US011346846B2

(12) United States Patent
Anderberg et al.

(10) Patent No.: US 11,346,846 B2
(45) Date of Patent: May 31, 2022

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Paul McPherson, Encinitas, CA (US); James Patrick Kampf, San Diego, CA (US); Kevin Nakamura, Cardiff by the Sea, CA (US); Jeff Gray, Solana Beach, CA (US); Thomas Kwan, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 16/483,519

(22) PCT Filed: Feb. 6, 2018

(86) PCT No.: PCT/US2018/017118
§ 371 (c)(1),
(2) Date: Aug. 5, 2019

(87) PCT Pub. No.: WO2018/145117
PCT Pub. Date: Aug. 9, 2018

(65) Prior Publication Data
US 2020/0103415 A1     Apr. 2, 2020

Related U.S. Application Data

(60) Provisional application No. 62/455,503, filed on Feb. 6, 2017.

(51) Int. Cl.
| G01N 33/68 | (2006.01) |
| G01N 33/543 | (2006.01) |
| G16B 25/10 | (2019.01) |
| G16B 40/20 | (2019.01) |

(52) U.S. Cl.
CPC ....... *G01N 33/6893* (2013.01); *G01N 33/543* (2013.01); *G16B 25/10* (2019.02); *G16B 40/20* (2019.02); *G01N 2333/521* (2013.01); *G01N 2333/96486* (2013.01); *G01N 2800/347* (2013.01); *G01N 2800/56* (2013.01)

(58) Field of Classification Search
CPC ....... G01N 33/6893; G01N 2333/8146; G01N 2800/56; G01N 33/53; G01N 33/543; G01N 2333/521; G01N 2333/96486; G01N 33/493; G01N 2800/347
See application file for complete search history.

(56) References Cited

U.S. PATENT DOCUMENTS

| 5,324,634 A | 6/1994 | Zucker |
| 6,218,122 B1 | 4/2001 | Friend et al. |
| 7,138,230 B2 | 11/2006 | Hu et al. |
| 8,252,905 B2 | 8/2012 | Furusako et al. |
| 8,778,615 B2 | 7/2014 | Anderberg et al. |
| 8,871,459 B2 | 10/2014 | Anderberg et al. |
| 8,993,250 B2 | 3/2015 | Anderberg et al. |
| 9,029,093 B2 | 5/2015 | Anderberg et al. |
| 9,057,735 B2 | 6/2015 | Anderberg et al. |
| 9,229,010 B2 | 1/2016 | Anderberg et al. |
| 9,360,488 B2 | 6/2016 | Anderberg et al. |
| 9,459,261 B2 | 10/2016 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | McPherson et al. |
| 2004/0029200 A1 | 2/2004 | Weimbs |
| 2004/0053309 A1 | 3/2004 | Holt et al. |
| 2004/0241744 A1 | 12/2004 | Kohno et al. |
| 2005/0158801 A1 | 7/2005 | Hu et al. |
| 2006/0240437 A1 | 10/2006 | Krolewski et al. |
| 2006/0246485 A1 | 11/2006 | Sarwal et al. |
| 2007/0087387 A1 | 4/2007 | Devarajan |

(Continued)

FOREIGN PATENT DOCUMENTS

| CN | 1791797 | 6/2006 |
| CN | 101010001 | 8/2007 |

(Continued)

OTHER PUBLICATIONS

Daubin et al. Urinary Biomarkers IGFBP7 and TIMP-2 for the Diagnostic Assessment of Transient and Persistent Acute Kidney Injury in Critically Ill Patients. PLoS ONE, 2017, 12(1): e0169674. https://doi.org/10.1371/journal.pone.0169674 (Year: 2017).*
Dewitte et al. Kinetic eGFR and Novel AKI Biomarkers to Predict Renal Recovery. Clin J Am Soc Nephrol 10: 1900-1910, 2015 (Year: 2015).*
Horstrup et al., "Elevation of serum and urine levels of TIMP-1 and tenascin in patients with renal disease," *Nephrol Dial Transplant*, 2002, 17:1005-1013.
International Search Report of the International Searching Authority issued in PCT/US18/171178 dated May 4, 2018.
Written Opinion of the International Searching Authority issued in PCT/US18/171178 dated May 4, 2018.

(Continued)

*Primary Examiner* — Vanessa L. Ford
*Assistant Examiner* — Sandrae Dillahunt
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using assays that detect one or more of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24 as diagnostic and prognostic biomarker assays in renal injuries.

20 Claims, No Drawings

Specification includes a Sequence Listing.

(56) References Cited

U.S. PATENT DOCUMENTS

| | | | |
|---|---|---|---|
| 2007/0166779 | A1 | 7/2007 | Belkowski et al. |
| 2007/0249002 | A1 | 10/2007 | Hu et al. |
| 2008/0206794 | A1 | 8/2008 | Hu et al. |
| 2008/0254485 | A1 | 10/2008 | Valkirs et al. |
| 2010/0279431 | A1 | 11/2010 | Amann-Zalan et al. |
| 2011/0111427 | A1 | 5/2011 | Kadomatsu et al. |
| 2011/0195429 | A1 | 8/2011 | Anderberg et al. |
| 2012/0142754 | A1 | 6/2012 | Niitsu et al. |
| 2012/0283128 | A1* | 11/2012 | Anderberg ......... G01N 33/6893 506/9 |
| 2013/0065239 | A1 | 3/2013 | Bodavilla Sandoval et al. |
| 2013/0157881 | A1 | 6/2013 | Anderberg et al. |
| 2013/0210041 | A1* | 8/2013 | Anderberg ......... G01N 33/6893 435/7.94 |
| 2013/0210043 | A1 | 8/2013 | Anderberg et al. |
| 2014/0323594 | A1 | 10/2014 | Anderberg et al. |
| 2014/0377777 | A1 | 12/2014 | Anderberg et al. |
| 2015/0355196 | A1* | 12/2015 | Anderberg ......... G01N 33/6893 435/7.92 |
| 2016/0146832 | A1 | 5/2016 | Chawla et al. |
| 2016/0274128 | A1 | 9/2016 | Anderberg et al. |
| 2016/0281083 | A1 | 9/2016 | Niitsu et al. |
| 2016/0297893 | A1 | 10/2016 | Vijayendran et al. |
| 2016/0303187 | A1 | 10/2016 | McPherson et al. |
| 2017/0248613 | A1 | 8/2017 | Anderberg et al. |
| 2018/0074054 | A1 | 3/2018 | McPherson et al. |
| 2018/0209990 | A1 | 7/2018 | Anderberg et al. |
| 2019/0263926 | A1 | 8/2019 | McPherson et al. |

FOREIGN PATENT DOCUMENTS

| | | |
|---|---|---|
| CN | 101358976 | 2/2009 |
| EP | 1970709 | 9/2008 |
| EP | 2479564 | 7/2012 |
| JP | H09-072906 | 3/1997 |
| JP | H09-274036 | 10/1997 |
| JP | 2005-120070 | 5/2005 |
| JP | 2008-224526 | 9/2008 |
| WO | WO 2001/028500 | 4/2001 |
| WO | WO 2001/088544 | 11/2001 |
| WO | WO 2001/090421 | 11/2001 |
| WO | WO 2004/088276 | 10/2004 |
| WO | WO 2005/002416 | 1/2005 |
| WO | WO 2005/121788 | 12/2005 |
| WO | WO 2007/024743 | 3/2007 |
| WO | WO 2007/039109 | 4/2007 |
| WO | WO 2007/084397 | 7/2007 |
| WO | WO 2007/093183 | 8/2007 |
| WO | WO 2007/144781 | 12/2007 |
| WO | WO 2008/061149 | 5/2008 |
| WO | WO 2008/084331 | 7/2008 |
| WO | WO 2008/116867 | 10/2008 |
| WO | WO 2009/062520 | 5/2009 |
| WO | WO 2010/048346 | 4/2010 |
| WO | WO 2010/048347 | 4/2010 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/064877 | 4/2016 |
| WO | WO 2016/164854 | 10/2016 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Casset et al., "A peptide mimetic of an anti-CD4 monoclonal antibody by rational design," Biochemical and Biophysical Research Communications, 2003, 307:198-205.

Ferrara et al., "Recombinant renewable polyclonal antibodies," mABs, 2015, 7(1):32-41.

MacCallum et al., "Antibody-antigen Interactions: Contact Analysis and Binding Site Topography," J Mol Biol, 1996, 262:732-745.

Paul, Fundamental Immunology, 3rd Edition, Raven Press, New York, 1993, Chapter 9, pp. 292-295.

Vajdos et al., "Comprehensive Functional Maps of the Antigen-binding Site of an Anti-ErbB2 Antibody Obtained with Shotgun Scanning Mutagenesis," J Mol Biol, 2002, 320:415-428.

Vijayan et al., "Clinical Use of the Urine Biomarker [TIMP-2] x [IGFBP7] for Acute Kidney Injury Risk Assessment," Am J Kidney Dis, 2016, 68(1):19-28.

Alatas et al., "Beneficial Effects of Allopurinol on Glutathione Levels and Glutathione Peroxidase Activity in Rat Ischaemic Acute Renal Failure," The Journal of International Medical Research, 1996, 24:33-39.

Allakhverdi et al., "Thymic stromal lymphopoietin is released by human epithelial cells in response to microbes, trauma, or inflammation and potently activates mast cells," J Exp Med, Feb. 19, 2007, 204(2):253-258.

Amar et al., "Potential clinical implications of recent matrix metalloproteinase inhibitor design strategies," Expert Rev Proteomics, 2015, 12(5):445-447.

Arthur et al., "Diagnostic and Prognostic Biomarkers in Acute Renal Failure," Contributions to Nephrology, Karger, Jan. 2008, 160:53-64.

Asanuma et al., "Selective modulation of the secretion of proteinases and their inhibitors by growth factors in cultured dlifferentiated podocytes," Kidney Int, Sep. 2002, 62(3):822-831.

Atkins et al., "Heat shock proteins in renal cell carcinomas," Contrib Nephrol, 2005, 148:35-56.

Berthier et al., "Metzincins, including matrix metalloproteinases and meprin, in kidney transplantation," Swiss Med Wkly, Dec. 23, 2006, 136:789-794.

Caron et al., "Ischemia injury alters endothelial cell properties of kidney cortex: stimulation of MMP-9," Exp Cell Res. Oct. 15, 2005;310(1):105-116.

Catania et al., "Role of matrix metalloproteinases in renal pathophysiologies," Am J Physiol Renal Physiol, Mar. 2007, 292(3):F905-F911.

Chang et al., "Levels in the Serum of Tissue Inhibitors of Metalloproteinaise-1 (TIMP-1) from Patients with Primary Nephrotic Syndrome," Chin J Integr Trad Western Nephrol, 2007, 10:600-601—English translation, abstract only.

Chatterjee et al., "Tempol, a membrane-permeable radical scavenger, reduces oxidant stress-mediated renal lysfunction and injury in the rat," Kidney Int, 2000, 58:658-673.

Chawla et al., "Identifying critically ill patients at high risk for developing acute renal failure: a pilot study," Kidney Int, 2005, 68:2274-2280.

Constantin et al., "Plasma neutrophil gelatinase-associated lipocalin is an early marker of acute kidney injury in adult critically ill patients: A prospective study," Journal of Critical Care, 2010, 25:176.e1-176.e6.

Cuadrado et al., "Vascular MMP-9/TIMP-2 and Neuronal MMP-10 Up-Regulation in Human Brain after Stroke: A Combined Laser Microdissection and Protein Array Study," J Proteome Res, 2009, 8:3191-3197.

Cwirla et al., "Peptides on phage: A vast library of peptides for identifying ligands," Proc Natl Arad Sci USA, Aug. 1990, 87:6378-6382.

Devarajan, "Neutrophil gelatinase-associated lipocalin (NGAL): A new marker of kidney disease," Scand J Clin Lab Invest Suppl, Jun. 2008, S241:89-94.

Edelstein, "Biomarkers of Acute Kidney Injury," Adv Chronic Kidney Dis, Jul. 2008, 15(3)222-234.

(56) References Cited

OTHER PUBLICATIONS

Eissa et al., "Noninvasive Diagnosis of Bladder Cancer by Detection of Matrix Metalloproteinases (MMP-2 and MMP-9) and Their Inhibitor (TIMP-2) in Urine," European Urology, 2007, 52:1388-1397.

Engers et al., "Rac Affects Invasion of Human Renal Cell Carcinomas by Up-regulating Tissue Inhibitor of Metalloproteinases (TIMP)-1 and TIMP-2 Expression," J Biol Chem, Nov. 9, 2001, 276(45):41889-41897.

Eremina et al., "Glomerular-specific alterations of VEGF-A expression lead to distinct congenital and acquired renal diseases," The Journal of Clinical Investigation, Mar. 2003, 111(5):707-716.

Fry et al., "Management of acute renal failure," Postgrad Med J, 2006, 82:106-116.

Fu et al., "Study on the expression of VEGF, MMP-2 and TIMP-2 in the progression of IgA nephropathy," J Clin Exp Pathol 2008, 24(5):573-576—includes English translation abstract only.

Gaggar et al., "Matrix metalloprotease-9 dysregulation in lower airway secretions of cystic fibrosis patients," Am J Physiol Lung Cell Mol Physiol, 2007, 293:L96-L104.

Grobmeyer et al., "Secretory leukocyte protease inhibitor, an inhibitor of neutrophil activiation, is elevated in serum in human sepsis and experimental endotoxema," Critical Care Medicine, 2000, 28(5):1276-1282.

Han et al., "An imbalance between matrix metalloproteinase-2 and tissue inhibitor of matrix metalloproteinase-2 contributes to the development of early diabetic nephropathy," Nephrol Dial Transplant, 2006, 21:2406-2416.

Hiemstra, "Novel roles of protease inhibitors in infection and inflammation," Biochem Soc Trans, Apr. 2002, 30(2):116-120.

Hollander et al., "Serum and bronchial lavage fluid concentrations of IL-8, SLPI, sCD14 and sICAM-1 in patients with COPD and Asthma," Respiratory Medicine, 2007, 101:1947-1953.

Iyoda et al., "Imatinib Suppresses Cryoglobulinemia and Secondary Membranoproliferative Glomerulonephritis," J Am Soc of Nephrol, Jan. 2009, 20(1):68-77.

Jalalah et al., "Inactive matrix metalloproteinase 2 in a normal constituent of human glomerular basement membrane. An immunoelectron microscopic study," J Pathol, 2000, 191:61-66.

Jin et al., "Correlation between Pathological Classification and Levels of TNF and sTNF-R in Sera from Patients with Lupus Nephritis," Clin Med J China, 2002, 9(1):7-8—English translation, abstract only.

Jo et al., "Heat preconditioning attenuates renal injury in ischemic ARF in rats: Role of heat-shock protein 70 on NF-kappa B-mediated inflammation and on tubular cell injury," J Am Soc Nephrology, 2006,17(11):3082-3092.

Jo et al., "Pharmacological Treatment of Acute Kidney Injury: Why Drugs Haven't Worked and What Is on the Horizon," Clin J Am Soc Nephrol, 2007, 2:356-365.

Journal of the Kanazawa University Juzen Medical Society, HISADA, "Expression of Matrix metalloproteinase-2 in Anti-Thy1.1 Glomerulonephritis in Rats," 1995;104:36-45—includes English translation abstract only.

Kallakury et al., "Increased Expression of Matrix Metalloproteinases 2 and 9 and Tissue Inhibitors of Metalloproteinases 1 and 2 Correlate with Poor Prognostic Variables in Renal Cell Carcinoma," Clin Cancer Res, Oct. 2001, 7:3113-3119.

Kawata et al., "Significant Relationship of Matrix Metalloproteinase 9 with Nuclear Grade and Prognostic Impact of Tissue Inhibitor of Metalloproteinase 2 for Incidental Clear Cell Renal Cell Carcinoma," Urology, 2007, 69(6):1049-1053.

Kellum, "Acute kidney injury," Crit Care Med, 2008, 36(4):S141-S145.

Kellum et al., "Definition and Classification of Acute Kidney Injury," Nephron Clin Pract, 2008, 109(4):c182-c187.

Kolkenbrock et al., "Biochemical Characterization of the Catalytic Domain of Membrane—Type 4 Matrix Metalloproteinase," Biol Chem, Sep. 1999, 380:1103-1108.

Laplante et al., "Modulation of matrix gelatinases and metalloproteinase-activating process in acute kidney rejection," Transpl Int, 2003, 16:262-269.

Lemancewicz et al., "Matrix metalloproteinase-2 and tissue inhibitor of metalloproteinase-2 urine levels in preterm labouring patients," Archives of Perinatal Medicine, 2007, 13(2):50-52.

Lenz et al., "Matrix Metalloproteinases in Renal Development and Disease," J Am Soc Nephrol, 2000, 11:574-581.

Lichte et al., "The recombinant catalytic domain of membrane-type matrix metalloproteinase-1 (MT1-MMP) induces activation of progelatinase A and progelatinase A complexed with TIMP-2," FEBS Lett, 1996, 397:277-282.

Lopes et al., "The RIFLE an AKIN classifications for acute kidney injury: a critical and comprehensive review," Clin Kidney J, 2013, 6(1):8-14.

Muhlfeld et al., "Overexpression of complement inhibitor Crry does not prevent cryoglobulin-associated membranoproliferative glomerulonephritis," Kidney International, 2004, 65:1214-1223.

Nguyen et al., "Biomarkers for the early detection of acute kidney injury," Pediatr Nephrol, 2008, 23(12):2151-2157.

Obata et al., "A one-step sandwich enzyme immunoassay for human matrix metalloproteinase 3 (stromelysin-1) using monoclonal antibodies," Clin Chim Acta, 1992, 211:59-72.

Ostermann et al., "Acute kidney injury 2016: diagnosis and diagnostic workup," Crit Care, 2016, 20(1):299.

Ramp et al., "Expression of heat shock protein 70 in renal cell carcinoma and its relation to tumor progression and prognosis," Histol Histopathol, 2007, 22):1099-1107.

Roy et al., "Urinary TIMP-1 and MMP-2 levels detect the presence of pancreatic malignancies," British Journal of Cancer, 2014, 111:1772-1779.

Rysz et al., "Serum matrix metalloproteinases MMP-2 and MMP-9 and metalloproteinase tissue inhibitors TIMP-1 and TIMP-2 in diabetic nephropathy," J Nephrol, 2007, 20:444-452.

Schaefer et al., "Tubular gelatinase A (MMP-2) and its tissue inhibitors in polycystic kidney disease in the Han:SPRD rat," Kidney Int, 1996, 49:75-81.

Schrijvers et al., "The role of vascular endothelial factor (VEGF) in renal pathophysiology," Kidney International, 2004, 65:2003-2017.

Scott et al., "Searching for Peptide Ligands with an Epitope Library," Science, 1990, 249:386-390.

Seo et al., "TIMP-2 Mediated Inhibition of Angiogenesis: An MMP-Independent Mechanism," Cell, Jul. 25, 2003, 114:171-180.

Shiba et al., "Chronic kidney disease and heart failure—Bidirectional close link and common therapeutic goal," J Cardiol, 2011, 57(1):8-17.

Taneda et al., "Cryoglobulinemic Glomerulonephritis in Thymic Stromal Lymphopoietin Transgenic Mice," Am J Path, 2001, 159(6):2355-2369.

Thiemermann et al., "High Density Lipoprotein (HDL) Reduces Renal Ischemia/Reperfusion Injury," J Am Soc Nephrol, 2003, 14:1833-1843.

Uchio-Yamada et al., "Decreased Expression of Matrix Metalloproteinases and Tissue Inhibitors of Metalloproteinase in the Kidneys of Hereditary Nephrotic (ICGN) Mice," J Vet Med Sci, Jan. 2005, 67(1):35-41.

Vaidya et al., "Mechanistic biomarkers for cytotoxic acute kidney injury," Expert Opin Drug Metab Toxicol, Oct. 2006, 2(5):697-713.

Vaidya et al., "Biomarkers of Acute Kidney Injury," Annu Rev Pharmacol Toxicol, Feb. 2008, 48:463-493.

Vasala, "Matrix metalloproteinase MMP-2 and MMP-9 and their inhibitors TIMP-1 and TIMP-2 in bladder carcinoma," Acta Univ Oul, Jan. 1, 2008, D 983:1-76, XP055552669.

Vasala et al., "Serum tissue inhibitor of metalloproteinase-2 (TIMP-2) and matrix metalloproteinase-2 in complex with the inhibitor (MMP-2:TIMP-2) as prognostic markers in bladder cancer," Clin Biochem, Jun. 1, 2007, 40(9-10):640-644.

Wagrowska-Danilewicz et al., "Aberrant Tubulointerstitial Immunoexpression of Matrix Metalloproteinases MMP-2, MMP-9 and Tissue Inhibitor of Matrix Proteinase-2 (TIMP-2) in Acute Cellular Rejection of Human Renal Allograft," Pol J Pathol, 2008, 59:189-194.

(56) References Cited

OTHER PUBLICATIONS

Waku et al., "Serum Level of Human Tissue Inhibitor Metalloproteinase-1 in Various Glomerulonephritides," J Kyorin Med Soc, 1997, 28:441-447—English translation, abstract only.

Wang et al., "Induction of heat shock protein 70 inhibits ischemic renal injury," Kidney International, 2011, 79:861-870.

Wasilewska et al., "Urinary levels of matrix metalloproteinases and their tissue inhibitors in nephrotic children," Pediatr Nephrol, Oct. 2008, 23:1795-1802.

When et al., "The expression and Significance of Serum TGF-beta1', MMP-9 and TIMP-1 in Patients with Chronic renal failure," Wanfang Data Knowledge Service Platform, 2007—English translation, abstract only.

Williamson et al., "Comparison of Biomarkers in Blood and Saliva in Healthy Adults," Nursing Research and Practice, 2012, vol. 2012, Article ID 246178, pp. 1-4.

Yan et al., "Expression of MMP-2 and TIMP-1 in Renal Tissue of Patients with Chronic Active Antibody-mediated Renal Graft Rejection," Diagn Pathol, 2012, 7:141.

Zhang et al., "Significance of MMP-2 and TIMP-2 mRNA Expressions on Glomerular Cells in the Development of Glomerulosclerosis," Chin Med Sci J, Jun. 2004, 19(2):84-88.

International Preliminary Report on Patentability issued in PCT/US18/171178 dated Aug. 15, 2019.

Anonymous, "Granulomatosis with polyangiitis", Wikipedia, Jan. 2, 2021, Retrieved from the Internet: https://en.wikipedia.org/wiki/Granulomatosis_with_polyangiitis.

Huang et al., "Chymase is Upregulated in Diabetic Nephropathy: Implications for an Alternative Pathway of Angiotensin II-Mediated Diabetic Renal and Vascular Disease," J Am Soc Nephrol, 2003, 14:1738-1747.

Koyner et al., "Tissue Inhibitor Metalloproteinase-2 (TIMP-2) IGF-Binding Protein-7 (IGFBP7) Levels Are Associated with Adverse Long-Term Outcomes in Patients with AKI," J Am Soc Nephrol, 2015, 26:1747-1754.

Malhotra et al., "Biomarkers for the Early Detection and Prognosis of Acute Kidney Injury," Clin J Am Soc Nephrol, 2016, 12:149-173.

Chlsson et al., "Increased expression of the secretory leukocyte proteinase inhibitor in Wegener's granulomatosis," Clin Exp Immunol, 2003, 131:190-196.

Extended European Search Report dated Mar. 9, 2021, issued in European application No. 18747952.2.

Supplementary Partial European Search Report dated Dec. 4, 2020, issued in European application No. 18747952.2.

\* cited by examiner

METHODS AND COMPOSITIONS FOR DIAGNOSIS AND PROGNOSIS OF RENAL INJURY AND RENAL FAILURE

The present application claims the benefit of U.S. Provisional Patent Application 62/455,503 filed Feb. 6, 2017, which is hereby incorporated by reference in its entirety including all tables, figures and claims.

SEQUENCE LISTING

This application contains a Sequence Listing which has been submitted in ASCII format via EFS-Web and is hereby incorporated by reference in its entirety. Said ASCII copy, created on Aug. 9, 2018, is named AST_8167_PCT_SeqListing.txt and is 10,751 bytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, *J Am Soc Nephrol* 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care*. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 µmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (>26.4 µmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine >354 µmol/L accompanied by an acute increase of at least 44 µmol/L OR urine output less than 0.3 mL/kg per hour for 24 hours or anuria for 12 hours.

The CIN Consensus Working Panel (McCollough et al, *Rev Cardiovasc Med.* 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24 (collectively referred to herein as 37 kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s) is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject having, or at risk of, an injury to renal function for future persistence of acute kidney injury. "Future persistence" as used herein refers to an existing acute renal injury that will continue for a period selected from the group consisting of 21 days, 14 days, 7 days, 5 days, 96 hours, 72 hours, 48 hours, 36 hours, 24 hours, and 12 hours. In certain embodiments the subject has an acute kidney injury at the time the sample is obtained. This is not meant to imply that the subject must have an acute kidney injury at the time the sample is obtained, but rather that the subject, upon onset of an acute kidney injury, suffers from an acute kidney injury that will persist. In various embodiments, the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the future persistence of the acute kidney injury in the subject. For example, the measured concentration(s) may be compared to a threshold value. For a positive going marker, when the measured concentration is above the threshold, a future persistence of acute kidney injury may be assigned to the subject; alternatively, when the measured concentration is below the threshold, afuture improvement of renal function may be assigned to the subject. For a negative going marker, when the measured concentration is below the threshold, a future persistence of acute kidney injury may be assigned to the subject; alternatively, when the measured concentration is above the threshold, a future improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s), for example a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24, is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^h$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of Metalloproteinase inhibitor 1, Metalloproteinase inhibitor 2, Metalloproteinase inhibitor 4, C—C motif chemokine 15, C—C motif chemokine 18, C—C motif chemokine 23, and/or, C—C motif chemokine 24 or one or more markers related thereto, and optionally one or more additional kidney injury markers known in the art, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (>8.8 μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (>26.4 μmol/1), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "Metalloproteinase inhibitor 1" refers to one or more polypeptides present in a biological sample that are derived from the Metalloproteinase inhibitor 1 precursor (Swiss-Prot P01033 (SEQ ID NO: 1)).

```
          10          20          30          40
  MAPFEPLASG  ILLLLWLIAP  SRACTCVPPH  PQTAFCNSDL 50          60          70          80
  VIRAKFVGTP  EVNQTTLYQR  YEIKMTKMYK  GFQALGDAAD 90         100         110         120
  IRFVYTPAME  SVCGYFHRSH  NRSEEFLIAG  KLQDGLLHIT 130         140         150         160
  TCSFVAPWNS  LSLAQRRGFT  KTYTVGCEEC  TVFPCLSIPC 170         180         190         200
  KLQSGTHCLW  TDQLLQGSEK  GFQSRHLACL  PREPGLCTWQ

SLRSQIA
```

The following domains have been identified in Metalloproteinase inhibitor 1:

| Residues | Length | Domain ID |
| --- | --- | --- |
| 1-23 | 23 | signal sequence |
| 24-207 | 184 | Metalloproteinase inhibitor 1 |

As used herein, the term "Metalloproteinase inhibitor 2" refers to one or more polypeptides present in a biological sample that are derived from the Metalloproteinase inhibitor 2 precursor (human precursor: Swiss-Prot P16035 (SEQ ID NO: 2)).

```
          10          20          30          40
  MGAAARTLRL  ALGLLLLATL  LRPADACSCS  PVHPQQAFCN 50          60          70          80
  ADVVIRAKAV  SEKEVDSGND  IYGNPIKRIQ  YEIKQIKMFK 90         100         110         120
  GPEKDIEFIY  TAPSSAVCGV  SLDVGGKKEY  LIAGKAEGDG 130         140         150         160
  KMHITLCDFI  VPWDTLSTTQ  KKSLNHRYQM  GCECKITRCP 170         180         190         200
  MIPCYISSPD  ECLWMDWVTE  KNINGHQAKF  FACIKRSDGS 210         220
  CAWYRGAAPP  KQEFLDIEDP
```

The following domains have been identified in Metalloproteinase inhibitor 2:

| Residues | Length | Domain ID |
| --- | --- | --- |
| 1-26 | 26 | Signal peptide |
| 27-220 | 194 | Metalloproteinase inhibitor 2 |

As used herein, the term "Metalloproteinase inhibitor 4" refers to one or polypeptides present in a biological sample that are derived from the Metalloproteinase inhibitor 4 precursor (human precursor: Swiss-Prot Q99727 (SEQ ID NO: 3)).

```
          10          20          30          40
  MPGSPRPAPS  WVLLLRLLAL  LRPPGLGEAC  SCAPAHPQQH 50          60          70          80
  ICHSALVIRA  KISSEKVVPA  SADPADTEKM  LRYEIKQIKM 90         100         110         120
  FKGFEKVKDV  QYIYTPFDSS  LCGVKLEANS  QKQYLLTGQV 130         140         150         160
  LSDGKVFIHL  CNYIEPWEDL  SLVQRESLNH  HYHLNCGCQI 170         180         190         200
  TTCYTVPCTI  SAPNECLWTD  WLLERKLYGY  QAQHYVCMKH
```

-continued

```
           210        220
VDGTCSWYRG HLPLRKEFVD IVQP
```

The following domains have been identified in Metalloproteinase inhibitor 4:

| Residues | Length | Domain ID |
| --- | --- | --- |
| 1-29 | 29 | Signal sequence |
| 30-224 | 195 | Metalloproteinase inhibitor 4 |

As used herein, the term "C—C motif chemokine 15" refers to one or more polypeptides present in a biological sample that are derived from the C—C motif chemokine 15 precursor (human precursor: Swiss-Prot Q16663 (SEQ ID NO: 4)).

```
           10         20         30         40
MKVSVAALSC LMLVAVLGSQ AQFINDAETE LMMSKLPLEN 50         60         70         80
PVVLNSFHFA ADCCTSYISQ SIPCSLMKSY FETSSECSKP 90         100        110
GVIFLTKKGR QVCAKPSGPG VQDCMKKLKP YSI
```

The following domains have been identified in C—C motif chemokine 15:

| Residues | Length | Domain ID |
| --- | --- | --- |
| 1-21 | 21 | Signal peptide |
| 22-113 | 92 | C-C motif chemokine 15 |
| 43-113 | 71 | C-C motif chemokine 15 (22-92) |
| 46-113 | 68 | C-C motif chemokine 15 (25-92) |
| 50-113 | 64 | C-C motif chemokine 15 (29-92) |

As used herein, the term "C—C motif chemokine 18" refers to one or more polypeptides present in a biological sample that are derived from the C—C motif chemokine 18 precursor (human precursor: Swiss-Prot P55774 (SEQ ID NO: 5)).

```
           10         20         30         40
MKGLAAALLV LVCTMALCSC AQVGTNKELC CLVYTSWQIP 50         60         70         80
QKFIVDYSET SPQCPKPGVI LLTKRGRQIC ADPNKKWVQK

YISDLKLNA
```

The following domains have been identified in C—C motif chemokine 18: Residues Length Domain ID

| Residues | Length | Domain ID |
| --- | --- | --- |
| 1-20 | 20 | Signal peptide |
| 21-89 | 69 | C-C motif chemokine 18 |
| 21-88 | 68 | CCL 18 (1-68) |
| 23-89 | 67 | CCL 18 (3-69) |
| 24-89 | 66 | CCL 18 (4-69) |

As used herein, the term "C—C motif chemokine 23" refers to one or more polypeptides present in a biological sample that are derived from the C—C motif chemokine 23 precursor (Swiss-Prot P55773 (SEQ ID NO: 6))

```
           10         20         30         40
MKVSVAALSC LMLVTALGSQ ARVTKDAETE FMMSKLPLEN 50         60         70         80
PVLLDRFHAT SADCCISYTP RSIPCSLLES YFETNSECSK 90         100        110        120
PGVIFLTKKG RRFCANPSDK QVQVCVRMLK LDTRIKTRKN
```

The following domains have been identified in C—C motif chemokine 23:

| Residues | Length | Domain ID |
| --- | --- | --- |
| 1-21 | 21 | signal peptide |
| 22-120 | 99 | C-C motif chemokine 23 |
| 40-120 | 81 | C-C motif chemokine 23 (19-99) |
| 43-120 | 78 | C-C motif chemokine 23 (22-99) |
| 48-120 | 73 | C-C motif chemokine 23 (27-99) |
| 51-120 | 70 | C-C motif chemokine 23 (30-99) |

As used herein, the term "C—C motif chemokine 24" refers to one or more polypeptides present in a biological sample that are derived from the C—C motif chemokine 24 precursor (Swiss-Prot O00175 (SEQ ID NO: 7))

```
           10         20         30         40
MAGLMTIVTS LLFLGVCAHH IIPTGSVVIP SPCCMFFVSK 50         60         70         80
RIPENRVVSY QLSSRSTCLK AGVIFTTKKG QQFCGDPKQE 90         100        110
WVQRYMKNLD AKQKKASPRA RAVAVKGPVQ RYPGNQTTC
```

The following domains have been identified in C—C motif chemokine 24:

| Residues | Length | Domain ID |
| --- | --- | --- |
| 1-26 | 26 | signal peptide |
| 27-119 | 93 | C-C motif chemokine 24 |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay.

The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $1012$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No.

6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection theroy developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1—specificity, the ROC graph is sometimes called the sensitivity vs (1—specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1.

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61769); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase 9 (Q16790); Casein Kinase 2 (P68400); Clusterin (P10909); Complement C3 (P01024); Cysteine-rich protein (CYR61, O00622); Cytochrome C (P99999); Epidermal growth factor (EGF, P01133); Endothelin-1 (PO5305); Exosomal Fetuin-A (P02765); Fatty acid-binding protein, heart (FABP3, P05413); Fatty acid-binding protein, liver (P07148); Ferritin (light chain, P02792; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P05019); Immunoglobulin G; Immunoglobulin Light Chains (Kappa and Lambda); Interferon gamma (P01579); Lysozyme (P61626); Interleukin-1 alpha (P01583); Interleukin-2 (P60568); Interleukin-4 (P05112); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine Ni-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, 000458); Isovaleryl-CoA dehydrogenase (IVD, P26440); I-TAC/CXCL11 (O14625); Keratin 19 (P08727); Kim-1 (Hepatitis A virus cellular receptor 1, Q96D42); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, 015244); Osteoprotegerin (O00300); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (P06870); RT1.B-1 (alpha) chain of the integral membrane protein (Q5Y7A8); soluble tumor necrosis factor receptor superfamily member 1A (sTNFR-I, P19438); soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m² can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;

undergoing a radiographic/angiographic procedure (such as a CT scan or coronary intervention) involving the intravascular administration of contrast media;

expected to be hospitalized for at least 48 hours after contrast administration.

able and willing to provide written informed consent for study participation and to comply with all study procedures.

Exclusion Criteria renal transplant recipients;

acutely worsening renal function prior to the contrast procedure;

already receiving dialysis (either acute or chronic) or in imminent need of dialysis at enrollment;

expected to undergo a major surgical procedure (such as involving cardiopulmonary bypass) or an additional imaging procedure with contrast media with significant risk for further renal insult within the 48 hrs following contrast administration;

participation in an interventional clinical study with an experimental therapy within the previous 30 days;

known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 $m^2$=2 points, 20-40 mL/min/1.73 $m^2$=4 points, <20 mL/min/1.73 $m^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2: Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria males and females 18 years of age or older;

undergoing cardiovascular surgery;

Toronto/Ottawa Predictive Risk Index for Renal Replacement risk score of at least 2 (Wijeysundera et al., JAMA 297: 1801-9, 2007); and able and willing to provide written informed consent for study participation and to comply with all study procedures.

Exclusion Criteria known pregnancy;

previous renal transplantation;

acutely worsening renal function prior to enrollment (e.g., any category of RIFLE criteria);

already receiving dialysis (either acute or chronic) or in imminent need of dialysis at enrollment;

currently enrolled in another clinical study or expected to be enrolled in another clinical study within 7 days of cardiac surgery that involves drug infusion or a therapeutic intervention for AKI;

known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3: Acutely Ill Subject Sample Collection

The objective of this study is to collect samples from acutely ill patients. Approximately 2200 adults expected to be in the ICU for at least 48 hours will be enrolled. To be enrolled in the study, each patient must meet all of the following inclusion criteria and none of the following exclusion criteria:

Inclusion Criteria males and females 18 years of age or older;

Study population 1: approximately 300 patients that have at least one of:

shock (SBP<90 mmHg and/or need for vasopressor support to maintain MAP>60 mmHg and/or documented drop in SBP of at least 40 mmHg); and sepsis;

Study population 2: approximately 300 patients that have at least one of:

IV antibiotics ordered in computerized physician order entry (CPOE) within 24 hours of enrollment;

contrast media exposure within 24 hours of enrollment;

increased Intra-Abdominal Pressure with acute decompensated heart failure; and severe trauma as the primary reason for ICU admission and likely to be hospitalized in the ICU for 48 hours after enrollment;

Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment;

Study population 4: approximately 1000 patients that are 21 years of age or older, within 24 hours of being admitted into the ICU, expected to have an indwelling urinary catheter for at least 48 hours after enrollment, and have at least one of the following acute conditions within 24 hours prior to enrollment:

(i) respiratory SOFA score of >2 (PaO2/FiO2<300), (ii) cardiovascular SOFA score of >1 (MAP<70 mm Hg and/or any vasopressor required).

Study population 5: approximately 300 patients that are 21 years of age or older, receiving care in the ICU, have an indwelling urinary catheter as standard care at the time of enrollment, have acute kidney injury (KDIGO stage 2 or stage 3) at the time of the first sample collection, and have their first sample collected within 36 hours of meeting KDIGO stage 2 criteria Exclusion Criteria
known pregnancy;
prisoners or institutionalized individuals;
previous renal transplantation;
comfort-measures-only status for study population 5;
known acutely worsening renal function prior to enrollment (e.g., any category of RIFLE criteria) for study populations 1, 2, 3, and 4;
received dialysis (either acute or chronic) within 5 days prior to enrollment or in imminent need of dialysis at the time of enrollment;
known infection with human immunodeficiency virus (HIV) or a hepatitis virus; meets any of the following in study populations 4 and 5:
  (i) active bleeding with an anticipated need for >4 units PRBC in a day;
  (ii) hemoglobin <7 g/dL;
  (iii) any other condition that in the physician's opinion would contraindicate drawing serial blood samples for clinical study purposes;
meets only the SBP <90 mmHg inclusion criterion set forth above, and does not have shock in the attending physician's or principal investigator's opinion.

After obtaining informed consent, an EDTA anti-coagulated blood sample (10 mL) and a urine sample (25-50 mL) are collected from each patient. Blood and urine samples are then collected at 4 (±0.5) and 8 (±1) hours after contrast administration (if applicable); at 12 (±1), 24 (±2), 36 (±2), 48 (±2), 60 (±2), 72 (±2), and 84 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4. Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Table of Swiss-Prot numbers, preferred names and units for the analytes in the examples below.

| Swiss-Prot Number | Preferred Name | Units |
|---|---|---|
| P01033 | Metalloproteinase inhibitor 1 | pg/ml |
| P16035 | Metalloproteinase inhibitor 2 | pg/ml |
| Q99727 | Metalloproteinase inhibitor 4 | pg/ml |
| Q16663 | C-C motif chemokine 15 | pg/ml |
| P55774 | C-C motif chemokine 18 | ng/ml |
| P55773 | C-C motif chemokine 23 | ng/ml |
| O00175 | C-C motif chemokine 24 | pg/ml |

Example 5. Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6. Use of Metalloproteinase Inhibitor 1 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 1 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 6.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 5950 | 17800 | 5970 | 17700 | 5950 | 17300 |
| Average | 9410 | 33100 | 8890 | 32200 | 8800 | 31800 |
| Stdev | 9010 | 35200 | 7930 | 34800 | 8170 | 34600 |
| p (t-test) | | 8.0E−7 | | 8.9E−6 | | 3.1E−5 |
| Min | 634 | 297 | 634 | 297 | 634 | 297 |
| Max | 39400 | 146000 | 32600 | 146000 | 32600 | 146000 |
| n (Patient) | 57 | 260 | 46 | 271 | 41 | 276 |
| sCr only | | | | | | |
| Median | 7940 | 18500 | 7940 | 18100 | 7940 | 18100 |
| Average | 12800 | 33700 | 13000 | 33500 | 11700 | 33500 |
| Stdev | 16300 | 35700 | 16400 | 35600 | 11300 | 35800 |
| p (t-test) | | 1.3E−6 | | 2.7E−6 | | 8.7E−7 |
| Min | 634 | 297 | 634 | 297 | 634 | 297 |
| Max | 116000 | 146000 | 116000 | 146000 | 65500 | 146000 |
| n (Patient) | 76 | 240 | 74 | 242 | 70 | 246 |
| UO only | | | | | | |
| Median | 10800 | 21300 | 9980 | 20500 | 9520 | 20800 |
| Average | 23500 | 37700 | 23000 | 36200 | 22100 | 35700 |
| Stdev | 30800 | 35700 | 30600 | 35400 | 29800 | 35400 |
| p (t-test) | | 2.2E−4 | | 4.4E−4 | | 2.7E−4 |
| Min | 297 | 399 | 297 | 399 | 297 | 399 |
| Max | 146000 | 140000 | 146000 | 140000 | 127000 | 146000 |
| n (Patient) | 194 | 121 | 173 | 142 | 156 | 159 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.75 | 0.70 | 0.66 | 0.75 | 0.69 |
| SE | 0.031 | 0.032 | 0.032 | 0.033 | 0.032 |
| p Value | 2.2E−16 | 2.7E−10 | 7.5E−7 | 6.6E−14 | 2.2E−9 |
| nCohort Recovered | 57 | 76 | 194 | 46 | 74 |
| nCohort Non-recovered | 260 | 240 | 121 | 271 | 242 |
| Cutoff Quartile 2 | 6030 | 6020 | 6080 | 6030 | 6020 |
| Sensitivity | 82% | 81% | 88% | 80% | 81% |
| Specificity | 54% | 43% | 34% | 52% | 43% |
| Cutoff Quartile 3 | 14200 | 14100 | 14200 | 14200 | 14100 |
| Sensitivity | 58% | 58% | 66% | 56% | 58% |
| Specificity | 84% | 76% | 60% | 87% | 76% |
| Cutoff Quartile 4 | 35900 | 35400 | 36300 | 35900 | 35400 |
| Sensitivity | 30% | 31% | 35% | 30% | 31% |

TABLE 6.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | |
|---|---|---|---|---|---|
| Specificity | 98% | 95% | 81% | 100% | 95% |
| OR Quartile 2 | 5.27 | 3.24 | 3.85 | 4.28 | 3.16 |
| p Value | 8.6E−8 | 3.5E−5 | 2.9E−5 | 1.1E−5 | 5.5E−5 |
| Lower limit of 95% CI | 2.87 | 1.86 | 2.05 | 2.24 | 1.81 |
| Upper limit of 95% CI | 9.67 | 5.64 | 7.24 | 8.21 | 5.53 |
| OR Quartile 3 | 7.27 | 4.51 | 2.90 | 8.64 | 4.27 |
| p Value | 2.4E−7 | 5.1E−7 | 1.0E−5 | 2.1E−6 | 1.4E−6 |
| Lower limit of 95% CI | 3.42 | 2.51 | 1.81 | 3.55 | 2.37 |
| Upper limit of 95% CI | 15.4 | 8.12 | 4.66 | 21.1 | 7.70 |
| OR Quartile 4 | 24.4 | 8.18 | 2.26 | 39.1 | 7.86 |
| p Value | 0.0017 | 7.8E−5 | 0.0021 | 0.010 | 1.1E−4 |
| Lower limit of 95% CI | 3.32 | 2.88 | 1.34 | 2.38 | 2.77 |
| Upper limit of 95% CI | 180 | 23.2 | 3.79 | 642 | 22.3 |

| | Recovery Period Duration (hr) | | | |
|---|---|---|---|---|
| | 48 | 72 | | |
| | UO only | sCr or UO | sCr only | UO only |
| AUC | 0.65 | 0.75 | 0.70 | 0.66 |
| SE | 0.031 | 0.035 | 0.032 | 0.030 |
| p Value | 8.9E−7 | 2.7E−13 | 8.0E−10 | 1.2E−7 |
| nCohort Recovered | 173 | 41 | 70 | 156 |
| nCohort Non-recovered | 142 | 276 | 246 | 159 |
| Cutoff Quartile 2 | 6080 | 6030 | 6020 | 6080 |
| Sensitivity | 86% | 79% | 80% | 85% |
| Specificity | 34% | 54% | 43% | 35% |
| Cutoff Quartile 3 | 14200 | 14200 | 14100 | 14200 |
| Sensitivity | 63% | 56% | 58% | 63% |
| Specificity | 61% | 88% | 77% | 63% |
| Cutoff Quartile 4 | 36300 | 35900 | 35400 | 36300 |
| Sensitivity | 33% | 29% | 31% | 33% |
| Specificity | 82% | 100% | 96% | 83% |
| OR Quartile 2 | 3.16 | 4.45 | 3.02 | 3.06 |
| p Value | 7.2E−5 | 1.7E−5 | 1.4E−4 | 5.6E−5 |
| Lower limit of 95% CI | 1.79 | 2.25 | 1.71 | 1.78 |
| Upper limit of 95% CI | 5.57 | 8.78 | 5.32 | 5.28 |
| OR Quartile 3 | 2.67 | 9.09 | 4.61 | 2.86 |
| p Value | 2.6E−5 | 7.4E−6 | 1.0E−6 | 6.4E−6 |
| Lower limit of 95% CI | 1.69 | 3.46 | 2.50 | 1.81 |
| Upper limit of 95% CI | 4.22 | 23.9 | 8.50 | 4.52 |
| OR Quartile 4 | 2.18 | 34.0 | 9.98 | 2.50 |
| p Value | 0.0033 | 0.014 | 1.5E−4 | 7.9E−4 |
| Lower limit of 95% CI | 1.30 | 2.07 | 3.04 | 1.46 |
| Upper limit of 95% CI | 3.66 | 559 | 32.7 | 4.27 |

TABLE 6.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 6460 | 20500 | 6980 | 19000 | 6510 | 18500 |
| Average | 13400 | 34900 | 14200 | 33700 | 14400 | 33000 |
| Stdev | 18900 | 35800 | 19900 | 35500 | 20800 | 35100 |
| p (t-test) | | 1.2E-7 | | 5.1E-6 | | 2.7E-5 |
| Min | 634 | 297 | 634 | 297 | 634 | 297 |
| Max | 110000 | 146000 | 110000 | 146000 | 110000 | 146000 |
| n (Patient) | 90 | 227 | 79 | 238 | 71 | 246 |
| | sCr only | | | | | |
| Median | 8310 | 20500 | 8310 | 20000 | 8210 | 19800 |
| Average | 15500 | 35500 | 15700 | 35200 | 14700 | 35200 |
| Stdev | 21000 | 36300 | 21100 | 36300 | 19000 | 36400 |
| p (t-test) | | 2.9E-7 | | 6.5E-7 | | 2.4E-7 |
| Min | 634 | 297 | 634 | 297 | 634 | 297 |
| Max | 116000 | 146000 | 116000 | 146000 | 110000 | 146000 |
| n (Patient) | 106 | 211 | 104 | 213 | 99 | 218 |
| | UO only | | | | | |
| Median | 11200 | 20500 | 11000 | 19200 | 11000 | 19300 |
| Average | 25400 | 36200 | 25900 | 33900 | 25000 | 34000 |
| Stdev | 31900 | 35500 | 32300 | 34700 | 31500 | 35300 |
| p (t-test) | | 0.0071 | | 0.039 | | 0.017 |
| Min | 297 | 399 | 297 | 399 | 297 | 399 |
| Max | 146000 | 140000 | 146000 | 140000 | 127000 | 146000 |
| n (Patient) | 212 | 103 | 194 | 121 | 178 | 137 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.74 | 0.70 | 0.64 | 0.71 | 0.69 |
| SE | 0.029 | 0.030 | 0.034 | 0.031 | 0.030 |
| p Value | 2.2E-16 | 1.5E-11 | 5.3E-5 | 4.3E-12 | 1.2E-10 |
| nCohort Recovered | 90 | 106 | 212 | 79 | 104 |
| nCohort Non-recovered | 227 | 211 | 103 | 238 | 213 |
| Cutoff Quartile 2 | 6030 | 6030 | 6080 | 6030 | 6030 |
| Sensitivity | 85% | 84% | 90% | 82% | 84% |
| Specificity | 49% | 42% | 33% | 47% | 42% |
| Cutoff Quartile 3 | 14200 | 14200 | 14200 | 14200 | 14200 |
| Sensitivity | 61% | 62% | 67% | 59% | 61% |
| Specificity | 78% | 73% | 58% | 76% | 72% |
| Cutoff Quartile 4 | 35900 | 35900 | 36300 | 35900 | 35900 |
| Sensitivity | 32% | 33% | 31% | 31% | 33% |
| Specificity | 92% | 91% | 78% | 91% | 90% |
| OR Quartile 2 | 5.25 | 3.84 | 4.49 | 4.11 | 3.73 |
| p Value | 3.1E-9 | 7.1E-7 | 3.7E-5 | 5.6E-7 | 1.2E-6 |
| Lower limit of 95% CI | 3.03 | 2.26 | 2.20 | 2.36 | 2.19 |
| Upper limit of 95% CI | 9.08 | 6.54 | 9.15 | 7.15 | 6.35 |
| OR Quartile 3 | 5.53 | 4.26 | 2.80 | 4.51 | 4.05 |
| p Value | 2.8E-9 | 2.4E-8 | 4.1E-5 | 3.1E-7 | 7.4E-8 |
| Lower limit of 95% CI | 3.14 | 2.56 | 1.71 | 2.53 | 2.43 |
| Upper limit of 95% CI | 9.72 | 7.09 | 4.59 | 8.03 | 6.74 |
| OR Quartile 4 | 5.62 | 4.77 | 1.58 | 4.55 | 4.60 |
| p Value | 3.7E-5 | 1.7E-5 | 0.089 | 3.1E-4 | 2.6E-5 |
| Lower limit of 95% CI | 2.48 | 2.34 | 0.933 | 2.00 | 2.26 |

TABLE 6.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | |
|---|---|---|---|---|
| Upper limit of 95% CI | 12.8 | 9.71 | 2.68 | 10.4 | 9.38 |

| | Recovery Period Duration (hr) | | | |
|---|---|---|---|---|
| | 48 | 72 | | |
| | UO only | sCr or UO | sCr only | UO only |
| AUC | 0.61 | 0.71 | 0.70 | 0.62 |
| SE | 0.033 | 0.032 | 0.030 | 0.032 |
| p Value | 5.9E−4 | 1.8E−11 | 2.2E−11 | 2.6E−4 |
| nCohort Recovered | 194 | 71 | 99 | 178 |
| nCohort Non-recovered | 121 | 246 | 218 | 137 |
| Cutoff Quartile 2 | 6080 | 6030 | 6030 | 6080 |
| Sensitivity | 87% | 82% | 83% | 85% |
| Specificity | 32% | 48% | 42% | 33% |
| Cutoff Quartile 3 | 14200 | 14200 | 14200 | 14200 |
| Sensitivity | 61% | 58% | 61% | 61% |
| Specificity | 57% | 77% | 74% | 58% |
| Cutoff Quartile 4 | 36300 | 35900 | 35900 | 36300 |
| Sensitivity | 29% | 30% | 33% | 31% |
| Specificity | 77% | 90% | 91% | 79% |
| OR Quartile 2 | 3.16 | 4.10 | 3.60 | 2.67 |
| p Value | 2.0E−4 | 1.0E−6 | 2.4E−6 | 6.0E−4 |
| Lower limit of 95% CI | 1.72 | 2.33 | 2.12 | 1.52 |
| Upper limit of 95% CI | 5.78 | 7.23 | 6.14 | 4.68 |
| OR Quartile 3 | 2.06 | 4.77 | 4.39 | 2.11 |
| p Value | 0.0022 | 5.5E−7 | 3.1E−8 | 0.0013 |
| Lower limit of 95% CI | 1.30 | 2.59 | 2.60 | 1.34 |
| Upper limit of 95% CI | 3.28 | 8.80 | 7.42 | 3.32 |
| OR Quartile 4 | 1.39 | 3.86 | 4.83 | 1.68 |
| p Value | 0.21 | 0.0014 | 3.1E−5 | 0.046 |
| Lower limit of 95% CI | 0.827 | 1.69 | 2.30 | 1.01 |
| Upper limit of 95% CI | 2.33 | 8.82 | 10.1 | 2.81 |

TABLE 6.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 7170 | 20500 | 7180 | 20200 | 7150 | 19300 |
| Average | 15100 | 36500 | 15400 | 35700 | 15800 | 34600 |
| Stdev | 20200 | 36700 | 20700 | 36400 | 21500 | 36000 |
| p (t-test) | | 1.9E−8 | | 1.9E−7 | | 2.6E−6 |
| Min | 475 | 297 | 475 | 297 | 475 | 297 |
| Max | 110000 | 146000 | 110000 | 146000 | 110000 | 146000 |
| n (Patient) | 114 | 203 | 107 | 210 | 97 | 220 |

TABLE 6.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | \multicolumn{6}{c}{sCr only} | | | | | |
|---|---|---|---|---|---|---|
| Median | 8610 | 20500 | 8810 | 20000 | 8610 | 19800 |
| Average | 16800 | 36900 | 17100 | 36400 | 16300 | 36300 |
| Stdev | 21800 | 37100 | 22000 | 37100 | 20400 | 37200 |
| p (t-test) | | 8.2E-8 | | 3.2E-7 | | 1.3E-7 |
| Min | 475 | 297 | 475 | 297 | 475 | 297 |
| Max | 116000 | 146000 | 116000 | 146000 | 110000 | 146000 |
| n (Patient) | 127 | 190 | 124 | 193 | 119 | 198 |
| | \multicolumn{6}{c}{UO only} | | | | | |
| Median | 11600 | 20500 | 11500 | 19400 | 11000 | 20500 |
| Average | 26000 | 35300 | 25900 | 34500 | 24700 | 35300 |
| Stdev | 32000 | 35500 | 32000 | 35400 | 31000 | 35900 |
| p (t-test) | | 0.021 | | 0.030 | | 0.0057 |
| Min | 297 | 399 | 297 | 399 | 297 | 399 |
| Max | 146000 | 140000 | 146000 | 140000 | 127000 | 146000 |
| n (Patient) | 214 | 101 | 204 | 111 | 190 | 125 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.72 | 0.69 | 0.62 | 0.71 | 0.68 |
| SE | 0.028 | 0.029 | 0.035 | 0.029 | 0.030 |
| p Value | 1.6E-15 | 2.6E-11 | 6.7E-4 | 2.9E-13 | 9.0E-10 |
| nCohort Recovered | 114 | 127 | 214 | 107 | 124 |
| nCohort Non-recovered | 203 | 190 | 101 | 210 | 193 |
| Cutoff Quartile 2 | 6030 | 6030 | 6080 | 6030 | 6030 |
| Sensitivity | 87% | 86% | 87% | 85% | 85% |
| Specificity | 46% | 41% | 31% | 45% | 40% |
| Cutoff Quartile 3 | 14200 | 14200 | 14200 | 14200 | 14200 |
| Sensitivity | 64% | 63% | 64% | 62% | 62% |
| Specificity | 74% | 69% | 57% | 73% | 69% |
| Cutoff Quartile 4 | 35900 | 35900 | 36300 | 35900 | 35900 |
| Sensitivity | 34% | 35% | 30% | 33% | 34% |
| Specificity | 90% | 89% | 77% | 90% | 89% |
| OR Quartile 2 | 5.47 | 4.19 | 3.02 | 4.70 | 3.82 |
| p Value | 1.2E-9 | 2.0E-7 | 8.7E-4 | 1.8E-8 | 8.4E-7 |
| Lower limit of 95% CI | 3.16 | 2.44 | 1.57 | 2.74 | 2.24 |
| Upper limit of 95% CI | 9.45 | 7.18 | 5.79 | 8.05 | 6.51 |
| OR Quartile 3 | 4.88 | 3.87 | 2.35 | 4.37 | 3.58 |
| p Value | 7.9E-10 | 3.0E-8 | 6.1E-4 | 1.4E-8 | 1.7E-7 |
| Lower limit of 95% CI | 2.94 | 2.40 | 1.44 | 2.63 | 2.22 |
| Upper limit of 95% CI | 8.09 | 6.24 | 3.83 | 7.27 | 5.78 |
| OR Quartile 4 | 4.82 | 4.30 | 1.42 | 4.27 | 4.08 |
| p Value | 7.0E-6 | 5.9E-6 | 0.19 | 3.5E-5 | 1.2E-5 |
| Lower limit of 95% CI | 2.43 | 2.29 | 0.835 | 2.15 | 2.17 |
| Upper limit of 95% CI | 9.58 | 8.07 | 2.42 | 8.49 | 7.67 |

| | Recovery Period Duration (hr) | | | |
|---|---|---|---|---|
| | 48 | 72 | | |
| | UO only | sCr or UO | sCr only | UO only |
| AUC | 0.61 | 0.70 | 0.69 | 0.63 |
| SE | 0.034 | 0.030 | 0.030 | 0.033 |
| p Value | 0.0013 | 6.9E-12 | 2.9E-10 | 1.2E-4 |
| nCohort Recovered | 204 | 97 | 119 | 190 |
| nCohort Non-recovered | 111 | 220 | 198 | 125 |

TABLE 6.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | |
|---|---|---|---|---|
| Cutoff Quartile 2 | 6080 | 6030 | 6030 | 6080 |
| Sensitivity | 86% | 84% | 84% | 85% |
| Specificity | 31% | 45% | 40% | 32% |
| Cutoff Quartile 3 | 14200 | 14200 | 14200 | 14200 |
| Sensitivity | 62% | 60% | 62% | 62% |
| Specificity | 56% | 73% | 70% | 58% |
| Cutoff Quartile 4 | 36300 | 35900 | 35900 | 36300 |
| Sensitivity | 29% | 31% | 34% | 32% |
| Specificity | 77% | 89% | 89% | 79% |
| OR Quartile 2 | 2.65 | 4.39 | 3.64 | 2.57 |
| p Value | 0.0016 | 7.5E−8 | 1.8E−6 | 0.0013 |
| Lower limit of 95% CI | 1.45 | 2.56 | 2.14 | 1.45 |
| Upper limit of 95% CI | 4.87 | 7.52 | 6.19 | 4.58 |
| OR Quartile 3 | 2.12 | 4.17 | 3.78 | 2.28 |
| p Value | 0.0018 | 9.2E−8 | 7.8E−8 | 4.7E−4 |
| Lower limit of 95% CI | 1.32 | 2.47 | 2.33 | 1.44 |
| Upper limit of 95% CI | 3.41 | 7.05 | 6.14 | 3.62 |
| OR Quartile 4 | 1.35 | 3.57 | 4.17 | 1.82 |
| p Value | 0.26 | 2.9E−4 | 1.5E−5 | 0.022 |
| Lower limit of 95% CI | 0.801 | 1.79 | 2.18 | 1.09 |
| Upper limit of 95% CI | 2.29 | 7.12 | 7.96 | 3.05 |

TABLE 6.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 8180 | 22000 | 8150 | 21100 | 7940 | 20000 |
| Average | 15800 | 38300 | 16200 | 37000 | 16600 | 35700 |
| Stdev | 21300 | 37200 | 21900 | 36900 | 22700 | 36300 |
| p (t-test) | | 1.1E−9 | | 2.9E−8 | | 6.2E−7 |
| Min | 419 | 297 | 419 | 297 | 419 | 297 |
| Max | 111000 | 146000 | 111000 | 146000 | 111000 | 146000 |
| n (Patient) | 134 | 183 | 125 | 192 | 114 | 203 |
| | sCr only | | | | | |
| Median | 8710 | 21900 | 8740 | 21300 | 8730 | 21600 |
| Average | 17200 | 38000 | 17400 | 37700 | 16600 | 37900 |
| Stdev | 22900 | 37300 | 23000 | 37200 | 21600 | 37500 |
| p (t-test) | | 1.6E−8 | | 4.2E−8 | | 9.3E−9 |
| Min | 419 | 297 | 419 | 297 | 419 | 297 |
| Max | 116000 | 146000 | 116000 | 146000 | 111000 | 146000 |
| n (Patient) | 140 | 177 | 138 | 179 | 135 | 182 |
| | UO only | | | | | |
| Median | 11600 | 21300 | 11200 | 20300 | 11000 | 20500 |
| Average | 25600 | 36300 | 25600 | 35400 | 24600 | 35900 |
| Stdev | 31900 | 35600 | 31800 | 35600 | 30800 | 36300 |
| p (t-test) | | 0.0076 | | 0.013 | | 0.0032 |
| Min | 297 | 399 | 297 | 399 | 297 | 399 |
| Max | 146000 | 140000 | 146000 | 140000 | 127000 | 146000 |
| n (Patient) | 216 | 99 | 207 | 108 | 194 | 121 |

TABLE 6.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  | Recovery Period Duration (hr) | | | | |
| --- | --- | --- | --- | --- | --- |
|  | 24 | | | 48 | |
|  | sCr or UO | sCr only | UO only | sCr or UO | sCr only |
| AUC | 0.73 | 0.71 | 0.63 | 0.72 | 0.70 |
| SE | 0.028 | 0.029 | 0.035 | 0.028 | 0.029 |
| p Value | 0 | 3.9E−13 | 1.9E−4 | 2.8E−14 | 4.1E−12 |
| nCohort Recovered | 134 | 140 | 216 | 125 | 138 |
| nCohort Non-recovered | 183 | 177 | 99 | 192 | 179 |
| Cutoff Quartile 2 | 6030 | 6030 | 6080 | 6030 | 6030 |
| Sensitivity | 88% | 87% | 88% | 86% | 87% |
| Specificity | 43% | 40% | 31% | 42% | 40% |
| Cutoff Quartile 3 | 14200 | 14200 | 14200 | 14200 | 14200 |
| Sensitivity | 67% | 66% | 66% | 64% | 65% |
| Specificity | 72% | 69% | 57% | 71% | 69% |
| Cutoff Quartile 4 | 35900 | 35900 | 36300 | 35900 | 35900 |
| Sensitivity | 37% | 36% | 33% | 35% | 36% |
| Specificity | 90% | 89% | 79% | 90% | 88% |
| OR Quartile 2 | 5.42 | 4.46 | 3.26 | 4.70 | 4.28 |
| p Value | 3.8E−9 | 1.2E−7 | 5.3E−4 | 2.6E−8 | 2.1E−7 |
| Lower limit of 95% CI | 3.09 | 2.57 | 1.67 | 2.73 | 2.47 |
| Upper limit of 95% CI | 9.50 | 7.76 | 6.36 | 8.10 | 7.41 |
| OR Quartile 3 | 5.24 | 4.29 | 2.53 | 4.41 | 4.07 |
| p Value | 2.8E−11 | 1.8E−9 | 2.4E−4 | 2.3E−9 | 6.2E−9 |
| Lower limit of 95% CI | 3.22 | 2.67 | 1.54 | 2.71 | 2.53 |
| Upper limit of 95% CI | 8.54 | 6.89 | 4.15 | 7.17 | 6.53 |
| OR Quartile 4 | 5.38 | 4.39 | 1.85 | 4.62 | 4.24 |
| p Value | 3.4E−7 | 1.6E−6 | 0.023 | 3.5E−6 | 2.7E−6 |
| Lower limit of 95% CI | 2.82 | 2.40 | 1.09 | 2.42 | 2.32 |
| Upper limit of 95% CI | 10.3 | 8.03 | 3.14 | 8.81 | 7.76 |

|  | Recovery Period Duration (hr) | | | |
| --- | --- | --- | --- | --- |
|  | 48 | 72 | | |
|  | UO only | sCr or UO | sCr only | UO only |
| AUC | 0.62 | 0.71 | 0.71 | 0.63 |
| SE | 0.034 | 0.029 | 0.029 | 0.033 |
| p Value | 2.7E−4 | 6.0E−13 | 5.8E−13 | 6.7E−5 |
| nCohort Recovered | 207 | 114 | 135 | 194 |
| nCohort Non-recovered | 108 | 203 | 182 | 121 |
| Cutoff Quartile 2 | 6080 | 6030 | 6030 | 6080 |
| Sensitivity | 88% | 85% | 86% | 86% |
| Specificity | 32% | 43% | 40% | 32% |
| Cutoff Quartile 3 | 14200 | 14200 | 14200 | 14200 |
| Sensitivity | 63% | 63% | 65% | 63% |
| Specificity | 57% | 72% | 70% | 58% |
| Cutoff Quartile 4 | 36300 | 35900 | 35900 | 36300 |
| Sensitivity | 31% | 33% | 36% | 33% |
| Specificity | 78% | 89% | 89% | 80% |
| OR Quartile 2 | 3.42 | 4.35 | 4.19 | 2.87 |
| p Value | 2.0E−4 | 7.9E−8 | 2.6E−7 | 5.1E−4 |
| Lower limit of 95% CI | 1.79 | 2.54 | 2.43 | 1.58 |
| Upper limit of 95% CI | 6.55 | 7.43 | 7.22 | 5.21 |
| OR Quartile 3 | 2.21 | 4.28 | 4.23 | 2.31 |
| p Value | 0.0011 | 1.0E−8 | 3.1E−9 | 4.4E−4 |
| Lower limit of 95% CI | 1.37 | 2.60 | 2.62 | 1.45 |

TABLE 6.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  |  |  |  |  |
|---|---|---|---|---|
| Upper limit of 95% CI | 3.56 | 7.04 | 6.81 | 3.68 |
| OR Quartile 4 | 1.65 | 3.83 | 4.44 | 1.96 |
| p Value | 0.060 | 4.8E−5 | 2.1E−6 | 0.011 |
| Lower limit of 95% CI | 0.980 | 2.00 | 2.40 | 1.17 |
| Upper limit of 95% CI | 2.79 | 7.31 | 8.23 | 3.29 |

TABLE 6.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 10600 | 20800 | 10000 | 20700 | 10000 | 20700 |
| Average | 22100 | 38700 | 22200 | 38200 | 22200 | 38200 |
| Stdev | 28300 | 37600 | 28500 | 37300 | 28500 | 37300 |
| p (t-test) | 9.9E−6 | | 2.0E−5 | | 2.0E−5 | |
| Min | 297 | 399 | 297 | 399 | 297 | 399 |
| Max | 127000 | 146000 | 127000 | 146000 | 127000 | 146000 |
| n (Patient) | 188 | 129 | 185 | 132 | 185 | 132 |
| | sCr only | | | | | |
| Median | 9400 | 22000 | 9350 | 22000 | 9330 | 22000 |
| Average | 18800 | 39100 | 18900 | 38600 | 18300 | 39000 |
| Stdev | 24400 | 37900 | 24600 | 37700 | 23400 | 38100 |
| p (t-test) | 3.0E−8 | | 8.7E−8 | | 1.5E−8 | |
| Min | 419 | 297 | 419 | 297 | 419 | 297 |
| Max | 116000 | 146000 | 116000 | 146000 | 111000 | 146000 |
| n (Patient) | 160 | 157 | 157 | 160 | 156 | 161 |
| | UO only | | | | | |
| Median | 11300 | 21500 | 11600 | 20800 | 11300 | 21100 |
| Average | 24300 | 38300 | 24500 | 37500 | 24500 | 37300 |
| Stdev | 29900 | 38000 | 30100 | 37800 | 30200 | 37400 |
| p (t-test) | 4.4E−4 | | 0.0010 | | 0.0012 | |
| Min | 297 | 399 | 297 | 399 | 297 | 399 |
| Max | 127000 | 146000 | 127000 | 146000 | 127000 | 146000 |
| n (Patient) | 211 | 104 | 208 | 107 | 205 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.70 | 0.64 | 0.66 | 0.69 | 0.63 | 0.66 | 0.70 | 0.63 |
| SE | 0.032 | 0.029 | 0.034 | 0.031 | 0.029 | 0.034 | 0.031 | 0.029 | 0.034 |
| p Value | 3.5E−7 | 1.9E−11 | 5.5E−5 | 3.6E−7 | 8.3E−11 | 1.1E−4 | 3.6E−7 | 1.5E−11 | 9.6E−5 |
| nCohort Recovered | 188 | 160 | 211 | 185 | 157 | 208 | 185 | 156 | 205 |
| nCohort Non-recovered | 129 | 157 | 104 | 132 | 160 | 107 | 132 | 161 | 110 |
| Cutoff Quartile 2 | 6030 | 6030 | 6080 | 6030 | 6030 | 6080 | 6030 | 6030 | 6080 |
| Sensitivity | 87% | 88% | 87% | 87% | 88% | 87% | 87% | 88% | 86% |
| Specificity | 33% | 38% | 31% | 34% | 38% | 31% | 34% | 38% | 31% |
| Cutoff Quartile 3 | 14200 | 14200 | 14200 | 14200 | 14200 | 14200 | 14200 | 14200 | 14200 |
| Sensitivity | 66% | 66% | 65% | 65% | 66% | 64% | 65% | 66% | 64% |
| Specificity | 61% | 66% | 57% | 61% | 66% | 57% | 61% | 66% | 57% |
| Cutoff Quartile 4 | 35900 | 35900 | 36300 | 35900 | 35900 | 36300 | 35900 | 35900 | 36300 |

TABLE 6.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 37% | 37% | 35% | 36% | 36% | 34% | 36% | 37% | 34% |
| Specificity | 83% | 86% | 80% | 83% | 86% | 79% | 83% | 87% | 80% |
| OR Quartile 2 | 3.24 | 4.36 | 2.86 | 3.41 | 4.21 | 3.02 | 3.41 | 4.29 | 2.87 |
| p Value | 1.0E−4 | 5.6E−7 | 0.0012 | 5.1E−5 | 7.3E−7 | 6.3E−4 | 5.1E−5 | 5.4E−7 | 8.4E−4 |
| Lower limit of 95% CI | 1.79 | 2.45 | 1.52 | 1.88 | 2.39 | 1.60 | 1.88 | 2.43 | 1.55 |
| Upper limit of 95% CI | 5.87 | 7.76 | 5.40 | 6.17 | 7.44 | 5.69 | 6.17 | 7.58 | 5.34 |
| OR Quartile 3 | 2.98 | 3.75 | 2.54 | 2.87 | 3.64 | 2.29 | 2.87 | 3.75 | 2.33 |
| p Value | 4.7E−6 | 2.5E−8 | 1.8E−4 | 8.5E−6 | 4.6E−8 | 7.3E−4 | 8.5E−6 | 2.5E−8 | 5.2E−4 |
| Lower limit of 95% CI | 1.87 | 2.35 | 1.56 | 1.80 | 2.29 | 1.41 | 1.80 | 2.35 | 1.44 |
| Upper limit of 95% CI | 4.75 | 5.96 | 4.13 | 4.56 | 5.79 | 3.69 | 4.56 | 5.96 | 3.75 |
| OR Quartile 4 | 2.89 | 3.67 | 2.07 | 2.73 | 3.49 | 1.95 | 2.73 | 3.72 | 1.97 |
| p Value | 6.7E−5 | 4.2E−6 | 0.0066 | 1.5E−4 | 9.8E−6 | 0.013 | 1.5E−4 | 4.4E−6 | 0.011 |
| Lower limit of 95% CI | 1.71 | 2.11 | 1.22 | 1.62 | 2.01 | 1.15 | 1.62 | 2.12 | 1.17 |
| Upper limit of 95% CI | 4.87 | 6.40 | 3.50 | 4.60 | 6.07 | 3.28 | 4.60 | 6.51 | 3.31 |

TABLE 6.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| *sCr or UO* | | | | | | |
| Median | 253000 | 499000 | 245000 | 494000 | 245000 | 472000 |
| Average | 314000 | 530000 | 280000 | 527000 | 285000 | 523000 |
| Stdev | 213000 | 274000 | 171000 | 275000 | 178000 | 275000 |
| p (t-test) | | 1.5E−7 | | 3.4E−8 | | 3.8E−7 |
| Min | 66700 | 13600 | 66700 | 13600 | 66700 | 13600 |
| Max | 975000 | 1120000 | 872000 | 1120000 | 872000 | 1120000 |
| n (Patient) | 52 | 275 | 42 | 285 | 38 | 289 |
| *sCr only* | | | | | | |
| Median | 257000 | 519000 | 257000 | 519000 | 257000 | 511000 |
| Average | 341000 | 535000 | 333000 | 535000 | 341000 | 530000 |
| Stdev | 237000 | 270000 | 231000 | 270000 | 236000 | 271000 |
| p (t-test) | | 1.1E−7 | | 4.6E−8 | | 5.7E−7 |
| Min | 66700 | 13600 | 66700 | 13600 | 66700 | 13600 |
| Max | 950000 | 1120000 | 950000 | 1120000 | 950000 | 1120000 |
| n (Patient) | 69 | 257 | 67 | 259 | 63 | 263 |
| *UO only* | | | | | | |
| Median | 359000 | 582000 | 343000 | 586000 | 342000 | 567000 |
| Average | 431000 | 598000 | 413000 | 596000 | 411000 | 580000 |
| Stdev | 248000 | 287000 | 239000 | 285000 | 241000 | 283000 |
| p (t-test) | | 5.3E−8 | | 1.1E−9 | | 1.9E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 197 | 128 | 176 | 149 | 159 | 166 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.74 | 0.72 | 0.67 | 0.78 | 0.73 |
| SE | 0.032 | 0.031 | 0.031 | 0.032 | 0.031 |

TABLE 6.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | |
|---|---|---|---|---|---|
| p Value | 7.8E−14 | 4.5E−13 | 8.1E−8 | 0 | 3.7E−14 |
| nCohort Recovered | 52 | 69 | 197 | 42 | 67 |
| nCohort Non-recovered | 275 | 257 | 128 | 285 | 259 |
| Cutoff Quartile 2 | 260000 | 260000 | 262000 | 260000 | 260000 |
| Sensitivity | 80% | 82% | 84% | 80% | 82% |
| Specificity | 52% | 51% | 31% | 57% | 52% |
| Cutoff Quartile 3 | 437000 | 433000 | 437000 | 437000 | 433000 |
| Sensitivity | 56% | 57% | 62% | 55% | 57% |
| Specificity | 81% | 75% | 58% | 83% | 76% |
| Cutoff Quartile 4 | 707000 | 704000 | 708000 | 707000 | 704000 |
| Sensitivity | 28% | 29% | 41% | 28% | 29% |
| Specificity | 92% | 88% | 85% | 98% | 90% |
| OR Quartile 2 | 4.32 | 4.60 | 2.42 | 5.22 | 4.93 |
| p Value | 3.6E−6 | 1.4E−7 | 0.0021 | 1.7E−6 | 5.1E−8 |
| Lower limit of 95% CI | 2.33 | 2.61 | 1.38 | 2.65 | 2.78 |
| Upper limit of 95% CI | 8.02 | 8.12 | 4.26 | 10.3 | 8.76 |
| OR Quartile 3 | 5.35 | 4.02 | 2.29 | 6.13 | 4.18 |
| p Value | 6.7E−6 | 5.6E−6 | 3.7E−4 | 2.6E−5 | 4.8E−6 |
| Lower limit of 95% CI | 2.58 | 2.21 | 1.45 | 2.64 | 2.27 |
| Upper limit of 95% CI | 11.1 | 7.34 | 3.61 | 14.3 | 7.72 |
| OR Quartile 4 | 4.75 | 3.08 | 4.09 | 16.3 | 3.49 |
| p Value | 0.0037 | 0.0049 | 1.7E−7 | 0.0063 | 0.0030 |
| Lower limit of 95% CI | 1.66 | 1.41 | 2.41 | 2.20 | 1.53 |
| Upper limit of 95% CI | 13.6 | 6.76 | 6.94 | 120 | 7.99 |

| | Recovery Period Duration (hr) | | | |
|---|---|---|---|---|
| | 48 | 72 | | |
| | UO only | sCr or UO | sCr only | UO only |
| AUC | 0.69 | 0.77 | 0.72 | 0.68 |
| SE | 0.030 | 0.034 | 0.032 | 0.030 |
| p Value | 5.0E−10 | 6.9E−15 | 1.3E−11 | 3.1E−9 |
| nCohort Recovered | 176 | 38 | 63 | 159 |
| nCohort Non-recovered | 149 | 289 | 263 | 166 |
| Cutoff Quartile 2 | 262000 | 260000 | 260000 | 262000 |
| Sensitivity | 85% | 79% | 81% | 85% |
| Specificity | 33% | 58% | 51% | 35% |
| Cutoff Quartile 3 | 437000 | 437000 | 433000 | 437000 |
| Sensitivity | 63% | 54% | 56% | 60% |
| Specificity | 61% | 82% | 75% | 60% |
| Cutoff Quartile 4 | 708000 | 707000 | 704000 | 708000 |
| Sensitivity | 40% | 28% | 29% | 37% |
| Specificity | 88% | 97% | 89% | 87% |
| OR Quartile 2 | 2.69 | 5.25 | 4.40 | 3.07 |
| p Value | 3.6E−4 | 3.9E−6 | 6.1E−7 | 4.1E−5 |
| Lower limit of 95% CI | 1.56 | 2.60 | 2.46 | 1.79 |
| Upper limit of 95% CI | 4.64 | 10.6 | 7.87 | 5.24 |
| OR Quartile 3 | 2.65 | 5.27 | 3.72 | 2.19 |
| p Value | 2.2E−5 | 1.3E−4 | 3.0E−5 | 5.2E−4 |
| Lower limit of 95% CI | 1.69 | 2.25 | 2.01 | 1.41 |
| Upper limit of 95% CI | 4.16 | 12.4 | 6.90 | 3.42 |
| OR Quartile 4 | 4.72 | 14.4 | 3.19 | 4.14 |
| p Value | 4.0E−8 | 0.0090 | 0.0061 | 8.0E−7 |
| Lower limit of 95% CI | 2.71 | 1.94 | 1.39 | 2.36 |
| Upper limit of 95% CI | 8.21 | 107 | 7.32 | 7.29 |

TABLE 6.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 279000 | 525000 | 277000 | 499000 | 279000 | 490000 |
| Average | 363000 | 543000 | 366000 | 534000 | 370000 | 529000 |
| Stdev | 233000 | 275000 | 239000 | 275000 | 245000 | 275000 |
| p (t-test) | | 1.0E−7 | | 2.4E−6 | | 1.7E−5 |
| Min | 66700 | 13600 | 66700 | 13600 | 66700 | 13600 |
| Max | 1040000 | 1120000 | 1040000 | 1120000 | 1040000 | 1120000 |
| n (Patient) | 87 | 240 | 76 | 251 | 69 | 258 |
| sCr only | | | | | | |
| Median | 282000 | 528000 | 282000 | 528000 | 291000 | 521000 |
| Average | 380000 | 547000 | 376000 | 547000 | 382000 | 541000 |
| Stdev | 248000 | 273000 | 245000 | 273000 | 249000 | 274000 |
| p (t-test) | | 3.0E−7 | | 1.7E−7 | | 1.8E−6 |
| Min | 66700 | 13600 | 66700 | 13600 | 66700 | 13600 |
| Max | 1040000 | 1120000 | 1040000 | 1120000 | 1040000 | 1120000 |
| n (Patient) | 101 | 226 | 99 | 228 | 94 | 233 |
| UO only | | | | | | |
| Median | 371000 | 598000 | 369000 | 576000 | 371000 | 534000 |
| Average | 437000 | 617000 | 434000 | 595000 | 433000 | 578000 |
| Stdev | 250000 | 287000 | 248000 | 289000 | 245000 | 292000 |
| p (t-test) | | 1.4E−8 | | 1.9E−7 | | 1.8E−6 |
| Min | 13600 | 135000 | 13600 | 135000 | 13600 | 135000 |
| Max | 1120000 | 1090000 | 1120000 | 1090000 | 1120000 | 1090000 |
| n (Patient) | 217 | 108 | 198 | 127 | 181 | 144 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.70 | 0.69 | 0.68 | 0.69 | 0.69 |
| SE | 0.030 | 0.030 | 0.033 | 0.032 | 0.030 |
| p Value | 4.7E−11 | 4.8E−10 | 1.9E−8 | 4.3E−9 | 1.6E−10 |
| nCohort Recovered | 87 | 101 | 217 | 76 | 99 |
| nCohort Non-recovered | 240 | 226 | 108 | 251 | 228 |
| Cutoff Quartile 2 | 260000 | 260000 | 262000 | 260000 | 260000 |
| Sensitivity | 81% | 82% | 87% | 80% | 82% |
| Specificity | 43% | 42% | 31% | 43% | 42% |
| Cutoff Quartile 3 | 437000 | 437000 | 437000 | 437000 | 437000 |
| Sensitivity | 57% | 58% | 65% | 56% | 58% |
| Specificity | 70% | 67% | 57% | 68% | 68% |
| Cutoff Quartile 4 | 707000 | 707000 | 708000 | 707000 | 707000 |
| Sensitivity | 30% | 31% | 44% | 29% | 31% |
| Specificity | 90% | 87% | 84% | 89% | 88% |
| OR Quartile 2 | 3.21 | 3.31 | 3.00 | 3.16 | 3.46 |
| p Value | 1.9E−5 | 7.2E−6 | 6.5E−4 | 4.1E−5 | 3.5E−6 |
| Lower limit of 95% CI | 1.88 | 1.96 | 1.60 | 1.82 | 2.05 |
| Upper limit of 95% CI | 5.47 | 5.58 | 5.64 | 5.49 | 5.85 |
| OR Quartile 3 | 3.17 | 2.84 | 2.46 | 2.73 | 2.88 |
| p Value | 1.7E−5 | 3.3E−5 | 2.3E−4 | 2.9E−4 | 3.0E−5 |
| Lower limit of 95% CI | 1.88 | 1.74 | 1.52 | 1.59 | 1.75 |
| Upper limit of 95% CI | 5.37 | 4.65 | 3.96 | 4.71 | 4.73 |
| OR Quartile 4 | 3.79 | 2.98 | 4.01 | 3.55 | 3.21 |
| p Value | 4.4E−4 | 9.7E−4 | 2.2E−7 | 0.0015 | 5.9E−4 |
| Lower limit of 95% CI | 1.80 | 1.56 | 2.37 | 1.63 | 1.65 |

TABLE 6.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | |
|---|---|---|---|---|---|
| Upper limit of 95% CI | 7.96 | 5.68 | 6.77 | 7.76 | 6.25 |

| | Recovery Period Duration (hr) | | | |
|---|---|---|---|---|
| | 48 | 72 | | |
| | UO only | sCr or UO | sCr only | UO only |
| AUC | 0.66 | 0.68 | 0.68 | 0.65 |
| SE | 0.031 | 0.033 | 0.031 | 0.031 |
| p Value | 2.4E−7 | 6.9E−8 | 7.1E−9 | 2.1E−6 |
| nCohort Recovered | 198 | 69 | 94 | 181 |
| nCohort Non-recovered | 127 | 258 | 233 | 144 |
| Cutoff Quartile 2 | 262000 | 260000 | 260000 | 262000 |
| Sensitivity | 85% | 80% | 82% | 84% |
| Specificity | 31% | 43% | 41% | 32% |
| Cutoff Quartile 3 | 437000 | 437000 | 437000 | 437000 |
| Sensitivity | 62% | 55% | 57% | 58% |
| Specificity | 58% | 68% | 67% | 56% |
| Cutoff Quartile 4 | 708000 | 707000 | 707000 | 708000 |
| Sensitivity | 39% | 29% | 30% | 37% |
| Specificity | 84% | 88% | 87% | 84% |
| OR Quartile 2 | 2.59 | 3.05 | 3.13 | 2.48 |
| p Value | 0.0011 | 1.1E−4 | 2.2E−5 | 0.0011 |
| Lower limit of 95% CI | 1.46 | 1.73 | 1.85 | 1.44 |
| Upper limit of 95% CI | 4.59 | 5.36 | 5.31 | 4.28 |
| OR Quartile 3 | 2.23 | 2.62 | 2.70 | 1.81 |
| p Value | 5.5E−4 | 8.1E−4 | 1.0E−4 | 0.0088 |
| Lower limit of 95% CI | 1.42 | 1.49 | 1.64 | 1.16 |
| Upper limit of 95% CI | 3.52 | 4.59 | 4.47 | 2.81 |
| OR Quartile 4 | 3.37 | 3.07 | 2.93 | 3.05 |
| p Value | 4.6E−6 | 0.0051 | 0.0016 | 2.8E−5 |
| Lower limit of 95% CI | 2.00 | 1.40 | 1.51 | 1.81 |
| Upper limit of 95% CI | 5.66 | 6.72 | 5.72 | 5.14 |

TABLE 6.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 280000 | 560000 | 279000 | 530000 | 279000 | 524000 |
| Average | 362000 | 564000 | 364000 | 557000 | 366000 | 547000 |
| Stdev | 224000 | 276000 | 229000 | 275000 | 235000 | 275000 |
| p (t-test) | | 1.2E−10 | | 1.5E−9 | | 4.4E−8 |
| Min | 13600 | 105000 | 13600 | 105000 | 13600 | 105000 |
| Max | 1040000 | 1120000 | 1040000 | 1120000 | 1040000 | 1120000 |
| n (Patient) | 111 | 216 | 104 | 223 | 94 | 233 |

TABLE 6.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | sCr only | | | | | |
|---|---|---|---|---|---|---|
| Median | 286000 | 564000 | 282000 | 564000 | 286000 | 552000 |
| Average | 376000 | 568000 | 372000 | 568000 | 376000 | 561000 |
| Stdev | 238000 | 273000 | 236000 | 273000 | 239000 | 274000 |
| p (t-test) | | 4.0E−10 | | 2.0E−10 | | 3.0E−9 |
| Min | 13600 | 105000 | 13600 | 105000 | 13600 | 105000 |
| Max | 1040000 | 1120000 | 1040000 | 1120000 | 1040000 | 1120000 |
| n (Patient) | 124 | 203 | 121 | 206 | 116 | 211 |
| | UO only | | | | | |
| Median | 367000 | 602000 | 363000 | 595000 | 367000 | 577000 |
| Average | 434000 | 627000 | 435000 | 608000 | 429000 | 596000 |
| Stdev | 247000 | 288000 | 249000 | 288000 | 243000 | 292000 |
| p (t-test) | | 1.4E−9 | | 2.8E−8 | | 4.6E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 219 | 106 | 208 | 117 | 193 | 132 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.72 | 0.71 | 0.70 | 0.71 | 0.71 |
| SE | 0.028 | 0.028 | 0.032 | 0.029 | 0.028 |
| p Value | 1.2E−14 | 1.7E−13 | 1.4E−9 | 2.1E−13 | 3.3E−14 |
| nCohort Recovered | 111 | 124 | 219 | 104 | 121 |
| nCohort Non-recovered | 216 | 203 | 106 | 223 | 206 |
| Cutoff Quartile 2 | 260000 | 260000 | 262000 | 260000 | 260000 |
| Sensitivity | 84% | 84% | 88% | 83% | 84% |
| Specificity | 42% | 40% | 31% | 43% | 41% |
| Cutoff Quartile 3 | 437000 | 437000 | 437000 | 437000 | 437000 |
| Sensitivity | 60% | 61% | 66% | 59% | 61% |
| Specificity | 68% | 67% | 58% | 69% | 68% |
| Cutoff Quartile 4 | 707000 | 707000 | 708000 | 707000 | 707000 |
| Sensitivity | 33% | 33% | 42% | 32% | 33% |
| Specificity | 91% | 89% | 83% | 90% | 89% |
| OR Quartile 2 | 3.80 | 3.61 | 3.22 | 3.83 | 3.83 |
| p Value | 5.5E−7 | 1.4E−6 | 4.0E−4 | 5.1E−7 | 4.8E−7 |
| Lower limit of 95% CI | 2.25 | 2.14 | 1.69 | 2.27 | 2.27 |
| Upper limit of 95% CI | 6.40 | 6.08 | 6.15 | 6.48 | 6.46 |
| OR Quartile 3 | 3.22 | 3.11 | 2.63 | 3.26 | 3.24 |
| p Value | 2.2E−6 | 2.0E−6 | 8.5E−5 | 2.8E−6 | 1.1E−6 |
| Lower limit of 95% CI | 1.98 | 1.95 | 1.63 | 1.99 | 2.02 |
| Upper limit of 95% CI | 5.22 | 4.97 | 4.27 | 5.35 | 5.21 |
| OR Quartile 4 | 5.05 | 3.96 | 3.63 | 4.48 | 4.18 |
| p Value | 7.5E−6 | 1.8E−5 | 1.3E−6 | 3.4E−5 | 1.3E−5 |
| Lower limit of 95% CI | 2.49 | 2.11 | 2.15 | 2.20 | 2.20 |
| Upper limit of 95% CI | 10.3 | 7.42 | 6.12 | 9.11 | 7.97 |

| | Recovery Period Duration (hr) | | | |
|---|---|---|---|---|
| | 48 | 72 | | |
| | UO only | sCr or UO | sCr only | UO only |
| AUC | 0.68 | 0.70 | 0.70 | 0.67 |
| SE | 0.032 | 0.030 | 0.029 | 0.031 |
| p Value | 2.6E−8 | 2.1E−11 | 1.9E−12 | 5.2E−8 |
| nCohort Recovered | 208 | 94 | 116 | 193 |
| nCohort Non-recovered | 117 | 233 | 211 | 132 |

TABLE 6.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

|  |  |  |  |  |
|---|---|---|---|---|
| Cutoff Quartile 2 | 262000 | 260000 | 260000 | 262000 |
| Sensitivity | 86% | 82% | 84% | 86% |
| Specificity | 31% | 44% | 41% | 32% |
| Cutoff Quartile 3 | 437000 | 437000 | 437000 | 437000 |
| Sensitivity | 65% | 58% | 60% | 62% |
| Specificity | 58% | 69% | 67% | 58% |
| Cutoff Quartile 4 | 708000 | 707000 | 707000 | 708000 |
| Sensitivity | 40% | 31% | 33% | 39% |
| Specificity | 83% | 89% | 89% | 84% |
| OR Quartile 2 | 2.87 | 3.62 | 3.67 | 2.81 |
| p Value | 6.2E−4 | 1.9E−6 | 9.7E−7 | 3.9E−4 |
| Lower limit of 95% CI | 1.57 | 2.13 | 2.18 | 1.59 |
| Upper limit of 95% CI | 5.25 | 6.15 | 6.19 | 4.99 |
| OR Quartile 3 | 2.58 | 3.09 | 3.04 | 2.27 |
| p Value | 7.6E−5 | 1.4E−5 | 4.5E−6 | 4.0E−4 |
| Lower limit of 95% CI | 1.61 | 1.86 | 1.89 | 1.44 |
| Upper limit of 95% CI | 4.12 | 5.14 | 4.89 | 3.57 |
| OR Quartile 4 | 3.32 | 3.76 | 3.85 | 3.53 |
| p Value | 5.7E−6 | 2.7E−4 | 4.2E−5 | 2.3E−6 |
| Lower limit of 95% CI | 1.98 | 1.84 | 2.02 | 2.09 |
| Upper limit of 95% CI | 5.57 | 7.66 | 7.34 | 5.96 |

TABLE 6.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 296000 | 564000 | 293000 | 536000 | 279000 | 529000 |
| Average | 383000 | 573000 | 381000 | 566000 | 372000 | 561000 |
| Stdev | 232000 | 278000 | 233000 | 277000 | 236000 | 274000 |
| p (t-test) | | 3.3E−10 | | 1.7E−9 | | 1.6E−9 |
| Min | 13600 | 105000 | 13600 | 105000 | 13600 | 105000 |
| Max | 1040000 | 1120000 | 1040000 | 1120000 | 1040000 | 1120000 |
| n (Patient) | 134 | 193 | 125 | 202 | 113 | 214 |
| | sCr only | | | | | |
| Median | 293000 | 567000 | 289000 | 567000 | 282000 | 565000 |
| Average | 381000 | 580000 | 377000 | 581000 | 376000 | 577000 |
| Stdev | 234000 | 275000 | 231000 | 275000 | 233000 | 274000 |
| p (t-test) | | 3.6E−11 | | 1.0E−11 | | 2.7E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 139 | 188 | 137 | 190 | 133 | 194 |
| | UO only | | | | | |
| Median | 373000 | 595000 | 371000 | 582000 | 369000 | 576000 |
| Average | 438000 | 621000 | 437000 | 609000 | 432000 | 599000 |
| Stdev | 249000 | 290000 | 248000 | 291000 | 246000 | 291000 |
| p (t-test) | | 1.1E−8 | | 4.2E−8 | | 5.9E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 220 | 105 | 211 | 114 | 198 | 127 |

TABLE 6.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  | Recovery Period Duration (hr) | | | | |
| --- | --- | --- | --- | --- | --- |
|  | 24 | | | 48 | |
|  | sCr or UO | sCr only | UO only | sCr or UO | sCr only |
| AUC | 0.70 | 0.71 | 0.69 | 0.70 | 0.72 |
| SE | 0.028 | 0.028 | 0.033 | 0.029 | 0.028 |
| p Value | 7.5E−13 | 2.6E−14 | 1.2E−8 | 2.5E−12 | 2.7E−15 |
| nCohort Recovered | 134 | 139 | 220 | 125 | 137 |
| nCohort Non-recovered | 193 | 188 | 105 | 202 | 190 |
| Cutoff Quartile 2 | 260000 | 260000 | 262000 | 260000 | 260000 |
| Sensitivity | 85% | 86% | 90% | 85% | 86% |
| Specificity | 40% | 40% | 32% | 42% | 40% |
| Cutoff Quartile 3 | 437000 | 437000 | 437000 | 437000 | 437000 |
| Sensitivity | 60% | 62% | 65% | 59% | 62% |
| Specificity | 64% | 65% | 57% | 65% | 66% |
| Cutoff Quartile 4 | 707000 | 707000 | 708000 | 707000 | 707000 |
| Sensitivity | 35% | 36% | 41% | 34% | 36% |
| Specificity | 90% | 89% | 82% | 90% | 90% |
| OR Quartile 2 | 3.98 | 3.90 | 3.99 | 4.08 | 4.05 |
| p Value | 3.1E−7 | 4.9E−7 | 7.7E−5 | 1.6E−7 | 2.5E−7 |
| Lower limit of 95% CI | 2.34 | 2.30 | 2.01 | 2.41 | 2.38 |
| Upper limit of 95% CI | 6.75 | 6.64 | 7.92 | 6.91 | 6.89 |
| OR Quartile 3 | 2.70 | 3.05 | 2.42 | 2.69 | 3.24 |
| p Value | 2.0E−5 | 1.7E−6 | 3.2E−4 | 2.6E−5 | 5.4E−7 |
| Lower limit of 95% CI | 1.71 | 1.93 | 1.49 | 1.70 | 2.05 |
| Upper limit of 95% CI | 4.26 | 4.82 | 3.91 | 4.28 | 5.14 |
| OR Quartile 4 | 4.66 | 4.58 | 3.22 | 4.47 | 4.90 |
| p Value | 1.5E−6 | 1.2E−6 | 1.1E−5 | 5.1E−6 | 6.9E−7 |
| Lower limit of 95% CI | 2.49 | 2.48 | 1.91 | 2.35 | 2.61 |
| Upper limit of 95% CI | 8.73 | 8.45 | 5.42 | 8.51 | 9.17 |

|  | Recovery Period Duration (hr) | | | |
| --- | --- | --- | --- | --- |
|  | 48 | 72 | | |
|  | UO only | sCr or UO | sCr only | UO only |
| AUC | 0.68 | 0.71 | 0.72 | 0.67 |
| SE | 0.032 | 0.029 | 0.028 | 0.031 |
| p Value | 5.0E−8 | 2.2E−13 | 6.7E−15 | 4.9E−8 |
| nCohort Recovered | 211 | 113 | 133 | 198 |
| nCohort Non-recovered | 114 | 214 | 194 | 127 |
| Cutoff Quartile 2 | 262000 | 260000 | 260000 | 262000 |
| Sensitivity | 88% | 85% | 86% | 87% |
| Specificity | 32% | 44% | 41% | 33% |
| Cutoff Quartile 3 | 437000 | 437000 | 437000 | 437000 |
| Sensitivity | 64% | 59% | 62% | 62% |
| Specificity | 57% | 67% | 67% | 58% |
| Cutoff Quartile 4 | 708000 | 707000 | 707000 | 708000 |
| Sensitivity | 40% | 33% | 35% | 39% |
| Specificity | 83% | 89% | 89% | 84% |
| OR Quartile 2 | 3.32 | 4.51 | 4.05 | 3.39 |
| p Value | 1.9E−4 | 2.2E−8 | 2.2E−7 | 7.1E−5 |
| Lower limit of 95% CI | 1.77 | 2.66 | 2.39 | 1.86 |
| Upper limit of 95% CI | 6.24 | 7.65 | 6.88 | 6.19 |
| OR Quartile 3 | 2.39 | 3.00 | 3.28 | 2.23 |
| p Value | 2.7E−4 | 6.8E−6 | 5.0E−7 | 5.5E−4 |
| Lower limit of 95% CI | 1.50 | 1.86 | 2.06 | 1.42 |

TABLE 6.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  |  |  |  |  |
|---|---|---|---|---|
| Upper limit of 95% CI | 3.83 | 4.84 | 5.21 | 3.52 |
| OR Quartile 4 | 3.29 | 4.09 | 4.59 | 3.37 |
| p Value | 6.8E−6 | 3.1E−5 | 1.9E−6 | 4.6E−6 |
| Lower limit of 95% CI | 1.96 | 2.11 | 2.45 | 2.00 |
| Upper limit of 95% CI | 5.52 | 7.94 | 8.59 | 5.66 |

TABLE 6.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 359000 | 572000 | 342000 | 576000 | 342000 | 577000 |
| Average | 421000 | 595000 | 416000 | 597000 | 415000 | 598000 |
| Stdev | 240000 | 290000 | 237000 | 289000 | 237000 | 289000 |
| p (t-test) | | 8.6E−9 | | 1.6E−9 | | 1.1E−9 |
| Min | 13600 | 105000 | 13600 | 105000 | 13600 | 105000 |
| Max | 1040000 | 1120000 | 1040000 | 1120000 | 1040000 | 1120000 |
| n (Patient) | 187 | 140 | 184 | 143 | 183 | 144 |
| | sCr only | | | | | |
| Median | 313000 | 564000 | 308000 | 564000 | 308000 | 564000 |
| Average | 402000 | 583000 | 399000 | 583000 | 399000 | 581000 |
| Stdev | 240000 | 280000 | 239000 | 279000 | 239000 | 279000 |
| p (t-test) | | 1.3E−9 | | 5.5E−10 | | 8.4E−10 |
| Min | 13600 | 105000 | 13600 | 105000 | 13600 | 105000 |
| Max | 1040000 | 1120000 | 1040000 | 1120000 | 1040000 | 1120000 |
| n (Patient) | 159 | 168 | 156 | 171 | 154 | 173 |
| | UO only | | | | | |
| Median | 375000 | 582000 | 369000 | 586000 | 359000 | 596000 |
| Average | 436000 | 616000 | 433000 | 617000 | 428000 | 622000 |
| Stdev | 245000 | 296000 | 243000 | 294000 | 241000 | 292000 |
| p (t-test) | | 1.4E−8 | | 4.2E−9 | | 3.7E−10 |
| Min | 13600 | 135000 | 13600 | 135000 | 13600 | 135000 |
| Max | 1040000 | 1120000 | 1040000 | 1120000 | 1040000 | 1120000 |
| n (Patient) | 215 | 110 | 212 | 113 | 209 | 116 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.69 | 0.68 | 0.68 | 0.70 | 0.69 | 0.69 | 0.69 | 0.70 |
| SE | 0.030 | 0.029 | 0.032 | 0.030 | 0.029 | 0.032 | 0.030 | 0.029 | 0.031 |
| p Value | 6.3E−9 | 3.9E−11 | 3.0E−8 | 8.4E−10 | 8.0E−12 | 6.3E−9 | 4.4E−10 | 1.5E−11 | 4.5E−10 |
| nCohort Recovered | 187 | 159 | 215 | 184 | 156 | 212 | 183 | 154 | 209 |
| nCohort Non-recovered | 140 | 168 | 110 | 143 | 171 | 113 | 144 | 173 | 116 |
| Cutoff Quartile 2 | 260000 | 260000 | 262000 | 260000 | 260000 | 262000 | 260000 | 260000 | 262000 |
| Sensitivity | 86% | 86% | 88% | 87% | 87% | 88% | 87% | 86% | 89% |
| Specificity | 34% | 37% | 32% | 34% | 38% | 32% | 34% | 38% | 33% |
| Cutoff Quartile 3 | 437000 | 437000 | 437000 | 437000 | 437000 | 437000 | 437000 | 437000 | 437000 |
| Sensitivity | 62% | 61% | 65% | 62% | 62% | 65% | 62% | 62% | 66% |
| Specificity | 59% | 62% | 57% | 59% | 63% | 58% | 60% | 63% | 58% |
| Cutoff Quartile 4 | 707000 | 707000 | 708000 | 707000 | 707000 | 708000 | 707000 | 707000 | 708000 |
| Sensitivity | 39% | 37% | 40% | 40% | 37% | 41% | 40% | 36% | 42% |

TABLE 6.10-continued

Comparison of marker levels and the area under the ROC curve (AUC) in EDTA samples for the "recovered"
and "non-recovered" cohorts where recovery starts within 168 hours after sample collection and renal
status is assessed by serum creatinine (sCr) only, urine output (UO) only, or serum creatinine or urine output RIFLE criteria.

| | | | | | | | | | |
|---|---|---|---|---|---|---|---|---|---|
| Specificity | 86% | 87% | 82% | 86% | 88% | 83% | 86% | 88% | 84% |
| OR Quartile 2 | 3.24 | 3.72 | 3.45 | 3.40 | 3.91 | 3.63 | 3.45 | 3.75 | 3.82 |
| p Value | 5.5E−5 | 2.3E−6 | 1.7E−4 | 2.7E−5 | 9.5E−7 | 9.1E−5 | 2.1E−5 | 1.6E−6 | 4.7E−5 |
| Lower limit of 95% CI | 1.83 | 2.16 | 1.81 | 1.92 | 2.27 | 1.90 | 1.95 | 2.18 | 2.00 |
| Upper limit of 95% CI | 5.73 | 6.41 | 6.59 | 6.01 | 6.75 | 6.93 | 6.11 | 6.44 | 7.29 |
| OR Quartile 3 | 2.35 | 2.55 | 2.43 | 2.40 | 2.76 | 2.47 | 2.45 | 2.76 | 2.66 |
| p Value | 2.0E−4 | 4.0E−5 | 2.4E−4 | 1.3E−4 | 9.3E−6 | 1.7E−4 | 8.6E−5 | 9.2E−6 | 4.6E−5 |
| Lower limit of 95% CI | 1.50 | 1.63 | 1.51 | 1.53 | 1.76 | 1.54 | 1.57 | 1.76 | 1.66 |
| Upper limit of 95% CI | 3.67 | 3.98 | 3.91 | 3.75 | 4.31 | 3.97 | 3.84 | 4.32 | 4.27 |
| OR Quartile 4 | 3.83 | 4.07 | 3.11 | 4.22 | 4.21 | 3.36 | 4.14 | 4.07 | 3.90 |
| p Value | 6.8E−7 | 1.1E−6 | 1.8E−5 | 1.6E−7 | 8.4E−7 | 4.8E−6 | 2.3E−7 | 1.5E−6 | 3.5E−7 |
| Lower limit of 95% CI | 2.26 | 2.31 | 1.85 | 2.46 | 2.37 | 2.00 | 2.42 | 2.30 | 2.31 |
| Upper limit of 95% CI | 6.52 | 7.14 | 5.21 | 7.22 | 7.45 | 5.64 | 7.09 | 7.21 | 6.58 |

Example 7. Use of Metalloproteinase Inhibitor 1 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 1 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 7.1

Comparison of marker levels and the area under the ROC curve (AUC) in urine samples for the "recovered"
and "non-recovered" cohorts where recovery starts within 24 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 7070 | 20000 | 6950 | 20000 | 6710 | 20500 |
| Average | 15900 | 35500 | 14900 | 35600 | 14800 | 35300 |
| Stdev | 23300 | 35800 | 21500 | 35900 | 21900 | 35700 |
| p (t-test) | | 4.7E−7 | | 1.2E−7 | | 2.2E−7 |
| Min | 475 | 297 | 475 | 297 | 475 | 297 |
| Max | 116000 | 146000 | 110000 | 146000 | 110000 | 146000 |
| n (Patient) | 108 | 209 | 104 | 213 | 100 | 217 |
| sCr only | | | | | | |
| Median | 8650 | 20500 | 8510 | 20500 | 8310 | 20500 |
| Average | 16400 | 36800 | 16400 | 36600 | 16500 | 36400 |
| Stdev | 22300 | 36800 | 22400 | 36700 | 22600 | 36500 |
| p (t-test) | | 5.2E−8 | | 8.5E−8 | | 1.3E−7 |
| Min | 475 | 297 | 475 | 297 | 475 | 297 |
| Max | 116000 | 146000 | 116000 | 146000 | 116000 | 146000 |
| n (Patient) | 126 | 190 | 124 | 192 | 122 | 194 |

TABLE 7.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 11300 | 21700 | 11000 | 21300 | 11000 | 20500 |
| Average | 24700 | 39200 | 24000 | 38700 | 24000 | 37300 |
| Stdev | 31100 | 36500 | 30700 | 36400 | 31000 | 35800 |
| p (t-test) | | 3.9E−4 | | 1.9E−4 | | 6.3E−4 |
| Min | 297 | 399 | 297 | 399 | 297 | 399 |
| Max | 146000 | 140000 | 146000 | 140000 | 146000 | 140000 |
| n (Patient) | 222 | 93 | 208 | 107 | 198 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.70 | 0.66 | 0.73 | 0.70 | 0.66 | 0.73 | 0.70 | 0.65 |
| SE | 0.029 | 0.029 | 0.035 | 0.028 | 0.029 | 0.033 | 0.028 | 0.029 | 0.033 |
| p Value | 3.8E−14 | 9.9E−12 | 6.3E−6 | 2.2E−15 | 8.2E−12 | 1.7E−6 | 2.2E−16 | 6.5E−12 | 4.3E−6 |
| nCohort Recovered | 108 | 126 | 222 | 104 | 124 | 208 | 100 | 122 | 198 |
| nCohort Non-recovered | 209 | 190 | 93 | 213 | 192 | 107 | 217 | 194 | 117 |
| Cutoff Quartile 2 | 6030 | 6020 | 6080 | 6030 | 6020 | 6080 | 6030 | 6020 | 6080 |
| Sensitivity | 85% | 84% | 89% | 85% | 84% | 89% | 85% | 85% | 87% |
| Specificity | 44% | 39% | 31% | 45% | 40% | 32% | 46% | 40% | 32% |
| Cutoff Quartile 3 | 14200 | 14100 | 14200 | 14200 | 14100 | 14200 | 14200 | 14100 | 14200 |
| Sensitivity | 63% | 64% | 68% | 62% | 64% | 66% | 63% | 63% | 64% |
| Specificity | 74% | 71% | 57% | 75% | 71% | 58% | 77% | 71% | 58% |
| Cutoff Quartile 4 | 35900 | 35400 | 36300 | 35900 | 35400 | 36300 | 35900 | 35400 | 36300 |
| Sensitivity | 33% | 35% | 35% | 33% | 34% | 36% | 32% | 34% | 35% |
| Specificity | 89% | 90% | 79% | 90% | 90% | 81% | 90% | 89% | 81% |
| OR Quartile 2 | 4.59 | 3.39 | 3.74 | 4.66 | 3.53 | 3.76 | 4.75 | 3.67 | 3.25 |
| p Value | 2.8E−8 | 6.1E−6 | 3.0E−4 | 2.1E−8 | 3.2E−6 | 9.9E−5 | 1.6E−8 | 1.6E−6 | 1.9E−4 |
| Lower limit of 95% CI | 2.68 | 2.00 | 1.83 | 2.72 | 2.08 | 1.93 | 2.77 | 2.16 | 1.75 |
| Upper limit of 95% CI | 7.87 | 5.76 | 7.65 | 7.99 | 6.00 | 7.33 | 8.15 | 6.24 | 6.03 |
| OR Quartile 3 | 4.80 | 4.22 | 2.81 | 4.99 | 4.26 | 2.74 | 5.62 | 4.31 | 2.47 |
| p Value | 2.2E−9 | 5.6E−9 | 7.2E−5 | 1.8E−9 | 5.3E−9 | 4.8E−5 | 3.9E−10 | 4.9E−9 | 1.7E−4 |
| Lower limit of 95% CI | 2.87 | 2.60 | 1.69 | 2.96 | 2.62 | 1.69 | 3.27 | 2.64 | 1.54 |
| Upper limit of 95% CI | 8.02 | 6.85 | 4.67 | 8.42 | 6.93 | 4.46 | 9.65 | 7.02 | 3.96 |
| OR Quartile 4 | 3.86 | 4.63 | 2.10 | 4.60 | 4.47 | 2.41 | 4.29 | 4.32 | 2.27 |
| p Value | 7.1E−5 | 3.5E−6 | 0.0064 | 2.6E−5 | 5.7E−6 | 9.9E−4 | 6.3E−5 | 9.3E−6 | 0.0019 |
| Lower limit of 95% CI | 1.98 | 2.42 | 1.23 | 2.26 | 2.34 | 1.43 | 2.10 | 2.26 | 1.35 |
| Upper limit of 95% CI | 7.51 | 8.84 | 3.59 | 9.38 | 8.54 | 4.07 | 8.74 | 8.26 | 3.82 |

TABLE 7.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 9010 | 20500 | 8810 | 20500 | 8420 | 20500 |
| Average | 17700 | 37200 | 17600 | 37000 | 16900 | 37000 |
| Stdev | 23400 | 37100 | 23500 | 37000 | 22300 | 37100 |
| p (t-test) | | 1.6E−7 | | 1.9E−7 | | 6.6E−8 |

TABLE 7.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 419 | 297 | 419 | 297 | 419 | 297 |
| Max | 116000 | 146000 | 116000 | 146000 | 110000 | 146000 |
| n (Patient) | 136 | 181 | 134 | 183 | 129 | 188 |
| | | | sCr only | | | |
| Median | 9350 | 20500 | 9380 | 20500 | 9380 | 20500 |
| Average | 18000 | 38400 | 18100 | 38200 | 18100 | 38000 |
| Stdev | 22800 | 38000 | 22900 | 38000 | 23000 | 37800 |
| p (t-test) | | 2.8E−8 | | 4.1E−8 | | 6.8E−8 |
| Min | 419 | 297 | 419 | 297 | 419 | 297 |
| Max | 116000 | 146000 | 116000 | 146000 | 116000 | 146000 |
| n (Patient) | 149 | 168 | 148 | 169 | 146 | 171 |
| | | | UO only | | | |
| Median | 11900 | 21700 | 11800 | 21300 | 11200 | 20900 |
| Average | 25200 | 38600 | 25300 | 37400 | 24900 | 36700 |
| Stdev | 31100 | 37200 | 31400 | 36500 | 31200 | 36200 |
| p (t-test) | | 0.0012 | | 0.0030 | | 0.0029 |
| Min | 297 | 399 | 297 | 399 | 297 | 399 |
| Max | 146000 | 140000 | 146000 | 140000 | 146000 | 140000 |
| n (Patient) | 226 | 89 | 220 | 95 | 207 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.64 | 0.69 | 0.68 | 0.64 | 0.70 | 0.68 | 0.64 |
| SE | 0.029 | 0.030 | 0.036 | 0.029 | 0.030 | 0.035 | 0.029 | 0.030 | 0.034 |
| p Value | 9.9E−11 | 1.0E−9 | 7.8E−5 | 5.0E−11 | 1.4E−9 | 9.6E−5 | 2.3E−12 | 1.4E−9 | 5.6E−5 |
| nCohort Recovered | 136 | 149 | 226 | 134 | 148 | 220 | 129 | 146 | 207 |
| nCohort Non-recovered | 181 | 168 | 89 | 183 | 169 | 95 | 188 | 171 | 108 |
| Cutoff Quartile 2 | 6030 | 6030 | 6080 | 6030 | 6030 | 6080 | 6030 | 6030 | 6080 |
| Sensitivity | 86% | 86% | 90% | 86% | 86% | 89% | 86% | 86% | 88% |
| Specificity | 40% | 37% | 31% | 40% | 37% | 31% | 41% | 38% | 32% |
| Cutoff Quartile 3 | 14200 | 14200 | 14200 | 14200 | 14200 | 14200 | 14200 | 14200 | 14200 |
| Sensitivity | 63% | 64% | 66% | 63% | 63% | 65% | 63% | 63% | 64% |
| Specificity | 67% | 65% | 56% | 67% | 65% | 56% | 69% | 65% | 57% |
| Cutoff Quartile 4 | 35900 | 35900 | 36300 | 35900 | 35900 | 36300 | 35900 | 35900 | 36300 |
| Sensitivity | 34% | 36% | 33% | 34% | 36% | 33% | 34% | 36% | 32% |
| Specificity | 87% | 87% | 78% | 87% | 87% | 78% | 88% | 87% | 79% |
| OR Quartile 2 | 4.11 | 3.51 | 3.99 | 4.27 | 3.57 | 3.88 | 4.35 | 3.70 | 3.42 |
| p Value | 3.6E−7 | 6.4E−6 | 2.7E−4 | 1.8E−7 | 4.8E−6 | 2.0E−4 | 1.1E−7 | 2.6E−6 | 2.0E−4 |
| Lower limit of 95% CI | 2.38 | 2.03 | 1.89 | 2.47 | 2.07 | 1.90 | 2.53 | 2.14 | 1.79 |
| Upper limit of 95% CI | 7.08 | 6.06 | 8.40 | 7.36 | 6.17 | 7.94 | 7.48 | 6.39 | 6.55 |
| OR Quartile 3 | 3.44 | 3.27 | 2.52 | 3.46 | 3.19 | 2.43 | 3.84 | 3.19 | 2.35 |
| p Value | 2.2E−7 | 4.6E−7 | 4.0E−4 | 2.1E−7 | 8.0E−7 | 5.0E−4 | 3.2E−8 | 7.9E−7 | 4.9E−4 |
| Lower limit of 95% CI | 2.16 | 2.06 | 1.51 | 2.16 | 2.01 | 1.47 | 2.38 | 2.01 | 1.45 |
| Upper limit of 95% CI | 5.49 | 5.19 | 4.21 | 5.53 | 5.05 | 4.00 | 6.18 | 5.06 | 3.79 |
| OR Quartile 4 | 3.42 | 3.90 | 1.70 | 3.61 | 3.83 | 1.74 | 3.65 | 3.71 | 1.78 |
| p Value | 3.7E−5 | 3.5E−6 | 0.055 | 2.2E−5 | 4.6E−6 | 0.043 | 2.7E−5 | 7.9E−6 | 0.031 |
| Lower limit of 95% CI | 1.91 | 2.19 | 0.988 | 2.00 | 2.16 | 1.02 | 1.99 | 2.09 | 1.05 |
| Upper limit of 95% CI | 6.12 | 6.93 | 2.93 | 6.54 | 6.81 | 2.96 | 6.67 | 6.59 | 3.00 |

TABLE 7.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 9010 | 21900 | 9010 | 21700 | 8870 | 21700 |
| Average | 18400 | 38700 | 18500 | 38300 | 18000 | 38300 |
| Stdev | 24700 | 37300 | 24900 | 37200 | 23900 | 37400 |
| p (t-test) | | 3.1E−8 | | 7.1E−8 | | 3.0E−8 |
| Min | 419 | 297 | 419 | 297 | 419 | 297 |
| Max | 116000 | 146000 | 116000 | 146000 | 111000 | 146000 |
| n (Patient) | 154 | 163 | 152 | 165 | 148 | 169 |
| | sCr only | | | | | |
| Median | 9310 | 22000 | 9160 | 21900 | 9310 | 21600 |
| Average | 18700 | 39200 | 18800 | 39000 | 18900 | 38800 |
| Stdev | 24500 | 37800 | 24600 | 37800 | 24700 | 37700 |
| p (t-test) | | 2.3E−8 | | 3.4E−8 | | 5.2E−8 |
| Min | 419 | 297 | 419 | 297 | 419 | 297 |
| Max | 116000 | 146000 | 116000 | 146000 | 116000 | 146000 |
| n (Patient) | 161 | 156 | 160 | 157 | 159 | 158 |
| | UO only | | | | | |
| Median | 11900 | 21300 | 11900 | 20900 | 11800 | 20500 |
| Average | 25600 | 37100 | 25700 | 36700 | 25300 | 36500 |
| Stdev | 31500 | 36700 | 31500 | 36600 | 31200 | 36500 |
| p (t-test) | | 0.0056 | | 0.0077 | | 0.0053 |
| Min | 297 | 399 | 297 | 399 | 297 | 399 |
| Max | 146000 | 140000 | 146000 | 140000 | 146000 | 140000 |
| n (Patient) | 224 | 91 | 223 | 92 | 212 | 103 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.69 | 0.63 | 0.70 | 0.69 | 0.62 | 0.70 | 0.69 | 0.62 |
| SE | 0.029 | 0.030 | 0.036 | 0.029 | 0.030 | 0.036 | 0.029 | 0.030 | 0.034 |
| p Value | 4.1E−12 | 8.7E−11 | 3.1E−4 | 1.3E−11 | 1.3E−10 | 6.4E−4 | 3.0E−12 | 2.1E−10 | 3.7E−4 |
| nCohort Recovered | 154 | 161 | 224 | 152 | 160 | 223 | 148 | 159 | 212 |
| nCohort Non-recovered | 163 | 156 | 91 | 165 | 157 | 92 | 169 | 158 | 103 |
| Cutoff Quartile 2 | 6030 | 6030 | 6080 | 6030 | 6030 | 6080 | 6030 | 6030 | 6080 |
| Sensitivity | 87% | 86% | 88% | 87% | 86% | 87% | 86% | 86% | 86% |
| Specificity | 37% | 35% | 30% | 38% | 36% | 30% | 38% | 36% | 31% |
| Cutoff Quartile 3 | 14200 | 14200 | 14200 | 14200 | 14200 | 14200 | 14200 | 14200 | 14200 |
| Sensitivity | 66% | 66% | 65% | 65% | 66% | 64% | 65% | 65% | 63% |
| Specificity | 67% | 65% | 56% | 66% | 65% | 56% | 67% | 65% | 56% |
| Cutoff Quartile 4 | 35900 | 35900 | 36300 | 35900 | 35900 | 36300 | 35900 | 35900 | 36300 |
| Sensitivity | 37% | 38% | 32% | 36% | 38% | 32% | 36% | 37% | 32% |
| Specificity | 87% | 87% | 78% | 87% | 87% | 78% | 87% | 87% | 78% |
| OR Quartile 2 | 3.77 | 3.34 | 3.17 | 3.90 | 3.40 | 2.86 | 3.86 | 3.45 | 2.81 |
| p Value | 2.9E−6 | 2.0E−5 | 0.0011 | 1.6E−6 | 1.6E−5 | 0.0021 | 1.5E−6 | 1.2E−5 | 0.0014 |
| Lower limit of 95% CI | 2.16 | 1.92 | 1.59 | 2.24 | 1.95 | 1.46 | 2.23 | 1.98 | 1.49 |
| Upper limit of 95% CI | 6.57 | 5.81 | 6.33 | 6.80 | 5.91 | 5.60 | 6.70 | 6.02 | 5.30 |
| OR Quartile 3 | 3.97 | 3.64 | 2.33 | 3.75 | 3.54 | 2.24 | 3.77 | 3.44 | 2.19 |
| p Value | 7.3E−9 | 4.6E−8 | 0.0010 | 2.5E−8 | 8.4E−8 | 0.0016 | 2.4E−8 | 1.5E−7 | 0.0015 |
| Lower limit of 95% CI | 2.49 | 2.29 | 1.41 | 2.36 | 2.23 | 1.36 | 2.36 | 2.17 | 1.35 |
| Upper limit of 95% CI | 6.33 | 5.79 | 3.86 | 5.97 | 5.63 | 3.70 | 6.00 | 5.46 | 3.55 |

TABLE 7.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

|  |  |  |  |  |  |  |  |  |  |
|---|---|---|---|---|---|---|---|---|---|
| OR Quartile 4 | 3.90 | 4.05 | 1.63 | 3.77 | 3.98 | 1.59 | 3.83 | 3.92 | 1.70 |
| p Value | 2.6E−6 | 1.0E−6 | 0.078 | 4.5E−6 | 1.4E−6 | 0.092 | 4.6E−6 | 1.8E−6 | 0.048 |
| Lower limit of 95% CI | 2.21 | 2.31 | 0.947 | 2.14 | 2.27 | 0.927 | 2.16 | 2.23 | 1.00 |
| Upper limit of 95% CI | 6.88 | 7.11 | 2.80 | 6.65 | 6.98 | 2.74 | 6.81 | 6.86 | 2.88 |

TABLE 7.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 9350 | 21900 | 9360 | 21500 | 9310 | 21500 |
| Average | 19200 | 39700 | 19400 | 39100 | 18900 | 39100 |
| Stdev | 24900 | 38100 | 25100 | 37900 | 24200 | 38100 |
| p (t-test) | | 2.3E−8 | | 7.9E−8 | | 3.5E−8 |
| Min | 419 | 297 | 419 | 297 | 419 | 297 |
| Max | 116000 | 146000 | 116000 | 146000 | 111000 | 146000 |
| n (Patient) | 168 | 149 | 165 | 152 | 161 | 156 |
| | sCr only | | | | | |
| Median | 9510 | 22000 | 9570 | 22000 | 9620 | 21900 |
| Average | 19400 | 40000 | 19500 | 39700 | 19600 | 39500 |
| Stdev | 24900 | 38400 | 24900 | 38400 | 25000 | 38300 |
| p (t-test) | | 2.4E−8 | | 3.7E−8 | | 5.7E−8 |
| Min | 419 | 297 | 419 | 297 | 419 | 297 |
| Max | 116000 | 146000 | 116000 | 146000 | 116000 | 146000 |
| n (Patient) | 172 | 145 | 171 | 146 | 170 | 147 |
| | UO only | | | | | |
| Median | 11800 | 21500 | 11900 | 21300 | 11800 | 20500 |
| Average | 25400 | 37400 | 25500 | 37200 | 25200 | 37000 |
| Stdev | 31500 | 36500 | 31500 | 36400 | 31100 | 36700 |
| p (t-test) | | 0.0036 | | 0.0046 | | 0.0033 |
| Min | 297 | 399 | 297 | 399 | 297 | 399 |
| Max | 146000 | 140000 | 146000 | 140000 | 146000 | 140000 |
| n (Patient) | 223 | 92 | 222 | 93 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.69 | 0.63 | 0.69 | 0.69 | 0.63 | 0.69 | 0.68 | 0.63 |
| SE | 0.030 | 0.030 | 0.036 | 0.030 | 0.030 | 0.035 | 0.029 | 0.030 | 0.034 |
| p Value | 3.9E−11 | 3.8E−10 | 1.9E−4 | 1.5E−10 | 5.6E−10 | 2.3E−4 | 4.7E−11 | 9.1E−10 | 1.6E−4 |
| nCohort Recovered | 168 | 172 | 223 | 165 | 171 | 222 | 161 | 170 | 214 |
| nCohort Non-recovered | 149 | 145 | 92 | 152 | 146 | 93 | 156 | 147 | 101 |
| Cutoff Quartile 2 | 6030 | 6030 | 6080 | 6030 | 6030 | 6080 | 6030 | 6030 | 6080 |
| Sensitivity | 87% | 86% | 88% | 88% | 86% | 88% | 87% | 86% | 88% |
| Specificity | 36% | 34% | 30% | 36% | 35% | 31% | 37% | 35% | 31% |
| Cutoff Quartile 3 | 14200 | 14200 | 14200 | 14200 | 14200 | 14200 | 14200 | 14200 | 14200 |
| Sensitivity | 68% | 68% | 65% | 66% | 67% | 65% | 66% | 67% | 63% |
| Specificity | 65% | 65% | 56% | 65% | 64% | 56% | 65% | 64% | 56% |
| Cutoff Quartile 4 | 35900 | 35900 | 36300 | 35900 | 35900 | 36300 | 35900 | 35900 | 36300 |
| Sensitivity | 38% | 38% | 35% | 37% | 38% | 34% | 37% | 37% | 34% |
| Specificity | 86% | 85% | 79% | 85% | 85% | 79% | 86% | 85% | 79% |
| OR Quartile 2 | 3.80 | 3.26 | 3.23 | 4.00 | 3.32 | 3.29 | 3.93 | 3.38 | 3.38 |
| p Value | 5.4E−6 | 4.4E−5 | 8.9E−4 | 2.4E−6 | 3.4E−5 | 7.3E−4 | 2.3E−6 | 2.7E−5 | 3.5E−4 |

TABLE 7.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.14 | 1.85 | 1.62 | 2.25 | 1.88 | 1.65 | 2.23 | 1.91 | 1.73 |
| Upper limit of 95% CI | 6.76 | 5.76 | 6.45 | 7.12 | 5.85 | 6.57 | 6.94 | 5.95 | 6.60 |
| OR Quartile 3 | 3.99 | 3.79 | 2.39 | 3.65 | 3.68 | 2.30 | 3.64 | 3.57 | 2.21 |
| p Value | 6.9E−9 | 2.3E−8 | 7.0E−4 | 4.5E−8 | 4.2E−8 | 0.0011 | 4.6E−8 | 7.7E−8 | 0.0014 |
| Lower limit of 95% CI | 2.50 | 2.38 | 1.44 | 2.30 | 2.31 | 1.39 | 2.29 | 2.25 | 1.36 |
| Upper limit of 95% CI | 6.37 | 6.06 | 3.96 | 5.81 | 5.87 | 3.80 | 5.79 | 5.69 | 3.59 |
| OR Quartile 4 | 3.61 | 3.59 | 2.00 | 3.43 | 3.53 | 1.95 | 3.45 | 3.47 | 1.91 |
| p Value | 3.8E−6 | 3.5E−6 | 0.011 | 9.1E−6 | 4.8E−6 | 0.014 | 9.5E−6 | 6.4E−6 | 0.017 |
| Lower limit of 95% CI | 2.10 | 2.09 | 1.17 | 1.99 | 2.06 | 1.14 | 2.00 | 2.02 | 1.12 |
| Upper limit of 95% CI | 6.23 | 6.17 | 3.41 | 5.90 | 6.06 | 3.34 | 5.98 | 5.95 | 3.23 |

TABLE 7.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 11100 | 21500 | 11100 | 21100 | 11000 | 20800 |
| Average | 23100 | 39100 | 23200 | 38600 | 23300 | 38300 |
| Stdev | 28900 | 38100 | 29000 | 38000 | 29000 | 37900 |
| p (t-test) | | 3.3E−5 | | 6.5E−5 | | 8.6E−5 |
| Min | 297 | 399 | 297 | 399 | 297 | 399 |
| Max | 127000 | 146000 | 127000 | 146000 | 127000 | 146000 |
| n (Patient) | 203 | 114 | 201 | 116 | 200 | 117 |
| sCr only | | | | | | |
| Median | 10900 | 22000 | 10900 | 22000 | 10900 | 22000 |
| Average | 20400 | 40600 | 20400 | 40600 | 20400 | 40600 |
| Stdev | 25100 | 39400 | 25100 | 39400 | 25100 | 39400 |
| p (t-test) | | 5.4E−8 | | 5.4E−8 | | 5.4E−8 |
| Min | 419 | 297 | 419 | 297 | 419 | 297 |
| Max | 116000 | 146000 | 116000 | 146000 | 116000 | 146000 |
| n (Patient) | 185 | 132 | 185 | 132 | 185 | 132 |
| UO only | | | | | | |
| Median | 11800 | 21500 | 11900 | 21300 | 11900 | 20800 |
| Average | 24500 | 38800 | 24600 | 38500 | 24700 | 37900 |
| Stdev | 29700 | 38800 | 29800 | 38700 | 29900 | 38500 |
| p (t-test) | | 4.1E−4 | | 5.5E−4 | | 9.8E−4 |
| Min | 297 | 399 | 297 | 399 | 297 | 399 |
| Max | 127000 | 146000 | 127000 | 146000 | 127000 | 146000 |
| n (Patient) | 217 | 98 | 216 | 99 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.67 | 0.63 | 0.65 | 0.67 | 0.63 | 0.64 | 0.67 | 0.63 |
| SE | 0.033 | 0.031 | 0.035 | 0.033 | 0.031 | 0.035 | 0.033 | 0.031 | 0.035 |
| p Value | 4.4E−6 | 2.0E−8 | 1.3E−4 | 8.7E−6 | 2.0E−8 | 1.5E−4 | 9.7E−6 | 2.0E−8 | 2.5E−4 |
| nCohort Recovered | 203 | 185 | 217 | 201 | 185 | 216 | 200 | 185 | 214 |
| nCohort Non-recovered | 114 | 132 | 98 | 116 | 132 | 99 | 117 | 132 | 101 |
| Cutoff Quartile 2 | 6030 | 6030 | 6080 | 6030 | 6030 | 6080 | 6030 | 6030 | 6080 |

TABLE 7.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 86% | 87% | 87% | 86% | 87% | 87% | 86% | 87% | 87% |
| Specificity | 31% | 34% | 30% | 31% | 34% | 31% | 32% | 34% | 31% |
| Cutoff Quartile 3 | 14200 | 14200 | 14200 | 14200 | 14200 | 14200 | 14200 | 14200 | 14200 |
| Sensitivity | 66% | 65% | 64% | 65% | 65% | 64% | 64% | 65% | 62% |
| Specificity | 59% | 61% | 56% | 58% | 61% | 56% | 58% | 61% | 56% |
| Cutoff Quartile 4 | 35900 | 35900 | 36300 | 35900 | 35900 | 36300 | 35900 | 35900 | 36300 |
| Sensitivity | 37% | 39% | 35% | 36% | 39% | 34% | 36% | 39% | 34% |
| Specificity | 81% | 84% | 79% | 81% | 84% | 79% | 81% | 84% | 79% |
| OR Quartile 2 | 2.76 | 3.41 | 2.86 | 2.85 | 3.41 | 2.91 | 2.90 | 3.41 | 3.02 |
| p Value | 0.0010 | 5.1E−5 | 0.0016 | 7.0E−4 | 5.1E−5 | 0.0013 | 5.7E−4 | 5.1E−5 | 8.7E−4 |
| Lower limit of 95% CI | 1.50 | 1.88 | 1.49 | 1.56 | 1.88 | 1.52 | 1.58 | 1.88 | 1.57 |
| Upper limit of 95% CI | 5.05 | 6.17 | 5.48 | 5.23 | 6.17 | 5.58 | 5.32 | 6.17 | 5.79 |
| OR Quartile 3 | 2.72 | 2.87 | 2.31 | 2.55 | 2.87 | 2.23 | 2.47 | 2.87 | 2.08 |
| p Value | 3.9E−5 | 8.5E−6 | 8.6E−4 | 1.1E−4 | 8.5E−6 | 0.0013 | 1.7E−4 | 8.5E−6 | 0.0031 |
| Lower limit of 95% CI | 1.69 | 1.80 | 1.41 | 1.59 | 1.80 | 1.37 | 1.54 | 1.80 | 1.28 |
| Upper limit of 95% CI | 4.39 | 4.56 | 3.78 | 4.09 | 4.56 | 3.64 | 3.95 | 4.56 | 3.37 |
| OR Quartile 4 | 2.53 | 3.39 | 2.03 | 2.43 | 3.39 | 1.99 | 2.39 | 3.39 | 1.91 |
| p Value | 4.5E−4 | 6.2E−6 | 0.0088 | 7.6E−4 | 6.2E−6 | 0.011 | 9.7E−4 | 6.2E−6 | 0.017 |
| Lower limit of 95% CI | 1.51 | 2.00 | 1.20 | 1.45 | 2.00 | 1.17 | 1.42 | 2.00 | 1.12 |
| Upper limit of 95% CI | 4.26 | 5.75 | 3.45 | 4.09 | 5.75 | 3.37 | 4.00 | 5.75 | 3.23 |

TABLE 7.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 274000 | 564000 | 275000 | 564000 | 270000 | 564000 |
| Average | 354000 | 562000 | 354000 | 560000 | 342000 | 561000 |
| Stdev | 231000 | 271000 | 231000 | 271000 | 222000 | 271000 |
| p (t-test) | | 5.2E−11 | | 1.3E−10 | | 1.0E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 105 | 222 | 102 | 225 | 98 | 229 |
| sCr only | | | | | | |
| Median | 279000 | 566000 | 279000 | 566000 | 275000 | 566000 |
| Average | 365000 | 569000 | 362000 | 569000 | 358000 | 570000 |
| Stdev | 235000 | 269000 | 235000 | 268000 | 232000 | 268000 |
| p (t-test) | | 2.1E−11 | | 1.4E−11 | | 4.4E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 121 | 205 | 119 | 207 | 117 | 209 |
| UO only | | | | | | |
| Median | 373000 | 605000 | 371000 | 598000 | 369000 | 595000 |
| Average | 445000 | 617000 | 439000 | 608000 | 433000 | 603000 |
| Stdev | 256000 | 284000 | 252000 | 287000 | 249000 | 286000 |
| p (t-test) | | 1.4E−7 | | 7.4E−8 | | 3.9E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 226 | 99 | 213 | 112 | 202 | 123 |

TABLE 7.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.72 | 0.67 | 0.73 | 0.73 | 0.67 | 0.74 | 0.73 | 0.67 |
| SE | 0.028 | 0.028 | 0.034 | 0.028 | 0.028 | 0.032 | 0.028 | 0.027 | 0.031 |
| p Value | 2.2E−16 | 4.4E−16 | 3.0E−7 | 1.3E−15 | 0 | 1.3E−7 | 0 | 0 | 4.0E−8 |
| nCohort Recovered | 105 | 121 | 226 | 102 | 119 | 213 | 98 | 117 | 202 |
| nCohort Non-recovered | 222 | 205 | 99 | 225 | 207 | 112 | 229 | 209 | 123 |
| Cutoff Quartile 2 | 260000 | 260000 | 262000 | 260000 | 260000 | 262000 | 260000 | 260000 | 262000 |
| Sensitivity | 84% | 85% | 85% | 84% | 86% | 85% | 84% | 86% | 85% |
| Specificity | 45% | 43% | 29% | 44% | 44% | 30% | 46% | 44% | 31% |
| Cutoff Quartile 3 | 437000 | 433000 | 437000 | 437000 | 433000 | 437000 | 437000 | 433000 | 437000 |
| Sensitivity | 60% | 62% | 66% | 60% | 62% | 64% | 60% | 62% | 63% |
| Specificity | 71% | 70% | 57% | 72% | 71% | 57% | 72% | 71% | 57% |
| Cutoff Quartile 4 | 707000 | 704000 | 708000 | 707000 | 704000 | 708000 | 707000 | 704000 | 708000 |
| Sensitivity | 33% | 34% | 44% | 32% | 33% | 42% | 33% | 33% | 41% |
| Specificity | 91% | 89% | 83% | 91% | 89% | 84% | 93% | 90% | 84% |
| OR Quartile 2 | 4.33 | 4.40 | 2.31 | 4.01 | 4.58 | 2.40 | 4.41 | 4.77 | 2.64 |
| p Value | 5.2E−8 | 4.0E−8 | 0.0081 | 2.3E−7 | 1.8E−8 | 0.0038 | 4.3E−8 | 8.2E−9 | 0.0011 |
| Lower limit of 95% CI | 2.55 | 2.59 | 1.24 | 2.37 | 2.70 | 1.33 | 2.59 | 2.81 | 1.48 |
| Upper limit of 95% CI | 7.34 | 7.46 | 4.29 | 6.79 | 7.78 | 4.35 | 7.49 | 8.12 | 4.73 |
| OR Quartile 3 | 3.81 | 3.84 | 2.50 | 3.78 | 3.89 | 2.41 | 3.92 | 3.94 | 2.26 |
| p Value | 1.8E−7 | 4.1E−8 | 2.6E−4 | 2.7E−7 | 3.8E−8 | 2.6E−4 | 2.2E−7 | 3.5E−8 | 5.1E−4 |
| Lower limit of 95% CI | 2.31 | 2.38 | 1.53 | 2.28 | 2.40 | 1.50 | 2.34 | 2.42 | 1.43 |
| Upper limit of 95% CI | 6.29 | 6.22 | 4.08 | 6.26 | 6.31 | 3.87 | 6.56 | 6.41 | 3.57 |
| OR Quartile 4 | 5.23 | 4.21 | 3.96 | 4.96 | 4.08 | 3.68 | 6.33 | 4.41 | 3.64 |
| p Value | 1.1E−5 | 1.2E−5 | 3.3E−7 | 2.1E−5 | 1.9E−5 | 1.0E−6 | 9.5E−6 | 1.2E−5 | 1.2E−6 |
| Lower limit of 95% CI | 2.50 | 2.21 | 2.33 | 2.37 | 2.14 | 2.18 | 2.80 | 2.27 | 2.16 |
| Upper limit of 95% CI | 10.9 | 8.03 | 6.71 | 10.4 | 7.77 | 6.20 | 14.3 | 8.55 | 6.13 |

TABLE 7.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 293000 | 568000 | 293000 | 571000 | 284000 | 568000 |
| Average | 379000 | 576000 | 376000 | 577000 | 370000 | 576000 |
| Stdev | 235000 | 274000 | 234000 | 273000 | 229000 | 274000 |
| p (t-test) | | 5.1E−11 | | 2.7E−11 | | 8.5E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 134 | 193 | 133 | 194 | 128 | 199 |
| | sCr only | | | | | |
| Median | 300000 | 576000 | 299000 | 577000 | 294000 | 577000 |
| Average | 386000 | 583000 | 384000 | 584000 | 380000 | 585000 |
| Stdev | 237000 | 274000 | 237000 | 274000 | 235000 | 273000 |
| p (t-test) | | 3.5E−11 | | 1.9E−11 | | 6.9E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 146 | 181 | 145 | 182 | 143 | 184 |

TABLE 7.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 375000 | 598000 | 375000 | 598000 | 369000 | 596000 |
| Average | 448000 | 619000 | 443000 | 618000 | 432000 | 616000 |
| Stdev | 256000 | 287000 | 253000 | 288000 | 247000 | 288000 |
| p (t-test) | | 2.5E−7 | | 7.7E−8 | | 4.4E−9 |
| Min | 13600 | 135000 | 13600 | 135000 | 13600 | 135000 |
| Max | 1120000 | 1090000 | 1120000 | 1090000 | 1120000 | 1090000 |
| n (Patient) | 231 | 94 | 225 | 100 | 210 | 115 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.71 | 0.67 | 0.72 | 0.72 | 0.68 | 0.72 | 0.72 | 0.69 |
| SE | 0.028 | 0.028 | 0.034 | 0.028 | 0.028 | 0.033 | 0.028 | 0.028 | 0.032 |
| p Value | 1.9E−14 | 4.0E−14 | 3.9E−7 | 5.3E−15 | 1.2E−14 | 9.9E−8 | 6.7E−16 | 2.0E−15 | 4.2E−9 |
| nCohort Recovered | 134 | 146 | 231 | 133 | 145 | 225 | 128 | 143 | 210 |
| nCohort Non-recovered | 193 | 181 | 94 | 194 | 182 | 100 | 199 | 184 | 115 |
| Cutoff Quartile 2 | 260000 | 260000 | 262000 | 260000 | 260000 | 262000 | 260000 | 260000 | 262000 |
| Sensitivity | 85% | 86% | 87% | 86% | 86% | 88% | 85% | 86% | 88% |
| Specificity | 40% | 39% | 30% | 41% | 39% | 31% | 41% | 40% | 32% |
| Cutoff Quartile 3 | 437000 | 437000 | 437000 | 437000 | 437000 | 437000 | 437000 | 437000 | 437000 |
| Sensitivity | 62% | 63% | 65% | 62% | 63% | 64% | 62% | 63% | 63% |
| Specificity | 67% | 66% | 56% | 68% | 66% | 56% | 68% | 66% | 57% |
| Cutoff Quartile 4 | 707000 | 707000 | 708000 | 707000 | 707000 | 708000 | 707000 | 707000 | 708000 |
| Sensitivity | 35% | 36% | 43% | 35% | 36% | 42% | 35% | 36% | 42% |
| Specificity | 89% | 88% | 82% | 89% | 88% | 82% | 90% | 89% | 84% |
| OR Quartile 2 | 3.98 | 4.00 | 2.91 | 4.05 | 4.07 | 3.24 | 4.14 | 4.22 | 3.38 |
| p Value | 3.1E−7 | 4.4E−7 | 0.0017 | 2.2E−7 | 3.2E−7 | 5.4E−4 | 1.3E−7 | 1.6E−7 | 1.5E−4 |
| Lower limit of 95% CI | 2.34 | 2.33 | 1.49 | 2.39 | 2.38 | 1.67 | 2.44 | 2.46 | 1.80 |
| Upper limit of 95% CI | 6.75 | 6.84 | 5.68 | 6.88 | 6.96 | 6.32 | 7.02 | 7.22 | 6.35 |
| OR Quartile 3 | 3.36 | 3.27 | 2.34 | 3.47 | 3.36 | 2.26 | 3.43 | 3.38 | 2.32 |
| p Value | 2.9E−7 | 3.6E−7 | 8.1E−4 | 1.6E−7 | 2.0E−7 | 9.9E−4 | 2.5E−7 | 2.0E−7 | 4.3E−4 |
| Lower limit of 95% CI | 2.12 | 2.07 | 1.42 | 2.18 | 2.13 | 1.39 | 2.15 | 2.13 | 1.45 |
| Upper limit of 95% CI | 5.34 | 5.15 | 3.84 | 5.52 | 5.31 | 3.68 | 5.49 | 5.34 | 3.70 |
| OR Quartile 4 | 4.22 | 4.25 | 3.33 | 4.15 | 4.18 | 3.35 | 4.70 | 4.44 | 3.71 |
| p Value | 4.2E−6 | 1.5E−6 | 7.9E−6 | 5.4E−6 | 2.0E−6 | 6.1E−6 | 2.5E−6 | 1.2E−6 | 8.5E−7 |
| Lower limit of 95% CI | 2.28 | 2.36 | 1.97 | 2.25 | 2.32 | 1.98 | 2.47 | 2.43 | 2.20 |
| Upper limit of 95% CI | 7.79 | 7.67 | 5.65 | 7.66 | 7.54 | 5.66 | 8.94 | 8.10 | 6.25 |

TABLE 7.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 303000 | 573000 | 300000 | 576000 | 296000 | 576000 |
| Average | 394000 | 586000 | 390000 | 587000 | 384000 | 587000 |
| Stdev | 239000 | 276000 | 238000 | 275000 | 232000 | 276000 |
| p (t-test) | | 1.0E−10 | | 2.8E−11 | | 7.0E−12 |

TABLE 7.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 13600 | 105000 | 13600 | 105000 | 13600 | 105000 |
| Max | 1040000 | 1120000 | 1040000 | 1120000 | 1040000 | 1120000 |
| n (Patient) | 154 | 173 | 152 | 175 | 148 | 179 | sCr only

| | | | | | | |
|---|---|---|---|---|---|---|
| Median | 304000 | 582000 | 303000 | 586000 | 301000 | 590000 |
| Average | 394000 | 594000 | 392000 | 594000 | 389000 | 596000 |
| Stdev | 239000 | 275000 | 238000 | 274000 | 236000 | 274000 |
| p (t-test) | | 1.4E−11 | | 7.8E−12 | | 2.2E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 161 | 166 | 160 | 167 | 159 | 168 |

UO only

| | | | | | | |
|---|---|---|---|---|---|---|
| Median | 373000 | 600000 | 373000 | 600000 | 367000 | 597000 |
| Average | 443000 | 627000 | 442000 | 627000 | 434000 | 621000 |
| Stdev | 254000 | 285000 | 252000 | 287000 | 248000 | 287000 |
| p (t-test) | | 2.5E−8 | | 1.7E−8 | | 3.3E−9 |
| Min | 13600 | 135000 | 13600 | 135000 | 13600 | 135000 |
| Max | 1120000 | 1090000 | 1120000 | 1090000 | 1120000 | 1090000 |
| n (Patient) | 230 | 95 | 228 | 97 | 215 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.71 | 0.69 | 0.71 | 0.72 | 0.69 | 0.72 | 0.72 | 0.69 |
| SE | 0.028 | 0.028 | 0.034 | 0.028 | 0.028 | 0.034 | 0.028 | 0.028 | 0.032 |
| p Value | 3.2E−13 | 3.4E−14 | 2.8E−8 | 3.4E−14 | 1.1E−14 | 2.3E−8 | 4.9E−15 | 2.0E−15 | 2.6E−9 |
| nCohort Recovered | 154 | 161 | 230 | 152 | 160 | 228 | 148 | 159 | 215 |
| nCohort Non-recovered | 173 | 166 | 95 | 175 | 167 | 97 | 179 | 168 | 110 |
| Cutoff Quartile 2 | 260000 | 260000 | 262000 | 260000 | 260000 | 262000 | 260000 | 260000 | 262000 |
| Sensitivity | 87% | 88% | 88% | 87% | 88% | 88% | 87% | 88% | 88% |
| Specificity | 39% | 39% | 30% | 39% | 39% | 30% | 40% | 39% | 32% |
| Cutoff Quartile 3 | 437000 | 437000 | 437000 | 437000 | 437000 | 437000 | 437000 | 437000 | 437000 |
| Sensitivity | 62% | 63% | 66% | 62% | 63% | 66% | 62% | 64% | 65% |
| Specificity | 63% | 63% | 57% | 64% | 64% | 57% | 64% | 64% | 57% |
| Cutoff Quartile 4 | 707000 | 707000 | 708000 | 707000 | 707000 | 708000 | 707000 | 707000 | 708000 |
| Sensitivity | 36% | 37% | 42% | 36% | 37% | 42% | 36% | 37% | 42% |
| Specificity | 87% | 87% | 82% | 88% | 87% | 82% | 89% | 87% | 83% |
| OR Quartile 2 | 4.38 | 4.57 | 3.34 | 4.54 | 4.65 | 3.07 | 4.50 | 4.73 | 3.45 |
| p Value | 1.6E−7 | 1.3E−7 | 5.9E−4 | 8.3E−8 | 9.8E−8 | 9.7E−4 | 7.4E−8 | 7.2E−8 | 1.7E−4 |
| Lower limit of 95% CI | 2.52 | 2.60 | 1.68 | 2.61 | 2.64 | 1.58 | 2.60 | 2.69 | 1.81 |
| Upper limit of 95% CI | 7.61 | 8.04 | 6.65 | 7.88 | 8.18 | 5.99 | 7.78 | 8.32 | 6.59 |
| OR Quartile 3 | 2.76 | 2.98 | 2.56 | 2.91 | 3.06 | 2.53 | 2.93 | 3.14 | 2.43 |
| p Value | 9.2E−6 | 2.0E−6 | 2.2E−4 | 3.3E−6 | 1.2E−6 | 2.4E−4 | 3.2E−6 | 6.9E−7 | 2.4E−4 |
| Lower limit of 95% CI | 1.76 | 1.90 | 1.55 | 1.86 | 1.95 | 1.54 | 1.86 | 2.00 | 1.51 |
| Upper limit of 95% CI | 4.32 | 4.67 | 4.22 | 4.57 | 4.80 | 4.15 | 4.60 | 4.93 | 3.91 |
| OR Quartile 4 | 3.74 | 3.87 | 3.26 | 3.94 | 3.81 | 3.34 | 4.39 | 4.07 | 3.57 |
| p Value | 4.4E−6 | 1.9E−6 | 1.1E−5 | 2.6E−6 | 2.5E−6 | 7.0E−6 | 8.8E−7 | 1.1E−6 | 1.7E−6 |
| Lower limit of 95% CI | 2.13 | 2.22 | 1.92 | 2.22 | 2.18 | 1.97 | 2.44 | 2.31 | 2.12 |
| Upper limit of 95% CI | 6.57 | 6.76 | 5.51 | 6.97 | 6.65 | 5.65 | 7.93 | 7.14 | 6.02 |

TABLE 7.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 318000 | 576000 | 313000 | 577000 | 304000 | 577000 |
| Average | 401000 | 592000 | 398000 | 592000 | 393000 | 593000 |
| Stdev | 243000 | 275000 | 243000 | 273000 | 238000 | 275000 |
| p (t-test) | | 1.3E−10 | | 4.8E−11 | | 1.3E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 166 | 161 | 163 | 164 | 159 | 168 |
| sCr only | | | | | | |
| Median | 313000 | 590000 | 311000 | 594000 | 309000 | 594000 |
| Average | 397000 | 600000 | 395000 | 601000 | 393000 | 603000 |
| Stdev | 242000 | 272000 | 242000 | 271000 | 240000 | 271000 |
| p (t-test) | | 6.4E−12 | | 3.5E−12 | | 9.9E−13 |
| Min | 13600 | 105000 | 13600 | 105000 | 13600 | 105000 |
| Max | 1040000 | 1120000 | 1040000 | 1120000 | 1040000 | 1120000 |
| n (Patient) | 169 | 158 | 168 | 159 | 167 | 160 |
| UO only | | | | | | |
| Median | 377000 | 598000 | 375000 | 596000 | 371000 | 596000 |
| Average | 441000 | 626000 | 441000 | 624000 | 436000 | 621000 |
| Stdev | 251000 | 289000 | 251000 | 288000 | 249000 | 287000 |
| p (t-test) | | 1.2E−8 | | 1.7E−8 | | 5.7E−9 |
| Min | 13600 | 135000 | 13600 | 135000 | 13600 | 135000 |
| Max | 1120000 | 1090000 | 1120000 | 1090000 | 1120000 | 1090000 |
| n (Patient) | 226 | 99 | 225 | 100 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.72 | 0.69 | 0.71 | 0.72 | 0.69 | 0.71 | 0.73 | 0.69 |
| SE | 0.029 | 0.028 | 0.033 | 0.028 | 0.028 | 0.033 | 0.028 | 0.028 | 0.032 |
| p Value | 8.9E−13 | 1.4E−14 | 1.3E−8 | 1.2E−13 | 4.9E−15 | 1.6E−8 | 2.3E−14 | 8.9E−16 | 3.9E−9 |
| nCohort Recovered | 166 | 169 | 226 | 163 | 168 | 225 | 159 | 167 | 217 |
| nCohort Non-recovered | 161 | 158 | 99 | 164 | 159 | 100 | 168 | 160 | 108 |
| Cutoff Quartile 2 | 260000 | 260000 | 262000 | 260000 | 260000 | 262000 | 260000 | 260000 | 262000 |
| Sensitivity | 88% | 89% | 90% | 88% | 89% | 90% | 88% | 89% | 90% |
| Specificity | 38% | 38% | 31% | 39% | 38% | 32% | 39% | 38% | 32% |
| Cutoff Quartile 3 | 437000 | 437000 | 437000 | 437000 | 437000 | 437000 | 437000 | 437000 | 437000 |
| Sensitivity | 63% | 65% | 66% | 63% | 65% | 65% | 63% | 66% | 64% |
| Specificity | 63% | 64% | 57% | 63% | 64% | 56% | 64% | 65% | 57% |
| Cutoff Quartile 4 | 707000 | 707000 | 708000 | 707000 | 707000 | 708000 | 707000 | 707000 | 708000 |
| Sensitivity | 37% | 37% | 41% | 37% | 37% | 41% | 37% | 38% | 42% |
| Specificity | 86% | 86% | 82% | 87% | 86% | 82% | 87% | 87% | 83% |
| OR Quartile 2 | 4.57 | 4.74 | 4.08 | 4.81 | 4.82 | 4.15 | 4.73 | 4.90 | 4.20 |
| p Value | 1.9E−7 | 1.5E−7 | 1.1E−4 | 7.7E−8 | 1.1E−7 | 8.8E−5 | 7.2E−8 | 8.3E−8 | 4.1E−5 |
| Lower limit of 95% CI | 2.58 | 2.65 | 2.00 | 2.71 | 2.70 | 2.04 | 2.69 | 2.74 | 2.12 |
| Upper limit of 95% CI | 8.10 | 8.47 | 8.30 | 8.53 | 8.62 | 8.45 | 8.32 | 8.77 | 8.33 |
| OR Quartile 3 | 2.90 | 3.32 | 2.50 | 2.98 | 3.40 | 2.41 | 2.98 | 3.49 | 2.32 |
| p Value | 3.4E−6 | 2.2E−7 | 2.6E−4 | 2.0E−6 | 1.3E−7 | 4.2E−4 | 2.0E−6 | 7.1E−8 | 5.4E−4 |
| Lower limit of 95% CI | 1.85 | 2.11 | 1.53 | 1.90 | 2.16 | 1.48 | 1.90 | 2.22 | 1.44 |
| Upper limit of 95% CI | 4.54 | 5.22 | 4.08 | 4.67 | 5.36 | 3.92 | 4.67 | 5.51 | 3.73 |
| OR Quartile 4 | 3.60 | 3.78 | 3.19 | 3.70 | 3.72 | 3.12 | 4.07 | 3.95 | 3.47 |
| p Value | 4.1E−6 | 1.7E−6 | 1.4E−5 | 3.2E−6 | 2.3E−6 | 2.0E−5 | 1.1E−6 | 1.0E−6 | 2.8E−6 |

TABLE 7.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.09 | 2.19 | 1.89 | 2.13 | 2.16 | 1.85 | 2.31 | 2.28 | 2.06 |
| Upper limit of 95% CI | 6.20 | 6.53 | 5.39 | 6.41 | 6.41 | 5.26 | 7.14 | 6.86 | 5.85 |

TABLE 7.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 358000 | 578000 | 350000 | 578000 | 342000 | 582000 |
| Average | 428000 | 607000 | 426000 | 607000 | 424000 | 609000 |
| Stdev | 246000 | 288000 | 246000 | 286000 | 244000 | 286000 |
| p (t-test) | | 5.2E−9 | | 4.0E−9 | | 1.4E−9 |
| Min | 13600 | 105000 | 13600 | 105000 | 13600 | 105000 |
| Max | 1040000 | 1120000 | 1040000 | 1120000 | 1040000 | 1120000 |
| n (Patient) | 204 | 123 | 202 | 125 | 201 | 126 |
| | sCr only | | | | | |
| Median | 328000 | 578000 | 328000 | 578000 | 328000 | 578000 |
| Average | 412000 | 603000 | 412000 | 603000 | 412000 | 603000 |
| Stdev | 242000 | 281000 | 242000 | 281000 | 242000 | 281000 |
| p (t-test) | | 1.8E−10 | | 1.8E−10 | | 1.8E−10 |
| Min | 13600 | 105000 | 13600 | 105000 | 13600 | 105000 |
| Max | 1040000 | 1120000 | 1040000 | 1120000 | 1040000 | 1120000 |
| n (Patient) | 184 | 143 | 184 | 143 | 184 | 143 |
| | UO only | | | | | |
| Median | 377000 | 586000 | 375000 | 582000 | 371000 | 590000 |
| Average | 439000 | 619000 | 439000 | 617000 | 436000 | 620000 |
| Stdev | 247000 | 295000 | 247000 | 295000 | 246000 | 293000 |
| p (t-test) | | 2.0E−8 | | 2.8E−8 | | 6.1E−9 |
| Min | 13600 | 135000 | 13600 | 135000 | 13600 | 135000 |
| Max | 1040000 | 1120000 | 1040000 | 1120000 | 1040000 | 1120000 |
| n (Patient) | 220 | 105 | 219 | 106 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.70 | 0.68 | 0.69 | 0.70 | 0.68 | 0.69 | 0.70 | 0.69 |
| SE | 0.031 | 0.030 | 0.033 | 0.031 | 0.030 | 0.033 | 0.031 | 0.030 | 0.032 |
| p Value | 3.2E−9 | 1.9E−11 | 3.8E−8 | 1.8E−9 | 1.9E−11 | 4.5E−8 | 5.7E−10 | 1.9E−11 | 8.2E−9 |
| nCohort Recovered | 204 | 184 | 220 | 202 | 184 | 219 | 201 | 184 | 217 |
| nCohort Non-recovered | 123 | 143 | 105 | 125 | 143 | 106 | 126 | 143 | 108 |
| Cutoff Quartile 2 | 260000 | 260000 | 262000 | 260000 | 260000 | 262000 | 260000 | 260000 | 262000 |
| Sensitivity | 89% | 88% | 89% | 89% | 88% | 89% | 89% | 88% | 89% |
| Specificity | 33% | 35% | 31% | 34% | 35% | 32% | 34% | 35% | 32% |
| Cutoff Quartile 3 | 437000 | 437000 | 437000 | 437000 | 437000 | 437000 | 437000 | 437000 | 437000 |
| Sensitivity | 64% | 64% | 65% | 64% | 64% | 64% | 64% | 64% | 65% |
| Specificity | 58% | 61% | 57% | 58% | 61% | 57% | 59% | 61% | 57% |
| Cutoff Quartile 4 | 707000 | 707000 | 708000 | 707000 | 707000 | 708000 | 707000 | 707000 | 708000 |
| Sensitivity | 39% | 38% | 40% | 39% | 38% | 40% | 40% | 38% | 41% |
| Specificity | 83% | 85% | 82% | 84% | 85% | 82% | 84% | 85% | 82% |
| OR Quartile 2 | 3.89 | 4.05 | 3.54 | 4.02 | 4.05 | 3.60 | 4.09 | 4.05 | 3.73 |
| p Value | 2.2E−5 | 3.4E−6 | 1.9E−4 | 1.4E−5 | 3.4E−6 | 1.6E−4 | 1.1E−5 | 3.4E−6 | 1.0E−4 |
| Lower limit of 95% CI | 2.08 | 2.24 | 1.82 | 2.15 | 2.24 | 1.85 | 2.18 | 2.24 | 1.92 |

TABLE 7.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 7.29 | 7.30 | 6.89 | 7.54 | 7.30 | 7.01 | 7.66 | 7.30 | 7.25 |
| OR Quartile 3 | 2.51 | 2.81 | 2.42 | 2.50 | 2.81 | 2.34 | 2.56 | 2.81 | 2.46 |
| p Value | 9.2E−5 | 7.8E−6 | 3.2E−4 | 9.7E−5 | 7.8E−6 | 5.1E−4 | 6.2E−5 | 7.8E−6 | 2.3E−4 |
| Lower limit of 95% CI | 1.58 | 1.78 | 1.49 | 1.58 | 1.78 | 1.45 | 1.62 | 1.78 | 1.52 |
| Upper limit of 95% CI | 3.99 | 4.41 | 3.91 | 3.96 | 4.41 | 3.77 | 4.05 | 4.41 | 3.96 |
| OR Quartile 4 | 3.20 | 3.63 | 3.00 | 3.30 | 3.63 | 2.94 | 3.47 | 3.63 | 3.24 |
| p Value | 1.0E−5 | 1.8E−6 | 3.4E−5 | 6.1E−6 | 1.8E−6 | 4.7E−5 | 2.6E−6 | 1.8E−6 | 9.3E−6 |
| Lower limit of 95% CI | 1.91 | 2.14 | 1.78 | 1.97 | 2.14 | 1.75 | 2.07 | 2.14 | 1.93 |
| Upper limit of 95% CI | 5.36 | 6.17 | 5.04 | 5.54 | 6.17 | 4.93 | 5.84 | 6.17 | 5.44 |

Example 8. Use of Metalloproteinase Inhibitor 1 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 1 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 8.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 10700 | 28600 | 10700 | 33800 | 11000 | 31700 |
| Average | 19900 | 45200 | 20100 | 48800 | 22000 | 48700 |
| Stdev | 25000 | 40000 | 25500 | 40200 | 27800 | 39800 |
| p (t-test) | | 2.2E−11 | | 2.4E−13 | | 1.7E−10 |
| Min | 297 | 873 | 297 | 873 | 297 | 873 |
| Max | 127000 | 146000 | 127000 | 146000 | 127000 | 146000 |
| n (Patient) | 205 | 112 | 221 | 96 | 236 | 81 |
| sCr only | | | | | | |
| Median | 11000 | 28600 | 10900 | 31500 | 11200 | 31500 |
| Average | 20000 | 45400 | 20300 | 48800 | 22200 | 47500 |
| Stdev | 24700 | 40600 | 24900 | 41400 | 27400 | 41100 |
| p (t-test) | | 2.8E−11 | | 6.1E−13 | | 1.2E−9 |
| Min | 297 | 873 | 297 | 873 | 297 | 873 |
| Max | 127000 | 146000 | 127000 | 146000 | 127000 | 146000 |
| n (Patient) | 208 | 108 | 223 | 93 | 235 | 81 |
| UO only | | | | | | |
| Median | 12400 | 25100 | 12500 | 28600 | 12700 | 30000 |
| Average | 26300 | 47200 | 26300 | 48500 | 26300 | 49300 |
| Stdev | 31200 | 42100 | 31100 | 43100 | 31000 | 43400 |

TABLE 8.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

|  | | | | | | | | | |
|---|---|---|---|---|---|---|---|---|---|
| p (t-test) | | 2.0E−4 | | | 1.3E−4 | | | 8.7E−5 | |
| Min | 297 | 873 | | 297 | 873 | | 297 | 873 | |
| Max | 146000 | 140000 | | 146000 | 140000 | | 146000 | 140000 | |
| n (Patient) | 275 | 40 | | 278 | 37 | | 279 | 36 | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.70 | 0.67 | 0.74 | 0.73 | 0.67 | 0.74 | 0.71 | 0.67 |
| SE | 0.031 | 0.032 | 0.049 | 0.032 | 0.033 | 0.051 | 0.035 | 0.036 | 0.052 |
| p Value | 9.6E−12 | 2.8E−10 | 5.0E−4 | 2.0E−14 | 3.4E−12 | 7.3E−4 | 1.0E−11 | 5.7E−9 | 7.4E−4 |
| nCohort Non-persistent | 205 | 208 | 275 | 221 | 223 | 278 | 236 | 235 | 279 |
| nCohort Persistent | 112 | 108 | 40 | 96 | 93 | 37 | 81 | 81 | 36 |
| Cutoff Quartile 2 | 6030 | 6020 | 6080 | 6030 | 6020 | 6080 | 6030 | 6020 | 6080 |
| Sensitivity | 89% | 88% | 92% | 92% | 90% | 92% | 93% | 90% | 92% |
| Specificity | 33% | 32% | 28% | 32% | 31% | 27% | 31% | 30% | 27% |
| Cutoff Quartile 3 | 14200 | 14100 | 14200 | 14200 | 14100 | 14200 | 14200 | 14100 | 14200 |
| Sensitivity | 71% | 69% | 70% | 76% | 74% | 70% | 78% | 74% | 69% |
| Specificity | 61% | 60% | 53% | 61% | 60% | 53% | 59% | 58% | 52% |
| Cutoff Quartile 4 | 35900 | 35400 | 36300 | 35900 | 35400 | 36300 | 35900 | 35400 | 36300 |
| Sensitivity | 46% | 45% | 45% | 50% | 48% | 46% | 49% | 47% | 47% |
| Specificity | 86% | 86% | 78% | 86% | 85% | 78% | 83% | 83% | 78% |
| OR Quartile 2 | 4.05 | 3.40 | 4.71 | 5.21 | 4.27 | 4.26 | 5.60 | 3.95 | 4.12 |
| p Value | 3.9E−5 | 2.2E−4 | 0.012 | 3.1E−5 | 1.3E−4 | 0.019 | 1.2E−4 | 5.7E−4 | 0.022 |
| Lower limit of 95% CI | 2.08 | 1.77 | 1.41 | 2.39 | 2.03 | 1.27 | 2.33 | 1.81 | 1.23 |
| Upper limit of 95% CI | 7.88 | 6.50 | 15.7 | 11.3 | 8.98 | 14.3 | 13.4 | 8.63 | 13.8 |
| OR Quartile 3 | 3.74 | 3.42 | 2.60 | 4.98 | 4.33 | 2.61 | 5.10 | 3.99 | 2.49 |
| p Value | 1.6E−7 | 1.1E−6 | 0.0089 | 6.0E−9 | 8.5E−8 | 0.011 | 4.6E−8 | 1.3E−6 | 0.016 |
| Lower limit of 95% CI | 2.28 | 2.09 | 1.27 | 2.90 | 2.53 | 1.24 | 2.84 | 2.28 | 1.18 |
| Upper limit of 95% CI | 6.13 | 5.61 | 5.33 | 8.56 | 7.40 | 5.50 | 9.16 | 7.00 | 5.27 |
| OR Quartile 4 | 5.07 | 4.93 | 2.87 | 5.91 | 5.21 | 2.96 | 4.78 | 4.18 | 3.13 |
| p Value | 4.0E−9 | 7.8E−9 | 0.0025 | 2.1E−10 | 3.2E−9 | 0.0026 | 2.9E−8 | 3.7E−7 | 0.0017 |
| Lower limit of 95% CI | 2.95 | 2.87 | 1.45 | 3.41 | 3.02 | 1.46 | 2.75 | 2.41 | 1.54 |
| Upper limit of 95% CI | 8.72 | 8.47 | 5.69 | 10.2 | 9.00 | 6.00 | 8.31 | 7.26 | 6.39 |

TABLE 8.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 10100 | 23400 | 10600 | 31500 | 10800 | 31500 |
| Average | 18900 | 42900 | 18900 | 46800 | 20700 | 46900 |
| Stdev | 23700 | 39500 | 23400 | 40500 | 26300 | 39900 |
| p (t-test) | | 7.7E−11 | | 9.3E−14 | | 2.4E−11 |
| Min | 419 | 297 | 297 | 399 | 297 | 399 |
| Max | 121000 | 146000 | 121000 | 146000 | 121000 | 146000 |
| n (Patient) | 186 | 131 | 204 | 113 | 219 | 98 |
| | sCr only | | | | | |
| Median | 11000 | 22400 | 10900 | 29300 | 11000 | 27300 |
| Average | 19500 | 42800 | 19400 | 46000 | 21400 | 44900 |

TABLE 8.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 23700 | 40400 | 23600 | 41200 | 26500 | 40600 |
| p (t-test) | | 4.0E−10 | | 2.3E−12 | | 2.6E−9 |
| Min | 419 | 297 | 297 | 399 | 297 | 399 |
| Max | 121000 | 146000 | 121000 | 146000 | 121000 | 146000 |
| n (Patient) | 192 | 124 | 206 | 110 | 218 | 98 |

UO only

| | | | | | | |
|---|---|---|---|---|---|---|
| Median | 12400 | 23400 | 12400 | 23400 | 12400 | 24700 |
| Average | 26000 | 42000 | 26000 | 42700 | 26000 | 43100 |
| Stdev | 31400 | 38800 | 31200 | 39800 | 31200 | 40000 |
| p (t-test) | | 8.4E−4 | | 7.3E−4 | | 5.6E−4 |
| Min | 297 | 399 | 297 | 399 | 297 | 399 |
| Max | 146000 | 140000 | 146000 | 140000 | 146000 | 140000 |
| n (Patient) | 256 | 59 | 260 | 55 | 261 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.65 | 0.73 | 0.71 | 0.65 | 0.73 | 0.70 | 0.65 |
| SE | 0.030 | 0.031 | 0.042 | 0.031 | 0.032 | 0.043 | 0.032 | 0.033 | 0.044 |
| p Value | 2.2E−11 | 7.7E−9 | 3.0E−4 | 4.2E−14 | 2.8E−11 | 6.8E−4 | 1.0E−12 | 3.7E−9 | 7.2E−4 |
| nCohort Non-persistent | 186 | 192 | 256 | 204 | 206 | 260 | 219 | 218 | 261 |
| nCohort Persistent | 131 | 124 | 59 | 113 | 110 | 55 | 98 | 98 | 54 |
| Cutoff Quartile 2 | 6030 | 6020 | 6080 | 6030 | 6020 | 6080 | 6030 | 6020 | 6080 |
| Sensitivity | 88% | 86% | 93% | 90% | 89% | 93% | 93% | 91% | 93% |
| Specificity | 34% | 32% | 29% | 33% | 33% | 29% | 33% | 32% | 29% |
| Cutoff Quartile 3 | 14200 | 14100 | 14200 | 14200 | 14100 | 14200 | 14200 | 14100 | 14200 |
| Sensitivity | 68% | 66% | 68% | 73% | 70% | 67% | 74% | 70% | 67% |
| Specificity | 62% | 60% | 54% | 62% | 61% | 53% | 61% | 59% | 53% |
| Cutoff Quartile 4 | 35900 | 35400 | 36300 | 35900 | 35400 | 36300 | 35900 | 35400 | 36300 |
| Sensitivity | 43% | 42% | 39% | 48% | 45% | 40% | 48% | 44% | 41% |
| Specificity | 87% | 86% | 78% | 87% | 86% | 78% | 85% | 83% | 78% |
| OR Quartile 2 | 3.68 | 3.00 | 5.70 | 4.64 | 3.94 | 5.17 | 6.37 | 4.68 | 5.04 |
| p Value | 2.4E−5 | 2.9E−4 | 0.0012 | 1.2E−5 | 5.6E−5 | 0.0022 | 9.4E−6 | 4.6E−5 | 0.0026 |
| Lower limit of 95% CI | 2.01 | 1.66 | 1.99 | 2.33 | 2.02 | 1.80 | 2.81 | 2.23 | 1.76 |
| Upper limit of 95% CI | 6.74 | 5.44 | 16.3 | 9.21 | 7.67 | 14.8 | 14.4 | 9.82 | 14.4 |
| OR Quartile 3 | 3.51 | 2.98 | 2.46 | 4.36 | 3.60 | 2.36 | 4.52 | 3.45 | 2.28 |
| p Value | 1.8E−7 | 5.6E−6 | 0.0032 | 8.2E−9 | 3.8E−7 | 0.0061 | 2.3E−8 | 2.0E−6 | 0.0088 |
| Lower limit of 95% CI | 2.19 | 1.86 | 1.35 | 2.64 | 2.20 | 1.28 | 2.66 | 2.07 | 1.23 |
| Upper limit of 95% CI | 5.63 | 4.77 | 4.48 | 7.20 | 5.90 | 4.36 | 7.66 | 5.75 | 4.22 |
| OR Quartile 4 | 5.04 | 4.41 | 2.28 | 6.27 | 5.09 | 2.37 | 5.19 | 3.95 | 2.46 |
| p Value | 8.7E−9 | 7.5E−8 | 0.0072 | 7.7E−11 | 4.4E−9 | 0.0058 | 2.6E−9 | 5.0E−7 | 0.0042 |
| Lower limit of 95% CI | 2.90 | 2.57 | 1.25 | 3.61 | 2.95 | 1.28 | 3.02 | 2.31 | 1.33 |
| Upper limit of 95% CI | 8.74 | 7.58 | 4.16 | 10.9 | 8.76 | 4.39 | 8.93 | 6.75 | 4.56 |

TABLE 8.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 9450 | 22000 | 9580 | 28600 | 9980 | 27300 |
| Average | 18500 | 41600 | 18300 | 44600 | 20200 | 44700 |
| Stdev | 23100 | 39200 | 22800 | 39900 | 25200 | 40100 |
| p (t-test) | | 2.5E−10 | | 9.6E−13 | | 1.2E−10 |
| Min | 419 | 297 | 297 | 399 | 297 | 399 |
| Max | 116000 | 146000 | 116000 | 146000 | 120000 | 146000 |
| n (Patient) | 175 | 142 | 190 | 127 | 205 | 112 |
| sCr only | | | | | | |
| Median | 10600 | 22000 | 9980 | 28600 | 10800 | 22700 |
| Average | 18900 | 41900 | 18700 | 44700 | 20600 | 44200 |
| Stdev | 23000 | 40000 | 22800 | 40600 | 25200 | 40800 |
| p (t-test) | | 4.4E−10 | | 3.1E−12 | | 8.4E−10 |
| Min | 419 | 297 | 297 | 399 | 297 | 399 |
| Max | 116000 | 146000 | 116000 | 146000 | 120000 | 146000 |
| n (Patient) | 182 | 134 | 195 | 121 | 208 | 108 |
| UO only | | | | | | |
| Median | 12400 | 21900 | 12400 | 22000 | 12400 | 22000 |
| Average | 25800 | 40300 | 25800 | 41300 | 25800 | 41300 |
| Stdev | 31100 | 38700 | 30900 | 39700 | 30900 | 39700 |
| p (t-test) | | 0.0014 | | 8.6E−4 | | 8.6E−4 |
| Min | 297 | 399 | 297 | 399 | 297 | 399 |
| Max | 146000 | 140000 | 146000 | 140000 | 146000 | 140000 |
| n (Patient) | 246 | 69 | 251 | 64 | 251 | 64 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.69 | 0.64 | 0.73 | 0.71 | 0.64 | 0.72 | 0.70 | 0.64 |
| SE | 0.030 | 0.031 | 0.039 | 0.030 | 0.031 | 0.041 | 0.031 | 0.032 | 0.041 |
| p Value | 1.2E−11 | 1.2E−9 | 5.0E−4 | 1.8E−14 | 3.1E−12 | 8.1E−4 | 6.4E−12 | 8.5E−10 | 8.1E−4 |
| nCohort Non-persistent | 175 | 182 | 246 | 190 | 195 | 251 | 205 | 208 | 251 |
| nCohort Persistent | 142 | 134 | 69 | 127 | 121 | 64 | 112 | 108 | 64 |
| Cutoff Quartile 2 | 6030 | 6020 | 6080 | 6030 | 6020 | 6080 | 6030 | 6020 | 6080 |
| Sensitivity | 87% | 86% | 91% | 90% | 88% | 91% | 91% | 90% | 91% |
| Specificity | 35% | 33% | 30% | 35% | 33% | 29% | 34% | 33% | 29% |
| Cutoff Quartile 3 | 14200 | 14100 | 14200 | 14200 | 14100 | 14200 | 14200 | 14100 | 14200 |
| Sensitivity | 67% | 66% | 64% | 70% | 69% | 64% | 71% | 69% | 64% |
| Specificity | 63% | 62% | 54% | 63% | 62% | 53% | 61% | 60% | 53% |
| Cutoff Quartile 4 | 35900 | 35400 | 36300 | 35900 | 35400 | 36300 | 35900 | 35400 | 36300 |
| Sensitivity | 40% | 40% | 36% | 44% | 44% | 38% | 44% | 43% | 38% |
| Specificity | 87% | 86% | 78% | 87% | 87% | 78% | 85% | 84% | 78% |
| OR Quartile 2 | 3.69 | 2.98 | 4.43 | 4.67 | 3.82 | 3.96 | 5.18 | 4.28 | 3.96 |
| p Value | 1.2E−5 | 2.0E−4 | 9.3E−4 | 3.0E−6 | 3.2E−5 | 0.0022 | 5.9E−6 | 3.4E−5 | 0.0022 |
| Lower limit of 95% CI | 2.06 | 1.67 | 1.84 | 2.44 | 2.03 | 1.64 | 2.54 | 2.15 | 1.64 |
| Upper limit of 95% CI | 6.61 | 5.29 | 10.7 | 8.91 | 7.19 | 9.59 | 10.5 | 8.52 | 9.59 |
| OR Quartile 3 | 3.51 | 3.24 | 2.04 | 4.02 | 3.71 | 2.04 | 3.74 | 3.42 | 2.04 |
| p Value | 1.3E−7 | 8.2E−7 | 0.011 | 1.5E−8 | 1.0E−7 | 0.014 | 1.6E−7 | 1.1E−6 | 0.014 |
| Lower limit of 95% CI | 2.20 | 2.03 | 1.17 | 2.48 | 2.29 | 1.16 | 2.28 | 2.09 | 1.16 |
| Upper limit of 95% CI | 5.58 | 5.17 | 3.54 | 6.49 | 6.02 | 3.60 | 6.13 | 5.61 | 3.60 |
| OR Quartile 4 | 4.43 | 4.24 | 2.02 | 5.46 | 5.07 | 2.14 | 4.37 | 3.93 | 2.14 |
| p Value | 1.3E−7 | 2.1E−7 | 0.017 | 1.8E−9 | 6.2E−9 | 0.011 | 6.4E−8 | 4.7E−7 | 0.011 |

TABLE 8.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.55 | 2.46 | 1.14 | 3.14 | 2.93 | 1.19 | 2.56 | 2.31 | 1.19 |
| Upper limit of 95% CI | 7.70 | 7.31 | 3.59 | 9.48 | 8.76 | 3.85 | 7.45 | 6.70 | 3.85 |

TABLE 8.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 9450 | 22000 | 9600 | 28600 | 9980 | 24700 |
| Average | 18300 | 41500 | 18400 | 44300 | 19800 | 44400 |
| Stdev | 22900 | 39100 | 22800 | 39900 | 24400 | 40500 |
| p (t-test) | | 2.0E−10 | | 2.1E−12 | | 6.9E−11 |
| Min | 419 | 297 | 297 | 399 | 297 | 399 |
| Max | 116000 | 146000 | 116000 | 146000 | 116000 | 146000 |
| n (Patient) | 173 | 144 | 189 | 128 | 201 | 116 |
| | sCr only | | | | | |
| Median | 10800 | 22000 | 10200 | 27300 | 10800 | 22700 |
| Average | 19100 | 41400 | 18800 | 43900 | 20200 | 44100 |
| Stdev | 23100 | 39900 | 22900 | 40400 | 24400 | 41100 |
| p (t-test) | | 1.4E−9 | | 1.3E−11 | | 3.8E−10 |
| Min | 419 | 297 | 297 | 399 | 297 | 399 |
| Max | 116000 | 146000 | 116000 | 146000 | 116000 | 146000 |
| n (Patient) | 180 | 136 | 192 | 124 | 204 | 112 |
| | UO only | | | | | |
| Median | 12100 | 22000 | 12100 | 22000 | 12100 | 22000 |
| Average | 25500 | 39700 | 25700 | 40200 | 25700 | 40200 |
| Stdev | 31400 | 37400 | 31200 | 38400 | 31200 | 38400 |
| p (t-test) | | 0.0012 | | 0.0013 | | 0.0013 |
| Min | 297 | 399 | 297 | 399 | 297 | 399 |
| Max | 146000 | 140000 | 146000 | 140000 | 146000 | 140000 |
| n (Patient) | 239 | 76 | 245 | 70 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.65 | 0.72 | 0.71 | 0.64 | 0.71 | 0.70 | 0.64 |
| SE | 0.030 | 0.031 | 0.038 | 0.030 | 0.031 | 0.039 | 0.031 | 0.032 | 0.039 |
| p Value | 1.4E−11 | 6.5E−9 | 1.3E−4 | 1.1E−13 | 1.4E−11 | 3.9E−4 | 1.1E−11 | 8.0E−10 | 3.9E−4 |
| nCohort Non-persistent | 173 | 180 | 239 | 189 | 192 | 245 | 201 | 204 | 245 |
| nCohort Persistent | 144 | 136 | 76 | 128 | 124 | 70 | 116 | 112 | 70 |
| Cutoff Quartile 2 | 6030 | 6020 | 6080 | 6030 | 6020 | 6080 | 6030 | 6020 | 6080 |
| Sensitivity | 87% | 85% | 91% | 89% | 88% | 90% | 91% | 89% | 90% |
| Specificity | 35% | 33% | 30% | 34% | 33% | 29% | 34% | 33% | 29% |
| Cutoff Quartile 3 | 14200 | 14100 | 14200 | 14200 | 14100 | 14200 | 14200 | 14100 | 14200 |
| Sensitivity | 67% | 65% | 66% | 70% | 69% | 66% | 70% | 69% | 66% |
| Specificity | 64% | 62% | 55% | 63% | 62% | 54% | 61% | 60% | 54% |
| Cutoff Quartile 4 | 35900 | 35400 | 36300 | 35900 | 35400 | 36300 | 35900 | 35400 | 36300 |
| Sensitivity | 40% | 40% | 38% | 44% | 43% | 39% | 43% | 42% | 39% |
| Specificity | 87% | 86% | 79% | 87% | 86% | 79% | 85% | 84% | 79% |
| OR Quartile 2 | 3.49 | 2.83 | 4.25 | 4.27 | 3.63 | 3.75 | 4.88 | 4.08 | 3.75 |
| p Value | 2.0E−5 | 3.3E−4 | 5.9E−4 | 6.6E−6 | 4.2E−5 | 0.0018 | 6.0E−6 | 3.6E−5 | 0.0018 |
| Lower limit of 95% CI | 1.97 | 1.60 | 1.86 | 2.27 | 1.96 | 1.64 | 2.46 | 2.09 | 1.64 |

TABLE 8.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 6.21 | 4.99 | 9.70 | 8.02 | 6.74 | 8.57 | 9.70 | 7.93 | 8.57 |
| OR Quartile 3 | 3.49 | 3.05 | 2.33 | 3.88 | 3.55 | 2.28 | 3.65 | 3.34 | 2.28 |
| p Value | 1.3E−7 | 2.5E−6 | 0.0020 | 2.8E−8 | 2.0E−7 | 0.0036 | 1.9E−7 | 1.3E−6 | 0.0036 |
| Lower limit of 95% CI | 2.19 | 1.92 | 1.36 | 2.40 | 2.20 | 1.31 | 2.24 | 2.05 | 1.31 |
| Upper limit of 95% CI | 5.56 | 4.84 | 3.99 | 6.26 | 5.73 | 3.96 | 5.94 | 5.44 | 3.96 |
| OR Quartile 4 | 4.63 | 4.08 | 2.33 | 5.35 | 4.77 | 2.33 | 4.32 | 3.89 | 2.33 |
| p Value | 7.2E−8 | 4.1E−7 | 0.0029 | 2.7E−9 | 2.0E−8 | 0.0036 | 8.1E−8 | 5.7E−7 | 0.0036 |
| Lower limit of 95% CI | 2.65 | 2.37 | 1.33 | 3.08 | 2.76 | 1.32 | 2.53 | 2.28 | 1.32 |
| Upper limit of 95% CI | 8.08 | 7.04 | 4.08 | 9.29 | 8.22 | 4.12 | 7.37 | 6.62 | 4.12 |

TABLE 8.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 9450 | 22000 | 9510 | 28600 | 9680 | 24700 |
| Average | 17900 | 41300 | 17700 | 44200 | 19600 | 43900 |
| Stdev | 22400 | 39000 | 22200 | 39600 | 24300 | 40100 |
| p (t-test) | | 1.5E−10 | | 4.6E−13 | | 8.4E−11 |
| Min | 419 | 297 | 297 | 399 | 297 | 399 |
| Max | 116000 | 146000 | 116000 | 146000 | 116000 | 146000 |
| n (Patient) | 169 | 148 | 184 | 133 | 197 | 120 |
| | sCr only | | | | | |
| Median | 10800 | 22000 | 10200 | 27300 | 10800 | 22700 |
| Average | 18700 | 41200 | 18500 | 43600 | 20000 | 43700 |
| Stdev | 22700 | 39800 | 22600 | 40300 | 24100 | 40900 |
| p (t-test) | | 1.0E−9 | | 1.0E−11 | | 3.2E−10 |
| Min | 419 | 297 | 297 | 399 | 297 | 399 |
| Max | 116000 | 146000 | 116000 | 146000 | 116000 | 146000 |
| n (Patient) | 176 | 140 | 188 | 128 | 200 | 116 |
| | UO only | | | | | |
| Median | 11900 | 23400 | 11900 | 22700 | 11900 | 22700 |
| Average | 24400 | 42200 | 24500 | 42400 | 24500 | 42400 |
| Stdev | 29800 | 39400 | 29800 | 39900 | 29800 | 39900 |
| p (t-test) | | 2.9E−5 | | 3.3E−5 | | 3.3E−5 |
| Min | 297 | 399 | 297 | 399 | 297 | 399 |
| Max | 127000 | 146000 | 127000 | 146000 | 127000 | 146000 |
| n (Patient) | 234 | 81 | 237 | 78 | 237 | 78 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.67 | 0.73 | 0.71 | 0.66 | 0.71 | 0.70 | 0.66 |
| SE | 0.030 | 0.031 | 0.037 | 0.029 | 0.030 | 0.037 | 0.031 | 0.032 | 0.037 |
| p Value | 1.4E−11 | 4.0E−9 | 5.2E−6 | 8.0E−15 | 8.8E−12 | 1.3E−5 | 5.9E−12 | 5.9E−10 | 1.3E−5 |
| nCohort Non-persistent | 169 | 176 | 234 | 184 | 188 | 237 | 197 | 200 | 237 |
| nCohort Persistent | 148 | 140 | 81 | 133 | 128 | 78 | 120 | 116 | 78 |
| Cutoff Quartile 2 | 6030 | 6020 | 6080 | 6030 | 6020 | 6080 | 6030 | 6020 | 6080 |
| Sensitivity | 86% | 86% | 91% | 89% | 88% | 91% | 90% | 90% | 91% |
| Specificity | 35% | 34% | 31% | 35% | 34% | 30% | 34% | 34% | 30% |

TABLE 8.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 3 | 14200 | 14100 | 14200 | 14200 | 14100 | 14200 | 14200 | 14100 | 14200 |
| Sensitivity | 66% | 65% | 68% | 70% | 68% | 68% | 70% | 68% | 68% |
| Specificity | 64% | 62% | 56% | 64% | 62% | 56% | 62% | 60% | 56% |
| Cutoff Quartile 4 | 35900 | 35400 | 36300 | 35900 | 35400 | 36300 | 35900 | 35400 | 36300 |
| Sensitivity | 40% | 39% | 40% | 44% | 42% | 40% | 42% | 41% | 40% |
| Specificity | 88% | 86% | 80% | 88% | 87% | 80% | 85% | 84% | 80% |
| OR Quartile 2 | 3.43 | 3.03 | 4.70 | 4.20 | 3.89 | 4.43 | 4.64 | 4.37 | 4.43 |
| p Value | 2.1E−5 | 1.3E−4 | 2.3E−4 | 5.2E−6 | 1.6E−5 | 4.1E−4 | 6.2E−6 | 1.4E−5 | 4.1E−4 |
| Lower limit of 95% CI | 1.95 | 1.72 | 2.06 | 2.26 | 2.10 | 1.94 | 2.38 | 2.24 | 1.94 |
| Upper limit of 95% CI | 6.06 | 5.34 | 10.7 | 7.78 | 7.21 | 10.1 | 9.02 | 8.50 | 10.1 |
| OR Quartile 3 | 3.47 | 3.02 | 2.69 | 4.16 | 3.50 | 2.67 | 3.80 | 3.27 | 2.67 |
| p Value | 1.4E−7 | 2.7E−6 | 2.7E−4 | 5.0E−9 | 2.3E−7 | 3.8E−4 | 7.0E−8 | 1.5E−6 | 3.8E−4 |
| Lower limit of 95% CI | 2.18 | 1.90 | 1.58 | 2.58 | 2.18 | 1.55 | 2.34 | 2.02 | 1.55 |
| Upper limit of 95% CI | 5.51 | 4.79 | 4.59 | 6.70 | 5.62 | 4.57 | 6.16 | 5.30 | 4.57 |
| OR Quartile 4 | 4.67 | 4.10 | 2.60 | 5.69 | 4.76 | 2.60 | 4.28 | 3.85 | 2.60 |
| p Value | 8.1E−8 | 4.6E−7 | 6.4E−4 | 1.3E−9 | 2.4E−8 | 7.2E−4 | 1.0E−7 | 6.9E−7 | 7.2E−4 |
| Lower limit of 95% CI | 2.66 | 2.37 | 1.50 | 3.25 | 2.75 | 1.49 | 2.51 | 2.26 | 1.49 |
| Upper limit of 95% CI | 8.21 | 7.09 | 4.50 | 9.99 | 8.23 | 4.52 | 7.31 | 6.55 | 4.52 |

TABLE 8.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 350000 | 595000 | 365000 | 595000 | 377000 | 605000 |
| Average | 435000 | 599000 | 444000 | 605000 | 451000 | 613000 |
| Stdev | 256000 | 279000 | 261000 | 277000 | 260000 | 285000 |
| p (t-test) | | 1.2E−7 | | 5.6E−7 | | 1.7E−6 |
| Min | 13600 | 105000 | 13600 | 135000 | 13600 | 135000 |
| Max | 1040000 | 1120000 | 1040000 | 1120000 | 1040000 | 1120000 |
| n (Patient) | 206 | 121 | 222 | 105 | 238 | 89 |
| *sCr only* | | | | | | |
| Median | 350000 | 596000 | 359000 | 594000 | 375000 | 590000 |
| Average | 432000 | 602000 | 443000 | 604000 | 450000 | 607000 |
| Stdev | 255000 | 276000 | 261000 | 273000 | 261000 | 278000 |
| p (t-test) | | 3.8E−8 | | 5.1E−7 | | 2.9E−6 |
| Min | 13600 | 105000 | 13600 | 151000 | 13600 | 154000 |
| Max | 1040000 | 1120000 | 1040000 | 1120000 | 1040000 | 1120000 |
| n (Patient) | 208 | 118 | 223 | 103 | 236 | 90 |
| *UO only* | | | | | | |
| Median | 404000 | 700000 | 404000 | 765000 | 406000 | 765000 |
| Average | 469000 | 677000 | 468000 | 691000 | 470000 | 693000 |
| Stdev | 264000 | 283000 | 264000 | 283000 | 264000 | 285000 |
| p (t-test) | | 2.3E−6 | | 7.2E−7 | | 1.1E−6 |
| Min | 13600 | 135000 | 13600 | 135000 | 13600 | 135000 |
| Max | 1120000 | 1090000 | 1120000 | 1090000 | 1120000 | 1090000 |
| n (Patient) | 281 | 44 | 283 | 42 | 285 | 40 |

TABLE 8.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.68 | 0.71 | 0.67 | 0.67 | 0.72 | 0.66 | 0.66 | 0.72 |
| SE | 0.032 | 0.032 | 0.046 | 0.033 | 0.033 | 0.047 | 0.035 | 0.035 | 0.048 |
| p Value | 9.0E−8 | 2.5E−8 | 7.4E−6 | 4.5E−7 | 3.3E−7 | 3.0E−6 | 3.2E−6 | 3.1E−6 | 5.1E−6 |
| nCohort Non-persistent | 206 | 208 | 281 | 222 | 223 | 283 | 238 | 236 | 285 |
| nCohort Persistent | 121 | 118 | 44 | 105 | 103 | 42 | 89 | 90 | 40 |
| Cutoff Quartile 2 | 260000 | 260000 | 262000 | 260000 | 260000 | 262000 | 260000 | 260000 | 262000 |
| Sensitivity | 85% | 86% | 91% | 86% | 86% | 90% | 85% | 87% | 90% |
| Specificity | 31% | 31% | 27% | 30% | 30% | 27% | 29% | 30% | 27% |
| Cutoff Quartile 3 | 437000 | 433000 | 437000 | 437000 | 433000 | 437000 | 437000 | 433000 | 437000 |
| Sensitivity | 66% | 68% | 75% | 67% | 67% | 79% | 67% | 68% | 80% |
| Specificity | 59% | 60% | 54% | 58% | 58% | 54% | 56% | 57% | 54% |
| Cutoff Quartile 4 | 707000 | 704000 | 708000 | 707000 | 704000 | 708000 | 707000 | 704000 | 708000 |
| Sensitivity | 39% | 39% | 50% | 39% | 39% | 52% | 42% | 39% | 52% |
| Specificity | 83% | 83% | 79% | 82% | 81% | 79% | 81% | 80% | 79% |
| OR Quartile 2 | 2.58 | 2.70 | 3.77 | 2.59 | 2.79 | 3.55 | 2.39 | 2.74 | 3.33 |
| p Value | 0.0014 | 1.0E−3 | 0.014 | 0.0025 | 0.0015 | 0.019 | 0.0089 | 0.0031 | 0.027 |
| Lower limit of 95% CI | 1.44 | 1.49 | 1.31 | 1.40 | 1.48 | 1.23 | 1.24 | 1.40 | 1.15 |
| Upper limit of 95% CI | 4.61 | 4.88 | 10.9 | 4.81 | 5.24 | 10.3 | 4.58 | 5.35 | 9.67 |
| OR Quartile 3 | 2.83 | 3.17 | 3.48 | 2.72 | 2.79 | 4.32 | 2.67 | 2.76 | 4.70 |
| p Value | 1.3E−5 | 2.0E−6 | 7.0E−4 | 5.2E−5 | 4.1E−5 | 2.1E−4 | 1.7E−4 | 9.9E−5 | 1.8E−4 |
| Lower limit of 95% CI | 1.77 | 1.97 | 1.69 | 1.68 | 1.71 | 1.99 | 1.60 | 1.66 | 2.09 |
| Upper limit of 95% CI | 4.52 | 5.10 | 7.17 | 4.42 | 4.54 | 9.35 | 4.45 | 4.61 | 10.6 |
| OR Quartile 4 | 3.10 | 3.05 | 3.68 | 2.83 | 2.74 | 4.09 | 3.05 | 2.56 | 4.06 |
| p Value | 1.7E−5 | 2.2E−5 | 9.9E−5 | 8.4E−5 | 1.5E−4 | 3.7E−5 | 3.9E−5 | 5.2E−4 | 5.7E−5 |
| Lower limit of 95% CI | 1.85 | 1.82 | 1.91 | 1.68 | 1.63 | 2.09 | 1.79 | 1.51 | 2.05 |
| Upper limit of 95% CI | 5.20 | 5.11 | 7.10 | 4.75 | 4.60 | 7.98 | 5.19 | 4.35 | 8.03 |

TABLE 8.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 338000 | 594000 | 359000 | 586000 | 371000 | 597000 |
| Average | 420000 | 596000 | 433000 | 599000 | 439000 | 609000 |
| Stdev | 248000 | 280000 | 253000 | 282000 | 253000 | 287000 |
| p (t-test) | | 5.0E−9 | | 7.2E−8 | | 1.0E−7 |
| Min | 13600 | 105000 | 13600 | 135000 | 13600 | 135000 |
| Max | 1040000 | 1120000 | 1040000 | 1120000 | 1040000 | 1120000 |
| n (Patient) | 187 | 140 | 204 | 123 | 219 | 108 |
| | sCr only | | | | | |
| Median | 341000 | 590000 | 359000 | 576000 | 371000 | 578000 |
| Average | 424000 | 593000 | 437000 | 589000 | 443000 | 594000 |
| Stdev | 253000 | 275000 | 259000 | 276000 | 259000 | 278000 |
| p (t-test) | | 2.7E−8 | | 1.0E−6 | | 2.0E−6 |
| Min | 13600 | 105000 | 13600 | 151000 | 13600 | 154000 |
| Max | 1040000 | 1120000 | 1040000 | 1120000 | 1040000 | 1120000 |
| n (Patient) | 192 | 134 | 205 | 121 | 217 | 109 |

TABLE 8.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

|  | UO only |  |  |  |  |  |
|---|---|---|---|---|---|---|
| Median | 398000 | 600000 | 400000 | 607000 | 402000 | 607000 |
| Average | 462000 | 638000 | 462000 | 646000 | 463000 | 646000 |
| Stdev | 262000 | 290000 | 260000 | 293000 | 260000 | 295000 |
| p (t-test) |  | 3.2E−6 |  | 1.5E−6 |  | 2.5E−6 |
| Min | 13600 | 135000 | 13600 | 135000 | 13600 | 135000 |
| Max | 1120000 | 1090000 | 1120000 | 1090000 | 1120000 | 1090000 |
| n (Patient) | 260 | 65 | 263 | 62 | 265 | 60 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.68 | 0.68 | 0.67 | 0.66 | 0.68 | 0.67 | 0.66 | 0.68 |
| SE | 0.030 | 0.031 | 0.040 | 0.031 | 0.032 | 0.040 | 0.033 | 0.033 | 0.041 |
| p Value | 1.3E−9 | 7.6E−9 | 6.7E−6 | 4.7E−8 | 4.9E−7 | 4.9E−6 | 1.3E−7 | 1.3E−6 | 8.7E−6 |
| nCohort Non-persistent | 187 | 192 | 260 | 204 | 205 | 263 | 219 | 217 | 265 |
| nCohort Persistent | 140 | 134 | 65 | 123 | 121 | 62 | 108 | 109 | 60 |
| Cutoff Quartile 2 | 260000 | 260000 | 262000 | 260000 | 260000 | 262000 | 260000 | 260000 | 262000 |
| Sensitivity | 86% | 86% | 89% | 86% | 86% | 89% | 86% | 86% | 88% |
| Specificity | 33% | 33% | 28% | 32% | 32% | 28% | 31% | 31% | 28% |
| Cutoff Quartile 3 | 437000 | 433000 | 437000 | 437000 | 433000 | 437000 | 437000 | 433000 | 437000 |
| Sensitivity | 66% | 66% | 68% | 65% | 64% | 69% | 66% | 65% | 70% |
| Specificity | 61% | 61% | 54% | 59% | 59% | 54% | 58% | 58% | 54% |
| Cutoff Quartile 4 | 707000 | 704000 | 708000 | 707000 | 704000 | 708000 | 707000 | 704000 | 708000 |
| Sensitivity | 38% | 37% | 43% | 38% | 36% | 45% | 40% | 37% | 45% |
| Specificity | 84% | 83% | 79% | 83% | 81% | 79% | 82% | 81% | 79% |
| OR Quartile 2 | 2.98 | 2.96 | 3.30 | 2.92 | 2.84 | 3.08 | 2.73 | 2.80 | 2.93 |
| p Value | 1.5E−4 | 2.0E−4 | 0.0048 | 3.8E−4 | 5.4E−4 | 0.0081 | 0.0014 | 0.0011 | 0.011 |
| Lower limit of 95% CI | 1.70 | 1.67 | 1.44 | 1.62 | 1.57 | 1.34 | 1.48 | 1.51 | 1.28 |
| Upper limit of 95% CI | 5.22 | 5.23 | 7.55 | 5.26 | 5.13 | 7.06 | 5.06 | 5.18 | 6.75 |
| OR Quartile 3 | 3.06 | 3.15 | 2.48 | 2.66 | 2.56 | 2.70 | 2.60 | 2.54 | 2.78 |
| p Value | 1.6E−6 | 1.1E−6 | 0.0019 | 3.6E−5 | 7.3E−5 | 0.0010 | 9.3E−5 | 1.3E−4 | 9.0E−4 |
| Lower limit of 95% CI | 1.94 | 1.99 | 1.40 | 1.67 | 1.61 | 1.49 | 1.61 | 1.58 | 1.52 |
| Upper limit of 95% CI | 4.83 | 5.00 | 4.41 | 4.23 | 4.08 | 4.87 | 4.20 | 4.09 | 5.07 |
| OR Quartile 4 | 3.32 | 2.98 | 2.89 | 2.99 | 2.51 | 3.19 | 3.05 | 2.42 | 3.12 |
| p Value | 6.9E−6 | 3.5E−5 | 3.0E−4 | 3.1E−5 | 4.1E−4 | 9.7E−5 | 2.4E−5 | 7.9E−4 | 1.5E−4 |
| Lower limit of 95% CI | 1.97 | 1.78 | 1.62 | 1.78 | 1.51 | 1.78 | 1.82 | 1.44 | 1.73 |
| Upper limit of 95% CI | 5.60 | 4.99 | 5.13 | 5.00 | 4.19 | 5.71 | 5.13 | 4.04 | 5.63 |

TABLE 8.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 323000 | 595000 | 339000 | 594000 | 342000 | 599000 |
| Average | 407000 | 598000 | 417000 | 603000 | 427000 | 610000 |
| Stdev | 244000 | 276000 | 246000 | 280000 | 249000 | 282000 |
| p (t-test) |  | 1.3E−10 |  | 6.4E−10 |  | 2.9E−9 |

TABLE 8.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 13600 | 105000 | 13600 | 135000 | 13600 | 135000 |
| Max | 1040000 | 1120000 | 1040000 | 1120000 | 1040000 | 1120000 |
| n (Patient) | 176 | 151 | 190 | 137 | 205 | 122 |
| | | | sCr only | | | |
| Median | 326000 | 594000 | 339000 | 582000 | 342000 | 586000 |
| Average | 411000 | 598000 | 422000 | 598000 | 432000 | 601000 |
| Stdev | 248000 | 272000 | 252000 | 274000 | 255000 | 275000 |
| p (t-test) | | 3.0E−10 | | 6.3E−9 | | 4.2E−8 |
| Min | 13600 | 105000 | 13600 | 151000 | 13600 | 154000 |
| Max | 1040000 | 1120000 | 1040000 | 1120000 | 1040000 | 1120000 |
| n (Patient) | 182 | 144 | 194 | 132 | 207 | 119 |
| | | | UO only | | | |
| Median | 380000 | 607000 | 382000 | 641000 | 389000 | 609000 |
| Average | 453000 | 642000 | 455000 | 647000 | 456000 | 643000 |
| Stdev | 258000 | 286000 | 257000 | 289000 | 258000 | 290000 |
| p (t-test) | | 9.1E−8 | | 1.1E−7 | | 2.6E−7 |
| Min | 13600 | 135000 | 13600 | 135000 | 13600 | 135000 |
| Max | 1120000 | 1090000 | 1120000 | 1090000 | 1120000 | 1090000 |
| n (Patient) | 249 | 76 | 253 | 72 | 254 | 71 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.69 | 0.69 | 0.69 | 0.69 | 0.69 | 0.68 | 0.69 |
| SE | 0.029 | 0.030 | 0.037 | 0.030 | 0.031 | 0.038 | 0.031 | 0.032 | 0.038 |
| p Value | 5.1E−12 | 1.7E−11 | 1.5E−7 | 1.3E−10 | 1.1E−9 | 2.8E−7 | 1.3E−9 | 1.3E−8 | 6.6E−7 |
| nCohort Non-persistent | 176 | 182 | 249 | 190 | 194 | 253 | 205 | 207 | 254 |
| nCohort Persistent | 151 | 144 | 76 | 137 | 132 | 72 | 122 | 119 | 71 |
| Cutoff Quartile 2 | 260000 | 260000 | 262000 | 260000 | 260000 | 262000 | 260000 | 260000 | 262000 |
| Sensitivity | 87% | 87% | 89% | 87% | 87% | 89% | 87% | 87% | 89% |
| Specificity | 35% | 35% | 29% | 34% | 34% | 29% | 32% | 32% | 29% |
| Cutoff Quartile 3 | 437000 | 433000 | 437000 | 437000 | 433000 | 437000 | 437000 | 433000 | 437000 |
| Sensitivity | 66% | 67% | 68% | 66% | 66% | 69% | 66% | 66% | 69% |
| Specificity | 64% | 64% | 55% | 61% | 61% | 55% | 60% | 59% | 55% |
| Cutoff Quartile 4 | 707000 | 704000 | 708000 | 707000 | 704000 | 708000 | 707000 | 704000 | 708000 |
| Sensitivity | 38% | 38% | 43% | 39% | 37% | 44% | 39% | 37% | 44% |
| Specificity | 86% | 85% | 80% | 85% | 83% | 80% | 83% | 82% | 80% |
| OR Quartile 2 | 3.56 | 3.48 | 3.53 | 3.36 | 3.41 | 3.24 | 3.15 | 3.32 | 3.18 |
| p Value | 9.8E−6 | 1.8E−5 | 0.0016 | 4.2E−5 | 4.6E−5 | 0.0032 | 1.9E−4 | 1.3E−4 | 0.0039 |
| Lower limit of 95% CI | 2.03 | 1.97 | 1.61 | 1.88 | 1.89 | 1.48 | 1.72 | 1.79 | 1.45 |
| Upper limit of 95% CI | 6.26 | 6.17 | 7.70 | 6.00 | 6.15 | 7.10 | 5.74 | 6.14 | 6.96 |
| OR Quartile 3 | 3.43 | 3.63 | 2.69 | 3.00 | 3.00 | 2.82 | 2.90 | 2.89 | 2.74 |
| p Value | 1.2E−7 | 4.3E−8 | 3.6E−4 | 2.5E−6 | 3.0E−6 | 2.9E−4 | 8.0E−6 | 9.8E−6 | 4.3E−4 |
| Lower limit of 95% CI | 2.17 | 2.29 | 1.56 | 1.90 | 1.89 | 1.61 | 1.82 | 1.81 | 1.56 |
| Upper limit of 95% CI | 5.41 | 5.75 | 4.64 | 4.74 | 4.76 | 4.93 | 4.64 | 4.63 | 4.79 |
| OR Quartile 4 | 3.66 | 3.30 | 3.13 | 3.50 | 2.88 | 3.25 | 3.26 | 2.61 | 3.08 |
| p Value | 2.1E−6 | 8.4E−6 | 4.8E−5 | 2.7E−6 | 5.6E−5 | 3.6E−5 | 7.4E−6 | 2.4E−4 | 8.2E−5 |
| Lower limit of 95% CI | 2.14 | 1.95 | 1.81 | 2.07 | 1.72 | 1.86 | 1.95 | 1.56 | 1.76 |
| Upper limit of 95% CI | 6.26 | 5.58 | 5.43 | 5.92 | 4.82 | 5.68 | 5.47 | 4.35 | 5.40 |

TABLE 8.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 321000 | 590000 | 339000 | 586000 | 342000 | 595000 |
| Average | 406000 | 595000 | 417000 | 601000 | 425000 | 606000 |
| Stdev | 246000 | 274000 | 247000 | 279000 | 250000 | 280000 |
| p (t-test) | | 1.9E−10 | | 9.9E−10 | | 3.2E−9 |
| Min | 13600 | 105000 | 13600 | 135000 | 13600 | 135000 |
| Max | 1040000 | 1120000 | 1040000 | 1120000 | 1040000 | 1120000 |
| n (Patient) | 173 | 154 | 188 | 139 | 200 | 127 |
| sCr only | | | | | | |
| Median | 326000 | 594000 | 334000 | 582000 | 341000 | 590000 |
| Average | 408000 | 598000 | 417000 | 600000 | 425000 | 605000 |
| Stdev | 247000 | 272000 | 250000 | 274000 | 252000 | 275000 |
| p (t-test) | | 1.5E−10 | | 1.2E−9 | | 3.9E−9 |
| Min | 13600 | 105000 | 13600 | 151000 | 13600 | 154000 |
| Max | 1040000 | 1120000 | 1040000 | 1120000 | 1040000 | 1120000 |
| n (Patient) | 179 | 147 | 190 | 136 | 202 | 124 |
| UO only | | | | | | |
| Median | 377000 | 596000 | 382000 | 602000 | 389000 | 600000 |
| Average | 449000 | 632000 | 451000 | 637000 | 453000 | 634000 |
| Stdev | 257000 | 285000 | 256000 | 289000 | 257000 | 290000 |
| p (t-test) | | 8.9E−8 | | 1.0E−7 | | 2.4E−7 |
| Min | 13600 | 135000 | 13600 | 135000 | 13600 | 135000 |
| Max | 1120000 | 1090000 | 1120000 | 1090000 | 1120000 | 1090000 |
| n (Patient) | 240 | 85 | 245 | 80 | 246 | 79 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.69 | 0.69 | 0.69 | 0.69 | 0.69 | 0.69 | 0.68 |
| SE | 0.029 | 0.029 | 0.035 | 0.030 | 0.030 | 0.036 | 0.031 | 0.031 | 0.036 |
| p Value | 5.3E−12 | 5.7E−12 | 9.1E−8 | 1.7E−10 | 1.3E−10 | 1.8E−7 | 1.0E−9 | 7.6E−10 | 4.3E−7 |
| nCohort Non-persistent | 173 | 179 | 240 | 188 | 190 | 245 | 200 | 202 | 246 |
| nCohort Persistent | 154 | 147 | 85 | 139 | 136 | 80 | 127 | 124 | 79 |
| Cutoff Quartile 2 | 260000 | 260000 | 262000 | 260000 | 260000 | 262000 | 260000 | 260000 | 262000 |
| Sensitivity | 87% | 87% | 91% | 87% | 88% | 90% | 87% | 88% | 90% |
| Specificity | 36% | 35% | 30% | 34% | 34% | 30% | 33% | 33% | 30% |
| Cutoff Quartile 3 | 437000 | 433000 | 437000 | 437000 | 433000 | 437000 | 437000 | 433000 | 437000 |
| Sensitivity | 66% | 67% | 67% | 65% | 66% | 68% | 66% | 67% | 67% |
| Specificity | 64% | 64% | 56% | 61% | 62% | 56% | 60% | 60% | 55% |
| Cutoff Quartile 4 | 707000 | 704000 | 708000 | 707000 | 704000 | 708000 | 707000 | 704000 | 708000 |
| Sensitivity | 37% | 37% | 41% | 38% | 38% | 42% | 39% | 38% | 42% |
| Specificity | 86% | 85% | 80% | 85% | 84% | 80% | 84% | 83% | 80% |
| OR Quartile 2 | 3.74 | 3.66 | 4.21 | 3.47 | 3.64 | 3.82 | 3.42 | 3.61 | 3.74 |
| p Value | 4.4E−6 | 8.6E−6 | 3.0E−4 | 2.6E−5 | 1.8E−5 | 7.6E−4 | 6.2E−5 | 4.2E−5 | 9.1E−4 |
| Lower limit of 95% CI | 2.13 | 2.07 | 1.93 | 1.94 | 2.02 | 1.75 | 1.87 | 1.95 | 1.72 |
| Upper limit of 95% CI | 6.57 | 6.48 | 9.16 | 6.20 | 6.57 | 8.33 | 6.23 | 6.66 | 8.17 |
| OR Quartile 3 | 3.51 | 3.71 | 2.57 | 2.99 | 3.14 | 2.59 | 2.93 | 3.09 | 2.52 |
| p Value | 6.8E−8 | 2.5E−8 | 3.6E−4 | 2.6E−6 | 1.1E−6 | 4.4E−4 | 5.5E−6 | 2.4E−6 | 6.7E−4 |
| Lower limit of 95% CI | 2.23 | 2.34 | 1.53 | 1.89 | 1.98 | 1.52 | 1.84 | 1.93 | 1.48 |
| Upper limit of 95% CI | 5.54 | 5.87 | 4.32 | 4.71 | 4.97 | 4.41 | 4.66 | 4.93 | 4.29 |
| OR Quartile 4 | 3.48 | 3.37 | 2.87 | 3.38 | 3.08 | 3.03 | 3.18 | 2.91 | 2.88 |
| p Value | 5.0E−6 | 6.7E−6 | 1.2E−4 | 5.1E−6 | 2.1E−5 | 6.4E−5 | 1.2E−5 | 4.6E−5 | 1.4E−4 |

TABLE 8.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.04 | 1.98 | 1.68 | 2.00 | 1.83 | 1.76 | 1.90 | 1.74 | 1.67 |
| Upper limit of 95% CI | 5.94 | 5.71 | 4.92 | 5.70 | 5.17 | 5.23 | 5.33 | 4.87 | 4.98 |

TABLE 8.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 314000 | 577000 | 327000 | 572000 | 339000 | 578000 |
| Average | 407000 | 590000 | 417000 | 595000 | 424000 | 602000 |
| Stdev | 248000 | 273000 | 250000 | 276000 | 252000 | 277000 |
| p (t-test) | | 6.5E−10 | | 2.6E−9 | | 5.7E−9 |
| Min | 13600 | 105000 | 13600 | 135000 | 13600 | 135000 |
| Max | 1040000 | 1120000 | 1040000 | 1120000 | 1040000 | 1120000 |
| n (Patient) | 169 | 158 | 183 | 144 | 196 | 131 |
| | sCr only | | | | | |
| Median | 321000 | 586000 | 328000 | 577000 | 340000 | 582000 |
| Average | 406000 | 595000 | 416000 | 597000 | 424000 | 602000 |
| Stdev | 246000 | 272000 | 249000 | 274000 | 252000 | 275000 |
| p (t-test) | | 1.8E−10 | | 1.4E−9 | | 5.1E−9 |
| Min | 13600 | 105000 | 13600 | 151000 | 13600 | 154000 |
| Max | 1040000 | 1120000 | 1040000 | 1120000 | 1040000 | 1120000 |
| n (Patient) | 175 | 151 | 186 | 140 | 198 | 128 |
| | UO only | | | | | |
| Median | 371000 | 602000 | 375000 | 607000 | 377000 | 605000 |
| Average | 442000 | 640000 | 443000 | 644000 | 444000 | 641000 |
| Stdev | 252000 | 287000 | 251000 | 289000 | 252000 | 289000 |
| p (t-test) | | 2.8E−9 | | 2.2E−9 | | 5.8E−9 |
| Min | 13600 | 135000 | 13600 | 135000 | 13600 | 135000 |
| Max | 1040000 | 1120000 | 1040000 | 1120000 | 1040000 | 1120000 |
| n (Patient) | 235 | 90 | 237 | 88 | 238 | 87 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.70 | 0.69 | 0.69 | 0.70 | 0.69 | 0.69 | 0.70 |
| SE | 0.029 | 0.029 | 0.034 | 0.030 | 0.030 | 0.034 | 0.031 | 0.031 | 0.035 |
| p Value | 1.4E−11 | 4.7E−12 | 2.7E−9 | 2.1E−10 | 1.2E−10 | 3.0E−9 | 9.8E−10 | 7.8E−10 | 8.1E−9 |
| nCohort Non-persistent | 169 | 175 | 235 | 183 | 186 | 237 | 196 | 198 | 238 |
| nCohort Persistent | 158 | 151 | 90 | 144 | 140 | 88 | 131 | 128 | 87 |
| Cutoff Quartile 2 | 260000 | 260000 | 262000 | 260000 | 260000 | 262000 | 260000 | 260000 | 262000 |
| Sensitivity | 87% | 87% | 91% | 88% | 87% | 91% | 88% | 88% | 91% |
| Specificity | 36% | 35% | 31% | 35% | 34% | 31% | 34% | 33% | 31% |
| Cutoff Quartile 3 | 437000 | 433000 | 437000 | 437000 | 433000 | 437000 | 437000 | 433000 | 437000 |
| Sensitivity | 66% | 67% | 68% | 65% | 66% | 68% | 66% | 66% | 68% |
| Specificity | 64% | 65% | 57% | 62% | 62% | 57% | 61% | 61% | 56% |
| Cutoff Quartile 4 | 707000 | 704000 | 708000 | 707000 | 704000 | 708000 | 707000 | 704000 | 708000 |
| Sensitivity | 36% | 37% | 42% | 37% | 37% | 43% | 37% | 38% | 43% |
| Specificity | 85% | 85% | 81% | 84% | 84% | 81% | 83% | 83% | 81% |
| OR Quartile 2 | 3.68 | 3.59 | 4.62 | 3.76 | 3.56 | 4.45 | 3.65 | 3.50 | 4.37 |
| p Value | 4.3E−6 | 8.6E−6 | 1.1E−4 | 7.4E−6 | 1.8E−5 | 1.7E−4 | 2.4E−5 | 4.5E−5 | 2.0E−4 |
| Lower limit of 95% CI | 2.11 | 2.05 | 2.12 | 2.11 | 1.99 | 2.05 | 2.00 | 1.92 | 2.01 |

TABLE 8.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 6.43 | 6.31 | 10.0 | 6.72 | 6.35 | 9.68 | 6.66 | 6.39 | 9.51 |
| OR Quartile 3 | 3.50 | 3.68 | 2.74 | 3.03 | 3.10 | 2.79 | 3.06 | 3.04 | 2.71 |
| p Value | 7.0E−8 | 2.6E−8 | 1.1E−4 | 1.7E−6 | 1.2E−6 | 1.0E−4 | 2.2E−6 | 2.7E−6 | 1.6E−4 |
| Lower limit of 95% CI | 2.22 | 2.33 | 1.64 | 1.93 | 1.96 | 1.66 | 1.92 | 1.91 | 1.62 |
| Upper limit of 95% CI | 5.52 | 5.83 | 4.58 | 4.78 | 4.91 | 4.67 | 4.85 | 4.84 | 4.56 |
| OR Quartile 4 | 3.25 | 3.38 | 3.17 | 3.09 | 3.07 | 3.33 | 2.95 | 2.89 | 3.17 |
| p Value | 1.5E−5 | 7.2E−6 | 2.1E−5 | 2.2E−5 | 2.3E−5 | 9.9E−6 | 3.8E−5 | 5.1E−5 | 2.3E−5 |
| Lower limit of 95% CI | 1.90 | 1.99 | 1.86 | 1.84 | 1.83 | 1.95 | 1.76 | 1.73 | 1.86 |
| Upper limit of 95% CI | 5.55 | 5.75 | 5.40 | 5.21 | 5.17 | 5.69 | 4.94 | 4.84 | 5.42 |

Example 9. Use of Metalloproteinase Inhibitor 1 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 1 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 9.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 7870 | 21100 | 9400 | 20500 | 9450 | 22400 |
| Average | 15500 | 36800 | 18800 | 38800 | 19400 | 41100 |
| Stdev | 22400 | 36200 | 24100 | 38000 | 25100 | 38400 |
| p (t-test) | | 1.6E−8 | | 4.3E−8 | | 3.9E−9 |
| Min | 475 | 297 | 419 | 297 | 419 | 297 |
| Max | 116000 | 146000 | 116000 | 146000 | 116000 | 146000 |
| n (Patient) | 119 | 198 | 158 | 159 | 179 | 138 |
| sCr only | | | | | | |
| Median | 8850 | 20700 | 9980 | 20700 | 9560 | 23100 |
| Average | 16600 | 37100 | 18200 | 39700 | 19100 | 42000 |
| Stdev | 22300 | 37000 | 22300 | 39000 | 24000 | 39400 |
| p (t-test) | | 3.2E−8 | | 3.4E−9 | | 5.1E−10 |
| Min | 475 | 297 | 419 | 297 | 399 | 297 |
| Max | 116000 | 146000 | 116000 | 146000 | 116000 | 146000 |
| n (Patient) | 130 | 186 | 162 | 154 | 184 | 132 |
| UO only | | | | | | |
| Median | 11800 | 27400 | 12100 | 29500 | 12100 | 31500 |
| Average | 24600 | 43300 | 25100 | 45500 | 25300 | 47500 |
| Stdev | 30500 | 38400 | 30600 | 39800 | 30600 | 40500 |

TABLE 9.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

|  | | | | | | | | | |
|---|---|---|---|---|---|---|---|---|---|
| p (t-test) | | 2.0E−5 | | | 1.9E−5 | | | 9.4E−6 | |
| Min | 297 | 873 | | 297 | 873 | | 297 | 873 | |
| Max | 146000 | 140000 | | 146000 | 140000 | | 146000 | 140000 | |
| n (Patient) | 241 | 74 | | 256 | 59 | | 263 | 52 | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.70 | 0.68 | 0.68 | 0.68 | 0.68 | 0.70 | 0.70 | 0.69 |
| SE | 0.028 | 0.029 | 0.038 | 0.030 | 0.030 | 0.041 | 0.030 | 0.030 | 0.043 |
| p Value | 6.7E−16 | 7.2E−12 | 1.0E−6 | 1.7E−9 | 2.5E−9 | 7.7E−6 | 2.7E−11 | 4.0E−11 | 7.8E−6 |
| nCohort Non-persistent | 119 | 130 | 241 | 158 | 162 | 256 | 179 | 184 | 263 |
| nCohort Persistent | 198 | 186 | 74 | 159 | 154 | 59 | 138 | 132 | 52 |
| Cutoff Quartile 2 | 6030 | 6020 | 6080 | 6030 | 6020 | 6080 | 6030 | 6020 | 6080 |
| Sensitivity | 86% | 84% | 92% | 86% | 85% | 92% | 88% | 86% | 90% |
| Specificity | 43% | 38% | 30% | 36% | 35% | 29% | 35% | 33% | 28% |
| Cutoff Quartile 3 | 14200 | 14100 | 14200 | 14200 | 14100 | 14200 | 14200 | 14100 | 14200 |
| Sensitivity | 65% | 65% | 70% | 64% | 64% | 71% | 69% | 70% | 73% |
| Specificity | 74% | 71% | 56% | 64% | 64% | 55% | 64% | 64% | 54% |
| Cutoff Quartile 4 | 35900 | 35400 | 36300 | 35900 | 35400 | 36300 | 35900 | 35400 | 36300 |
| Sensitivity | 34% | 35% | 39% | 37% | 38% | 41% | 40% | 41% | 42% |
| Specificity | 90% | 89% | 79% | 87% | 88% | 79% | 86% | 86% | 78% |
| OR Quartile 2 | 4.55 | 3.38 | 4.92 | 3.51 | 3.01 | 4.39 | 3.77 | 3.14 | 3.68 |
| p Value | 3.8E−8 | 6.8E−6 | 3.8E−4 | 9.1E−6 | 8.3E−5 | 0.0024 | 1.2E−5 | 1.2E−4 | 0.0078 |
| Lower limit of 95% CI | 2.65 | 1.99 | 2.05 | 2.02 | 1.74 | 1.69 | 2.08 | 1.75 | 1.41 |
| Upper limit of 95% CI | 7.81 | 5.75 | 11.9 | 6.12 | 5.21 | 11.4 | 6.83 | 5.63 | 9.62 |
| OR Quartile 3 | 5.19 | 4.40 | 3.01 | 3.17 | 3.14 | 2.98 | 3.97 | 4.11 | 3.23 |
| p Value | 1.3E−10 | 1.8E−9 | 1.1E−4 | 8.2E−7 | 1.0E−6 | 5.0E−4 | 1.1E−8 | 6.8E−9 | 4.8E−4 |
| Lower limit of 95% CI | 3.14 | 2.72 | 1.72 | 2.00 | 1.98 | 1.61 | 2.48 | 2.55 | 1.67 |
| Upper limit of 95% CI | 8.58 | 7.13 | 5.27 | 5.02 | 4.97 | 5.51 | 6.37 | 6.63 | 6.25 |
| OR Quartile 4 | 4.66 | 4.45 | 2.46 | 3.85 | 4.41 | 2.51 | 4.08 | 4.40 | 2.65 |
| p Value | 5.6E−6 | 3.5E−6 | 0.0016 | 2.5E−6 | 3.3E−7 | 0.0026 | 3.8E−7 | 1.0E−7 | 0.0022 |
| Lower limit of 95% CI | 2.40 | 2.37 | 1.40 | 2.20 | 2.49 | 1.38 | 2.37 | 2.55 | 1.42 |
| Upper limit of 95% CI | 9.07 | 8.37 | 4.31 | 6.74 | 7.80 | 4.56 | 7.02 | 7.60 | 4.94 |

TABLE 9.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 7070 | 20500 | 9020 | 20700 | 9010 | 22400 |
| Average | 15500 | 36100 | 17600 | 38500 | 18200 | 40400 |
| Stdev | 22900 | 35900 | 22700 | 37800 | 24100 | 37900 |
| p (t-test) | | 7.2E−8 | | 1.2E−8 | | 1.2E−9 |
| Min | 475 | 297 | 419 | 297 | 419 | 297 |
| Max | 116000 | 146000 | 116000 | 146000 | 116000 | 146000 |
| n (Patient) | 112 | 205 | 147 | 170 | 165 | 152 |
| | sCr only | | | | | |
| Median | 8650 | 20500 | 9980 | 20500 | 9450 | 22000 |
| Average | 16600 | 36700 | 18300 | 38600 | 18900 | 39900 |

TABLE 9.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 22600 | 36700 | 22800 | 38400 | 24300 | 38400 |
| p (t-test) | | 9.4E−8 | | 3.1E−8 | | 1.0E−8 |
| Min | 475 | 297 | 419 | 297 | 419 | 297 |
| Max | 116000 | 146000 | 116000 | 146000 | 116000 | 146000 |
| n (Patient) | 126 | 190 | 154 | 162 | 169 | 147 |

UO only

| | | | | | | |
|---|---|---|---|---|---|---|
| Median | 11600 | 21900 | 12100 | 21900 | 12100 | 24700 |
| Average | 24400 | 39900 | 25100 | 41000 | 25200 | 41900 |
| Stdev | 30500 | 37400 | 30600 | 38700 | 30600 | 39300 |
| p (t-test) | | 1.6E−4 | | 2.6E−4 | | 2.0E−4 |
| Min | 297 | 399 | 297 | 399 | 297 | 399 |
| Max | 146000 | 140000 | 146000 | 140000 | 146000 | 140000 |
| n (Patient) | 222 | 93 | 238 | 77 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.70 | 0.66 | 0.69 | 0.68 | 0.65 | 0.71 | 0.69 | 0.65 |
| SE | 0.028 | 0.029 | 0.035 | 0.029 | 0.030 | 0.038 | 0.029 | 0.030 | 0.039 |
| p Value | 4.4E−16 | 1.7E−11 | 3.2E−6 | 4.3E−11 | 3.8E−9 | 5.3E−5 | 1.1E−13 | 1.1E−10 | 7.5E−5 |
| nCohort Non-persistent | 112 | 126 | 222 | 147 | 154 | 238 | 165 | 169 | 245 |
| nCohort Persistent | 205 | 190 | 93 | 170 | 162 | 77 | 152 | 147 | 70 |
| Cutoff Quartile 2 | 6030 | 6020 | 6080 | 6030 | 6020 | 6080 | 6030 | 6020 | 6080 |
| Sensitivity | 86% | 84% | 92% | 87% | 86% | 92% | 89% | 87% | 91% |
| Specificity | 45% | 39% | 32% | 39% | 36% | 31% | 38% | 36% | 30% |
| Cutoff Quartile 3 | 14200 | 14100 | 14200 | 14200 | 14100 | 14200 | 14200 | 14100 | 14200 |
| Sensitivity | 63% | 64% | 67% | 64% | 63% | 66% | 68% | 67% | 67% |
| Specificity | 74% | 71% | 57% | 65% | 64% | 55% | 66% | 64% | 55% |
| Cutoff Quartile 4 | 35900 | 35400 | 36300 | 35900 | 35400 | 36300 | 35900 | 35400 | 36300 |
| Sensitivity | 34% | 34% | 37% | 36% | 36% | 36% | 39% | 38% | 37% |
| Specificity | 90% | 89% | 80% | 88% | 87% | 79% | 87% | 86% | 78% |
| OR Quartile 2 | 4.89 | 3.39 | 5.90 | 4.26 | 3.45 | 5.24 | 4.78 | 3.71 | 4.53 |
| p Value | 9.0E−9 | 6.1E−6 | 2.2E−5 | 3.5E−7 | 1.0E−5 | 2.2E−4 | 2.5E−7 | 8.1E−6 | 7.8E−4 |
| Lower limit of 95% CI | 2.85 | 2.00 | 2.60 | 2.44 | 1.99 | 2.18 | 2.64 | 2.09 | 1.88 |
| Upper limit of 95% CI | 8.41 | 5.76 | 13.4 | 7.44 | 5.99 | 12.6 | 8.66 | 6.60 | 10.9 |
| OR Quartile 3 | 4.96 | 4.22 | 2.63 | 3.28 | 2.98 | 2.40 | 4.09 | 3.63 | 2.47 |
| p Value | 7.2E−10 | 5.6E−9 | 1.9E−4 | 4.5E−7 | 3.0E−6 | 0.0014 | 3.8E−9 | 5.6E−8 | 0.0015 |
| Lower limit of 95% CI | 2.98 | 2.60 | 1.58 | 2.07 | 1.88 | 1.40 | 2.56 | 2.28 | 1.41 |
| Upper limit of 95% CI | 8.26 | 6.85 | 4.36 | 5.20 | 4.70 | 4.11 | 6.54 | 5.79 | 4.31 |
| OR Quartile 4 | 4.66 | 4.16 | 2.27 | 4.11 | 3.84 | 2.10 | 4.35 | 3.91 | 2.14 |
| p Value | 1.1E−5 | 9.6E−6 | 0.0027 | 2.0E−6 | 3.5E−6 | 0.0094 | 3.0E−7 | 1.3E−6 | 0.0091 |
| Lower limit of 95% CI | 2.34 | 2.21 | 1.33 | 2.29 | 2.17 | 1.20 | 2.48 | 2.25 | 1.21 |
| Upper limit of 95% CI | 9.25 | 7.82 | 3.87 | 7.38 | 6.78 | 3.66 | 7.63 | 6.78 | 3.79 |

TABLE 9.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 6980 | 20500 | 9010 | 20500 | 9010 | 21900 |
| Average | 15500 | 36000 | 17500 | 38200 | 18400 | 39200 |
| Stdev | 23000 | 35800 | 22800 | 37600 | 24500 | 37600 |
| p (t-test) | | 9.9E−8 | | 1.7E−8 | | 1.4E−8 |
| Min | 475 | 297 | 419 | 297 | 419 | 297 |
| Max | 116000 | 146000 | 116000 | 146000 | 116000 | 146000 |
| n (Patient) | 111 | 206 | 144 | 173 | 158 | 159 |
| | sCr only | | | | | |
| Median | 8510 | 20500 | 9450 | 20500 | 9450 | 20800 |
| Average | 16800 | 36400 | 18400 | 38100 | 19200 | 38700 |
| Stdev | 22700 | 36700 | 23000 | 38200 | 24700 | 38100 |
| p (t-test) | | 1.8E−7 | | 7.7E−8 | | 1.1E−7 |
| Min | 475 | 297 | 419 | 297 | 419 | 297 |
| Max | 116000 | 146000 | 116000 | 146000 | 116000 | 146000 |
| n (Patient) | 124 | 192 | 151 | 165 | 163 | 153 |
| | UO only | | | | | |
| Median | 11600 | 20500 | 11900 | 20900 | 12000 | 21700 |
| Average | 24900 | 37300 | 25300 | 38000 | 25500 | 38600 |
| Stdev | 31100 | 36600 | 31100 | 37300 | 31100 | 37800 |
| p (t-test) | | 0.0019 | | 0.0022 | | 0.0021 |
| Min | 297 | 399 | 297 | 399 | 297 | 399 |
| Max | 146000 | 140000 | 146000 | 140000 | 146000 | 140000 |
| n (Patient) | 212 | 103 | 225 | 90 | 232 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.69 | 0.64 | 0.70 | 0.67 | 0.63 | 0.70 | 0.68 | 0.63 |
| SE | 0.028 | 0.029 | 0.034 | 0.029 | 0.030 | 0.036 | 0.029 | 0.030 | 0.037 |
| p Value | 6.7E−16 | 3.3E−11 | 6.2E−5 | 1.3E−11 | 5.2E−9 | 2.8E−4 | 3.1E−12 | 1.5E−9 | 4.3E−4 |
| nCohort Non-persistent | 111 | 124 | 212 | 144 | 151 | 225 | 158 | 163 | 232 |
| nCohort Persistent | 206 | 192 | 103 | 173 | 165 | 90 | 159 | 153 | 83 |
| Cutoff Quartile 2 | 6030 | 6020 | 6080 | 6030 | 6020 | 6080 | 6030 | 6020 | 6080 |
| Sensitivity | 86% | 84% | 89% | 87% | 86% | 89% | 87% | 86% | 88% |
| Specificity | 45% | 40% | 32% | 40% | 37% | 31% | 37% | 36% | 30% |
| Cutoff Quartile 3 | 14200 | 14100 | 14200 | 14200 | 14100 | 14200 | 14200 | 14100 | 14200 |
| Sensitivity | 63% | 63% | 63% | 64% | 62% | 63% | 66% | 65% | 64% |
| Specificity | 74% | 70% | 56% | 66% | 64% | 55% | 66% | 64% | 55% |
| Cutoff Quartile 4 | 35900 | 35400 | 36300 | 35900 | 35400 | 36300 | 35900 | 35400 | 36300 |
| Sensitivity | 33% | 34% | 34% | 36% | 36% | 34% | 38% | 37% | 35% |
| Specificity | 90% | 89% | 79% | 88% | 87% | 79% | 87% | 86% | 78% |
| OR Quartile 2 | 5.00 | 3.53 | 3.95 | 4.50 | 3.64 | 3.54 | 4.14 | 3.47 | 3.09 |
| p Value | 5.9E−9 | 3.2E−6 | 9.2E−5 | 1.3E−7 | 4.2E−6 | 5.4E−4 | 9.8E−7 | 1.4E−5 | 0.0021 |
| Lower limit of 95% CI | 2.91 | 2.08 | 1.98 | 2.57 | 2.10 | 1.73 | 2.34 | 1.98 | 1.51 |
| Upper limit of 95% CI | 8.60 | 6.00 | 7.86 | 7.86 | 6.31 | 7.24 | 7.32 | 6.09 | 6.34 |
| OR Quartile 3 | 4.84 | 4.01 | 2.19 | 3.39 | 2.90 | 2.12 | 3.74 | 3.23 | 2.14 |
| p Value | 1.3E−9 | 1.8E−8 | 0.0015 | 2.5E−7 | 5.0E−6 | 0.0034 | 2.5E−8 | 5.9E−7 | 0.0040 |
| Lower limit of 95% CI | 2.91 | 2.47 | 1.35 | 2.13 | 1.84 | 1.28 | 2.35 | 2.04 | 1.27 |
| Upper limit of 95% CI | 8.05 | 6.50 | 3.55 | 5.38 | 4.58 | 3.51 | 5.96 | 5.12 | 3.58 |

TABLE 9.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 4.58 | 4.02 | 1.97 | 4.28 | 3.65 | 1.94 | 4.18 | 3.51 | 1.95 |
| p Value | 1.4E−5 | 1.6E−5 | 0.012 | 1.6E−6 | 8.1E−6 | 0.016 | 8.0E−7 | 7.6E−6 | 0.017 |
| Lower limit of 95% CI | 2.30 | 2.14 | 1.16 | 2.36 | 2.07 | 1.13 | 2.37 | 2.03 | 1.13 |
| Upper limit of 95% CI | 9.10 | 7.56 | 3.32 | 7.74 | 6.43 | 3.32 | 7.38 | 6.09 | 3.39 |

TABLE 9.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 7070 | 20500 | 9010 | 20500 | 9010 | 21700 |
| Average | 15600 | 35900 | 17600 | 38000 | 18500 | 38800 |
| Stdev | 23000 | 35800 | 22900 | 37600 | 24600 | 37500 |
| p (t-test) | | 1.5E−7 | | 2.8E−8 | | 2.9E−8 |
| Min | 475 | 297 | 419 | 297 | 419 | 297 |
| Max | 116000 | 146000 | 116000 | 146000 | 116000 | 146000 |
| n (Patient) | 110 | 207 | 143 | 174 | 156 | 161 |
| | sCr only | | | | | |
| Median | 8510 | 20500 | 9980 | 19900 | 9560 | 20700 |
| Average | 16800 | 36400 | 18500 | 37900 | 19300 | 38500 |
| Stdev | 22700 | 36700 | 23000 | 38200 | 24700 | 38100 |
| p (t-test) | | 1.8E−7 | | 1.3E−7 | | 1.8E−7 |
| Min | 475 | 297 | 419 | 297 | 419 | 297 |
| Max | 116000 | 146000 | 116000 | 146000 | 116000 | 146000 |
| n (Patient) | 124 | 192 | 150 | 166 | 162 | 154 |
| | UO only | | | | | |
| Median | 11800 | 20500 | 11900 | 20500 | 11900 | 21300 |
| Average | 25100 | 36400 | 25300 | 37300 | 25500 | 37600 |
| Stdev | 31300 | 36300 | 31300 | 36700 | 31400 | 36900 |
| p (t-test) | | 0.0044 | | 0.0034 | | 0.0038 |
| Min | 297 | 399 | 297 | 399 | 297 | 399 |
| Max | 146000 | 140000 | 146000 | 140000 | 146000 | 140000 |
| n (Patient) | 208 | 107 | 220 | 95 | 226 | 89 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.72 | 0.69 | 0.62 | 0.69 | 0.67 |
| SE | 0.028 | 0.029 | 0.034 | 0.029 | 0.030 |
| p Value | 2.7E−15 | 3.3E−11 | 2.3E−4 | 5.1E−11 | 1.6E−8 |
| nCohort Non-persistent | 110 | 124 | 208 | 143 | 150 |
| nCohort Persistent | 207 | 192 | 107 | 174 | 166 |
| Cutoff Quartile 2 | 6030 | 6020 | 6080 | 6030 | 6020 |
| Sensitivity | 86% | 84% | 88% | 87% | 86% |
| Specificity | 45% | 40% | 32% | 39% | 37% |
| Cutoff Quartile 3 | 14200 | 14100 | 14200 | 14200 | 14100 |
| Sensitivity | 63% | 63% | 62% | 63% | 62% |
| Specificity | 74% | 70% | 56% | 66% | 63% |
| Cutoff Quartile 4 | 35900 | 35400 | 36300 | 35900 | 35400 |
| Sensitivity | 33% | 34% | 34% | 36% | 36% |

TABLE 9.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | |
|---|---|---|---|---|---|
| Specificity | 90% | 89% | 79% | 88% | 87% |
| OR Quartile 2 | 4.74 | 3.53 | 3.36 | 4.23 | 3.43 |
| p Value | 1.6E−8 | 3.2E−6 | 2.5E−4 | 3.2E−7 | 9.6E−6 |
| Lower limit of 95% CI | 2.76 | 2.08 | 1.76 | 2.43 | 1.99 |
| Upper limit of 95% CI | 8.13 | 6.00 | 6.43 | 7.34 | 5.91 |
| OR Quartile 3 | 4.72 | 4.01 | 2.03 | 3.30 | 2.82 |
| p Value | 2.4E−9 | 1.8E−8 | 0.0036 | 4.4E−7 | 8.4E−6 |
| Lower limit of 95% CI | 2.83 | 2.47 | 1.26 | 2.08 | 1.79 |
| Upper limit of 95% CI | 7.85 | 6.50 | 3.27 | 5.24 | 4.46 |
| OR Quartile 4 | 4.50 | 4.02 | 1.95 | 4.21 | 3.58 |
| p Value | 1.8E−5 | 1.6E−5 | 0.013 | 2.1E−6 | 1.1E−5 |
| Lower limit of 95% CI | 2.26 | 2.14 | 1.15 | 2.32 | 2.03 |
| Upper limit of 95% CI | 8.94 | 7.56 | 3.28 | 7.61 | 6.33 |

| | Persistence Period Duration (hr) | | | |
|---|---|---|---|---|
| | 48 | 72 | | |
| | UO only | sCr or UO | sCr only | UO only |
| AUC | 0.63 | 0.70 | 0.68 | 0.63 |
| SE | 0.035 | 0.029 | 0.030 | 0.036 |
| p Value | 2.9E−4 | 8.7E−12 | 5.0E−9 | 4.1E−4 |
| nCohort Non-persistent | 220 | 156 | 162 | 226 |
| nCohort Persistent | 95 | 161 | 154 | 89 |
| Cutoff Quartile 2 | 6080 | 6030 | 6020 | 6080 |
| Sensitivity | 88% | 87% | 86% | 88% |
| Specificity | 31% | 37% | 35% | 30% |
| Cutoff Quartile 3 | 14200 | 14200 | 14100 | 14200 |
| Sensitivity | 63% | 66% | 64% | 64% |
| Specificity | 55% | 66% | 64% | 55% |
| Cutoff Quartile 4 | 36300 | 35900 | 35400 | 36300 |
| Sensitivity | 35% | 37% | 36% | 35% |
| Specificity | 79% | 87% | 86% | 79% |
| OR Quartile 2 | 3.42 | 3.95 | 3.26 | 3.05 |
| p Value | 4.9E−4 | 1.7E−6 | 3.0E−5 | 0.0016 |
| Lower limit of 95% CI | 1.71 | 2.25 | 1.87 | 1.53 |
| Upper limit of 95% CI | 6.81 | 6.92 | 5.67 | 6.10 |
| OR Quartile 3 | 2.13 | 3.75 | 3.14 | 2.20 |
| p Value | 0.0027 | 2.5E−8 | 1.0E−6 | 0.0022 |
| Lower limit of 95% CI | 1.30 | 2.35 | 1.98 | 1.33 |
| Upper limit of 95% CI | 3.50 | 5.96 | 4.97 | 3.66 |
| OR Quartile 4 | 2.01 | 4.04 | 3.45 | 1.98 |
| p Value | 0.010 | 1.4E−6 | 1.0E−5 | 0.013 |
| Lower limit of 95% CI | 1.18 | 2.29 | 1.99 | 1.15 |
| Upper limit of 95% CI | 3.43 | 7.13 | 5.99 | 3.40 |

TABLE 9.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 6950 | 20500 | 8810 | 20500 | 8870 | 21300 |
| Average | 14700 | 35900 | 17100 | 37900 | 18100 | 38500 |
| Stdev | 21600 | 35900 | 22000 | 37600 | 24000 | 37500 |
| p (t-test) | | 4.5E−8 | | 1.7E−8 | | 3.0E−8 |
| Min | 475 | 297 | 419 | 297 | 419 | 297 |
| Max | 116000 | 146000 | 116000 | 146000 | 116000 | 146000 |
| n (Patient) | 106 | 211 | 138 | 179 | 150 | 167 |
| sCr only | | | | | | |
| Median | 8210 | 20500 | 9380 | 20500 | 9380 | 21100 |
| Average | 15900 | 36600 | 17700 | 38100 | 18600 | 38700 |
| Stdev | 21400 | 36800 | 22000 | 38200 | 23900 | 38000 |
| p (t-test) | | 3.8E−8 | | 2.7E−8 | | 4.1E−8 |
| Min | 475 | 297 | 419 | 297 | 419 | 297 |
| Max | 116000 | 146000 | 116000 | 146000 | 116000 | 146000 |
| n (Patient) | 121 | 195 | 146 | 170 | 158 | 158 |
| UO only | | | | | | |
| Median | 11200 | 21300 | 11600 | 21300 | 11800 | 21500 |
| Average | 23600 | 38400 | 24100 | 39000 | 24400 | 39000 |
| Stdev | 29300 | 38100 | 29600 | 38400 | 29800 | 38700 |
| p (t-test) | | 1.5E−4 | | 1.9E−4 | | 2.9E−4 |
| Min | 297 | 399 | 297 | 399 | 297 | 399 |
| Max | 127000 | 146000 | 127000 | 146000 | 127000 | 146000 |
| n (Patient) | 202 | 113 | 212 | 103 | 217 | 98 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.73 | 0.70 | 0.65 | 0.69 | 0.68 |
| SE | 0.028 | 0.029 | 0.033 | 0.029 | 0.030 |
| p Value | 2.2E−16 | 1.9E−12 | 7.3E−6 | 2.6E−11 | 1.1E−9 |
| nCohort Non-persistent | 106 | 121 | 202 | 138 | 146 |
| nCohort Persistent | 211 | 195 | 113 | 179 | 170 |
| Cutoff Quartile 2 | 6030 | 6020 | 6080 | 6030 | 6020 |
| Sensitivity | 85% | 85% | 88% | 87% | 86% |
| Specificity | 45% | 40% | 33% | 40% | 38% |
| Cutoff Quartile 3 | 14200 | 14100 | 14200 | 14200 | 14100 |
| Sensitivity | 63% | 63% | 64% | 63% | 62% |
| Specificity | 75% | 71% | 57% | 66% | 64% |
| Cutoff Quartile 4 | 35900 | 35400 | 36300 | 35900 | 35400 |
| Sensitivity | 34% | 34% | 35% | 36% | 36% |
| Specificity | 92% | 90% | 80% | 88% | 88% |
| OR Quartile 2 | 4.81 | 3.74 | 3.73 | 4.28 | 3.68 |
| p Value | 1.2E−8 | 1.2E−6 | 6.8E−5 | 2.1E−7 | 3.0E−6 |
| Lower limit of 95% CI | 2.80 | 2.20 | 1.95 | 2.47 | 2.13 |
| Upper limit of 95% CI | 8.25 | 6.37 | 7.14 | 7.41 | 6.35 |
| OR Quartile 3 | 4.89 | 4.20 | 2.37 | 3.24 | 2.99 |
| p Value | 2.0E−9 | 8.9E−9 | 3.6E−4 | 7.1E−7 | 2.9E−6 |
| Lower limit of 95% CI | 2.91 | 2.57 | 1.47 | 2.03 | 1.89 |
| Upper limit of 95% CI | 8.21 | 6.84 | 3.81 | 5.15 | 4.74 |
| OR Quartile 4 | 5.47 | 4.75 | 2.13 | 4.24 | 3.98 |
| p Value | 6.9E−6 | 4.4E−6 | 0.0042 | 2.7E−6 | 3.6E−6 |
| Lower limit of | 2.61 | 2.44 | 1.27 | 2.32 | 2.22 |

TABLE 9.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | |
|---|---|---|---|---|---|
| 95% CI Upper limit of 95% CI | | 11.5 | 9.25 | 3.59 | 7.76 | 7.14 |

| | | Persistence Period Duration (hr) | | | |
|---|---|---|---|---|---|
| | | 48 | 72 | | |
| | | UO only | sCr or UO | sCr only | UO only |
| AUC | | 0.65 | 0.70 | 0.69 | 0.64 |
| SE | | 0.034 | 0.029 | 0.030 | 0.035 |
| p Value | | 1.7E−5 | 1.0E−11 | 3.7E−10 | 3.5E−5 |
| nCohort Non-persistent | | 212 | 150 | 158 | 217 |
| nCohort Persistent | | 103 | 167 | 158 | 98 |
| Cutoff Quartile 2 | | 6080 | 6030 | 6020 | 6080 |
| Sensitivity | | 89% | 87% | 86% | 89% |
| Specificity | | 32% | 38% | 36% | 31% |
| Cutoff Quartile 3 | | 14200 | 14200 | 14100 | 14200 |
| Sensitivity | | 64% | 65% | 65% | 64% |
| Specificity | | 57% | 66% | 65% | 56% |
| Cutoff Quartile 4 | | 36300 | 35900 | 35400 | 36300 |
| Sensitivity | | 35% | 37% | 37% | 35% |
| Specificity | | 80% | 87% | 87% | 79% |
| OR Quartile 2 | | 3.95 | 4.04 | 3.49 | 3.61 |
| p Value | | 9.2E−5 | 8.8E−7 | 1.0E−5 | 2.6E−4 |
| Lower limit of 95% CI | | 1.98 | 2.32 | 2.00 | 1.81 |
| Upper limit of 95% CI | | 7.86 | 7.05 | 6.08 | 7.19 |
| OR Quartile 3 | | 2.33 | 3.55 | 3.32 | 2.31 |
| p Value | | 6.5E−4 | 8.2E−8 | 3.4E−7 | 8.6E−4 |
| Lower limit of 95% CI | | 1.43 | 2.24 | 2.09 | 1.41 |
| Upper limit of 95% CI | | 3.78 | 5.65 | 5.26 | 3.78 |
| OR Quartile 4 | | 2.11 | 3.97 | 3.78 | 2.03 |
| p Value | | 0.0053 | 2.6E−6 | 3.4E−6 | 0.0088 |
| Lower limit of 95% CI | | 1.25 | 2.23 | 2.16 | 1.20 |
| Upper limit of 95% CI | | 3.57 | 7.05 | 6.64 | 3.45 |

TABLE 9.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 279000 | 564000 | 321000 | 571000 | 342000 | 577000 |
| Average | 363000 | 566000 | 410000 | 572000 | 418000 | 589000 |
| Stdev | 236000 | 270000 | 253000 | 274000 | 249000 | 279000 |
| p (t-test) | | 5.9E−11 | | 6.3E−8 | | 1.3E−8 |
| Min | 13600 | 105000 | 13600 | 105000 | 13600 | 105000 |
| Max | 1040000 | 1120000 | 1040000 | 1120000 | 1040000 | 1120000 |
| n (Patient) | 114 | 213 | 155 | 172 | 179 | 148 |

TABLE 9.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr only | | | | | |
|---|---|---|---|---|---|---|
| Median | 280000 | 567000 | 314000 | 586000 | 340000 | 594000 |
| Average | 365000 | 572000 | 394000 | 586000 | 409000 | 600000 |
| Stdev | 235000 | 268000 | 237000 | 276000 | 244000 | 276000 |
| p (t-test) | | 9.2E−12 | | 8.8E−11 | | 1.6E−10 |
| Min | 13600 | 105000 | 13600 | 105000 | 13600 | 105000 |
| Max | 1040000 | 1120000 | 1040000 | 1120000 | 1040000 | 1120000 |
| n (Patient) | 124 | 202 | 157 | 169 | 182 | 144 |
| | UO only | | | | | |
| Median | 400000 | 595000 | 402000 | 660000 | 400000 | 693000 |
| Average | 457000 | 619000 | 461000 | 643000 | 460000 | 673000 |
| Stdev | 260000 | 289000 | 261000 | 288000 | 261000 | 280000 |
| p (t-test) | | 3.7E−6 | | 1.5E−6 | | 8.5E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 245 | 80 | 261 | 64 | 269 | 56 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.72 | 0.73 | 0.66 | 0.68 | 0.70 |
| SE | 0.028 | 0.028 | 0.037 | 0.029 | 0.029 |
| p Value | 1.1E−15 | 2.2E−16 | 8.6E−6 | 2.5E−9 | 1.1E−12 |
| nCohort Non-persistent | 114 | 124 | 245 | 155 | 157 |
| nCohort Persistent | 213 | 202 | 80 | 172 | 169 |
| Cutoff Quartile 2 | 260000 | 260000 | 262000 | 260000 | 260000 |
| Sensitivity | 85% | 86% | 85% | 85% | 86% |
| Specificity | 43% | 43% | 28% | 36% | 37% |
| Cutoff Quartile 3 | 437000 | 433000 | 437000 | 437000 | 433000 |
| Sensitivity | 61% | 62% | 65% | 62% | 63% |
| Specificity | 70% | 70% | 55% | 63% | 64% |
| Cutoff Quartile 4 | 707000 | 704000 | 708000 | 707000 | 704000 |
| Sensitivity | 33% | 34% | 44% | 34% | 37% |
| Specificity | 90% | 90% | 81% | 85% | 87% |
| OR Quartile 2 | 4.11 | 4.45 | 2.22 | 3.18 | 3.54 |
| p Value | 1.3E−7 | 3.4E−8 | 0.020 | 2.0E−5 | 4.5E−6 |
| Lower limit of 95% CI | 2.43 | 2.62 | 1.13 | 1.87 | 2.06 |
| Upper limit of 95% CI | 6.95 | 7.57 | 4.36 | 5.40 | 6.07 |
| OR Quartile 3 | 3.69 | 3.90 | 2.24 | 2.69 | 3.11 |
| p Value | 1.5E−7 | 2.5E−8 | 0.0025 | 1.5E−5 | 8.6E−7 |
| Lower limit of 95% CI | 2.27 | 2.42 | 1.33 | 1.72 | 1.98 |
| Upper limit of 95% CI | 6.00 | 6.29 | 3.79 | 4.20 | 4.89 |
| OR Quartile 4 | 4.68 | 4.43 | 3.28 | 3.00 | 3.97 |
| p Value | 9.7E−6 | 5.9E−6 | 1.9E−5 | 7.5E−5 | 1.7E−6 |
| Lower limit of 95% CI | 2.36 | 2.33 | 1.90 | 1.74 | 2.26 |
| Upper limit of 95% CI | 9.28 | 8.43 | 5.65 | 5.16 | 6.98 |

| | Persistence Period Duration (hr) | | | |
|---|---|---|---|---|
| | 48 | 72 | | |
| | UO only | sCr or UO | sCr only | UO only |
| AUC | 0.68 | 0.68 | 0.70 | 0.71 |
| SE | 0.040 | 0.030 | 0.029 | 0.041 |
| p Value | 4.0E−6 | 2.2E−9 | 8.8E−12 | 2.1E−7 |
| nCohort Non-persistent | 261 | 179 | 182 | 269 |
| nCohort | 64 | 148 | 144 | 56 |

TABLE 9.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | |
|---|---|---|---|---|
| Persistent | | | | |
| Cutoff Quartile 2 | 262000 | 260000 | 260000 | 262000 |
| Sensitivity | 89% | 86% | 88% | 91% |
| Specificity | 28% | 35% | 35% | 28% |
| Cutoff Quartile 3 | 437000 | 437000 | 433000 | 437000 |
| Sensitivity | 69% | 63% | 65% | 75% |
| Specificity | 54% | 60% | 62% | 55% |
| Cutoff Quartile 4 | 708000 | 707000 | 704000 | 708000 |
| Sensitivity | 47% | 38% | 40% | 50% |
| Specificity | 80% | 85% | 86% | 80% |
| OR Quartile 2 | 3.22 | 3.39 | 3.80 | 4.02 |
| p Value | 0.0057 | 2.1E−5 | 6.6E−6 | 0.0044 |
| Lower limit of 95% CI | 1.41 | 1.93 | 2.13 | 1.54 |
| Upper limit of 95% CI | 7.39 | 5.95 | 6.78 | 10.4 |
| OR Quartile 3 | 2.63 | 2.57 | 2.92 | 3.67 |
| p Value | 0.0012 | 3.6E−5 | 3.7E−6 | 9.0E−5 |
| Lower limit of 95% CI | 1.47 | 1.64 | 1.85 | 1.91 |
| Upper limit of 95% CI | 4.70 | 4.03 | 4.59 | 7.03 |
| OR Quartile 4 | 3.55 | 3.58 | 4.11 | 3.98 |
| p Value | 1.7E−5 | 2.6E−6 | 2.6E−7 | 7.0E−6 |
| Lower limit of 95% CI | 1.99 | 2.10 | 2.40 | 2.18 |
| Upper limit of 95% CI | 6.32 | 6.10 | 7.05 | 7.28 |

TABLE 9.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 272000 | 565000 | 300000 | 573000 | 314000 | 578000 |
| Average | 348000 | 568000 | 389000 | 579000 | 397000 | 594000 |
| Stdev | 224000 | 270000 | 237000 | 276000 | 237000 | 278000 |
| p (t-test) | | 2.1E−12 | | 1.9E−10 | | 3.2E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 108 | 219 | 144 | 183 | 164 | 163 |
| sCr only | | | | | | |
| Median | 277000 | 571000 | 299000 | 578000 | 314000 | 582000 |
| Average | 356000 | 574000 | 385000 | 585000 | 399000 | 592000 |
| Stdev | 228000 | 268000 | 236000 | 273000 | 241000 | 274000 |
| p (t-test) | | 7.4E−13 | | 1.2E−11 | | 6.4E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 120 | 206 | 149 | 177 | 166 | 160 |
| UO only | | | | | | |
| Median | 375000 | 590000 | 382000 | 602000 | 377000 | 609000 |
| Average | 446000 | 612000 | 451000 | 629000 | 451000 | 644000 |
| Stdev | 254000 | 290000 | 256000 | 290000 | 256000 | 287000 |
| p (t-test) | | 3.7E−7 | | 2.3E−7 | | 4.7E−8 |
| Min | 13600 | 135000 | 13600 | 135000 | 13600 | 135000 |
| Max | 1120000 | 1090000 | 1120000 | 1090000 | 1120000 | 1090000 |

TABLE 9.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| n (Patient) | 225 | 100 | 241 | 84 | 248 | 77 |
|---|---|---|---|---|---|---|

| | Persistence Period Duration (hr) | | | | | |
|---|---|---|---|---|---|---|
| | 24 | | | 48 | | |
| | sCr or UO | sCr only | UO only | sCr or UO | sCr only | |
| AUC | 0.74 | 0.74 | 0.67 | 0.70 | 0.72 | |
| SE | 0.027 | 0.027 | 0.034 | 0.028 | 0.028 | |
| p Value | 0 | 0 | 6.4E−7 | 5.3E−13 | 1.2E−14 | |
| nCohort Non-persistent | 108 | 120 | 225 | 144 | 149 | |
| nCohort Persistent | 219 | 206 | 100 | 183 | 177 | |
| Cutoff Quartile 2 | 260000 | 260000 | 262000 | 260000 | 260000 | |
| Sensitivity | 85% | 86% | 86% | 86% | 86% | |
| Specificity | 45% | 44% | 30% | 39% | 39% | |
| Cutoff Quartile 3 | 437000 | 433000 | 437000 | 437000 | 433000 | |
| Sensitivity | 61% | 63% | 63% | 62% | 64% | |
| Specificity | 72% | 72% | 56% | 65% | 66% | |
| Cutoff Quartile 4 | 707000 | 704000 | 708000 | 707000 | 704000 | |
| Sensitivity | 33% | 34% | 42% | 35% | 36% | |
| Specificity | 92% | 90% | 82% | 88% | 87% | |
| OR Quartile 2 | 4.68 | 4.83 | 2.60 | 3.84 | 4.06 | |
| p Value | 1.1E−8 | 7.0E−9 | 0.0030 | 7.5E−7 | 4.0E−7 | |
| Lower limit of 95% CI | 2.76 | 2.83 | 1.38 | 2.25 | 2.36 | |
| Upper limit of 95% CI | 7.95 | 8.23 | 4.91 | 6.55 | 6.99 | |
| OR Quartile 3 | 4.10 | 4.24 | 2.13 | 3.11 | 3.50 | |
| p Value | 3.4E−8 | 6.3E−9 | 0.0022 | 1.1E−6 | 8.4E−8 | |
| Lower limit of 95% CI | 2.48 | 2.60 | 1.31 | 1.97 | 2.21 | |
| Upper limit of 95% CI | 6.77 | 6.90 | 3.45 | 4.90 | 5.53 | |
| OR Quartile 4 | 5.50 | 4.63 | 3.35 | 3.76 | 3.78 | |
| p Value | 6.0E−6 | 5.7E−6 | 6.1E−6 | 7.4E−6 | 5.0E−6 | |
| Lower limit of 95% CI | 2.63 | 2.39 | 1.98 | 2.11 | 2.14 | |
| Upper limit of 95% CI | 11.5 | 8.98 | 5.66 | 6.72 | 6.69 | |

| | Persistence Period Duration (hr) | | | |
|---|---|---|---|---|
| | 48 | 72 | | |
| | UO only | sCr or UO | sCr only | UO only |
| AUC | 0.68 | 0.71 | 0.71 | 0.69 |
| SE | 0.036 | 0.029 | 0.029 | 0.037 |
| p Value | 4.7E−7 | 2.8E−13 | 5.1E−13 | 9.9E−8 |
| nCohort Non-persistent | 241 | 164 | 166 | 248 |
| nCohort Persistent | 84 | 163 | 160 | 77 |
| Cutoff Quartile 2 | 262000 | 260000 | 260000 | 262000 |
| Sensitivity | 89% | 88% | 88% | 90% |
| Specificity | 30% | 38% | 37% | 29% |
| Cutoff Quartile 3 | 437000 | 437000 | 433000 | 437000 |
| Sensitivity | 65% | 63% | 64% | 69% |
| Specificity | 55% | 63% | 63% | 56% |
| Cutoff Quartile 4 | 708000 | 707000 | 704000 | 708000 |
| Sensitivity | 44% | 37% | 37% | 45% |
| Specificity | 81% | 87% | 86% | 81% |
| OR Quartile 2 | 3.55 | 4.35 | 4.17 | 3.60 |
| p Value | 8.5E−4 | 3.4E−7 | 7.0E−7 | 0.0013 |
| Lower limit of 95% CI | 1.69 | 2.47 | 2.37 | 1.65 |
| Upper limit of 95% CI | 7.47 | 7.64 | 7.34 | 7.86 |
| OR Quartile 3 | 2.34 | 2.90 | 3.03 | 2.77 |

TABLE 9.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

|  |  |  |  |  |
|---|---|---|---|---|
| p Value | 0.0013 | 3.4E−6 | 1.5E−6 | 2.4E−4 |
| Lower limit of 95% CI | 1.39 | 1.85 | 1.93 | 1.61 |
| Upper limit of 95% CI | 3.91 | 4.54 | 4.75 | 4.77 |
| OR Quartile 4 | 3.43 | 4.07 | 3.63 | 3.56 |
| p Value | 7.4E−6 | 7.8E−7 | 3.5E−6 | 5.8E−6 |
| Lower limit of 95% CI | 2.00 | 2.33 | 2.11 | 2.06 |
| Upper limit of 95% CI | 5.88 | 7.11 | 6.26 | 6.17 |

TABLE 9.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

|  | Persistence Period Duration (hr) | | | | | |
|---|---|---|---|---|---|---|
|  | 24 | | 48 | | 72 | |
|  | Non-persistent Cohort | Persistent Cohort | Non-persistent Cohort | Persistent Cohort | Non-persistent Cohort | Persistent Cohort |
| sCr or UO | | | | | | |
| Median | 270000 | 565000 | 298000 | 573000 | 303000 | 578000 |
| Average | 345000 | 569000 | 386000 | 579000 | 394000 | 590000 |
| Stdev | 223000 | 270000 | 238000 | 275000 | 238000 | 276000 |
| p (t-test) |  | 9.8E−13 |  | 1.2E−10 |  | 3.2E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 107 | 220 | 142 | 185 | 158 | 169 |
| sCr only | | | | | | |
| Median | 275000 | 574000 | 295000 | 582000 | 300000 | 590000 |
| Average | 349000 | 576000 | 379000 | 587000 | 388000 | 595000 |
| Stdev | 223000 | 268000 | 233000 | 271000 | 235000 | 273000 |
| p (t-test) |  | 7.8E−14 |  | 2.2E−12 |  | 2.0E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 118 | 208 | 146 | 180 | 160 | 166 |
| UO only | | | | | | |
| Median | 371000 | 595000 | 373000 | 598000 | 371000 | 602000 |
| Average | 440000 | 609000 | 446000 | 620000 | 447000 | 633000 |
| Stdev | 253000 | 286000 | 256000 | 285000 | 256000 | 283000 |
| p (t-test) |  | 1.1E−7 |  | 1.5E−7 |  | 3.7E−8 |
| Min | 13600 | 135000 | 13600 | 135000 | 13600 | 135000 |
| Max | 1120000 | 1090000 | 1120000 | 1090000 | 1120000 | 1090000 |
| n (Patient) | 216 | 109 | 230 | 95 | 237 | 88 |

|  | Persistence Period Duration (hr) | | | | |
|---|---|---|---|---|---|
|  | 24 | | | 48 | |
|  | sCr or UO | sCr only | UO only | sCr or UO | sCr only |
| AUC | 0.75 | 0.75 | 0.67 | 0.71 | 0.72 |
| SE | 0.027 | 0.027 | 0.033 | 0.028 | 0.028 |
| p Value | 0 | 0 | 1.1E−7 | 1.7E−13 | 4.4E−16 |
| nCohort Non-persistent | 107 | 118 | 216 | 142 | 146 |
| nCohort Persistent | 220 | 208 | 109 | 185 | 180 |
| Cutoff Quartile 2 | 260000 | 260000 | 262000 | 260000 | 260000 |

TABLE 9.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | |
|---|---|---|---|---|---|
| Sensitivity | 85% | 86% | 86% | 86% | 87% |
| Specificity | 46% | 45% | 31% | 39% | 40% |
| Cutoff Quartile 3 | 437000 | 433000 | 437000 | 437000 | 433000 |
| Sensitivity | 61% | 63% | 63% | 62% | 64% |
| Specificity | 73% | 73% | 56% | 65% | 67% |
| Cutoff Quartile 4 | 707000 | 704000 | 708000 | 707000 | 704000 |
| Sensitivity | 33% | 34% | 40% | 35% | 36% |
| Specificity | 92% | 91% | 82% | 87% | 88% |
| OR Quartile 2 | 4.79 | 5.03 | 2.76 | 3.98 | 4.28 |
| p Value | 7.3E−9 | 3.1E−9 | 0.0013 | 3.9E−7 | 1.5E−7 |
| Lower limit of 95% CI | 2.82 | 2.95 | 1.49 | 2.33 | 2.49 |
| Upper limit of 95% CI | 8.14 | 8.59 | 5.11 | 6.79 | 7.37 |
| OR Quartile 3 | 4.27 | 4.57 | 2.24 | 3.12 | 3.61 |
| p Value | 1.8E−8 | 1.6E−9 | 8.5E−4 | 1.0E−6 | 4.5E−8 |
| Lower limit of 95% CI | 2.58 | 2.79 | 1.39 | 1.98 | 2.28 |
| Upper limit of 95% CI | 7.08 | 7.49 | 3.59 | 4.92 | 5.72 |
| OR Quartile 4 | 5.41 | 5.04 | 3.17 | 3.64 | 3.92 |
| p Value | 7.4E−6 | 3.5E−6 | 1.3E−5 | 1.2E−5 | 3.9E−6 |
| Lower limit of 95% CI | 2.58 | 2.54 | 1.89 | 2.04 | 2.20 |
| Upper limit of 95% CI | 11.3 | 9.99 | 5.33 | 6.51 | 7.01 |

| | Persistence Period Duration (hr) | | | |
|---|---|---|---|---|
| | 48 | 72 | | |
| | UO only | sCr or UO | sCr only | UO only |
| AUC | 0.68 | 0.71 | 0.72 | 0.69 |
| SE | 0.034 | 0.028 | 0.028 | 0.035 |
| p Value | 1.7E−7 | 8.4E−14 | 2.0E−15 | 4.2E−8 |
| nCohort Non-persistent | 230 | 158 | 160 | 237 |
| nCohort Persistent | 95 | 169 | 166 | 88 |
| Cutoff Quartile 2 | 262000 | 260000 | 260000 | 262000 |
| Sensitivity | 88% | 88% | 88% | 89% |
| Specificity | 30% | 39% | 39% | 30% |
| Cutoff Quartile 3 | 437000 | 437000 | 433000 | 437000 |
| Sensitivity | 65% | 63% | 64% | 68% |
| Specificity | 56% | 63% | 64% | 57% |
| Cutoff Quartile 4 | 708000 | 707000 | 704000 | 708000 |
| Sensitivity | 41% | 36% | 37% | 42% |
| Specificity | 81% | 87% | 87% | 81% |
| OR Quartile 2 | 3.34 | 4.43 | 4.62 | 3.34 |
| p Value | 5.9E−4 | 1.7E−7 | 1.1E−7 | 9.5E−4 |
| Lower limit of 95% CI | 1.68 | 2.54 | 2.62 | 1.63 |
| Upper limit of 95% CI | 6.65 | 7.74 | 8.13 | 6.82 |
| OR Quartile 3 | 2.40 | 2.90 | 3.19 | 2.79 |
| p Value | 5.4E−4 | 3.4E−6 | 5.0E−7 | 1.0E−4 |
| Lower limit of 95% CI | 1.46 | 1.85 | 2.03 | 1.66 |
| Upper limit of 95% CI | 3.94 | 4.55 | 5.02 | 4.67 |
| OR Quartile 4 | 3.03 | 3.68 | 3.85 | 3.10 |
| p Value | 3.7E−5 | 4.3E−6 | 2.1E−6 | 3.3E−5 |
| Lower limit of 95% CI | 1.79 | 2.11 | 2.20 | 1.82 |
| Upper limit of 95% CI | 5.13 | 6.43 | 6.71 | 5.28 |

TABLE 9.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 272000 | 565000 | 296000 | 568000 | 301000 | 574000 |
| Average | 346000 | 567000 | 386000 | 577000 | 393000 | 587000 |
| Stdev | 224000 | 270000 | 239000 | 274000 | 240000 | 275000 |
| p (t-test) | | 2.2E−12 | | 1.7E−10 | | 6.5E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 106 | 221 | 140 | 187 | 155 | 172 |
| sCr only | | | | | | |
| Median | 275000 | 574000 | 293000 | 577000 | 300000 | 582000 |
| Average | 349000 | 576000 | 378000 | 585000 | 388000 | 593000 |
| Stdev | 223000 | 268000 | 234000 | 271000 | 236000 | 272000 |
| p (t-test) | | 7.8E−14 | | 3.0E−12 | | 3.0E−12 |
| Min | 13600 | 105000 | 13600 | 105000 | 13600 | 105000 |
| Max | 1040000 | 1120000 | 1040000 | 1120000 | 1040000 | 1120000 |
| n (Patient) | 118 | 208 | 144 | 182 | 158 | 168 |
| UO only | | | | | | |
| Median | 375000 | 577000 | 375000 | 590000 | 375000 | 595000 |
| Average | 443000 | 597000 | 445000 | 612000 | 445000 | 620000 |
| Stdev | 255000 | 286000 | 255000 | 286000 | 256000 | 284000 |
| p (t-test) | | 1.0E−6 | | 2.6E−7 | | 1.1E−7 |
| Min | 13600 | 135000 | 13600 | 135000 | 13600 | 135000 |
| Max | 1120000 | 1090000 | 1120000 | 1090000 | 1120000 | 1090000 |
| n (Patient) | 211 | 114 | 223 | 102 | 229 | 96 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.74 | 0.75 | 0.66 | 0.71 | 0.72 |
| SE | 0.027 | 0.027 | 0.033 | 0.028 | 0.028 |
| p Value | 0 | 0 | 9.4E−7 | 1.7E−13 | 4.4E−16 |
| nCohort Non-persistent | 106 | 118 | 211 | 140 | 144 |
| nCohort Persistent | 221 | 208 | 114 | 187 | 182 |
| Cutoff Quartile 2 | 260000 | 260000 | 262000 | 260000 | 260000 |
| Sensitivity | 85% | 86% | 86% | 86% | 87% |
| Specificity | 45% | 45% | 31% | 40% | 40% |
| Cutoff Quartile 3 | 437000 | 433000 | 437000 | 437000 | 433000 |
| Sensitivity | 61% | 63% | 61% | 62% | 64% |
| Specificity | 73% | 73% | 56% | 66% | 67% |
| Cutoff Quartile 4 | 707000 | 704000 | 708000 | 707000 | 704000 |
| Sensitivity | 33% | 34% | 39% | 34% | 35% |
| Specificity | 92% | 91% | 82% | 87% | 88% |
| OR Quartile 2 | 4.55 | 5.03 | 2.73 | 4.13 | 4.44 |
| p Value | 2.0E−8 | 3.1E−9 | 0.0011 | 2.0E−7 | 7.6E−8 |
| Lower limit of 95% CI | 2.68 | 2.95 | 1.49 | 2.42 | 2.58 |
| Upper limit of 95% CI | 7.73 | 8.59 | 4.99 | 7.05 | 7.64 |
| OR Quartile 3 | 4.17 | 4.57 | 2.02 | 3.13 | 3.63 |
| p Value | 3.1E−8 | 1.6E−9 | 0.0031 | 9.9E−7 | 4.3E−8 |
| Lower limit of 95% CI | 2.51 | 2.79 | 1.27 | 1.98 | 2.29 |
| Upper limit of 95% CI | 6.91 | 7.49 | 3.21 | 4.95 | 5.75 |
| OR Quartile 4 | 5.32 | 5.04 | 2.86 | 3.53 | 3.80 |
| p Value | 9.2E−6 | 3.5E−6 | 6.3E−5 | 2.0E−5 | 6.6E−6 |
| Lower limit of | 2.54 | 2.54 | 1.71 | 1.97 | 2.13 |

TABLE 9.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | |
|---|---|---|---|---|
| 95% CI Upper limit of 95% CI | 11.1 | 9.99 | 4.79 | 6.30 | 6.78 |

| | Persistence Period Duration (hr) | | | |
|---|---|---|---|---|
| | 48 | 72 | | |
| | UO only | sCr or UO | sCr only | UO only |
| AUC | 0.67 | 0.71 | 0.72 | 0.68 |
| SE | 0.033 | 0.028 | 0.028 | 0.034 |
| p Value | 2.2E−7 | 1.2E−13 | 2.2E−15 | 8.9E−8 |
| nCohort Non-persistent | 223 | 155 | 158 | 229 |
| nCohort Persistent | 102 | 172 | 168 | 96 |
| Cutoff Quartile 2 | 262000 | 260000 | 260000 | 262000 |
| Sensitivity | 89% | 88% | 88% | 90% |
| Specificity | 31% | 39% | 39% | 31% |
| Cutoff Quartile 3 | 437000 | 437000 | 433000 | 437000 |
| Sensitivity | 64% | 62% | 64% | 66% |
| Specificity | 56% | 63% | 65% | 56% |
| Cutoff Quartile 4 | 708000 | 707000 | 704000 | 708000 |
| Sensitivity | 39% | 35% | 36% | 40% |
| Specificity | 81% | 86% | 87% | 81% |
| OR Quartile 2 | 3.78 | 4.67 | 4.78 | 3.86 |
| p Value | 1.4E−4 | 6.6E−8 | 6.0E−8 | 2.0E−4 |
| Lower limit of 95% CI | 1.90 | 2.67 | 2.71 | 1.90 |
| Upper limit of 95% CI | 7.52 | 8.16 | 8.41 | 7.88 |
| OR Quartile 3 | 2.24 | 2.83 | 3.19 | 2.46 |
| p Value | 0.0010 | 5.6E−6 | 5.0E−7 | 3.6E−4 |
| Lower limit of 95% CI | 1.38 | 1.81 | 2.03 | 1.50 |
| Upper limit of 95% CI | 3.63 | 4.43 | 5.03 | 4.04 |
| OR Quartile 4 | 2.78 | 3.51 | 3.72 | 2.75 |
| p Value | 1.2E−4 | 9.8E−6 | 3.7E−6 | 1.5E−4 |
| Lower limit of 95% CI | 1.65 | 2.01 | 2.13 | 1.63 |
| Upper limit of 95% CI | 4.68 | 6.11 | 6.49 | 4.66 |

TABLE 9.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 272000 | 564000 | 293000 | 565000 | 294000 | 571000 |
| Average | 347000 | 562000 | 383000 | 575000 | 389000 | 585000 |
| Stdev | 227000 | 271000 | 238000 | 274000 | 239000 | 274000 |
| p (t-test) | | 1.6E−11 | | 1.9E−10 | | 4.2E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 102 | 225 | 135 | 192 | 149 | 178 |

TABLE 9.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | \multicolumn{6}{c}{sCr only} |
|---|---|---|---|---|---|---|
| Median | 275000 | 568000 | 293000 | 571000 | 303000 | 574000 |
| Average | 351000 | 571000 | 381000 | 579000 | 390000 | 586000 |
| Stdev | 225000 | 269000 | 236000 | 272000 | 238000 | 273000 |
| p (t-test) | | 8.4E−13 | | 3.2E−11 | | 3.4E−11 |
| Min | 13600 | 105000 | 13600 | 105000 | 13600 | 105000 |
| Max | 1040000 | 1120000 | 1040000 | 1120000 | 1040000 | 1120000 |
| n (Patient) | 115 | 211 | 140 | 186 | 154 | 172 |
| | \multicolumn{6}{c}{UO only} |
| Median | 369000 | 576000 | 363000 | 595000 | 367000 | 595000 |
| Average | 436000 | 601000 | 434000 | 618000 | 436000 | 623000 |
| Stdev | 250000 | 288000 | 249000 | 286000 | 250000 | 285000 |
| p (t-test) | | 1.1E−7 | | 5.6E−9 | | 4.2E−9 |
| Min | 13600 | 135000 | 13600 | 135000 | 13600 | 135000 |
| Max | 1040000 | 1120000 | 1040000 | 1120000 | 1040000 | 1120000 |
| n (Patient) | 204 | 121 | 214 | 111 | 219 | 106 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.74 | 0.74 | 0.67 | 0.71 | 0.72 |
| SE | 0.028 | 0.027 | 0.032 | 0.028 | 0.028 |
| p Value | 0 | 0 | 8.0E−8 | 1.3E−13 | 1.4E−14 |
| nCohort Non-persistent | 102 | 115 | 204 | 135 | 140 |
| nCohort Persistent | 225 | 211 | 121 | 192 | 186 |
| Cutoff Quartile 2 | 260000 | 260000 | 262000 | 260000 | 260000 |
| Sensitivity | 84% | 85% | 87% | 86% | 86% |
| Specificity | 45% | 44% | 32% | 41% | 40% |
| Cutoff Quartile 3 | 437000 | 433000 | 437000 | 437000 | 433000 |
| Sensitivity | 60% | 62% | 62% | 62% | 63% |
| Specificity | 73% | 72% | 57% | 67% | 67% |
| Cutoff Quartile 4 | 707000 | 704000 | 708000 | 707000 | 704000 |
| Sensitivity | 32% | 34% | 39% | 34% | 34% |
| Specificity | 91% | 90% | 83% | 87% | 87% |
| OR Quartile 2 | 4.31 | 4.63 | 3.07 | 4.20 | 4.10 |
| p Value | 5.9E−8 | 1.4E−8 | 2.7E−4 | 1.3E−7 | 2.3E−7 |
| Lower limit of 95% CI | 2.54 | 2.72 | 1.68 | 2.47 | 2.40 |
| Upper limit of 95% CI | 7.31 | 7.86 | 5.61 | 7.15 | 7.00 |
| OR Quartile 3 | 4.04 | 4.25 | 2.15 | 3.26 | 3.47 |
| p Value | 8.3E−8 | 9.3E−9 | 0.0011 | 5.2E−7 | 1.3E−7 |
| Lower limit of 95% CI | 2.42 | 2.59 | 1.36 | 2.06 | 2.18 |
| Upper limit of 95% CI | 6.73 | 6.96 | 3.40 | 5.17 | 5.50 |
| OR Quartile 4 | 4.96 | 4.79 | 3.07 | 3.55 | 3.56 |
| p Value | 2.1E−5 | 7.0E−6 | 2.1E−5 | 2.5E−5 | 1.8E−5 |
| Lower limit of 95% CI | 2.37 | 2.42 | 1.83 | 1.97 | 1.99 |
| Upper limit of 95% CI | 10.4 | 9.50 | 5.14 | 6.41 | 6.35 |

| | Persistence Period Duration (hr) | | | |
|---|---|---|---|---|
| | 48 | 72 | | |
| | UO only | sCr or UO | sCr only | UO only |
| AUC | 0.69 | 0.71 | 0.71 | 0.69 |
| SE | 0.032 | 0.028 | 0.028 | 0.032 |
| p Value | 3.1E−9 | 3.4E−14 | 6.5E−14 | 2.0E−9 |
| nCohort Non-persistent | 214 | 149 | 154 | 219 |
| nCohort | 111 | 178 | 172 | 106 |

TABLE 9.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| Persistent | | | | |
|---|---|---|---|---|
| Cutoff Quartile 2 | 262000 | 260000 | 260000 | 262000 |
| Sensitivity | 90% | 88% | 87% | 91% |
| Specificity | 33% | 40% | 39% | 32% |
| Cutoff Quartile 3 | 437000 | 437000 | 433000 | 437000 |
| Sensitivity | 65% | 62% | 63% | 66% |
| Specificity | 57% | 64% | 64% | 58% |
| Cutoff Quartile 4 | 708000 | 707000 | 704000 | 708000 |
| Sensitivity | 41% | 35% | 35% | 41% |
| Specificity | 83% | 87% | 86% | 82% |
| OR Quartile 2 | 4.42 | 4.78 | 4.35 | 4.61 |
| p Value | 2.1E−5 | 3.0E−8 | 1.8E−7 | 2.5E−5 |
| Lower limit of 95% CI | 2.23 | 2.75 | 2.50 | 2.26 |
| Upper limit of 95% CI | 8.77 | 8.32 | 7.56 | 9.37 |
| OR Quartile 3 | 2.50 | 3.00 | 3.04 | 2.63 |
| p Value | 1.6E−4 | 1.9E−6 | 1.4E−6 | 8.5E−5 |
| Lower limit of 95% CI | 1.55 | 1.91 | 1.93 | 1.63 |
| Upper limit of 95% CI | 4.01 | 4.72 | 4.77 | 4.27 |
| OR Quartile 4 | 3.26 | 3.75 | 3.48 | 3.15 |
| p Value | 7.9E−6 | 5.8E−6 | 1.1E−5 | 1.5E−5 |
| Lower limit of 95% CI | 1.94 | 2.12 | 2.00 | 1.87 |
| Upper limit of 95% CI | 5.48 | 6.64 | 6.07 | 5.30 |

Example 10. Use of Metalloproteinase Inhibitor 2 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 10.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 9920 | 16000 | 10100 | 15400 | 10000 | 15100 |
| Average | 12700 | 33200 | 13500 | 32200 | 13000 | 31900 |
| Stdev | 10100 | 58100 | 10900 | 57100 | 10500 | 56600 |
| p (t-test) | 0.0084 | | 0.027 | | 0.034 | |

TABLE 10.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 200 | 658 | 200 | 658 | 200 | 658 |
| Max | 42400 | 465000 | 42400 | 465000 | 38600 | 465000 |
| n (Patient) | 57 | 260 | 46 | 271 | 41 | 276 |
| | | sCr only | | | | |
| Median | 12000 | 14800 | 12000 | 14800 | 11600 | 14800 |
| Average | 16600 | 33200 | 16600 | 33100 | 15800 | 33100 |
| Stdev | 13400 | 60100 | 13600 | 59900 | 12500 | 59400 |
| p (t-test) | | 0.017 | | 0.020 | | 0.016 |
| Min | 200 | 658 | 200 | 658 | 200 | 658 |
| Max | 63200 | 465000 | 63200 | 465000 | 63200 | 465000 |
| n (Patient) | 76 | 240 | 74 | 242 | 70 | 246 |
| | | UO only | | | | |
| Median | 10600 | 21700 | 10300 | 21200 | 10100 | 19600 |
| Average | 19200 | 46300 | 19200 | 42300 | 19300 | 39700 |
| Stdev | 38500 | 68200 | 40400 | 63900 | 42200 | 61000 |
| p (t-test) | | 9.9E−6 | | 1.1E−4 | | 6.3E−4 |
| Min | 200 | 2170 | 200 | 2170 | 200 | 2170 |
| Max | 465000 | 428000 | 465000 | 428000 | 465000 | 428000 |
| n (Patient) | 194 | 121 | 173 | 142 | 156 | 159 |

| | Recovery Period Duration (hr) | | | | |
|---|---|---|---|---|---|
| | 24 | | | 48 | |
| | sCr or UO | sCr only | UO only | sCr or UO | sCr only |
| AUC | 0.67 | 0.58 | 0.74 | 0.65 | 0.57 |
| SE | 0.036 | 0.037 | 0.030 | 0.040 | 0.037 |
| p Value | 2.8E−6 | 0.037 | 6.7E−16 | 2.7E−4 | 0.042 |
| nCohort Recovered | 57 | 76 | 194 | 46 | 74 |
| nCohort Non-recovered | 260 | 240 | 121 | 271 | 242 |
| Cutoff Quartile 2 | 7990 | 7980 | 8020 | 7990 | 7980 |
| Sensitivity | 79% | 77% | 93% | 78% | 77% |
| Specificity | 42% | 30% | 37% | 41% | 31% |
| Cutoff Quartile 3 | 13500 | 13500 | 13500 | 13500 | 13500 |
| Sensitivity | 54% | 52% | 69% | 53% | 52% |
| Specificity | 68% | 57% | 62% | 67% | 57% |
| Cutoff Quartile 4 | 28900 | 28100 | 29400 | 28900 | 28100 |
| Sensitivity | 28% | 28% | 40% | 27% | 28% |
| Specificity | 89% | 84% | 85% | 87% | 84% |
| OR Quartile 2 | 2.71 | 1.43 | 8.15 | 2.47 | 1.50 |
| p Value | 0.0012 | 0.23 | 1.1E−7 | 0.0066 | 0.17 |
| Lower limit of 95% CI | 1.48 | 0.803 | 3.76 | 1.29 | 0.842 |
| Upper limit of 95% CI | 4.96 | 2.53 | 17.7 | 4.76 | 2.66 |
| OR Quartile 3 | 2.57 | 1.42 | 3.68 | 2.34 | 1.43 |
| p Value | 0.0024 | 0.19 | 1.2E−7 | 0.012 | 0.19 |
| Lower limit of 95% CI | 1.40 | 0.842 | 2.27 | 1.21 | 0.844 |
| Upper limit of 95% CI | 4.72 | 2.38 | 5.97 | 4.54 | 2.41 |
| OR Quartile 4 | 3.38 | 2.07 | 3.72 | 2.50 | 1.98 |
| p Value | 0.0071 | 0.036 | 1.3E−6 | 0.045 | 0.049 |
| Lower limit of 95% CI | 1.39 | 1.05 | 2.19 | 1.02 | 1.00 |
| Upper limit of 95% CI | 8.22 | 4.07 | 6.33 | 6.15 | 3.90 |

| | Recovery Period Duration (hr) | | | |
|---|---|---|---|---|
| | 48 | 72 | | |
| | UO only | sCr or UO | sCr only | UO only |
| AUC | 0.73 | 0.66 | 0.59 | 0.72 |
| SE | 0.029 | 0.042 | 0.037 | 0.029 |
| p Value | 5.1E−15 | 1.6E−4 | 0.018 | 1.6E−14 |
| nCohort | 173 | 41 | 70 | 156 |

TABLE 10.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

|  |  |  |  |  |
|---|---|---|---|---|
| Recovered nCohort Non-recovered | 142 | 276 | 246 | 159 |
| Cutoff Quartile 2 | 8020 | 7990 | 7980 | 8020 |
| Sensitivity | 91% | 78% | 77% | 89% |
| Specificity | 38% | 44% | 33% | 39% |
| Cutoff Quartile 3 | 13500 | 13500 | 13500 | 13500 |
| Sensitivity | 67% | 53% | 52% | 66% |
| Specificity | 64% | 68% | 57% | 66% |
| Cutoff Quartile 4 | 29400 | 28900 | 28100 | 29400 |
| Sensitivity | 37% | 27% | 28% | 35% |
| Specificity | 85% | 88% | 86% | 85% |
| OR Quartile 2 | 6.12 | 2.76 | 1.66 | 5.03 |
| p Value | 4.2E−8 | 0.0034 | 0.087 | 6.8E−8 |
| Lower limit of 95% CI | 3.20 | 1.40 | 0.929 | 2.80 |
| Upper limit of 95% CI | 11.7 | 5.44 | 2.97 | 9.04 |
| OR Quartile 3 | 3.53 | 2.42 | 1.45 | 3.78 |
| p Value | 1.2E−7 | 0.013 | 0.18 | 2.3E−8 |
| Lower limit of 95% CI | 2.21 | 1.20 | 0.847 | 2.37 |
| Upper limit of 95% CI | 5.63 | 4.87 | 2.47 | 6.02 |
| OR Quartile 4 | 3.37 | 2.69 | 2.34 | 2.91 |
| p Value | 9.8E−6 | 0.046 | 0.022 | 1.2E−4 |
| Lower limit of 95% CI | 1.97 | 1.02 | 1.13 | 1.69 |
| Upper limit of 95% CI | 5.77 | 7.10 | 4.83 | 5.01 |

TABLE 10.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 10600 | 18100 | 10900 | 17200 | 10600 | 16100 |
| Average | 13600 | 35800 | 14200 | 34600 | 13700 | 34100 |
| Stdev | 11500 | 61500 | 12100 | 60300 | 12000 | 59500 |
| p (t-test) | | 8.0E−4 | | 0.0031 | | 0.0045 |
| Min | 200 | 658 | 200 | 658 | 200 | 658 |
| Max | 76000 | 465000 | 76000 | 465000 | 76000 | 465000 |
| n (Patient) | 90 | 227 | 79 | 238 | 71 | 246 |
| sCr only | | | | | | |
| Median | 12000 | 16000 | 12000 | 16000 | 11400 | 16600 |
| Average | 16700 | 35900 | 16700 | 35600 | 16000 | 35600 |
| Stdev | 14200 | 63700 | 14300 | 63400 | 13600 | 62800 |
| p (t-test) | | 0.0023 | | 0.0028 | | 0.0022 |
| Min | 200 | 658 | 200 | 658 | 200 | 658 |
| Max | 76000 | 465000 | 76000 | 465000 | 76000 | 465000 |
| n (Patient) | 106 | 211 | 104 | 213 | 99 | 218 |
| UO only | | | | | | |
| Median | 11400 | 21700 | 11200 | 21100 | 10900 | 19500 |
| Average | 20000 | 49400 | 19900 | 45100 | 19900 | 42300 |
| Stdev | 37100 | 73200 | 38400 | 68700 | 39800 | 65300 |
| p (t-test) | | 3.4E−6 | | 3.9E−5 | | 2.0E−4 |
| Min | 200 | 2170 | 200 | 2170 | 200 | 2170 |
| Max | 465000 | 428000 | 465000 | 428000 | 465000 | 428000 |

TABLE 10.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| n (Patient) | 212 | 103 | 194 | 121 | 178 | 137 |
|---|---|---|---|---|---|---|

| | Recovery Period Duration (hr) | | | | |
|---|---|---|---|---|---|
| | 24 | | | 48 | |
| | sCr or UO | sCr only | UO only | sCr or UO | sCr only |
| AUC | 0.66 | 0.59 | 0.71 | 0.64 | 0.59 |
| SE | 0.032 | 0.033 | 0.032 | 0.034 | 0.033 |
| p Value | 5.3E−7 | 0.0065 | 7.9E−11 | 3.3E−5 | 0.0075 |
| nCohort Recovered | 90 | 106 | 212 | 79 | 104 |
| nCohort Non-recovered | 227 | 211 | 103 | 238 | 213 |
| Cutoff Quartile 2 | 7990 | 7990 | 8020 | 7990 | 7990 |
| Sensitivity | 79% | 77% | 90% | 78% | 77% |
| Specificity | 34% | 28% | 33% | 34% | 29% |
| Cutoff Quartile 3 | 13500 | 13500 | 13500 | 13500 | 13500 |
| Sensitivity | 56% | 54% | 68% | 55% | 54% |
| Specificity | 66% | 57% | 58% | 65% | 57% |
| Cutoff Quartile 4 | 28900 | 28900 | 29400 | 28900 | 28900 |
| Sensitivity | 31% | 30% | 41% | 30% | 30% |
| Specificity | 90% | 85% | 83% | 89% | 85% |
| OR Quartile 2 | 1.96 | 1.31 | 4.49 | 1.86 | 1.36 |
| p Value | 0.014 | 0.32 | 3.7E−5 | 0.029 | 0.26 |
| Lower limit of 95% CI | 1.14 | 0.768 | 2.20 | 1.06 | 0.798 |
| Upper limit of 95% CI | 3.36 | 2.22 | 9.15 | 3.24 | 2.31 |
| OR Quartile 3 | 2.46 | 1.50 | 2.99 | 2.23 | 1.51 |
| p Value | 5.1E−4 | 0.089 | 1.5E−5 | 0.0029 | 0.087 |
| Lower limit of 95% CI | 1.48 | 0.940 | 1.82 | 1.32 | 0.942 |
| Upper limit of 95% CI | 4.09 | 2.41 | 4.91 | 3.78 | 2.42 |
| OR Quartile 4 | 4.10 | 2.45 | 3.26 | 3.31 | 2.36 |
| p Value | 2.0E−4 | 0.0039 | 1.2E−5 | 0.0017 | 0.0056 |
| Lower limit of 95% CI | 1.95 | 1.33 | 1.92 | 1.57 | 1.29 |
| Upper limit of 95% CI | 8.62 | 4.50 | 5.53 | 6.98 | 4.34 |

| | Recovery Period Duration (hr) | | | |
|---|---|---|---|---|
| | 48 | 72 | | |
| | UO only | sCr or UO | sCr only | UO only |
| AUC | 0.69 | 0.65 | 0.60 | 0.69 |
| SE | 0.031 | 0.035 | 0.033 | 0.030 |
| p Value | 6.2E−10 | 9.4E−6 | 0.0018 | 7.6E−10 |
| nCohort Recovered | 194 | 71 | 99 | 178 |
| nCohort Non-recovered | 121 | 246 | 218 | 137 |
| Cutoff Quartile 2 | 8020 | 7990 | 7990 | 8020 |
| Sensitivity | 88% | 78% | 78% | 87% |
| Specificity | 34% | 37% | 30% | 34% |
| Cutoff Quartile 3 | 13500 | 13500 | 13500 | 13500 |
| Sensitivity | 65% | 54% | 54% | 65% |
| Specificity | 59% | 65% | 58% | 61% |
| Cutoff Quartile 4 | 29400 | 28900 | 28900 | 29400 |
| Sensitivity | 38% | 30% | 31% | 36% |
| Specificity | 83% | 90% | 87% | 83% |
| OR Quartile 2 | 3.85 | 2.10 | 1.50 | 3.45 |
| p Value | 2.9E−5 | 0.011 | 0.14 | 3.3E−5 |
| Lower limit of 95% CI | 2.05 | 1.19 | 0.879 | 1.92 |
| Upper limit of 95% CI | 7.24 | 3.72 | 2.56 | 6.18 |
| OR Quartile 3 | 2.74 | 2.20 | 1.57 | 2.93 |
| p Value | 2.8E−5 | 0.0048 | 0.064 | 5.3E−6 |

TABLE 10.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | |
|---|---|---|---|---|
| Lower limit of 95% CI | 1.71 | 1.27 | 0.973 | 1.84 |
| Upper limit of 95% CI | 4.39 | 3.81 | 2.54 | 4.65 |
| OR Quartile 4 | 2.99 | 3.86 | 2.94 | 2.75 |
| p Value | 4.2E-5 | 0.0014 | 0.0012 | 1.6E-4 |
| Lower limit of 95% CI | 1.77 | 1.69 | 1.53 | 1.62 |
| Upper limit of 95% CI | 5.06 | 8.82 | 5.62 | 4.65 |

TABLE 10.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11300 | 18600 | 11300 | 18100 | 11000 | 17900 |
| Average | 15000 | 37600 | 15200 | 36800 | 14600 | 36000 |
| Stdev | 13100 | 64600 | 13400 | 63700 | 12800 | 62400 |
| p (t-test) | | 2.5E-4 | | 5.9E-4 | | 9.1E-4 |
| Min | 200 | 658 | 200 | 658 | 200 | 658 |
| Max | 76000 | 465000 | 76000 | 465000 | 76000 | 465000 |
| n (Patient) | 114 | 203 | 107 | 210 | 97 | 220 |
| | sCr only | | | | | |
| Median | 11900 | 18000 | 12000 | 17900 | 11600 | 17900 |
| Average | 16800 | 38000 | 17000 | 37500 | 16400 | 37400 |
| Stdev | 14800 | 66600 | 14900 | 66100 | 14300 | 65400 |
| p (t-test) | | 4.9E-4 | | 7.4E-4 | | 6.3E-4 |
| Min | 200 | 658 | 200 | 658 | 200 | 658 |
| Max | 76000 | 465000 | 76000 | 465000 | 76000 | 465000 |
| n (Patient) | 127 | 190 | 124 | 193 | 119 | 198 |
| | UO only | | | | | |
| Median | 11600 | 21500 | 11500 | 21400 | 11300 | 20600 |
| Average | 20700 | 48500 | 20800 | 45900 | 20100 | 44000 |
| Stdev | 37700 | 73600 | 38500 | 70900 | 38900 | 67800 |
| p (t-test) | | 1.3E-5 | | 5.7E-5 | | 8.9E-5 |
| Min | 200 | 2170 | 200 | 2170 | 200 | 2170 |
| Max | 465000 | 428000 | 465000 | 428000 | 465000 | 428000 |
| n (Patient) | 214 | 101 | 204 | 111 | 190 | 125 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.61 | 0.69 | 0.64 | 0.60 | 0.68 | 0.64 | 0.61 | 0.68 |
| SE | 0.031 | 0.032 | 0.033 | 0.032 | 0.032 | 0.033 | 0.032 | 0.032 | 0.031 |
| p Value | 2.5E-6 | 8.2E-4 | 1.7E-8 | 1.3E-5 | 0.0016 | 4.5E-8 | 6.7E-6 | 5.3E-4 | 7.1E-9 |
| nCohort Recovered | 114 | 127 | 214 | 107 | 124 | 204 | 97 | 119 | 190 |
| nCohort Non-recovered | 203 | 190 | 101 | 210 | 193 | 111 | 220 | 198 | 125 |
| Cutoff Quartile 2 | 7990 | 7990 | 8020 | 7990 | 7990 | 8020 | 7990 | 7990 | 8020 |
| Sensitivity | 80% | 79% | 87% | 80% | 79% | 86% | 80% | 79% | 86% |
| Specificity | 34% | 31% | 31% | 35% | 31% | 31% | 36% | 32% | 33% |
| Cutoff Quartile 3 | 13500 | 13500 | 13500 | 13500 | 13500 | 13500 | 13500 | 13500 | 13500 |
| Sensitivity | 57% | 55% | 65% | 57% | 55% | 64% | 56% | 55% | 64% |

TABLE 10.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| Specificity | 62% | 57% | 57% | 63% | 57% | 57% | 63% | 58% | 59% |
|---|---|---|---|---|---|---|---|---|---|
| Cutoff Quartile 4 | 28900 | 28900 | 29400 | 28900 | 28900 | 29400 | 28900 | 28900 | 29400 |
| Sensitivity | 33% | 32% | 41% | 31% | 32% | 39% | 31% | 32% | 38% |
| Specificity | 88% | 85% | 82% | 87% | 85% | 82% | 89% | 87% | 83% |
| OR Quartile 2 | 2.12 | 1.78 | 3.02 | 2.11 | 1.76 | 2.93 | 2.26 | 1.80 | 3.08 |
| p Value | 0.0046 | 0.028 | 8.7E−4 | 0.0050 | 0.032 | 6.8E−4 | 0.0026 | 0.026 | 2.1E−4 |
| Lower limit of 95% CI | 1.26 | 1.06 | 1.57 | 1.25 | 1.05 | 1.57 | 1.33 | 1.07 | 1.70 |
| Upper limit of 95% CI | 3.56 | 2.98 | 5.79 | 3.57 | 2.94 | 5.44 | 3.84 | 3.01 | 5.58 |
| OR Quartile 3 | 2.20 | 1.67 | 2.50 | 2.19 | 1.63 | 2.39 | 2.15 | 1.69 | 2.55 |
| p Value | 9.9E−4 | 0.027 | 2.5E−4 | 0.0013 | 0.035 | 3.5E−4 | 0.0022 | 0.025 | 8.0E−5 |
| Lower limit of 95% CI | 1.38 | 1.06 | 1.53 | 1.36 | 1.04 | 1.48 | 1.32 | 1.07 | 1.60 |
| Upper limit of 95% CI | 3.52 | 2.63 | 4.09 | 3.53 | 2.57 | 3.84 | 3.51 | 2.68 | 4.07 |
| OR Quartile 4 | 3.44 | 2.69 | 3.16 | 3.04 | 2.55 | 2.95 | 3.57 | 3.07 | 2.98 |
| p Value | 1.3E−4 | 7.5E−4 | 2.0E−5 | 5.7E−4 | 0.0014 | 5.3E−5 | 2.9E−4 | 2.7E−4 | 4.7E−5 |
| Lower limit of 95% CI | 1.83 | 1.51 | 1.86 | 1.62 | 1.44 | 1.75 | 1.79 | 1.68 | 1.76 |
| Upper limit of 95% CI | 6.47 | 4.78 | 5.38 | 5.73 | 4.54 | 4.99 | 7.12 | 5.63 | 5.03 |

TABLE 10.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11400 | 18600 | 11300 | 18400 | 10900 | 18200 |
| Average | 17300 | 38500 | 17300 | 37400 | 17000 | 36500 |
| Stdev | 22300 | 66200 | 22900 | 64900 | 23500 | 63300 |
| p (t-test) | | 4.3E−4 | | 9.4E−4 | | 0.0017 |
| Min | 200 | 658 | 200 | 658 | 200 | 658 |
| Max | 215000 | 465000 | 215000 | 465000 | 215000 | 465000 |
| n (Patient) | 134 | 183 | 125 | 192 | 114 | 203 |
| | sCr only | | | | | |
| Median | 11800 | 18200 | 11800 | 18100 | 11600 | 18100 |
| Average | 18000 | 38600 | 18100 | 38300 | 17800 | 38200 |
| Stdev | 22400 | 67300 | 22600 | 66900 | 22400 | 66500 |
| p (t-test) | | 6.0E−4 | | 7.8E−4 | | 6.9E−4 |
| Min | 200 | 658 | 200 | 658 | 200 | 658 |
| Max | 215000 | 465000 | 215000 | 465000 | 215000 | 465000 |
| n (Patient) | 140 | 177 | 138 | 179 | 135 | 182 |
| | UO only | | | | | |
| Median | 11600 | 21400 | 11400 | 21500 | 11400 | 20600 |
| Average | 20700 | 49000 | 20600 | 46900 | 20200 | 44700 |
| Stdev | 37500 | 74400 | 38100 | 71700 | 38500 | 68700 |
| p (t-test) | | 1.0E−5 | | 2.8E−5 | | 6.8E−5 |
| Min | 200 | 2170 | 200 | 2170 | 200 | 2170 |
| Max | 465000 | 428000 | 465000 | 428000 | 465000 | 428000 |
| n (Patient) | 216 | 99 | 207 | 108 | 194 | 121 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.68 | 0.64 | 0.62 | 0.68 | 0.65 | 0.62 | 0.67 |

TABLE 10.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| SE | 0.031 | 0.031 | 0.034 | 0.031 | 0.031 | 0.033 | 0.031 | 0.031 | 0.032 |
| p Value | 3.5E−6 | 9.1E−5 | 9.1E−8 | 5.6E−6 | 1.4E−4 | 4.5E−8 | 2.0E−6 | 7.2E−5 | 4.2E−8 |
| nCohort Recovered | 134 | 140 | 216 | 125 | 138 | 207 | 114 | 135 | 194 |
| nCohort Non-recovered | 183 | 177 | 99 | 192 | 179 | 108 | 203 | 182 | 121 |
| Cutoff Quartile 2 | 7990 | 7990 | 8020 | 7990 | 7990 | 8020 | 7990 | 7990 | 8020 |
| Sensitivity | 82% | 82% | 86% | 82% | 82% | 86% | 82% | 81% | 85% |
| Specificity | 34% | 34% | 30% | 35% | 33% | 31% | 37% | 33% | 31% |
| Cutoff Quartile 3 | 13500 | 13500 | 13500 | 13500 | 13500 | 13500 | 13500 | 13500 | 13500 |
| Sensitivity | 57% | 56% | 65% | 57% | 56% | 65% | 57% | 56% | 64% |
| Specificity | 60% | 57% | 56% | 61% | 57% | 57% | 61% | 58% | 58% |
| Cutoff Quartile 4 | 28900 | 28900 | 29400 | 28900 | 28900 | 29400 | 28900 | 28900 | 29400 |
| Sensitivity | 33% | 33% | 41% | 32% | 33% | 40% | 32% | 34% | 38% |
| Specificity | 86% | 85% | 82% | 86% | 85% | 83% | 86% | 86% | 83% |
| OR Quartile 2 | 2.38 | 2.29 | 2.61 | 2.44 | 2.21 | 2.77 | 2.62 | 2.18 | 2.62 |
| p Value | 0.0011 | 0.0018 | 0.0031 | 7.6E−4 | 0.0026 | 0.0013 | 3.0E−4 | 0.0032 | 0.0012 |
| Lower limit of 95% CI | 1.41 | 1.36 | 1.38 | 1.45 | 1.32 | 1.49 | 1.55 | 1.30 | 1.46 |
| Upper limit of 95% CI | 3.99 | 3.85 | 4.94 | 4.09 | 3.71 | 5.16 | 4.41 | 3.65 | 4.71 |
| OR Quartile 3 | 1.99 | 1.69 | 2.37 | 2.08 | 1.69 | 2.49 | 2.08 | 1.74 | 2.44 |
| p Value | 0.0028 | 0.021 | 5.8E−4 | 0.0018 | 0.021 | 2.0E−4 | 0.0022 | 0.015 | 1.8E−4 |
| Lower limit of 95% CI | 1.27 | 1.08 | 1.45 | 1.31 | 1.08 | 1.54 | 1.30 | 1.11 | 1.53 |
| Upper limit of 95% CI | 3.14 | 2.65 | 3.88 | 3.29 | 2.65 | 4.03 | 3.32 | 2.74 | 3.90 |
| OR Quartile 4 | 3.03 | 2.83 | 3.31 | 2.84 | 2.74 | 3.14 | 2.82 | 3.08 | 2.99 |
| p Value | 1.6E−4 | 2.6E−4 | 1.0E−5 | 4.7E−4 | 4.1E−4 | 2.1E−5 | 7.9E−4 | 1.3E−4 | 4.2E−5 |
| Lower limit of 95% CI | 1.70 | 1.62 | 1.95 | 1.58 | 1.57 | 1.86 | 1.54 | 1.73 | 1.77 |
| Upper limit of 95% CI | 5.38 | 4.96 | 5.63 | 5.08 | 4.79 | 5.32 | 5.17 | 5.47 | 5.06 |

TABLE 10.5

Comparison of marker levels and the area under the ROC curve (AUC) in urine samples for the "recovered" and "non-recovered" cohorts where recovery stalls within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 11900 | 19800 | 11900 | 20000 | 11900 | 20000 |
| Average | 20700 | 42300 | 20600 | 42000 | 20600 | 42000 |
| Stdev | 38800 | 67400 | 39100 | 66700 | 39100 | 66700 |
| p (t-test) | | 3.4E−4 | | 3.9E−4 | | 3.9E−4 |
| Min | 200 | 1490 | 200 | 1490 | 200 | 1490 |
| Max | 465000 | 428000 | 465000 | 428000 | 465000 | 428000 |
| n (Patient) | 188 | 129 | 185 | 132 | 185 | 132 |
| sCr only | | | | | | |
| Median | 11800 | 18800 | 12000 | 18300 | 12000 | 18500 |
| Average | 18600 | 40600 | 18700 | 40000 | 18500 | 40200 |
| Stdev | 22400 | 70800 | 22500 | 70200 | 22300 | 70000 |
| p (t-test) | | 2.0E−4 | | 3.4E−4 | | 2.6E−4 |
| Min | 200 | 658 | 200 | 658 | 200 | 658 |
| Max | 215000 | 465000 | 215000 | 465000 | 215000 | 465000 |
| n (Patient) | 160 | 157 | 160 | 156 | 160 | 161 |
| UO only | | | | | | |
| Median | 11500 | 21500 | 11500 | 21500 | 11400 | 21500 |
| Average | 20500 | 48000 | 20500 | 47400 | 20000 | 47400 |
| Stdev | 37700 | 72900 | 37900 | 72000 | 37500 | 71500 |
| p (t-test) | | 1.4E−5 | | 1.8E−5 | | 1.1E−5 |
| Min | 200 | 2170 | 200 | 2170 | 200 | 2170 |
| Max | 465000 | 428000 | 465000 | 428000 | 465000 | 428000 |

TABLE 10.5-continued

Comparison of marker levels and the area under the ROC curve (AUC) in urine samples for the "recovered" and "non-recovered" cohorts where recovery stalls within 168 hours after sample collection and renal status is assessed by serum creatinine (sCr) only, urine output (UO) only, or serum creatinine or urine output RIFLE criteria.

| n (Patient) | 211 | 104 | 208 | 107 | 205 | 110 |
|---|---|---|---|---|---|---|

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.62 | 0.68 | 0.64 | 0.61 | 0.68 | 0.64 | 0.62 | 0.68 |
| SE | 0.032 | 0.031 | 0.033 | 0.032 | 0.031 | 0.033 | 0.032 | 0.031 | 0.033 |
| p Value | 3.2E−5 | 1.8E−4 | 9.2E−8 | 1.6E−5 | 4.8E−4 | 5.0E−8 | 1.6E−5 | 2.4E−4 | 2.9E−8 |
| nCohort Recovered | 188 | 160 | 211 | 185 | 157 | 208 | 185 | 156 | 205 |
| nCohort Non-recovered | 129 | 157 | 104 | 132 | 160 | 107 | 132 | 161 | 110 |
| Cutoff Quartile 2 | 7990 | 7990 | 8020 | 7990 | 7990 | 8020 | 7990 | 7990 | 8020 |
| Sensitivity | 83% | 82% | 85% | 83% | 81% | 85% | 83% | 81% | 85% |
| Specificity | 30% | 31% | 30% | 31% | 31% | 30% | 31% | 31% | 30% |
| Cutoff Quartile 3 | 13500 | 13500 | 13500 | 13500 | 13500 | 13500 | 13500 | 13500 | 13500 |
| Sensitivity | 60% | 57% | 65% | 60% | 56% | 65% | 60% | 56% | 65% |
| Specificity | 56% | 56% | 57% | 57% | 55% | 58% | 57% | 56% | 58% |
| Cutoff Quartile 4 | 28900 | 28900 | 29400 | 28900 | 28900 | 29400 | 28900 | 28900 | 29400 |
| Sensitivity | 36% | 34% | 41% | 36% | 34% | 41% | 36% | 34% | 41% |
| Specificity | 82% | 84% | 83% | 82% | 83% | 83% | 82% | 84% | 83% |
| OR Quartile 2 | 2.12 | 2.01 | 2.34 | 2.23 | 1.97 | 2.47 | 2.23 | 2.00 | 2.37 |
| p Value | 0.0080 | 0.0092 | 0.0062 | 0.0046 | 0.011 | 0.0035 | 0.0046 | 0.0092 | 0.0046 |
| Lower limit of 95% CI | 1.22 | 1.19 | 1.27 | 1.28 | 1.17 | 1.35 | 1.28 | 1.19 | 1.31 |
| Upper limit of 95% CI | 3.68 | 3.39 | 4.30 | 3.87 | 3.31 | 4.54 | 3.87 | 3.37 | 4.31 |
| OR Quartile 3 | 1.91 | 1.68 | 2.54 | 1.96 | 1.56 | 2.58 | 1.96 | 1.60 | 2.62 |
| p Value | 0.0051 | 0.022 | 1.8E−4 | 0.0037 | 0.050 | 1.2E−4 | 0.0037 | 0.038 | 8.6E−5 |
| Lower limit of 95% CI | 1.21 | 1.08 | 1.56 | 1.24 | 1.00 | 1.59 | 1.24 | 1.03 | 1.62 |
| Upper limit of 95% CI | 3.02 | 2.62 | 4.13 | 3.08 | 2.43 | 4.19 | 3.08 | 2.49 | 4.24 |
| OR Quartile 4 | 2.51 | 2.70 | 3.43 | 2.55 | 2.57 | 3.45 | 2.55 | 2.72 | 3.48 |
| p Value | 4.9E−4 | 2.6E−4 | 5.3E−6 | 4.1E−4 | 5.3E−4 | 4.5E−6 | 4.1E−4 | 2.7E−4 | 3.8E−6 |
| Lower limit of 95% CI | 1.50 | 1.58 | 2.02 | 1.52 | 1.51 | 2.03 | 1.52 | 1.59 | 2.05 |
| Upper limit of 95% CI | 4.21 | 4.61 | 5.82 | 4.28 | 4.38 | 5.86 | 4.28 | 4.65 | 5.91 |

TABLE 10.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 94400 | 115000 | 94100 | 114000 | 92400 | 114000 |
| Average | 101000 | 126000 | 101000 | 125000 | 99500 | 125000 |
| Stdev | 32200 | 45000 | 31900 | 44800 | 32900 | 44600 |
| p (t-test) | | 2.7E−4 | | 0.0010 | | 8.8E−4 |
| Min | 57600 | 57000 | 57600 | 57000 | 57600 | 57000 |
| Max | 213000 | 299000 | 213000 | 299000 | 213000 | 299000 |
| n (Patient) | 52 | 275 | 42 | 285 | 38 | 289 |
| | sCr only | | | | | |
| Median | 96000 | 116000 | 96000 | 116000 | 96000 | 115000 |
| Average | 101000 | 127000 | 101000 | 127000 | 101000 | 127000 |
| Stdev | 26600 | 46300 | 26000 | 46300 | 26400 | 46100 |
| p (t-test) | | 1.3E−5 | | 1.1E−5 | | 2.6E−5 |
| Min | 57600 | 57000 | 57600 | 57000 | 57600 | 57000 |

TABLE 10.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 213000 | 299000 | 213000 | 299000 | 213000 | 299000 |
| n (Patient) | 69 | 257 | 67 | 259 | 63 | 263 |
| UO only | | | | | | |
| Median | 104000 | 121000 | 104000 | 120000 | 102000 | 119000 |
| Average | 117000 | 130000 | 115000 | 131000 | 115000 | 129000 |
| Stdev | 43200 | 44400 | 41100 | 46100 | 41900 | 45300 |
| p (t-test) | | 0.0058 | | 9.9E−4 | | 0.0047 |
| Min | 57000 | 64800 | 57000 | 64800 | 57600 | 57000 |
| Max | 299000 | 281000 | 299000 | 281000 | 299000 | 281000 |
| n (Patient) | 197 | 128 | 176 | 149 | 159 | 166 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.61 | 0.70 | 0.69 | 0.62 | 0.72 | 0.69 | 0.61 |
| SE | 0.035 | 0.033 | 0.032 | 0.039 | 0.033 | 0.031 | 0.038 | 0.034 | 0.031 |
| p Value | 2.0E−8 | 2.3E−8 | 3.9E−4 | 4.2E−7 | 1.6E−8 | 1.4E−4 | 1.6E−8 | 4.7E−8 | 3.3E−4 |
| nCohort Recovered | 52 | 69 | 197 | 42 | 67 | 176 | 38 | 63 | 159 |
| nCohort Non-recovered | 275 | 257 | 128 | 285 | 259 | 149 | 289 | 263 | 166 |
| Cutoff Quartile 2 | 90200 | 90200 | 90200 | 90200 | 90200 | 90200 | 90200 | 90200 | 90200 |
| Sensitivity | 78% | 78% | 85% | 78% | 78% | 84% | 78% | 78% | 83% |
| Specificity | 42% | 38% | 31% | 43% | 37% | 32% | 47% | 38% | 33% |
| Cutoff Quartile 3 | 109000 | 109000 | 109000 | 109000 | 109000 | 109000 | 109000 | 109000 | 109000 |
| Sensitivity | 55% | 56% | 60% | 54% | 56% | 60% | 54% | 55% | 58% |
| Specificity | 77% | 71% | 56% | 76% | 72% | 58% | 79% | 71% | 58% |
| Cutoff Quartile 4 | 137000 | 137000 | 137000 | 137000 | 137000 | 137000 | 137000 | 137000 | 137000 |
| Sensitivity | 28% | 30% | 32% | 28% | 30% | 32% | 27% | 30% | 30% |
| Specificity | 92% | 93% | 79% | 93% | 94% | 80% | 92% | 94% | 79% |
| OR Quartile 2 | 2.63 | 2.17 | 2.63 | 2.59 | 2.11 | 2.49 | 3.16 | 2.18 | 2.46 |
| p Value | 0.0023 | 0.0077 | 9.1E−4 | 0.0055 | 0.011 | 8.9E−4 | 0.0012 | 0.0094 | 7.3E−4 |
| Lower limit of 95% CI | 1.41 | 1.23 | 1.49 | 1.32 | 1.19 | 1.46 | 1.58 | 1.21 | 1.46 |
| Upper limit of 95% CI | 4.89 | 3.84 | 4.67 | 5.07 | 3.75 | 4.28 | 6.34 | 3.91 | 4.16 |
| OR Quartile 3 | 4.12 | 3.07 | 1.95 | 3.76 | 3.16 | 2.04 | 4.40 | 3.07 | 1.98 |
| p Value | 5.4E−5 | 1.3E−4 | 0.0038 | 5.1E−4 | 1.1E−4 | 0.0016 | 3.6E−4 | 2.4E−4 | 0.0024 |
| Lower limit of 95% CI | 2.07 | 1.73 | 1.24 | 1.78 | 1.76 | 1.31 | 1.95 | 1.69 | 1.27 |
| Upper limit of 95% CI | 8.19 | 5.46 | 3.06 | 7.94 | 5.68 | 3.19 | 9.92 | 5.59 | 3.08 |
| OR Quartile 4 | 4.75 | 5.48 | 1.79 | 4.99 | 6.79 | 1.86 | 4.39 | 6.22 | 1.60 |
| p Value | 0.0037 | 4.4E−4 | 0.024 | 0.0088 | 3.3E−4 | 0.017 | 0.016 | 6.2E−4 | 0.070 |
| Lower limit of 95% CI | 1.66 | 2.12 | 1.08 | 1.50 | 2.39 | 1.12 | 1.31 | 2.18 | 0.962 |
| Upper limit of 95% CI | 13.6 | 14.1 | 2.97 | 16.6 | 19.3 | 3.08 | 14.7 | 17.7 | 2.66 |

TABLE 10.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 97900 | 116000 | 97400 | 115000 | 96000 | 114000 |
| Average | 108000 | 127000 | 110000 | 125000 | 110000 | 125000 |
| Stdev | 35600 | 45800 | 37400 | 45400 | 38900 | 44900 |
| p (t-test) | | 4.8E−4 | | 0.0059 | | 0.012 |

TABLE 10.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 57600 | 57000 | 57600 | 57000 | 57600 | 57000 |
| Max | 257000 | 299000 | 257000 | 299000 | 257000 | 299000 |
| n (Patient) | 87 | 240 | 76 | 251 | 69 | 258 | sCr only

| | | | | | | |
|---|---|---|---|---|---|---|
| Median | 98100 | 117000 | 98100 | 117000 | 98000 | 117000 |
| Average | 107000 | 129000 | 106000 | 128000 | 107000 | 128000 |
| Stdev | 32600 | 46900 | 32400 | 46800 | 32900 | 46600 |
| p (t-test) | | 2.4E−5 | | 2.4E−5 | | 8.9E−5 |
| Min | 57600 | 57000 | 57600 | 57000 | 57600 | 57000 |
| Max | 257000 | 299000 | 257000 | 299000 | 257000 | 299000 |
| n (Patient) | 101 | 226 | 99 | 228 | 94 | 233 |

UO only

| | | | | | | |
|---|---|---|---|---|---|---|
| Median | 105000 | 123000 | 105000 | 120000 | 104000 | 120000 |
| Average | 117000 | 133000 | 116000 | 131000 | 116000 | 129000 |
| Stdev | 42700 | 45300 | 42100 | 45900 | 42900 | 44600 |
| p (t-test) | | 0.0019 | | 0.0029 | | 0.0066 |
| Min | 57600 | 57000 | 57600 | 57000 | 57600 | 57000 |
| Max | 299000 | 281000 | 299000 | 281000 | 299000 | 281000 |
| n (Patient) | 217 | 108 | 198 | 127 | 181 | 144 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.66 | 0.62 | 0.62 | 0.66 | 0.61 | 0.63 | 0.65 | 0.61 |
| SE | 0.033 | 0.031 | 0.034 | 0.035 | 0.031 | 0.032 | 0.036 | 0.032 | 0.032 |
| p Value | 5.8E−6 | 4.8E−7 | 2.1E−4 | 3.4E−4 | 4.5E−7 | 5.1E−4 | 4.5E−4 | 3.5E−6 | 3.6E−4 |
| nCohort Recovered | 87 | 101 | 217 | 76 | 99 | 198 | 69 | 94 | 181 |
| nCohort Non-recovered | 240 | 226 | 108 | 251 | 228 | 127 | 258 | 233 | 144 |
| Cutoff Quartile 2 | 90200 | 90200 | 90200 | 90200 | 90200 | 90200 | 90200 | 90200 | 90200 |
| Sensitivity | 78% | 79% | 86% | 78% | 79% | 84% | 78% | 79% | 84% |
| Specificity | 34% | 35% | 30% | 34% | 34% | 31% | 36% | 34% | 32% |
| Cutoff Quartile 3 | 109000 | 109000 | 109000 | 109000 | 109000 | 109000 | 109000 | 109000 | 109000 |
| Sensitivity | 57% | 58% | 62% | 55% | 57% | 60% | 54% | 57% | 59% |
| Specificity | 69% | 66% | 56% | 66% | 67% | 56% | 65% | 66% | 57% |
| Cutoff Quartile 4 | 137000 | 137000 | 137000 | 137000 | 137000 | 137000 | 137000 | 137000 | 137000 |
| Sensitivity | 29% | 30% | 34% | 27% | 30% | 32% | 27% | 30% | 31% |
| Specificity | 85% | 86% | 79% | 83% | 87% | 79% | 81% | 86% | 79% |
| OR Quartile 2 | 1.90 | 2.02 | 2.71 | 1.81 | 1.96 | 2.38 | 2.00 | 1.89 | 2.48 |
| p Value | 0.019 | 0.0082 | 0.0015 | 0.037 | 0.012 | 0.0026 | 0.017 | 0.018 | 0.0011 |
| Lower limit of 95% CI | 1.11 | 1.20 | 1.46 | 1.03 | 1.16 | 1.35 | 1.13 | 1.11 | 1.44 |
| Upper limit of 95% CI | 3.26 | 3.40 | 5.02 | 3.17 | 3.31 | 4.19 | 3.55 | 3.21 | 4.28 |
| OR Quartile 3 | 2.96 | 2.67 | 2.06 | 2.35 | 2.70 | 1.90 | 2.22 | 2.53 | 1.90 |
| p Value | 4.6E−5 | 8.6E−5 | 0.0027 | 0.0018 | 7.9E−5 | 0.0054 | 0.0046 | 2.6E−4 | 0.0045 |
| Lower limit of 95% CI | 1.76 | 1.64 | 1.28 | 1.38 | 1.65 | 1.21 | 1.28 | 1.54 | 1.22 |
| Upper limit of 95% CI | 4.98 | 4.35 | 3.30 | 4.01 | 4.42 | 2.99 | 3.87 | 4.17 | 2.96 |
| OR Quartile 4 | 2.30 | 2.67 | 1.99 | 1.84 | 2.87 | 1.83 | 1.57 | 2.62 | 1.66 |
| p Value | 0.012 | 0.0023 | 0.0088 | 0.070 | 0.0014 | 0.020 | 0.18 | 0.0036 | 0.050 |
| Lower limit of 95% CI | 1.20 | 1.42 | 1.19 | 0.951 | 1.50 | 1.10 | 0.810 | 1.37 | 1.00 |
| Upper limit of 95% CI | 4.41 | 5.03 | 3.33 | 3.55 | 5.49 | 3.03 | 3.05 | 5.02 | 2.74 |

TABLE 10.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| Recovery Period Duration (hr) | | |
|---|---|---|
| 24 | 48 | 72 |

TABLE 10.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

|   | Recovered Cohort | Non-recovered Cohort | Recovered Cohort | Non-recovered Cohort | Recovered Cohort | Non-recovered Cohort |
|---|---|---|---|---|---|---|
|   | sCr or UO | | | | | |
| Median | 98600 | 117000 | 98600 | 117000 | 98000 | 116000 |
| Average | 112000 | 127000 | 112000 | 126000 | 112000 | 126000 |
| Stdev | 40700 | 45000 | 40800 | 44900 | 41900 | 44400 |
| p (t-test) | | 0.0049 | | 0.0082 | | 0.012 |
| Min | 57600 | 57000 | 57600 | 57000 | 57600 | 57000 |
| Max | 257000 | 299000 | 257000 | 299000 | 257000 | 299000 |
| n (Patient) | 111 | 216 | 104 | 223 | 94 | 233 |
|   | sCr only | | | | | |
| Median | 98600 | 118000 | 98600 | 118000 | 98600 | 118000 |
| Average | 111000 | 129000 | 110000 | 129000 | 109000 | 129000 |
| Stdev | 38500 | 45900 | 37700 | 46000 | 37600 | 46000 |
| p (t-test) | | 2.8E−4 | | 1.2E−4 | | 1.6E−4 |
| Min | 57600 | 57000 | 57600 | 57000 | 57600 | 57000 |
| Max | 257000 | 299000 | 257000 | 299000 | 257000 | 299000 |
| n (Patient) | 124 | 203 | 121 | 206 | 116 | 211 |
|   | UO only | | | | | |
| Median | 104000 | 125000 | 103000 | 125000 | 101000 | 123000 |
| Average | 115000 | 137000 | 114000 | 136000 | 114000 | 134000 |
| Stdev | 41400 | 46000 | 40600 | 46800 | 41200 | 45800 |
| p (t-test) | | 1.9E−5 | | 1.7E−5 | | 7.8E−5 |
| Min | 57600 | 57000 | 57600 | 57000 | 57600 | 57000 |
| Max | 299000 | 281000 | 299000 | 281000 | 299000 | 281000 |
| n (Patient) | 219 | 106 | 208 | 117 | 193 | 132 |

|   | Recovery Period Duration (hr) | | | | | | | | |
|---|---|---|---|---|---|---|---|---|---|
|   | 24 | | | 48 | | | 72 | | |
|   | sCr or UO | sCr only | UO only | sCr or UO | sCr only | UO only | sCr or UO | sCr only | UO only |
| AUC | 0.62 | 0.64 | 0.67 | 0.62 | 0.65 | 0.66 | 0.62 | 0.64 | 0.65 |
| SE | 0.032 | 0.031 | 0.033 | 0.032 | 0.031 | 0.032 | 0.033 | 0.031 | 0.031 |
| p Value | 9.1E−5 | 5.0E−6 | 5.3E−7 | 2.7E−4 | 1.7E−6 | 5.8E−7 | 2.2E−4 | 3.4E−6 | 8.7E−7 |
| nCohort Recovered | 111 | 124 | 219 | 104 | 121 | 208 | 94 | 116 | 193 |
| nCohort Non-recovered | 216 | 203 | 106 | 223 | 206 | 117 | 233 | 211 | 132 |
| Cutoff Quartile 2 | 90200 | 90200 | 90200 | 90200 | 90200 | 90200 | 90200 | 90200 | 90200 |
| Sensitivity | 78% | 79% | 89% | 78% | 79% | 87% | 78% | 78% | 86% |
| Specificity | 32% | 31% | 32% | 31% | 31% | 32% | 33% | 31% | 33% |
| Cutoff Quartile 3 | 109000 | 109000 | 109000 | 109000 | 109000 | 109000 | 109000 | 109000 | 109000 |
| Sensitivity | 58% | 59% | 66% | 57% | 59% | 65% | 57% | 59% | 64% |
| Specificity | 66% | 65% | 58% | 65% | 65% | 58% | 66% | 66% | 59% |
| Cutoff Quartile 4 | 137000 | 137000 | 137000 | 137000 | 137000 | 137000 | 137000 | 137000 | 137000 |
| Sensitivity | 29% | 31% | 39% | 29% | 31% | 37% | 28% | 31% | 34% |
| Specificity | 83% | 84% | 81% | 83% | 85% | 81% | 82% | 85% | 81% |
| OR Quartile 2 | 1.66 | 1.71 | 3.60 | 1.54 | 1.69 | 3.16 | 1.76 | 1.61 | 3.07 |
| p Value | 0.055 | 0.039 | 1.6E−4 | 0.11 | 0.044 | 2.5E−4 | 0.037 | 0.066 | 1.6E−4 |
| Lower limit of 95% CI | 0.990 | 1.03 | 1.85 | 0.912 | 1.01 | 1.71 | 1.03 | 0.968 | 1.72 |
| Upper limit of 95% CI | 2.77 | 2.83 | 7.01 | 2.59 | 2.80 | 5.85 | 2.98 | 2.69 | 5.49 |
| OR Quartile 3 | 2.69 | 2.63 | 2.63 | 2.55 | 2.73 | 2.58 | 2.53 | 2.71 | 2.53 |
| p Value | 4.7E−5 | 4.2E−5 | 8.5E−5 | 1.5E−4 | 2.4E−5 | 7.6E−5 | 2.6E−4 | 3.4E−5 | 6.9E−5 |
| Lower limit of 95% CI | 1.67 | 1.66 | 1.63 | 1.57 | 1.71 | 1.61 | 1.54 | 1.69 | 1.60 |
| Upper limit of 95% CI | 4.33 | 4.17 | 4.27 | 4.13 | 4.35 | 4.12 | 4.17 | 4.34 | 3.99 |
| OR Quartile 4 | 1.99 | 2.29 | 2.74 | 1.92 | 2.58 | 2.52 | 1.75 | 2.59 | 2.18 |
| p Value | 0.019 | 0.0041 | 1.4E−4 | 0.028 | 0.0014 | 4.1E−4 | 0.066 | 0.0016 | 0.0026 |
| Lower limit of 95% CI | 1.12 | 1.30 | 1.63 | 1.07 | 1.44 | 1.51 | 0.964 | 1.43 | 1.31 |
| Upper limit of 95% CI | 3.54 | 4.02 | 4.60 | 3.45 | 4.61 | 4.20 | 3.19 | 4.69 | 3.62 |

TABLE 10.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 98600 | 119000 | 98600 | 118000 | 98100 | 118000 |
| Average | 112000 | 128000 | 112000 | 128000 | 111000 | 128000 |
| Stdev | 40900 | 45100 | 41200 | 44900 | 39400 | 45300 |
| p (t-test) | | 0.0012 | | 0.0023 | | 8.2E−4 |
| Min | 57600 | 57000 | 57600 | 57000 | 57600 | 57000 |
| Max | 269000 | 299000 | 269000 | 299000 | 257000 | 299000 |
| n (Patient) | 134 | 193 | 125 | 202 | 113 | 214 |
| sCr only | | | | | | |
| Median | 98700 | 120000 | 98600 | 121000 | 98700 | 120000 |
| Average | 111000 | 130000 | 110000 | 130000 | 110000 | 130000 |
| Stdev | 39400 | 45800 | 38700 | 45900 | 38400 | 46000 |
| p (t-test) | | 1.2E−4 | | 3.3E−5 | | 5.7E−5 |
| Min | 57600 | 57000 | 57600 | 57000 | 57600 | 57000 |
| Max | 269000 | 299000 | 269000 | 299000 | 269000 | 299000 |
| n (Patient) | 139 | 188 | 137 | 190 | 133 | 194 |
| UO only | | | | | | |
| Median | 103000 | 128000 | 103000 | 124000 | 103000 | 123000 |
| Average | 114000 | 139000 | 114000 | 136000 | 114000 | 134000 |
| Stdev | 39800 | 47800 | 40400 | 47200 | 41200 | 46000 |
| p (t-test) | | 9.4E−7 | | 1.2E−5 | | 7.2E−5 |
| Min | 57600 | 57000 | 57600 | 57000 | 57600 | 57000 |
| Max | 299000 | 281000 | 299000 | 281000 | 299000 | 281000 |
| n (Patient) | 220 | 105 | 211 | 114 | 198 | 127 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.65 | 0.68 | 0.63 | 0.66 | 0.66 | 0.64 | 0.65 | 0.65 |
| SE | 0.031 | 0.030 | 0.033 | 0.031 | 0.030 | 0.032 | 0.031 | 0.030 | 0.032 |
| p Value | 8.4E−6 | 9.0E−7 | 4.4E−8 | 2.0E−5 | 1.2E−7 | 5.9E−7 | 5.3E−6 | 5.9E−7 | 1.1E−6 |
| nCohort Recovered | 134 | 139 | 220 | 125 | 137 | 211 | 113 | 133 | 198 |
| nCohort Non-recovered | 193 | 188 | 105 | 202 | 190 | 114 | 214 | 194 | 127 |
| Cutoff Quartile 2 | 90200 | 90200 | 90200 | 90200 | 90200 | 90200 | 90200 | 90200 | 90200 |
| Sensitivity | 80% | 80% | 89% | 80% | 81% | 87% | 80% | 79% | 86% |
| Specificity | 33% | 32% | 31% | 33% | 33% | 31% | 35% | 32% | 32% |
| Cutoff Quartile 3 | 109000 | 109000 | 109000 | 109000 | 109000 | 109000 | 109000 | 109000 | 109000 |
| Sensitivity | 61% | 62% | 67% | 60% | 62% | 64% | 59% | 61% | 64% |
| Specificity | 66% | 65% | 58% | 66% | 66% | 57% | 66% | 66% | 59% |
| Cutoff Quartile 4 | 137000 | 137000 | 137000 | 137000 | 137000 | 137000 | 137000 | 137000 | 137000 |
| Sensitivity | 31% | 32% | 40% | 30% | 33% | 38% | 30% | 32% | 35% |
| Specificity | 83% | 84% | 82% | 83% | 85% | 82% | 84% | 86% | 81% |
| OR Quartile 2 | 1.99 | 1.95 | 3.54 | 1.92 | 2.02 | 3.00 | 2.10 | 1.78 | 2.83 |
| p Value | 0.0075 | 0.0094 | 1.9E−4 | 0.012 | 0.0064 | 4.7E−4 | 0.0046 | 0.026 | 4.6E−4 |
| Lower limit of 95% CI | 1.20 | 1.18 | 1.82 | 1.15 | 1.22 | 1.62 | 1.26 | 1.07 | 1.58 |
| Upper limit of 95% CI | 3.31 | 3.24 | 6.89 | 3.18 | 3.35 | 5.56 | 3.50 | 2.94 | 5.05 |
| OR Quartile 3 | 3.01 | 3.05 | 2.73 | 2.85 | 3.24 | 2.39 | 2.83 | 3.10 | 2.49 |
| p Value | 2.6E−6 | 1.7E−6 | 5.1E−5 | 9.8E−6 | 5.4E−7 | 2.7E−4 | 1.9E−5 | 1.5E−6 | 9.8E−5 |
| Lower limit of 95% CI | 1.90 | 1.93 | 1.68 | 1.79 | 2.05 | 1.50 | 1.76 | 1.96 | 1.57 |
| Upper limit of 95% CI | 4.76 | 4.82 | 4.44 | 4.53 | 5.14 | 3.83 | 4.55 | 4.92 | 3.94 |

TABLE 10.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 2.12 | 2.49 | 3.00 | 2.14 | 2.83 | 2.67 | 2.25 | 2.89 | 2.23 |
| p Value | 0.0066 | 0.0011 | 3.4E−5 | 0.0073 | 2.9E−4 | 1.8E−4 | 0.0063 | 2.8E−4 | 0.0020 |
| Lower limit of 95% CI | 1.23 | 1.44 | 1.78 | 1.23 | 1.61 | 1.60 | 1.26 | 1.63 | 1.34 |
| Upper limit of 95% CI | 3.66 | 4.32 | 5.04 | 3.74 | 4.98 | 4.47 | 4.03 | 5.11 | 3.71 |

TABLE 10.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 101000 | 119000 | 101000 | 120000 | 101000 | 119000 |
| Average | 114000 | 132000 | 114000 | 132000 | 114000 | 131000 |
| Stdev | 40800 | 46600 | 40900 | 46200 | 40900 | 46200 |
| p (t-test) | | 4.5E−4 | | 3.1E−4 | | 4.3E−4 |
| Min | 57600 | 57000 | 57600 | 57000 | 57600 | 57000 |
| Max | 299000 | 281000 | 299000 | 281000 | 299000 | 281000 |
| n (Patient) | 187 | 140 | 184 | 143 | 183 | 144 |
| | sCr only | | | | | |
| Median | 101000 | 118000 | 99700 | 120000 | 100000 | 119000 |
| Average | 113000 | 130000 | 112000 | 131000 | 112000 | 130000 |
| Stdev | 38800 | 47200 | 37800 | 47400 | 37900 | 47400 |
| p (t-test) | | 4.7E−4 | | 6.7E−5 | | 1.5E−4 |
| Min | 57600 | 57000 | 57600 | 57000 | 57600 | 57000 |
| Max | 269000 | 299000 | 269000 | 299000 | 269000 | 299000 |
| n (Patient) | 159 | 168 | 156 | 171 | 154 | 173 |
| | UO only | | | | | |
| Median | 103000 | 124000 | 103000 | 125000 | 103000 | 124000 |
| Average | 114000 | 138000 | 114000 | 137000 | 114000 | 137000 |
| Stdev | 39600 | 48200 | 39800 | 47700 | 40100 | 47300 |
| p (t-test) | | 3.0E−6 | | 3.1E−6 | | 5.1E−6 |
| Min | 57600 | 57000 | 57600 | 57000 | 57600 | 57000 |
| Max | 299000 | 281000 | 299000 | 281000 | 299000 | 281000 |
| n (Patient) | 215 | 110 | 212 | 113 | 209 | 116 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.62 | 0.66 | 0.63 | 0.64 | 0.67 | 0.63 | 0.63 | 0.67 |
| SE | 0.031 | 0.031 | 0.033 | 0.031 | 0.030 | 0.032 | 0.031 | 0.031 | 0.032 |
| p Value | 5.0E−5 | 8.3E−5 | 4.7E−7 | 1.9E−5 | 8.0E−6 | 2.1E−7 | 3.2E−5 | 3.2E−5 | 2.0E−7 |
| nCohort Recovered | 187 | 159 | 215 | 184 | 156 | 212 | 183 | 154 | 209 |
| nCohort Non-recovered | 140 | 168 | 110 | 143 | 171 | 113 | 144 | 173 | 116 |
| Cutoff Quartile 2 | 90200 | 90200 | 90200 | 90200 | 90200 | 90200 | 90200 | 90200 | 90200 |
| Sensitivity | 83% | 80% | 86% | 83% | 81% | 87% | 83% | 80% | 87% |
| Specificity | 31% | 31% | 31% | 32% | 31% | 31% | 31% | 31% | 32% |
| Cutoff Quartile 3 | 109000 | 109000 | 109000 | 109000 | 109000 | 109000 | 109000 | 109000 | 109000 |
| Sensitivity | 61% | 60% | 65% | 61% | 60% | 65% | 60% | 60% | 66% |
| Specificity | 58% | 60% | 58% | 58% | 61% | 58% | 58% | 60% | 58% |
| Cutoff Quartile 4 | 137000 | 137000 | 137000 | 137000 | 137000 | 137000 | 137000 | 137000 | 137000 |
| Sensitivity | 33% | 32% | 39% | 34% | 33% | 39% | 33% | 33% | 38% |
| Specificity | 81% | 82% | 82% | 82% | 84% | 82% | 81% | 84% | 82% |
| OR Quartile 2 | 2.17 | 1.82 | 2.81 | 2.28 | 1.92 | 2.95 | 2.15 | 1.73 | 3.11 |
| p Value | 0.0047 | 0.021 | 0.0010 | 0.0026 | 0.012 | 5.7E−4 | 0.0048 | 0.033 | 3.1E−4 |

TABLE 10.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.27 | 1.10 | 1.51 | 1.33 | 1.15 | 1.59 | 1.26 | 1.04 | 1.68 |
| Upper limit of 95% CI | 3.72 | 3.03 | 5.20 | 3.91 | 3.18 | 5.47 | 3.67 | 2.87 | 5.75 |
| OR Quartile 3 | 2.11 | 2.18 | 2.58 | 2.16 | 2.36 | 2.62 | 2.10 | 2.24 | 2.66 |
| p Value | 0.0010 | 5.4E−4 | 9.8E−5 | 7.1E−4 | 1.5E−4 | 6.7E−5 | 0.0011 | 3.5E−4 | 4.6E−5 |
| Lower limit of 95% CI | 1.35 | 1.40 | 1.60 | 1.38 | 1.51 | 1.63 | 1.35 | 1.44 | 1.66 |
| Upper limit of 95% CI | 3.30 | 3.40 | 4.16 | 3.37 | 3.68 | 4.21 | 3.28 | 3.49 | 4.27 |
| OR Quartile 4 | 2.05 | 2.22 | 2.90 | 2.23 | 2.62 | 2.92 | 2.19 | 2.54 | 2.75 |
| p Value | 0.0054 | 0.0028 | 5.5E−5 | 0.0020 | 4.0E−4 | 4.7E−5 | 0.0025 | 6.2E−4 | 1.1E−4 |
| Lower limit of 95% CI | 1.24 | 1.32 | 1.73 | 1.34 | 1.54 | 1.74 | 1.32 | 1.49 | 1.64 |
| Upper limit of 95% CI | 3.41 | 3.73 | 4.86 | 3.71 | 4.46 | 4.89 | 3.64 | 4.32 | 4.60 |

Example 11. Use of Metalloproteinase Inhibitor 2 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 11.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 10600 | 17900 | 10400 | 17900 | 10100 | 17900 |
| Average | 15300 | 36900 | 14700 | 36700 | 14500 | 36400 |
| Stdev | 13900 | 63700 | 13300 | 63200 | 13300 | 62700 |
| p (t-test) | | 5.8E−4 | | 5.1E−4 | | 6.3E−4 |
| Min | 200 | 658 | 200 | 658 | 200 | 658 |
| Max | 76000 | 465000 | 76000 | 465000 | 76000 | 465000 |
| n (Patient) | 108 | 209 | 104 | 213 | 100 | 217 |
| sCr only | | | | | | |
| Median | 12000 | 16000 | 11800 | 16000 | 11500 | 16600 |
| Average | 17000 | 37300 | 17000 | 37100 | 17000 | 36900 |
| Stdev | 14700 | 66400 | 14800 | 66100 | 14900 | 65800 |
| p (t-test) | | 8.2E−4 | | 9.5E−4 | | 0.0011 |
| Min | 200 | 658 | 200 | 658 | 200 | 658 |
| Max | 76000 | 465000 | 76000 | 465000 | 76000 | 465000 |
| n (Patient) | 126 | 190 | 124 | 192 | 122 | 194 |

TABLE 11.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 11400 | 25100 | 11000 | 22700 | 11000 | 21700 |
| Average | 20500 | 51500 | 19900 | 48500 | 19900 | 46000 |
| Stdev | 38100 | 74800 | 38900 | 70600 | 39600 | 68200 |
| p (t-test) | | 1.9E−6 | | 5.3E−6 | | 2.4E−5 |
| Min | 200 | 2170 | 200 | 2170 | 200 | 2170 |
| Max | 465000 | 428000 | 465000 | 428000 | 465000 | 428000 |
| n (Patient) | 222 | 93 | 208 | 107 | 198 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.59 | 0.74 | 0.66 | 0.60 | 0.74 | 0.66 | 0.60 | 0.72 |
| SE | 0.031 | 0.032 | 0.033 | 0.031 | 0.032 | 0.031 | 0.031 | 0.032 | 0.031 |
| p Value | 1.6E−6 | 0.0031 | 5.1E−13 | 2.3E−7 | 0.0023 | 5.3E−15 | 1.3E−7 | 0.0017 | 2.8E−13 |
| nCohort Recovered | 108 | 126 | 222 | 104 | 124 | 208 | 100 | 122 | 198 |
| nCohort Non-recovered | 209 | 190 | 93 | 213 | 192 | 107 | 217 | 194 | 117 |
| Cutoff Quartile 2 | 7990 | 7980 | 8020 | 7990 | 7980 | 8020 | 7990 | 7980 | 8020 |
| Sensitivity | 81% | 79% | 92% | 82% | 79% | 93% | 82% | 79% | 91% |
| Specificity | 37% | 31% | 32% | 38% | 31% | 35% | 39% | 32% | 34% |
| Cutoff Quartile 3 | 13500 | 13500 | 13500 | 13500 | 13500 | 13500 | 13500 | 13500 | 13500 |
| Sensitivity | 56% | 53% | 71% | 56% | 54% | 69% | 57% | 54% | 68% |
| Specificity | 61% | 55% | 59% | 62% | 56% | 60% | 64% | 57% | 60% |
| Cutoff Quartile 4 | 28900 | 28100 | 29400 | 28900 | 28100 | 29400 | 28900 | 28100 | 29400 |
| Sensitivity | 32% | 32% | 44% | 32% | 32% | 43% | 32% | 31% | 41% |
| Specificity | 87% | 86% | 83% | 88% | 85% | 84% | 89% | 85% | 84% |
| OR Quartile 2 | 2.56 | 1.68 | 5.90 | 2.79 | 1.74 | 7.56 | 2.83 | 1.81 | 5.04 |
| p Value | 4.2E−4 | 0.048 | 2.2E−5 | 1.3E−4 | 0.034 | 1.2E−6 | 1.1E−4 | 0.024 | 3.9E−6 |
| Lower limit of 95% CI | 1.52 | 1.01 | 2.60 | 1.65 | 1.04 | 3.34 | 1.67 | 1.08 | 2.54 |
| Upper limit of 95% CI | 4.33 | 2.81 | 13.4 | 4.72 | 2.92 | 17.1 | 4.80 | 3.03 | 10.0 |
| OR Quartile 3 | 2.00 | 1.37 | 3.45 | 2.15 | 1.45 | 3.31 | 2.33 | 1.54 | 3.13 |
| p Value | 0.0042 | 0.17 | 3.2E−6 | 0.0018 | 0.11 | 2.1E−6 | 7.1E−4 | 0.065 | 3.2E−6 |
| Lower limit of 95% CI | 1.24 | 0.874 | 2.05 | 1.33 | 0.922 | 2.02 | 1.43 | 0.974 | 1.94 |
| Upper limit of 95% CI | 3.21 | 2.16 | 5.82 | 3.48 | 2.29 | 5.43 | 3.79 | 2.42 | 5.06 |
| OR Quartile 4 | 3.10 | 2.84 | 3.82 | 3.60 | 2.74 | 4.00 | 3.77 | 2.65 | 3.75 |
| p Value | 4.6E−4 | 4.7E−4 | 1.1E−6 | 1.7E−4 | 7.2E−4 | 3.6E−7 | 1.6E−4 | 0.0011 | 1.1E−6 |
| Lower limit of 95% CI | 1.65 | 1.58 | 2.23 | 1.85 | 1.53 | 2.35 | 1.89 | 1.48 | 2.20 |
| Upper limit of 95% CI | 5.83 | 5.09 | 6.54 | 7.01 | 4.92 | 6.82 | 7.51 | 4.76 | 6.38 |

TABLE 11.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11300 | 19300 | 11100 | 19300 | 11000 | 19300 |
| Average | 15500 | 40000 | 15400 | 39800 | 14900 | 39500 |
| Stdev | 13800 | 67800 | 13800 | 67400 | 13300 | 66600 |
| p (t-test) | | 4.4E−5 | | 4.7E−5 | | 4.7E−5 |

TABLE 11.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 200 | 658 | 200 | 658 | 200 | 658 |
| Max | 76000 | 465000 | 76000 | 465000 | 76000 | 465000 |
| n (Patient) | 136 | 181 | 134 | 183 | 129 | 188 | sCr only

| | | | | | | |
|---|---|---|---|---|---|---|
| Median | 12000 | 18700 | 12000 | 18600 | 11800 | 18200 |
| Average | 16900 | 40600 | 16900 | 40500 | 16900 | 40200 |
| Stdev | 14700 | 70200 | 14700 | 70000 | 14800 | 69600 |
| p (t-test) | | 6.5E−5 | | 7.4E−5 | | 8.9E−5 |
| Min | 200 | 658 | 200 | 658 | 200 | 658 |
| Max | 76000 | 465000 | 76000 | 465000 | 76000 | 465000 |
| n (Patient) | 149 | 168 | 148 | 169 | 146 | 171 |

UO only

| | | | | | | |
|---|---|---|---|---|---|---|
| Median | 11600 | 22100 | 11400 | 22100 | 11300 | 21700 |
| Average | 20600 | 52500 | 20300 | 51100 | 20100 | 47800 |
| Stdev | 37600 | 76500 | 38000 | 74400 | 38800 | 70600 |
| p (t-test) | | 1.3E−6 | | 1.9E−6 | | 9.6E−6 |
| Min | 200 | 2170 | 200 | 2170 | 200 | 2170 |
| Max | 465000 | 428000 | 465000 | 428000 | 465000 | 428000 |
| n (Patient) | 226 | 89 | 220 | 95 | 207 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.61 | 0.72 | 0.66 | 0.61 | 0.72 | 0.67 | 0.62 | 0.71 |
| SE | 0.030 | 0.031 | 0.034 | 0.030 | 0.031 | 0.033 | 0.030 | 0.031 | 0.032 |
| p Value | 4.5E−7 | 3.4E−4 | 2.3E−10 | 1.8E−7 | 3.2E−4 | 2.0E−11 | 3.8E−8 | 2.4E−4 | 3.5E−11 |
| nCohort Recovered | 136 | 149 | 226 | 134 | 148 | 220 | 129 | 146 | 207 |
| nCohort Non-recovered | 181 | 168 | 89 | 183 | 169 | 95 | 188 | 171 | 108 |
| Cutoff Quartile 2 | 7990 | 7990 | 8020 | 7990 | 7990 | 8020 | 7990 | 7990 | 8020 |
| Sensitivity | 81% | 79% | 89% | 81% | 79% | 89% | 81% | 80% | 88% |
| Specificity | 33% | 30% | 31% | 34% | 30% | 31% | 34% | 30% | 32% |
| Cutoff Quartile 3 | 13500 | 13500 | 13500 | 13500 | 13500 | 13500 | 13500 | 13500 | 13500 |
| Sensitivity | 59% | 56% | 69% | 59% | 56% | 68% | 60% | 57% | 68% |
| Specificity | 61% | 56% | 57% | 62% | 57% | 58% | 64% | 58% | 59% |
| Cutoff Quartile 4 | 28900 | 28900 | 29400 | 28900 | 28900 | 29400 | 28900 | 28900 | 29400 |
| Sensitivity | 34% | 35% | 44% | 34% | 34% | 44% | 35% | 34% | 43% |
| Specificity | 87% | 85% | 82% | 87% | 85% | 83% | 88% | 85% | 84% |
| OR Quartile 2 | 2.14 | 1.59 | 3.47 | 2.22 | 1.62 | 3.88 | 2.26 | 1.68 | 3.42 |
| p Value | 0.0039 | 0.075 | 6.6E−4 | 0.0026 | 0.065 | 2.0E−4 | 0.0020 | 0.048 | 2.0E−4 |
| Lower limit of 95% CI | 1.28 | 0.954 | 1.70 | 1.32 | 0.970 | 1.90 | 1.35 | 1.00 | 1.79 |
| Upper limit of 95% CI | 3.58 | 2.66 | 7.11 | 3.72 | 2.70 | 7.94 | 3.80 | 2.80 | 6.55 |
| OR Quartile 3 | 2.21 | 1.64 | 2.90 | 2.34 | 1.68 | 2.96 | 2.57 | 1.78 | 2.99 |
| p Value | 6.1E−4 | 0.029 | 5.9E−5 | 2.6E−4 | 0.022 | 2.9E−5 | 6.2E−5 | 0.012 | 1.1E−5 |
| Lower limit of 95% CI | 1.41 | 1.05 | 1.72 | 1.48 | 1.08 | 1.78 | 1.62 | 1.14 | 1.84 |
| Upper limit of 95% CI | 3.49 | 2.56 | 4.87 | 3.70 | 2.63 | 4.92 | 4.08 | 2.78 | 4.88 |
| OR Quartile 4 | 3.42 | 3.04 | 3.63 | 3.61 | 2.99 | 3.92 | 4.02 | 2.89 | 3.91 |
| p Value | 3.7E−5 | 8.0E−5 | 3.0E−6 | 2.2E−5 | 1.0E−4 | 6.3E−7 | 9.9E−6 | 1.7E−4 | 5.2E−7 |
| Lower limit of 95% CI | 1.91 | 1.75 | 2.11 | 2.00 | 1.72 | 2.29 | 2.17 | 1.66 | 2.30 |
| Upper limit of 95% CI | 6.12 | 5.29 | 6.23 | 6.54 | 5.20 | 6.71 | 7.44 | 5.03 | 6.67 |

TABLE 11.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| *sCr or UO* | | | | | | |
| Median | 11300 | 19300 | 11300 | 19300 | 11000 | 19300 |
| Average | 17200 | 41100 | 17300 | 40700 | 16800 | 40600 |
| Stdev | 21500 | 69500 | 21700 | 69200 | 21600 | 68400 |
| p (t-test) | | 5.7E−5 | | 7.8E−5 | | 6.3E−5 |
| Min | 200 | 658 | 200 | 658 | 200 | 658 |
| Max | 215000 | 465000 | 215000 | 465000 | 215000 | 465000 |
| n (Patient) | 154 | 163 | 152 | 165 | 148 | 169 |
| *sCr only* | | | | | | |
| Median | 11500 | 19000 | 11500 | 18900 | 11400 | 18800 |
| Average | 17900 | 41500 | 17900 | 41300 | 17900 | 41200 |
| Stdev | 21500 | 71000 | 21600 | 70800 | 21600 | 70600 |
| p (t-test) | | 7.0E−5 | | 8.0E−5 | | 8.9E−5 |
| Min | 200 | 658 | 200 | 658 | 200 | 658 |
| Max | 215000 | 465000 | 215000 | 465000 | 215000 | 465000 |
| n (Patient) | 161 | 156 | 160 | 157 | 159 | 158 |
| *UO only* | | | | | | |
| Median | 11900 | 21500 | 11900 | 21500 | 11500 | 21500 |
| Average | 21500 | 49500 | 21600 | 49100 | 21200 | 46900 |
| Stdev | 38600 | 75700 | 38600 | 75400 | 39400 | 71800 |
| p (t-test) | | 2.1E−5 | | 2.7E−5 | | 5.4E−5 |
| Min | 200 | 2170 | 200 | 2170 | 200 | 2170 |
| Max | 465000 | 428000 | 465000 | 428000 | 465000 | 428000 |
| n (Patient) | 224 | 91 | 223 | 92 | 212 | 103 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.63 | 0.68 | 0.65 | 0.63 | 0.68 | 0.67 | 0.63 | 0.69 |
| SE | 0.030 | 0.031 | 0.035 | 0.030 | 0.031 | 0.035 | 0.030 | 0.031 | 0.033 |
| p Value | 3.0E−7 | 2.0E−5 | 2.2E−7 | 4.5E−7 | 1.8E−5 | 3.3E−7 | 3.5E−8 | 1.6E−5 | 1.3E−8 |
| nCohort Recovered | 154 | 161 | 224 | 152 | 160 | 223 | 148 | 159 | 212 |
| nCohort Non-recovered | 163 | 156 | 91 | 165 | 157 | 92 | 169 | 158 | 103 |
| Cutoff Quartile 2 | 7990 | 7990 | 8020 | 7990 | 7990 | 8020 | 7990 | 7990 | 8020 |
| Sensitivity | 83% | 81% | 86% | 83% | 82% | 86% | 83% | 82% | 87% |
| Specificity | 33% | 31% | 29% | 34% | 31% | 30% | 34% | 31% | 31% |
| Cutoff Quartile 3 | 13500 | 13500 | 13500 | 13500 | 13500 | 13500 | 13500 | 13500 | 13500 |
| Sensitivity | 60% | 58% | 66% | 60% | 59% | 65% | 61% | 59% | 66% |
| Specificity | 60% | 58% | 56% | 61% | 58% | 56% | 62% | 58% | 58% |
| Cutoff Quartile 4 | 28900 | 28900 | 29400 | 28900 | 28900 | 29400 | 28900 | 28900 | 29400 |
| Sensitivity | 36% | 37% | 42% | 36% | 36% | 41% | 36% | 36% | 41% |
| Specificity | 86% | 86% | 82% | 86% | 86% | 82% | 87% | 86% | 83% |
| OR Quartile 2 | 2.39 | 1.97 | 2.51 | 2.47 | 2.01 | 2.55 | 2.65 | 2.04 | 3.13 |
| p Value | 0.0012 | 0.011 | 0.0059 | 7.8E−4 | 0.0092 | 0.0049 | 3.1E−4 | 0.0076 | 5.8E−4 |
| Lower limit of 95% CI | 1.41 | 1.17 | 1.30 | 1.46 | 1.19 | 1.33 | 1.56 | 1.21 | 1.63 |
| Upper limit of 95% CI | 4.05 | 3.33 | 4.82 | 4.19 | 3.39 | 4.91 | 4.49 | 3.45 | 6.00 |
| OR Quartile 3 | 2.30 | 1.91 | 2.49 | 2.30 | 1.96 | 2.39 | 2.56 | 2.02 | 2.63 |
| p Value | 2.9E−4 | 0.0043 | 4.3E−4 | 2.9E−4 | 0.0030 | 7.0E−4 | 4.8E−5 | 0.0021 | 1.1E−4 |
| Lower limit of 95% CI | 1.47 | 1.23 | 1.50 | 1.47 | 1.26 | 1.44 | 1.63 | 1.29 | 1.61 |
| Upper limit of 95% CI | 3.61 | 2.99 | 4.13 | 3.61 | 3.07 | 3.96 | 4.04 | 3.15 | 4.30 |

TABLE 11.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.59 | 3.45 | 3.20 | 3.47 | 3.40 | 3.12 | 3.83 | 3.34 | 3.26 |
| p Value | 7.7E−6 | 9.5E−6 | 2.2E−5 | 1.3E−5 | 1.3E−5 | 3.1E−5 | 4.6E−6 | 1.7E−5 | 1.2E−5 |
| Lower limit of 95% CI | 2.05 | 2.00 | 1.87 | 1.98 | 1.96 | 1.83 | 2.16 | 1.93 | 1.92 |
| Upper limit of 95% CI | 6.29 | 5.98 | 5.47 | 6.08 | 5.88 | 5.34 | 6.81 | 5.77 | 5.53 |

TABLE 11.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11500 | 19100 | 11400 | 19000 | 11300 | 19200 |
| Average | 19000 | 41300 | 18900 | 40900 | 18600 | 40800 |
| Stdev | 25200 | 71400 | 25300 | 70700 | 25400 | 69900 |
| p (t-test) | | 1.8E−4 | | 2.2E−4 | | 1.8E−4 |
| Min | 200 | 658 | 200 | 658 | 200 | 658 |
| Max | 215000 | 465000 | 215000 | 465000 | 215000 | 465000 |
| n (Patient) | 168 | 149 | 165 | 152 | 161 | 156 |
| | sCr only | | | | | |
| Median | 11900 | 18800 | 11900 | 18700 | 11800 | 18600 |
| Average | 19300 | 41600 | 19300 | 41400 | 19300 | 41200 |
| Stdev | 25100 | 72300 | 25100 | 72100 | 25200 | 71900 |
| p (t-test) | | 1.9E−4 | | 2.2E−4 | | 2.4E−4 |
| Min | 200 | 658 | 200 | 658 | 200 | 658 |
| Max | 215000 | 465000 | 215000 | 465000 | 215000 | 465000 |
| n (Patient) | 172 | 145 | 171 | 146 | 170 | 147 |
| | UO only | | | | | |
| Median | 11900 | 21500 | 11800 | 21500 | 11500 | 21500 |
| Average | 21600 | 49100 | 21500 | 49100 | 21300 | 47200 |
| Stdev | 38600 | 75500 | 38600 | 75100 | 39200 | 72500 |
| p (t-test) | | 2.6E−5 | | 2.4E−5 | | 5.3E−5 |
| Min | 200 | 2170 | 200 | 2170 | 200 | 2170 |
| Max | 465000 | 428000 | 465000 | 428000 | 465000 | 428000 |
| n (Patient) | 223 | 92 | 222 | 93 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.67 | 0.64 | 0.62 | 0.68 | 0.65 | 0.62 | 0.68 |
| SE | 0.031 | 0.032 | 0.035 | 0.031 | 0.032 | 0.035 | 0.031 | 0.032 | 0.033 |
| p Value | 1.0E−5 | 1.2E−4 | 6.6E−7 | 7.2E−6 | 1.1E−4 | 2.8E−7 | 8.9E−7 | 1.0E−4 | 5.3E−8 |
| nCohort Recovered | 168 | 172 | 223 | 165 | 171 | 222 | 161 | 170 | 214 |
| nCohort Non-recovered | 149 | 145 | 92 | 152 | 146 | 93 | 156 | 147 | 101 |
| Cutoff Quartile 2 | 7990 | 7990 | 8020 | 7990 | 7990 | 8020 | 7990 | 7990 | 8020 |
| Sensitivity | 83% | 81% | 85% | 83% | 82% | 85% | 83% | 82% | 86% |
| Specificity | 32% | 30% | 29% | 32% | 30% | 29% | 33% | 31% | 30% |
| Cutoff Quartile 3 | 13500 | 13500 | 13500 | 13500 | 13500 | 13500 | 13500 | 13500 | 13500 |
| Sensitivity | 60% | 58% | 65% | 60% | 58% | 66% | 61% | 59% | 66% |
| Specificity | 58% | 56% | 56% | 59% | 57% | 56% | 60% | 57% | 57% |
| Cutoff Quartile 4 | 28900 | 28900 | 29400 | 28900 | 28900 | 29400 | 28900 | 28900 | 29400 |
| Sensitivity | 36% | 37% | 41% | 36% | 36% | 42% | 36% | 36% | 41% |
| Specificity | 84% | 84% | 82% | 84% | 84% | 82% | 85% | 84% | 82% |
| OR Quartile 2 | 2.18 | 1.89 | 2.29 | 2.29 | 1.93 | 2.34 | 2.45 | 1.96 | 2.71 |
| p Value | 0.0042 | 0.018 | 0.011 | 0.0023 | 0.015 | 0.0091 | 9.9E−4 | 0.013 | 0.0021 |

TABLE 11.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| Lower limit of 95% CI | 1.28 | 1.11 | 1.21 | 1.34 | 1.13 | 1.23 | 1.44 | 1.15 | 1.44 |
|---|---|---|---|---|---|---|---|---|---|
| Upper limit of 95% CI | 3.72 | 3.22 | 4.34 | 3.91 | 3.27 | 4.42 | 4.19 | 3.33 | 5.12 |
| OR Quartile 3 | 2.08 | 1.78 | 2.39 | 2.13 | 1.83 | 2.46 | 2.36 | 1.87 | 2.66 |
| p Value | 0.0014 | 0.011 | 7.0E−4 | 9.7E−4 | 0.0082 | 4.7E−4 | 1.9E−4 | 0.0059 | 1.0E−4 |
| Lower limit of 95% CI | 1.33 | 1.14 | 1.44 | 1.36 | 1.17 | 1.48 | 1.50 | 1.20 | 1.63 |
| Upper limit of 95% CI | 3.25 | 2.78 | 3.96 | 3.33 | 2.86 | 4.06 | 3.70 | 2.93 | 4.36 |
| OR Quartile 4 | 2.88 | 3.09 | 3.12 | 2.95 | 3.04 | 3.29 | 3.20 | 2.99 | 3.16 |
| p Value | 9.3E−5 | 3.2E−5 | 3.1E−5 | 7.4E−5 | 4.2E−5 | 1.3E−5 | 2.8E−5 | 5.5E−5 | 2.0E−5 |
| Lower limit of 95% CI | 1.70 | 1.82 | 1.83 | 1.73 | 1.79 | 1.92 | 1.86 | 1.76 | 1.86 |
| Upper limit of 95% CI | 4.90 | 5.27 | 5.34 | 5.03 | 5.17 | 5.61 | 5.50 | 5.08 | 5.38 |

TABLE 11.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11900 | 20900 | 11900 | 20900 | 11800 | 21100 |
| Average | 21500 | 43700 | 21400 | 43400 | 21400 | 43300 |
| Stdev | 39800 | 69300 | 39900 | 68800 | 40000 | 68500 |
| p (t-test) | | 3.4E−4 | | 3.7E−4 | | 4.0E−4 |
| Min | 200 | 1490 | 200 | 1490 | 200 | 1490 |
| Max | 465000 | 428000 | 465000 | 428000 | 465000 | 428000 |
| n (Patient) | 203 | 114 | 201 | 116 | 200 | 117 |
| | sCr only | | | | | |
| Median | 11900 | 19000 | 11900 | 19000 | 11900 | 19000 |
| Average | 19100 | 44000 | 19100 | 44000 | 19100 | 44000 |
| Stdev | 24400 | 75300 | 24400 | 75300 | 24400 | 75300 |
| p (t-test) | | 3.4E−5 | | 3.4E−5 | | 3.4E−5 |
| Min | 200 | 658 | 200 | 658 | 200 | 658 |
| Max | 215000 | 465000 | 215000 | 465000 | 215000 | 465000 |
| n (Patient) | 185 | 132 | 185 | 132 | 185 | 132 |
| | UO only | | | | | |
| Median | 11800 | 21500 | 11700 | 21500 | 11700 | 21500 |
| Average | 21700 | 47200 | 21600 | 47200 | 21600 | 46600 |
| Stdev | 39100 | 73500 | 39200 | 73100 | 39400 | 72500 |
| p (t-test) | | 7.4E−5 | | 6.6E−5 | | 9.6E−5 |
| Min | 200 | 2170 | 200 | 2170 | 200 | 2170 |
| Max | 465000 | 428000 | 465000 | 428000 | 465000 | 428000 |
| n (Patient) | 217 | 98 | 216 | 99 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.63 | 0.67 | 0.64 | 0.63 | 0.67 | 0.65 | 0.63 | 0.67 |
| SE | 0.033 | 0.032 | 0.034 | 0.033 | 0.032 | 0.034 | 0.033 | 0.032 | 0.034 |
| p Value | 1.4E−5 | 4.9E−5 | 1.2E−6 | 1.1E−5 | 4.9E−5 | 5.1E−7 | 8.0E−6 | 4.9E−5 | 6.9E−7 |
| nCohort Recovered | 203 | 185 | 217 | 201 | 185 | 216 | 200 | 185 | 214 |
| nCohort Non-recovered | 114 | 132 | 98 | 116 | 132 | 99 | 117 | 132 | 101 |
| Cutoff Quartile 2 | 7990 | 7990 | 8020 | 7990 | 7990 | 8020 | 7990 | 7990 | 8020 |

TABLE 11.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 83% | 83% | 84% | 84% | 83% | 84% | 84% | 83% | 84% |
| Specificity | 30% | 30% | 29% | 30% | 30% | 29% | 30% | 30% | 29% |
| Cutoff Quartile 3 | 13500 | 13500 | 13500 | 13500 | 13500 | 13500 | 13500 | 13500 | 13500 |
| Sensitivity | 62% | 59% | 65% | 62% | 59% | 66% | 62% | 59% | 65% |
| Specificity | 57% | 56% | 57% | 57% | 56% | 57% | 57% | 56% | 57% |
| Cutoff Quartile 4 | 28900 | 28900 | 29400 | 28900 | 28900 | 29400 | 28900 | 28900 | 29400 |
| Sensitivity | 39% | 39% | 41% | 39% | 39% | 41% | 38% | 39% | 41% |
| Specificity | 82% | 84% | 82% | 83% | 84% | 82% | 82% | 84% | 82% |
| OR Quartile 2 | 2.10 | 2.06 | 2.10 | 2.17 | 2.06 | 2.14 | 2.21 | 2.06 | 2.22 |
| p Value | 0.012 | 0.0099 | 0.017 | 0.0084 | 0.0099 | 0.015 | 0.0070 | 0.0099 | 0.011 |
| Lower limit of 95% CI | 1.18 | 1.19 | 1.14 | 1.22 | 1.19 | 1.16 | 1.24 | 1.19 | 1.20 |
| Upper limit of 95% CI | 3.74 | 3.56 | 3.86 | 3.87 | 3.56 | 3.93 | 3.94 | 3.56 | 4.08 |
| OR Quartile 3 | 2.16 | 1.85 | 2.46 | 2.14 | 1.85 | 2.53 | 2.20 | 1.85 | 2.50 |
| p Value | 0.0013 | 0.0075 | 3.6E−4 | 0.0014 | 0.0075 | 2.4E−4 | 9.5E−4 | 0.0075 | 2.5E−4 |
| Lower limit of 95% CI | 1.35 | 1.18 | 1.50 | 1.34 | 1.18 | 1.54 | 1.38 | 1.18 | 1.53 |
| Upper limit of 95% CI | 3.45 | 2.92 | 4.04 | 3.42 | 2.92 | 4.15 | 3.51 | 2.92 | 4.09 |
| OR Quartile 4 | 2.92 | 3.39 | 3.15 | 3.01 | 3.39 | 3.31 | 2.95 | 3.39 | 3.16 |
| p Value | 5.8E−5 | 6.2E−6 | 2.3E−5 | 3.6E−5 | 6.2E−6 | 1.0E−5 | 4.8E−5 | 6.2E−6 | 2.0E−5 |
| Lower limit of 95% CI | 1.73 | 2.00 | 1.85 | 1.78 | 2.00 | 1.95 | 1.75 | 2.00 | 1.86 |
| Upper limit of 95% CI | 4.91 | 5.75 | 5.36 | 5.07 | 5.75 | 5.63 | 4.96 | 5.75 | 5.38 |

TABLE 11.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 97900 | 117000 | 97500 | 117000 | 97500 | 117000 |
| Average | 107000 | 129000 | 107000 | 128000 | 107000 | 128000 |
| Stdev | 34500 | 46400 | 34800 | 46300 | 35400 | 46100 |
| p (t-test) | | 2.0E−5 | | 4.4E−5 | | 1.0E−4 |
| Min | 57600 | 57000 | 57600 | 57000 | 57600 | 57000 |
| Max | 257000 | 299000 | 257000 | 299000 | 257000 | 299000 |
| n (Patient) | 105 | 222 | 102 | 225 | 98 | 229 |
| | sCr only | | | | | |
| Median | 97900 | 120000 | 97900 | 120000 | 97900 | 120000 |
| Average | 106000 | 131000 | 106000 | 131000 | 106000 | 131000 |
| Stdev | 32400 | 47500 | 32700 | 47300 | 32600 | 47200 |
| p (t-test) | | 5.5E−7 | | 7.3E−7 | | 6.2E−7 |
| Min | 57600 | 57000 | 57600 | 57000 | 57600 | 57000 |
| Max | 257000 | 299000 | 257000 | 299000 | 257000 | 299000 |
| n (Patient) | 121 | 205 | 119 | 207 | 117 | 209 |
| | UO only | | | | | |
| Median | 106000 | 123000 | 105000 | 124000 | 104000 | 123000 |
| Average | 118000 | 132000 | 116000 | 134000 | 115000 | 133000 |
| Stdev | 43100 | 45000 | 41300 | 46900 | 41800 | 46000 |
| p (t-test) | | 0.0068 | | 2.9E−4 | | 6.0E−4 |
| Min | 57000 | 70200 | 57000 | 70200 | 57000 | 70200 |
| Max | 299000 | 281000 | 299000 | 281000 | 299000 | 281000 |
| n (Patient) | 226 | 99 | 213 | 112 | 202 | 123 |

TABLE 11.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.68 | 0.62 | 0.66 | 0.68 | 0.63 | 0.66 | 0.68 | 0.63 |
| SE | 0.031 | 0.030 | 0.035 | 0.031 | 0.030 | 0.033 | 0.031 | 0.030 | 0.032 |
| p Value | 7.3E−8 | 1.9E−9 | 9.0E−4 | 2.6E−7 | 1.6E−9 | 4.9E−5 | 7.9E−7 | 9.3E−10 | 5.1E−5 |
| nCohort Recovered | 105 | 121 | 226 | 102 | 119 | 213 | 98 | 117 | 202 |
| nCohort Non-recovered | 222 | 205 | 99 | 225 | 207 | 112 | 229 | 209 | 123 |
| Cutoff Quartile 2 | 90200 | 90200 | 90200 | 90200 | 90200 | 90200 | 90200 | 90200 | 90200 |
| Sensitivity | 80% | 80% | 86% | 80% | 80% | 87% | 79% | 80% | 86% |
| Specificity | 35% | 34% | 30% | 35% | 34% | 31% | 35% | 34% | 32% |
| Cutoff Quartile 3 | 109000 | 109000 | 109000 | 109000 | 109000 | 109000 | 109000 | 109000 | 109000 |
| Sensitivity | 59% | 60% | 61% | 58% | 60% | 62% | 58% | 60% | 60% |
| Specificity | 68% | 67% | 54% | 68% | 67% | 56% | 67% | 68% | 56% |
| Cutoff Quartile 4 | 137000 | 137000 | 137000 | 137000 | 137000 | 137000 | 137000 | 137000 | 137000 |
| Sensitivity | 32% | 33% | 35% | 31% | 33% | 37% | 31% | 33% | 34% |
| Specificity | 89% | 88% | 79% | 88% | 88% | 81% | 88% | 89% | 80% |
| OR Quartile 2 | 2.14 | 2.05 | 2.56 | 2.12 | 2.13 | 2.90 | 2.00 | 2.07 | 2.89 |
| p Value | 0.0039 | 0.0057 | 0.0036 | 0.0045 | 0.0037 | 7.0E−4 | 0.0093 | 0.0053 | 4.4E−4 |
| Lower limit of 95% CI | 1.28 | 1.23 | 1.36 | 1.26 | 1.28 | 1.57 | 1.19 | 1.24 | 1.60 |
| Upper limit of 95% CI | 3.59 | 3.41 | 4.82 | 3.57 | 3.54 | 5.38 | 3.38 | 3.44 | 5.23 |
| OR Quartile 3 | 2.95 | 3.04 | 1.84 | 2.91 | 3.06 | 2.03 | 2.81 | 3.09 | 1.92 |
| p Value | 1.4E−5 | 3.7E−6 | 0.013 | 2.1E−5 | 3.5E−6 | 0.0029 | 4.7E−5 | 3.3E−6 | 0.0051 |
| Lower limit of 95% CI | 1.81 | 1.90 | 1.14 | 1.78 | 1.91 | 1.27 | 1.71 | 1.92 | 1.22 |
| Upper limit of 95% CI | 4.81 | 4.86 | 2.97 | 4.77 | 4.92 | 3.24 | 4.61 | 4.98 | 3.02 |
| OR Quartile 4 | 3.57 | 3.79 | 2.08 | 3.39 | 3.67 | 2.42 | 3.16 | 3.94 | 2.10 |
| p Value | 1.7E−4 | 3.2E−5 | 0.0059 | 3.2E−4 | 5.0E−5 | 7.3E−4 | 7.2E−4 | 3.0E−5 | 0.0042 |
| Lower limit of 95% CI | 1.84 | 2.02 | 1.24 | 1.74 | 1.96 | 1.45 | 1.62 | 2.07 | 1.26 |
| Upper limit of 95% CI | 6.94 | 7.11 | 3.51 | 6.59 | 6.88 | 4.05 | 6.14 | 7.51 | 3.49 |

TABLE 11.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 98000 | 120000 | 97900 | 119000 | 98000 | 118000 |
| Average | 111000 | 129000 | 111000 | 129000 | 112000 | 128000 |
| Stdev | 41500 | 44400 | 41600 | 44300 | 42200 | 44200 |
| p (t-test) | | 2.4E−4 | | 2.5E−4 | | 8.6E−4 |
| Min | 57600 | 57000 | 57600 | 57000 | 57600 | 57000 |
| Max | 299000 | 281000 | 299000 | 281000 | 299000 | 281000 |
| n (Patient) | 134 | 193 | 133 | 194 | 128 | 199 |
| | sCr only | | | | | |
| Median | 98600 | 121000 | 98600 | 121000 | 98600 | 121000 |
| Average | 110000 | 131000 | 110000 | 131000 | 110000 | 131000 |
| Stdev | 39300 | 45700 | 39400 | 45600 | 39500 | 45400 |
| p (t-test) | | 1.9E−5 | | 2.1E−5 | | 2.0E−5 |
| Min | 57600 | 57000 | 57600 | 57000 | 57600 | 57000 |
| Max | 299000 | 281000 | 299000 | 281000 | 299000 | 281000 |
| n (Patient) | 146 | 181 | 145 | 182 | 143 | 184 |

TABLE 11.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 104000 | 124000 | 104000 | 125000 | 104000 | 125000 |
| Average | 116000 | 136000 | 115000 | 138000 | 115000 | 135000 |
| Stdev | 41900 | 46400 | 40800 | 47500 | 41300 | 46100 |
| p (t-test) | | 1.5E−4 | | 1.5E−5 | | 4.3E−5 |
| Min | 57600 | 57000 | 57600 | 57000 | 57600 | 57000 |
| Max | 299000 | 281000 | 299000 | 281000 | 299000 | 281000 |
| n (Patient) | 231 | 94 | 225 | 100 | 210 | 115 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.66 | 0.65 | 0.66 | 0.66 | 0.67 | 0.65 | 0.66 | 0.66 |
| SE | 0.030 | 0.030 | 0.035 | 0.030 | 0.030 | 0.034 | 0.030 | 0.030 | 0.032 |
| p Value | 2.0E−7 | 4.7E−8 | 1.3E−5 | 1.7E−7 | 4.0E−8 | 1.0E−6 | 1.6E−6 | 2.8E−8 | 9.4E−7 |
| nCohort Recovered | 134 | 146 | 231 | 133 | 145 | 225 | 128 | 143 | 210 |
| nCohort Non-recovered | 193 | 181 | 94 | 194 | 182 | 100 | 199 | 184 | 115 |
| Cutoff Quartile 2 | 90200 | 90200 | 90200 | 90200 | 90200 | 90200 | 90200 | 90200 | 90200 |
| Sensitivity | 82% | 82% | 88% | 82% | 82% | 89% | 81% | 82% | 87% |
| Specificity | 35% | 34% | 30% | 35% | 34% | 31% | 34% | 34% | 31% |
| Cutoff Quartile 3 | 109000 | 109000 | 109000 | 109000 | 109000 | 109000 | 109000 | 109000 | 109000 |
| Sensitivity | 61% | 62% | 65% | 61% | 62% | 66% | 60% | 62% | 64% |
| Specificity | 66% | 64% | 56% | 66% | 65% | 57% | 66% | 65% | 58% |
| Cutoff Quartile 4 | 137000 | 137000 | 137000 | 137000 | 137000 | 137000 | 137000 | 137000 | 137000 |
| Sensitivity | 31% | 33% | 38% | 31% | 32% | 39% | 30% | 33% | 37% |
| Specificity | 84% | 84% | 80% | 83% | 84% | 81% | 83% | 85% | 81% |
| OR Quartile 2 | 2.44 | 2.27 | 3.28 | 2.48 | 2.30 | 3.65 | 2.22 | 2.23 | 3.06 |
| p Value | 6.1E−4 | 0.0017 | 7.2E−4 | 4.8E−4 | 0.0013 | 2.2E−4 | 0.0021 | 0.0020 | 3.8E−4 |
| Lower limit of 95% CI | 1.46 | 1.36 | 1.65 | 1.49 | 1.38 | 1.84 | 1.34 | 1.34 | 1.65 |
| Upper limit of 95% CI | 4.06 | 3.77 | 6.53 | 4.14 | 3.84 | 7.26 | 3.69 | 3.71 | 5.66 |
| OR Quartile 3 | 3.01 | 2.93 | 2.34 | 3.10 | 3.02 | 2.56 | 2.90 | 3.03 | 2.45 |
| p Value | 2.6E−6 | 3.1E−6 | 8.1E−4 | 1.5E−6 | 1.8E−6 | 1.7E−4 | 6.4E−6 | 1.8E−6 | 1.8E−4 |
| Lower limit of 95% CI | 1.90 | 1.87 | 1.42 | 1.96 | 1.92 | 1.57 | 1.83 | 1.92 | 1.53 |
| Upper limit of 95% CI | 4.76 | 4.61 | 3.84 | 4.92 | 4.75 | 4.18 | 4.60 | 4.77 | 3.92 |
| OR Quartile 4 | 2.30 | 2.59 | 2.50 | 2.26 | 2.54 | 2.71 | 2.08 | 2.66 | 2.45 |
| p Value | 0.0030 | 6.0E−4 | 6.6E−4 | 0.0036 | 7.5E−4 | 1.8E−4 | 0.0091 | 4.7E−4 | 6.3E−4 |
| Lower limit of 95% CI | 1.33 | 1.50 | 1.47 | 1.30 | 1.48 | 1.61 | 1.20 | 1.54 | 1.46 |
| Upper limit of 95% CI | 3.98 | 4.45 | 4.23 | 3.91 | 4.38 | 4.56 | 3.60 | 4.61 | 4.08 |

TABLE 11.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 98800 | 120000 | 98600 | 120000 | 98600 | 120000 |
| Average | 114000 | 129000 | 114000 | 129000 | 114000 | 128000 |
| Stdev | 42700 | 44200 | 43000 | 43900 | 43300 | 43800 |
| p (t-test) | | 0.0018 | | 0.0017 | | 0.0029 |
| Min | 57600 | 57000 | 57600 | 57000 | 57600 | 57000 |

TABLE 11.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 299000 | 281000 | 299000 | 281000 | 299000 | 281000 |
| n (Patient) | 154 | 173 | 152 | 175 | 148 | 179 | sCr only

| | | | | | | |
|---|---|---|---|---|---|---|
| Median | 99200 | 122000 | 99100 | 121000 | 99000 | 122000 |
| Average | 113000 | 131000 | 113000 | 131000 | 112000 | 131000 |
| Stdev | 41100 | 45200 | 41200 | 45000 | 41200 | 45000 |
| p (t-test) | | 1.7E−4 | | 1.9E−4 | | 1.3E−4 |
| Min | 57600 | 57000 | 57600 | 57000 | 57600 | 57000 |
| Max | 299000 | 281000 | 299000 | 281000 | 299000 | 281000 |
| n (Patient) | 161 | 166 | 160 | 167 | 159 | 168 |

UO only

| | | | | | | |
|---|---|---|---|---|---|---|
| Median | 104000 | 124000 | 104000 | 125000 | 103000 | 127000 |
| Average | 115000 | 138000 | 115000 | 139000 | 114000 | 138000 |
| Stdev | 41100 | 47300 | 40900 | 47000 | 40200 | 47200 |
| p (t-test) | | 2.2E−5 | | 7.1E−6 | | 2.8E−6 |
| Min | 57600 | 57000 | 57600 | 57000 | 57600 | 57000 |
| Max | 299000 | 281000 | 299000 | 281000 | 299000 | 281000 |
| n (Patient) | 230 | 95 | 228 | 97 | 215 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.65 | 0.66 | 0.64 | 0.65 | 0.67 | 0.63 | 0.65 | 0.68 |
| SE | 0.030 | 0.030 | 0.034 | 0.030 | 0.030 | 0.034 | 0.030 | 0.030 | 0.033 |
| p Value | 1.0E−5 | 1.1E−6 | 2.2E−6 | 5.4E−6 | 9.6E−7 | 4.5E−7 | 1.1E−5 | 4.2E−7 | 6.7E−8 |
| nCohort Recovered | 154 | 161 | 230 | 152 | 160 | 228 | 148 | 159 | 215 |
| nCohort Non-recovered | 173 | 166 | 95 | 175 | 167 | 97 | 179 | 168 | 110 |
| Cutoff Quartile 2 | 90200 | 90200 | 90200 | 90200 | 90200 | 90200 | 90200 | 90200 | 90200 |
| Sensitivity | 83% | 83% | 88% | 83% | 83% | 89% | 82% | 83% | 87% |
| Specificity | 34% | 33% | 30% | 34% | 33% | 31% | 34% | 33% | 31% |
| Cutoff Quartile 3 | 109000 | 109000 | 109000 | 109000 | 109000 | 109000 | 109000 | 109000 | 109000 |
| Sensitivity | 62% | 63% | 66% | 62% | 63% | 67% | 62% | 63% | 67% |
| Specificity | 63% | 63% | 57% | 64% | 63% | 57% | 64% | 64% | 59% |
| Cutoff Quartile 4 | 137000 | 137000 | 137000 | 137000 | 137000 | 137000 | 137000 | 137000 | 137000 |
| Sensitivity | 31% | 33% | 39% | 30% | 32% | 40% | 30% | 33% | 39% |
| Specificity | 81% | 83% | 80% | 81% | 82% | 81% | 81% | 83% | 82% |
| OR Quartile 2 | 2.43 | 2.32 | 3.34 | 2.51 | 2.36 | 3.46 | 2.34 | 2.40 | 3.10 |
| p Value | 7.5E−4 | 0.0015 | 5.9E−4 | 4.7E−4 | 0.0012 | 4.0E−4 | 0.0011 | 9.5E−4 | 4.3E−4 |
| Lower limit of 95% CI | 1.45 | 1.38 | 1.68 | 1.50 | 1.40 | 1.74 | 1.40 | 1.43 | 1.65 |
| Upper limit of 95% CI | 4.07 | 3.89 | 6.65 | 4.21 | 3.96 | 6.89 | 3.91 | 4.02 | 5.83 |
| OR Quartile 3 | 2.76 | 2.82 | 2.56 | 2.91 | 2.90 | 2.69 | 2.93 | 2.98 | 2.91 |
| p Value | 9.2E−6 | 5.7E−6 | 2.2E−4 | 3.3E−6 | 3.4E−6 | 9.5E−5 | 3.2E−6 | 2.0E−6 | 1.4E−5 |
| Lower limit of 95% CI | 1.76 | 1.80 | 1.55 | 1.86 | 1.85 | 1.64 | 1.86 | 1.90 | 1.80 |
| Upper limit of 95% CI | 4.32 | 4.42 | 4.22 | 4.57 | 4.54 | 4.43 | 4.60 | 4.67 | 4.71 |
| OR Quartile 4 | 1.90 | 2.29 | 2.62 | 1.84 | 2.25 | 2.89 | 1.85 | 2.38 | 2.90 |
| p Value | 0.015 | 0.0018 | 3.2E−4 | 0.021 | 0.0022 | 7.1E−5 | 0.020 | 0.0012 | 5.5E−5 |
| Lower limit of 95% CI | 1.13 | 1.36 | 1.55 | 1.10 | 1.34 | 1.71 | 1.10 | 1.41 | 1.73 |
| Upper limit of 95% CI | 3.19 | 3.86 | 4.44 | 3.09 | 3.79 | 4.89 | 3.12 | 4.02 | 4.86 |

TABLE 11.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 99100 | 120000 | 98700 | 120000 | 98700 | 120000 |
| Average | 114000 | 130000 | 114000 | 130000 | 114000 | 129000 |
| Stdev | 42500 | 44300 | 42900 | 44000 | 43200 | 43800 |
| p (t-test) | | 9.0E−4 | | 0.0010 | | 0.0018 |
| Min | 57600 | 57000 | 57600 | 57000 | 57600 | 57000 |
| Max | 299000 | 281000 | 299000 | 281000 | 299000 | 281000 |
| n (Patient) | 166 | 161 | 163 | 164 | 159 | 168 |
| sCr only | | | | | | |
| Median | 99200 | 122000 | 99100 | 121000 | 99000 | 122000 |
| Average | 113000 | 131000 | 113000 | 131000 | 113000 | 131000 |
| Stdev | 41400 | 44900 | 41600 | 44800 | 41500 | 44700 |
| p (t-test) | | 1.2E−4 | | 1.4E−4 | | 9.3E−5 |
| Min | 57600 | 57000 | 57600 | 57000 | 57600 | 57000 |
| Max | 299000 | 281000 | 299000 | 281000 | 299000 | 281000 |
| n (Patient) | 169 | 158 | 168 | 159 | 167 | 160 |
| UO only | | | | | | |
| Median | 103000 | 130000 | 103000 | 129000 | 103000 | 128000 |
| Average | 114000 | 141000 | 114000 | 141000 | 114000 | 139000 |
| Stdev | 39500 | 48200 | 39500 | 48100 | 40000 | 47400 |
| p (t-test) | | 1.1E−7 | | 1.6E−7 | | 9.5E−7 |
| Min | 57600 | 57000 | 57600 | 57000 | 57600 | 57000 |
| Max | 299000 | 281000 | 299000 | 281000 | 299000 | 281000 |
| n (Patient) | 226 | 99 | 225 | 100 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.65 | 0.70 | 0.64 | 0.65 | 0.69 | 0.64 | 0.66 | 0.68 |
| SE | 0.030 | 0.030 | 0.033 | 0.030 | 0.030 | 0.033 | 0.030 | 0.030 | 0.033 |
| p Value | 4.6E−6 | 5.4E−7 | 3.6E−9 | 3.0E−6 | 4.8E−7 | 5.6E−9 | 6.3E−6 | 2.1E−7 | 1.9E−8 |
| nCohort Recovered | 166 | 169 | 226 | 163 | 168 | 225 | 159 | 167 | 217 |
| nCohort Non-recovered | 161 | 158 | 99 | 164 | 159 | 100 | 168 | 160 | 108 |
| Cutoff Quartile 2 | 90200 | 90200 | 90200 | 90200 | 90200 | 90200 | 90200 | 90200 | 90200 |
| Sensitivity | 83% | 83% | 89% | 83% | 83% | 89% | 82% | 83% | 87% |
| Specificity | 33% | 33% | 31% | 33% | 33% | 31% | 33% | 33% | 31% |
| Cutoff Quartile 3 | 109000 | 109000 | 109000 | 109000 | 109000 | 109000 | 109000 | 109000 | 109000 |
| Sensitivity | 63% | 63% | 69% | 63% | 64% | 68% | 62% | 64% | 68% |
| Specificity | 62% | 62% | 58% | 63% | 62% | 58% | 63% | 63% | 59% |
| Cutoff Quartile 4 | 137000 | 137000 | 137000 | 137000 | 137000 | 137000 | 137000 | 137000 | 137000 |
| Sensitivity | 32% | 33% | 42% | 31% | 33% | 42% | 31% | 33% | 40% |
| Specificity | 81% | 82% | 82% | 81% | 82% | 82% | 81% | 83% | 82% |
| OR Quartile 2 | 2.29 | 2.34 | 3.59 | 2.41 | 2.38 | 3.65 | 2.24 | 2.42 | 3.00 |
| p Value | 0.0018 | 0.0015 | 2.7E−4 | 9.6E−4 | 0.0012 | 2.2E−4 | 0.0022 | 9.7E−4 | 6.5E−4 |
| Lower limit of 95% CI | 1.36 | 1.39 | 1.81 | 1.43 | 1.41 | 1.84 | 1.34 | 1.43 | 1.60 |
| Upper limit of 95% CI | 3.86 | 3.96 | 7.14 | 4.05 | 4.02 | 7.26 | 3.74 | 4.09 | 5.64 |
| OR Quartile 3 | 2.75 | 2.83 | 3.02 | 2.82 | 2.90 | 2.91 | 2.82 | 2.98 | 2.94 |
| p Value | 9.3E−6 | 5.6E−6 | 1.4E−5 | 5.7E−6 | 3.3E−6 | 2.5E−5 | 5.7E−6 | 2.0E−6 | 1.3E−5 |
| Lower limit of 95% CI | 1.76 | 1.81 | 1.83 | 1.80 | 1.85 | 1.77 | 1.80 | 1.90 | 1.81 |
| Upper limit of 95% CI | 4.31 | 4.43 | 4.99 | 4.42 | 4.55 | 4.78 | 4.42 | 4.67 | 4.78 |

TABLE 11.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 2.02 | 2.27 | 3.43 | 1.92 | 2.24 | 3.35 | 1.93 | 2.36 | 3.02 |
| p Value | 0.0072 | 0.0018 | 4.3E−6 | 0.012 | 0.0022 | 6.1E−6 | 0.012 | 0.0012 | 2.9E−5 |
| Lower limit of 95% CI | 1.21 | 1.36 | 2.03 | 1.15 | 1.34 | 1.98 | 1.15 | 1.40 | 1.80 |
| Upper limit of 95% CI | 3.37 | 3.81 | 5.79 | 3.21 | 3.74 | 5.66 | 3.22 | 3.96 | 5.07 |

TABLE 11.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| *sCr or UO* | | | | | | |
| Median | 101000 | 123000 | 101000 | 123000 | 101000 | 123000 |
| Average | 114000 | 135000 | 114000 | 135000 | 114000 | 135000 |
| Stdev | 40600 | 46500 | 40800 | 46200 | 40800 | 46100 |
| p (t-test) | | 1.8E−5 | | 2.1E−5 | | 1.7E−5 |
| Min | 57600 | 57000 | 57600 | 57000 | 57600 | 57000 |
| Max | 299000 | 281000 | 299000 | 281000 | 299000 | 281000 |
| n (Patient) | 204 | 123 | 202 | 125 | 201 | 126 |
| *sCr only* | | | | | | |
| Median | 101000 | 121000 | 101000 | 121000 | 101000 | 121000 |
| Average | 114000 | 131000 | 114000 | 131000 | 114000 | 131000 |
| Stdev | 41500 | 45600 | 41500 | 45600 | 41500 | 45600 |
| p (t-test) | | 4.5E−4 | | 4.5E−4 | | 4.5E−4 |
| Min | 57600 | 57000 | 57600 | 57000 | 57600 | 57000 |
| Max | 299000 | 281000 | 299000 | 281000 | 299000 | 281000 |
| n (Patient) | 184 | 143 | 184 | 143 | 184 | 143 |
| *UO only* | | | | | | |
| Median | 103000 | 125000 | 103000 | 125000 | 102000 | 126000 |
| Average | 114000 | 139000 | 114000 | 139000 | 114000 | 139000 |
| Stdev | 39400 | 48400 | 39500 | 48400 | 39600 | 47900 |
| p (t-test) | | 6.0E−7 | | 8.8E−7 | | 6.3E−7 |
| Min | 57600 | 57000 | 57600 | 57000 | 57600 | 57000 |
| Max | 299000 | 281000 | 299000 | 281000 | 299000 | 281000 |
| n (Patient) | 220 | 105 | 219 | 106 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.64 | 0.68 | 0.66 | 0.64 | 0.68 | 0.66 | 0.64 | 0.68 |
| SE | 0.032 | 0.031 | 0.033 | 0.032 | 0.031 | 0.033 | 0.031 | 0.031 | 0.033 |
| p Value | 3.6E−7 | 1.4E−5 | 5.9E−8 | 2.8E−7 | 1.4E−5 | 8.4E−8 | 1.5E−7 | 1.4E−5 | 2.5E−8 |
| nCohort Recovered | 204 | 184 | 220 | 202 | 184 | 219 | 201 | 184 | 217 |
| nCohort Non-recovered | 123 | 143 | 105 | 125 | 143 | 106 | 126 | 143 | 108 |
| Cutoff Quartile 2 | 90200 | 90200 | 90200 | 90200 | 90200 | 90200 | 90200 | 90200 | 90200 |
| Sensitivity | 86% | 83% | 87% | 86% | 83% | 87% | 87% | 83% | 87% |
| Specificity | 32% | 31% | 30% | 32% | 31% | 31% | 32% | 31% | 31% |
| Cutoff Quartile 3 | 109000 | 109000 | 109000 | 109000 | 109000 | 109000 | 109000 | 109000 | 109000 |
| Sensitivity | 65% | 62% | 68% | 65% | 62% | 67% | 65% | 62% | 68% |
| Specificity | 59% | 59% | 58% | 59% | 59% | 58% | 59% | 59% | 59% |
| Cutoff Quartile 4 | 137000 | 137000 | 137000 | 137000 | 137000 | 137000 | 137000 | 137000 | 137000 |
| Sensitivity | 36% | 34% | 40% | 35% | 34% | 40% | 36% | 34% | 40% |
| Specificity | 81% | 82% | 82% | 81% | 82% | 82% | 82% | 82% | 82% |
| OR Quartile 2 | 2.92 | 2.12 | 2.85 | 3.01 | 2.12 | 2.90 | 3.06 | 2.12 | 3.00 |
| p Value | 3.8E−4 | 0.0058 | 0.0012 | 2.5E−4 | 0.0058 | 9.6E−4 | 2.0E−4 | 0.0058 | 6.5E−4 |

TABLE 11.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.62 | 1.24 | 1.51 | 1.67 | 1.24 | 1.54 | 1.70 | 1.24 | 1.60 |
| Upper limit of 95% CI | 5.26 | 3.61 | 5.35 | 5.44 | 3.61 | 5.45 | 5.53 | 3.61 | 5.64 |
| OR Quartile 3 | 2.66 | 2.40 | 2.91 | 2.64 | 2.40 | 2.80 | 2.70 | 2.40 | 2.94 |
| p Value | 3.6E−5 | 1.3E−4 | 1.9E−5 | 3.8E−5 | 1.3E−4 | 3.2E−5 | 2.4E−5 | 1.3E−4 | 1.3E−5 |
| Lower limit of 95% CI | 1.67 | 1.53 | 1.78 | 1.66 | 1.53 | 1.72 | 1.70 | 1.53 | 1.81 |
| Upper limit of 95% CI | 4.23 | 3.75 | 4.74 | 4.19 | 3.75 | 4.55 | 4.29 | 3.75 | 4.78 |
| OR Quartile 4 | 2.43 | 2.23 | 3.00 | 2.34 | 2.23 | 2.94 | 2.46 | 2.23 | 3.02 |
| p Value | 6.3E−4 | 0.0020 | 3.4E−5 | 0.0010 | 0.0020 | 4.7E−5 | 5.3E−4 | 0.0020 | 2.9E−5 |
| Lower limit of 95% CI | 1.46 | 1.34 | 1.78 | 1.41 | 1.34 | 1.75 | 1.48 | 1.34 | 1.80 |
| Upper limit of 95% CI | 4.05 | 3.71 | 5.04 | 3.90 | 3.71 | 4.93 | 4.10 | 3.71 | 5.07 |

Example 12. Use of Metalloproteinase Inhibitor 2 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 12.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 11600 | 23500 | 11600 | 25700 | 11900 | 28900 |
| Average | 17800 | 50100 | 18300 | 54600 | 20900 | 53600 |
| Stdev | 21800 | 77800 | 22100 | 82600 | 35200 | 78100 |
| p (t-test) | | 5.7E−8 | | 3.8E−9 | | 5.5E−7 |
| Min | 200 | 2940 | 200 | 2940 | 200 | 3000 |
| Max | 183000 | 428000 | 183000 | 428000 | 396000 | 428000 |
| n (Patient) | 205 | 112 | 221 | 96 | 236 | 81 |
| sCr only | | | | | | |
| Median | 11800 | 21800 | 11800 | 25200 | 12000 | 24300 |
| Average | 19900 | 46400 | 20500 | 49500 | 23200 | 45800 |
| Stdev | 35400 | 70300 | 35500 | 73900 | 44300 | 65800 |
| p (t-test) | | 1.1E−5 | | 3.7E−6 | | 5.9E−4 |
| Min | 200 | 2940 | 200 | 2940 | 200 | 2940 |
| Max | 428000 | 396000 | 428000 | 396000 | 428000 | 371000 |
| n (Patient) | 208 | 108 | 223 | 93 | 235 | 81 |

TABLE 12.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 12300 | 39600 | 12800 | 38200 | 12800 | 39600 |
| Average | 22100 | 79400 | 22400 | 81600 | 22400 | 83600 |
| Stdev | 34300 | 102000 | 34300 | 106000 | 34300 | 106000 |
| p (t-test) | | 1.3E−11 | | 1.4E−11 | | 4.9E−12 |
| Min | 200 | 5410 | 200 | 5410 | 200 | 5410 |
| Max | 396000 | 428000 | 396000 | 428000 | 396000 | 428000 |
| n (Patient) | 275 | 40 | 278 | 37 | 279 | 36 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.79 | 0.71 | 0.69 | 0.78 | 0.72 | 0.67 | 0.78 |
| SE | 0.032 | 0.033 | 0.044 | 0.033 | 0.034 | 0.047 | 0.035 | 0.036 | 0.047 |
| p Value | 1.5E−9 | 3.6E−7 | 1.3E−10 | 8.6E−11 | 1.4E−8 | 3.6E−9 | 7.4E−10 | 2.7E−6 | 1.2E−9 |
| nCohort Non-persistent | 205 | 208 | 275 | 221 | 223 | 278 | 236 | 235 | 279 |
| nCohort Persistent | 112 | 108 | 40 | 96 | 93 | 37 | 81 | 81 | 36 |
| Cutoff Quartile 2 | 7990 | 7980 | 8020 | 7990 | 7980 | 8020 | 7990 | 7980 | 8020 |
| Sensitivity | 85% | 83% | 90% | 89% | 87% | 89% | 90% | 86% | 89% |
| Specificity | 30% | 29% | 27% | 31% | 30% | 27% | 30% | 29% | 27% |
| Cutoff Quartile 3 | 13500 | 13500 | 13500 | 13500 | 13500 | 13500 | 13500 | 13500 | 13500 |
| Sensitivity | 66% | 64% | 82% | 69% | 68% | 81% | 70% | 67% | 83% |
| Specificity | 59% | 57% | 55% | 58% | 57% | 54% | 57% | 56% | 54% |
| Cutoff Quartile 4 | 28900 | 28100 | 29400 | 28900 | 28100 | 29400 | 28900 | 28100 | 29400 |
| Sensitivity | 46% | 44% | 65% | 49% | 47% | 65% | 51% | 46% | 67% |
| Specificity | 86% | 85% | 81% | 85% | 84% | 80% | 83% | 82% | 80% |
| OR Quartile 2 | 2.42 | 2.07 | 3.37 | 3.43 | 2.90 | 3.05 | 3.93 | 2.59 | 2.94 |
| p Value | 0.0036 | 0.015 | 0.025 | 4.6E−4 | 0.0019 | 0.041 | 6.0E−4 | 0.0073 | 0.049 |
| Lower limit of 95% CI | 1.34 | 1.15 | 1.16 | 1.72 | 1.48 | 1.04 | 1.80 | 1.29 | 1.01 |
| Upper limit of 95% CI | 4.40 | 3.73 | 9.81 | 6.85 | 5.67 | 8.89 | 8.58 | 5.19 | 8.60 |
| OR Quartile 3 | 2.75 | 2.37 | 5.66 | 3.03 | 2.83 | 5.02 | 3.12 | 2.52 | 5.90 |
| p Value | 3.6E−5 | 4.3E−4 | 6.4E−5 | 1.9E−5 | 6.3E−5 | 2.2E−4 | 3.9E−5 | 6.2E−4 | 1.3E−4 |
| Lower limit of 95% CI | 1.70 | 1.46 | 2.42 | 1.82 | 1.70 | 2.13 | 1.81 | 1.48 | 2.38 |
| Upper limit of 95% CI | 4.44 | 3.82 | 13.2 | 5.03 | 4.71 | 11.8 | 5.36 | 4.28 | 14.6 |
| OR Quartile 4 | 5.07 | 4.24 | 7.78 | 5.46 | 4.82 | 7.49 | 5.18 | 3.86 | 8.15 |
| p Value | 4.0E−9 | 1.2E−7 | 1.9E−8 | 1.0E−9 | 1.4E−8 | 8.5E−8 | 6.3E−9 | 1.5E−6 | 4.8E−8 |
| Lower limit of 95% CI | 2.95 | 2.48 | 3.80 | 3.17 | 2.80 | 3.58 | 2.97 | 2.23 | 3.84 |
| Upper limit of 95% CI | 8.72 | 7.24 | 15.9 | 9.42 | 8.31 | 15.6 | 9.02 | 6.70 | 17.3 |

TABLE 12.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 11600 | 21200 | 11600 | 21900 | 11600 | 24800 |
| Average | 17500 | 45900 | 17600 | 50200 | 20300 | 49200 |
| Stdev | 21300 | 73300 | 21200 | 77700 | 35600 | 72600 |

TABLE 12.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 9.8E−7 | | 4.0E−8 | | 3.1E−6 |
| Min | 200 | 658 | 200 | 2170 | 200 | 2170 |
| Max | 183000 | 428000 | 183000 | 428000 | 396000 | 428000 |
| n (Patient) | 186 | 131 | 204 | 113 | 219 | 98 | sCr only

| | | | | | | |
|---|---|---|---|---|---|---|
| Median | 11900 | 19800 | 11800 | 21200 | 11900 | 21300 |
| Average | 20600 | 42000 | 20300 | 45200 | 23000 | 42300 |
| Stdev | 36700 | 66600 | 35800 | 69700 | 45200 | 61600 |
| p (t-test) | | 2.7E−4 | | 3.7E−5 | | 0.0020 |
| Min | 200 | 658 | 200 | 2170 | 200 | 2170 |
| Max | 428000 | 396000 | 428000 | 396000 | 428000 | 371000 |
| n (Patient) | 192 | 124 | 206 | 110 | 218 | 98 |

UO only

| | | | | | | |
|---|---|---|---|---|---|---|
| Median | 12000 | 32200 | 12500 | 32200 | 12300 | 32400 |
| Average | 21600 | 62900 | 22000 | 64300 | 21900 | 65300 |
| Stdev | 34500 | 88900 | 34500 | 91700 | 34400 | 92300 |
| p (t-test) | | 1.6E−8 | | 1.8E−8 | | 1.0E−8 |
| Min | 200 | 2170 | 200 | 2170 | 200 | 2170 |
| Max | 396000 | 428000 | 396000 | 428000 | 396000 | 428000 |
| n (Patient) | 256 | 59 | 260 | 55 | 261 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.63 | 0.71 | 0.69 | 0.66 | 0.70 | 0.70 | 0.66 | 0.70 |
| SE | 0.031 | 0.032 | 0.040 | 0.032 | 0.033 | 0.042 | 0.033 | 0.034 | 0.042 |
| p Value | 6.8E−8 | 5.2E−5 | 1.4E−7 | 1.2E−9 | 1.1E−6 | 1.8E−6 | 7.7E−10 | 6.4E−6 | 1.2E−6 |
| nCohort Non-persistent | 186 | 192 | 256 | 204 | 206 | 260 | 219 | 218 | 261 |
| nCohort Persistent | 131 | 124 | 59 | 113 | 110 | 55 | 98 | 98 | 54 |
| Cutoff Quartile 2 | 7990 | 7980 | 8020 | 7990 | 7980 | 8020 | 7990 | 7980 | 8020 |
| Sensitivity | 82% | 81% | 83% | 85% | 84% | 82% | 88% | 85% | 81% |
| Specificity | 30% | 29% | 27% | 30% | 30% | 27% | 31% | 29% | 26% |
| Cutoff Quartile 3 | 13500 | 13500 | 13500 | 13500 | 13500 | 13500 | 13500 | 13500 | 13500 |
| Sensitivity | 63% | 60% | 71% | 65% | 63% | 69% | 67% | 63% | 70% |
| Specificity | 59% | 56% | 55% | 58% | 57% | 54% | 58% | 56% | 54% |
| Cutoff Quartile 4 | 28900 | 28100 | 29400 | 28900 | 28100 | 29400 | 28900 | 28100 | 29400 |
| Sensitivity | 41% | 39% | 53% | 45% | 42% | 53% | 47% | 42% | 54% |
| Specificity | 86% | 84% | 81% | 86% | 84% | 81% | 84% | 83% | 81% |
| OR Quartile 2 | 2.02 | 1.67 | 1.81 | 2.47 | 2.15 | 1.63 | 3.16 | 2.30 | 1.58 |
| p Value | 0.012 | 0.064 | 0.11 | 0.0030 | 0.011 | 0.20 | 7.5E−4 | 0.0087 | 0.22 |
| Lower limit of 95% CI | 1.17 | 0.971 | 0.868 | 1.36 | 1.20 | 0.777 | 1.62 | 1.23 | 0.755 |
| Upper limit of 95% CI | 3.50 | 2.88 | 3.77 | 4.47 | 3.87 | 3.40 | 6.17 | 4.28 | 3.31 |
| OR Quartile 3 | 2.37 | 1.90 | 2.98 | 2.66 | 2.21 | 2.61 | 2.79 | 2.19 | 2.79 |
| p Value | 2.3E−4 | 0.0059 | 5.0E−4 | 6.0E−5 | 0.0010 | 0.0025 | 5.6E−5 | 0.0017 | 0.0015 |
| Lower limit of 95% CI | 1.50 | 1.20 | 1.61 | 1.65 | 1.38 | 1.40 | 1.69 | 1.34 | 1.48 |
| Upper limit of 95% CI | 3.75 | 3.01 | 5.51 | 4.28 | 3.56 | 4.86 | 4.61 | 3.57 | 5.25 |
| OR Quartile 4 | 4.32 | 3.28 | 4.80 | 4.96 | 3.77 | 4.68 | 4.81 | 3.41 | 4.90 |
| p Value | 1.2E−7 | 1.0E−5 | 3.0E−7 | 6.1E−9 | 9.8E−7 | 7.8E−7 | 1.1E−8 | 6.4E−6 | 4.6E−7 |
| Lower limit of 95% CI | 2.51 | 1.94 | 2.63 | 2.89 | 2.22 | 2.54 | 2.81 | 2.00 | 2.64 |
| Upper limit of 95% CI | 7.41 | 5.56 | 8.74 | 8.52 | 6.41 | 8.64 | 8.26 | 5.80 | 9.08 |

TABLE 12.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 11500 | 21100 | 11400 | 21400 | 11600 | 21600 |
| Average | 16700 | 44800 | 16500 | 48300 | 19900 | 46400 |
| Stdev | 18500 | 71600 | 18100 | 74800 | 35100 | 69800 |
| p (t-test) | | 9.8E−7 | | 4.3E−8 | | 9.5E−6 |
| Min | 200 | 658 | 200 | 2170 | 200 | 2170 |
| Max | 183000 | 428000 | 183000 | 428000 | 396000 | 428000 |
| n (Patient) | 175 | 142 | 190 | 127 | 205 | 112 |
| sCr only | | | | | | |
| Median | 11800 | 19600 | 11600 | 20600 | 11800 | 20900 |
| Average | 19700 | 41600 | 19900 | 43600 | 23100 | 40400 |
| Stdev | 35700 | 65400 | 36300 | 67100 | 46100 | 59200 |
| p (t-test) | | 1.6E−4 | | 6.2E−5 | | 0.0044 |
| Min | 200 | 658 | 200 | 2170 | 200 | 2170 |
| Max | 428000 | 396000 | 428000 | 396000 | 428000 | 371000 |
| n (Patient) | 182 | 134 | 195 | 121 | 208 | 108 |
| UO only | | | | | | |
| Median | 12000 | 25100 | 12000 | 27000 | 12000 | 27000 |
| Average | 21200 | 58500 | 21500 | 60100 | 21500 | 60100 |
| Stdev | 33800 | 84800 | 33700 | 87500 | 33700 | 87500 |
| p (t-test) | | 6.6E−8 | | 6.0E−8 | | 6.0E−8 |
| Min | 200 | 2170 | 200 | 2170 | 200 | 2170 |
| Max | 396000 | 428000 | 396000 | 428000 | 396000 | 428000 |
| n (Patient) | 246 | 69 | 251 | 64 | 251 | 64 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.64 | 0.69 | 0.70 | 0.66 | 0.68 | 0.69 | 0.65 | 0.68 |
| SE | 0.031 | 0.032 | 0.038 | 0.031 | 0.032 | 0.040 | 0.032 | 0.033 | 0.040 |
| p Value | 2.5E−8 | 2.0E−5 | 4.0E−7 | 2.2E−10 | 4.0E−7 | 4.7E−6 | 2.6E−9 | 6.4E−6 | 4.7E−6 |
| nCohort Non-persistent | 175 | 182 | 246 | 190 | 195 | 251 | 205 | 208 | 251 |
| nCohort Persistent | 142 | 134 | 69 | 127 | 121 | 64 | 112 | 108 | 64 |
| Cutoff Quartile 2 | 7990 | 7980 | 8020 | 7990 | 7980 | 8020 | 7990 | 7980 | 8020 |
| Sensitivity | 82% | 81% | 83% | 85% | 83% | 81% | 87% | 84% | 81% |
| Specificity | 31% | 29% | 27% | 32% | 30% | 27% | 31% | 30% | 27% |
| Cutoff Quartile 3 | 13500 | 13500 | 13500 | 13500 | 13500 | 13500 | 13500 | 13500 | 13500 |
| Sensitivity | 63% | 60% | 70% | 65% | 63% | 67% | 66% | 63% | 67% |
| Specificity | 60% | 57% | 55% | 60% | 58% | 54% | 59% | 57% | 54% |
| Cutoff Quartile 4 | 28900 | 28100 | 29400 | 28900 | 28100 | 29400 | 28900 | 28100 | 29400 |
| Sensitivity | 39% | 38% | 48% | 43% | 40% | 48% | 43% | 40% | 48% |
| Specificity | 86% | 85% | 81% | 86% | 85% | 81% | 84% | 83% | 81% |
| OR Quartile 2 | 2.09 | 1.71 | 1.78 | 2.62 | 2.19 | 1.58 | 2.94 | 2.27 | 1.58 |
| p Value | 0.0073 | 0.050 | 0.099 | 0.0010 | 0.0069 | 0.19 | 6.5E−4 | 0.0070 | 0.19 |
| Lower limit of 95% CI | 1.22 | 1.00 | 0.898 | 1.48 | 1.24 | 0.794 | 1.58 | 1.25 | 0.794 |
| Upper limit of 95% CI | 3.58 | 2.91 | 3.52 | 4.67 | 3.87 | 3.14 | 5.45 | 4.13 | 3.14 |
| OR Quartile 3 | 2.52 | 1.98 | 2.83 | 2.83 | 2.33 | 2.42 | 2.75 | 2.23 | 2.42 |
| p Value | 6.9E−5 | 0.0032 | 3.6E−4 | 1.3E−5 | 3.8E−4 | 0.0027 | 3.6E−5 | 1.0E−3 | 0.0027 |
| Lower limit of 95% CI | 1.60 | 1.26 | 1.60 | 1.77 | 1.46 | 1.36 | 1.70 | 1.38 | 1.36 |
| Upper limit of 95% CI | 3.97 | 3.11 | 5.00 | 4.51 | 3.71 | 4.32 | 4.44 | 3.59 | 4.32 |

TABLE 12.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 4.10 | 3.38 | 3.99 | 4.67 | 3.74 | 3.97 | 4.05 | 3.16 | 3.97 |
| p Value | 4.3E−7 | 7.4E−6 | 2.1E−6 | 2.7E−8 | 1.2E−6 | 3.5E−6 | 2.4E−7 | 1.9E−5 | 3.5E−6 |
| Lower limit of 95% CI | 2.37 | 1.98 | 2.25 | 2.71 | 2.20 | 2.22 | 2.38 | 1.87 | 2.22 |
| Upper limit of 95% CI | 7.08 | 5.76 | 7.05 | 8.03 | 6.37 | 7.11 | 6.90 | 5.35 | 7.11 |

TABLE 12.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 11400 | 21100 | 11400 | 21300 | 11500 | 21500 |
| Average | 16700 | 44400 | 16600 | 48000 | 18100 | 48500 |
| Stdev | 18600 | 71100 | 18200 | 74600 | 23400 | 76100 |
| p (t-test) | | 1.3E−6 | | 5.7E−8 | | 2.8E−7 |
| Min | 200 | 658 | 200 | 2170 | 200 | 2170 |
| Max | 183000 | 428000 | 183000 | 428000 | 215000 | 428000 |
| n (Patient) | 173 | 144 | 189 | 128 | 201 | 116 |
| | sCr only | | | | | |
| Median | 11700 | 19400 | 11500 | 20400 | 11600 | 20900 |
| Average | 19700 | 41300 | 19200 | 44100 | 20600 | 44300 |
| Stdev | 35900 | 65000 | 34900 | 67300 | 37100 | 68300 |
| p (t-test) | | 2.1E−4 | | 2.1E−5 | | 8.1E−5 |
| Min | 200 | 658 | 200 | 2170 | 200 | 2170 |
| Max | 428000 | 396000 | 428000 | 396000 | 428000 | 396000 |
| n (Patient) | 180 | 136 | 192 | 124 | 204 | 112 |
| | UO only | | | | | |
| Median | 11900 | 24000 | 12000 | 27000 | 12000 | 27000 |
| Average | 20900 | 56100 | 21300 | 57800 | 21300 | 57800 |
| Stdev | 34000 | 81300 | 33900 | 84200 | 33900 | 84200 |
| p (t-test) | | 1.5E−7 | | 1.1E−7 | | 1.1E−7 |
| Min | 200 | 2170 | 200 | 2170 | 200 | 2170 |
| Max | 396000 | 428000 | 396000 | 428000 | 396000 | 428000 |
| n (Patient) | 239 | 76 | 245 | 70 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.64 | 0.70 | 0.69 | 0.67 | 0.69 | 0.69 | 0.66 | 0.69 |
| SE | 0.031 | 0.032 | 0.037 | 0.031 | 0.032 | 0.038 | 0.032 | 0.033 | 0.038 |
| p Value | 1.9E−8 | 1.9E−5 | 3.5E−8 | 2.7E−10 | 1.3E−7 | 7.3E−7 | 2.7E−9 | 8.0E−7 | 7.3E−7 |
| nCohort Non-persistent | 173 | 180 | 239 | 189 | 192 | 245 | 201 | 204 | 245 |
| nCohort Persistent | 144 | 136 | 76 | 128 | 124 | 70 | 116 | 112 | 70 |
| Cutoff Quartile 2 | 7990 | 7980 | 8020 | 7990 | 7980 | 8020 | 7990 | 7980 | 8020 |
| Sensitivity | 83% | 81% | 84% | 85% | 84% | 83% | 86% | 85% | 83% |
| Specificity | 31% | 29% | 28% | 32% | 31% | 27% | 31% | 30% | 27% |
| Cutoff Quartile 3 | 13500 | 13500 | 13500 | 13500 | 13500 | 13500 | 13500 | 13500 | 13500 |
| Sensitivity | 62% | 60% | 70% | 65% | 63% | 67% | 66% | 63% | 67% |
| Specificity | 60% | 57% | 56% | 60% | 58% | 55% | 59% | 57% | 55% |
| Cutoff Quartile 4 | 28900 | 28100 | 29400 | 28900 | 28100 | 29400 | 28900 | 28100 | 29400 |
| Sensitivity | 39% | 38% | 47% | 42% | 40% | 49% | 42% | 40% | 49% |
| Specificity | 86% | 84% | 82% | 86% | 85% | 82% | 85% | 83% | 82% |
| OR Quartile 2 | 2.16 | 1.77 | 2.08 | 2.67 | 2.31 | 1.82 | 2.85 | 2.44 | 1.82 |
| p Value | 0.0050 | 0.037 | 0.035 | 8.3E−4 | 0.0039 | 0.086 | 7.0E−4 | 0.0034 | 0.086 |

TABLE 12.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.26 | 1.03 | 1.05 | 1.50 | 1.31 | 0.920 | 1.56 | 1.34 | 0.920 |
| Upper limit of 95% CI | 3.70 | 3.01 | 4.09 | 4.74 | 4.07 | 3.60 | 5.23 | 4.43 | 3.60 |
| OR Quartile 3 | 2.51 | 1.97 | 2.94 | 2.74 | 2.37 | 2.47 | 2.70 | 2.33 | 2.47 |
| p Value | 7.1E−5 | 0.0033 | 1.3E−4 | 2.1E−5 | 2.6E−4 | 0.0015 | 4.1E−5 | 4.7E−4 | 0.0015 |
| Lower limit of 95% CI | 1.59 | 1.25 | 1.69 | 1.72 | 1.49 | 1.41 | 1.68 | 1.45 | 1.41 |
| Upper limit of 95% CI | 3.96 | 3.10 | 5.11 | 4.37 | 3.77 | 4.31 | 4.34 | 3.74 | 4.31 |
| OR Quartile 4 | 3.95 | 3.26 | 4.10 | 4.57 | 3.80 | 4.20 | 4.01 | 3.36 | 4.20 |
| p Value | 8.1E−7 | 1.4E−5 | 7.2E−7 | 4.0E−8 | 9.5E−7 | 7.9E−7 | 3.0E−7 | 6.8E−6 | 7.9E−7 |
| Lower limit of 95% CI | 2.29 | 1.91 | 2.35 | 2.66 | 2.23 | 2.38 | 2.36 | 1.98 | 2.38 |
| Upper limit of 95% CI | 6.82 | 5.54 | 7.17 | 7.87 | 6.48 | 7.42 | 6.82 | 5.69 | 7.42 |

TABLE 12.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 11400 | 20900 | 11300 | 21400 | 11400 | 21600 |
| Average | 16600 | 43600 | 16500 | 46900 | 18100 | 47600 |
| Stdev | 18800 | 70300 | 18300 | 73400 | 23600 | 75000 |
| p (t-test) | | 2.5E−6 | | 1.2E−7 | | 5.2E−7 |
| Min | 200 | 658 | 200 | 2170 | 200 | 2170 |
| Max | 183000 | 428000 | 183000 | 428000 | 215000 | 428000 |
| n (Patient) | 169 | 148 | 184 | 133 | 197 | 120 |
| | sCr only | | | | | |
| Median | 11600 | 19200 | 11500 | 20000 | 11600 | 20400 |
| Average | 19800 | 40600 | 19300 | 43300 | 20700 | 43300 |
| Stdev | 36300 | 64200 | 35200 | 66400 | 37400 | 67300 |
| p (t-test) | | 3.4E−4 | | 3.9E−5 | | 1.5E−4 |
| Min | 200 | 658 | 200 | 2170 | 200 | 2170 |
| Max | 428000 | 396000 | 428000 | 396000 | 428000 | 396000 |
| n (Patient) | 176 | 140 | 188 | 128 | 200 | 116 |
| | UO only | | | | | |
| Median | 11700 | 25100 | 11900 | 24000 | 11900 | 24000 |
| Average | 20700 | 54400 | 21100 | 54500 | 21100 | 54500 |
| Stdev | 34300 | 79100 | 34400 | 80400 | 34400 | 80400 |
| p (t-test) | | 2.6E−7 | | 4.8E−7 | | 4.8E−7 |
| Min | 200 | 2170 | 200 | 2170 | 200 | 2170 |
| Max | 396000 | 428000 | 396000 | 428000 | 396000 | 428000 |
| n (Patient) | 234 | 81 | 237 | 78 | 237 | 78 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.63 | 0.71 | 0.70 | 0.66 | 0.70 | 0.69 | 0.66 | 0.70 |
| SE | 0.030 | 0.032 | 0.035 | 0.030 | 0.032 | 0.036 | 0.031 | 0.033 | 0.036 |
| p Value | 2.7E−8 | 2.8E−5 | 1.9E−9 | 1.3E−10 | 2.1E−7 | 2.6E−8 | 1.8E−9 | 1.4E−6 | 2.6E−8 |
| nCohort Non-persistent | 169 | 176 | 234 | 184 | 188 | 237 | 197 | 200 | 237 |
| nCohort Persistent | 148 | 140 | 81 | 133 | 128 | 78 | 120 | 116 | 78 |
| Cutoff Quartile 2 | 7990 | 7980 | 8020 | 7990 | 7980 | 8020 | 7990 | 7980 | 8020 |

TABLE 12.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 82% | 81% | 85% | 85% | 84% | 85% | 86% | 84% | 85% |
| Specificity | 31% | 30% | 29% | 32% | 31% | 28% | 31% | 30% | 28% |
| Cutoff Quartile 3 | 13500 | 13500 | 13500 | 13500 | 13500 | 13500 | 13500 | 13500 | 13500 |
| Sensitivity | 62% | 59% | 72% | 65% | 62% | 71% | 66% | 63% | 71% |
| Specificity | 60% | 57% | 57% | 61% | 59% | 57% | 59% | 57% | 57% |
| Cutoff Quartile 4 | 28900 | 28100 | 29400 | 28900 | 28100 | 29400 | 28900 | 28100 | 29400 |
| Sensitivity | 39% | 37% | 47% | 41% | 40% | 46% | 42% | 40% | 46% |
| Specificity | 86% | 85% | 82% | 86% | 85% | 82% | 85% | 84% | 82% |
| OR Quartile 2 | 2.14 | 1.76 | 2.31 | 2.67 | 2.27 | 2.17 | 2.78 | 2.39 | 2.17 |
| p Value | 0.0051 | 0.038 | 0.015 | 7.0E-4 | 0.0041 | 0.025 | 7.4E-4 | 0.0036 | 0.025 |
| Lower limit of 95% CI | 1.26 | 1.03 | 1.17 | 1.51 | 1.30 | 1.10 | 1.54 | 1.33 | 1.10 |
| Upper limit of 95% CI | 3.66 | 2.98 | 4.53 | 4.70 | 3.98 | 4.27 | 5.04 | 4.29 | 4.27 |
| OR Quartile 3 | 2.50 | 1.96 | 3.38 | 2.94 | 2.35 | 3.11 | 2.82 | 2.30 | 3.11 |
| p Value | 7.3E-5 | 0.0034 | 1.3E-5 | 5.2E-6 | 2.8E-4 | 5.3E-5 | 1.7E-5 | 5.2E-4 | 5.3E-5 |
| Lower limit of 95% CI | 1.59 | 1.25 | 1.95 | 1.85 | 1.48 | 1.79 | 1.76 | 1.44 | 1.79 |
| Upper limit of 95% CI | 3.93 | 3.08 | 5.85 | 4.68 | 3.73 | 5.39 | 4.52 | 3.67 | 5.39 |
| OR Quartile 4 | 3.98 | 3.26 | 4.16 | 4.48 | 3.78 | 3.87 | 3.98 | 3.33 | 3.87 |
| p Value | 8.9E-7 | 1.5E-5 | 4.0E-7 | 6.7E-8 | 1.1E-6 | 1.7E-6 | 3.6E-7 | 7.9E-6 | 1.7E-6 |
| Lower limit of 95% CI | 2.29 | 1.91 | 2.40 | 2.60 | 2.22 | 2.22 | 2.34 | 1.96 | 2.22 |
| Upper limit of 95% CI | 6.89 | 5.56 | 7.22 | 7.73 | 6.46 | 6.73 | 6.77 | 5.63 | 6.73 |

TABLE 12.6

Comparison of marker levels and the area under the ROC curve (AUC) in EDTA samples for the "persistent" and "non-persistent" cohorts where persistence starrts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 104000 | 123000 | 105000 | 120000 | 106000 | 120000 |
| Average | 115000 | 133000 | 118000 | 130000 | 118000 | 132000 |
| Stdev | 41600 | 45900 | 43500 | 44400 | 42600 | 46500 |
| p (t-test) | | 4.0E-4 | | 0.027 | | 0.014 |
| Min | 57000 | 64800 | 57000 | 64800 | 57000 | 64800 |
| Max | 299000 | 281000 | 299000 | 281000 | 299000 | 281000 |
| n (Patient) | 206 | 121 | 222 | 105 | 238 | 89 |
| | sCr only | | | | | |
| Median | 104000 | 123000 | 105000 | 120000 | 106000 | 119000 |
| Average | 115000 | 134000 | 119000 | 128000 | 119000 | 129000 |
| Stdev | 41400 | 46300 | 44800 | 42000 | 44300 | 43000 |
| p (t-test) | | 2.3E-4 | | 0.074 | | 0.082 |
| Min | 57000 | 64800 | 57000 | 64800 | 57000 | 64800 |
| Max | 299000 | 281000 | 299000 | 270000 | 299000 | 270000 |
| n (Patient) | 208 | 118 | 223 | 103 | 236 | 90 |
| | UO only | | | | | |
| Median | 106000 | 139000 | 106000 | 145000 | 106000 | 145000 |
| Average | 118000 | 149000 | 118000 | 151000 | 118000 | 153000 |
| Stdev | 41500 | 50100 | 41400 | 50200 | 41300 | 50900 |
| p (t-test) | | 7.7E-6 | | 2.4E-6 | | 2.0E-6 |
| Min | 57000 | 82200 | 57000 | 82200 | 57000 | 82200 |
| Max | 299000 | 281000 | 299000 | 281000 | 299000 | 281000 |
| n (Patient) | 281 | 44 | 283 | 42 | 285 | 40 |

TABLE 12.6-continued

Comparison of marker levels and the area under the ROC curve (AUC) in EDTA samples for the "persistent" and "non-persistent" cohorts where persistence starrts within 24 hours after sample collection and renal status is assessed by serum creatinine (sCr) only, urine output (UO) only, or serum creatinine or urine output RIFLE criteria.

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.64 | 0.71 | 0.60 | 0.59 | 0.72 | 0.60 | 0.59 | 0.72 |
| SE | 0.032 | 0.033 | 0.046 | 0.034 | 0.034 | 0.047 | 0.036 | 0.036 | 0.048 |
| p Value | 2.6E−5 | 1.6E−5 | 6.7E−6 | 0.0036 | 0.0067 | 2.1E−6 | 0.0049 | 0.017 | 2.9E−6 |
| nCohort Non-persistent | 206 | 208 | 281 | 222 | 223 | 283 | 238 | 236 | 285 |
| nCohort Persistent | 121 | 118 | 44 | 105 | 103 | 42 | 89 | 90 | 40 |
| Cutoff Quartile 2 | 90400 | 90300 | 90600 | 90400 | 90300 | 90600 | 90400 | 90300 | 90600 |
| Sensitivity | 84% | 84% | 91% | 83% | 83% | 90% | 82% | 81% | 90% |
| Specificity | 31% | 30% | 27% | 29% | 29% | 27% | 28% | 28% | 27% |
| Cutoff Quartile 3 | 109000 | 109000 | 109000 | 109000 | 109000 | 109000 | 109000 | 109000 | 109000 |
| Sensitivity | 63% | 64% | 73% | 60% | 59% | 76% | 61% | 59% | 78% |
| Specificity | 57% | 58% | 53% | 55% | 54% | 54% | 54% | 53% | 54% |
| Cutoff Quartile 4 | 137000 | 137000 | 137000 | 137000 | 137000 | 137000 | 137000 | 137000 | 137000 |
| Sensitivity | 34% | 35% | 50% | 30% | 30% | 52% | 34% | 32% | 52% |
| Specificity | 80% | 80% | 79% | 77% | 77% | 79% | 78% | 78% | 79% |
| OR Quartile 2 | 2.37 | 2.26 | 3.77 | 1.96 | 1.90 | 3.55 | 1.75 | 1.63 | 3.33 |
| p Value | 0.0032 | 0.0052 | 0.014 | 0.024 | 0.032 | 0.019 | 0.072 | 0.11 | 0.027 |
| Lower limit of 95% CI | 1.33 | 1.28 | 1.31 | 1.09 | 1.06 | 1.23 | 0.950 | 0.896 | 1.15 |
| Upper limit of 95% CI | 4.19 | 4.02 | 10.9 | 3.51 | 3.41 | 10.3 | 3.23 | 2.97 | 9.67 |
| OR Quartile 3 | 2.26 | 2.38 | 3.05 | 1.80 | 1.72 | 3.71 | 1.80 | 1.64 | 3.99 |
| p Value | 5.0E−4 | 2.6E−4 | 0.0019 | 0.015 | 0.024 | 5.8E−4 | 0.021 | 0.048 | 4.9E−4 |
| Lower limit of 95% CI | 1.43 | 1.49 | 1.51 | 1.12 | 1.07 | 1.76 | 1.09 | 1.00 | 1.83 |
| Upper limit of 95% CI | 3.59 | 3.79 | 6.17 | 2.88 | 2.77 | 7.84 | 2.95 | 2.68 | 8.69 |
| OR Quartile 4 | 2.06 | 2.17 | 3.68 | 1.51 | 1.45 | 4.09 | 1.82 | 1.64 | 4.06 |
| p Value | 0.0053 | 0.0029 | 9.9E−5 | 0.12 | 0.16 | 3.7E−5 | 0.029 | 0.071 | 5.7E−5 |
| Lower limit of 95% CI | 1.24 | 1.30 | 1.91 | 0.895 | 0.860 | 2.09 | 1.06 | 0.959 | 2.05 |
| Upper limit of 95% CI | 3.43 | 3.61 | 7.10 | 2.54 | 2.45 | 7.98 | 3.11 | 2.81 | 8.03 |

TABLE 12.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 103000 | 122000 | 104000 | 121000 | 104000 | 123000 |
| Average | 115000 | 131000 | 117000 | 130000 | 116000 | 133000 |
| Stdev | 41800 | 45200 | 43100 | 44400 | 41900 | 46200 |
| p (t-test) | | 5.6E−4 | | 0.0070 | | 0.0013 |
| Min | 57600 | 57000 | 57600 | 57000 | 57600 | 57000 |
| Max | 299000 | 281000 | 299000 | 281000 | 299000 | 281000 |
| n (Patient) | 187 | 140 | 204 | 123 | 219 | 108 |
| | sCr only | | | | | |
| Median | 103000 | 123000 | 104000 | 120000 | 105000 | 120000 |
| Average | 115000 | 132000 | 117000 | 130000 | 117000 | 131000 |
| Stdev | 41500 | 45800 | 43100 | 44800 | 42100 | 46400 |
| p (t-test) | | 4.2E−4 | | 0.013 | | 0.0051 |
| Min | 57600 | 57000 | 57600 | 57000 | 57600 | 57000 |
| Max | 299000 | 281000 | 299000 | 281000 | 299000 | 281000 |
| n (Patient) | 192 | 134 | 205 | 121 | 217 | 109 |

TABLE 12.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 106000 | 132000 | 105000 | 133000 | 105000 | 133000 |
| Average | 117000 | 144000 | 116000 | 146000 | 116000 | 147000 |
| Stdev | 40900 | 49600 | 40700 | 49700 | 40600 | 50200 |
| p (t-test) | | 5.7E−6 | | 1.2E−6 | | 1.1E−6 |
| Min | 57600 | 57000 | 57600 | 57000 | 57600 | 57000 |
| Max | 299000 | 281000 | 299000 | 281000 | 299000 | 281000 |
| n (Patient) | 260 | 65 | 263 | 62 | 265 | 60 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.63 | 0.68 | 0.61 | 0.60 | 0.70 | 0.63 | 0.61 | 0.70 |
| SE | 0.031 | 0.032 | 0.039 | 0.033 | 0.033 | 0.040 | 0.034 | 0.034 | 0.040 |
| p Value | 1.6E−5 | 2.0E−5 | 3.8E−6 | 4.5E−4 | 0.0015 | 7.0E−7 | 1.8E−4 | 0.0014 | 1.1E−6 |
| nCohort Non-persistent | 187 | 192 | 260 | 204 | 205 | 263 | 219 | 217 | 265 |
| nCohort Persistent | 140 | 134 | 65 | 123 | 121 | 62 | 108 | 109 | 60 |
| Cutoff Quartile 2 | 90400 | 90300 | 90600 | 90400 | 90300 | 90600 | 90400 | 90300 | 90600 |
| Sensitivity | 84% | 83% | 89% | 83% | 82% | 89% | 83% | 82% | 88% |
| Specificity | 32% | 31% | 28% | 30% | 29% | 28% | 29% | 29% | 28% |
| Cutoff Quartile 3 | 109000 | 109000 | 109000 | 109000 | 109000 | 109000 | 109000 | 109000 | 109000 |
| Sensitivity | 61% | 62% | 68% | 60% | 59% | 71% | 61% | 59% | 72% |
| Specificity | 58% | 58% | 54% | 56% | 55% | 55% | 55% | 54% | 55% |
| Cutoff Quartile 4 | 137000 | 137000 | 137000 | 137000 | 137000 | 137000 | 137000 | 137000 | 137000 |
| Sensitivity | 34% | 34% | 45% | 33% | 31% | 47% | 36% | 34% | 47% |
| Specificity | 81% | 81% | 80% | 79% | 79% | 80% | 80% | 79% | 80% |
| OR Quartile 2 | 2.34 | 2.14 | 3.30 | 2.07 | 1.86 | 3.08 | 2.06 | 1.78 | 2.93 |
| p Value | 0.0021 | 0.0061 | 0.0048 | 0.010 | 0.027 | 0.0081 | 0.015 | 0.046 | 0.011 |
| Lower limit of 95% CI | 1.36 | 1.24 | 1.44 | 1.19 | 1.07 | 1.34 | 1.15 | 1.01 | 1.28 |
| Upper limit of 95% CI | 4.04 | 3.69 | 7.55 | 3.62 | 3.23 | 7.06 | 3.70 | 3.14 | 6.75 |
| OR Quartile 3 | 2.23 | 2.28 | 2.48 | 1.91 | 1.74 | 2.96 | 1.94 | 1.70 | 3.06 |
| p Value | 4.6E−4 | 3.5E−4 | 0.0019 | 0.0052 | 0.016 | 3.9E−4 | 0.0057 | 0.026 | 3.4E−4 |
| Lower limit of 95% CI | 1.42 | 1.45 | 1.40 | 1.21 | 1.11 | 1.62 | 1.21 | 1.06 | 1.66 |
| Upper limit of 95% CI | 3.48 | 3.58 | 4.41 | 3.01 | 2.75 | 5.39 | 3.10 | 2.70 | 5.63 |
| OR Quartile 4 | 2.19 | 2.12 | 3.15 | 1.86 | 1.68 | 3.48 | 2.31 | 1.96 | 3.42 |
| p Value | 0.0024 | 0.0037 | 9.3E−5 | 0.017 | 0.047 | 2.7E−5 | 0.0014 | 0.010 | 4.3E−5 |
| Lower limit of 95% CI | 1.32 | 1.28 | 1.77 | 1.12 | 1.01 | 1.94 | 1.38 | 1.17 | 1.90 |
| Upper limit of 95% CI | 3.65 | 3.52 | 5.59 | 3.09 | 2.79 | 6.24 | 3.87 | 3.29 | 6.16 |

TABLE 12.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 100000 | 120000 | 103000 | 120000 | 103000 | 122000 |
| Average | 114000 | 131000 | 116000 | 130000 | 115000 | 133000 |
| Stdev | 41600 | 44900 | 42800 | 44300 | 41600 | 45900 |
| p (t-test) | | 2.4E−4 | | 0.0026 | | 3.9E−4 |

TABLE 12.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 57600 | 57000 | 57600 | 57000 | 57600 | 57000 |
| Max | 299000 | 281000 | 299000 | 281000 | 299000 | 281000 |
| n (Patient) | 176 | 151 | 190 | 137 | 205 | 122 | sCr only

| | | | | | | |
|---|---|---|---|---|---|---|
| Median | 101000 | 122000 | 104000 | 119000 | 104000 | 120000 |
| Average | 114000 | 132000 | 116000 | 130000 | 116000 | 132000 |
| Stdev | 41100 | 45700 | 42600 | 45000 | 41500 | 46600 |
| p (t-test) | | 1.6E−4 | | 0.0046 | | 0.0014 |
| Min | 57600 | 57000 | 57600 | 57000 | 57600 | 57000 |
| Max | 299000 | 281000 | 299000 | 281000 | 299000 | 281000 |
| n (Patient) | 182 | 144 | 194 | 132 | 207 | 119 |

UO only

| | | | | | | |
|---|---|---|---|---|---|---|
| Median | 104000 | 133000 | 104000 | 133000 | 104000 | 133000 |
| Average | 115000 | 145000 | 115000 | 146000 | 115000 | 146000 |
| Stdev | 40400 | 48000 | 40200 | 48400 | 40200 | 48700 |
| p (t-test) | | 1.6E−7 | | 4.8E−8 | | 7.4E−8 |
| Min | 57600 | 57000 | 57600 | 57000 | 57600 | 57000 |
| Max | 299000 | 281000 | 299000 | 281000 | 299000 | 281000 |
| n (Patient) | 249 | 76 | 253 | 72 | 254 | 71 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.64 | 0.71 | 0.62 | 0.61 | 0.72 | 0.64 | 0.62 | 0.71 |
| SE | 0.031 | 0.031 | 0.036 | 0.032 | 0.032 | 0.037 | 0.032 | 0.033 | 0.037 |
| p Value | 2.3E−6 | 3.7E−6 | 1.1E−8 | 7.6E−5 | 3.9E−4 | 3.7E−9 | 2.4E−5 | 3.2E−4 | 9.2E−9 |
| nCohort Non-persistent | 176 | 182 | 249 | 190 | 194 | 253 | 205 | 207 | 254 |
| nCohort Persistent | 151 | 144 | 76 | 137 | 132 | 72 | 122 | 119 | 71 |
| Cutoff Quartile 2 | 90400 | 90300 | 90600 | 90400 | 90300 | 90600 | 90400 | 90300 | 90600 |
| Sensitivity | 83% | 83% | 91% | 82% | 82% | 90% | 83% | 82% | 90% |
| Specificity | 32% | 31% | 30% | 31% | 30% | 29% | 30% | 29% | 29% |
| Cutoff Quartile 3 | 109000 | 109000 | 109000 | 109000 | 109000 | 109000 | 109000 | 109000 | 109000 |
| Sensitivity | 62% | 62% | 71% | 61% | 60% | 74% | 62% | 60% | 73% |
| Specificity | 60% | 60% | 56% | 58% | 57% | 57% | 57% | 56% | 56% |
| Cutoff Quartile 4 | 137000 | 137000 | 137000 | 137000 | 137000 | 137000 | 137000 | 137000 | 137000 |
| Sensitivity | 34% | 34% | 46% | 33% | 32% | 47% | 36% | 34% | 46% |
| Specificity | 82% | 82% | 81% | 81% | 79% | 81% | 81% | 80% | 81% |
| OR Quartile 2 | 2.41 | 2.17 | 4.17 | 2.07 | 1.92 | 3.84 | 2.04 | 1.80 | 3.76 |
| p Value | 0.0012 | 0.0044 | 6.8E−4 | 0.0081 | 0.018 | 0.0014 | 0.012 | 0.037 | 0.0017 |
| Lower limit of 95% CI | 1.42 | 1.27 | 1.83 | 1.21 | 1.12 | 1.68 | 1.17 | 1.04 | 1.65 |
| Upper limit of 95% CI | 4.11 | 3.70 | 9.50 | 3.54 | 3.29 | 8.76 | 3.56 | 3.12 | 8.58 |
| OR Quartile 3 | 2.50 | 2.49 | 3.15 | 2.18 | 1.95 | 3.63 | 2.20 | 1.85 | 3.53 |
| p Value | 5.9E−5 | 6.9E−5 | 5.1E−5 | 6.6E−4 | 0.0035 | 1.3E−5 | 7.8E−4 | 0.0085 | 2.1E−5 |
| Lower limit of 95% CI | 1.60 | 1.59 | 1.81 | 1.39 | 1.25 | 2.03 | 1.39 | 1.17 | 1.97 |
| Upper limit of 95% CI | 3.90 | 3.90 | 5.49 | 3.41 | 3.06 | 6.48 | 3.48 | 2.92 | 6.30 |
| OR Quartile 4 | 2.39 | 2.33 | 3.67 | 2.02 | 1.80 | 3.82 | 2.48 | 2.13 | 3.63 |
| p Value | 9.1E−4 | 0.0012 | 3.9E−6 | 0.0064 | 0.023 | 2.6E−6 | 4.9E−4 | 0.0037 | 6.5E−6 |
| Lower limit of 95% CI | 1.43 | 1.40 | 2.11 | 1.22 | 1.08 | 2.18 | 1.49 | 1.28 | 2.07 |
| Upper limit of 95% CI | 3.99 | 3.88 | 6.37 | 3.35 | 2.98 | 6.69 | 4.13 | 3.54 | 6.37 |

TABLE 12.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 99600 | 120000 | 103000 | 120000 | 103000 | 123000 |
| Average | 113000 | 132000 | 115000 | 131000 | 114000 | 134000 |
| Stdev | 40000 | 46100 | 41400 | 45700 | 40300 | 47100 |
| p (t-test) | | 4.6E−5 | | 5.8E−4 | | 1.0E−4 |
| Min | 57600 | 57000 | 57600 | 57000 | 57600 | 57000 |
| Max | 299000 | 281000 | 299000 | 281000 | 299000 | 281000 |
| n (Patient) | 173 | 154 | 188 | 139 | 200 | 127 |
| sCr only | | | | | | |
| Median | 101000 | 123000 | 103000 | 120000 | 104000 | 123000 |
| Average | 112000 | 133000 | 115000 | 132000 | 114000 | 134000 |
| Stdev | 39400 | 46800 | 41200 | 46200 | 40100 | 47600 |
| p (t-test) | | 1.8E−5 | | 5.9E−4 | | 1.0E−4 |
| Min | 57600 | 57000 | 57600 | 57000 | 57600 | 57000 |
| Max | 299000 | 281000 | 299000 | 281000 | 299000 | 281000 |
| n (Patient) | 179 | 147 | 190 | 136 | 202 | 124 |
| UO only | | | | | | |
| Median | 103000 | 133000 | 103000 | 134000 | 104000 | 133000 |
| Average | 114000 | 146000 | 114000 | 148000 | 114000 | 148000 |
| Stdev | 39200 | 48500 | 38900 | 49000 | 38900 | 49300 |
| p (t-test) | | 3.9E−9 | | 7.3E−10 | | 1.2E−9 |
| Min | 57600 | 57000 | 57600 | 57000 | 57600 | 57000 |
| Max | 299000 | 281000 | 299000 | 281000 | 299000 | 281000 |
| n (Patient) | 240 | 85 | 245 | 80 | 246 | 79 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.66 | 0.72 | 0.63 | 0.63 | 0.73 | 0.64 | 0.64 | 0.73 |
| SE | 0.030 | 0.031 | 0.034 | 0.031 | 0.032 | 0.035 | 0.032 | 0.032 | 0.035 |
| p Value | 4.6E−7 | 3.6E−7 | 5.7E−11 | 2.1E−5 | 3.7E−5 | 1.3E−11 | 9.2E−6 | 1.7E−5 | 3.9E−11 |
| nCohort Non-persistent | 173 | 179 | 240 | 188 | 190 | 245 | 200 | 202 | 246 |
| nCohort Persistent | 154 | 147 | 85 | 139 | 136 | 80 | 127 | 124 | 79 |
| Cutoff Quartile 2 | 90400 | 90300 | 90600 | 90400 | 90300 | 90600 | 90400 | 90300 | 90600 |
| Sensitivity | 84% | 83% | 92% | 83% | 82% | 91% | 83% | 82% | 91% |
| Specificity | 33% | 32% | 31% | 31% | 31% | 30% | 30% | 30% | 30% |
| Cutoff Quartile 3 | 109000 | 109000 | 109000 | 109000 | 109000 | 109000 | 109000 | 109000 | 109000 |
| Sensitivity | 63% | 63% | 73% | 62% | 61% | 75% | 62% | 61% | 75% |
| Specificity | 61% | 61% | 58% | 59% | 58% | 58% | 57% | 57% | 58% |
| Cutoff Quartile 4 | 137000 | 137000 | 137000 | 137000 | 137000 | 137000 | 137000 | 137000 | 137000 |
| Sensitivity | 34% | 35% | 47% | 33% | 33% | 49% | 36% | 36% | 48% |
| Specificity | 83% | 83% | 82% | 81% | 81% | 82% | 82% | 82% | 82% |
| OR Quartile 2 | 2.54 | 2.28 | 4.97 | 2.14 | 2.05 | 4.51 | 2.05 | 1.96 | 4.43 |
| p Value | 6.2E−4 | 0.0024 | 1.3E−4 | 0.0056 | 0.0089 | 3.3E−4 | 0.011 | 0.017 | 3.9E−4 |
| Lower limit of 95% CI | 1.49 | 1.34 | 2.19 | 1.25 | 1.20 | 1.98 | 1.18 | 1.13 | 1.94 |
| Upper limit of 95% CI | 4.32 | 3.89 | 11.3 | 3.66 | 3.51 | 10.3 | 3.55 | 3.40 | 10.1 |
| OR Quartile 3 | 2.69 | 2.68 | 3.71 | 2.29 | 2.15 | 4.14 | 2.23 | 2.09 | 4.03 |
| p Value | 1.5E−5 | 1.7E−5 | 2.2E−6 | 3.0E−4 | 8.2E−4 | 8.9E−7 | 5.7E−4 | 0.0015 | 1.4E−6 |
| Lower limit of 95% CI | 1.72 | 1.71 | 2.16 | 1.46 | 1.37 | 2.35 | 1.41 | 1.33 | 2.29 |
| Upper limit of 95% CI | 4.21 | 4.21 | 6.38 | 3.58 | 3.37 | 7.28 | 3.51 | 3.30 | 7.10 |
| OR Quartile 4 | 2.43 | 2.54 | 4.19 | 2.09 | 2.04 | 4.47 | 2.59 | 2.54 | 4.25 |
| p Value | 7.5E−4 | 4.0E−4 | 2.1E−7 | 0.0044 | 0.0056 | 8.7E−8 | 2.7E−4 | 3.5E−4 | 2.3E−7 |
| Lower limit of 95% CI | 1.45 | 1.52 | 2.44 | 1.26 | 1.23 | 2.58 | 1.55 | 1.52 | 2.46 |

TABLE 12.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 4.07 | 4.24 | 7.20 | 3.47 | 3.39 | 7.73 | 4.31 | 4.23 | 7.37 |

TABLE 12.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 99600 | 120000 | 102000 | 120000 | 103000 | 121000 |
| Average | 112000 | 132000 | 114000 | 131000 | 114000 | 133000 |
| Stdev | 39700 | 46200 | 41300 | 45600 | 40100 | 47100 |
| p (t-test) | | 5.0E−5 | | 5.8E−4 | | 1.0E−4 |
| Min | 57600 | 57000 | 57600 | 57000 | 57600 | 57000 |
| Max | 299000 | 281000 | 299000 | 281000 | 299000 | 281000 |
| n (Patient) | 169 | 158 | 183 | 144 | 196 | 131 |
| | sCr only | | | | | |
| Median | 101000 | 123000 | 103000 | 120000 | 104000 | 122000 |
| Average | 113000 | 132000 | 115000 | 131000 | 115000 | 133000 |
| Stdev | 39700 | 46600 | 41500 | 45900 | 40400 | 47300 |
| p (t-test) | | 4.6E−5 | | 0.0013 | | 2.6E−4 |
| Min | 57600 | 57000 | 57600 | 57000 | 57600 | 57000 |
| Max | 299000 | 281000 | 299000 | 281000 | 299000 | 281000 |
| n (Patient) | 175 | 151 | 186 | 140 | 198 | 128 |
| | UO only | | | | | |
| Median | 103000 | 132000 | 102000 | 132000 | 103000 | 132000 |
| Average | 114000 | 144000 | 114000 | 145000 | 114000 | 145000 |
| Stdev | 39500 | 48000 | 39400 | 48000 | 39400 | 48300 |
| p (t-test) | | 2.0E−8 | | 6.3E−9 | | 1.0E−8 |
| Min | 57600 | 57000 | 57600 | 57000 | 57600 | 57000 |
| Max | 299000 | 281000 | 299000 | 281000 | 299000 | 281000 |
| n (Patient) | 235 | 90 | 237 | 88 | 238 | 87 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.65 | 0.72 | 0.63 | 0.62 | 0.72 | 0.64 | 0.63 | 0.72 |
| SE | 0.030 | 0.031 | 0.034 | 0.031 | 0.032 | 0.034 | 0.032 | 0.032 | 0.034 |
| p Value | 8.4E−7 | 1.2E−6 | 1.8E−10 | 2.1E−5 | 1.0E−4 | 3.5E−11 | 1.1E−5 | 4.9E−5 | 9.8E−11 |
| nCohort Non-persistent | 169 | 175 | 235 | 183 | 186 | 237 | 196 | 198 | 238 |
| nCohort Persistent | 158 | 151 | 90 | 144 | 140 | 88 | 131 | 128 | 87 |
| Cutoff Quartile 2 | 90400 | 90300 | 90600 | 90400 | 90300 | 90600 | 90400 | 90300 | 90600 |
| Sensitivity | 83% | 82% | 91% | 83% | 81% | 91% | 82% | 81% | 91% |
| Specificity | 33% | 31% | 31% | 31% | 30% | 31% | 30% | 29% | 31% |
| Cutoff Quartile 3 | 109000 | 109000 | 109000 | 109000 | 109000 | 109000 | 109000 | 109000 | 109000 |
| Sensitivity | 63% | 63% | 72% | 62% | 61% | 74% | 62% | 61% | 74% |
| Specificity | 62% | 61% | 58% | 59% | 58% | 59% | 58% | 57% | 58% |
| Cutoff Quartile 4 | 137000 | 137000 | 137000 | 137000 | 137000 | 137000 | 137000 | 137000 | 137000 |
| Sensitivity | 34% | 34% | 44% | 33% | 32% | 45% | 36% | 35% | 45% |
| Specificity | 83% | 82% | 82% | 81% | 80% | 82% | 82% | 81% | 82% |
| OR Quartile 2 | 2.34 | 2.10 | 4.62 | 2.15 | 1.89 | 4.45 | 2.02 | 1.80 | 4.37 |
| p Value | 0.0015 | 0.0054 | 1.1E−4 | 0.0048 | 0.018 | 1.7E−4 | 0.011 | 0.033 | 2.0E−4 |
| Lower limit of 95% CI | 1.39 | 1.25 | 2.12 | 1.26 | 1.11 | 2.05 | 1.17 | 1.05 | 2.01 |
| Upper limit of 95% CI | 3.96 | 3.56 | 10.0 | 3.67 | 3.20 | 9.68 | 3.48 | 3.08 | 9.51 |

TABLE 12.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| OR Quartile 3 | 2.68 | 2.67 | 3.63 | 2.33 | 2.14 | 4.01 | 2.21 | 2.07 | 3.91 |
|---|---|---|---|---|---|---|---|---|---|
| p Value | 1.5E−5 | 1.8E−5 | 1.8E−6 | 2.1E−4 | 8.5E−4 | 5.0E−7 | 6.1E−4 | 0.0016 | 8.2E−7 |
| Lower limit of 95% CI | 1.72 | 1.70 | 2.14 | 1.49 | 1.37 | 2.33 | 1.40 | 1.32 | 2.27 |
| Upper limit of 95% CI | 4.20 | 4.18 | 6.17 | 3.64 | 3.35 | 6.89 | 3.47 | 3.26 | 6.72 |
| OR Quartile 4 | 2.44 | 2.37 | 3.68 | 2.05 | 1.91 | 3.87 | 2.57 | 2.36 | 3.68 |
| p Value | 7.6E−4 | 0.0010 | 1.7E−6 | 0.0056 | 0.012 | 7.5E−7 | 2.9E−4 | 9.6E−4 | 1.9E−6 |
| Lower limit of 95% CI | 1.45 | 1.42 | 2.16 | 1.23 | 1.15 | 2.26 | 1.54 | 1.42 | 2.16 |
| Upper limit of 95% CI | 4.09 | 3.96 | 6.27 | 3.40 | 3.16 | 6.61 | 4.29 | 3.93 | 6.30 |

Example 13. Use of Metalloproteinase Inhibitor 2 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 2 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 13.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 11300 | 18000 | 11500 | 19500 | 11400 | 20900 |
| Average | 15600 | 37400 | 16300 | 42100 | 17400 | 44700 |
| Stdev | 13600 | 63200 | 14600 | 69300 | 20800 | 71900 |
| p (t-test) | | 2.5E−4 | | 6.9E−6 | | 2.1E−6 |
| Min | 200 | 658 | 200 | 658 | 200 | 658 |
| Max | 76000 | 428000 | 76000 | 428000 | 215000 | 428000 |
| n (Patient) | 119 | 198 | 158 | 159 | 179 | 138 |
| sCr only | | | | | | |
| Median | 12000 | 16000 | 11900 | 19200 | 11900 | 19600 |
| Average | 17300 | 37100 | 16800 | 41900 | 18500 | 43600 |
| Stdev | 14800 | 64900 | 14600 | 70200 | 22500 | 72900 |
| p (t-test) | | 7.0E−4 | | 1.2E−5 | | 1.6E−5 |
| Min | 200 | 658 | 200 | 658 | 200 | 658 |
| Max | 76000 | 428000 | 76000 | 428000 | 215000 | 428000 |
| n (Patient) | 130 | 186 | 162 | 154 | 184 | 132 |
| UO only | | | | | | |
| Median | 11600 | 31200 | 12000 | 32600 | 12000 | 35500 |
| Average | 20100 | 59500 | 20800 | 66400 | 21300 | 70300 |
| Stdev | 33400 | 81800 | 33200 | 89300 | 33300 | 93700 |
| p (t-test) | | 4.6E−9 | | 3.6E−10 | | 1.4E−10 |
| Min | 200 | 5410 | 200 | 5410 | 200 | 5410 |

TABLE 13.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Max | 396000 | 428000 | 396000 | 428000 | 396000 | 428000 | | | |
| n (Patient) | 241 | 74 | 256 | 59 | 263 | 52 | | | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.59 | 0.76 | 0.65 | 0.63 | 0.76 | 0.67 | 0.64 | 0.76 |
| SE | 0.031 | 0.032 | 0.035 | 0.031 | 0.031 | 0.038 | 0.031 | 0.032 | 0.041 |
| p Value | 2.1E−5 | 0.0066 | 6.1E−14 | 1.5E−6 | 5.4E−5 | 8.5E−12 | 5.2E−8 | 7.3E−6 | 9.5E−11 |
| nCohort Non-persistent | 119 | 130 | 241 | 158 | 162 | 256 | 179 | 184 | 263 |
| nCohort Persistent | 198 | 186 | 74 | 159 | 154 | 59 | 138 | 132 | 52 |
| Cutoff Quartile 2 | 7990 | 7980 | 8020 | 7990 | 7980 | 8020 | 7990 | 7980 | 8020 |
| Sensitivity | 80% | 78% | 93% | 82% | 81% | 92% | 85% | 84% | 90% |
| Specificity | 34% | 30% | 31% | 32% | 30% | 29% | 32% | 32% | 28% |
| Cutoff Quartile 3 | 13500 | 13500 | 13500 | 13500 | 13500 | 13500 | 13500 | 13500 | 13500 |
| Sensitivity | 56% | 53% | 76% | 60% | 58% | 76% | 63% | 61% | 77% |
| Specificity | 60% | 55% | 58% | 59% | 57% | 56% | 60% | 58% | 55% |
| Cutoff Quartile 4 | 28900 | 28100 | 29400 | 28900 | 28100 | 29400 | 28900 | 28100 | 29400 |
| Sensitivity | 33% | 32% | 51% | 36% | 36% | 54% | 39% | 38% | 58% |
| Specificity | 87% | 85% | 83% | 85% | 85% | 82% | 85% | 84% | 81% |
| OR Quartile 2 | 2.06 | 1.56 | 6.11 | 2.08 | 1.79 | 4.39 | 2.67 | 2.43 | 3.68 |
| p Value | 0.0060 | 0.087 | 1.8E−4 | 0.0063 | 0.028 | 0.0024 | 5.9E−4 | 0.0019 | 0.0078 |
| Lower limit of 95% CI | 1.23 | 0.937 | 2.37 | 1.23 | 1.06 | 1.69 | 1.53 | 1.39 | 1.41 |
| Upper limit of 95% CI | 3.46 | 2.61 | 15.8 | 3.50 | 3.02 | 11.4 | 4.68 | 4.26 | 9.62 |
| OR Quartile 3 | 1.89 | 1.37 | 4.24 | 2.18 | 1.85 | 4.07 | 2.54 | 2.09 | 4.10 |
| p Value | 0.0070 | 0.17 | 1.6E−6 | 6.6E−4 | 0.0071 | 2.2E−5 | 6.6E−5 | 0.0015 | 6.1E−5 |
| Lower limit of 95% CI | 1.19 | 0.873 | 2.35 | 1.39 | 1.18 | 2.13 | 1.61 | 1.33 | 2.06 |
| Upper limit of 95% CI | 2.99 | 2.15 | 7.64 | 3.41 | 2.88 | 7.78 | 4.00 | 3.30 | 8.16 |
| OR Quartile 4 | 3.39 | 2.56 | 5.15 | 3.28 | 3.19 | 5.27 | 3.78 | 3.26 | 5.96 |
| p Value | 1.1E−4 | 0.0012 | 1.4E−8 | 2.2E−5 | 2.9E−5 | 6.3E−8 | 1.3E−6 | 1.2E−5 | 3.1E−8 |
| Lower limit of 95% CI | 1.83 | 1.45 | 2.92 | 1.90 | 1.85 | 2.89 | 2.21 | 1.92 | 3.17 |
| Upper limit of 95% CI | 6.28 | 4.51 | 9.07 | 5.68 | 5.51 | 9.62 | 6.48 | 5.54 | 11.2 |

TABLE 13.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 10600 | 17900 | 11400 | 19300 | 11300 | 20000 |
| Average | 15200 | 36900 | 16000 | 40700 | 17100 | 42500 |
| Stdev | 13700 | 62200 | 14300 | 67300 | 21100 | 69000 |
| p (t-test) | | 3.0E−4 | | 1.7E−5 | | 9.1E−6 |
| Min | 200 | 658 | 200 | 658 | 200 | 658 |
| Max | 76000 | 428000 | 76000 | 428000 | 215000 | 428000 |
| n (Patient) | 112 | 205 | 147 | 170 | 165 | 152 |
| | sCr only | | | | | |
| Median | 11800 | 15700 | 11800 | 18800 | 11600 | 19300 |
| Average | 17200 | 36800 | 16800 | 40600 | 17800 | 41800 |
| Stdev | 14900 | 64200 | 14700 | 68700 | 21200 | 70000 |
| p (t-test) | | 8.5E−4 | | 3.4E−5 | | 2.9E−5 |

TABLE 13.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 200 | 658 | 200 | 658 | 200 | 658 |
| Max | 76000 | 428000 | 76000 | 428000 | 215000 | 428000 |
| n (Patient) | 126 | 190 | 154 | 162 | 169 | 147 |

UO only

| | | | | | | |
|---|---|---|---|---|---|---|
| Median | 11400 | 22900 | 11700 | 22900 | 11900 | 27000 |
| Average | 19900 | 52100 | 20700 | 56200 | 21200 | 58100 |
| Stdev | 34300 | 74900 | 34000 | 80800 | 34100 | 83900 |
| p (t-test) | | 2.9E−7 | | 9.4E−8 | | 8.4E−8 |
| Min | 200 | 2170 | 200 | 2170 | 200 | 2170 |
| Max | 396000 | 428000 | 396000 | 428000 | 396000 | 428000 |
| n (Patient) | 222 | 93 | 238 | 77 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.59 | 0.73 | 0.65 | 0.62 | 0.72 | 0.67 | 0.64 | 0.71 |
| SE | 0.031 | 0.032 | 0.033 | 0.031 | 0.031 | 0.036 | 0.030 | 0.031 | 0.038 |
| p Value | 1.6E−6 | 0.0039 | 1.9E−12 | 7.9E−7 | 1.1E−4 | 1.3E−9 | 1.7E−8 | 9.4E−6 | 1.8E−8 |
| nCohort Non-persistent | 112 | 126 | 222 | 147 | 154 | 238 | 165 | 169 | 245 |
| nCohort Persistent | 205 | 190 | 93 | 170 | 162 | 77 | 152 | 147 | 70 |
| Cutoff Quartile 2 | 7990 | 7980 | 8020 | 7990 | 7980 | 8020 | 7990 | 7980 | 8020 |
| Sensitivity | 81% | 79% | 89% | 81% | 80% | 87% | 84% | 82% | 86% |
| Specificity | 36% | 31% | 31% | 32% | 30% | 29% | 33% | 31% | 28% |
| Cutoff Quartile 3 | 13500 | 13500 | 13500 | 13500 | 13500 | 13500 | 13500 | 13500 | 13500 |
| Sensitivity | 57% | 54% | 71% | 60% | 57% | 70% | 62% | 59% | 70% |
| Specificity | 62% | 56% | 59% | 61% | 58% | 56% | 61% | 58% | 56% |
| Cutoff Quartile 4 | 28900 | 28100 | 29400 | 28900 | 28100 | 29400 | 28900 | 28100 | 29400 |
| Sensitivity | 33% | 32% | 46% | 35% | 35% | 47% | 38% | 37% | 49% |
| Specificity | 88% | 85% | 84% | 86% | 85% | 82% | 86% | 85% | 82% |
| OR Quartile 2 | 2.36 | 1.68 | 3.74 | 2.03 | 1.66 | 2.74 | 2.67 | 2.13 | 2.35 |
| p Value | 0.0012 | 0.048 | 3.0E−4 | 0.0075 | 0.052 | 0.0062 | 4.0E−4 | 0.0056 | 0.021 |
| Lower limit of 95% CI | 1.40 | 1.01 | 1.83 | 1.21 | 0.995 | 1.33 | 1.55 | 1.25 | 1.14 |
| Upper limit of 95% CI | 3.98 | 2.81 | 7.65 | 3.40 | 2.79 | 5.63 | 4.59 | 3.63 | 4.86 |
| OR Quartile 3 | 2.22 | 1.45 | 3.45 | 2.37 | 1.85 | 3.03 | 2.63 | 2.00 | 2.91 |
| p Value | 9.5E−4 | 0.11 | 3.2E−6 | 1.8E−4 | 0.0071 | 8.3E−5 | 3.0E−5 | 0.0024 | 2.4E−4 |
| Lower limit of 95% CI | 1.38 | 0.921 | 2.05 | 1.51 | 1.18 | 1.74 | 1.67 | 1.28 | 1.65 |
| Upper limit of 95% CI | 3.55 | 2.28 | 5.82 | 3.72 | 2.88 | 5.25 | 4.14 | 3.14 | 5.15 |
| OR Quartile 4 | 3.70 | 2.60 | 4.44 | 3.19 | 3.01 | 3.98 | 3.70 | 3.34 | 4.20 |
| p Value | 7.6E−5 | 0.0012 | 6.8E−8 | 4.9E−5 | 8.3E−5 | 1.1E−6 | 3.0E−6 | 1.2E−5 | 7.9E−7 |
| Lower limit of 95% CI | 1.93 | 1.46 | 2.58 | 1.82 | 1.74 | 2.28 | 2.14 | 1.95 | 2.38 |
| Upper limit of 95% CI | 7.07 | 4.62 | 7.64 | 5.58 | 5.21 | 6.95 | 6.42 | 5.75 | 7.42 |

TABLE 13.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort | sCr or UO

| | | | | | | |
|---|---|---|---|---|---|---|
| Median | 10600 | 18000 | 11400 | 19300 | 11400 | 19300 |
| Average | 15200 | 36900 | 16000 | 40300 | 17300 | 41100 |
| Stdev | 13700 | 62000 | 14400 | 66800 | 21400 | 67800 |

TABLE 13.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 3.3E−4 | | 2.3E−5 | | 3.4E−5 |
| Min | 200 | 658 | 200 | 658 | 200 | 658 |
| Max | 76000 | 428000 | 76000 | 428000 | 215000 | 428000 |
| n (Patient) | 111 | 206 | 144 | 173 | 158 | 159 | sCr only

| | | | | | | |
|---|---|---|---|---|---|---|
| Median | 11500 | 16000 | 11600 | 18600 | 11600 | 18800 |
| Average | 17200 | 36600 | 16900 | 40100 | 18100 | 40600 |
| Stdev | 15000 | 63900 | 14800 | 68100 | 21500 | 68900 |
| p (t-test) | | 9.8E−4 | | 5.3E−5 | | 8.5E−5 |
| Min | 200 | 658 | 200 | 658 | 200 | 658 |
| Max | 76000 | 428000 | 76000 | 428000 | 215000 | 428000 |
| n (Patient) | 124 | 192 | 151 | 165 | 163 | 153 |

UO only

| | | | | | | |
|---|---|---|---|---|---|---|
| Median | 11400 | 21700 | 11600 | 21700 | 11800 | 21700 |
| Average | 20000 | 48700 | 20700 | 51100 | 21200 | 52200 |
| Stdev | 34800 | 72100 | 34700 | 76000 | 34700 | 78500 |
| p (t-test) | | 2.8E−6 | | 1.8E−6 | | 2.0E−6 |
| Min | 200 | 2170 | 200 | 2170 | 200 | 2170 |
| Max | 396000 | 428000 | 396000 | 428000 | 396000 | 428000 |
| n (Patient) | 212 | 103 | 225 | 90 | 232 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.60 | 0.71 | 0.65 | 0.62 | 0.70 | 0.65 | 0.63 | 0.69 |
| SE | 0.031 | 0.032 | 0.033 | 0.031 | 0.031 | 0.034 | 0.031 | 0.031 | 0.036 |
| p Value | 1.2E−6 | 0.0030 | 1.8E−10 | 8.5E−7 | 1.7E−4 | 1.3E−8 | 5.0E−7 | 6.1E−5 | 1.7E−7 |
| nCohort Non-persistent | 111 | 124 | 212 | 144 | 151 | 225 | 158 | 163 | 232 |
| nCohort Persistent | 206 | 192 | 103 | 173 | 165 | 90 | 159 | 153 | 83 |
| Cutoff Quartile 2 | 7990 | 7980 | 8020 | 7990 | 7980 | 8020 | 7990 | 7980 | 8020 |
| Sensitivity | 81% | 79% | 87% | 81% | 79% | 86% | 82% | 81% | 84% |
| Specificity | 36% | 31% | 31% | 32% | 30% | 29% | 32% | 31% | 28% |
| Cutoff Quartile 3 | 13500 | 13500 | 13500 | 13500 | 13500 | 13500 | 13500 | 13500 | 13500 |
| Sensitivity | 57% | 54% | 68% | 60% | 58% | 68% | 61% | 59% | 67% |
| Specificity | 63% | 56% | 58% | 62% | 58% | 57% | 61% | 58% | 56% |
| Cutoff Quartile 4 | 28900 | 28100 | 29400 | 28900 | 28100 | 29400 | 28900 | 28100 | 29400 |
| Sensitivity | 33% | 31% | 43% | 35% | 34% | 43% | 36% | 35% | 45% |
| Specificity | 88% | 85% | 83% | 86% | 85% | 82% | 86% | 85% | 82% |
| OR Quartile 2 | 2.41 | 1.74 | 3.13 | 1.99 | 1.64 | 2.46 | 2.23 | 1.89 | 2.14 |
| p Value | 9.3E−4 | 0.034 | 5.8E−4 | 0.0089 | 0.060 | 0.0070 | 0.0029 | 0.017 | 0.023 |
| Lower limit of 95% CI | 1.43 | 1.04 | 1.63 | 1.19 | 0.979 | 1.28 | 1.32 | 1.12 | 1.11 |
| Upper limit of 95% CI | 4.06 | 2.92 | 6.00 | 3.34 | 2.73 | 4.73 | 3.78 | 3.19 | 4.13 |
| OR Quartile 3 | 2.29 | 1.53 | 2.99 | 2.44 | 1.90 | 2.78 | 2.42 | 2.00 | 2.64 |
| p Value | 6.2E−4 | 0.066 | 1.5E−5 | 1.2E−4 | 0.0051 | 1.0E−4 | 1.2E−4 | 0.0025 | 3.0E−4 |
| Lower limit of 95% CI | 1.42 | 0.972 | 1.82 | 1.55 | 1.21 | 1.66 | 1.54 | 1.28 | 1.56 |
| Upper limit of 95% CI | 3.68 | 2.41 | 4.91 | 3.84 | 2.96 | 4.64 | 3.80 | 3.12 | 4.48 |
| OR Quartile 4 | 3.63 | 2.51 | 3.77 | 3.29 | 2.86 | 3.54 | 3.55 | 3.01 | 3.64 |
| p Value | 9.5E−5 | 0.0017 | 1.0E−6 | 3.8E−5 | 1.7E−4 | 4.4E−6 | 7.4E−6 | 6.3E−5 | 3.7E−6 |
| Lower limit of 95% CI | 1.90 | 1.41 | 2.21 | 1.87 | 1.65 | 2.06 | 2.04 | 1.75 | 2.11 |
| Upper limit of 95% CI | 6.95 | 4.47 | 6.43 | 5.80 | 4.95 | 6.06 | 6.18 | 5.17 | 6.29 |

TABLE 13.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 10600 | 17900 | 11300 | 19300 | 11300 | 19300 |
| Average | 15300 | 36700 | 16000 | 40200 | 17300 | 40800 |
| Stdev | 13700 | 61900 | 14400 | 66700 | 21500 | 67500 |
| p (t-test) | | 4.0E−4 | | 2.7E−5 | | 4.3E−5 |
| Min | 200 | 658 | 200 | 658 | 200 | 658 |
| Max | 76000 | 428000 | 76000 | 428000 | 215000 | 428000 |
| n (Patient) | 110 | 207 | 143 | 174 | 156 | 161 |
| sCr only | | | | | | |
| Median | 11500 | 16000 | 11600 | 18600 | 11500 | 18700 |
| Average | 17200 | 36600 | 16900 | 39900 | 18100 | 40400 |
| Stdev | 15000 | 63900 | 14900 | 68000 | 21600 | 68700 |
| p (t-test) | | 9.8E−4 | | 6.2E−5 | | 1.0E−4 |
| Min | 200 | 658 | 200 | 658 | 200 | 658 |
| Max | 76000 | 428000 | 76000 | 428000 | 215000 | 428000 |
| n (Patient) | 124 | 192 | 150 | 166 | 162 | 154 |
| UO only | | | | | | |
| Median | 11400 | 21700 | 11600 | 21500 | 11700 | 21500 |
| Average | 20200 | 47300 | 20800 | 49200 | 21300 | 49800 |
| Stdev | 35100 | 71100 | 35000 | 74400 | 35200 | 76400 |
| p (t-test) | | 8.5E−6 | | 5.9E−6 | | 8.6E−6 |
| Min | 200 | 2170 | 200 | 2170 | 200 | 2170 |
| Max | 396000 | 428000 | 396000 | 428000 | 396000 | 428000 |
| n (Patient) | 208 | 107 | 220 | 95 | 226 | 89 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.65 | 0.60 | 0.69 | 0.65 | 0.62 |
| SE | 0.031 | 0.032 | 0.033 | 0.031 | 0.031 |
| p Value | 3.2E−6 | 0.0030 | 3.4E−9 | 9.4E−7 | 1.8E−4 |
| nCohort Non-persistent | 110 | 124 | 208 | 143 | 150 |
| nCohort Persistent | 207 | 192 | 107 | 174 | 166 |
| Cutoff Quartile 2 | 7990 | 7980 | 8020 | 7990 | 7980 |
| Sensitivity | 81% | 79% | 86% | 81% | 80% |
| Specificity | 35% | 31% | 31% | 32% | 30% |
| Cutoff Quartile 3 | 13500 | 13500 | 13500 | 13500 | 13500 |
| Sensitivity | 57% | 54% | 66% | 60% | 57% |
| Specificity | 63% | 56% | 58% | 62% | 58% |
| Cutoff Quartile 4 | 28900 | 28100 | 29400 | 28900 | 28100 |
| Sensitivity | 32% | 31% | 41% | 34% | 34% |
| Specificity | 88% | 85% | 83% | 86% | 85% |
| OR Quartile 2 | 2.29 | 1.74 | 2.73 | 2.03 | 1.66 |
| p Value | 0.0018 | 0.034 | 0.0015 | 0.0074 | 0.052 |
| Lower limit of 95% CI | 1.36 | 1.04 | 1.47 | 1.21 | 0.995 |
| Upper limit of 95% CI | 3.86 | 2.92 | 5.07 | 3.40 | 2.78 |
| OR Quartile 3 | 2.23 | 1.53 | 2.74 | 2.38 | 1.85 |
| p Value | 9.1E−4 | 0.066 | 4.8E−5 | 1.8E−4 | 0.0071 |
| Lower limit of 95% CI | 1.39 | 0.972 | 1.69 | 1.51 | 1.18 |
| Upper limit of 95% CI | 3.59 | 2.41 | 4.46 | 3.74 | 2.89 |
| OR Quartile 4 | 3.57 | 2.51 | 3.45 | 3.24 | 2.81 |
| p Value | 1.2E−4 | 0.0017 | 4.5E−6 | 4.8E−5 | 2.2E−4 |
| Lower limit of 95% CI | 1.87 | 1.41 | 2.03 | 1.84 | 1.62 |

TABLE 13.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | |
|---|---|---|---|---|---|
| Upper limit of 95% CI | 6.83 | 4.47 | 5.86 | 5.70 | 4.86 |

| | Persistence Period Duration (hr) | | | |
|---|---|---|---|---|
| | 48 | | 72 | |
| | UO only | sCr or UO | sCr only | UO only |
| AUC | 0.69 | 0.65 | 0.63 | 0.68 |
| SE | 0.034 | 0.031 | 0.031 | 0.035 |
| p Value | 4.8E−8 | 3.8E−7 | 6.6E−5 | 4.3E−7 |
| nCohort Non-persistent | 220 | 156 | 162 | 226 |
| nCohort Persistent | 95 | 161 | 154 | 89 |
| Cutoff Quartile 2 | 8020 | 7990 | 7980 | 8020 |
| Sensitivity | 85% | 83% | 81% | 84% |
| Specificity | 30% | 33% | 31% | 29% |
| Cutoff Quartile 3 | 13500 | 13500 | 13500 | 13500 |
| Sensitivity | 66% | 61% | 58% | 66% |
| Specificity | 57% | 61% | 58% | 56% |
| Cutoff Quartile 4 | 29400 | 28900 | 28100 | 29400 |
| Sensitivity | 42% | 36% | 35% | 43% |
| Specificity | 82% | 86% | 85% | 82% |
| OR Quartile 2 | 2.43 | 2.31 | 1.92 | 2.16 |
| p Value | 0.0064 | 0.0019 | 0.014 | 0.018 |
| Lower limit of 95% CI | 1.28 | 1.36 | 1.14 | 1.14 |
| Upper limit of 95% CI | 4.59 | 3.91 | 3.25 | 4.10 |
| OR Quartile 3 | 2.59 | 2.42 | 1.94 | 2.52 |
| p Value | 2.0E−4 | 1.2E−4 | 0.0036 | 4.0E−4 |
| Lower limit of 95% CI | 1.57 | 1.54 | 1.24 | 1.51 |
| Upper limit of 95% CI | 4.28 | 3.80 | 3.04 | 4.21 |
| OR Quartile 4 | 3.38 | 3.43 | 2.96 | 3.36 |
| p Value | 8.1E−6 | 1.3E−5 | 8.1E−5 | 1.1E−5 |
| Lower limit of 95% CI | 1.98 | 1.97 | 1.73 | 1.96 |
| Upper limit of 95% CI | 5.76 | 5.97 | 5.08 | 5.77 |

TABLE 13.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 10700 | 17900 | 11300 | 19300 | 11300 | 19300 |
| Average | 14900 | 36400 | 15500 | 39800 | 17000 | 40300 |
| Stdev | 12600 | 61500 | 13600 | 65900 | 21300 | 66500 |
| p (t-test) | | 4.3E−4 | | 2.6E−5 | | 5.1E−5 |
| Min | 200 | 658 | 200 | 658 | 200 | 658 |
| Max | 61200 | 428000 | 61200 | 428000 | 215000 | 428000 |
| n (Patient) | 106 | 211 | 138 | 179 | 150 | 167 |

TABLE 13.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | sCr only | | | | | |
|---|---|---|---|---|---|---|
| Median | 11600 | 16000 | 11600 | 18600 | 11500 | 18700 |
| Average | 16800 | 36500 | 16500 | 39700 | 17700 | 40200 |
| Stdev | 14200 | 63600 | 14100 | 67300 | 21300 | 68000 |
| p (t-test) | | 8.9E−4 | | 5.4E−5 | | 9.1E−5 |
| Min | 200 | 658 | 200 | 658 | 200 | 658 |
| Max | 63200 | 428000 | 63200 | 428000 | 215000 | 428000 |
| n (Patient) | 121 | 195 | 146 | 170 | 158 | 158 |
| | UO only | | | | | |
| Median | 11200 | 21700 | 11400 | 21700 | 11500 | 21700 |
| Average | 19700 | 46600 | 20400 | 47800 | 21000 | 47900 |
| Stdev | 35400 | 69400 | 35400 | 71800 | 35700 | 73200 |
| p (t-test) | | 7.4E−6 | | 8.7E−6 | | 1.5E−5 |
| Min | 200 | 2170 | 200 | 2170 | 200 | 2170 |
| Max | 396000 | 428000 | 396000 | 428000 | 396000 | 428000 |
| n (Patient) | 202 | 113 | 212 | 103 | 217 | 98 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.64 | 0.60 | 0.71 | 0.65 | 0.62 |
| SE | 0.032 | 0.032 | 0.032 | 0.030 | 0.031 |
| p Value | 8.4E−6 | 0.0031 | 3.8E−11 | 4.1E−7 | 1.1E−4 |
| nCohort Non-persistent | 106 | 121 | 202 | 138 | 146 |
| nCohort Persistent | 211 | 195 | 113 | 179 | 170 |
| Cutoff Quartile 2 | 7990 | 7980 | 8020 | 7990 | 7980 |
| Sensitivity | 80% | 79% | 87% | 81% | 79% |
| Specificity | 35% | 31% | 32% | 33% | 30% |
| Cutoff Quartile 3 | 13500 | 13500 | 13500 | 13500 | 13500 |
| Sensitivity | 56% | 54% | 68% | 60% | 57% |
| Specificity | 62% | 56% | 60% | 62% | 58% |
| Cutoff Quartile 4 | 28900 | 28100 | 29400 | 28900 | 28100 |
| Sensitivity | 32% | 31% | 42% | 35% | 34% |
| Specificity | 89% | 85% | 84% | 87% | 86% |
| OR Quartile 2 | 2.16 | 1.72 | 3.03 | 2.06 | 1.66 |
| p Value | 0.0040 | 0.039 | 4.5E−4 | 0.0059 | 0.052 |
| Lower limit of 95% CI | 1.28 | 1.03 | 1.63 | 1.23 | 0.996 |
| Upper limit of 95% CI | 3.64 | 2.88 | 5.63 | 3.46 | 2.78 |
| OR Quartile 3 | 2.13 | 1.50 | 3.20 | 2.46 | 1.85 |
| p Value | 0.0019 | 0.083 | 2.7E−6 | 1.1E−4 | 0.0070 |
| Lower limit of 95% CI | 1.32 | 0.948 | 1.97 | 1.56 | 1.18 |
| Upper limit of 95% CI | 3.44 | 2.36 | 5.19 | 3.88 | 2.90 |
| OR Quartile 4 | 3.72 | 2.60 | 3.78 | 3.53 | 3.08 |
| p Value | 1.1E−4 | 0.0013 | 9.3E−7 | 2.2E−5 | 8.3E−5 |
| Lower limit of 95% CI | 1.91 | 1.45 | 2.22 | 1.97 | 1.76 |
| Upper limit of 95% CI | 7.25 | 4.68 | 6.44 | 6.33 | 5.40 |

| | Persistence Period Duration (hr) | | | |
|---|---|---|---|---|
| | 48 | 72 | | |
| | UO only | sCr or UO | sCr only | UO only |
| AUC | 0.70 | 0.66 | 0.63 | 0.69 |
| SE | 0.033 | 0.030 | 0.031 | 0.034 |
| p Value | 1.3E−9 | 3.0E−7 | 4.2E−5 | 1.1E−8 |
| nCohort Non-persistent | 212 | 150 | 158 | 217 |
| nCohort Persistent | 103 | 167 | 158 | 98 |
| Cutoff Quartile 2 | 8020 | 7990 | 7980 | 8020 |

TABLE 13.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | |
|---|---|---|---|---|
| Sensitivity | 86% | 83% | 81% | 86% |
| Specificity | 31% | 33% | 31% | 30% |
| Cutoff Quartile 3 | 13500 | 13500 | 13500 | 13500 |
| Sensitivity | 68% | 60% | 58% | 68% |
| Specificity | 58% | 61% | 58% | 58% |
| Cutoff Quartile 4 | 29400 | 28900 | 28100 | 29400 |
| Sensitivity | 42% | 36% | 35% | 42% |
| Specificity | 83% | 87% | 85% | 82% |
| OR Quartile 2 | 2.81 | 2.38 | 1.92 | 2.57 |
| p Value | 0.0014 | 0.0012 | 0.014 | 0.0037 |
| Lower limit of 95% CI | 1.49 | 1.41 | 1.14 | 1.36 |
| Upper limit of 95% CI | 5.30 | 4.02 | 3.23 | 4.85 |
| OR Quartile 3 | 2.99 | 2.43 | 1.94 | 2.99 |
| p Value | 1.5E−5 | 1.2E−4 | 0.0036 | 2.0E−5 |
| Lower limit of 95% CI | 1.82 | 1.54 | 1.24 | 1.81 |
| Upper limit of 95% CI | 4.91 | 3.81 | 3.04 | 4.95 |
| OR Quartile 4 | 3.50 | 3.64 | 3.22 | 3.39 |
| p Value | 3.7E−6 | 7.8E−6 | 3.0E−5 | 7.1E−6 |
| Lower limit of 95% CI | 2.06 | 2.07 | 1.86 | 1.99 |
| Upper limit of 95% CI | 5.96 | 6.43 | 5.58 | 5.77 |

TABLE 13.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 98000 | 117000 | 98700 | 119000 | 102000 | 120000 |
| Average | 109000 | 129000 | 113000 | 129000 | 116000 | 129000 |
| Stdev | 37500 | 45800 | 42900 | 43700 | 44400 | 42800 |
| p (t-test) | | 8.6E−5 | | 9.6E−4 | | 0.012 |
| Min | 57600 | 57000 | 57000 | 64800 | 57000 | 64800 |
| Max | 277000 | 299000 | 299000 | 281000 | 299000 | 281000 |
| n (Patient) | 114 | 213 | 155 | 172 | 179 | 148 |
| | sCr only | | | | | |
| Median | 98000 | 120000 | 98700 | 123000 | 103000 | 122000 |
| Average | 107000 | 131000 | 112000 | 131000 | 117000 | 128000 |
| Stdev | 35400 | 46600 | 41700 | 44300 | 45900 | 41000 |
| p (t-test) | | 2.4E−6 | | 6.5E−5 | | 0.025 |
| Min | 57600 | 57000 | 57000 | 64800 | 57000 | 64800 |
| Max | 277000 | 299000 | 299000 | 281000 | 299000 | 270000 |
| n (Patient) | 124 | 202 | 157 | 169 | 182 | 144 |
| | UO only | | | | | |
| Median | 106000 | 125000 | 106000 | 129000 | 105000 | 132000 |
| Average | 118000 | 134000 | 118000 | 140000 | 117000 | 145000 |
| Stdev | 42500 | 46600 | 41900 | 48100 | 41600 | 48700 |
| p (t-test) | | 0.0039 | | 2.4E−4 | | 1.6E−5 |
| Min | 57000 | 70200 | 57000 | 70200 | 57000 | 77400 |
| Max | 299000 | 281000 | 299000 | 281000 | 299000 | 281000 |
| n (Patient) | 245 | 80 | 261 | 64 | 269 | 56 |

TABLE 13.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

|  | Persistence Period Duration (hr) | | | | |
| --- | --- | --- | --- | --- | --- |
|  | 24 | | | 48 | |
|  | sCr or UO | sCr only | UO only | sCr or UO | sCr only |
| AUC | 0.65 | 0.67 | 0.62 | 0.64 | 0.66 |
| SE | 0.031 | 0.030 | 0.037 | 0.030 | 0.030 |
| p Value | 4.4E−7 | 4.0E−9 | 0.0013 | 2.8E−6 | 6.2E−8 |
| nCohort Non-persistent | 114 | 124 | 245 | 155 | 157 |
| nCohort Persistent | 213 | 202 | 80 | 172 | 169 |
| Cutoff Quartile 2 | 90400 | 90300 | 90600 | 90400 | 90300 |
| Sensitivity | 80% | 80% | 85% | 83% | 83% |
| Specificity | 34% | 34% | 28% | 34% | 34% |
| Cutoff Quartile 3 | 109000 | 109000 | 109000 | 109000 | 109000 |
| Sensitivity | 58% | 60% | 62% | 61% | 63% |
| Specificity | 65% | 66% | 54% | 62% | 64% |
| Cutoff Quartile 4 | 137000 | 137000 | 137000 | 137000 | 137000 |
| Sensitivity | 31% | 33% | 38% | 31% | 33% |
| Specificity | 87% | 88% | 79% | 81% | 83% |
| OR Quartile 2 | 2.06 | 2.07 | 2.22 | 2.56 | 2.46 |
| p Value | 0.0058 | 0.0049 | 0.020 | 3.8E−4 | 6.7E−4 |
| Lower limit of 95% CI | 1.23 | 1.25 | 1.13 | 1.52 | 1.46 |
| Upper limit of 95% CI | 3.43 | 3.45 | 4.36 | 4.31 | 4.13 |
| OR Quartile 3 | 2.58 | 2.92 | 1.95 | 2.55 | 2.95 |
| p Value | 8.2E−5 | 6.8E−6 | 0.012 | 3.9E−5 | 2.5E−6 |
| Lower limit of 95% CI | 1.61 | 1.83 | 1.16 | 1.63 | 1.88 |
| Upper limit of 95% CI | 4.13 | 4.65 | 3.27 | 3.98 | 4.63 |
| OR Quartile 4 | 3.03 | 3.61 | 2.23 | 1.94 | 2.50 |
| p Value | 4.2E−4 | 4.2E−5 | 0.0041 | 0.012 | 7.0E−4 |
| Lower limit of 95% CI | 1.64 | 1.95 | 1.29 | 1.15 | 1.47 |
| Upper limit of 95% CI | 5.60 | 6.66 | 3.85 | 3.25 | 4.24 |

|  | Persistence Period Duration (hr) | | | |
| --- | --- | --- | --- | --- |
|  | 48 | 72 | | |
|  | UO only | sCr or UO | sCr only | UO only |
| AUC | 0.66 | 0.62 | 0.62 | 0.69 |
| SE | 0.040 | 0.031 | 0.031 | 0.042 |
| p Value | 9.2E−5 | 1.6E−4 | 2.2E−4 | 5.8E−6 |
| nCohort Non-persistent | 261 | 179 | 182 | 269 |
| nCohort Persistent | 64 | 148 | 144 | 56 |
| Cutoff Quartile 2 | 90600 | 90400 | 90300 | 90600 |
| Sensitivity | 89% | 83% | 82% | 91% |
| Specificity | 28% | 32% | 31% | 28% |
| Cutoff Quartile 3 | 109000 | 109000 | 109000 | 109000 |
| Sensitivity | 66% | 63% | 63% | 71% |
| Specificity | 54% | 60% | 60% | 54% |
| Cutoff Quartile 4 | 137000 | 137000 | 137000 | 137000 |
| Sensitivity | 41% | 31% | 32% | 45% |
| Specificity | 79% | 80% | 80% | 79% |
| OR Quartile 2 | 3.22 | 2.30 | 2.02 | 4.02 |
| p Value | 0.0057 | 0.0022 | 0.0093 | 0.0044 |
| Lower limit of 95% CI | 1.41 | 1.35 | 1.19 | 1.54 |
| Upper limit of 95% CI | 7.39 | 3.92 | 3.42 | 10.4 |
| OR Quartile 3 | 2.21 | 2.57 | 2.62 | 2.97 |
| p Value | 0.0065 | 3.6E−5 | 2.7E−5 | 6.8E−4 |
| Lower limit of 95% CI | 1.25 | 1.64 | 1.67 | 1.58 |
| Upper limit of 95% CI | 3.91 | 4.03 | 4.12 | 5.56 |

TABLE 13.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

|  |  |  |  |  |
|---|---|---|---|---|
| OR Quartile 4 | 2.50 | 1.79 | 1.90 | 3.00 |
| p Value | 0.0019 | 0.024 | 0.013 | 3.5E−4 |
| Lower limit of 95% CI | 1.40 | 1.08 | 1.15 | 1.64 |
| Upper limit of 95% CI | 4.47 | 2.97 | 3.16 | 5.48 |

TABLE 13.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

|  | Persistence Period Duration (hr) | | | | | |
|---|---|---|---|---|---|---|
|  | 24 | | 48 | | 72 | |
|  | Non-persistent Cohort | Persistent Cohort | Non-persistent Cohort | Persistent Cohort | Non-persistent Cohort | Persistent Cohort |
| sCr or UO | | | | | | |
| Median | 97100 | 118000 | 98500 | 120000 | 99700 | 120000 |
| Average | 106000 | 130000 | 112000 | 129000 | 115000 | 129000 |
| Stdev | 33300 | 46500 | 42700 | 43700 | 44300 | 42800 |
| p (t-test) |  | 2.8E−6 |  | 5.3E−4 |  | 0.0050 |
| Min | 57600 | 57000 | 57600 | 57000 | 57600 | 57000 |
| Max | 252000 | 299000 | 299000 | 281000 | 299000 | 281000 |
| n (Patient) | 108 | 219 | 144 | 183 | 164 | 163 |
| sCr only | | | | | | |
| Median | 97500 | 120000 | 98700 | 121000 | 100000 | 121000 |
| Average | 105000 | 132000 | 111000 | 131000 | 115000 | 129000 |
| Stdev | 31200 | 47500 | 41100 | 44700 | 43800 | 43300 |
| p (t-test) |  | 8.4E−8 |  | 6.2E−5 |  | 0.0032 |
| Min | 57600 | 57000 | 57600 | 57000 | 57600 | 57000 |
| Max | 252000 | 299000 | 299000 | 281000 | 299000 | 281000 |
| n (Patient) | 120 | 206 | 149 | 177 | 166 | 160 |
| UO only | | | | | | |
| Median | 104000 | 124000 | 104000 | 128000 | 104000 | 130000 |
| Average | 116000 | 135000 | 116000 | 139000 | 116000 | 142000 |
| Stdev | 42300 | 45600 | 41600 | 46700 | 41300 | 47200 |
| p (t-test) |  | 5.8E−4 |  | 3.7E−5 |  | 5.6E−6 |
| Min | 57600 | 57000 | 57600 | 57000 | 57600 | 57000 |
| Max | 299000 | 281000 | 299000 | 281000 | 299000 | 281000 |
| n (Patient) | 225 | 100 | 241 | 84 | 248 | 77 |

|  | Persistence Period Duration (hr) | | | | |
|---|---|---|---|---|---|
|  | 24 | | | 48 | |
|  | sCr or UO | sCr only | UO only | sCr or UO | sCr only |
| AUC | 0.68 | 0.69 | 0.64 | 0.65 | 0.66 |
| SE | 0.030 | 0.029 | 0.034 | 0.030 | 0.030 |
| p Value | 2.2E−9 | 6.2E−11 | 4.3E−5 | 5.8E−7 | 9.0E−8 |
| nCohort Non-persistent | 108 | 120 | 225 | 144 | 149 |
| nCohort Persistent | 219 | 206 | 100 | 183 | 177 |
| Cutoff Quartile 2 | 90400 | 90300 | 90600 | 90400 | 90300 |
| Sensitivity | 80% | 81% | 86% | 83% | 82% |
| Specificity | 36% | 35% | 30% | 35% | 34% |
| Cutoff Quartile 3 | 109000 | 109000 | 109000 | 109000 | 109000 |
| Sensitivity | 59% | 61% | 64% | 61% | 62% |
| Specificity | 69% | 68% | 56% | 64% | 64% |
| Cutoff Quartile 4 | 137000 | 137000 | 137000 | 137000 | 137000 |
| Sensitivity | 32% | 33% | 38% | 31% | 33% |
| Specificity | 89% | 89% | 80% | 83% | 84% |

TABLE 13.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | |
|---|---|---|---|---|---|
| OR Quartile 2 | 2.31 | 2.23 | 2.60 | 2.51 | 2.29 |
| p Value | 0.0014 | 0.0020 | 0.0030 | 4.4E−4 | 0.0015 |
| Lower limit of 95% CI | 1.38 | 1.34 | 1.38 | 1.50 | 1.37 |
| Upper limit of 95% CI | 3.87 | 3.72 | 4.91 | 4.19 | 3.82 |
| OR Quartile 3 | 3.18 | 3.33 | 2.26 | 2.79 | 2.97 |
| p Value | 3.3E−6 | 7.1E−7 | 9.9E−4 | 8.4E−6 | 2.4E−6 |
| Lower limit of 95% CI | 1.95 | 2.07 | 1.39 | 1.78 | 1.89 |
| Upper limit of 95% CI | 5.18 | 5.36 | 3.68 | 4.38 | 4.68 |
| OR Quartile 4 | 3.76 | 4.15 | 2.52 | 2.15 | 2.54 |
| p Value | 9.3E−5 | 1.5E−5 | 5.1E−4 | 0.0048 | 6.9E−4 |
| Lower limit of 95% CI | 1.93 | 2.18 | 1.50 | 1.26 | 1.48 |
| Upper limit of 95% CI | 7.30 | 7.90 | 4.25 | 3.67 | 4.35 |

| | Persistence Period Duration (hr) | | | |
|---|---|---|---|---|
| | 48 | 72 | | |
| | UO only | sCr or UO | sCr only | UO only |
| AUC | 0.67 | 0.63 | 0.63 | 0.69 |
| SE | 0.036 | 0.031 | 0.031 | 0.037 |
| p Value | 2.3E−6 | 2.2E−5 | 2.1E−5 | 4.1E−7 |
| nCohort Non-persistent | 241 | 164 | 166 | 248 |
| nCohort Persistent | 84 | 163 | 160 | 77 |
| Cutoff Quartile 2 | 90600 | 90400 | 90300 | 90600 |
| Sensitivity | 89% | 83% | 82% | 90% |
| Specificity | 30% | 33% | 32% | 29% |
| Cutoff Quartile 3 | 109000 | 109000 | 109000 | 109000 |
| Sensitivity | 67% | 63% | 62% | 70% |
| Specificity | 56% | 62% | 62% | 56% |
| Cutoff Quartile 4 | 137000 | 137000 | 137000 | 137000 |
| Sensitivity | 40% | 31% | 32% | 43% |
| Specificity | 80% | 81% | 81% | 80% |
| OR Quartile 2 | 3.55 | 2.37 | 2.12 | 3.60 |
| p Value | 8.5E−4 | 0.0012 | 0.0045 | 0.0013 |
| Lower limit of 95% CI | 1.69 | 1.41 | 1.26 | 1.65 |
| Upper limit of 95% CI | 7.47 | 3.99 | 3.56 | 7.86 |
| OR Quartile 3 | 2.50 | 2.75 | 2.72 | 2.99 |
| p Value | 5.4E−4 | 9.3E−6 | 1.2E−5 | 9.0E−5 |
| Lower limit of 95% CI | 1.49 | 1.76 | 1.74 | 1.73 |
| Upper limit of 95% CI | 4.21 | 4.30 | 4.26 | 5.18 |
| OR Quartile 4 | 2.73 | 1.95 | 2.04 | 3.05 |
| p Value | 2.5E−4 | 0.010 | 0.0065 | 7.0E−5 |
| Lower limit of 95% CI | 1.60 | 1.17 | 1.22 | 1.76 |
| Upper limit of 95% CI | 4.68 | 3.26 | 3.40 | 5.27 |

TABLE 13.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 97000 | 118000 | 98300 | 119000 | 99100 | 120000 |
| Average | 106000 | 130000 | 112000 | 129000 | 114000 | 129000 |
| Stdev | 33500 | 46400 | 43000 | 43500 | 44100 | 42900 |
| p (t-test) | | 2.8E−6 | | 6.3E−4 | | 0.0036 |
| Min | 57600 | 57000 | 57600 | 57000 | 57600 | 57000 |
| Max | 252000 | 299000 | 299000 | 281000 | 299000 | 281000 |
| n (Patient) | 107 | 220 | 142 | 185 | 158 | 169 |
| | sCr only | | | | | |
| Median | 97100 | 120000 | 98500 | 121000 | 99100 | 121000 |
| Average | 104000 | 132000 | 111000 | 131000 | 113000 | 130000 |
| Stdev | 31100 | 47300 | 41300 | 44400 | 42900 | 43700 |
| p (t-test) | | 4.6E−8 | | 5.1E−5 | | 5.6E−4 |
| Min | 57600 | 57000 | 57600 | 57000 | 57600 | 57000 |
| Max | 252000 | 299000 | 299000 | 281000 | 299000 | 281000 |
| n (Patient) | 118 | 208 | 146 | 180 | 160 | 166 |
| | UO only | | | | | |
| Median | 104000 | 123000 | 104000 | 125000 | 104000 | 127000 |
| Average | 115000 | 135000 | 115000 | 138000 | 115000 | 141000 |
| Stdev | 41900 | 45600 | 41400 | 46400 | 41000 | 46900 |
| p (t-test) | | 1.6E−4 | | 1.6E−5 | | 2.7E−6 |
| Min | 57600 | 57000 | 57600 | 57000 | 57600 | 57000 |
| Max | 299000 | 281000 | 299000 | 281000 | 299000 | 281000 |
| n (Patient) | 216 | 109 | 230 | 95 | 237 | 88 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.68 | 0.70 | 0.65 | 0.65 | 0.66 |
| SE | 0.030 | 0.029 | 0.033 | 0.030 | 0.030 |
| p Value | 1.4E−9 | 8.6E−12 | 6.1E−6 | 4.8E−7 | 2.8E−8 |
| nCohort Non-persistent | 107 | 118 | 216 | 142 | 146 |
| nCohort Persistent | 220 | 208 | 109 | 185 | 180 |
| Cutoff Quartile 2 | 90400 | 90300 | 90600 | 90400 | 90300 |
| Sensitivity | 80% | 81% | 86% | 83% | 82% |
| Specificity | 36% | 36% | 31% | 35% | 34% |
| Cutoff Quartile 3 | 109000 | 109000 | 109000 | 109000 | 109000 |
| Sensitivity | 60% | 61% | 64% | 61% | 62% |
| Specificity | 69% | 69% | 57% | 64% | 65% |
| Cutoff Quartile 4 | 137000 | 137000 | 137000 | 137000 | 137000 |
| Sensitivity | 32% | 34% | 38% | 31% | 33% |
| Specificity | 89% | 90% | 81% | 82% | 84% |
| OR Quartile 2 | 2.36 | 2.32 | 2.76 | 2.60 | 2.41 |
| p Value | 0.0011 | 0.0012 | 0.0013 | 2.7E−4 | 7.8E−4 |
| Lower limit of 95% CI | 1.41 | 1.39 | 1.49 | 1.55 | 1.44 |
| Upper limit of 95% CI | 3.95 | 3.87 | 5.11 | 4.34 | 4.02 |
| OR Quartile 3 | 3.30 | 3.57 | 2.37 | 2.80 | 3.07 |
| p Value | 1.8E−6 | 2.1E−7 | 3.6E−4 | 8.2E−6 | 1.3E−6 |
| Lower limit of 95% CI | 2.02 | 2.21 | 1.48 | 1.78 | 1.95 |
| Upper limit of 95% CI | 5.39 | 5.78 | 3.82 | 4.40 | 4.83 |

TABLE 13.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | |
|---|---|---|---|---|---|
| OR Quartile 4 | 3.69 | 4.48 | 2.57 | 2.08 | 2.61 |
| p Value | 1.1E−4 | 9.2E−6 | 3.3E−4 | 0.0069 | 5.4E−4 |
| Lower limit of 95% CI | 1.90 | 2.31 | 1.54 | 1.22 | 1.51 |
| Upper limit of 95% CI | 7.18 | 8.69 | 4.31 | 3.55 | 4.49 |

| | Persistence Period Duration (hr) | | | |
|---|---|---|---|---|
| | 48 | 72 | | |
| | UO only | sCr or UO | sCr only | UO only |
| AUC | 0.67 | 0.63 | 0.65 | 0.69 |
| SE | 0.034 | 0.030 | 0.030 | 0.035 |
| p Value | 4.7E−7 | 1.1E−5 | 1.4E−6 | 8.8E−8 |
| nCohort Non-persistent | 230 | 158 | 160 | 237 |
| nCohort Persistent | 95 | 169 | 166 | 88 |
| Cutoff Quartile 2 | 90600 | 90400 | 90300 | 90600 |
| Sensitivity | 89% | 83% | 83% | 90% |
| Specificity | 31% | 34% | 33% | 30% |
| Cutoff Quartile 3 | 109000 | 109000 | 109000 | 109000 |
| Sensitivity | 66% | 62% | 63% | 69% |
| Specificity | 57% | 63% | 63% | 57% |
| Cutoff Quartile 4 | 137000 | 137000 | 137000 | 137000 |
| Sensitivity | 39% | 31% | 33% | 41% |
| Specificity | 80% | 81% | 82% | 81% |
| OR Quartile 2 | 3.80 | 2.44 | 2.34 | 3.83 |
| p Value | 2.4E−4 | 7.6E−4 | 0.0013 | 4.0E−4 |
| Lower limit of 95% CI | 1.86 | 1.45 | 1.39 | 1.82 |
| Upper limit of 95% CI | 7.74 | 4.09 | 3.93 | 8.05 |
| OR Quartile 3 | 2.56 | 2.75 | 2.87 | 2.99 |
| p Value | 2.2E−4 | 9.3E−6 | 4.2E−6 | 3.8E−5 |
| Lower limit of 95% CI | 1.55 | 1.76 | 1.83 | 1.78 |
| Upper limit of 95% CI | 4.22 | 4.31 | 4.50 | 5.03 |
| OR Quartile 4 | 2.62 | 1.90 | 2.27 | 2.87 |
| p Value | 3.2E−4 | 0.015 | 0.0020 | 1.0E−4 |
| Lower limit of 95% CI | 1.55 | 1.13 | 1.35 | 1.69 |
| Upper limit of 95% CI | 4.44 | 3.17 | 3.83 | 4.90 |

TABLE 13.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 96500 | 118000 | 98000 | 120000 | 98700 | 120000 |
| Average | 106000 | 129000 | 111000 | 130000 | 113000 | 129000 |
| Stdev | 33600 | 46300 | 41000 | 44600 | 42500 | 44100 |
| p (t-test) | | 3.6E−6 | | 1.1E−4 | | 9.9E−4 |
| Min | 57600 | 57000 | 57600 | 57000 | 57600 | 57000 |
| Max | 252000 | 299000 | 299000 | 281000 | 299000 | 281000 |
| n (Patient) | 106 | 221 | 140 | 187 | 155 | 172 |

TABLE 13.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | sCr only | | | |
|---|---|---|---|---|---|---|
| Median | 97100 | 120000 | 98300 | 122000 | 98800 | 122000 |
| Average | 104000 | 132000 | 110000 | 131000 | 112000 | 131000 |
| Stdev | 31100 | 47300 | 39100 | 45500 | 41100 | 44900 |
| p (t-test) | | 4.6E−8 | | 7.0E−6 | | 1.0E−4 |
| Min | 57600 | 57000 | 57600 | 57000 | 57600 | 57000 |
| Max | 252000 | 299000 | 299000 | 281000 | 299000 | 281000 |
| n (Patient) | 118 | 208 | 144 | 182 | 158 | 168 |
| | | | UO only | | | |
| Median | 104000 | 124000 | 103000 | 127000 | 103000 | 129000 |
| Average | 114000 | 136000 | 114000 | 139000 | 114000 | 141000 |
| Stdev | 40300 | 47300 | 39900 | 47600 | 39700 | 48000 |
| p (t-test) | | 2.3E−5 | | 8.8E−7 | | 1.7E−7 |
| Min | 57600 | 57000 | 57600 | 57000 | 57600 | 57000 |
| Max | 299000 | 281000 | 299000 | 281000 | 299000 | 281000 |
| n (Patient) | 211 | 114 | 223 | 102 | 229 | 96 |

| | Persistence Period Duration (hr) | | | | |
|---|---|---|---|---|---|
| | 24 | | | 48 | |
| | sCr or UO | sCr only | UO only | sCr or UO | sCr only |
| AUC | 0.68 | 0.70 | 0.66 | 0.66 | 0.67 |
| SE | 0.030 | 0.029 | 0.033 | 0.030 | 0.029 |
| p Value | 2.0E−9 | 8.6E−12 | 1.9E−6 | 7.3E−8 | 3.3E−9 |
| nCohort Non-persistent | 106 | 118 | 211 | 140 | 144 |
| nCohort Persistent | 221 | 208 | 114 | 187 | 182 |
| Cutoff Quartile 2 | 90400 | 90300 | 90600 | 90400 | 90300 |
| Sensitivity | 81% | 81% | 86% | 83% | 82% |
| Specificity | 37% | 36% | 31% | 36% | 35% |
| Cutoff Quartile 3 | 109000 | 109000 | 109000 | 109000 | 109000 |
| Sensitivity | 59% | 61% | 64% | 61% | 63% |
| Specificity | 69% | 69% | 57% | 65% | 66% |
| Cutoff Quartile 4 | 137000 | 137000 | 137000 | 137000 | 137000 |
| Sensitivity | 32% | 34% | 38% | 31% | 33% |
| Specificity | 89% | 90% | 82% | 83% | 85% |
| OR Quartile 2 | 2.41 | 2.32 | 2.73 | 2.69 | 2.49 |
| p Value | 8.5E−4 | 0.0012 | 0.0011 | 1.6E−4 | 4.8E−4 |
| Lower limit of 95% CI | 1.44 | 1.39 | 1.49 | 1.61 | 1.49 |
| Upper limit of 95% CI | 4.04 | 3.87 | 4.99 | 4.50 | 4.17 |
| OR Quartile 3 | 3.22 | 3.57 | 2.39 | 2.97 | 3.25 |
| p Value | 3.0E−6 | 2.1E−7 | 2.7E−4 | 2.9E−6 | 4.3E−7 |
| Lower limit of 95% CI | 1.97 | 2.21 | 1.50 | 1.88 | 2.06 |
| Upper limit of 95% CI | 5.26 | 5.78 | 3.83 | 4.68 | 5.13 |
| OR Quartile 4 | 3.63 | 4.48 | 2.67 | 2.17 | 2.73 |
| p Value | 1.4E−4 | 9.2E−6 | 1.8E−4 | 0.0047 | 3.4E−4 |
| Lower limit of 95% CI | 1.87 | 2.31 | 1.60 | 1.27 | 1.57 |
| Upper limit of 95% CI | 7.06 | 8.69 | 4.47 | 3.72 | 4.72 |

| | Persistence Period Duration (hr) | | | |
|---|---|---|---|---|
| | 48 | 72 | | |
| | UO only | sCr or UO | sCr only | UO only |
| AUC | 0.69 | 0.64 | 0.65 | 0.70 |
| SE | 0.033 | 0.030 | 0.030 | 0.034 |
| p Value | 2.1E−8 | 2.9E−6 | 2.6E−7 | 4.8E−9 |
| nCohort Non-persistent | 223 | 155 | 158 | 229 |
| nCohort Persistent | 102 | 172 | 168 | 96 |
| Cutoff Quartile 2 | 90600 | 90400 | 90300 | 90600 |
| Sensitivity | 89% | 83% | 83% | 90% |

TABLE 13.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

|  |  |  |  |  |
|---|---|---|---|---|
| Specificity | 31% | 34% | 34% | 31% |
| Cutoff Quartile 3 | 109000 | 109000 | 109000 | 109000 |
| Sensitivity | 68% | 62% | 63% | 70% |
| Specificity | 58% | 63% | 64% | 58% |
| Cutoff Quartile 4 | 137000 | 137000 | 137000 | 137000 |
| Sensitivity | 40% | 31% | 33% | 42% |
| Specificity | 82% | 81% | 83% | 82% |
| OR Quartile 2 | 3.78 | 2.56 | 2.42 | 3.86 |
| p Value | 1.4E−4 | 3.8E−4 | 8.4E−4 | 2.0E−4 |
| Lower limit of 95% CI | 1.90 | 1.52 | 1.44 | 1.90 |
| Upper limit of 95% CI | 7.52 | 4.31 | 4.06 | 7.88 |
| OR Quartile 3 | 2.87 | 2.83 | 3.03 | 3.20 |
| p Value | 2.7E−5 | 5.6E−6 | 1.5E−6 | 7.4E−6 |
| Lower limit of 95% CI | 1.75 | 1.81 | 1.93 | 1.92 |
| Upper limit of 95% CI | 4.70 | 4.43 | 4.76 | 5.32 |
| OR Quartile 4 | 2.98 | 1.94 | 2.36 | 3.18 |
| p Value | 3.9E−5 | 0.012 | 0.0013 | 1.6E−5 |
| Lower limit of 95% CI | 1.77 | 1.15 | 1.40 | 1.88 |
| Upper limit of 95% CI | 5.02 | 3.25 | 3.99 | 5.38 |

TABLE 13.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 96500 | 118000 | 97900 | 119000 | 98600 | 120000 |
| Average | 105000 | 129000 | 111000 | 130000 | 113000 | 129000 |
| Stdev | 32700 | 46400 | 40700 | 44700 | 42500 | 44000 |
| p (t-test) | | 3.3E−6 | | 1.0E−4 | | 8.3E−4 |
| Min | 57600 | 57000 | 57600 | 57000 | 57600 | 57000 |
| Max | 252000 | 299000 | 299000 | 281000 | 299000 | 281000 |
| n (Patient) | 102 | 225 | 135 | 192 | 149 | 178 |
| *sCr only* | | | | | | |
| Median | 97200 | 120000 | 98500 | 120000 | 99100 | 120000 |
| Average | 105000 | 131000 | 110000 | 130000 | 113000 | 130000 |
| Stdev | 31400 | 47200 | 39500 | 45500 | 41400 | 44900 |
| p (t-test) | | 1.6E−7 | | 3.3E−5 | | 4.1E−4 |
| Min | 57600 | 57000 | 57600 | 57000 | 57600 | 57000 |
| Max | 252000 | 299000 | 299000 | 281000 | 299000 | 281000 |
| n (Patient) | 115 | 211 | 140 | 186 | 154 | 172 |
| *UO only* | | | | | | |
| Median | 104000 | 123000 | 103000 | 125000 | 103000 | 125000 |
| Average | 115000 | 134000 | 114000 | 137000 | 114000 | 138000 |
| Stdev | 40800 | 46800 | 40500 | 46800 | 40200 | 47400 |
| p (t-test) | | 1.3E−4 | | 5.9E−6 | | 3.3E−6 |
| Min | 57600 | 57000 | 57600 | 57000 | 57600 | 57000 |
| Max | 299000 | 281000 | 299000 | 281000 | 299000 | 281000 |
| n (Patient) | 204 | 121 | 214 | 111 | 219 | 106 |

TABLE 13.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

|  | Persistence Period Duration (hr) | | | | |
|---|---|---|---|---|---|
|  | 24 | | | 48 | |
|  | sCr or UO | sCr only | UO only | sCr or UO | sCr only |
| AUC | 0.68 | 0.69 | 0.64 | 0.66 | 0.66 |
| SE | 0.030 | 0.029 | 0.032 | 0.030 | 0.030 |
| p Value | 3.3E−9 | 1.0E−10 | 1.2E−5 | 7.8E−8 | 7.2E−8 |
| nCohort Non-persistent | 102 | 115 | 204 | 135 | 140 |
| nCohort Persistent | 225 | 211 | 121 | 192 | 186 |
| Cutoff Quartile 2 | 90400 | 90300 | 90600 | 90400 | 90300 |
| Sensitivity | 80% | 80% | 84% | 82% | 81% |
| Specificity | 36% | 35% | 30% | 36% | 34% |
| Cutoff Quartile 3 | 109000 | 109000 | 109000 | 109000 | 109000 |
| Sensitivity | 59% | 60% | 63% | 61% | 61% |
| Specificity | 69% | 69% | 57% | 65% | 65% |
| Cutoff Quartile 4 | 137000 | 137000 | 137000 | 137000 | 137000 |
| Sensitivity | 32% | 33% | 36% | 31% | 32% |
| Specificity | 89% | 90% | 81% | 84% | 84% |
| OR Quartile 2 | 2.28 | 2.15 | 2.34 | 2.56 | 2.18 |
| p Value | 0.0019 | 0.0034 | 0.0036 | 3.1E−4 | 0.0026 |
| Lower limit of 95% CI | 1.35 | 1.29 | 1.32 | 1.54 | 1.31 |
| Upper limit of 95% CI | 3.83 | 3.58 | 4.16 | 4.28 | 3.62 |
| OR Quartile 3 | 3.10 | 3.32 | 2.27 | 2.92 | 2.94 |
| p Value | 7.4E−6 | 1.0E−6 | 4.9E−4 | 4.4E−6 | 3.5E−6 |
| Lower limit of 95% CI | 1.89 | 2.05 | 1.43 | 1.85 | 1.86 |
| Upper limit of 95% CI | 5.10 | 5.37 | 3.60 | 4.62 | 4.64 |
| OR Quartile 4 | 3.81 | 4.26 | 2.33 | 2.33 | 2.55 |
| p Value | 1.3E−4 | 1.8E−5 | 0.0011 | 0.0025 | 8.2E−4 |
| Lower limit of 95% CI | 1.92 | 2.20 | 1.40 | 1.35 | 1.47 |
| Upper limit of 95% CI | 7.57 | 8.27 | 3.89 | 4.04 | 4.42 |

|  | Persistence Period Duration (hr) | | | |
|---|---|---|---|---|
|  | 48 | 72 | | |
|  | UO only | sCr or UO | sCr only | UO only |
| AUC | 0.67 | 0.64 | 0.64 | 0.68 |
| SE | 0.032 | 0.030 | 0.030 | 0.033 |
| p Value | 8.5E−8 | 1.9E−6 | 3.4E−6 | 1.0E−7 |
| nCohort Non-persistent | 214 | 149 | 154 | 219 |
| nCohort Persistent | 111 | 178 | 172 | 106 |
| Cutoff Quartile 2 | 90600 | 90400 | 90300 | 90600 |
| Sensitivity | 87% | 83% | 81% | 87% |
| Specificity | 31% | 34% | 32% | 31% |
| Cutoff Quartile 3 | 109000 | 109000 | 109000 | 109000 |
| Sensitivity | 67% | 62% | 62% | 68% |
| Specificity | 58% | 64% | 63% | 58% |
| Cutoff Quartile 4 | 137000 | 137000 | 137000 | 137000 |
| Sensitivity | 38% | 31% | 32% | 39% |
| Specificity | 81% | 82% | 82% | 81% |
| OR Quartile 2 | 3.16 | 2.47 | 2.10 | 2.90 |
| p Value | 3.5E−4 | 5.8E−4 | 0.0044 | 9.6E−4 |
| Lower limit of 95% CI | 1.68 | 1.48 | 1.26 | 1.54 |
| Upper limit of 95% CI | 5.93 | 4.13 | 3.51 | 5.45 |

TABLE 13.10-continued

Comparison of marker levels and the area under the ROC curve (AUC) in
EDTA samples for the "persistent" and "non-persistent"
cohorts where persistence starts within 168 hours after sample collection
and renal status is assessed by serum creatinine (sCr) only, urine output
(UO) only, or serum creatinine or urine output RIFLE criteria.

| | | | | |
|---|---|---|---|---|
| OR Quartile 3 | 2.81 | 2.85 | 2.73 | 2.98 |
| p Value | 2.4E−5 | 5.4E−6 | 1.1E−5 | 1.2E−5 |
| Lower limit of 95% CI | 1.74 | 1.81 | 1.74 | 1.83 |
| Upper limit of 95% CI | 4.54 | 4.47 | 4.28 | 4.85 |
| OR Quartile 4 | 2.65 | 2.02 | 2.21 | 2.74 |
| p Value | 2.1E−4 | 0.0086 | 0.0030 | 1.4E−4 |
| Lower limit of 95% CI | 1.58 | 1.20 | 1.31 | 1.63 |
| Upper limit of 95% CI | 4.43 | 3.41 | 3.74 | 4.60 |

Example 14. Use of Metalloproteinase Inhibitor 4 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 14.1

Comparison of marker levels and the area under the ROC curve (AUC) in urine samples for the "recovered"
and "non-recovered" cohorts where recovery starts within 24 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11.1 | 29.5 | 11.8 | 29.0 | 11.1 | 28.9 |
| Average | 17.9 | 190 | 18.2 | 183 | 17.1 | 180 |
| Stdev | 21.6 | 850 | 21.6 | 834 | 22.3 | 826 |
| p (t-test) | | 0.13 | | 0.18 | | 0.21 |
| Min | 0.00110 | 0.00167 | 0.00167 | 0.00110 | 0.00167 | 0.00110 |
| Max | 108 | 9030 | 108 | 9030 | 108 | 9030 |
| n (Patient) | 57 | 260 | 46 | 271 | 41 | 276 |
| | sCr only | | | | | |
| Median | 13.0 | 29.0 | 13.3 | 28.8 | 13.3 | 28.8 |
| Average | 22.6 | 203 | 23.1 | 201 | 21.3 | 199 |
| Stdev | 27.4 | 884 | 27.6 | 880 | 21.5 | 873 |
| p (t-test) | | 0.077 | | 0.083 | | 0.091 |
| Min | 0.00110 | 0.00167 | 0.00167 | 0.00110 | 0.00167 | 0.00110 |
| Max | 173 | 9030 | 173 | 9030 | 108 | 9030 |
| n (Patient) | 76 | 240 | 74 | 242 | 70 | 246 |
| | UO only | | | | | |
| Median | 17.0 | 38.8 | 16.9 | 34.6 | 15.7 | 33.7 |
| Average | 97.5 | 261 | 98.2 | 236 | 98.8 | 220 |
| Stdev | 655 | 931 | 691 | 863 | 725 | 819 |

TABLE 14.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.069 | | | 0.12 | | | 0.16 | |
| Min | 0.00110 | | 0.00277 | 0.00110 | | 0.00273 | 0.00110 | | 0.00273 |
| Max | 9030 | | 7570 | 9030 | | 7570 | 9030 | | 7570 |
| n (Patient) | 194 | | 121 | 173 | | 142 | 156 | | 159 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.66 | 0.66 | 0.69 | 0.65 | 0.66 | 0.70 | 0.65 | 0.66 |
| SE | 0.034 | 0.034 | 0.032 | 0.038 | 0.034 | 0.031 | 0.038 | 0.035 | 0.030 |
| p Value | 1.3E−9 | 3.4E−6 | 4.9E−7 | 9.4E−7 | 1.9E−5 | 5.3E−7 | 1.2E−7 | 1.8E−5 | 7.3E−8 |
| nCohort Recovered | 57 | 76 | 194 | 46 | 74 | 173 | 41 | 70 | 156 |
| nCohort Non-recovered | 260 | 240 | 121 | 271 | 242 | 142 | 276 | 246 | 159 |
| Cutoff Quartile 2 | 8.33 | 8.31 | 8.36 | 8.33 | 8.31 | 8.36 | 8.33 | 8.31 | 8.36 |
| Sensitivity | 80% | 78% | 88% | 78% | 77% | 86% | 78% | 77% | 85% |
| Specificity | 46% | 33% | 33% | 43% | 32% | 34% | 46% | 31% | 35% |
| Cutoff Quartile 3 | 24.1 | 23.6 | 24.1 | 24.1 | 23.6 | 24.1 | 24.1 | 23.6 | 24.1 |
| Sensitivity | 55% | 55% | 64% | 54% | 54% | 62% | 55% | 54% | 62% |
| Specificity | 74% | 64% | 59% | 74% | 64% | 60% | 80% | 64% | 62% |
| Cutoff Quartile 4 | 60.9 | 60.8 | 61.8 | 60.9 | 60.8 | 61.8 | 60.9 | 60.8 | 61.8 |
| Sensitivity | 30% | 31% | 36% | 29% | 31% | 33% | 28% | 31% | 33% |
| Specificity | 96% | 95% | 81% | 96% | 95% | 82% | 95% | 96% | 83% |
| OR Quartile 2 | 3.28 | 1.69 | 3.48 | 2.76 | 1.63 | 3.16 | 3.11 | 1.52 | 3.06 |
| p Value | 1.1E−4 | 0.070 | 7.7E−5 | 0.0022 | 0.093 | 7.2E−5 | 0.0010 | 0.16 | 5.6E−5 |
| Lower limit of 95% CI | 1.79 | 0.958 | 1.88 | 1.44 | 0.921 | 1.79 | 1.58 | 0.847 | 1.78 |
| Upper limit of 95% CI | 5.98 | 2.97 | 6.45 | 5.30 | 2.89 | 5.57 | 6.12 | 2.73 | 5.28 |
| OR Quartile 3 | 3.48 | 2.18 | 2.58 | 3.36 | 2.05 | 2.40 | 4.98 | 2.12 | 2.71 |
| p Value | 1.3E−4 | 0.0042 | 7.3E−5 | 6.9E−4 | 0.0085 | 1.6E−4 | 9.8E−5 | 0.0074 | 1.8E−5 |
| Lower limit of 95% CI | 1.84 | 1.28 | 1.62 | 1.67 | 1.20 | 1.52 | 2.22 | 1.22 | 1.72 |
| Upper limit of 95% CI | 6.58 | 3.72 | 4.13 | 6.77 | 3.51 | 3.78 | 11.2 | 3.67 | 4.28 |
| OR Quartile 4 | 11.8 | 8.18 | 2.42 | 8.89 | 7.86 | 2.18 | 7.68 | 9.98 | 2.32 |
| p Value | 7.6E−4 | 7.8E−5 | 8.5E−4 | 0.0030 | 1.1E−4 | 0.0033 | 0.0057 | 1.5E−4 | 0.0019 |
| Lower limit of 95% CI | 2.80 | 2.88 | 1.44 | 2.10 | 2.77 | 1.30 | 1.81 | 3.04 | 1.37 |
| Upper limit of 95% CI | 49.5 | 23.2 | 4.07 | 37.6 | 22.3 | 3.66 | 32.6 | 32.7 | 3.95 |

TABLE 14.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 11.2 | 33.4 | 12.3 | 29.7 | 11.2 | 29.7 |
| Average | 21.2 | 214 | 22.6 | 205 | 21.7 | 199 |
| Stdev | 26.7 | 908 | 27.7 | 887 | 28.6 | 873 |
| p (t-test) | | 0.045 | | 0.070 | | 0.089 |
| Min | 0.00110 | 0.00167 | 0.00167 | 0.00110 | 0.00167 | 0.00110 |
| Max | 121 | 9030 | 121 | 9030 | 121 | 9030 |
| n (Patient) | 90 | 227 | 79 | 238 | 71 | 246 |
| | sCr only | | | | | |
| Median | 12.5 | 33.7 | 12.7 | 33.4 | 12.7 | 33.6 |
| Average | 25.3 | 227 | 25.7 | 225 | 24.4 | 221 |

TABLE 14.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | |
|---|---|---|---|---|---|---|---|
| Stdev | 32.9 | 940 | 33.1 | 936 | 30.2 | 926 |
| p (t-test) | | 0.028 | | 0.031 | | 0.036 |
| Min | 0.00110 | 0.00167 | 0.00167 | 0.00110 | 0.00167 | 0.00110 |
| Max | 173 | 9030 | 173 | 9030 | 172 | 9030 |
| n (Patient) | 106 | 211 | 104 | 213 | 99 | 218 |

UO only

| | | | | | | |
|---|---|---|---|---|---|---|
| Median | 18.2 | 33.4 | 18.5 | 30.7 | 17.2 | 33.2 |
| Average | 111 | 262 | 117 | 229 | 109 | 226 |
| Stdev | 645 | 986 | 674 | 913 | 690 | 871 |
| p (t-test) | | 0.10 | | 0.21 | | 0.18 |
| Min | 0.00110 | 0.00277 | 0.00110 | 0.00273 | 0.00110 | 0.00273 |
| Max | 9030 | 7570 | 9030 | 7570 | 9030 | 7570 |
| n (Patient) | 212 | 103 | 194 | 121 | 178 | 137 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.68 | 0.64 | 0.68 | 0.67 | 0.61 | 0.69 | 0.67 | 0.62 |
| SE | 0.030 | 0.030 | 0.034 | 0.032 | 0.031 | 0.033 | 0.032 | 0.031 | 0.032 |
| p Value | 2.8E−12 | 7.0E−9 | 7.9E−5 | 2.9E−8 | 5.4E−8 | 0.0012 | 2.0E−9 | 3.6E−8 | 1.9E−4 |
| nCohort Recovered | 90 | 106 | 212 | 79 | 104 | 194 | 71 | 99 | 178 |
| nCohort Non-recovered | 227 | 211 | 103 | 238 | 213 | 121 | 246 | 218 | 137 |
| Cutoff Quartile 2 | 8.33 | 8.33 | 8.36 | 8.33 | 8.33 | 8.36 | 8.33 | 8.33 | 8.36 |
| Sensitivity | 83% | 81% | 89% | 81% | 81% | 86% | 81% | 80% | 85% |
| Specificity | 44% | 37% | 32% | 42% | 37% | 32% | 45% | 36% | 33% |
| Cutoff Quartile 3 | 24.1 | 24.1 | 24.1 | 24.1 | 24.1 | 24.1 | 24.1 | 24.1 | 24.1 |
| Sensitivity | 58% | 57% | 62% | 56% | 57% | 59% | 57% | 57% | 60% |
| Specificity | 70% | 64% | 56% | 68% | 63% | 55% | 73% | 65% | 57% |
| Cutoff Quartile 4 | 60.9 | 60.9 | 61.8 | 60.9 | 60.9 | 61.8 | 60.9 | 60.9 | 61.8 |
| Sensitivity | 33% | 34% | 33% | 31% | 33% | 30% | 30% | 33% | 31% |
| Specificity | 93% | 92% | 79% | 92% | 91% | 78% | 93% | 92% | 79% |
| OR Quartile 2 | 3.86 | 2.49 | 3.95 | 2.99 | 2.42 | 2.87 | 3.47 | 2.33 | 2.90 |
| p Value | 9.7E−7 | 6.5E−4 | 9.2E−5 | 9.5E−5 | 9.9E−4 | 5.1E−4 | 1.6E−5 | 0.0017 | 2.4E−4 |
| Lower limit of 95% CI | 2.25 | 1.47 | 1.98 | 1.73 | 1.43 | 1.58 | 1.97 | 1.37 | 1.64 |
| Upper limit of 95% CI | 6.62 | 4.20 | 7.86 | 5.19 | 4.08 | 5.21 | 6.11 | 3.94 | 5.12 |
| OR Quartile 3 | 3.24 | 2.41 | 2.06 | 2.78 | 2.28 | 1.75 | 3.61 | 2.41 | 2.00 |
| p Value | 1.0E−5 | 3.5E−4 | 0.0033 | 2.0E−4 | 7.9E−4 | 0.017 | 1.6E−5 | 4.5E−4 | 0.0027 |
| Lower limit of 95% CI | 1.92 | 1.49 | 1.27 | 1.62 | 1.41 | 1.10 | 2.02 | 1.48 | 1.27 |
| Upper limit of 95% CI | 5.47 | 3.89 | 3.33 | 4.77 | 3.70 | 2.76 | 6.47 | 3.94 | 3.15 |
| OR Quartile 4 | 6.77 | 5.47 | 1.83 | 5.49 | 5.28 | 1.49 | 5.79 | 5.61 | 1.68 |
| p Value | 1.8E−5 | 6.9E−6 | 0.025 | 1.4E−4 | 1.1E−5 | 0.13 | 2.9E−4 | 1.3E−5 | 0.046 |
| Lower limit of 95% CI | 2.83 | 2.61 | 1.08 | 2.29 | 2.52 | 0.887 | 2.24 | 2.58 | 1.01 |
| Upper limit of 95% CI | 16.2 | 11.5 | 3.10 | 13.2 | 11.1 | 2.49 | 15.0 | 12.2 | 2.81 |

TABLE 14.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 12.3 | 33.7 | 12.3 | 33.5 | 12.3 | 33.4 |
| Average | 24.0 | 235 | 24.5 | 228 | 24.1 | 219 |
| Stdev | 32.3 | 958 | 32.9 | 942 | 33.8 | 922 |
| p (t-test) | | 0.019 | | 0.026 | | 0.038 |
| Min | 0.00110 | 0.00167 | 0.00167 | 0.00110 | 0.00167 | 0.00110 |
| Max | 223 | 9030 | 223 | 9030 | 223 | 9030 |
| n (Patient) | 114 | 203 | 107 | 210 | 97 | 220 |
| sCr only | | | | | | |
| Median | 12.7 | 35.5 | 13.3 | 33.4 | 13.3 | 34.0 |
| Average | 27.3 | 248 | 27.8 | 244 | 26.9 | 239 |
| Stdev | 36.2 | 989 | 36.5 | 982 | 34.6 | 970 |
| p (t-test) | | 0.013 | | 0.015 | | 0.018 |
| Min | 0.00110 | 0.00167 | 0.00167 | 0.00110 | 0.00167 | 0.00110 |
| Max | 223 | 9030 | 223 | 9030 | 223 | 9030 |
| n (Patient) | 127 | 190 | 124 | 193 | 119 | 198 |
| UO only | | | | | | |
| Median | 18.1 | 33.4 | 17.7 | 33.4 | 16.9 | 33.7 |
| Average | 112 | 263 | 115 | 243 | 106 | 243 |
| Stdev | 642 | 996 | 658 | 952 | 669 | 910 |
| p (t-test) | | 0.11 | | 0.16 | | 0.12 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 214 | 101 | 204 | 111 | 190 | 125 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.62 | 0.69 | 0.66 | 0.61 | 0.69 | 0.66 | 0.64 |
| SE | 0.029 | 0.030 | 0.035 | 0.030 | 0.030 | 0.034 | 0.030 | 0.030 | 0.032 |
| p Value | 4.9E−12 | 4.5E−9 | 4.7E−4 | 3.2E−10 | 1.1E−7 | 9.4E−4 | 2.2E−10 | 9.3E−8 | 1.1E−5 |
| nCohort Recovered | 114 | 127 | 214 | 107 | 124 | 204 | 97 | 119 | 190 |
| nCohort Non-recovered | 203 | 190 | 101 | 210 | 193 | 111 | 220 | 198 | 125 |
| Cutoff Quartile 2 | 8.33 | 8.33 | 8.36 | 8.33 | 8.33 | 8.36 | 8.33 | 8.33 | 8.36 |
| Sensitivity | 84% | 82% | 86% | 82% | 81% | 85% | 82% | 81% | 86% |
| Specificity | 40% | 35% | 30% | 39% | 35% | 30% | 40% | 34% | 32% |
| Cutoff Quartile 3 | 24.1 | 24.1 | 24.1 | 24.1 | 24.1 | 24.1 | 24.1 | 24.1 | 24.1 |
| Sensitivity | 60% | 59% | 62% | 60% | 58% | 62% | 60% | 58% | 65% |
| Specificity | 68% | 63% | 56% | 68% | 62% | 56% | 71% | 63% | 59% |
| Cutoff Quartile 4 | 60.9 | 60.9 | 61.8 | 60.9 | 60.9 | 61.8 | 60.9 | 60.9 | 61.8 |
| Sensitivity | 34% | 35% | 32% | 33% | 35% | 30% | 33% | 34% | 32% |
| Specificity | 91% | 90% | 78% | 91% | 90% | 77% | 92% | 90% | 79% |
| OR Quartile 2 | 3.48 | 2.52 | 2.71 | 3.02 | 2.32 | 2.41 | 3.03 | 2.21 | 2.81 |
| p Value | 3.6E−6 | 4.9E−4 | 0.0021 | 3.8E−5 | 0.0015 | 0.0038 | 4.4E−5 | 0.0026 | 5.3E−4 |
| Lower limit of 95% CI | 2.05 | 1.50 | 1.44 | 1.79 | 1.38 | 1.33 | 1.78 | 1.32 | 1.57 |
| Upper limit of 95% CI | 5.91 | 4.23 | 5.12 | 5.11 | 3.88 | 4.38 | 5.15 | 3.71 | 5.04 |
| OR Quartile 3 | 3.13 | 2.44 | 2.08 | 3.16 | 2.27 | 2.12 | 3.63 | 2.36 | 2.70 |
| p Value | 3.4E−6 | 1.5E−4 | 0.0031 | 4.5E−6 | 5.2E−4 | 0.0018 | 9.5E−7 | 3.1E−4 | 3.1E−5 |
| Lower limit of 95% CI | 1.94 | 1.54 | 1.28 | 1.93 | 1.43 | 1.32 | 2.17 | 1.48 | 1.69 |
| Upper limit of 95% CI | 5.08 | 3.88 | 3.37 | 5.16 | 3.60 | 3.41 | 6.07 | 3.77 | 4.31 |

TABLE 14.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 5.47 | 4.78 | 1.65 | 4.85 | 4.54 | 1.45 | 5.41 | 4.66 | 1.82 |
| p Value | 2.7E−6 | 2.1E−6 | 0.065 | 1.4E−5 | 4.5E−6 | 0.16 | 2.0E−5 | 5.6E−6 | 0.022 |
| Lower limit of 95% CI | 2.69 | 2.50 | 0.970 | 2.38 | 2.38 | 0.861 | 2.49 | 2.40 | 1.09 |
| Upper limit of 95% CI | 11.1 | 9.12 | 2.80 | 9.88 | 8.67 | 2.45 | 11.8 | 9.07 | 3.05 |

TABLE 14.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 12.3 | 37.0 | 12.3 | 36.1 | 11.9 | 33.7 |
| Average | 26.8 | 256 | 27.5 | 245 | 27.6 | 233 |
| Stdev | 42.8 | 1010 | 44.0 | 984 | 45.6 | 958 |
| p (t-test) | 0.0088 | | 0.014 | | 0.023 | |
| Min | 0.00110 | 0.00167 | 0.00167 | 0.00110 | 0.00167 | 0.00110 |
| Max | 337 | 9030 | 337 | 9030 | 337 | 9030 |
| n (Patient) | 134 | 183 | 125 | 192 | 114 | 203 |
| sCr only | | | | | | |
| Median | 12.5 | 37.0 | 12.7 | 36.7 | 12.7 | 36.6 |
| Average | 28.8 | 263 | 29.1 | 260 | 28.2 | 257 |
| Stdev | 43.9 | 1020 | 44.1 | 1020 | 42.8 | 1010 |
| p (t-test) | 0.0073 | | 0.0082 | | 0.0090 | |
| Min | 0.00110 | 0.00167 | 0.00110 | 0.00167 | 0.00110 | 0.00167 |
| Max | 337 | 9030 | 337 | 9030 | 337 | 9030 |
| n (Patient) | 140 | 177 | 138 | 179 | 135 | 182 |
| UO only | | | | | | |
| Median | 18.1 | 38.8 | 17.3 | 36.3 | 17.0 | 35.8 |
| Average | 110 | 270 | 113 | 251 | 104 | 251 |
| Stdev | 640 | 1000 | 653 | 964 | 662 | 924 |
| p (t-test) | 0.089 | | 0.13 | | 0.10 | |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 216 | 99 | 207 | 108 | 194 | 121 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.69 | 0.64 | 0.70 | 0.68 | 0.63 | 0.70 | 0.69 | 0.65 |
| SE | 0.028 | 0.029 | 0.035 | 0.029 | 0.030 | 0.034 | 0.029 | 0.029 | 0.032 |
| p Value | 6.0E−14 | 5.9E−11 | 7.2E−5 | 9.9E−12 | 5.2E−10 | 8.2E−5 | 2.5E−11 | 2.4E−10 | 5.1E−6 |
| nCohort Recovered | 134 | 140 | 216 | 125 | 138 | 207 | 114 | 135 | 194 |
| nCohort Non-recovered | 183 | 177 | 99 | 192 | 179 | 108 | 203 | 182 | 121 |
| Cutoff Quartile 2 | 8.33 | 8.33 | 8.36 | 8.33 | 8.33 | 8.36 | 8.33 | 8.33 | 8.36 |
| Sensitivity | 85% | 84% | 86% | 83% | 83% | 86% | 83% | 83% | 86% |
| Specificity | 38% | 36% | 30% | 38% | 36% | 31% | 39% | 36% | 32% |
| Cutoff Quartile 3 | 24.1 | 24.1 | 24.1 | 24.1 | 24.1 | 24.1 | 24.1 | 24.1 | 24.1 |
| Sensitivity | 62% | 60% | 64% | 61% | 60% | 64% | 61% | 60% | 65% |
| Specificity | 66% | 63% | 56% | 67% | 62% | 57% | 69% | 63% | 59% |
| Cutoff Quartile 4 | 60.9 | 60.9 | 61.8 | 60.9 | 60.9 | 61.8 | 60.9 | 60.9 | 61.8 |
| Sensitivity | 37% | 37% | 34% | 35% | 36% | 32% | 34% | 36% | 33% |
| Specificity | 90% | 89% | 79% | 90% | 89% | 79% | 90% | 90% | 80% |
| OR Quartile 2 | 3.40 | 2.84 | 2.61 | 3.01 | 2.73 | 2.77 | 3.02 | 2.69 | 2.87 |
| p Value | 6.6E−6 | 1.1E−4 | 0.0031 | 3.8E−5 | 1.7E−4 | 0.0013 | 3.6E−5 | 2.1E−4 | 5.1E−4 |

TABLE 14.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 2.00 | 1.67 | 1.38 | 1.78 | 1.62 | 1.49 | 1.79 | 1.59 | 1.58 |
| Upper limit of 95% CI | 5.79 | 4.80 | 4.94 | 5.09 | 4.62 | 5.16 | 5.10 | 4.53 | 5.21 |
| OR Quartile 3 | 3.27 | 2.59 | 2.23 | 3.27 | 2.46 | 2.35 | 3.54 | 2.54 | 2.74 |
| p Value | 6.6E−7 | 4.5E−5 | 0.0013 | 9.4E−7 | 1.1E−4 | 4.9E−4 | 3.7E−7 | 6.7E−5 | 2.8E−5 |
| Lower limit of 95% CI | 2.05 | 1.64 | 1.37 | 2.04 | 1.56 | 1.45 | 2.18 | 1.61 | 1.71 |
| Upper limit of 95% CI | 5.21 | 4.08 | 3.64 | 5.24 | 3.88 | 3.79 | 5.77 | 4.01 | 4.39 |
| OR Quartile 4 | 5.38 | 4.84 | 1.99 | 4.62 | 4.68 | 1.78 | 4.82 | 4.92 | 1.96 |
| p Value | 3.4E−7 | 5.4E−7 | 0.011 | 3.5E−6 | 9.4E−7 | 0.031 | 7.0E−6 | 7.4E−7 | 0.011 |
| Lower limit of 95% CI | 2.82 | 2.61 | 1.17 | 2.42 | 2.52 | 1.05 | 2.43 | 2.62 | 1.17 |
| Upper limit of 95% CI | 10.3 | 8.96 | 3.37 | 8.81 | 8.66 | 3.00 | 9.58 | 9.24 | 3.29 |

TABLE 14.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 16.8 | 37.0 | 16.5 | 36.9 | 16.5 | 36.9 |
| Average | 101 | 244 | 102 | 239 | 102 | 239 |
| Stdev | 672 | 896 | 677 | 886 | 677 | 886 |
| p (t-test) | | 0.11 | | 0.12 | | 0.12 |
| Min | 0.00110 | 0.00169 | 0.00110 | 0.00169 | 0.00110 | 0.00169 |
| Max | 9030 | 7570 | 9030 | 7570 | 9030 | 7570 |
| n (Patient) | 188 | 129 | 185 | 132 | 185 | 132 |
| sCr only | | | | | | |
| Median | 15.1 | 38.6 | 15.4 | 37.8 | 15.1 | 38.6 |
| Average | 36.5 | 284 | 36.8 | 280 | 35.9 | 279 |
| Stdev | 67.1 | 1080 | 67.5 | 1070 | 66.9 | 1070 |
| p (t-test) | | 0.0041 | | 0.0050 | | 0.0050 |
| Min | 0.00110 | 0.00167 | 0.00110 | 0.00167 | 0.00110 | 0.00167 |
| Max | 453 | 9030 | 453 | 9030 | 453 | 9030 |
| n (Patient) | 160 | 157 | 157 | 160 | 156 | 161 |
| UO only | | | | | | |
| Median | 18.2 | 39.1 | 18.5 | 37.0 | 18.1 | 37.9 |
| Average | 104 | 275 | 105 | 268 | 105 | 262 |
| Stdev | 643 | 985 | 647 | 972 | 652 | 959 |
| p (t-test) | | 0.065 | | 0.077 | | 0.086 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 211 | 104 | 208 | 107 | 205 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.68 | 0.64 | 0.65 | 0.67 | 0.63 | 0.65 | 0.68 | 0.64 |
| SE | 0.032 | 0.030 | 0.034 | 0.032 | 0.030 | 0.034 | 0.032 | 0.030 | 0.033 |
| p Value | 3.1E−6 | 1.5E−9 | 3.4E−5 | 2.5E−6 | 8.1E−9 | 6.6E−5 | 2.5E−6 | 2.3E−9 | 2.3E−5 |
| nCohort Recovered | 188 | 160 | 211 | 185 | 157 | 208 | 185 | 156 | 205 |
| nCohort Non-recovered | 129 | 157 | 104 | 132 | 160 | 107 | 132 | 161 | 110 |
| Cutoff Quartile 2 | 8.33 | 8.33 | 8.36 | 8.33 | 8.33 | 8.36 | 8.33 | 8.33 | 8.36 |

TABLE 14.5-continued

Comparison of marker levels and the area under the ROC curve (AUC) in urine samples for the "recovered"
and "non-recovered" cohorts where recovery starts within 168 hours after sample collection and renal status
is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 84% | 84% | 86% | 85% | 83% | 86% | 85% | 83% | 86% |
| Specificity | 31% | 34% | 30% | 32% | 33% | 31% | 32% | 33% | 31% |
| Cutoff Quartile 3 | 24.1 | 24.1 | 24.1 | 24.1 | 24.1 | 24.1 | 24.1 | 24.1 | 24.1 |
| Sensitivity | 63% | 62% | 63% | 63% | 62% | 63% | 63% | 62% | 64% |
| Specificity | 59% | 62% | 56% | 59% | 62% | 56% | 59% | 62% | 57% |
| Cutoff Quartile 4 | 60.9 | 60.9 | 61.8 | 60.9 | 60.9 | 61.8 | 60.9 | 60.9 | 61.8 |
| Sensitivity | 37% | 38% | 36% | 37% | 38% | 35% | 37% | 38% | 35% |
| Specificity | 83% | 87% | 80% | 83% | 87% | 80% | 83% | 88% | 80% |
| OR Quartile 2 | 2.49 | 2.69 | 2.58 | 2.62 | 2.44 | 2.73 | 2.62 | 2.48 | 2.87 |
| p Value | 0.0016 | 3.2E−4 | 0.0027 | 8.7E−4 | 9.9E−4 | 0.0015 | 8.7E−4 | 7.9E−4 | 8.4E−4 |
| Lower limit of 95% CI | 1.41 | 1.57 | 1.39 | 1.49 | 1.43 | 1.47 | 1.49 | 1.46 | 1.55 |
| Upper limit of 95% CI | 4.40 | 4.61 | 4.81 | 4.62 | 4.15 | 5.07 | 4.62 | 4.22 | 5.34 |
| OR Quartile 3 | 2.38 | 2.70 | 2.25 | 2.43 | 2.62 | 2.15 | 2.43 | 2.70 | 2.33 |
| p Value | 2.2E−4 | 1.9E−5 | 0.0010 | 1.5E−4 | 3.0E−5 | 0.0017 | 1.5E−4 | 1.9E−5 | 5.2E−4 |
| Lower limit of 95% CI | 1.50 | 1.71 | 1.39 | 1.54 | 1.67 | 1.34 | 1.54 | 1.71 | 1.44 |
| Upper limit of 95% CI | 3.77 | 4.24 | 3.64 | 3.84 | 4.13 | 3.47 | 3.84 | 4.24 | 3.75 |
| OR Quartile 4 | 2.89 | 3.98 | 2.22 | 2.93 | 4.11 | 2.09 | 2.93 | 4.40 | 2.11 |
| p Value | 6.7E−5 | 1.4E−6 | 0.0029 | 5.5E−5 | 1.1E−6 | 0.0057 | 5.5E−5 | 4.6E−7 | 0.0049 |
| Lower limit of 95% CI | 1.71 | 2.27 | 1.31 | 1.74 | 2.33 | 1.24 | 1.74 | 2.47 | 1.25 |
| Upper limit of 95% CI | 4.87 | 6.98 | 3.76 | 4.95 | 7.25 | 3.52 | 4.95 | 7.82 | 3.55 |

TABLE 14.6

Comparison of marker levels and the area under the ROC curve (AUC) in EDTA samples for the "recovered"
and "non-recovered" cohorts where recovery starts within 24 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3180 | 3320 | 3180 | 3320 | 3180 | 3300 |
| Average | 3270 | 3980 | 3200 | 3970 | 3220 | 3950 |
| Stdev | 1390 | 2560 | 1240 | 2540 | 1270 | 2530 |
| p (t-test) | | 0.050 | | 0.057 | | 0.079 |
| Min | 1080 | 863 | 1080 | 863 | 1080 | 863 |
| Max | 7920 | 19700 | 5620 | 19700 | 5620 | 19700 |
| n (Patient) | 52 | 275 | 42 | 285 | 38 | 289 |
| sCr only | | | | | | |
| Median | 3140 | 3320 | 3130 | 3330 | 3130 | 3320 |
| Average | 3340 | 4000 | 3240 | 4020 | 3280 | 4000 |
| Stdev | 1570 | 2590 | 1380 | 2610 | 1390 | 2600 |
| p (t-test) | | 0.046 | | 0.018 | | 0.035 |
| Min | 1080 | 863 | 1080 | 863 | 1080 | 863 |
| Max | 9820 | 19700 | 7920 | 19700 | 7920 | 19700 |
| n (Patient) | 69 | 257 | 67 | 259 | 63 | 263 |
| UO only | | | | | | |
| Median | 3010 | 3910 | 2980 | 3860 | 3030 | 3770 |
| Average | 3430 | 4530 | 3380 | 4430 | 3390 | 4320 |
| Stdev | 1930 | 2890 | 1940 | 2770 | 1990 | 2680 |
| p (t-test) | | 4.5E−5 | | 8.0E−5 | | 4.8E−4 |
| Min | 893 | 863 | 893 | 863 | 893 | 863 |
| Max | 19700 | 18800 | 19700 | 18800 | 19700 | 18800 |
| n (Patient) | 197 | 128 | 176 | 149 | 159 | 166 |

TABLE 14.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.56 | 0.62 | 0.56 | 0.57 | 0.62 | 0.56 | 0.56 | 0.61 |
| SE | 0.042 | 0.038 | 0.032 | 0.046 | 0.038 | 0.031 | 0.048 | 0.039 | 0.031 |
| p Value | 0.13 | 0.12 | 2.5E−4 | 0.16 | 0.062 | 1.5E−4 | 0.22 | 0.12 | 5.5E−4 |
| nCohort Recovered | 52 | 69 | 197 | 42 | 67 | 176 | 38 | 63 | 159 |
| nCohort Non-recovered | 275 | 257 | 128 | 285 | 259 | 149 | 289 | 263 | 166 |
| Cutoff Quartile 2 | 2320 | 2320 | 2330 | 2320 | 2320 | 2330 | 2320 | 2320 | 2330 |
| Sensitivity | 76% | 76% | 83% | 76% | 76% | 82% | 76% | 76% | 82% |
| Specificity | 33% | 30% | 30% | 33% | 31% | 31% | 32% | 30% | 32% |
| Cutoff Quartile 3 | 3280 | 3280 | 3280 | 3280 | 3280 | 3280 | 3280 | 3280 | 3280 |
| Sensitivity | 51% | 51% | 60% | 51% | 51% | 59% | 51% | 51% | 57% |
| Specificity | 52% | 52% | 56% | 52% | 54% | 57% | 53% | 54% | 57% |
| Cutoff Quartile 4 | 4720 | 4710 | 4720 | 4720 | 4710 | 4720 | 4720 | 4710 | 4720 |
| Sensitivity | 27% | 28% | 32% | 27% | 28% | 31% | 26% | 27% | 30% |
| Specificity | 85% | 84% | 79% | 86% | 85% | 80% | 84% | 84% | 79% |
| OR Quartile 2 | 1.57 | 1.41 | 2.06 | 1.60 | 1.48 | 2.00 | 1.44 | 1.37 | 2.14 |
| p Value | 0.17 | 0.26 | 0.010 | 0.19 | 0.19 | 0.0098 | 0.33 | 0.31 | 0.0039 |
| Lower limit of 95% CI | 0.825 | 0.781 | 1.19 | 0.795 | 0.821 | 1.18 | 0.692 | 0.746 | 1.28 |
| Upper limit of 95% CI | 2.98 | 2.53 | 3.57 | 3.20 | 2.67 | 3.38 | 3.01 | 2.52 | 3.59 |
| OR Quartile 3 | 1.10 | 1.12 | 1.95 | 1.12 | 1.21 | 1.94 | 1.13 | 1.22 | 1.70 |
| p Value | 0.74 | 0.68 | 0.0038 | 0.73 | 0.49 | 0.0033 | 0.72 | 0.48 | 0.017 |
| Lower limit of 95% CI | 0.610 | 0.656 | 1.24 | 0.587 | 0.704 | 1.25 | 0.576 | 0.702 | 1.10 |
| Upper limit of 95% CI | 2.00 | 1.90 | 3.06 | 2.15 | 2.07 | 3.02 | 2.23 | 2.11 | 2.64 |
| OR Quartile 4 | 2.02 | 2.01 | 1.79 | 2.18 | 2.19 | 1.74 | 1.90 | 2.00 | 1.60 |
| p Value | 0.084 | 0.050 | 0.024 | 0.090 | 0.034 | 0.032 | 0.17 | 0.062 | 0.070 |
| Lower limit of 95% CI | 0.911 | 0.999 | 1.08 | 0.884 | 1.06 | 1.05 | 0.766 | 0.965 | 0.962 |
| Upper limit of 95% CI | 4.50 | 4.05 | 2.97 | 5.38 | 4.53 | 2.88 | 4.73 | 4.14 | 2.66 |

TABLE 14.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3040 | 3390 | 3070 | 3350 | 3040 | 3390 |
| Average | 3300 | 4070 | 3330 | 4030 | 3290 | 4020 |
| Stdev | 1510 | 2660 | 1560 | 2610 | 1600 | 2580 |
| p (t-test) | 0.011 | | 0.026 | | 0.026 | |
| Min | 1080 | 863 | 1080 | 863 | 1080 | 863 |
| Max | 9100 | 19700 | 9100 | 19700 | 9100 | 19700 |
| n (Patient) | 87 | 240 | 76 | 251 | 69 | 258 |
| | sCr only | | | | | |
| Median | 3040 | 3390 | 3040 | 3440 | 2980 | 3430 |
| Average | 3380 | 4090 | 3310 | 4110 | 3330 | 4090 |
| Stdev | 1640 | 2680 | 1520 | 2700 | 1530 | 2680 |
| p (t-test) | 0.015 | | 0.0059 | | 0.011 | |
| Min | 1080 | 863 | 1080 | 863 | 1080 | 863 |
| Max | 9820 | 19700 | 9100 | 19700 | 9100 | 19700 |
| n (Patient) | 101 | 226 | 99 | 228 | 94 | 233 |

TABLE 14.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 3060 | 3890 | 3050 | 3720 | 3070 | 3720 |
| Average | 3520 | 4540 | 3510 | 4400 | 3490 | 4330 |
| Stdev | 2070 | 2880 | 2090 | 2760 | 2120 | 2670 |
| p (t-test) | | 2.9E-4 | | 0.0011 | | 0.0018 |
| Min | 893 | 863 | 893 | 863 | 893 | 863 |
| Max | 19700 | 18800 | 19700 | 18800 | 19700 | 18800 |
| n (Patient) | 217 | 108 | 198 | 127 | 181 | 144 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.57 | 0.61 | 0.57 | 0.58 | 0.60 | 0.58 | 0.57 | 0.60 |
| SE | 0.035 | 0.034 | 0.034 | 0.036 | 0.034 | 0.033 | 0.037 | 0.034 | 0.032 |
| p Value | 0.026 | 0.037 | 9.7E-4 | 0.055 | 0.019 | 0.0023 | 0.030 | 0.030 | 0.0019 |
| nCohort Recovered | 87 | 101 | 217 | 76 | 99 | 198 | 69 | 94 | 181 |
| nCohort Non-recovered | 240 | 226 | 108 | 251 | 228 | 127 | 258 | 233 | 144 |
| Cutoff Quartile 2 | 2320 | 2320 | 2330 | 2320 | 2320 | 2330 | 2320 | 2320 | 2330 |
| Sensitivity | 78% | 78% | 82% | 78% | 78% | 80% | 78% | 78% | 81% |
| Specificity | 33% | 32% | 29% | 34% | 32% | 28% | 35% | 32% | 30% |
| Cutoff Quartile 3 | 3280 | 3280 | 3280 | 3280 | 3280 | 3280 | 3280 | 3280 | 3280 |
| Sensitivity | 52% | 53% | 60% | 52% | 53% | 58% | 53% | 53% | 57% |
| Specificity | 56% | 55% | 55% | 57% | 57% | 55% | 59% | 57% | 55% |
| Cutoff Quartile 4 | 4720 | 4720 | 4720 | 4720 | 4720 | 4720 | 4720 | 4720 | 4720 |
| Sensitivity | 29% | 29% | 33% | 28% | 29% | 32% | 28% | 28% | 31% |
| Specificity | 85% | 83% | 79% | 84% | 84% | 79% | 84% | 83% | 80% |
| OR Quartile 2 | 1.76 | 1.63 | 1.87 | 1.81 | 1.70 | 1.61 | 1.84 | 1.63 | 1.84 |
| p Value | 0.039 | 0.067 | 0.033 | 0.037 | 0.048 | 0.082 | 0.038 | 0.071 | 0.023 |
| Lower limit of 95% CI | 1.03 | 0.967 | 1.05 | 1.03 | 1.01 | 0.942 | 1.03 | 0.958 | 1.09 |
| Upper limit of 95% CI | 3.03 | 2.76 | 3.33 | 3.17 | 2.87 | 2.75 | 3.27 | 2.78 | 3.12 |
| OR Quartile 3 | 1.43 | 1.38 | 1.84 | 1.42 | 1.47 | 1.71 | 1.63 | 1.54 | 1.63 |
| p Value | 0.16 | 0.18 | 0.011 | 0.18 | 0.11 | 0.020 | 0.075 | 0.082 | 0.029 |
| Lower limit of 95% CI | 0.870 | 0.864 | 1.15 | 0.848 | 0.916 | 1.09 | 0.952 | 0.947 | 1.05 |
| Upper limit of 95% CI | 2.33 | 2.22 | 2.93 | 2.39 | 2.37 | 2.68 | 2.80 | 2.49 | 2.54 |
| OR Quartile 4 | 2.30 | 1.99 | 1.86 | 2.06 | 2.11 | 1.83 | 2.00 | 1.93 | 1.77 |
| p Value | 0.012 | 0.023 | 0.018 | 0.036 | 0.016 | 0.020 | 0.052 | 0.035 | 0.027 |
| Lower limit of 95% CI | 1.20 | 1.10 | 1.11 | 1.05 | 1.15 | 1.10 | 0.994 | 1.05 | 1.07 |
| Upper limit of 95% CI | 4.41 | 3.62 | 3.11 | 4.05 | 3.88 | 3.03 | 4.03 | 3.54 | 2.93 |

TABLE 14.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3040 | 3470 | 3100 | 3450 | 2990 | 3470 |
| Average | 3390 | 4120 | 3430 | 4080 | 3390 | 4060 |
| Stdev | 1820 | 2650 | 1870 | 2620 | 1940 | 2580 |
| p (t-test) | | 0.0097 | | 0.024 | | 0.024 |

TABLE 14.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 1080 | 863 | 1080 | 863 | 1080 | 863 |
| Max | 14500 | 19700 | 14500 | 19700 | 14500 | 19700 |
| n (Patient) | 111 | 216 | 104 | 223 | 94 | 233 | sCr only

| | | | | | | |
|---|---|---|---|---|---|---|
| Median | 2990 | 3490 | 2950 | 3500 | 2930 | 3490 |
| Average | 3380 | 4170 | 3340 | 4180 | 3350 | 4160 |
| Stdev | 1880 | 2670 | 1800 | 2680 | 1820 | 2660 |
| p (t-test) | | 0.0046 | | 0.0023 | | 0.0037 |
| Min | 1080 | 863 | 1080 | 863 | 1080 | 863 |
| Max | 14500 | 19700 | 14500 | 19700 | 14500 | 19700 |
| n (Patient) | 124 | 203 | 121 | 206 | 116 | 211 |

UO only

| | | | | | | |
|---|---|---|---|---|---|---|
| Median | 3090 | 3710 | 3100 | 3700 | 3040 | 3770 |
| Average | 3540 | 4530 | 3550 | 4420 | 3480 | 4420 |
| Stdev | 2060 | 2910 | 2080 | 2830 | 2080 | 2740 |
| p (t-test) | | 4.8E-4 | | 0.0017 | | 5.5E-4 |
| Min | 893 | 863 | 893 | 863 | 893 | 863 |
| Max | 19700 | 18800 | 19700 | 18800 | 19700 | 18800 |
| n (Patient) | 219 | 106 | 208 | 117 | 193 | 132 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.59 | 0.60 | 0.57 | 0.60 | 0.59 | 0.58 | 0.60 | 0.61 |
| SE | 0.033 | 0.032 | 0.034 | 0.033 | 0.032 | 0.033 | 0.034 | 0.032 | 0.032 |
| p Value | 0.013 | 0.0032 | 0.0029 | 0.034 | 0.0020 | 0.0070 | 0.013 | 0.0028 | 8.2E-4 |
| nCohort Recovered | 111 | 124 | 219 | 104 | 121 | 208 | 94 | 116 | 193 |
| nCohort Non-recovered | 216 | 203 | 106 | 223 | 206 | 117 | 233 | 211 | 132 |
| Cutoff Quartile 2 | 2320 | 2320 | 2330 | 2320 | 2320 | 2330 | 2320 | 2320 | 2330 |
| Sensitivity | 79% | 80% | 83% | 78% | 80% | 81% | 79% | 80% | 82% |
| Specificity | 32% | 34% | 29% | 33% | 34% | 28% | 34% | 34% | 30% |
| Cutoff Quartile 3 | 3280 | 3280 | 3280 | 3280 | 3280 | 3280 | 3280 | 3280 | 3280 |
| Sensitivity | 53% | 54% | 58% | 52% | 54% | 56% | 54% | 55% | 58% |
| Specificity | 56% | 56% | 53% | 55% | 57% | 53% | 59% | 58% | 55% |
| Cutoff Quartile 4 | 4720 | 4720 | 4720 | 4720 | 4720 | 4720 | 4720 | 4720 | 4720 |
| Sensitivity | 29% | 30% | 31% | 28% | 30% | 30% | 27% | 29% | 31% |
| Specificity | 83% | 83% | 78% | 82% | 83% | 77% | 81% | 83% | 79% |
| OR Quartile 2 | 1.77 | 2.09 | 1.97 | 1.77 | 2.06 | 1.71 | 1.89 | 1.98 | 1.89 |
| p Value | 0.029 | 0.0045 | 0.023 | 0.031 | 0.0053 | 0.057 | 0.018 | 0.0088 | 0.021 |
| Lower limit of 95% CI | 1.06 | 1.26 | 1.10 | 1.05 | 1.24 | 0.983 | 1.11 | 1.19 | 1.10 |
| Upper limit of 95% CI | 2.97 | 3.47 | 3.55 | 2.98 | 3.43 | 2.97 | 3.21 | 3.30 | 3.24 |
| OR Quartile 3 | 1.44 | 1.53 | 1.55 | 1.34 | 1.58 | 1.48 | 1.63 | 1.64 | 1.65 |
| p Value | 0.12 | 0.063 | 0.064 | 0.22 | 0.047 | 0.091 | 0.047 | 0.034 | 0.027 |
| Lower limit of 95% CI | 0.909 | 0.978 | 0.974 | 0.839 | 1.01 | 0.939 | 1.01 | 1.04 | 1.06 |
| Upper limit of 95% CI | 2.28 | 2.40 | 2.48 | 2.14 | 2.49 | 2.34 | 2.65 | 2.59 | 2.58 |
| OR Quartile 4 | 1.99 | 2.11 | 1.57 | 1.76 | 2.17 | 1.46 | 1.60 | 2.00 | 1.67 |
| p Value | 0.019 | 0.0087 | 0.090 | 0.054 | 0.0070 | 0.15 | 0.12 | 0.017 | 0.046 |
| Lower limit of 95% CI | 1.12 | 1.21 | 0.933 | 0.990 | 1.24 | 0.876 | 0.887 | 1.13 | 1.01 |
| Upper limit of 95% CI | 3.54 | 3.68 | 2.64 | 3.14 | 3.82 | 2.44 | 2.88 | 3.52 | 2.77 |

TABLE 14.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3150 | 3430 | 3160 | 3350 | 3040 | 3470 |
| Average | 3450 | 4160 | 3500 | 4100 | 3430 | 4100 |
| Stdev | 1790 | 2750 | 1830 | 2710 | 1910 | 2640 |
| p (t-test) | | 0.0098 | | 0.028 | | 0.018 |
| Min | 1080 | 863 | 1080 | 863 | 1080 | 863 |
| Max | 14500 | 19700 | 14500 | 19700 | 14500 | 19700 |
| n (Patient) | 134 | 193 | 125 | 202 | 113 | 214 |
| sCr only | | | | | | |
| Median | 3130 | 3450 | 3130 | 3450 | 3110 | 3470 |
| Average | 3470 | 4170 | 3430 | 4190 | 3430 | 4170 |
| Stdev | 1860 | 2740 | 1790 | 2760 | 1800 | 2740 |
| p (t-test) | | 0.0099 | | 0.0054 | | 0.0061 |
| Min | 1080 | 863 | 1080 | 863 | 1080 | 863 |
| Max | 14500 | 19700 | 14500 | 19700 | 14500 | 19700 |
| n (Patient) | 139 | 188 | 137 | 190 | 133 | 194 |
| UO only | | | | | | |
| Median | 3080 | 3720 | 3090 | 3620 | 3020 | 3860 |
| Average | 3510 | 4600 | 3520 | 4480 | 3470 | 4470 |
| Stdev | 2030 | 2940 | 2050 | 2870 | 2070 | 2760 |
| p (t-test) | | 1.3E−4 | | 5.7E−4 | | 2.2E−4 |
| Min | 893 | 863 | 893 | 863 | 893 | 863 |
| Max | 19700 | 18800 | 19700 | 18800 | 19700 | 18800 |
| n (Patient) | 220 | 105 | 211 | 114 | 198 | 127 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.57 | 0.61 | 0.55 | 0.57 | 0.60 | 0.58 | 0.58 | 0.62 |
| SE | 0.032 | 0.032 | 0.034 | 0.032 | 0.032 | 0.033 | 0.033 | 0.032 | 0.032 |
| p Value | 0.044 | 0.026 | 0.0012 | 0.10 | 0.021 | 0.0034 | 0.016 | 0.017 | 2.9E−4 |
| nCohort Recovered | 134 | 139 | 220 | 125 | 137 | 211 | 113 | 133 | 198 |
| nCohort Non-recovered | 193 | 188 | 105 | 202 | 190 | 114 | 214 | 194 | 127 |
| Cutoff Quartile 2 | 2320 | 2320 | 2330 | 2320 | 2320 | 2330 | 2320 | 2320 | 2330 |
| Sensitivity | 78% | 79% | 84% | 78% | 79% | 83% | 79% | 79% | 83% |
| Specificity | 29% | 31% | 29% | 30% | 31% | 29% | 33% | 31% | 30% |
| Cutoff Quartile 3 | 3280 | 3280 | 3280 | 3280 | 3280 | 3280 | 3280 | 3280 | 3280 |
| Sensitivity | 52% | 52% | 57% | 51% | 52% | 56% | 54% | 53% | 58% |
| Specificity | 52% | 53% | 53% | 51% | 53% | 53% | 57% | 53% | 55% |
| Cutoff Quartile 4 | 4720 | 4720 | 4720 | 4720 | 4720 | 4720 | 4720 | 4720 | 4720 |
| Sensitivity | 30% | 30% | 32% | 28% | 30% | 31% | 28% | 29% | 31% |
| Specificity | 81% | 81% | 78% | 80% | 82% | 78% | 80% | 81% | 79% |
| OR Quartile 2 | 1.43 | 1.71 | 2.12 | 1.47 | 1.66 | 2.08 | 1.83 | 1.66 | 2.19 |
| p Value | 0.16 | 0.037 | 0.013 | 0.14 | 0.049 | 0.012 | 0.021 | 0.048 | 0.0057 |
| Lower limit of 95% CI | 0.865 | 1.03 | 1.17 | 0.883 | 1.00 | 1.17 | 1.10 | 1.00 | 1.26 |
| Upper limit of 95% CI | 2.37 | 2.83 | 3.85 | 2.44 | 2.74 | 3.70 | 3.05 | 2.75 | 3.83 |
| OR Quartile 3 | 1.18 | 1.20 | 1.51 | 1.09 | 1.21 | 1.45 | 1.52 | 1.27 | 1.71 |
| p Value | 0.47 | 0.41 | 0.082 | 0.70 | 0.41 | 0.11 | 0.075 | 0.29 | 0.020 |
| Lower limit of 95% CI | 0.757 | 0.776 | 0.948 | 0.699 | 0.776 | 0.916 | 0.959 | 0.816 | 1.09 |
| Upper limit of 95% CI | 1.83 | 1.87 | 2.42 | 1.71 | 1.87 | 2.29 | 2.40 | 1.98 | 2.68 |

TABLE 14.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.83 | 1.84 | 1.72 | 1.57 | 1.92 | 1.55 | 1.49 | 1.80 | 1.71 |
| p Value | 0.027 | 0.023 | 0.041 | 0.097 | 0.016 | 0.096 | 0.15 | 0.031 | 0.038 |
| Lower limit of 95% CI | 1.07 | 1.09 | 1.02 | 0.921 | 1.13 | 0.925 | 0.862 | 1.05 | 1.03 |
| Upper limit of 95% CI | 3.12 | 3.13 | 2.88 | 2.68 | 3.27 | 2.58 | 2.57 | 3.06 | 2.83 |

TABLE 14.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3090 | 3510 | 3080 | 3520 | 3070 | 3620 |
| Average | 3520 | 4330 | 3520 | 4320 | 3510 | 4320 |
| Stdev | 2090 | 2750 | 2110 | 2730 | 2110 | 2720 |
| p (t-test) | 0.0027 | | 0.0028 | | 0.0027 | |
| Min | 1080 | 863 | 1080 | 863 | 1080 | 863 |
| Max | 19700 | 18800 | 19700 | 18800 | 19700 | 18800 |
| n (Patient) | 187 | 140 | 184 | 143 | 183 | 144 |
| sCr only | | | | | | |
| Median | 3130 | 3450 | 3140 | 3430 | 3140 | 3430 |
| Average | 3520 | 4200 | 3520 | 4190 | 3530 | 4170 |
| Stdev | 1810 | 2860 | 1820 | 2840 | 1820 | 2830 |
| p (t-test) | 0.010 | | 0.012 | | 0.016 | |
| Min | 1080 | 863 | 1080 | 863 | 1080 | 863 |
| Max | 14500 | 19700 | 14500 | 19700 | 14500 | 19700 |
| n (Patient) | 159 | 168 | 156 | 171 | 154 | 173 |
| UO only | | | | | | |
| Median | 3040 | 3790 | 3040 | 3720 | 3010 | 3890 |
| Average | 3480 | 4600 | 3480 | 4590 | 3440 | 4620 |
| Stdev | 2030 | 2890 | 2040 | 2860 | 2030 | 2840 |
| p (t-test) | 6.4E-5 | | 6.5E-5 | | 1.9E-5 | |
| Min | 893 | 863 | 893 | 863 | 893 | 863 |
| Max | 19700 | 18800 | 19700 | 18800 | 19700 | 18800 |
| n (Patient) | 215 | 110 | 212 | 113 | 209 | 116 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.56 | 0.62 | 0.59 | 0.56 | 0.62 | 0.59 | 0.55 | 0.63 |
| SE | 0.032 | 0.032 | 0.034 | 0.032 | 0.032 | 0.033 | 0.032 | 0.032 | 0.033 |
| p Value | 0.0081 | 0.071 | 3.9E-4 | 0.0063 | 0.072 | 2.7E-4 | 0.0052 | 0.094 | 4.6E-5 |
| nCohort Recovered | 187 | 159 | 215 | 184 | 156 | 212 | 183 | 154 | 209 |
| nCohort Non-recovered | 140 | 168 | 110 | 143 | 171 | 113 | 144 | 173 | 116 |
| Cutoff Quartile 2 | 2320 | 2320 | 2330 | 2320 | 2320 | 2330 | 2320 | 2320 | 2330 |
| Sensitivity | 81% | 79% | 85% | 82% | 79% | 85% | 82% | 79% | 85% |
| Specificity | 30% | 30% | 30% | 30% | 29% | 30% | 31% | 29% | 31% |
| Cutoff Quartile 3 | 3280 | 3280 | 3280 | 3280 | 3280 | 3280 | 3280 | 3280 | 3280 |
| Sensitivity | 55% | 52% | 57% | 55% | 52% | 58% | 56% | 52% | 59% |
| Specificity | 53% | 52% | 53% | 54% | 52% | 54% | 54% | 52% | 55% |
| Cutoff Quartile 4 | 4720 | 4720 | 4720 | 4720 | 4720 | 4720 | 4720 | 4720 | 4720 |
| Sensitivity | 31% | 29% | 32% | 31% | 29% | 32% | 31% | 29% | 34% |
| Specificity | 79% | 79% | 78% | 79% | 79% | 78% | 79% | 79% | 79% |
| OR Quartile 2 | 1.87 | 1.59 | 2.32 | 1.97 | 1.57 | 2.44 | 2.00 | 1.52 | 2.57 |
| p Value | 0.020 | 0.070 | 0.0055 | 0.012 | 0.080 | 0.0032 | 0.010 | 0.10 | 0.0018 |

TABLE 14.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| Lower limit of 95% CI | 1.10 | 0.963 | 1.28 | 1.16 | 0.948 | 1.35 | 1.18 | 0.918 | 1.42 |
| --- | --- | --- | --- | --- | --- | --- | --- | --- | --- |
| Upper limit of 95% CI | 3.18 | 2.64 | 4.20 | 3.34 | 2.59 | 4.42 | 3.39 | 2.51 | 4.65 |
| OR Quartile 3 | 1.40 | 1.20 | 1.54 | 1.44 | 1.17 | 1.58 | 1.47 | 1.17 | 1.70 |
| p Value | 0.13 | 0.41 | 0.067 | 0.10 | 0.47 | 0.053 | 0.084 | 0.47 | 0.023 |
| Lower limit of 95% CI | 0.905 | 0.778 | 0.970 | 0.927 | 0.759 | 0.994 | 0.950 | 0.759 | 1.07 |
| Upper limit of 95% CI | 2.18 | 1.85 | 2.45 | 2.23 | 1.81 | 2.50 | 2.28 | 1.81 | 2.69 |
| OR Quartile 4 | 1.68 | 1.57 | 1.67 | 1.71 | 1.60 | 1.69 | 1.68 | 1.55 | 1.96 |
| p Value | 0.043 | 0.081 | 0.052 | 0.037 | 0.070 | 0.046 | 0.044 | 0.092 | 0.010 |
| Lower limit of 95% CI | 1.02 | 0.946 | 0.996 | 1.03 | 0.962 | 1.01 | 1.01 | 0.931 | 1.17 |
| Upper limit of 95% CI | 2.78 | 2.61 | 2.79 | 2.83 | 2.67 | 2.82 | 2.78 | 2.58 | 3.26 |

Example 15. Use of Metalloproteinase Inhibitor 4 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 15.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
| --- | --- | --- | --- | --- | --- | --- |
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 12.5 | 34.6 | 12.5 | 33.4 | 12.5 | 33.4 |
| Average | 27.4 | 227 | 26.4 | 224 | 26.5 | 221 |
| Stdev | 47.8 | 945 | 46.5 | 936 | 47.2 | 928 |
| p (t-test) | 0.029 | | 0.032 | | 0.038 | |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 108 | 209 | 104 | 213 | 100 | 217 |
| sCr only | | | | | | |
| Median | 13.3 | 34.9 | 13.3 | 34.9 | 13.3 | 34.9 |
| Average | 29.0 | 246 | 29.0 | 244 | 29.0 | 241 |
| Stdev | 46.7 | 989 | 47.0 | 984 | 47.3 | 979 |
| p (t-test) | 0.014 | | 0.016 | | 0.017 | |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 126 | 190 | 124 | 192 | 122 | 194 |

TABLE 15.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 18.5 | 39.3 | 18.1 | 39.3 | 18.1 | 36.7 |
| Average | 99.9 | 304 | 101 | 275 | 104 | 255 |
| Stdev | 623 | 1040 | 643 | 976 | 658 | 936 |
| p (t-test) | | 0.033 | | 0.059 | | 0.094 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 222 | 93 | 208 | 107 | 198 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.65 | 0.69 | 0.67 | 0.66 | 0.69 | 0.67 | 0.64 |
| SE | 0.030 | 0.030 | 0.035 | 0.030 | 0.030 | 0.033 | 0.030 | 0.030 | 0.033 |
| p Value | 4.8E−10 | 3.2E−8 | 2.2E−5 | 4.2E−10 | 3.7E−8 | 3.5E−6 | 6.4E−10 | 2.9E−8 | 3.6E−5 |
| nCohort Recovered | 108 | 126 | 222 | 104 | 124 | 208 | 100 | 122 | 198 |
| nCohort Non-recovered | 209 | 190 | 93 | 213 | 192 | 107 | 217 | 194 | 117 |
| Cutoff Quartile 2 | 8.33 | 8.31 | 8.36 | 8.33 | 8.31 | 8.36 | 8.33 | 8.31 | 8.36 |
| Sensitivity | 82% | 81% | 86% | 82% | 81% | 86% | 82% | 81% | 84% |
| Specificity | 39% | 33% | 30% | 39% | 34% | 31% | 40% | 34% | 30% |
| Cutoff Quartile 3 | 24.1 | 23.6 | 24.1 | 24.1 | 23.6 | 24.1 | 24.1 | 23.6 | 24.1 |
| Sensitivity | 58% | 58% | 65% | 58% | 58% | 64% | 58% | 58% | 61% |
| Specificity | 66% | 63% | 56% | 66% | 63% | 57% | 67% | 63% | 56% |
| Cutoff Quartile 4 | 60.9 | 60.8 | 61.8 | 60.9 | 60.8 | 61.8 | 60.9 | 60.8 | 61.8 |
| Sensitivity | 33% | 35% | 39% | 33% | 35% | 37% | 33% | 35% | 36% |
| Specificity | 91% | 90% | 81% | 91% | 90% | 81% | 91% | 90% | 81% |
| OR Quartile 2 | 2.96 | 2.07 | 2.60 | 3.00 | 2.15 | 2.73 | 3.04 | 2.23 | 2.24 |
| p Value | 5.2E−5 | 0.0058 | 0.0041 | 4.5E−5 | 0.0038 | 0.0015 | 3.8E−5 | 0.0024 | 0.0061 |
| Lower limit of 95% CI | 1.75 | 1.23 | 1.36 | 1.77 | 1.28 | 1.47 | 1.79 | 1.33 | 1.26 |
| Upper limit of 95% CI | 5.00 | 3.46 | 5.00 | 5.08 | 3.60 | 5.07 | 5.17 | 3.74 | 3.99 |
| OR Quartile 3 | 2.69 | 2.36 | 2.30 | 2.75 | 2.37 | 2.29 | 2.81 | 2.39 | 1.97 |
| p Value | 6.0E−5 | 2.7E−4 | 0.0011 | 5.2E−5 | 2.6E−4 | 7.3E−4 | 4.5E−5 | 2.5E−4 | 0.0043 |
| Lower limit of 95% CI | 1.66 | 1.49 | 1.39 | 1.68 | 1.49 | 1.41 | 1.71 | 1.50 | 1.24 |
| Upper limit of 95% CI | 4.36 | 3.75 | 3.80 | 4.48 | 3.77 | 3.69 | 4.62 | 3.80 | 3.14 |
| OR Quartile 4 | 4.94 | 5.17 | 2.63 | 5.28 | 5.00 | 2.59 | 4.92 | 4.84 | 2.44 |
| p Value | 1.1E−5 | 1.3E−6 | 3.9E−4 | 1.1E−5 | 2.1E−6 | 3.8E−4 | 2.5E−5 | 3.4E−6 | 7.9E−4 |
| Lower limit of 95% CI | 2.42 | 2.66 | 1.54 | 2.52 | 2.57 | 1.53 | 2.34 | 2.49 | 1.45 |
| Upper limit of 95% CI | 10.1 | 10.1 | 4.48 | 11.1 | 9.73 | 4.37 | 10.3 | 9.41 | 4.10 |

TABLE 15.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 13.3 | 36.5 | 13.3 | 33.4 | 13.3 | 33.4 |
| Average | 29.4 | 257 | 29.6 | 254 | 28.6 | 249 |
| Stdev | 47.4 | 1010 | 47.7 | 1010 | 46.7 | 994 |

TABLE 15.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.0093 | | 0.010 | | 0.012 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 136 | 181 | 134 | 183 | 129 | 188 | sCr only

| | | | | | | |
|---|---|---|---|---|---|---|
| Median | 15.4 | 36.9 | 15.9 | 36.7 | 15.9 | 36.7 |
| Average | 30.5 | 274 | 30.7 | 272 | 30.6 | 269 |
| Stdev | 47.1 | 1050 | 47.2 | 1050 | 47.4 | 1040 |
| p (t-test) | | 0.0050 | | 0.0054 | | 0.0060 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 149 | 168 | 148 | 169 | 146 | 171 |

UO only

| | | | | | | |
|---|---|---|---|---|---|---|
| Median | 18.2 | 39.3 | 18.2 | 38.8 | 18.1 | 33.4 |
| Average | 107 | 297 | 108 | 282 | 111 | 254 |
| Stdev | 625 | 1060 | 633 | 1030 | 653 | 964 |
| p (t-test) | | 0.050 | | 0.067 | | 0.12 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 226 | 89 | 220 | 95 | 207 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.67 | 0.65 | 0.68 | 0.67 | 0.64 | 0.68 | 0.67 | 0.63 |
| SE | 0.030 | 0.030 | 0.036 | 0.030 | 0.030 | 0.035 | 0.030 | 0.030 | 0.034 |
| p Value | 1.0E−9 | 1.6E−8 | 4.7E−5 | 1.5E−9 | 3.0E−8 | 7.1E−5 | 7.1E−10 | 2.7E−8 | 1.7E−4 |
| nCohort Recovered | 136 | 149 | 226 | 134 | 148 | 220 | 129 | 146 | 207 |
| nCohort Non-recovered | 181 | 168 | 89 | 183 | 169 | 95 | 188 | 171 | 108 |
| Cutoff Quartile 2 | 8.33 | 8.33 | 8.36 | 8.33 | 8.33 | 8.36 | 8.33 | 8.33 | 8.36 |
| Sensitivity | 83% | 82% | 88% | 84% | 82% | 87% | 84% | 82% | 86% |
| Specificity | 36% | 32% | 30% | 37% | 32% | 30% | 37% | 33% | 31% |
| Cutoff Quartile 3 | 24.1 | 24.1 | 24.1 | 24.1 | 24.1 | 24.1 | 24.1 | 24.1 | 24.1 |
| Sensitivity | 60% | 60% | 65% | 60% | 59% | 63% | 60% | 59% | 61% |
| Specificity | 62% | 60% | 56% | 63% | 60% | 55% | 64% | 60% | 56% |
| Cutoff Quartile 4 | 60.9 | 60.9 | 61.8 | 60.9 | 60.9 | 61.8 | 60.9 | 60.9 | 61.8 |
| Sensitivity | 36% | 38% | 36% | 36% | 38% | 35% | 36% | 37% | 33% |
| Specificity | 90% | 89% | 79% | 90% | 89% | 79% | 90% | 89% | 79% |
| OR Quartile 2 | 2.83 | 2.10 | 3.05 | 2.94 | 2.14 | 3.03 | 3.00 | 2.21 | 2.77 |
| p Value | 1.0E−4 | 0.0051 | 0.0016 | 5.9E−5 | 0.0042 | 0.0012 | 4.1E−5 | 0.0028 | 0.0013 |
| Lower limit of 95% CI | 1.68 | 1.25 | 1.53 | 1.74 | 1.27 | 1.55 | 1.77 | 1.31 | 1.49 |
| Upper limit of 95% CI | 4.79 | 3.53 | 6.10 | 4.98 | 3.59 | 5.92 | 5.07 | 3.72 | 5.16 |
| OR Quartile 3 | 2.47 | 2.24 | 2.36 | 2.47 | 2.19 | 2.13 | 2.57 | 2.19 | 1.96 |
| p Value | 1.1E−4 | 4.4E−4 | 9.6E−4 | 1.1E−4 | 6.5E−4 | 0.0027 | 6.2E−5 | 6.5E−4 | 0.0053 |
| Lower limit of 95% CI | 1.56 | 1.43 | 1.42 | 1.57 | 1.39 | 1.30 | 1.62 | 1.40 | 1.22 |
| Upper limit of 95% CI | 3.89 | 3.52 | 3.92 | 3.91 | 3.43 | 3.50 | 4.08 | 3.43 | 3.16 |
| OR Quartile 4 | 5.00 | 5.12 | 2.14 | 4.84 | 5.03 | 2.01 | 4.94 | 4.86 | 1.91 |
| p Value | 5.6E−7 | 1.2E−7 | 0.0057 | 9.6E−7 | 1.7E−7 | 0.010 | 1.3E−6 | 3.0E−7 | 0.015 |
| Lower limit of 95% CI | 2.66 | 2.79 | 1.25 | 2.57 | 2.75 | 1.18 | 2.59 | 2.65 | 1.13 |
| Upper limit of 95% CI | 9.39 | 9.37 | 3.67 | 9.08 | 9.21 | 3.43 | 9.43 | 8.90 | 3.22 |

TABLE 15.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 13.0 | 38.8 | 13.0 | 37.0 | 13.0 | 37.0 |
| Average | 31.8 | 280 | 32.0 | 277 | 31.4 | 271 |
| Stdev | 53.3 | 1060 | 53.6 | 1060 | 52.9 | 1050 |
| p (t-test) | | 0.0041 | | 0.0047 | | 0.0056 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 154 | 163 | 152 | 165 | 148 | 169 |
| sCr only | | | | | | |
| Median | 14.3 | 38.2 | 14.5 | 37.0 | 14.7 | 37.0 |
| Average | 32.2 | 290 | 32.4 | 289 | 32.5 | 287 |
| Stdev | 52.3 | 1090 | 52.4 | 1080 | 52.6 | 1080 |
| p (t-test) | | 0.0028 | | 0.0030 | | 0.0032 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 161 | 156 | 160 | 157 | 159 | 158 |
| UO only | | | | | | |
| Median | 18.1 | 38.8 | 18.2 | 37.8 | 18.1 | 33.4 |
| Average | 109 | 286 | 110 | 283 | 112 | 259 |
| Stdev | 628 | 1050 | 629 | 1040 | 645 | 986 |
| p (t-test) | | 0.066 | | 0.071 | | 0.11 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 224 | 91 | 223 | 92 | 212 | 103 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.63 | 0.69 | 0.68 | 0.62 | 0.69 | 0.68 | 0.62 |
| SE | 0.029 | 0.030 | 0.036 | 0.029 | 0.030 | 0.036 | 0.029 | 0.030 | 0.034 |
| p Value | 3.0E−11 | 7.2E−10 | 3.1E−4 | 9.6E−11 | 1.5E−9 | 5.7E−4 | 1.0E−10 | 2.7E−9 | 6.4E−4 |
| nCohort Recovered | 154 | 161 | 224 | 152 | 160 | 223 | 148 | 159 | 212 |
| nCohort Non-recovered | 163 | 156 | 91 | 165 | 157 | 92 | 169 | 158 | 103 |
| Cutoff Quartile 2 | 8.33 | 8.33 | 8.36 | 8.33 | 8.33 | 8.36 | 8.33 | 8.33 | 8.36 |
| Sensitivity | 85% | 83% | 87% | 85% | 83% | 86% | 85% | 84% | 84% |
| Specificity | 35% | 33% | 30% | 36% | 33% | 30% | 36% | 33% | 30% |
| Cutoff Quartile 3 | 24.1 | 24.1 | 24.1 | 24.1 | 24.1 | 24.1 | 24.1 | 24.1 | 24.1 |
| Sensitivity | 63% | 62% | 64% | 62% | 62% | 63% | 62% | 61% | 62% |
| Specificity | 64% | 61% | 55% | 63% | 61% | 55% | 64% | 61% | 56% |
| Cutoff Quartile 4 | 60.9 | 60.9 | 61.8 | 60.9 | 60.9 | 61.8 | 60.9 | 60.9 | 61.8 |
| Sensitivity | 37% | 38% | 33% | 37% | 38% | 33% | 37% | 38% | 32% |
| Specificity | 88% | 88% | 78% | 88% | 88% | 78% | 88% | 87% | 78% |
| OR Quartile 2 | 2.98 | 2.45 | 2.81 | 3.09 | 2.50 | 2.55 | 3.07 | 2.54 | 2.30 |
| p Value | 7.2E−5 | 9.9E−4 | 0.0026 | 4.3E−5 | 7.9E−4 | 0.0049 | 4.2E−5 | 6.3E−4 | 0.0074 |
| Lower limit of 95% CI | 1.74 | 1.44 | 1.44 | 1.80 | 1.46 | 1.33 | 1.79 | 1.49 | 1.25 |
| Upper limit of 95% CI | 5.11 | 4.19 | 5.50 | 5.29 | 4.26 | 4.91 | 5.25 | 4.33 | 4.23 |
| OR Quartile 3 | 3.00 | 2.63 | 2.18 | 2.85 | 2.56 | 2.10 | 2.86 | 2.49 | 2.06 |
| p Value | 2.4E−6 | 3.0E−5 | 0.0024 | 6.8E−6 | 4.8E−5 | 0.0036 | 6.7E−6 | 7.7E−5 | 0.0033 |
| Lower limit of 95% CI | 1.90 | 1.67 | 1.32 | 1.81 | 1.63 | 1.27 | 1.81 | 1.58 | 1.27 |
| Upper limit of 95% CI | 4.75 | 4.13 | 3.60 | 4.49 | 4.02 | 3.46 | 4.51 | 3.91 | 3.33 |

TABLE 15.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 4.25 | 4.41 | 1.76 | 4.11 | 4.33 | 1.72 | 4.18 | 4.26 | 1.70 |
| p Value | 8.4E−7 | 3.2E−7 | 0.041 | 1.5E−6 | 4.3E−7 | 0.049 | 1.5E−6 | 5.9E−7 | 0.048 |
| Lower limit of 95% CI | 2.39 | 2.50 | 1.02 | 2.31 | 2.45 | 1.00 | 2.33 | 2.41 | 1.00 |
| Upper limit of 95% CI | 7.56 | 7.78 | 3.01 | 7.30 | 7.64 | 2.95 | 7.50 | 7.51 | 2.88 |

TABLE 15.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 15.1 | 38.8 | 15.4 | 37.0 | 15.4 | 36.9 |
| Average | 36.0 | 298 | 36.4 | 293 | 35.9 | 287 |
| Stdev | 62.4 | 1110 | 62.9 | 1100 | 62.7 | 1090 |
| p (t-test) | | 0.0024 | | 0.0030 | | 0.0037 |
| Min | 0.00110 | 0.00167 | 0.00110 | 0.00167 | 0.00110 | 0.00167 |
| Max | 453 | 9030 | 453 | 9030 | 453 | 9030 |
| n (Patient) | 168 | 149 | 165 | 152 | 161 | 156 |
| | sCr only | | | | | |
| Median | 15.9 | 37.0 | 16.3 | 37.0 | 16.3 | 37.0 |
| Average | 36.4 | 305 | 36.6 | 303 | 36.7 | 301 |
| Stdev | 61.8 | 1130 | 61.9 | 1120 | 62.1 | 1120 |
| p (t-test) | | 0.0019 | | 0.0021 | | 0.0023 |
| Min | 0.00110 | 0.00167 | 0.00110 | 0.00167 | 0.00110 | 0.00167 |
| Max | 453 | 9030 | 453 | 9030 | 453 | 9030 |
| n (Patient) | 172 | 145 | 171 | 146 | 170 | 147 |
| | UO only | | | | | |
| Median | 18.2 | 39.1 | 18.1 | 38.8 | 18.1 | 36.7 |
| Average | 108 | 286 | 109 | 283 | 111 | 265 |
| Stdev | 630 | 1040 | 631 | 1040 | 642 | 995 |
| p (t-test) | | 0.065 | | 0.069 | | 0.10 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 223 | 92 | 222 | 93 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.67 | 0.64 | 0.67 | 0.67 | 0.64 | 0.67 | 0.66 | 0.63 |
| SE | 0.030 | 0.031 | 0.035 | 0.030 | 0.031 | 0.035 | 0.030 | 0.031 | 0.035 |
| p Value | 2.6E−9 | 3.2E−8 | 1.1E−4 | 6.9E−9 | 5.9E−8 | 1.2E−4 | 8.2E−9 | 1.0E−7 | 1.9E−4 |
| nCohort Recovered | 168 | 172 | 223 | 165 | 171 | 222 | 161 | 170 | 214 |
| nCohort Non-recovered | 149 | 145 | 92 | 152 | 146 | 93 | 156 | 147 | 101 |
| Cutoff Quartile 2 | 8.33 | 8.33 | 8.36 | 8.33 | 8.33 | 8.36 | 8.33 | 8.33 | 8.36 |
| Sensitivity | 84% | 83% | 86% | 84% | 83% | 86% | 84% | 83% | 85% |
| Specificity | 33% | 31% | 30% | 33% | 32% | 30% | 34% | 32% | 30% |
| Cutoff Quartile 3 | 24.1 | 24.1 | 24.1 | 24.1 | 24.1 | 24.1 | 24.1 | 24.1 | 24.1 |
| Sensitivity | 63% | 62% | 64% | 62% | 62% | 65% | 62% | 61% | 63% |
| Specificity | 61% | 60% | 56% | 61% | 60% | 56% | 61% | 59% | 56% |
| Cutoff Quartile 4 | 60.9 | 60.9 | 61.8 | 60.9 | 60.9 | 61.8 | 60.9 | 60.9 | 61.8 |
| Sensitivity | 38% | 38% | 35% | 37% | 38% | 34% | 37% | 37% | 34% |
| Specificity | 86% | 85% | 79% | 85% | 85% | 79% | 86% | 85% | 79% |
| OR Quartile 2 | 2.54 | 2.20 | 2.55 | 2.67 | 2.23 | 2.60 | 2.64 | 2.27 | 2.45 |

TABLE 15.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 7.8E-4 | 0.0041 | 0.0049 | 4.0E-4 | 0.0034 | 0.0041 | 4.0E-4 | 0.0028 | 0.0048 |
| Lower limit of 95% CI | 1.47 | 1.28 | 1.33 | 1.55 | 1.30 | 1.36 | 1.54 | 1.33 | 1.31 |
| Upper limit of 95% CI | 4.36 | 3.76 | 4.91 | 4.59 | 3.83 | 5.00 | 4.53 | 3.89 | 4.55 |
| OR Quartile 3 | 2.71 | 2.44 | 2.24 | 2.63 | 2.38 | 2.30 | 2.63 | 2.31 | 2.21 |
| p Value | 1.8E-5 | 1.1E-4 | 0.0016 | 3.0E-5 | 1.8E-4 | 0.0011 | 3.0E-5 | 2.8E-4 | 0.0014 |
| Lower limit of 95% CI | 1.72 | 1.55 | 1.36 | 1.67 | 1.51 | 1.39 | 1.67 | 1.47 | 1.36 |
| Upper limit of 95% CI | 4.27 | 3.84 | 3.70 | 4.14 | 3.73 | 3.80 | 4.13 | 3.63 | 3.59 |
| OR Quartile 4 | 3.61 | 3.59 | 2.00 | 3.43 | 3.53 | 1.95 | 3.45 | 3.47 | 1.91 |
| p Value | 3.8E-6 | 3.5E-6 | 0.011 | 9.1E-6 | 4.8E-6 | 0.014 | 9.5E-6 | 6.4E-6 | 0.017 |
| Lower limit of 95% CI | 2.10 | 2.09 | 1.17 | 1.99 | 2.06 | 1.14 | 2.00 | 2.02 | 1.12 |
| Upper limit of 95% CI | 6.23 | 6.17 | 3.41 | 5.90 | 6.06 | 3.34 | 5.98 | 5.95 | 3.23 |

TABLE 15.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 18.1 | 36.9 | 18.1 | 36.3 | 18.1 | 35.9 |
| Average | 98.8 | 267 | 99.6 | 263 | 100 | 261 |
| Stdev | 646 | 951 | 650 | 943 | 651 | 939 |
| p (t-test) | | 0.063 | | 0.070 | | 0.074 |
| Min | 0.00110 | 0.00169 | 0.00110 | 0.00169 | 0.00110 | 0.00169 |
| Max | 9030 | 7570 | 9030 | 7570 | 9030 | 7570 |
| n (Patient) | 203 | 114 | 201 | 116 | 200 | 117 |
| | sCr only | | | | | |
| Median | 17.0 | 36.9 | 17.0 | 36.9 | 17.0 | 36.9 |
| Average | 41.1 | 325 | 41.1 | 325 | 41.1 | 325 |
| Stdev | 69.2 | 1180 | 69.2 | 1180 | 69.2 | 1180 |
| p (t-test) | | 0.0012 | | 0.0012 | | 0.0012 |
| Min | 0.00110 | 0.00169 | 0.00110 | 0.00169 | 0.00110 | 0.00169 |
| Max | 453 | 9030 | 453 | 9030 | 453 | 9030 |
| n (Patient) | 185 | 132 | 185 | 132 | 185 | 132 |
| | UO only | | | | | |
| Median | 18.8 | 37.9 | 18.5 | 37.0 | 19.1 | 36.7 |
| Average | 103 | 287 | 103 | 284 | 104 | 279 |
| Stdev | 634 | 1010 | 635 | 1010 | 638 | 999 |
| p (t-test) | | 0.051 | | 0.054 | | 0.061 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 217 | 98 | 216 | 99 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.65 | 0.63 | 0.63 | 0.65 | 0.63 | 0.62 | 0.65 | 0.63 |
| SE | 0.033 | 0.032 | 0.035 | 0.033 | 0.032 | 0.035 | 0.033 | 0.032 | 0.035 |
| p Value | 1.1E-4 | 2.2E-6 | 1.5E-4 | 1.4E-4 | 2.2E-6 | 1.5E-4 | 1.9E-4 | 2.2E-6 | 2.8E-4 |

TABLE 15.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Recovered | 203 | 185 | 217 | 201 | 185 | 216 | 200 | 185 | 214 |
| nCohort Non-recovered | 114 | 132 | 98 | 116 | 132 | 99 | 117 | 132 | 101 |
| Cutoff Quartile 2 | 8.33 | 8.33 | 8.36 | 8.33 | 8.33 | 8.36 | 8.33 | 8.33 | 8.36 |
| Sensitivity | 82% | 83% | 85% | 83% | 83% | 85% | 83% | 83% | 85% |
| Specificity | 29% | 30% | 29% | 29% | 30% | 30% | 30% | 30% | 30% |
| Cutoff Quartile 3 | 24.1 | 24.1 | 24.1 | 24.1 | 24.1 | 24.1 | 24.1 | 24.1 | 24.1 |
| Sensitivity | 63% | 62% | 63% | 63% | 62% | 64% | 62% | 62% | 62% |
| Specificity | 57% | 58% | 56% | 57% | 58% | 56% | 57% | 58% | 56% |
| Cutoff Quartile 4 | 60.9 | 60.9 | 61.8 | 60.9 | 60.9 | 61.8 | 60.9 | 60.9 | 61.8 |
| Sensitivity | 36% | 38% | 35% | 35% | 38% | 34% | 35% | 38% | 34% |
| Specificity | 81% | 84% | 79% | 81% | 84% | 79% | 80% | 84% | 79% |
| OR Quartile 2 | 1.93 | 2.06 | 2.31 | 1.99 | 2.06 | 2.36 | 2.03 | 2.06 | 2.45 |
| p Value | 0.024 | 0.0099 | 0.0082 | 0.017 | 0.0099 | 0.0069 | 0.015 | 0.0099 | 0.0048 |
| Lower limit of 95% CI | 1.09 | 1.19 | 1.24 | 1.13 | 1.19 | 1.27 | 1.15 | 1.19 | 1.31 |
| Upper limit of 95% CI | 3.40 | 3.56 | 4.31 | 3.52 | 3.56 | 4.39 | 3.59 | 3.56 | 4.55 |
| OR Quartile 3 | 2.29 | 2.30 | 2.17 | 2.27 | 2.30 | 2.23 | 2.20 | 2.30 | 2.08 |
| p Value | 5.9E−4 | 3.6E−4 | 0.0019 | 6.1E−4 | 3.6E−4 | 0.0013 | 9.5E−4 | 3.6E−4 | 0.0031 |
| Lower limit of 95% CI | 1.43 | 1.46 | 1.33 | 1.42 | 1.46 | 1.37 | 1.38 | 1.46 | 1.28 |
| Upper limit of 95% CI | 3.66 | 3.63 | 3.54 | 3.63 | 3.63 | 3.64 | 3.51 | 3.63 | 3.37 |
| OR Quartile 4 | 2.36 | 3.15 | 2.03 | 2.27 | 3.15 | 1.99 | 2.23 | 3.15 | 1.91 |
| p Value | 0.0011 | 1.9E−5 | 0.0088 | 0.0019 | 1.9E−5 | 0.011 | 0.0024 | 1.9E−5 | 0.017 |
| Lower limit of 95% CI | 1.41 | 1.86 | 1.20 | 1.35 | 1.86 | 1.17 | 1.33 | 1.86 | 1.12 |
| Upper limit of 95% CI | 3.96 | 5.33 | 3.45 | 3.81 | 5.33 | 3.37 | 3.73 | 5.33 | 3.23 |

TABLE 15.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 2870 | 3520 | 2850 | 3520 | 2870 | 3510 |
| Average | 3160 | 4200 | 3150 | 4200 | 3170 | 4170 |
| Stdev | 1580 | 2680 | 1550 | 2670 | 1570 | 2660 |
| p (t-test) | | 2.7E−4 | | 2.6E−4 | | 6.2E−4 |
| Min | 1080 | 863 | 1080 | 863 | 1080 | 863 |
| Max | 9100 | 19700 | 9100 | 19700 | 9100 | 19700 |
| n (Patient) | 105 | 222 | 102 | 225 | 98 | 229 |
| sCr only | | | | | | |
| Median | 2950 | 3510 | 2920 | 3510 | 2870 | 3510 |
| Average | 3290 | 4200 | 3260 | 4210 | 3200 | 4230 |
| Stdev | 1660 | 2730 | 1640 | 2720 | 1540 | 2740 |
| p (t-test) | | 0.0011 | | 5.7E−4 | | 1.9E−4 |
| Min | 1080 | 863 | 1080 | 863 | 1080 | 863 |
| Max | 9820 | 19700 | 9820 | 19700 | 9100 | 19700 |
| n (Patient) | 121 | 205 | 119 | 207 | 117 | 209 |
| UO only | | | | | | |
| Median | 3020 | 3940 | 3000 | 3940 | 3030 | 3910 |
| Average | 3470 | 4770 | 3410 | 4710 | 3410 | 4610 |
| Stdev | 1940 | 3070 | 1910 | 2980 | 1910 | 2920 |
| p (t-test) | | 5.8E−6 | | 3.0E−6 | | 1.1E−5 |
| Min | 893 | 863 | 893 | 863 | 893 | 863 |

TABLE 15.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Max | 19700 | | 18800 | 19700 | | 18800 | 19700 | | 18800 |
| n (Patient) | 226 | | 99 | 213 | | 112 | 202 | | 123 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.61 | 0.64 | 0.63 | 0.62 | 0.64 | 0.63 | 0.62 | 0.63 |
| SE | 0.032 | 0.032 | 0.034 | 0.032 | 0.031 | 0.033 | 0.032 | 0.031 | 0.032 |
| p Value | 2.8E-5 | 7.4E-4 | 5.9E-5 | 2.3E-5 | 2.4E-4 | 1.3E-5 | 9.2E-5 | 8.3E-5 | 5.6E-5 |
| nCohort Recovered | 105 | 121 | 226 | 102 | 119 | 213 | 98 | 117 | 202 |
| nCohort Non-recovered | 222 | 205 | 99 | 225 | 207 | 112 | 229 | 209 | 123 |
| Cutoff Quartile 2 | 2320 | 2320 | 2330 | 2320 | 2320 | 2330 | 2320 | 2320 | 2330 |
| Sensitivity | 82% | 81% | 85% | 81% | 81% | 86% | 81% | 81% | 84% |
| Specificity | 39% | 36% | 29% | 39% | 36% | 31% | 39% | 37% | 30% |
| Cutoff Quartile 3 | 3280 | 3280 | 3280 | 3280 | 3280 | 3280 | 3280 | 3280 | 3280 |
| Sensitivity | 55% | 55% | 65% | 56% | 55% | 64% | 55% | 56% | 61% |
| Specificity | 61% | 58% | 56% | 62% | 59% | 57% | 61% | 60% | 56% |
| Cutoff Quartile 4 | 4720 | 4710 | 4720 | 4720 | 4710 | 4720 | 4720 | 4710 | 4720 |
| Sensitivity | 30% | 31% | 35% | 30% | 31% | 35% | 30% | 31% | 34% |
| Specificity | 86% | 84% | 79% | 86% | 85% | 80% | 86% | 85% | 80% |
| OR Quartile 2 | 2.83 | 2.35 | 2.31 | 2.81 | 2.44 | 2.64 | 2.66 | 2.53 | 2.23 |
| p Value | 8.4E-5 | 0.0010 | 0.0081 | 9.8E-5 | 6.4E-4 | 0.0017 | 2.4E-4 | 3.8E-4 | 0.0055 |
| Lower limit of 95% CI | 1.68 | 1.41 | 1.24 | 1.67 | 1.46 | 1.44 | 1.58 | 1.52 | 1.27 |
| Upper limit of 95% CI | 4.75 | 3.91 | 4.29 | 4.73 | 4.06 | 4.82 | 4.49 | 4.23 | 3.92 |
| OR Quartile 3 | 1.94 | 1.65 | 2.35 | 2.02 | 1.75 | 2.41 | 1.93 | 1.86 | 2.02 |
| p Value | 0.0061 | 0.030 | 6.3E-4 | 0.0040 | 0.016 | 2.6E-4 | 0.0075 | 0.0082 | 0.0025 |
| Lower limit of 95% CI | 1.21 | 1.05 | 1.44 | 1.25 | 1.11 | 1.50 | 1.19 | 1.17 | 1.28 |
| Upper limit of 95% CI | 3.11 | 2.60 | 3.82 | 3.26 | 2.76 | 3.87 | 3.13 | 2.94 | 3.20 |
| OR Quartile 4 | 2.59 | 2.38 | 2.08 | 2.72 | 2.51 | 2.11 | 2.53 | 2.66 | 2.10 |
| p Value | 0.0025 | 0.0030 | 0.0059 | 0.0019 | 0.0019 | 0.0043 | 0.0040 | 0.0012 | 0.0042 |
| Lower limit of 95% CI | 1.40 | 1.34 | 1.24 | 1.45 | 1.40 | 1.26 | 1.35 | 1.47 | 1.26 |
| Upper limit of 95% CI | 4.81 | 4.22 | 3.51 | 5.12 | 4.49 | 3.53 | 4.77 | 4.80 | 3.49 |

TABLE 15.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 2930 | 3560 | 2920 | 3630 | 2980 | 3520 |
| Average | 3230 | 4310 | 3210 | 4320 | 3250 | 4270 |
| Stdev | 1540 | 2810 | 1520 | 2800 | 1530 | 2790 |
| p (t-test) | | 6.5E-5 | | 3.8E-5 | | 1.7E-4 |
| Min | 1080 | 863 | 1080 | 863 | 1080 | 863 |
| Max | 9100 | 19700 | 9100 | 19700 | 9100 | 19700 |
| n (Patient) | 134 | 193 | 133 | 194 | 128 | 199 |
| | sCr only | | | | | |
| Median | 2980 | 3520 | 2950 | 3540 | 2920 | 3540 |
| Average | 3310 | 4320 | 3290 | 4330 | 3240 | 4360 |
| Stdev | 1610 | 2850 | 1590 | 2850 | 1510 | 2860 |

TABLE 15.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | |
|---|---|---|---|---|---|---|---|
| p (t-test) | | 1.5E−4 | | 8.7E−5 | | 2.7E−5 | |
| Min | 1080 | 863 | 1080 | 863 | 1080 | 863 | |
| Max | 9820 | 19700 | 9820 | 19700 | 9100 | 19700 | |
| n (Patient) | 146 | 181 | 145 | 182 | 143 | 184 | |

UO only

| | | | | | | |
|---|---|---|---|---|---|---|
| Median | 3060 | 3890 | 3040 | 3930 | 3050 | 3920 |
| Average | 3530 | 4670 | 3500 | 4670 | 3460 | 4600 |
| Stdev | 2060 | 2970 | 2060 | 2910 | 2040 | 2840 |
| p (t-test) | | 9.7E−5 | | 5.0E−5 | | 3.9E−5 |
| Min | 893 | 863 | 893 | 863 | 893 | 863 |
| Max | 19700 | 18800 | 19700 | 18800 | 19700 | 18800 |
| n (Patient) | 231 | 94 | 225 | 100 | 210 | 115 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.62 | 0.61 | 0.62 | 0.63 | 0.62 | 0.63 | 0.61 | 0.62 | 0.63 |
| SE | 0.031 | 0.031 | 0.035 | 0.031 | 0.031 | 0.034 | 0.031 | 0.031 | 0.033 |
| p Value | 6.4E−5 | 2.9E−4 | 4.3E−4 | 2.8E−5 | 1.4E−4 | 1.1E−4 | 2.5E−4 | 5.3E−5 | 8.3E−5 |
| nCohort Recovered | 134 | 146 | 231 | 133 | 145 | 225 | 128 | 143 | 210 |
| nCohort Non-recovered | 193 | 181 | 94 | 194 | 182 | 100 | 199 | 184 | 115 |
| Cutoff Quartile 2 | 2320 | 2320 | 2330 | 2320 | 2320 | 2330 | 2320 | 2320 | 2330 |
| Sensitivity | 82% | 82% | 86% | 82% | 82% | 87% | 81% | 82% | 84% |
| Specificity | 35% | 34% | 29% | 35% | 34% | 30% | 34% | 34% | 30% |
| Cutoff Quartile 3 | 3280 | 3280 | 3280 | 3280 | 3280 | 3280 | 3280 | 3280 | 3280 |
| Sensitivity | 56% | 56% | 62% | 56% | 56% | 62% | 55% | 57% | 60% |
| Specificity | 58% | 57% | 55% | 59% | 57% | 55% | 58% | 58% | 55% |
| Cutoff Quartile 4 | 4720 | 4720 | 4720 | 4720 | 4720 | 4720 | 4720 | 4720 | 4720 |
| Sensitivity | 32% | 32% | 33% | 32% | 32% | 34% | 31% | 33% | 35% |
| Specificity | 84% | 84% | 78% | 85% | 84% | 79% | 84% | 85% | 80% |
| OR Quartile 2 | 2.44 | 2.27 | 2.60 | 2.48 | 2.30 | 2.90 | 2.22 | 2.39 | 2.31 |
| p Value | 6.1E−4 | 0.0017 | 0.0040 | 4.8E−4 | 0.0013 | 0.0013 | 0.0021 | 8.6E−4 | 0.0049 |
| Lower limit of 95% CI | 1.46 | 1.36 | 1.36 | 1.49 | 1.38 | 1.52 | 1.34 | 1.43 | 1.29 |
| Upper limit of 95% CI | 4.06 | 3.77 | 4.98 | 4.14 | 3.84 | 5.54 | 3.69 | 3.98 | 4.14 |
| OR Quartile 3 | 1.77 | 1.66 | 1.93 | 1.82 | 1.71 | 2.00 | 1.69 | 1.80 | 1.85 |
| p Value | 0.012 | 0.023 | 0.0084 | 0.0087 | 0.017 | 0.0047 | 0.021 | 0.0092 | 0.0089 |
| Lower limit of 95% CI | 1.13 | 1.07 | 1.18 | 1.16 | 1.10 | 1.24 | 1.08 | 1.16 | 1.17 |
| Upper limit of 95% CI | 2.76 | 2.58 | 3.16 | 2.84 | 2.65 | 3.24 | 2.65 | 2.80 | 2.94 |
| OR Quartile 4 | 2.49 | 2.40 | 1.74 | 2.65 | 2.54 | 1.90 | 2.44 | 2.66 | 2.13 |
| p Value | 0.0013 | 0.0014 | 0.041 | 6.8E−4 | 7.5E−4 | 0.016 | 0.0019 | 4.7E−4 | 0.0037 |
| Lower limit of 95% CI | 1.43 | 1.40 | 1.02 | 1.51 | 1.48 | 1.13 | 1.39 | 1.54 | 1.28 |
| Upper limit of 95% CI | 4.34 | 4.10 | 2.95 | 4.66 | 4.38 | 3.20 | 4.29 | 4.61 | 3.56 |

TABLE 15.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3100 | 3490 | 3080 | 3510 | 3120 | 3470 |
| Average | 3460 | 4230 | 3430 | 4250 | 3470 | 4200 |
| Stdev | 1830 | 2810 | 1810 | 2800 | 1820 | 2790 |
| p (t-test) | | 0.0042 | | 0.0021 | | 0.0060 |
| Min | 1080 | 863 | 1080 | 863 | 1080 | 863 |
| Max | 14500 | 19700 | 14500 | 19700 | 14500 | 19700 |
| n (Patient) | 154 | 173 | 152 | 175 | 148 | 179 |
| sCr only | | | | | | |
| Median | 3110 | 3480 | 3100 | 3490 | 3090 | 3500 |
| Average | 3500 | 4230 | 3480 | 4240 | 3440 | 4280 |
| Stdev | 1870 | 2830 | 1860 | 2820 | 1790 | 2850 |
| p (t-test) | | 0.0060 | | 0.0042 | | 0.0017 |
| Min | 1080 | 863 | 1080 | 863 | 1080 | 863 |
| Max | 14500 | 19700 | 14500 | 19700 | 14500 | 19700 |
| n (Patient) | 161 | 166 | 160 | 167 | 159 | 168 |
| UO only | | | | | | |
| Median | 3080 | 3720 | 3050 | 3720 | 3070 | 3720 |
| Average | 3540 | 4640 | 3520 | 4670 | 3490 | 4580 |
| Stdev | 2050 | 2980 | 2040 | 2970 | 2040 | 2890 |
| p (t-test) | | 1.7E−4 | | 6.3E−5 | | 1.1E−4 |
| Min | 893 | 863 | 893 | 863 | 893 | 863 |
| Max | 19700 | 18800 | 19700 | 18800 | 19700 | 18800 |
| n (Patient) | 230 | 95 | 228 | 97 | 215 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.57 | 0.61 | 0.59 | 0.58 | 0.62 | 0.57 | 0.58 | 0.62 |
| SE | 0.031 | 0.032 | 0.035 | 0.031 | 0.031 | 0.035 | 0.032 | 0.031 | 0.034 |
| p Value | 0.015 | 0.020 | 0.0012 | 0.0062 | 0.013 | 3.8E−4 | 0.022 | 0.0075 | 4.7E−4 |
| nCohort Recovered | 154 | 161 | 230 | 152 | 160 | 228 | 148 | 159 | 215 |
| nCohort Non-recovered | 173 | 166 | 95 | 175 | 167 | 97 | 179 | 168 | 110 |
| Cutoff Quartile 2 | 2320 | 2320 | 2330 | 2320 | 2320 | 2330 | 2320 | 2320 | 2330 |
| Sensitivity | 80% | 81% | 85% | 81% | 81% | 86% | 80% | 81% | 85% |
| Specificity | 31% | 31% | 29% | 32% | 31% | 29% | 31% | 31% | 30% |
| Cutoff Quartile 3 | 3280 | 3280 | 3280 | 3280 | 3280 | 3280 | 3280 | 3280 | 3280 |
| Sensitivity | 53% | 53% | 59% | 54% | 53% | 60% | 53% | 54% | 58% |
| Specificity | 53% | 53% | 53% | 54% | 53% | 54% | 53% | 53% | 54% |
| Cutoff Quartile 4 | 4720 | 4720 | 4720 | 4720 | 4720 | 4720 | 4720 | 4720 | 4720 |
| Sensitivity | 29% | 30% | 32% | 30% | 30% | 33% | 29% | 30% | 33% |
| Specificity | 79% | 80% | 77% | 80% | 80% | 78% | 80% | 81% | 79% |
| OR Quartile 2 | 1.85 | 1.89 | 2.38 | 1.91 | 1.92 | 2.47 | 1.79 | 1.95 | 2.32 |
| p Value | 0.017 | 0.015 | 0.0075 | 0.012 | 0.012 | 0.0052 | 0.024 | 0.010 | 0.0055 |
| Lower limit of 95% CI | 1.12 | 1.13 | 1.26 | 1.15 | 1.15 | 1.31 | 1.08 | 1.17 | 1.28 |
| Upper limit of 95% CI | 3.07 | 3.14 | 4.49 | 3.18 | 3.19 | 4.65 | 2.97 | 3.25 | 4.20 |
| OR Quartile 3 | 1.29 | 1.26 | 1.65 | 1.36 | 1.29 | 1.74 | 1.23 | 1.33 | 1.63 |
| p Value | 0.25 | 0.29 | 0.042 | 0.17 | 0.25 | 0.024 | 0.35 | 0.20 | 0.039 |
| Lower limit of 95% CI | 0.837 | 0.817 | 1.02 | 0.879 | 0.837 | 1.08 | 0.797 | 0.858 | 1.02 |
| Upper limit of 95% CI | 2.00 | 1.95 | 2.68 | 2.10 | 2.00 | 2.82 | 1.91 | 2.05 | 2.59 |

TABLE 15.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.55 | 1.62 | 1.58 | 1.72 | 1.71 | 1.75 | 1.61 | 1.80 | 1.79 |
| p Value | 0.092 | 0.061 | 0.092 | 0.039 | 0.039 | 0.037 | 0.069 | 0.024 | 0.027 |
| Lower limit of 95% CI | 0.931 | 0.978 | 0.928 | 1.03 | 1.03 | 1.03 | 0.963 | 1.08 | 1.07 |
| Upper limit of 95% CI | 2.58 | 2.70 | 2.69 | 2.88 | 2.85 | 2.97 | 2.69 | 3.00 | 2.99 |

TABLE 15.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3080 | 3510 | 3040 | 3520 | 3090 | 3500 |
| Average | 3460 | 4290 | 3430 | 4310 | 3460 | 4250 |
| Stdev | 1790 | 2890 | 1780 | 2870 | 1790 | 2850 |
| p (t-test) | | 0.0020 | | 9.9E−4 | | 0.0030 |
| Min | 1080 | 863 | 1080 | 863 | 1080 | 863 |
| Max | 14500 | 19700 | 14500 | 19700 | 14500 | 19700 |
| n (Patient) | 166 | 161 | 163 | 164 | 159 | 168 |
| | sCr only | | | | | |
| Median | 3110 | 3500 | 3100 | 3510 | 3090 | 3510 |
| Average | 3510 | 4250 | 3490 | 4270 | 3460 | 4300 |
| Stdev | 1850 | 2880 | 1840 | 2880 | 1780 | 2900 |
| p (t-test) | | 0.0056 | | 0.0038 | | 0.0015 |
| Min | 1080 | 863 | 1080 | 863 | 1080 | 863 |
| Max | 14500 | 19700 | 14500 | 19700 | 14500 | 19700 |
| n (Patient) | 169 | 158 | 168 | 159 | 167 | 160 |
| | UO only | | | | | |
| Median | 3050 | 3860 | 3040 | 3790 | 3070 | 3720 |
| Average | 3500 | 4690 | 3500 | 4680 | 3500 | 4590 |
| Stdev | 2020 | 2980 | 2030 | 2960 | 2040 | 2910 |
| p (t-test) | | 3.3E−5 | | 3.6E−5 | | 1.1E−4 |
| Min | 893 | 863 | 893 | 863 | 893 | 863 |
| Max | 19700 | 18800 | 19700 | 18800 | 19700 | 18800 |
| n (Patient) | 226 | 99 | 225 | 100 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.57 | 0.63 | 0.59 | 0.57 | 0.63 | 0.58 | 0.58 | 0.62 |
| SE | 0.032 | 0.032 | 0.035 | 0.031 | 0.032 | 0.034 | 0.032 | 0.032 | 0.034 |
| p Value | 0.013 | 0.031 | 3.0E−4 | 0.0046 | 0.021 | 2.7E−4 | 0.017 | 0.012 | 6.2E−4 |
| nCohort Recovered | 166 | 169 | 226 | 163 | 168 | 225 | 159 | 167 | 217 |
| nCohort Non-recovered | 161 | 158 | 99 | 164 | 159 | 100 | 168 | 160 | 108 |
| Cutoff Quartile 2 | 2320 | 2320 | 2330 | 2320 | 2320 | 2330 | 2320 | 2320 | 2330 |
| Sensitivity | 80% | 80% | 86% | 80% | 80% | 86% | 80% | 80% | 85% |
| Specificity | 30% | 30% | 30% | 31% | 30% | 30% | 30% | 30% | 30% |
| Cutoff Quartile 3 | 3280 | 3280 | 3280 | 3280 | 3280 | 3280 | 3280 | 3280 | 3280 |
| Sensitivity | 54% | 53% | 59% | 55% | 53% | 59% | 54% | 54% | 57% |
| Specificity | 54% | 53% | 54% | 55% | 53% | 54% | 53% | 53% | 53% |
| Cutoff Quartile 4 | 4720 | 4720 | 4720 | 4720 | 4720 | 4720 | 4720 | 4720 | 4720 |
| Sensitivity | 29% | 29% | 33% | 30% | 30% | 33% | 29% | 30% | 32% |
| Specificity | 79% | 79% | 78% | 80% | 79% | 78% | 79% | 80% | 78% |
| OR Quartile 2 | 1.74 | 1.65 | 2.56 | 1.83 | 1.68 | 2.60 | 1.70 | 1.71 | 2.46 |

TABLE 15.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 0.034 | 0.053 | 0.0036 | 0.021 | 0.046 | 0.0030 | 0.039 | 0.039 | 0.0036 |
| Lower limit of 95% CI | 1.04 | 0.994 | 1.36 | 1.10 | 1.01 | 1.38 | 1.03 | 1.03 | 1.34 |
| Upper limit of 95% CI | 2.89 | 2.75 | 4.82 | 3.04 | 2.80 | 4.91 | 2.83 | 2.85 | 4.50 |
| OR Quartile 3 | 1.36 | 1.26 | 1.63 | 1.46 | 1.29 | 1.67 | 1.33 | 1.33 | 1.55 |
| p Value | 0.17 | 0.29 | 0.045 | 0.087 | 0.25 | 0.034 | 0.20 | 0.20 | 0.066 |
| Lower limit of 95% CI | 0.880 | 0.818 | 1.01 | 0.946 | 0.838 | 1.04 | 0.858 | 0.859 | 0.972 |
| Upper limit of 95% CI | 2.10 | 1.95 | 2.63 | 2.26 | 2.00 | 2.70 | 2.05 | 2.05 | 2.47 |
| OR Quartile 4 | 1.54 | 1.52 | 1.81 | 1.68 | 1.59 | 1.77 | 1.57 | 1.68 | 1.73 |
| p Value | 0.092 | 0.10 | 0.027 | 0.046 | 0.070 | 0.033 | 0.081 | 0.045 | 0.037 |
| Lower limit of 95% CI | 0.932 | 0.917 | 1.07 | 1.01 | 0.963 | 1.05 | 0.946 | 1.01 | 1.03 |
| Upper limit of 95% CI | 2.56 | 2.51 | 3.05 | 2.79 | 2.64 | 2.99 | 2.61 | 2.78 | 2.91 |

TABLE 15.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3100 | 3510 | 3080 | 3520 | 3090 | 3510 |
| Average | 3560 | 4390 | 3550 | 4390 | 3550 | 4380 |
| Stdev | 2090 | 2830 | 2100 | 2810 | 2100 | 2800 |
| p (t-test) | | 0.0026 | | 0.0020 | | 0.0025 |
| Min | 1080 | 863 | 1080 | 863 | 1080 | 863 |
| Max | 19700 | 18800 | 19700 | 18800 | 19700 | 18800 |
| n (Patient) | 204 | 123 | 202 | 125 | 201 | 126 |
| sCr only | | | | | | |
| Median | 3080 | 3510 | 3080 | 3510 | 3080 | 3510 |
| Average | 3480 | 4370 | 3480 | 4370 | 3480 | 4370 |
| Stdev | 1770 | 3010 | 1770 | 3010 | 1770 | 3010 |
| p (t-test) | | 8.8E-4 | | 8.8E-4 | | 8.8E-4 |
| Min | 1080 | 863 | 1080 | 863 | 1080 | 863 |
| Max | 14500 | 19700 | 14500 | 19700 | 14500 | 19700 |
| n (Patient) | 184 | 143 | 184 | 143 | 184 | 143 |
| UO only | | | | | | |
| Median | 3040 | 3860 | 3040 | 3790 | 3040 | 3790 |
| Average | 3470 | 4670 | 3470 | 4660 | 3470 | 4650 |
| Stdev | 2030 | 2910 | 2030 | 2900 | 2030 | 2880 |
| p (t-test) | | 2.3E-5 | | 2.5E-5 | | 2.3E-5 |
| Min | 893 | 863 | 893 | 863 | 893 | 863 |
| Max | 19700 | 18800 | 19700 | 18800 | 19700 | 18800 |
| n (Patient) | 220 | 105 | 219 | 106 | 217 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.58 | 0.63 | 0.59 | 0.58 | 0.63 | 0.59 | 0.58 | 0.63 |
| SE | 0.033 | 0.032 | 0.034 | 0.033 | 0.032 | 0.034 | 0.033 | 0.032 | 0.034 |
| p Value | 0.011 | 0.013 | 1.2E-4 | 0.0064 | 0.013 | 1.1E-4 | 0.0079 | 0.013 | 8.0E-5 |
| nCohort Recovered | 204 | 184 | 220 | 202 | 184 | 219 | 201 | 184 | 217 |

TABLE 15.10-continued

Comparison of marker levels and the area under the ROC curve (AUC) in EDTA samples for the "recovered"
and "non-recovered" cohorts where recovery starts within 168 hours after sample collection and renal status
is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-recovered | 123 | 143 | 105 | 125 | 143 | 106 | 126 | 143 | 108 |
| Cutoff Quartile 2 | 2320 | 2320 | 2330 | 2320 | 2320 | 2330 | 2320 | 2320 | 2330 |
| Sensitivity | 83% | 82% | 87% | 83% | 82% | 87% | 83% | 82% | 87% |
| Specificity | 30% | 30% | 30% | 30% | 30% | 31% | 30% | 30% | 31% |
| Cutoff Quartile 3 | 3280 | 3280 | 3280 | 3280 | 3280 | 3280 | 3280 | 3280 | 3280 |
| Sensitivity | 55% | 55% | 58% | 56% | 55% | 58% | 56% | 55% | 58% |
| Specificity | 53% | 53% | 54% | 53% | 53% | 54% | 53% | 53% | 54% |
| Cutoff Quartile 4 | 4720 | 4720 | 4720 | 4720 | 4720 | 4720 | 4720 | 4720 | 4720 |
| Sensitivity | 29% | 30% | 32% | 30% | 30% | 32% | 29% | 30% | 32% |
| Specificity | 77% | 79% | 78% | 78% | 79% | 78% | 78% | 79% | 78% |
| OR Quartile 2 | 2.07 | 1.97 | 2.85 | 2.14 | 1.97 | 2.90 | 2.18 | 1.97 | 3.00 |
| p Value | 0.010 | 0.012 | 0.0012 | 0.0073 | 0.012 | 9.6E−4 | 0.0061 | 0.012 | 6.5E−4 |
| Lower limit of 95% CI | 1.19 | 1.16 | 1.51 | 1.23 | 1.16 | 1.54 | 1.25 | 1.16 | 1.60 |
| Upper limit of 95% CI | 3.62 | 3.34 | 5.35 | 3.74 | 3.34 | 5.45 | 3.80 | 3.34 | 5.64 |
| OR Quartile 3 | 1.39 | 1.37 | 1.60 | 1.46 | 1.37 | 1.65 | 1.42 | 1.37 | 1.64 |
| p Value | 0.15 | 0.16 | 0.049 | 0.097 | 0.16 | 0.037 | 0.12 | 0.16 | 0.038 |
| Lower limit of 95% CI | 0.887 | 0.882 | 1.00 | 0.934 | 0.882 | 1.03 | 0.910 | 0.882 | 1.03 |
| Upper limit of 95% CI | 2.18 | 2.12 | 2.57 | 2.29 | 2.12 | 2.63 | 2.23 | 2.12 | 2.61 |
| OR Quartile 4 | 1.42 | 1.60 | 1.72 | 1.47 | 1.60 | 1.68 | 1.44 | 1.60 | 1.73 |
| p Value | 0.18 | 0.067 | 0.041 | 0.14 | 0.067 | 0.049 | 0.16 | 0.067 | 0.037 |
| Lower limit of 95% CI | 0.855 | 0.967 | 1.02 | 0.883 | 0.967 | 1.00 | 0.868 | 0.967 | 1.03 |
| Upper limit of 95% CI | 2.36 | 2.64 | 2.88 | 2.44 | 2.64 | 2.83 | 2.39 | 2.64 | 2.91 |

Example 16. Use of Metalloproteinase Inhibitor 4 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 16.1

Comparison of marker levels and the area under the ROC curve (AUC) in urine samples for the "persistent"
and "non-persistent" cohorts where persistence starts within 24 hours after sample collection and renal
status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 16.3 | 51.9 | 16.5 | 61.5 | 17.0 | 56.6 |
| Average | 37.9 | 382 | 37.4 | 440 | 78.7 | 394 |
| Stdev | 62.5 | 1270 | 60.8 | 1370 | 589 | 1120 |
| p (t-test) | | 1.3E−4 | | 1.6E−5 | | 0.0014 |
| Min | 0.00110 | 0.00167 | 0.00110 | 0.00167 | 0.00110 | 0.00167 |

TABLE 16.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 409 | 9030 | 409 | 9030 | 9030 | 7570 |
| n (Patient) | 205 | 112 | 221 | 96 | 236 | 81 | sCr only

| | | | | | | |
|---|---|---|---|---|---|---|
| Median | 16.9 | 48.7 | 16.9 | 56.6 | 18.2 | 53.0 |
| Average | 38.8 | 392 | 38.9 | 449 | 80.3 | 389 |
| Stdev | 62.9 | 1290 | 61.8 | 1390 | 590 | 1130 |
| p (t-test) | | 1.0E−4 | | 1.4E−5 | | 0.0019 |
| Min | 0.00110 | 0.00167 | 0.00110 | 0.00167 | 0.00110 | 0.00167 |
| Max | 409 | 9030 | 409 | 9030 | 9030 | 7570 |
| n (Patient) | 208 | 108 | 223 | 93 | 235 | 81 |

UO only

| | | | | | | |
|---|---|---|---|---|---|---|
| Median | 20.5 | 54.3 | 20.7 | 55.6 | 20.8 | 57.9 |
| Average | 99.1 | 580 | 98.5 | 624 | 98.3 | 640 |
| Stdev | 568 | 1540 | 565 | 1590 | 564 | 1610 |
| p (t-test) | | 2.2E−4 | | 9.2E−5 | | 6.7E−5 |
| Min | 0.00110 | 1.76 | 0.00110 | 1.76 | 0.00110 | 1.76 |
| Max | 9030 | 7570 | 9030 | 7570 | 9030 | 7570 |
| n (Patient) | 275 | 40 | 278 | 37 | 279 | 36 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.69 | 0.69 | 0.74 | 0.72 | 0.69 | 0.73 | 0.70 | 0.70 |
| SE | 0.031 | 0.032 | 0.049 | 0.032 | 0.033 | 0.050 | 0.035 | 0.036 | 0.051 |
| p Value | 2.1E−11 | 1.8E−9 | 8.2E−5 | 6.9E−14 | 4.2E−11 | 1.3E−4 | 2.0E−11 | 3.0E−8 | 1.2E−4 |
| nCohort Non-persistent | 205 | 208 | 275 | 221 | 223 | 278 | 236 | 235 | 279 |
| nCohort Persistent | 112 | 108 | 40 | 96 | 93 | 37 | 81 | 81 | 36 |
| Cutoff Quartile 2 | 8.33 | 8.31 | 8.36 | 8.33 | 8.31 | 8.36 | 8.33 | 8.31 | 8.36 |
| Sensitivity | 86% | 84% | 88% | 89% | 87% | 86% | 89% | 86% | 86% |
| Specificity | 31% | 30% | 27% | 31% | 30% | 27% | 30% | 29% | 27% |
| Cutoff Quartile 3 | 24.1 | 23.6 | 24.1 | 24.1 | 23.6 | 24.1 | 24.1 | 23.6 | 24.1 |
| Sensitivity | 71% | 69% | 80% | 74% | 72% | 78% | 77% | 73% | 78% |
| Specificity | 61% | 60% | 54% | 60% | 59% | 54% | 59% | 58% | 53% |
| Cutoff Quartile 4 | 60.9 | 60.8 | 61.8 | 60.9 | 60.8 | 61.8 | 60.9 | 60.8 | 61.8 |
| Sensitivity | 46% | 45% | 45% | 50% | 48% | 46% | 48% | 46% | 47% |
| Specificity | 86% | 86% | 78% | 86% | 85% | 78% | 83% | 82% | 78% |
| OR Quartile 2 | 2.66 | 2.27 | 2.58 | 3.43 | 2.90 | 2.32 | 3.37 | 2.59 | 2.24 |
| p Value | 0.0016 | 0.0070 | 0.057 | 4.6E−4 | 0.0019 | 0.092 | 0.0014 | 0.0073 | 0.11 |
| Lower limit of 95% CI | 1.45 | 1.25 | 0.973 | 1.72 | 1.48 | 0.872 | 1.60 | 1.29 | 0.839 |
| Upper limit of 95% CI | 4.88 | 4.13 | 6.83 | 6.85 | 5.67 | 6.18 | 7.12 | 5.19 | 5.97 |
| OR Quartile 3 | 3.74 | 3.21 | 4.73 | 4.29 | 3.74 | 4.19 | 4.68 | 3.68 | 4.01 |
| p Value | 1.6E−7 | 3.3E−6 | 1.7E−4 | 6.9E−8 | 8.9E−7 | 6.0E−4 | 1.5E−7 | 3.9E−6 | 9.0E−4 |
| Lower limit of 95% CI | 2.28 | 1.97 | 2.10 | 2.53 | 2.21 | 1.85 | 2.63 | 2.12 | 1.77 |
| Upper limit of 95% CI | 6.13 | 5.25 | 10.6 | 7.29 | 6.32 | 9.48 | 8.32 | 6.41 | 9.11 |
| OR Quartile 4 | 5.07 | 4.93 | 2.87 | 5.91 | 5.21 | 2.96 | 4.42 | 3.86 | 3.13 |
| p Value | 4.0E−9 | 7.8E−9 | 0.0025 | 2.1E−10 | 3.2E−9 | 0.0026 | 1.3E−7 | 1.5E−6 | 0.0017 |
| Lower limit of 95% CI | 2.95 | 2.87 | 1.45 | 3.41 | 3.02 | 1.46 | 2.55 | 2.23 | 1.54 |
| Upper limit of 95% CI | 8.72 | 8.47 | 5.69 | 10.2 | 9.00 | 6.00 | 7.66 | 6.70 | 6.39 |

TABLE 16.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 16.3 | 43.9 | 16.3 | 56.6 | 16.5 | 56.1 |
| Average | 35.1 | 336 | 34.1 | 385 | 78.4 | 340 |
| Stdev | 57.4 | 1180 | 55.3 | 1260 | 611 | 1030 |
| p (t-test) | | 5.9E−4 | | 9.1E−5 | | 0.0052 |
| Min | 0.00110 | 0.00167 | 0.00110 | 0.00167 | 0.00110 | 0.00167 |
| Max | 409 | 9030 | 409 | 9030 | 9030 | 7570 |
| n (Patient) | 186 | 131 | 204 | 113 | 219 | 98 |
| sCr only | | | | | | |
| Median | 16.9 | 42.2 | 16.7 | 51.9 | 17.0 | 46.3 |
| Average | 37.9 | 348 | 36.9 | 389 | 81.6 | 332 |
| Stdev | 60.8 | 1210 | 59.2 | 1280 | 612 | 1030 |
| p (t-test) | | 4.7E−4 | | 1.0E−4 | | 0.0075 |
| Min | 0.00110 | 0.00167 | 0.00110 | 0.00167 | 0.00110 | 0.00167 |
| Max | 409 | 9030 | 409 | 9030 | 9030 | 7570 |
| n (Patient) | 192 | 124 | 206 | 110 | 218 | 98 |
| UO only | | | | | | |
| Median | 20.0 | 43.9 | 20.4 | 50.8 | 20.5 | 51.9 |
| Average | 101 | 416 | 100 | 443 | 100 | 451 |
| Stdev | 588 | 1280 | 584 | 1330 | 583 | 1340 |
| p (t-test) | | 0.0048 | | 0.0027 | | 0.0023 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 256 | 59 | 260 | 55 | 261 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.67 | 0.66 | 0.73 | 0.71 | 0.66 | 0.73 | 0.69 | 0.66 |
| SE | 0.030 | 0.032 | 0.042 | 0.031 | 0.032 | 0.043 | 0.032 | 0.034 | 0.043 |
| p Value | 6.6E−11 | 3.6E−8 | 1.0E−4 | 2.6E−14 | 8.9E−11 | 1.4E−4 | 1.3E−12 | 2.5E−8 | 1.4E−4 |
| nCohort Non-persistent | 186 | 192 | 256 | 204 | 206 | 260 | 219 | 218 | 261 |
| nCohort Persistent | 131 | 124 | 59 | 113 | 110 | 55 | 98 | 98 | 54 |
| Cutoff Quartile 2 | 8.33 | 8.31 | 8.36 | 8.33 | 8.31 | 8.36 | 8.33 | 8.31 | 8.36 |
| Sensitivity | 85% | 83% | 86% | 87% | 85% | 85% | 88% | 86% | 85% |
| Specificity | 32% | 30% | 28% | 31% | 31% | 27% | 31% | 30% | 27% |
| Cutoff Quartile 3 | 24.1 | 23.6 | 24.1 | 24.1 | 23.6 | 24.1 | 24.1 | 23.6 | 24.1 |
| Sensitivity | 66% | 65% | 71% | 72% | 69% | 71% | 73% | 68% | 70% |
| Specificity | 61% | 59% | 55% | 62% | 60% | 54% | 60% | 58% | 54% |
| Cutoff Quartile 4 | 60.9 | 60.8 | 61.8 | 60.9 | 60.8 | 61.8 | 60.9 | 60.8 | 61.8 |
| Sensitivity | 43% | 42% | 41% | 48% | 45% | 42% | 47% | 43% | 43% |
| Specificity | 87% | 86% | 79% | 87% | 86% | 78% | 84% | 83% | 79% |
| OR Quartile 2 | 2.58 | 2.12 | 2.45 | 2.99 | 2.59 | 2.21 | 3.16 | 2.55 | 2.15 |
| p Value | 0.0011 | 0.0086 | 0.027 | 5.3E−4 | 0.0021 | 0.052 | 7.5E−4 | 0.0039 | 0.061 |
| Lower limit of 95% CI | 1.46 | 1.21 | 1.11 | 1.61 | 1.41 | 0.994 | 1.62 | 1.35 | 0.967 |
| Upper limit of 95% CI | 4.55 | 3.72 | 5.41 | 5.54 | 4.75 | 4.90 | 6.17 | 4.81 | 4.78 |
| OR Quartile 3 | 3.13 | 2.66 | 2.98 | 4.09 | 3.38 | 2.89 | 4.20 | 3.02 | 2.79 |
| p Value | 1.7E−6 | 4.1E−5 | 5.0E−4 | 2.8E−8 | 1.2E−6 | 9.9E−4 | 7.8E−8 | 1.7E−5 | 0.0015 |
| Lower limit of 95% CI | 1.96 | 1.67 | 1.61 | 2.49 | 2.07 | 1.54 | 2.49 | 1.82 | 1.48 |
| Upper limit of 95% CI | 5.00 | 4.24 | 5.51 | 6.72 | 5.52 | 5.43 | 7.09 | 4.99 | 5.25 |

TABLE 16.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 5.04 | 4.41 | 2.51 | 6.27 | 5.09 | 2.62 | 4.81 | 3.67 | 2.72 |
| p Value | 8.7E−9 | 7.5E−8 | 0.0026 | 7.7E−11 | 4.4E−9 | 0.0021 | 1.1E−8 | 1.8E−6 | 0.0015 |
| Lower limit of 95% CI | 2.90 | 2.57 | 1.38 | 3.61 | 2.95 | 1.42 | 2.81 | 2.15 | 1.47 |
| Upper limit of 95% CI | 8.74 | 7.58 | 4.56 | 10.9 | 8.76 | 4.83 | 8.26 | 6.26 | 5.02 |

TABLE 16.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 15.8 | 42.0 | 16.0 | 53.0 | 16.3 | 51.9 |
| Average | 33.1 | 315 | 32.1 | 350 | 79.7 | 305 |
| Stdev | 52.8 | 1140 | 51.2 | 1200 | 631 | 967 |
| p (t-test) | | 0.0012 | | 3.0E−4 | | 0.013 |
| Min | 0.00110 | 0.00167 | 0.00110 | 0.00167 | 0.00110 | 0.00167 |
| Max | 409 | 9030 | 409 | 9030 | 9030 | 7570 |
| n (Patient) | 175 | 142 | 190 | 127 | 205 | 112 |
| | sCr only | | | | | |
| Median | 16.4 | 42.0 | 16.3 | 46.5 | 17.0 | 45.0 |
| Average | 34.5 | 329 | 34.8 | 360 | 81.7 | 309 |
| Stdev | 53.5 | 1170 | 54.9 | 1230 | 626 | 985 |
| p (t-test) | | 7.6E−4 | | 2.5E−4 | | 0.013 |
| Min | 0.00110 | 0.00167 | 0.00110 | 0.00167 | 0.00110 | 0.00167 |
| Max | 409 | 9030 | 409 | 9030 | 9030 | 7570 |
| n (Patient) | 182 | 134 | 195 | 121 | 208 | 108 |
| | UO only | | | | | |
| Median | 19.1 | 40.3 | 19.6 | 47.4 | 19.6 | 47.4 |
| Average | 103 | 365 | 101 | 391 | 101 | 391 |
| Stdev | 600 | 1190 | 594 | 1240 | 594 | 1240 |
| p (t-test) | | 0.013 | | 0.0075 | | 0.0075 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 246 | 69 | 251 | 64 | 251 | 64 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.65 | 0.72 | 0.70 | 0.66 | 0.71 | 0.68 | 0.66 |
| SE | 0.030 | 0.031 | 0.039 | 0.030 | 0.031 | 0.040 | 0.031 | 0.033 | 0.040 |
| p Value | 9.5E−11 | 9.9E−9 | 1.3E−4 | 4.7E−14 | 4.9E−11 | 1.0E−4 | 1.8E−11 | 1.9E−8 | 1.0E−4 |
| nCohort Non-persistent | 175 | 182 | 246 | 190 | 195 | 251 | 205 | 208 | 251 |
| nCohort Persistent | 142 | 134 | 69 | 127 | 121 | 64 | 112 | 108 | 64 |
| Cutoff Quartile 2 | 8.33 | 8.31 | 8.36 | 8.33 | 8.31 | 8.36 | 8.33 | 8.31 | 8.36 |
| Sensitivity | 85% | 83% | 86% | 87% | 85% | 84% | 87% | 85% | 84% |
| Specificity | 33% | 31% | 28% | 33% | 31% | 27% | 31% | 30% | 27% |
| Cutoff Quartile 3 | 24.1 | 23.6 | 24.1 | 24.1 | 23.6 | 24.1 | 24.1 | 23.6 | 24.1 |
| Sensitivity | 65% | 64% | 70% | 69% | 68% | 70% | 70% | 67% | 70% |
| Specificity | 62% | 60% | 55% | 63% | 61% | 55% | 60% | 59% | 55% |
| Cutoff Quartile 4 | 60.9 | 60.8 | 61.8 | 60.9 | 60.8 | 61.8 | 60.9 | 60.8 | 61.8 |
| Sensitivity | 41% | 41% | 39% | 45% | 44% | 41% | 44% | 42% | 41% |
| Specificity | 87% | 87% | 79% | 88% | 87% | 79% | 85% | 84% | 79% |
| OR Quartile 2 | 2.63 | 2.14 | 2.30 | 3.13 | 2.60 | 2.05 | 2.94 | 2.50 | 2.05 |

TABLE 16.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 6.0E−4 | 0.0064 | 0.024 | 1.6E−4 | 0.0013 | 0.054 | 6.5E−4 | 0.0031 | 0.054 |
| Lower limit of 95% CI | 1.51 | 1.24 | 1.11 | 1.73 | 1.45 | 0.987 | 1.58 | 1.36 | 0.987 |
| Upper limit of 95% CI | 4.58 | 3.71 | 4.75 | 5.68 | 4.68 | 4.25 | 5.45 | 4.59 | 4.25 |
| OR Quartile 3 | 3.13 | 2.74 | 2.83 | 3.78 | 3.29 | 2.89 | 3.51 | 2.84 | 2.89 |
| p Value | 1.2E−6 | 1.9E−5 | 3.6E−4 | 4.9E−8 | 1.0E−6 | 4.3E−4 | 5.2E−7 | 2.6E−5 | 4.3E−4 |
| Lower limit of 95% CI | 1.98 | 1.73 | 1.60 | 2.34 | 2.04 | 1.60 | 2.15 | 1.75 | 1.60 |
| Upper limit of 95% CI | 4.97 | 4.34 | 5.00 | 6.10 | 5.31 | 5.22 | 5.74 | 4.61 | 5.22 |
| OR Quartile 4 | 4.80 | 4.58 | 2.40 | 5.91 | 5.07 | 2.56 | 4.37 | 3.66 | 2.56 |
| p Value | 3.6E−8 | 5.9E−8 | 0.0027 | 4.6E−10 | 6.2E−9 | 0.0016 | 6.4E−8 | 1.7E−6 | 0.0016 |
| Lower limit of 95% CI | 2.75 | 2.64 | 1.35 | 3.38 | 2.93 | 1.43 | 2.56 | 2.15 | 1.43 |
| Upper limit of 95% CI | 8.39 | 7.95 | 4.25 | 10.3 | 8.76 | 4.58 | 7.45 | 6.21 | 4.58 |

TABLE 16.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 15.8 | 42.0 | 16.3 | 51.9 | 16.3 | 48.7 |
| Average | 32.9 | 311 | 32.2 | 347 | 36.2 | 373 |
| Stdev | 53.0 | 1130 | 51.3 | 1190 | 59.1 | 1250 |
| p (t-test) | | 0.0013 | | 3.4E−4 | | 1.6E−4 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 173 | 144 | 189 | 128 | 201 | 116 |
| *sCr only* | | | | | | |
| Median | 16.7 | 41.1 | 16.3 | 46.3 | 17.0 | 45.0 |
| Average | 34.8 | 324 | 33.8 | 354 | 37.6 | 381 |
| Stdev | 53.8 | 1160 | 52.5 | 1210 | 59.9 | 1270 |
| p (t-test) | | 9.2E−4 | | 3.0E−4 | | 1.4E−4 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 180 | 136 | 192 | 124 | 204 | 112 |
| *UO only* | | | | | | |
| Median | 18.2 | 42.1 | 18.8 | 47.4 | 18.8 | 47.4 |
| Average | 104 | 337 | 102 | 363 | 102 | 363 |
| Stdev | 608 | 1140 | 601 | 1180 | 601 | 1180 |
| p (t-test) | | 0.022 | | 0.013 | | 0.013 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 239 | 76 | 245 | 70 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.66 | 0.72 | 0.70 | 0.66 | 0.71 | 0.69 | 0.66 |
| SE | 0.030 | 0.031 | 0.038 | 0.030 | 0.031 | 0.039 | 0.031 | 0.032 | 0.039 |
| p Value | 8.7E−11 | 3.9E−8 | 2.5E−5 | 1.6E−13 | 6.9E−11 | 3.7E−5 | 3.8E−11 | 6.9E−9 | 3.7E−5 |
| nCohort Non-persistent | 173 | 180 | 239 | 189 | 192 | 245 | 201 | 204 | 245 |

TABLE 16.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| nCohort | 144 | 136 | 76 | 128 | 124 | 70 | 116 | 112 | 70 |
|---|---|---|---|---|---|---|---|---|---|
| Persistent | | | | | | | | | |
| Cutoff Quartile 2 | 8.33 | 8.31 | 8.36 | 8.33 | 8.31 | 8.36 | 8.33 | 8.31 | 8.36 |
| Sensitivity | 84% | 82% | 86% | 86% | 85% | 84% | 86% | 85% | 84% |
| Specificity | 32% | 31% | 28% | 32% | 31% | 28% | 31% | 30% | 28% |
| Cutoff Quartile 3 | 24.1 | 23.6 | 24.1 | 24.1 | 23.6 | 24.1 | 24.1 | 23.6 | 24.1 |
| Sensitivity | 65% | 63% | 70% | 69% | 67% | 70% | 68% | 66% | 70% |
| Specificity | 62% | 60% | 56% | 62% | 61% | 56% | 60% | 59% | 56% |
| Cutoff Quartile 4 | 60.9 | 60.8 | 61.8 | 60.9 | 60.8 | 61.8 | 60.9 | 60.8 | 61.8 |
| Sensitivity | 41% | 40% | 39% | 45% | 44% | 40% | 43% | 42% | 40% |
| Specificity | 88% | 87% | 79% | 88% | 87% | 79% | 85% | 84% | 79% |
| OR Quartile 2 | 2.52 | 2.05 | 2.35 | 2.91 | 2.51 | 2.06 | 2.85 | 2.44 | 2.06 |
| p Value | 9.5E−4 | 0.0094 | 0.016 | 3.4E−4 | 0.0017 | 0.043 | 7.0E−4 | 0.0034 | 0.043 |
| Lower limit of 95% CI | 1.46 | 1.19 | 1.17 | 1.62 | 1.41 | 1.02 | 1.56 | 1.34 | 1.02 |
| Upper limit of 95% CI | 4.36 | 3.53 | 4.72 | 5.22 | 4.47 | 4.16 | 5.23 | 4.43 | 4.16 |
| OR Quartile 3 | 3.12 | 2.58 | 2.94 | 3.66 | 3.16 | 2.91 | 3.23 | 2.78 | 2.91 |
| p Value | 1.3E−6 | 5.1E−5 | 1.3E−4 | 9.2E−8 | 1.9E−6 | 2.4E−4 | 1.9E−6 | 3.0E−5 | 2.4E−4 |
| Lower limit of 95% CI | 1.97 | 1.63 | 1.69 | 2.27 | 1.97 | 1.65 | 1.99 | 1.72 | 1.65 |
| Upper limit of 95% CI | 4.95 | 4.08 | 5.11 | 5.88 | 5.07 | 5.15 | 5.23 | 4.50 | 5.15 |
| OR Quartile 4 | 5.02 | 4.41 | 2.53 | 5.79 | 5.15 | 2.54 | 4.32 | 3.89 | 2.54 |
| p Value | 2.1E−8 | 1.2E−7 | 0.0011 | 6.9E−10 | 5.2E−9 | 0.0013 | 8.1E−8 | 5.7E−7 | 0.0013 |
| Lower limit of 95% CI | 2.86 | 2.55 | 1.45 | 3.32 | 2.97 | 1.44 | 2.53 | 2.28 | 1.44 |
| Upper limit of 95% CI | 8.83 | 7.65 | 4.41 | 10.1 | 8.93 | 4.48 | 7.37 | 6.62 | 4.48 |

TABLE 16.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 15.8 | 41.1 | 15.8 | 50.8 | 16.3 | 46.3 |
| Average | 32.4 | 304 | 31.4 | 336 | 36.1 | 362 |
| Stdev | 52.7 | 1110 | 50.9 | 1170 | 59.5 | 1230 |
| p (t-test) | | 0.0017 | | 4.8E−4 | | 2.5E−4 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 169 | 148 | 184 | 133 | 197 | 120 |
| sCr only | | | | | | |
| Median | 16.4 | 40.2 | 16.3 | 45.0 | 16.7 | 43.2 |
| Average | 34.4 | 317 | 33.4 | 345 | 37.3 | 370 |
| Stdev | 53.5 | 1140 | 52.2 | 1190 | 59.8 | 1250 |
| p (t-test) | | 0.0012 | | 4.1E−4 | | 2.0E−4 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 176 | 140 | 188 | 128 | 200 | 116 |
| UO only | | | | | | |
| Median | 18.1 | 46.1 | 18.2 | 48.4 | 18.2 | 48.4 |
| Average | 97.3 | 342 | 96.6 | 354 | 96.6 | 354 |
| Stdev | 611 | 1110 | 607 | 1130 | 607 | 1130 |
| p (t-test) | | 0.014 | | 0.011 | | 0.011 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 234 | 81 | 237 | 78 | 237 | 78 |

TABLE 16.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.68 | 0.72 | 0.70 | 0.68 | 0.71 | 0.68 | 0.68 |
| SE | 0.030 | 0.031 | 0.036 | 0.029 | 0.031 | 0.037 | 0.031 | 0.032 | 0.037 |
| p Value | 8.1E−11 | 3.4E−8 | 1.2E−6 | 2.5E−14 | 6.5E−11 | 1.6E−6 | 3.6E−11 | 7.2E−9 | 1.6E−6 |
| nCohort Non-persistent | 169 | 176 | 234 | 184 | 188 | 237 | 197 | 200 | 237 |
| nCohort Persistent | 148 | 140 | 81 | 133 | 128 | 78 | 120 | 116 | 78 |
| Cutoff Quartile 2 | 8.33 | 8.31 | 8.36 | 8.33 | 8.31 | 8.36 | 8.33 | 8.31 | 8.36 |
| Sensitivity | 84% | 82% | 86% | 86% | 84% | 86% | 86% | 84% | 86% |
| Specificity | 33% | 31% | 29% | 33% | 31% | 29% | 31% | 30% | 29% |
| Cutoff Quartile 3 | 24.1 | 23.6 | 24.1 | 24.1 | 23.6 | 24.1 | 24.1 | 23.6 | 24.1 |
| Sensitivity | 65% | 63% | 70% | 69% | 66% | 71% | 68% | 66% | 71% |
| Specificity | 63% | 60% | 57% | 64% | 61% | 57% | 61% | 59% | 57% |
| Cutoff Quartile 4 | 60.9 | 60.8 | 61.8 | 60.9 | 60.8 | 61.8 | 60.9 | 60.8 | 61.8 |
| Sensitivity | 41% | 40% | 41% | 44% | 43% | 41% | 42% | 41% | 41% |
| Specificity | 88% | 87% | 80% | 89% | 87% | 80% | 85% | 84% | 80% |
| OR Quartile 2 | 2.49 | 2.04 | 2.61 | 2.90 | 2.47 | 2.45 | 2.78 | 2.39 | 2.45 |
| p Value | 9.7E−4 | 0.0096 | 0.0069 | 2.8E−4 | 0.0018 | 0.012 | 7.4E−4 | 0.0036 | 0.012 |
| Lower limit of 95% CI | 1.45 | 1.19 | 1.30 | 1.63 | 1.40 | 1.22 | 1.54 | 1.33 | 1.22 |
| Upper limit of 95% CI | 4.29 | 3.49 | 5.23 | 5.16 | 4.36 | 4.92 | 5.04 | 4.29 | 4.92 |
| OR Quartile 3 | 3.11 | 2.56 | 3.13 | 3.92 | 3.11 | 3.11 | 3.36 | 2.73 | 3.11 |
| p Value | 1.3E−6 | 5.4E−5 | 3.8E−5 | 1.7E−8 | 2.1E−6 | 5.3E−5 | 7.1E−7 | 3.4E−5 | 5.3E−5 |
| Lower limit of 95% CI | 1.96 | 1.62 | 1.82 | 2.44 | 1.95 | 1.79 | 2.08 | 1.70 | 1.79 |
| Upper limit of 95% CI | 4.92 | 4.05 | 5.38 | 6.30 | 4.98 | 5.39 | 5.43 | 4.40 | 5.39 |
| OR Quartile 4 | 5.08 | 4.43 | 2.81 | 6.19 | 5.15 | 2.81 | 4.28 | 3.85 | 2.81 |
| p Value | 2.4E−8 | 1.3E−7 | 2.2E−4 | 3.4E−10 | 6.4E−9 | 2.5E−4 | 1.0E−7 | 6.9E−7 | 2.5E−4 |
| Lower limit of 95% CI | 2.87 | 2.55 | 1.62 | 3.50 | 2.96 | 1.62 | 2.51 | 2.26 | 1.62 |
| Upper limit of 95% CI | 8.99 | 7.71 | 4.86 | 10.9 | 8.95 | 4.89 | 7.31 | 6.55 | 4.89 |

TABLE 16.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3120 | 3720 | 3140 | 3810 | 3150 | 3810 |
| Average | 3490 | 4520 | 3560 | 4520 | 3630 | 4500 |
| Stdev | 1640 | 3270 | 1820 | 3280 | 2090 | 3090 |
| p (t-test) | | 2.0E−4 | | 8.7E−4 | | 0.0039 |
| Min | 1080 | 863 | 1080 | 863 | 1080 | 863 |
| Max | 9820 | 19700 | 14500 | 19700 | 19700 | 18800 |
| n (Patient) | 206 | 121 | 222 | 105 | 238 | 89 |
| | sCr only | | | | | |
| Median | 3100 | 3620 | 3090 | 3860 | 3120 | 3670 |
| Average | 3470 | 4540 | 3530 | 4580 | 3620 | 4490 |
| Stdev | 1630 | 3310 | 1810 | 3300 | 2080 | 3080 |
| p (t-test) | | 1.1E−4 | | 2.7E−4 | | 0.0035 |
| Min | 1080 | 863 | 1080 | 863 | 1080 | 863 |

TABLE 16.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 9820 | 19700 | 14500 | 19700 | 19700 | 18800 |
| n (Patient) | 208 | 118 | 223 | 103 | 236 | 90 |
| | | | UO only | | | |
| Median | 3140 | 4580 | 3150 | 4610 | 3140 | 4750 |
| Average | 3580 | 5670 | 3580 | 5740 | 3570 | 5940 |
| Stdev | 2020 | 3670 | 2010 | 3740 | 2010 | 3720 |
| p (t-test) | | 5.0E−8 | | 3.4E−8 | | 2.5E−9 |
| Min | 893 | 863 | 893 | 863 | 893 | 863 |
| Max | 19700 | 18800 | 19700 | 18800 | 19700 | 18800 |
| n (Patient) | 281 | 44 | 283 | 42 | 285 | 40 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.58 | 0.69 | 0.57 | 0.59 | 0.69 | 0.57 | 0.57 | 0.72 |
| SE | 0.033 | 0.033 | 0.047 | 0.034 | 0.035 | 0.048 | 0.036 | 0.036 | 0.048 |
| p Value | 0.022 | 0.018 | 5.4E−5 | 0.036 | 0.013 | 8.5E−5 | 0.048 | 0.039 | 5.3E−6 |
| nCohort Non-persistent | 206 | 208 | 281 | 222 | 223 | 283 | 238 | 236 | 285 |
| nCohort Persistent | 121 | 118 | 44 | 105 | 103 | 42 | 89 | 90 | 40 |
| Cutoff Quartile 2 | 2320 | 2320 | 2330 | 2320 | 2320 | 2330 | 2320 | 2320 | 2330 |
| Sensitivity | 79% | 79% | 91% | 80% | 80% | 90% | 80% | 79% | 95% |
| Specificity | 28% | 27% | 27% | 27% | 27% | 27% | 27% | 27% | 28% |
| Cutoff Quartile 3 | 3280 | 3280 | 3280 | 3280 | 3280 | 3280 | 3280 | 3280 | 3280 |
| Sensitivity | 56% | 56% | 68% | 56% | 57% | 67% | 57% | 57% | 70% |
| Specificity | 53% | 53% | 53% | 53% | 53% | 52% | 53% | 53% | 53% |
| Cutoff Quartile 4 | 4720 | 4710 | 4720 | 4720 | 4710 | 4720 | 4720 | 4710 | 4720 |
| Sensitivity | 33% | 34% | 45% | 33% | 35% | 48% | 33% | 33% | 50% |
| Specificity | 80% | 80% | 78% | 79% | 79% | 78% | 78% | 78% | 78% |
| OR Quartile 2 | 1.47 | 1.40 | 3.77 | 1.52 | 1.47 | 3.55 | 1.45 | 1.36 | 7.29 |
| p Value | 0.16 | 0.21 | 0.014 | 0.15 | 0.18 | 0.019 | 0.22 | 0.30 | 0.0071 |
| Lower limit of 95% CI | 0.860 | 0.821 | 1.31 | 0.864 | 0.838 | 1.23 | 0.803 | 0.760 | 1.72 |
| Upper limit of 95% CI | 2.51 | 2.40 | 10.9 | 2.66 | 2.58 | 10.3 | 2.62 | 2.44 | 30.9 |
| OR Quartile 3 | 1.47 | 1.45 | 2.38 | 1.43 | 1.53 | 2.19 | 1.48 | 1.45 | 2.59 |
| p Value | 0.094 | 0.11 | 0.012 | 0.13 | 0.075 | 0.024 | 0.11 | 0.14 | 0.0090 |
| Lower limit of 95% CI | 0.936 | 0.922 | 1.21 | 0.896 | 0.958 | 1.11 | 0.909 | 0.888 | 1.27 |
| Upper limit of 95% CI | 2.31 | 2.29 | 4.69 | 2.28 | 2.46 | 4.34 | 2.43 | 2.36 | 5.30 |
| OR Quartile 4 | 1.93 | 2.03 | 2.94 | 1.86 | 2.07 | 3.24 | 1.69 | 1.77 | 3.60 |
| p Value | 0.011 | 0.0066 | 0.0013 | 0.019 | 0.0061 | 5.6E−4 | 0.057 | 0.037 | 2.3E−4 |
| Lower limit of 95% CI | 1.16 | 1.22 | 1.53 | 1.11 | 1.23 | 1.66 | 0.985 | 1.04 | 1.82 |
| Upper limit of 95% CI | 3.21 | 3.37 | 5.68 | 3.13 | 3.47 | 6.32 | 2.89 | 3.02 | 7.10 |

TABLE 16.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3110 | 3720 | 3120 | 3810 | 3140 | 3770 |
| Average | 3420 | 4470 | 3510 | 4470 | 3600 | 4420 |
| Stdev | 1590 | 3130 | 1800 | 3120 | 2090 | 2930 |

TABLE 16.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | |
|---|---|---|---|---|---|---|---|
| p (t-test) | | 9.5E-5 | | 4.3E-4 | | | 0.0035 |
| Min | 1080 | 863 | 1080 | 863 | 1080 | 863 | |
| Max | 9820 | 19700 | 14500 | 19700 | 19700 | 18800 | |
| n (Patient) | 187 | 140 | 204 | 123 | 219 | 108 | | sCr only

| | | | | | | |
|---|---|---|---|---|---|---|
| Median | 3100 | 3620 | 3090 | 3810 | 3130 | 3520 |
| Average | 3420 | 4490 | 3490 | 4480 | 3600 | 4380 |
| Stdev | 1580 | 3180 | 1790 | 3140 | 2090 | 2930 |
| p (t-test) | | 8.1E-5 | | 3.4E-4 | | 0.0059 |
| Min | 1080 | 863 | 1080 | 863 | 1080 | 863 |
| Max | 9820 | 19700 | 14500 | 19700 | 19700 | 18800 |
| n (Patient) | 192 | 134 | 205 | 121 | 217 | 109 |

UO only

| | | | | | | |
|---|---|---|---|---|---|---|
| Median | 3140 | 3990 | 3140 | 4150 | 3130 | 4350 |
| Average | 3570 | 5020 | 3570 | 5090 | 3560 | 5210 |
| Stdev | 2040 | 3300 | 2030 | 3360 | 2030 | 3360 |
| p (t-test) | | 1.2E-5 | | 5.8E-6 | | 1.2E-6 |
| Min | 893 | 863 | 893 | 863 | 893 | 863 |
| Max | 19700 | 18800 | 19700 | 18800 | 19700 | 18800 |
| n (Patient) | 260 | 65 | 263 | 62 | 265 | 60 |

| | Persistence Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.59 | 0.59 | 0.64 | 0.58 | 0.59 | 0.64 | 0.58 | 0.57 | 0.66 |
| SE | 0.032 | 0.032 | 0.040 | 0.033 | 0.033 | 0.041 | 0.034 | 0.034 | 0.041 |
| p Value | 0.0062 | 0.0078 | 7.5E-4 | 0.010 | 0.0084 | 6.1E-4 | 0.025 | 0.039 | 1.0E-4 |
| nCohort Non-persistent | 187 | 192 | 260 | 204 | 205 | 263 | 219 | 217 | 265 |
| nCohort Persistent | 140 | 134 | 65 | 123 | 121 | 62 | 108 | 109 | 60 |
| Cutoff Quartile 2 | 2320 | 2320 | 2330 | 2320 | 2320 | 2330 | 2320 | 2320 | 2330 |
| Sensitivity | 80% | 80% | 88% | 81% | 81% | 89% | 81% | 81% | 92% |
| Specificity | 29% | 29% | 28% | 29% | 29% | 28% | 28% | 28% | 29% |
| Cutoff Quartile 3 | 3280 | 3280 | 3280 | 3280 | 3280 | 3280 | 3280 | 3280 | 3280 |
| Sensitivity | 56% | 55% | 62% | 56% | 56% | 61% | 56% | 55% | 63% |
| Specificity | 54% | 54% | 53% | 53% | 54% | 52% | 53% | 53% | 53% |
| Cutoff Quartile 4 | 4720 | 4710 | 4720 | 4720 | 4710 | 4720 | 4720 | 4710 | 4720 |
| Sensitivity | 32% | 32% | 35% | 33% | 32% | 37% | 31% | 30% | 38% |
| Specificity | 80% | 80% | 77% | 79% | 79% | 78% | 78% | 77% | 78% |
| OR Quartile 2 | 1.62 | 1.59 | 2.78 | 1.77 | 1.72 | 3.08 | 1.74 | 1.64 | 4.42 |
| p Value | 0.068 | 0.083 | 0.011 | 0.040 | 0.051 | 0.0081 | 0.056 | 0.084 | 0.0022 |
| Lower limit of 95% CI | 0.964 | 0.941 | 1.27 | 1.03 | 0.998 | 1.34 | 0.985 | 0.935 | 1.70 |
| Upper limit of 95% CI | 2.73 | 2.69 | 6.12 | 3.05 | 2.97 | 7.06 | 3.07 | 2.87 | 11.5 |
| OR Quartile 3 | 1.48 | 1.43 | 1.78 | 1.47 | 1.49 | 1.75 | 1.46 | 1.36 | 1.93 |
| p Value | 0.082 | 0.12 | 0.042 | 0.096 | 0.086 | 0.053 | 0.11 | 0.20 | 0.025 |
| Lower limit of 95% CI | 0.951 | 0.916 | 1.02 | 0.935 | 0.945 | 0.993 | 0.919 | 0.854 | 1.09 |
| Upper limit of 95% CI | 2.29 | 2.22 | 3.11 | 2.30 | 2.33 | 3.08 | 2.32 | 2.15 | 3.45 |
| OR Quartile 4 | 1.92 | 1.85 | 1.87 | 1.86 | 1.79 | 2.04 | 1.64 | 1.49 | 2.17 |
| p Value | 0.011 | 0.017 | 0.037 | 0.017 | 0.025 | 0.018 | 0.062 | 0.13 | 0.011 |
| Lower limit of 95% CI | 1.16 | 1.12 | 1.04 | 1.12 | 1.08 | 1.13 | 0.976 | 0.887 | 1.20 |
| Upper limit of 95% CI | 3.18 | 3.07 | 3.35 | 3.09 | 2.98 | 3.68 | 2.75 | 2.50 | 3.94 |

TABLE 16.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3100 | 3510 | 3100 | 3520 | 3140 | 3620 |
| Average | 3400 | 4420 | 3460 | 4440 | 3550 | 4400 |
| Stdev | 1530 | 3080 | 1740 | 3060 | 2060 | 2870 |
| p (t-test) | | 1.2E−4 | | 2.8E−4 | | 0.0021 |
| Min | 1080 | 863 | 1080 | 863 | 1080 | 863 |
| Max | 9100 | 19700 | 14500 | 19700 | 19700 | 18800 |
| n (Patient) | 176 | 151 | 190 | 137 | 205 | 122 |
| | sCr only | | | | | |
| Median | 3100 | 3500 | 3100 | 3510 | 3130 | 3510 |
| Average | 3420 | 4420 | 3490 | 4410 | 3590 | 4330 |
| Stdev | 1590 | 3100 | 1780 | 3070 | 2100 | 2860 |
| p (t-test) | | 2.2E−4 | | 6.9E−4 | | 0.0078 |
| Min | 1080 | 863 | 1080 | 863 | 1080 | 863 |
| Max | 9820 | 19700 | 14500 | 19700 | 19700 | 18800 |
| n (Patient) | 182 | 144 | 194 | 132 | 207 | 119 |
| | UO only | | | | | |
| Median | 3100 | 3960 | 3110 | 3960 | 3110 | 3990 |
| Average | 3510 | 5010 | 3540 | 5000 | 3530 | 5050 |
| Stdev | 2000 | 3190 | 2030 | 3200 | 2030 | 3200 |
| p (t-test) | | 1.6E−6 | | 3.9E−6 | | 1.9E−6 |
| Min | 893 | 863 | 893 | 863 | 893 | 863 |
| Max | 19700 | 18800 | 19700 | 18800 | 19700 | 18800 |
| n (Patient) | 249 | 76 | 253 | 72 | 254 | 71 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.58 | 0.65 | 0.59 | 0.58 | 0.65 | 0.58 | 0.57 | 0.65 |
| SE | 0.032 | 0.032 | 0.038 | 0.032 | 0.032 | 0.039 | 0.033 | 0.033 | 0.039 |
| p Value | 0.0079 | 0.012 | 8.4E−5 | 0.0071 | 0.013 | 1.6E−4 | 0.014 | 0.042 | 6.7E−5 |
| nCohort Non-persistent | 176 | 182 | 249 | 190 | 194 | 253 | 205 | 207 | 254 |
| nCohort Persistent | 151 | 144 | 76 | 137 | 132 | 72 | 122 | 119 | 71 |
| Cutoff Quartile 2 | 2320 | 2320 | 2330 | 2320 | 2320 | 2330 | 2320 | 2320 | 2330 |
| Sensitivity | 80% | 80% | 88% | 82% | 81% | 89% | 82% | 81% | 90% |
| Specificity | 30% | 29% | 29% | 30% | 29% | 29% | 29% | 29% | 29% |
| Cutoff Quartile 3 | 3280 | 3280 | 3280 | 3280 | 3280 | 3280 | 3280 | 3280 | 3280 |
| Sensitivity | 54% | 53% | 61% | 54% | 54% | 60% | 55% | 54% | 61% |
| Specificity | 53% | 53% | 53% | 53% | 53% | 53% | 53% | 52% | 53% |
| Cutoff Quartile 4 | 4720 | 4710 | 4720 | 4720 | 4710 | 4720 | 4720 | 4710 | 4720 |
| Sensitivity | 31% | 31% | 36% | 32% | 32% | 36% | 31% | 30% | 37% |
| Specificity | 80% | 80% | 78% | 80% | 79% | 78% | 79% | 78% | 78% |
| OR Quartile 2 | 1.69 | 1.63 | 3.03 | 1.92 | 1.78 | 3.24 | 1.88 | 1.66 | 3.76 |
| p Value | 0.045 | 0.065 | 0.0037 | 0.016 | 0.034 | 0.0032 | 0.025 | 0.068 | 0.0017 |
| Lower limit of 95% CI | 1.01 | 0.971 | 1.43 | 1.13 | 1.04 | 1.48 | 1.08 | 0.964 | 1.65 |
| Upper limit of 95% CI | 2.83 | 2.73 | 6.40 | 3.27 | 3.04 | 7.10 | 3.26 | 2.87 | 8.58 |
| OR Quartile 3 | 1.30 | 1.28 | 1.73 | 1.31 | 1.29 | 1.64 | 1.36 | 1.27 | 1.71 |
| p Value | 0.24 | 0.27 | 0.040 | 0.24 | 0.26 | 0.067 | 0.18 | 0.30 | 0.049 |
| Lower limit of 95% CI | 0.839 | 0.828 | 1.03 | 0.840 | 0.828 | 0.966 | 0.865 | 0.808 | 1.00 |
| Upper limit of 95% CI | 2.00 | 1.99 | 2.92 | 2.03 | 2.01 | 2.80 | 2.13 | 1.99 | 2.93 |

TABLE 16.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.82 | 1.78 | 1.94 | 1.89 | 1.80 | 1.99 | 1.66 | 1.52 | 2.04 |
| p Value | 0.020 | 0.025 | 0.019 | 0.013 | 0.023 | 0.017 | 0.052 | 0.11 | 0.013 |
| Lower limit of 95% CI | 1.10 | 1.08 | 1.11 | 1.14 | 1.08 | 1.13 | 0.996 | 0.911 | 1.16 |
| Upper limit of 95% CI | 3.02 | 2.95 | 3.39 | 3.14 | 2.98 | 3.50 | 2.75 | 2.53 | 3.60 |

TABLE 16.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3090 | 3510 | 3100 | 3520 | 3120 | 3520 |
| Average | 3390 | 4400 | 3460 | 4420 | 3490 | 4470 |
| Stdev | 1540 | 3060 | 1740 | 3040 | 1740 | 3140 |
| p (t-test) | | 1.5E−4 | | 3.9E−4 | | 3.6E−4 |
| Min | 1080 | 863 | 1080 | 863 | 1080 | 863 |
| Max | 9100 | 19700 | 14500 | 19700 | 14500 | 19700 |
| n (Patient) | 173 | 154 | 188 | 139 | 200 | 127 |
| | sCr only | | | | | |
| Median | 3090 | 3510 | 3080 | 3620 | 3100 | 3620 |
| Average | 3390 | 4430 | 3450 | 4430 | 3480 | 4480 |
| Stdev | 1520 | 3110 | 1740 | 3060 | 1730 | 3170 |
| p (t-test) | | 9.8E−5 | | 2.9E−4 | | 2.7E−4 |
| Min | 1080 | 863 | 1080 | 863 | 1080 | 863 |
| Max | 9100 | 19700 | 14500 | 19700 | 14500 | 19700 |
| n (Patient) | 179 | 147 | 190 | 136 | 202 | 124 |
| | UO only | | | | | |
| Median | 3080 | 3990 | 3100 | 3960 | 3100 | 3990 |
| Average | 3480 | 4930 | 3510 | 4930 | 3510 | 4970 |
| Stdev | 2000 | 3080 | 2020 | 3110 | 2020 | 3110 |
| p (t-test) | | 1.4E−6 | | 4.0E−6 | | 2.0E−6 |
| Min | 893 | 863 | 893 | 863 | 893 | 863 |
| Max | 19700 | 18800 | 19700 | 18800 | 19700 | 18800 |
| n (Patient) | 240 | 85 | 245 | 80 | 246 | 79 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.58 | 0.65 | 0.58 | 0.59 | 0.64 | 0.58 | 0.58 | 0.65 |
| SE | 0.032 | 0.032 | 0.036 | 0.032 | 0.032 | 0.037 | 0.033 | 0.033 | 0.037 |
| p Value | 0.0072 | 0.0081 | 3.0E−5 | 0.0087 | 0.0072 | 9.2E−5 | 0.017 | 0.015 | 3.8E−5 |
| nCohort Non-persistent | 173 | 179 | 240 | 188 | 190 | 245 | 200 | 202 | 246 |
| nCohort Persistent | 154 | 147 | 85 | 139 | 136 | 80 | 127 | 124 | 79 |
| Cutoff Quartile 2 | 2320 | 2320 | 2330 | 2320 | 2320 | 2330 | 2320 | 2320 | 2330 |
| Sensitivity | 80% | 80% | 88% | 81% | 81% | 89% | 81% | 81% | 90% |
| Specificity | 29% | 29% | 30% | 30% | 29% | 29% | 29% | 29% | 30% |
| Cutoff Quartile 3 | 3280 | 3280 | 3280 | 3280 | 3280 | 3280 | 3280 | 3280 | 3280 |
| Sensitivity | 54% | 54% | 61% | 54% | 54% | 60% | 54% | 55% | 61% |
| Specificity | 53% | 53% | 54% | 53% | 53% | 53% | 52% | 53% | 53% |
| Cutoff Quartile 4 | 4720 | 4710 | 4720 | 4720 | 4710 | 4720 | 4720 | 4710 | 4720 |
| Sensitivity | 31% | 31% | 35% | 32% | 32% | 36% | 31% | 31% | 37% |
| Specificity | 80% | 80% | 78% | 80% | 79% | 78% | 78% | 78% | 78% |
| OR Quartile 2 | 1.66 | 1.60 | 3.15 | 1.84 | 1.77 | 3.28 | 1.75 | 1.68 | 3.74 |

TABLE 16.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| p Value | 0.053 | 0.075 | 0.0017 | 0.023 | 0.035 | 0.0018 | 0.041 | 0.060 | 9.1E−4 |
|---|---|---|---|---|---|---|---|---|---|
| Lower limit of 95% CI | 0.994 | 0.954 | 1.54 | 1.09 | 1.04 | 1.56 | 1.02 | 0.978 | 1.72 |
| Upper limit of 95% CI | 2.77 | 2.67 | 6.45 | 3.13 | 3.00 | 6.92 | 3.01 | 2.88 | 8.17 |
| OR Quartile 3 | 1.33 | 1.31 | 1.83 | 1.30 | 1.35 | 1.70 | 1.31 | 1.37 | 1.76 |
| p Value | 0.20 | 0.22 | 0.019 | 0.24 | 0.18 | 0.044 | 0.23 | 0.17 | 0.031 |
| Lower limit of 95% CI | 0.859 | 0.848 | 1.11 | 0.840 | 0.871 | 1.02 | 0.842 | 0.873 | 1.05 |
| Upper limit of 95% CI | 2.05 | 2.03 | 3.03 | 2.02 | 2.11 | 2.83 | 2.05 | 2.14 | 2.96 |
| OR Quartile 4 | 1.73 | 1.81 | 1.97 | 1.83 | 1.79 | 2.06 | 1.62 | 1.59 | 2.11 |
| p Value | 0.033 | 0.021 | 0.014 | 0.019 | 0.024 | 0.0097 | 0.062 | 0.075 | 0.0076 |
| Lower limit of 95% CI | 1.04 | 1.09 | 1.15 | 1.10 | 1.08 | 1.19 | 0.976 | 0.955 | 1.22 |
| Upper limit of 95% CI | 2.87 | 3.00 | 3.39 | 3.03 | 2.97 | 3.56 | 2.68 | 2.64 | 3.66 |

TABLE 16.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3040 | 3520 | 3040 | 3770 | 3080 | 3720 |
| Average | 3370 | 4400 | 3430 | 4430 | 3480 | 4460 |
| Stdev | 1540 | 3020 | 1750 | 2990 | 1750 | 3100 |
| p (t-test) | | 1.1E−4 | | 2.1E−4 | | 3.0E−4 |
| Min | 1080 | 863 | 1080 | 863 | 1080 | 863 |
| Max | 9100 | 19700 | 14500 | 19700 | 14500 | 19700 |
| n (Patient) | 169 | 158 | 183 | 144 | 196 | 131 |
| | sCr only | | | | | |
| Median | 3040 | 3520 | 3040 | 3770 | 3050 | 3770 |
| Average | 3360 | 4450 | 3420 | 4450 | 3450 | 4500 |
| Stdev | 1510 | 3080 | 1740 | 3030 | 1730 | 3120 |
| p (t-test) | | 4.2E−5 | | 1.4E−4 | | 1.3E−4 |
| Min | 1080 | 863 | 1080 | 863 | 1080 | 863 |
| Max | 9100 | 19700 | 14500 | 19700 | 14500 | 19700 |
| n (Patient) | 175 | 151 | 186 | 140 | 198 | 128 |
| | UO only | | | | | |
| Median | 3040 | 4030 | 3040 | 4180 | 3040 | 4300 |
| Average | 3460 | 4920 | 3450 | 4970 | 3440 | 5000 |
| Stdev | 1990 | 3030 | 1990 | 3050 | 1980 | 3040 |
| p (t-test) | | 6.1E−7 | | 2.9E−7 | | 1.4E−7 |
| Min | 893 | 863 | 893 | 863 | 893 | 863 |
| Max | 19700 | 18800 | 19700 | 18800 | 19700 | 18800 |
| n (Patient) | 235 | 90 | 237 | 88 | 238 | 87 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.59 | 0.60 | 0.66 | 0.60 | 0.60 | 0.66 | 0.59 | 0.59 | 0.67 |
| SE | 0.031 | 0.032 | 0.035 | 0.032 | 0.032 | 0.035 | 0.032 | 0.033 | 0.035 |
| p Value | 0.0032 | 0.0022 | 7.1E−6 | 0.0024 | 0.0019 | 3.7E−6 | 0.0084 | 0.0044 | 1.3E−6 |
| nCohort Non-persistent | 169 | 175 | 235 | 183 | 186 | 237 | 196 | 198 | 238 |

TABLE 16.10-continued

Comparison of marker levels and the area under the ROC curve (AUC) in EDTA samples for the "persistent"
and "non-persistent" cohorts where persistence starts within 168 hours after sample collection and renal
status is assessed by serum creatinine (sCr) only, urine output (UO) only, or serum creatinine or urine output RIFLE criteria.

| nCohort | 158 | 151 | 90 | 144 | 140 | 88 | 131 | 128 | 87 |
|---|---|---|---|---|---|---|---|---|---|
| Persistent | | | | | | | | | |
| Cutoff Quartile 2 | 2320 | 2320 | 2330 | 2320 | 2320 | 2330 | 2320 | 2320 | 2330 |
| Sensitivity | 80% | 80% | 89% | 82% | 81% | 90% | 82% | 81% | 91% |
| Specificity | 30% | 30% | 30% | 31% | 30% | 30% | 30% | 29% | 31% |
| Cutoff Quartile 3 | 3280 | 3280 | 3280 | 3280 | 3280 | 3280 | 3280 | 3280 | 3280 |
| Sensitivity | 54% | 55% | 62% | 55% | 56% | 62% | 55% | 56% | 63% |
| Specificity | 54% | 54% | 54% | 54% | 54% | 54% | 53% | 54% | 55% |
| Cutoff Quartile 4 | 4720 | 4710 | 4720 | 4720 | 4710 | 4720 | 4720 | 4710 | 4720 |
| Sensitivity | 30% | 32% | 36% | 31% | 32% | 36% | 30% | 31% | 37% |
| Specificity | 80% | 81% | 79% | 80% | 80% | 79% | 78% | 79% | 79% |
| OR Quartile 2 | 1.77 | 1.71 | 3.46 | 2.00 | 1.89 | 3.83 | 1.87 | 1.80 | 4.37 |
| p Value | 0.029 | 0.042 | 6.5E−4 | 0.010 | 0.018 | 4.0E−4 | 0.022 | 0.033 | 2.0E−4 |
| Lower limit of 95% CI | 1.06 | 1.02 | 1.70 | 1.18 | 1.11 | 1.82 | 1.09 | 1.05 | 2.01 |
| Upper limit of 95% CI | 2.95 | 2.85 | 7.07 | 3.39 | 3.20 | 8.05 | 3.21 | 3.08 | 9.51 |
| OR Quartile 3 | 1.39 | 1.45 | 1.97 | 1.40 | 1.49 | 1.99 | 1.38 | 1.51 | 2.07 |
| p Value | 0.14 | 0.096 | 0.0075 | 0.13 | 0.074 | 0.0071 | 0.16 | 0.070 | 0.0048 |
| Lower limit of 95% CI | 0.902 | 0.936 | 1.20 | 0.904 | 0.962 | 1.21 | 0.885 | 0.967 | 1.25 |
| Upper limit of 95% CI | 2.15 | 2.24 | 3.24 | 2.17 | 2.32 | 3.29 | 2.15 | 2.36 | 3.43 |
| OR Quartile 4 | 1.73 | 1.93 | 2.04 | 1.79 | 1.91 | 2.14 | 1.51 | 1.69 | 2.19 |
| p Value | 0.033 | 0.011 | 0.0087 | 0.023 | 0.012 | 0.0054 | 0.11 | 0.042 | 0.0042 |
| Lower limit of 95% CI | 1.04 | 1.16 | 1.20 | 1.08 | 1.15 | 1.25 | 0.911 | 1.02 | 1.28 |
| Upper limit of 95% CI | 2.87 | 3.21 | 3.48 | 2.97 | 3.16 | 3.65 | 2.50 | 2.80 | 3.74 |

Example 17. Use of Metalloproteinase Inhibitor 4 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. Metalloproteinase inhibitor 4 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 17.1

Comparison of marker levels and the area under the ROC curve (AUC) in urine samples for
the "persistent" and "non-persistent" cohorts where persistence starts
within 24 hours after sample collection and renal status is assessed by serum creatinine
(sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 12.7 | 36.2 | 15.6 | 37.0 | 15.4 | 42.2 |
| Average | 26.9 | 239 | 34.3 | 284 | 35.2 | 320 |
| Stdev | 45.9 | 969 | 57.0 | 1080 | 59.2 | 1150 |
| p (t-test) | | 0.018 | | 0.0039 | | 0.0010 |
| Min | 0.00110 | 0.00167 | 0.00110 | 0.00167 | 0.00110 | 0.00167 |

TABLE 17.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Max | 409 | 9030 | 409 | 9030 | 409 | 9030 |
| n (Patient) | 119 | 198 | 158 | 159 | 179 | 138 | sCr only

| | | | | | | |
|---|---|---|---|---|---|---|
| Median | 13.3 | 35.4 | 16.0 | 37.0 | 16.0 | 42.2 |
| Average | 29.3 | 250 | 31.2 | 294 | 33.1 | 336 |
| Stdev | 46.8 | 999 | 46.8 | 1090 | 51.4 | 1180 |
| p (t-test) | | 0.012 | | 0.0024 | | 5.6E−4 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 130 | 186 | 162 | 154 | 184 | 132 |

UO only

| | | | | | | |
|---|---|---|---|---|---|---|
| Median | 18.2 | 41.0 | 19.1 | 53.0 | 19.3 | 57.9 |
| Average | 96.3 | 368 | 99.9 | 422 | 99.5 | 467 |
| Stdev | 598 | 1160 | 588 | 1280 | 581 | 1360 |
| p (t-test) | | 0.0081 | | 0.0038 | | 0.0017 |
| Min | 0.00110 | 1.76 | 0.00110 | 1.76 | 0.00110 | 1.76 |
| Max | 9030 | 7570 | 9030 | 7570 | 9030 | 7570 |
| n (Patient) | 241 | 74 | 256 | 59 | 263 | 52 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.68 | 0.67 | 0.67 | 0.69 | 0.69 | 0.69 | 0.70 |
| SE | 0.029 | 0.030 | 0.038 | 0.030 | 0.030 | 0.041 | 0.030 | 0.031 | 0.043 |
| p Value | 9.3E−11 | 2.2E−8 | 2.6E−6 | 2.2E−8 | 2.5E−8 | 3.9E−6 | 1.1E−10 | 2.2E−10 | 2.0E−6 |
| nCohort Non-persistent | 119 | 130 | 241 | 158 | 162 | 256 | 179 | 184 | 263 |
| nCohort Persistent | 198 | 186 | 74 | 159 | 154 | 59 | 138 | 132 | 52 |
| Cutoff Quartile 2 | 8.33 | 8.31 | 8.36 | 8.33 | 8.31 | 8.36 | 8.33 | 8.31 | 8.36 |
| Sensitivity | 82% | 81% | 88% | 82% | 81% | 88% | 86% | 85% | 88% |
| Specificity | 36% | 33% | 29% | 32% | 31% | 28% | 33% | 32% | 28% |
| Cutoff Quartile 3 | 24.1 | 23.6 | 24.1 | 24.1 | 23.6 | 24.1 | 24.1 | 23.6 | 24.1 |
| Sensitivity | 60% | 59% | 69% | 60% | 60% | 73% | 64% | 64% | 77% |
| Specificity | 66% | 63% | 56% | 60% | 60% | 55% | 61% | 60% | 55% |
| Cutoff Quartile 4 | 60.9 | 60.8 | 61.8 | 60.9 | 60.8 | 61.8 | 60.9 | 60.8 | 61.8 |
| Sensitivity | 35% | 35% | 42% | 38% | 40% | 44% | 41% | 42% | 46% |
| Specificity | 92% | 90% | 80% | 88% | 89% | 79% | 87% | 87% | 79% |
| OR Quartile 2 | 2.55 | 2.06 | 2.96 | 2.23 | 1.92 | 2.91 | 2.90 | 2.64 | 2.95 |
| p Value | 4.3E−4 | 0.0060 | 0.0046 | 0.0029 | 0.014 | 0.012 | 2.3E−4 | 7.9E−4 | 0.018 |
| Lower limit of 95% CI | 1.51 | 1.23 | 1.40 | 1.32 | 1.14 | 1.26 | 1.65 | 1.50 | 1.21 |
| Upper limit of 95% CI | 4.28 | 3.45 | 6.26 | 3.78 | 3.25 | 6.70 | 5.12 | 4.66 | 7.19 |
| OR Quartile 3 | 2.81 | 2.47 | 2.78 | 2.30 | 2.28 | 3.30 | 2.83 | 2.75 | 4.10 |
| p Value | 1.9E−5 | 1.2E−4 | 3.0E−4 | 2.9E−4 | 3.5E−4 | 1.8E−4 | 9.5E−6 | 1.8E−5 | 6.1E−5 |
| Lower limit of 95% CI | 1.75 | 1.56 | 1.60 | 1.47 | 1.45 | 1.76 | 1.79 | 1.73 | 2.06 |
| Upper limit of 95% CI | 4.50 | 3.92 | 4.83 | 3.60 | 3.57 | 6.15 | 4.48 | 4.37 | 8.16 |
| OR Quartile 4 | 5.96 | 4.95 | 2.90 | 4.55 | 5.25 | 3.02 | 4.41 | 4.76 | 3.24 |
| p Value | 8.3E−7 | 1.3E−6 | 1.9E−4 | 2.5E−7 | 3.1E−8 | 2.8E−4 | 1.1E−7 | 2.9E−8 | 2.1E−4 |
| Lower limit of 95% CI | 2.93 | 2.59 | 1.66 | 2.56 | 2.92 | 1.66 | 2.55 | 2.74 | 1.74 |
| Upper limit of 95% CI | 12.1 | 9.45 | 5.07 | 8.10 | 9.44 | 5.48 | 7.63 | 8.26 | 6.03 |

TABLE 17.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 12.5 | 34.8 | 14.7 | 37.0 | 13.3 | 41.1 |
| Average | 27.2 | 231 | 30.5 | 271 | 31.7 | 298 |
| Stdev | 47.1 | 953 | 48.1 | 1040 | 52.4 | 1100 |
| p (t-test) | | 0.024 | | 0.0056 | | 0.0021 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 112 | 205 | 147 | 170 | 165 | 152 |
| sCr only | | | | | | |
| Median | 13.3 | 34.9 | 16.3 | 36.9 | 15.4 | 40.1 |
| Average | 29.5 | 246 | 31.6 | 281 | 32.9 | 305 |
| Stdev | 47.4 | 989 | 47.8 | 1070 | 52.3 | 1120 |
| p (t-test) | | 0.015 | | 0.0041 | | 0.0017 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 126 | 190 | 154 | 162 | 169 | 147 |
| UO only | | | | | | |
| Median | 18.1 | 39.3 | 18.2 | 40.3 | 18.2 | 47.4 |
| Average | 99.3 | 306 | 103 | 338 | 102 | 363 |
| Stdev | 622 | 1040 | 609 | 1130 | 601 | 1180 |
| p (t-test) | | 0.031 | | 0.020 | | 0.013 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 222 | 93 | 238 | 77 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.66 | 0.66 | 0.68 | 0.66 | 0.66 | 0.70 | 0.68 | 0.67 |
| SE | 0.030 | 0.030 | 0.035 | 0.029 | 0.030 | 0.037 | 0.029 | 0.030 | 0.039 |
| p Value | 2.2E−10 | 5.2E−8 | 4.9E−6 | 1.6E−9 | 9.6E−8 | 1.4E−5 | 3.0E−12 | 1.4E−9 | 1.1E−5 |
| nCohort Non-persistent | 112 | 126 | 222 | 147 | 154 | 238 | 165 | 169 | 245 |
| nCohort Persistent | 205 | 190 | 93 | 170 | 162 | 77 | 152 | 147 | 70 |
| Cutoff Quartile 2 | 8.33 | 8.31 | 8.36 | 8.33 | 8.31 | 8.36 | 8.33 | 8.31 | 8.36 |
| Sensitivity | 82% | 81% | 87% | 83% | 81% | 87% | 86% | 84% | 87% |
| Specificity | 38% | 33% | 30% | 34% | 32% | 29% | 35% | 33% | 29% |
| Cutoff Quartile 3 | 24.1 | 23.6 | 24.1 | 24.1 | 23.6 | 24.1 | 24.1 | 23.6 | 24.1 |
| Sensitivity | 59% | 58% | 67% | 61% | 59% | 69% | 64% | 62% | 71% |
| Specificity | 66% | 63% | 57% | 62% | 60% | 56% | 62% | 60% | 56% |
| Cutoff Quartile 4 | 60.9 | 60.8 | 61.8 | 60.9 | 60.8 | 61.8 | 60.9 | 60.8 | 61.8 |
| Sensitivity | 34% | 35% | 38% | 38% | 38% | 39% | 39% | 39% | 40% |
| Specificity | 91% | 90% | 80% | 89% | 88% | 79% | 88% | 87% | 79% |
| OR Quartile 2 | 2.72 | 2.07 | 2.92 | 2.51 | 2.05 | 2.74 | 3.38 | 2.67 | 2.71 |
| p Value | 1.7E−4 | 0.0058 | 0.0017 | 6.1E−4 | 0.0069 | 0.0062 | 2.1E−5 | 4.4E−4 | 0.0094 |
| Lower limit of 95% CI | 1.62 | 1.23 | 1.49 | 1.48 | 1.22 | 1.33 | 1.93 | 1.54 | 1.28 |
| Upper limit of 95% CI | 4.59 | 3.46 | 5.71 | 4.24 | 3.46 | 5.63 | 5.92 | 4.62 | 5.76 |
| OR Quartile 3 | 2.81 | 2.36 | 2.63 | 2.50 | 2.16 | 2.80 | 2.93 | 2.47 | 3.17 |
| p Value | 2.5E−5 | 2.7E−4 | 1.9E−4 | 7.5E−5 | 7.9E−4 | 2.2E−4 | 4.0E−6 | 9.1E−5 | 8.8E−5 |
| Lower limit of 95% CI | 1.74 | 1.49 | 1.58 | 1.59 | 1.38 | 1.62 | 1.86 | 1.57 | 1.78 |
| Upper limit of 95% CI | 4.53 | 3.75 | 4.36 | 3.93 | 3.38 | 4.83 | 4.63 | 3.89 | 5.65 |
| OR Quartile 4 | 5.29 | 4.63 | 2.44 | 4.94 | 4.56 | 2.46 | 4.73 | 4.23 | 2.54 |
| p Value | 4.4E−6 | 3.5E−6 | 0.0010 | 2.2E−7 | 3.7E−7 | 0.0015 | 9.0E−8 | 3.9E−7 | 0.0013 |
| Lower limit of 95% CI | 2.60 | 2.42 | 1.43 | 2.70 | 2.54 | 1.41 | 2.68 | 2.42 | 1.44 |

TABLE 17.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 10.8 | 8.84 | 4.16 | 9.05 | 8.19 | 4.29 | 8.36 | 7.39 | 4.48 |

TABLE 17.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 12.3 | 34.7 | 13.3 | 36.7 | 13.3 | 37.0 |
| Average | 27.2 | 230 | 30.6 | 266 | 32.4 | 285 |
| Stdev | 47.3 | 951 | 48.6 | 1030 | 53.4 | 1080 |
| p (t-test) | | 0.025 | | 0.0066 | | 0.0034 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 111 | 206 | 144 | 173 | 158 | 159 |
| | sCr only | | | | | |
| Median | 13.3 | 34.7 | 16.3 | 36.5 | 15.4 | 37.0 |
| Average | 29.7 | 243 | 31.8 | 276 | 33.6 | 293 |
| Stdev | 47.7 | 984 | 48.2 | 1060 | 53.1 | 1100 |
| p (t-test) | | 0.016 | | 0.0049 | | 0.0027 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 124 | 192 | 151 | 165 | 163 | 153 |
| | UO only | | | | | |
| Median | 18.1 | 37.0 | 18.2 | 39.1 | 18.5 | 39.3 |
| Average | 102 | 279 | 106 | 295 | 106 | 312 |
| Stdev | 637 | 995 | 626 | 1050 | 617 | 1090 |
| p (t-test) | | 0.057 | | 0.051 | | 0.037 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 212 | 103 | 225 | 90 | 232 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.66 | 0.64 | 0.68 | 0.66 | 0.64 | 0.69 | 0.67 | 0.64 |
| SE | 0.030 | 0.030 | 0.034 | 0.030 | 0.030 | 0.036 | 0.030 | 0.030 | 0.037 |
| p Value | 1.8E−10 | 8.1E−8 | 5.9E−5 | 1.0E−9 | 1.4E−7 | 1.5E−4 | 1.2E−10 | 2.2E−8 | 1.6E−4 |
| nCohort Non-persistent | 111 | 124 | 212 | 144 | 151 | 225 | 158 | 163 | 232 |
| nCohort Persistent | 206 | 192 | 103 | 173 | 165 | 90 | 159 | 153 | 83 |
| Cutoff Quartile 2 | 8.33 | 8.31 | 8.36 | 8.33 | 8.31 | 8.36 | 8.33 | 8.31 | 8.36 |
| Sensitivity | 82% | 81% | 85% | 83% | 82% | 86% | 85% | 84% | 86% |
| Specificity | 38% | 34% | 30% | 35% | 32% | 29% | 35% | 33% | 29% |
| Cutoff Quartile 3 | 24.1 | 23.6 | 24.1 | 24.1 | 23.6 | 24.1 | 24.1 | 23.6 | 24.1 |
| Sensitivity | 59% | 58% | 63% | 61% | 59% | 64% | 63% | 61% | 66% |
| Specificity | 67% | 63% | 56% | 63% | 60% | 56% | 63% | 60% | 56% |
| Cutoff Quartile 4 | 60.9 | 60.8 | 61.8 | 60.9 | 60.8 | 61.8 | 60.9 | 60.8 | 61.8 |
| Sensitivity | 34% | 34% | 35% | 37% | 37% | 36% | 38% | 37% | 36% |

TABLE 17.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| Specificity | 91% | 90% | 80% | 89% | 88% | 79% | 87% | 87% | 79% |
|---|---|---|---|---|---|---|---|---|---|
| OR Quartile 2 | 2.78 | 2.15 | 2.54 | 2.64 | 2.16 | 2.46 | 3.00 | 2.54 | 2.40 |
| p Value | 1.3E−4 | 0.0038 | 0.0033 | 3.0E−4 | 0.0038 | 0.0070 | 7.4E−5 | 7.1E−4 | 0.011 |
| Lower limit of 95% CI | 1.65 | 1.28 | 1.36 | 1.56 | 1.28 | 1.28 | 1.74 | 1.48 | 1.22 |
| Upper limit of 95% CI | 4.69 | 3.60 | 4.72 | 4.47 | 3.64 | 4.73 | 5.17 | 4.35 | 4.72 |
| OR Quartile 3 | 2.90 | 2.37 | 2.19 | 2.72 | 2.22 | 2.27 | 2.84 | 2.34 | 2.46 |
| p Value | 1.5E−5 | 2.6E−4 | 0.0015 | 1.8E−5 | 5.2E−4 | 0.0015 | 6.9E−6 | 2.3E−4 | 7.5E−4 |
| Lower limit of 95% CI | 1.79 | 1.49 | 1.35 | 1.72 | 1.41 | 1.37 | 1.80 | 1.49 | 1.46 |
| Upper limit of 95% CI | 4.71 | 3.77 | 3.55 | 4.29 | 3.48 | 3.76 | 4.48 | 3.67 | 4.15 |
| OR Quartile 4 | 5.20 | 4.47 | 2.11 | 4.70 | 4.33 | 2.09 | 4.18 | 3.81 | 2.11 |
| p Value | 5.5E−6 | 5.7E−6 | 0.0053 | 5.3E−7 | 9.0E−7 | 0.0073 | 8.0E−7 | 2.5E−6 | 0.0074 |
| Lower limit of 95% CI | 2.55 | 2.34 | 1.25 | 2.57 | 2.41 | 1.22 | 2.37 | 2.18 | 1.22 |
| Upper limit of 95% CI | 10.6 | 8.54 | 3.57 | 8.60 | 7.78 | 3.58 | 7.38 | 6.64 | 3.66 |

TABLE 17.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 12.5 | 34.6 | 13.3 | 36.6 | 13.3 | 37.0 |
| Average | 27.4 | 229 | 30.8 | 265 | 32.5 | 282 |
| Stdev | 47.5 | 949 | 48.7 | 1030 | 53.7 | 1070 |
| p (t-test) | | 0.027 | | 0.0071 | | 0.0039 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 110 | 207 | 143 | 174 | 156 | 161 |
| | sCr only | | | | | |
| Median | 13.3 | 34.7 | 16.3 | 34.9 | 15.9 | 36.9 |
| Average | 29.7 | 243 | 32.0 | 275 | 33.7 | 292 |
| Stdev | 47.7 | 984 | 48.4 | 1060 | 53.3 | 1090 |
| p (t-test) | | 0.016 | | 0.0052 | | 0.0029 |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 124 | 192 | 150 | 166 | 162 | 154 |
| | UO only | | | | | |
| Median | 18.2 | 36.7 | 18.2 | 37.0 | 18.2 | 38.8 |
| Average | 104 | 270 | 108 | 281 | 108 | 294 |
| Stdev | 643 | 977 | 633 | 1030 | 625 | 1060 |
| p (t-test) | | 0.071 | | 0.068 | | 0.055 |
| Min | 0.00110 | 0.00277 | 0.00110 | 0.00277 | 0.00110 | 0.00277 |
| Max | 9030 | 7570 | 9030 | 7570 | 9030 | 7570 |
| n (Patient) | 208 | 107 | 220 | 95 | 226 | 89 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.66 | 0.63 | 0.68 | 0.66 | 0.63 | 0.69 | 0.67 | 0.63 |
| SE | 0.030 | 0.030 | 0.034 | 0.030 | 0.030 | 0.035 | 0.030 | 0.030 | 0.036 |
| p Value | 6.1E−10 | 8.1E−8 | 1.5E−4 | 2.3E−9 | 2.7E−7 | 1.9E−4 | 1.9E−10 | 4.7E−8 | 1.7E−4 |

TABLE 17.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-persistent | 110 | 124 | 208 | 143 | 150 | 220 | 156 | 162 | 226 |
| nCohort Persistent | 207 | 192 | 107 | 174 | 166 | 95 | 161 | 154 | 89 |
| Cutoff Quartile 2 | 8.33 | 8.31 | 8.36 | 8.33 | 8.31 | 8.36 | 8.33 | 8.31 | 8.36 |
| Sensitivity | 82% | 81% | 84% | 83% | 81% | 85% | 84% | 83% | 85% |
| Specificity | 37% | 34% | 30% | 34% | 32% | 30% | 35% | 33% | 29% |
| Cutoff Quartile 3 | 24.1 | 23.6 | 24.1 | 24.1 | 23.6 | 24.1 | 24.1 | 23.6 | 24.1 |
| Sensitivity | 59% | 58% | 62% | 61% | 59% | 63% | 63% | 60% | 65% |
| Specificity | 66% | 63% | 56% | 63% | 60% | 55% | 63% | 60% | 56% |
| Cutoff Quartile 4 | 60.9 | 60.8 | 61.8 | 60.9 | 60.8 | 61.8 | 60.9 | 60.8 | 61.8 |
| Sensitivity | 34% | 34% | 35% | 37% | 37% | 35% | 37% | 37% | 35% |
| Specificity | 91% | 90% | 80% | 89% | 88% | 79% | 87% | 86% | 79% |
| OR Quartile 2 | 2.64 | 2.15 | 2.25 | 2.50 | 2.05 | 2.43 | 2.88 | 2.39 | 2.41 |
| p Value | 2.7E−4 | 0.0038 | 0.0079 | 5.9E−4 | 0.0068 | 0.0064 | 1.2E−4 | 0.0014 | 0.0084 |
| Lower limit of 95% CI | 1.57 | 1.28 | 1.24 | 1.48 | 1.22 | 1.28 | 1.68 | 1.40 | 1.25 |
| Upper limit of 95% CI | 4.46 | 3.60 | 4.09 | 4.22 | 3.45 | 4.59 | 4.94 | 4.08 | 4.64 |
| OR Quartile 3 | 2.83 | 2.37 | 2.03 | 2.65 | 2.16 | 2.13 | 2.84 | 2.28 | 2.36 |
| p Value | 2.4E−5 | 2.6E−4 | 0.0036 | 2.9E−5 | 7.8E−4 | 0.0027 | 6.9E−6 | 3.5E−4 | 9.6E−4 |
| Lower limit of 95% CI | 1.75 | 1.49 | 1.26 | 1.68 | 1.38 | 1.30 | 1.80 | 1.45 | 1.42 |
| Upper limit of 95% CI | 4.59 | 3.77 | 3.27 | 4.18 | 3.39 | 3.50 | 4.49 | 3.57 | 3.92 |
| OR Quartile 4 | 5.11 | 4.47 | 2.09 | 4.62 | 4.26 | 2.01 | 4.04 | 3.74 | 1.98 |
| p Value | 6.9E−6 | 5.7E−6 | 0.0057 | 7.0E−7 | 1.2E−6 | 0.010 | 1.4E−6 | 3.3E−6 | 0.013 |
| Lower limit of 95% CI | 2.51 | 2.34 | 1.24 | 2.52 | 2.37 | 1.18 | 2.29 | 2.14 | 1.15 |
| Upper limit of 95% CI | 10.4 | 8.54 | 3.52 | 8.45 | 7.65 | 3.43 | 7.13 | 6.52 | 3.40 |

TABLE 17.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 12.5 | 34.6 | 14.0 | 35.9 | 13.3 | 36.7 |
| Average | 26.9 | 226 | 30.6 | 259 | 32.6 | 273 |
| Stdev | 47.5 | 940 | 49.0 | 1020 | 54.2 | 1050 |
| p (t-test) | 0.030 | | 0.0090 | | 0.0055 | |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 106 | 211 | 138 | 179 | 150 | 167 |
| sCr only | | | | | | |
| Median | 13.3 | 34.8 | 15.9 | 36.2 | 15.1 | 36.9 |
| Average | 29.1 | 240 | 31.5 | 269 | 33.3 | 286 |
| Stdev | 47.7 | 977 | 48.5 | 1040 | 53.5 | 1080 |
| p (t-test) | 0.018 | | 0.0063 | | 0.0036 | |
| Min | 0.00110 | 0.00167 | 0.00110 | 0.00167 | 0.00110 | 0.00167 |
| Max | 409 | 9030 | 409 | 9030 | 409 | 9030 |
| n (Patient) | 121 | 195 | 146 | 170 | 158 | 158 |
| UO only | | | | | | |
| Median | 17.7 | 37.0 | 18.1 | 37.0 | 18.2 | 37.9 |
| Average | 97.1 | 273 | 103 | 279 | 103 | 287 |
| Stdev | 648 | 955 | 641 | 990 | 634 | 1010 |

TABLE 17.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.053 | | | 0.058 | | | 0.050 | |
| Min | 0.00110 | | 0.00277 | 0.00110 | | 0.00277 | 0.00110 | | 0.00277 |
| Max | 9030 | | 7570 | 9030 | | 7570 | 9030 | | 7570 |
| n (Patient) | 202 | | 113 | 212 | | 103 | 217 | | 98 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.67 | 0.65 | 0.67 | 0.66 | 0.64 | 0.68 | 0.67 | 0.64 |
| SE | 0.030 | 0.030 | 0.033 | 0.030 | 0.030 | 0.034 | 0.030 | 0.030 | 0.035 |
| p Value | 5.2E−10 | 2.6E−8 | 1.1E−5 | 5.1E−9 | 8.2E−8 | 2.9E−5 | 7.4E−10 | 1.4E−8 | 3.8E−5 |
| nCohort Non-persistent | 106 | 121 | 202 | 138 | 146 | 212 | 150 | 158 | 217 |
| nCohort Persistent | 211 | 195 | 113 | 179 | 170 | 103 | 167 | 158 | 98 |
| Cutoff Quartile 2 | 8.33 | 8.31 | 8.36 | 8.33 | 8.31 | 8.36 | 8.33 | 8.31 | 8.36 |
| Sensitivity | 82% | 81% | 85% | 83% | 82% | 86% | 84% | 84% | 87% |
| Specificity | 38% | 35% | 31% | 35% | 33% | 31% | 35% | 34% | 30% |
| Cutoff Quartile 3 | 24.1 | 23.6 | 24.1 | 24.1 | 23.6 | 24.1 | 24.1 | 23.6 | 24.1 |
| Sensitivity | 59% | 58% | 63% | 60% | 59% | 63% | 62% | 61% | 64% |
| Specificity | 67% | 64% | 57% | 63% | 61% | 56% | 63% | 61% | 56% |
| Cutoff Quartile 4 | 60.9 | 60.8 | 61.8 | 60.9 | 60.8 | 61.8 | 60.9 | 60.8 | 61.8 |
| Sensitivity | 34% | 34% | 35% | 36% | 36% | 35% | 37% | 37% | 35% |
| Specificity | 92% | 90% | 81% | 89% | 88% | 80% | 87% | 87% | 79% |
| OR Quartile 2 | 2.67 | 2.27 | 2.50 | 2.55 | 2.20 | 2.81 | 2.96 | 2.56 | 2.86 |
| p Value | 2.4E−4 | 0.0019 | 0.0026 | 4.5E−4 | 0.0030 | 0.0014 | 7.1E−5 | 5.6E−4 | 0.0016 |
| Lower limit of 95% CI | 1.58 | 1.35 | 1.38 | 1.51 | 1.31 | 1.49 | 1.73 | 1.50 | 1.49 |
| Upper limit of 95% CI | 4.52 | 3.81 | 4.54 | 4.29 | 3.70 | 5.30 | 5.06 | 4.37 | 5.48 |
| OR Quartile 3 | 2.89 | 2.46 | 2.23 | 2.59 | 2.29 | 2.19 | 2.70 | 2.40 | 2.31 |
| p Value | 2.1E−5 | 1.6E−4 | 8.5E−4 | 4.4E−5 | 3.4E−4 | 0.0015 | 1.8E−5 | 1.5E−4 | 8.6E−4 |
| Lower limit of 95% CI | 1.77 | 1.54 | 1.39 | 1.64 | 1.45 | 1.35 | 1.71 | 1.53 | 1.41 |
| Upper limit of 95% CI | 4.71 | 3.93 | 3.58 | 4.10 | 3.59 | 3.55 | 4.26 | 3.77 | 3.78 |
| OR Quartile 4 | 5.47 | 4.75 | 2.29 | 4.68 | 4.36 | 2.11 | 3.97 | 3.78 | 2.03 |
| p Value | 6.9E−6 | 4.4E−6 | 0.0018 | 9.4E−7 | 1.2E−6 | 0.0053 | 2.6E−6 | 3.4E−6 | 0.0088 |
| Lower limit of 95% CI | 2.61 | 2.44 | 1.36 | 2.52 | 2.40 | 1.25 | 2.23 | 2.16 | 1.20 |
| Upper limit of 95% CI | 11.5 | 9.25 | 3.85 | 8.66 | 7.89 | 3.57 | 7.05 | 6.64 | 3.45 |

TABLE 17.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 2870 | 3560 | 3000 | 3640 | 3110 | 3520 |
| Average | 3210 | 4220 | 3360 | 4330 | 3520 | 4290 |
| Stdev | 1650 | 2690 | 1670 | 2880 | 1860 | 2920 |
| p (t-test) | | 2.8E−4 | | 2.5E−4 | | 0.0044 |
| Min | 1080 | 863 | 1080 | 863 | 1080 | 863 |
| Max | 9820 | 19700 | 9820 | 19700 | 14500 | 19700 |
| n (Patient) | 114 | 213 | 155 | 172 | 179 | 148 |

TABLE 17.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | sCr only | | | | | |
|---|---|---|---|---|---|---|
| Median | 2930 | 3510 | 2950 | 3560 | 3070 | 3670 |
| Average | 3290 | 4210 | 3310 | 4370 | 3460 | 4360 |
| Stdev | 1640 | 2750 | 1580 | 2920 | 1810 | 2960 |
| p (t-test) | | 7.5E−4 | | 6.7E−5 | | 8.3E−4 |
| Min | 1080 | 863 | 1080 | 863 | 1080 | 863 |
| Max | 9820 | 19700 | 9820 | 19700 | 14500 | 19700 |
| n (Patient) | 124 | 202 | 157 | 169 | 182 | 144 |
| | UO only | | | | | |
| Median | 3040 | 4350 | 3100 | 4340 | 3100 | 4390 |
| Average | 3520 | 4910 | 3570 | 5040 | 3570 | 5240 |
| Stdev | 2050 | 3060 | 2050 | 3280 | 2050 | 3390 |
| p (t-test) | | 6.0E−6 | | 1.0E−5 | | 1.8E−6 |
| Min | 893 | 863 | 893 | 863 | 893 | 863 |
| Max | 19700 | 18800 | 19700 | 18800 | 19700 | 18800 |
| n (Patient) | 245 | 80 | 261 | 64 | 269 | 56 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.61 | 0.65 | 0.61 | 0.61 | 0.64 | 0.57 | 0.59 | 0.66 |
| SE | 0.031 | 0.031 | 0.037 | 0.031 | 0.031 | 0.040 | 0.032 | 0.032 | 0.042 |
| p Value | 3.1E−5 | 6.1E−4 | 2.8E−5 | 5.8E−4 | 2.9E−4 | 3.6E−4 | 0.027 | 0.0057 | 1.3E−4 |
| nCohort Non-persistent | 114 | 124 | 245 | 155 | 157 | 261 | 179 | 182 | 269 |
| nCohort Persistent | 213 | 202 | 80 | 172 | 169 | 64 | 148 | 144 | 56 |
| Cutoff Quartile 2 | 2320 | 2320 | 2330 | 2320 | 2320 | 2330 | 2320 | 2320 | 2330 |
| Sensitivity | 81% | 81% | 85% | 81% | 82% | 86% | 80% | 80% | 88% |
| Specificity | 37% | 35% | 28% | 32% | 32% | 28% | 29% | 29% | 28% |
| Cutoff Quartile 3 | 3280 | 3280 | 3280 | 3280 | 3280 | 3280 | 3280 | 3280 | 3280 |
| Sensitivity | 56% | 55% | 66% | 56% | 56% | 64% | 55% | 56% | 66% |
| Specificity | 61% | 58% | 55% | 57% | 57% | 53% | 54% | 54% | 53% |
| Cutoff Quartile 4 | 4720 | 4710 | 4720 | 4720 | 4710 | 4720 | 4720 | 4710 | 4720 |
| Sensitivity | 31% | 31% | 39% | 32% | 33% | 36% | 30% | 33% | 38% |
| Specificity | 86% | 85% | 79% | 83% | 83% | 77% | 79% | 81% | 77% |
| OR Quartile 2 | 2.52 | 2.22 | 2.22 | 2.08 | 2.14 | 2.33 | 1.61 | 1.63 | 2.66 |
| p Value | 4.1E−4 | 0.0021 | 0.020 | 0.0049 | 0.0036 | 0.028 | 0.069 | 0.065 | 0.022 |
| Lower limit of 95% CI | 1.51 | 1.33 | 1.13 | 1.25 | 1.28 | 1.09 | 0.963 | 0.971 | 1.15 |
| Upper limit of 95% CI | 4.21 | 3.69 | 4.36 | 3.47 | 3.58 | 4.95 | 2.69 | 2.73 | 6.13 |
| OR Quartile 3 | 2.05 | 1.69 | 2.41 | 1.70 | 1.68 | 2.03 | 1.40 | 1.49 | 2.21 |
| p Value | 0.0024 | 0.023 | 0.0011 | 0.018 | 0.020 | 0.014 | 0.13 | 0.075 | 0.0099 |
| Lower limit of 95% CI | 1.29 | 1.08 | 1.42 | 1.10 | 1.08 | 1.15 | 0.903 | 0.961 | 1.21 |
| Upper limit of 95% CI | 3.27 | 2.65 | 4.08 | 2.63 | 2.60 | 3.58 | 2.16 | 2.31 | 4.04 |
| OR Quartile 4 | 2.75 | 2.50 | 2.41 | 2.23 | 2.50 | 1.92 | 1.68 | 2.04 | 2.05 |
| p Value | 0.0010 | 0.0017 | 0.0016 | 0.0027 | 7.0E−4 | 0.029 | 0.044 | 0.0060 | 0.022 |
| Lower limit of 95% CI | 1.50 | 1.41 | 1.39 | 1.32 | 1.47 | 1.07 | 1.01 | 1.23 | 1.11 |
| Upper limit of 95% CI | 5.03 | 4.44 | 4.15 | 3.76 | 4.24 | 3.46 | 2.77 | 3.38 | 3.77 |

TABLE 17.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

|  | Persistence Period Duration (hr) | | | | | |
|---|---|---|---|---|---|---|
|  | 24 | | 48 | | 72 | |
|  | Non-persistent Cohort | Persistent Cohort | Non-persistent Cohort | Persistent Cohort | Non-persistent Cohort | Persistent Cohort |
| | sCr or UO | | | | | |
| Median | 2820 | 3560 | 2910 | 3720 | 3080 | 3520 |
| Average | 3120 | 4240 | 3230 | 4370 | 3450 | 4300 |
| Stdev | 1530 | 2690 | 1500 | 2860 | 1780 | 2880 |
| p (t-test) |  | 6.7E−5 |  | 1.8E−5 |  | 0.0015 |
| Min | 1080 | 863 | 1080 | 863 | 1080 | 863 |
| Max | 9100 | 19700 | 9100 | 19700 | 14500 | 19700 |
| n (Patient) | 108 | 219 | 144 | 183 | 164 | 163 |
| | sCr only | | | | | |
| Median | 2900 | 3510 | 2950 | 3520 | 3100 | 3500 |
| Average | 3260 | 4210 | 3290 | 4340 | 3490 | 4240 |
| Stdev | 1640 | 2730 | 1590 | 2870 | 1860 | 2860 |
| p (t-test) |  | 5.8E−4 |  | 9.0E−5 |  | 0.0052 |
| Min | 1080 | 863 | 1080 | 863 | 1080 | 863 |
| Max | 9820 | 19700 | 9820 | 19700 | 14500 | 19700 |
| n (Patient) | 120 | 206 | 149 | 177 | 166 | 160 |
| | UO only | | | | | |
| Median | 3030 | 3960 | 3070 | 3930 | 3080 | 3930 |
| Average | 3460 | 4760 | 3520 | 4830 | 3530 | 4930 |
| Stdev | 2020 | 2930 | 2030 | 3090 | 2020 | 3150 |
| p (t-test) |  | 5.6E−6 |  | 1.5E−5 |  | 5.9E−6 |
| Min | 893 | 863 | 893 | 863 | 893 | 863 |
| Max | 19700 | 18800 | 19700 | 18800 | 19700 | 18800 |
| n (Patient) | 225 | 100 | 241 | 84 | 248 | 77 |

|  | Persistence Period Duration (hr) | | | | | | | | |
|---|---|---|---|---|---|---|---|---|---|
|  | 24 | | | 48 | | | 72 | | |
|  | sCr or UO | sCr only | UO only | sCr or UO | sCr only | UO only | sCr or UO | sCr only | UO only |
| AUC | 0.65 | 0.61 | 0.65 | 0.63 | 0.61 | 0.63 | 0.58 | 0.57 | 0.64 |
| SE | 0.031 | 0.031 | 0.034 | 0.031 | 0.031 | 0.037 | 0.031 | 0.032 | 0.038 |
| p Value | 2.9E−6 | 2.6E−4 | 1.6E−5 | 2.8E−5 | 2.2E−4 | 2.6E−4 | 0.011 | 0.022 | 1.5E−4 |
| nCohort Non-persistent | 108 | 120 | 225 | 144 | 149 | 241 | 164 | 166 | 248 |
| nCohort Persistent | 219 | 206 | 100 | 183 | 177 | 84 | 163 | 160 | 77 |
| Cutoff Quartile 2 | 2320 | 2320 | 2330 | 2320 | 2320 | 2330 | 2320 | 2320 | 2330 |
| Sensitivity | 82% | 81% | 86% | 82% | 82% | 87% | 80% | 80% | 88% |
| Specificity | 39% | 36% | 30% | 34% | 34% | 29% | 30% | 30% | 29% |
| Cutoff Quartile 3 | 3280 | 3280 | 3280 | 3280 | 3280 | 3280 | 3280 | 3280 | 3280 |
| Sensitivity | 57% | 55% | 64% | 57% | 56% | 62% | 55% | 54% | 62% |
| Specificity | 63% | 59% | 56% | 58% | 57% | 54% | 54% | 54% | 54% |
| Cutoff Quartile 4 | 4720 | 4710 | 4720 | 4720 | 4710 | 4720 | 4720 | 4710 | 4720 |
| Sensitivity | 31% | 31% | 36% | 33% | 32% | 33% | 31% | 30% | 34% |
| Specificity | 87% | 85% | 80% | 85% | 83% | 78% | 80% | 80% | 77% |
| OR Quartile 2 | 2.85 | 2.39 | 2.60 | 2.34 | 2.29 | 2.72 | 1.68 | 1.72 | 3.09 |
| p Value | 7.2E−5 | 8.2E−4 | 0.0030 | 0.0011 | 0.0015 | 0.0047 | 0.046 | 0.036 | 0.0031 |
| Lower limit of 95% CI | 1.70 | 1.44 | 1.38 | 1.41 | 1.37 | 1.36 | 1.01 | 1.04 | 1.46 |
| Upper limit of 95% CI | 4.78 | 3.98 | 4.91 | 3.91 | 3.82 | 5.43 | 2.79 | 2.87 | 6.53 |
| OR Quartile 3 | 2.22 | 1.80 | 2.26 | 1.84 | 1.69 | 1.90 | 1.43 | 1.34 | 1.91 |
| p Value | 9.6E−4 | 0.012 | 9.9E−4 | 0.0067 | 0.020 | 0.013 | 0.11 | 0.18 | 0.015 |
| Lower limit of 95% CI | 1.38 | 1.14 | 1.39 | 1.18 | 1.09 | 1.15 | 0.924 | 0.869 | 1.13 |
| Upper limit of 95% CI | 3.56 | 2.83 | 3.68 | 2.87 | 2.62 | 3.16 | 2.21 | 2.08 | 3.23 |

TABLE 17.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.02 | 2.55 | 2.19 | 2.71 | 2.36 | 1.73 | 1.83 | 1.66 | 1.75 |
| p Value | 5.8E−4 | 0.0016 | 0.0032 | 3.8E−4 | 0.0016 | 0.049 | 0.021 | 0.049 | 0.050 |
| Lower limit of 95% CI | 1.61 | 1.43 | 1.30 | 1.56 | 1.38 | 1.00 | 1.10 | 1.00 | 1.00 |
| Upper limit of 95% CI | 5.68 | 4.57 | 3.69 | 4.68 | 4.01 | 2.99 | 3.04 | 2.76 | 3.05 |

TABLE 17.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 2800 | 3540 | 2910 | 3560 | 3100 | 3490 |
| Average | 3120 | 4240 | 3230 | 4360 | 3440 | 4270 |
| Stdev | 1540 | 2680 | 1510 | 2850 | 1800 | 2840 |
| p (t-test) | | 7.6E−5 | | 2.7E−5 | | 0.0021 |
| Min | 1080 | 863 | 1080 | 863 | 1080 | 863 |
| Max | 9100 | 19700 | 9100 | 19700 | 14500 | 19700 |
| n (Patient) | 107 | 220 | 142 | 185 | 158 | 169 |
| *sCr only* | | | | | | |
| Median | 2870 | 3510 | 2930 | 3520 | 3100 | 3480 |
| Average | 3210 | 4230 | 3260 | 4350 | 3440 | 4270 |
| Stdev | 1540 | 2740 | 1510 | 2880 | 1790 | 2860 |
| p (t-test) | | 2.1E−4 | | 4.0E−5 | | 0.0021 |
| Min | 1080 | 863 | 1080 | 863 | 1080 | 863 |
| Max | 9100 | 19700 | 9100 | 19700 | 14500 | 19700 |
| n (Patient) | 118 | 208 | 146 | 180 | 160 | 166 |
| *UO only* | | | | | | |
| Median | 3010 | 3920 | 3100 | 3720 | 3100 | 3790 |
| Average | 3440 | 4700 | 3520 | 4690 | 3530 | 4770 |
| Stdev | 2020 | 2870 | 2020 | 3020 | 2020 | 3070 |
| p (t-test) | | 6.4E−6 | | 6.1E−5 | | 3.1E−5 |
| Min | 893 | 863 | 893 | 863 | 893 | 863 |
| Max | 19700 | 18800 | 19700 | 18800 | 19700 | 18800 |
| n (Patient) | 216 | 109 | 230 | 95 | 237 | 88 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.62 | 0.65 | 0.63 | 0.62 | 0.62 | 0.58 | 0.58 | 0.62 |
| SE | 0.031 | 0.031 | 0.033 | 0.031 | 0.031 | 0.035 | 0.031 | 0.032 | 0.036 |
| p Value | 3.1E−6 | 1.1E−4 | 1.1E−5 | 4.0E−5 | 1.3E−4 | 8.9E−4 | 0.010 | 0.012 | 6.2E−4 |
| nCohort Non-persistent | 107 | 118 | 216 | 142 | 146 | 230 | 158 | 160 | 237 |
| nCohort Persistent | 220 | 208 | 109 | 185 | 180 | 95 | 169 | 166 | 88 |
| Cutoff Quartile 2 | 2320 | 2320 | 2330 | 2320 | 2320 | 2330 | 2320 | 2320 | 2330 |
| Sensitivity | 82% | 81% | 86% | 82% | 82% | 85% | 80% | 81% | 86% |
| Specificity | 39% | 36% | 31% | 35% | 34% | 29% | 31% | 31% | 29% |
| Cutoff Quartile 3 | 3280 | 3280 | 3280 | 3280 | 3280 | 3280 | 3280 | 3280 | 3280 |
| Sensitivity | 56% | 55% | 61% | 56% | 56% | 58% | 53% | 53% | 58% |
| Specificity | 63% | 59% | 56% | 58% | 57% | 53% | 53% | 53% | 53% |
| Cutoff Quartile 4 | 4720 | 4710 | 4720 | 4720 | 4710 | 4720 | 4720 | 4710 | 4720 |
| Sensitivity | 31% | 31% | 36% | 32% | 32% | 33% | 30% | 30% | 33% |
| Specificity | 87% | 86% | 80% | 85% | 84% | 78% | 80% | 80% | 78% |

TABLE 17.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 2.91 | 2.48 | 2.76 | 2.43 | 2.41 | 2.38 | 1.85 | 1.90 | 2.60 |
| p Value | 5.3E−5 | 4.9E−4 | 0.0013 | 6.8E−4 | 7.8E−4 | 0.0075 | 0.017 | 0.013 | 0.0052 |
| Lower limit of 95% CI | 1.73 | 1.49 | 1.49 | 1.46 | 1.44 | 1.26 | 1.11 | 1.14 | 1.33 |
| Upper limit of 95% CI | 4.88 | 4.14 | 5.11 | 4.05 | 4.02 | 4.49 | 3.08 | 3.17 | 5.08 |
| OR Quartile 3 | 2.16 | 1.80 | 1.99 | 1.75 | 1.65 | 1.55 | 1.29 | 1.28 | 1.54 |
| p Value | 0.0014 | 0.012 | 0.0040 | 0.013 | 0.026 | 0.074 | 0.25 | 0.27 | 0.088 |
| Lower limit of 95% CI | 1.35 | 1.14 | 1.25 | 1.13 | 1.06 | 0.959 | 0.837 | 0.828 | 0.939 |
| Upper limit of 95% CI | 3.47 | 2.85 | 3.19 | 2.73 | 2.56 | 2.52 | 2.00 | 1.98 | 2.52 |
| OR Quartile 4 | 2.97 | 2.70 | 2.24 | 2.62 | 2.42 | 1.70 | 1.77 | 1.72 | 1.71 |
| p Value | 7.1E−4 | 1.0E−3 | 0.0021 | 5.9E−4 | 0.0013 | 0.050 | 0.029 | 0.036 | 0.052 |
| Lower limit of 95% CI | 1.58 | 1.49 | 1.34 | 1.51 | 1.41 | 1.00 | 1.06 | 1.04 | 0.995 |
| Upper limit of 95% CI | 5.58 | 4.88 | 3.75 | 4.53 | 4.14 | 2.89 | 2.95 | 2.87 | 2.93 |

TABLE 17.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 2820 | 3520 | 2910 | 3560 | 3090 | 3500 |
| Average | 3130 | 4230 | 3240 | 4340 | 3440 | 4250 |
| Stdev | 1540 | 2680 | 1520 | 2840 | 1810 | 2820 |
| p (t-test) | | 1.1E−4 | | 3.6E−5 | | 0.0024 |
| Min | 1080 | 863 | 1080 | 863 | 1080 | 863 |
| Max | 9100 | 19700 | 9100 | 19700 | 14500 | 19700 |
| n (Patient) | 106 | 221 | 140 | 187 | 155 | 172 |
| | sCr only | | | | | |
| Median | 2870 | 3510 | 2930 | 3520 | 3100 | 3480 |
| Average | 3210 | 4230 | 3260 | 4340 | 3450 | 4250 |
| Stdev | 1540 | 2740 | 1520 | 2870 | 1800 | 2850 |
| p (t-test) | | 2.1E−4 | | 5.4E−5 | | 0.0027 |
| Min | 1080 | 863 | 1080 | 863 | 1080 | 863 |
| Max | 9100 | 19700 | 9100 | 19700 | 14500 | 19700 |
| n (Patient) | 118 | 208 | 144 | 182 | 158 | 168 |
| | UO only | | | | | |
| Median | 3010 | 3880 | 3070 | 3790 | 3070 | 3890 |
| Average | 3450 | 4610 | 3490 | 4670 | 3490 | 4740 |
| Stdev | 2040 | 2840 | 2020 | 2960 | 2020 | 2990 |
| p (t-test) | | 2.8E−5 | | 3.5E−5 | | 1.7E−5 |
| Min | 893 | 863 | 893 | 863 | 893 | 863 |
| Max | 19700 | 18800 | 19700 | 18800 | 19700 | 18800 |
| n (Patient) | 211 | 114 | 223 | 102 | 229 | 96 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.63 | 0.62 | 0.62 | 0.62 | 0.58 | 0.58 | 0.63 |
| SE | 0.031 | 0.031 | 0.033 | 0.031 | 0.031 | 0.034 | 0.031 | 0.032 | 0.035 |
| p Value | 6.5E−6 | 1.1E−4 | 5.7E−5 | 5.1E−5 | 1.7E−4 | 3.4E−4 | 0.0094 | 0.014 | 1.7E−4 |
| nCohort Non-persistent | 106 | 118 | 211 | 140 | 144 | 223 | 155 | 158 | 229 |

TABLE 17.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Persistent | 221 | 208 | 114 | 187 | 182 | 102 | 172 | 168 | 96 |
| Cutoff Quartile 2 | 2320 | 2320 | 2330 | 2320 | 2320 | 2330 | 2320 | 2320 | 2330 |
| Sensitivity | 81% | 81% | 85% | 82% | 82% | 85% | 80% | 80% | 86% |
| Specificity | 39% | 36% | 30% | 34% | 34% | 30% | 31% | 31% | 30% |
| Cutoff Quartile 3 | 3280 | 3280 | 3280 | 3280 | 3280 | 3280 | 3280 | 3280 | 3280 |
| Sensitivity | 56% | 55% | 60% | 56% | 55% | 58% | 53% | 53% | 58% |
| Specificity | 62% | 59% | 55% | 58% | 57% | 53% | 54% | 53% | 53% |
| Cutoff Quartile 4 | 4720 | 4710 | 4720 | 4720 | 4710 | 4720 | 4720 | 4710 | 4720 |
| Sensitivity | 31% | 31% | 34% | 32% | 32% | 33% | 30% | 30% | 33% |
| Specificity | 87% | 86% | 80% | 84% | 83% | 78% | 80% | 80% | 78% |
| OR Quartile 2 | 2.77 | 2.48 | 2.48 | 2.35 | 2.33 | 2.44 | 1.82 | 1.84 | 2.70 |
| p Value | 1.1E−4 | 4.9E−4 | 0.0026 | 0.0010 | 0.0012 | 0.0048 | 0.020 | 0.019 | 0.0028 |
| Lower limit of 95% CI | 1.65 | 1.49 | 1.37 | 1.41 | 1.40 | 1.31 | 1.10 | 1.11 | 1.41 |
| Upper limit of 95% CI | 4.65 | 4.14 | 4.50 | 3.91 | 3.88 | 4.53 | 3.02 | 3.06 | 5.16 |
| OR Quartile 3 | 2.11 | 1.80 | 1.81 | 1.76 | 1.65 | 1.57 | 1.33 | 1.28 | 1.60 |
| p Value | 0.0020 | 0.012 | 0.012 | 0.012 | 0.026 | 0.062 | 0.20 | 0.27 | 0.057 |
| Lower limit of 95% CI | 1.31 | 1.14 | 1.14 | 1.13 | 1.06 | 0.978 | 0.858 | 0.828 | 0.986 |
| Upper limit of 95% CI | 3.39 | 2.85 | 2.87 | 2.74 | 2.56 | 2.52 | 2.05 | 1.98 | 2.58 |
| OR Quartile 4 | 2.92 | 2.70 | 2.03 | 2.53 | 2.34 | 1.82 | 1.69 | 1.67 | 1.79 |
| p Value | 8.7E−4 | 1.0E−3 | 0.0066 | 9.0E−4 | 0.0020 | 0.024 | 0.045 | 0.049 | 0.031 |
| Lower limit of 95% CI | 1.55 | 1.49 | 1.22 | 1.46 | 1.37 | 1.08 | 1.01 | 1.00 | 1.06 |
| Upper limit of 95% CI | 5.49 | 4.88 | 3.39 | 4.39 | 4.00 | 3.07 | 2.81 | 2.78 | 3.03 |

TABLE 17.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 2850 | 3510 | 2920 | 3520 | 3090 | 3480 |
| Average | 3150 | 4200 | 3240 | 4310 | 3440 | 4230 |
| Stdev | 1570 | 2670 | 1540 | 2810 | 1830 | 2790 |
| p (t-test) | | 2.7E−4 | | 8.1E−5 | | 0.0034 |
| Min | 1080 | 863 | 1080 | 863 | 1080 | 863 |
| Max | 9100 | 19700 | 9100 | 19700 | 14500 | 19700 |
| n (Patient) | 102 | 225 | 135 | 192 | 149 | 178 |
| | sCr only | | | | | |
| Median | 2920 | 3500 | 2980 | 3510 | 3120 | 3450 |
| Average | 3230 | 4210 | 3270 | 4310 | 3460 | 4220 |
| Stdev | 1550 | 2730 | 1530 | 2850 | 1810 | 2830 |
| p (t-test) | | 4.6E−4 | | 1.1E−4 | | 0.0048 |
| Min | 1080 | 863 | 1080 | 863 | 1080 | 863 |
| Max | 9100 | 19700 | 9100 | 19700 | 14500 | 19700 |
| n (Patient) | 115 | 211 | 140 | 186 | 154 | 172 |

TABLE 17.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

UO only

|  |  |  |  |  |  |  |
|---|---|---|---|---|---|---|
| Median | 3010 | 3910 | 3050 | 3860 | 3040 | 3890 |
| Average | 3430 | 4580 | 3470 | 4620 | 3470 | 4670 |
| Stdev | 2030 | 2810 | 2010 | 2900 | 2020 | 2910 |
| p (t-test) |  | 2.7E−5 |  | 3.4E−5 |  | 2.0E−5 |
| Min | 893 | 863 | 893 | 863 | 893 | 863 |
| Max | 19700 | 18800 | 19700 | 18800 | 19700 | 18800 |
| n (Patient) | 204 | 121 | 214 | 111 | 219 | 106 |

Persistence Period Duration (hr)

|  | 24 | | | 48 | | | 72 | | |
|---|---|---|---|---|---|---|---|---|---|
|  | sCr or UO | sCr only | UO only | sCr or UO | sCr only | UO only | sCr or UO | sCr only | UO only |
| AUC | 0.63 | 0.61 | 0.63 | 0.62 | 0.61 | 0.62 | 0.58 | 0.57 | 0.63 |
| SE | 0.032 | 0.032 | 0.032 | 0.031 | 0.031 | 0.033 | 0.031 | 0.032 | 0.034 |
| p Value | 2.8E−5 | 3.8E−4 | 4.3E−5 | 1.0E−4 | 3.8E−4 | 2.2E−4 | 0.010 | 0.024 | 1.0E−4 |
| nCohort Non-persistent | 102 | 115 | 204 | 135 | 140 | 214 | 149 | 154 | 219 |
| nCohort Persistent | 225 | 211 | 121 | 192 | 186 | 111 | 178 | 172 | 106 |
| Cutoff Quartile 2 | 2320 | 2320 | 2330 | 2320 | 2320 | 2330 | 2320 | 2320 | 2330 |
| Sensitivity | 81% | 81% | 84% | 82% | 81% | 85% | 80% | 80% | 86% |
| Specificity | 38% | 36% | 30% | 35% | 34% | 30% | 32% | 31% | 30% |
| Cutoff Quartile 3 | 3280 | 3280 | 3280 | 3280 | 3280 | 3280 | 3280 | 3280 | 3280 |
| Sensitivity | 55% | 55% | 60% | 55% | 55% | 58% | 53% | 52% | 58% |
| Specificity | 61% | 58% | 55% | 57% | 56% | 54% | 53% | 53% | 54% |
| Cutoff Quartile 4 | 4720 | 4710 | 4720 | 4720 | 4710 | 4720 | 4720 | 4710 | 4720 |
| Sensitivity | 30% | 31% | 34% | 31% | 31% | 33% | 29% | 29% | 33% |
| Specificity | 86% | 85% | 80% | 84% | 83% | 79% | 80% | 79% | 79% |
| OR Quartile 2 | 2.62 | 2.30 | 2.34 | 2.40 | 2.18 | 2.36 | 1.88 | 1.72 | 2.62 |
| p Value | 2.8E−4 | 0.0014 | 0.0036 | 7.8E−4 | 0.0026 | 0.0046 | 0.014 | 0.036 | 0.0023 |
| Lower limit of 95% CI | 1.56 | 1.38 | 1.32 | 1.44 | 1.31 | 1.30 | 1.14 | 1.04 | 1.41 |
| Upper limit of 95% CI | 4.41 | 3.83 | 4.16 | 3.99 | 3.62 | 4.27 | 3.12 | 2.85 | 4.85 |
| OR Quartile 3 | 1.90 | 1.67 | 1.82 | 1.64 | 1.57 | 1.58 | 1.26 | 1.22 | 1.65 |
| p Value | 0.0081 | 0.028 | 0.0097 | 0.030 | 0.044 | 0.052 | 0.29 | 0.37 | 0.037 |
| Lower limit of 95% CI | 1.18 | 1.06 | 1.16 | 1.05 | 1.01 | 0.996 | 0.817 | 0.788 | 1.03 |
| Upper limit of 95% CI | 3.06 | 2.65 | 2.88 | 2.55 | 2.45 | 2.51 | 1.95 | 1.88 | 2.63 |
| OR Quartile 4 | 2.72 | 2.57 | 2.04 | 2.33 | 2.19 | 1.88 | 1.64 | 1.56 | 1.80 |
| p Value | 0.0019 | 0.0018 | 0.0061 | 0.0025 | 0.0043 | 0.016 | 0.060 | 0.086 | 0.025 |
| Lower limit of 95% CI | 1.45 | 1.42 | 1.22 | 1.35 | 1.28 | 1.12 | 0.979 | 0.938 | 1.08 |
| Upper limit of 95% CI | 5.12 | 4.64 | 3.39 | 4.04 | 3.75 | 3.14 | 2.74 | 2.60 | 3.03 |

Example 18. Use of C—C Motif Chemokine 15 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 15 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 18.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 22.0 | 289 | 10.3 | 274 | 0.0534 | 237 |
| Average | 144 | 2060 | 118 | 1990 | 120 | 1950 |
| Stdev | 265 | 6000 | 245 | 5890 | 260 | 5840 |
| p (t-test) | | 0.017 | | 0.032 | | 0.046 |
| Min | 0.0116 | 0.0116 | 0.0187 | 0.0116 | 0.0187 | 0.0116 |
| Max | 1160 | 53500 | 1160 | 53500 | 1160 | 53500 |
| n (Patient) | 57 | 259 | 46 | 270 | 41 | 275 |
| sCr only | | | | | | |
| Median | 7.54 | 338 | 7.54 | 338 | 7.54 | 316 |
| Average | 169 | 2210 | 173 | 2190 | 180 | 2160 |
| Stdev | 314 | 6230 | 317 | 6200 | 325 | 6160 |
| p (t-test) | | 0.0046 | | 0.0054 | | 0.0076 |
| Min | 0.0116 | 0.0116 | 0.0116 | 0.0116 | 0.0187 | 0.0116 |
| Max | 1300 | 53500 | 1300 | 53500 | 1300 | 53500 |
| n (Patient) | 76 | 239 | 74 | 241 | 70 | 245 |
| UO only | | | | | | |
| Median | 118 | 248 | 104 | 275 | 103 | 237 |
| Average | 1880 | 1470 | 1750 | 1690 | 1460 | 1980 |
| Stdev | 6590 | 3060 | 6510 | 3970 | 5360 | 5640 |
| p (t-test) | | 0.53 | | 0.92 | | 0.41 |
| Min | 0.0116 | 0.0116 | 0.0187 | 0.0116 | 0.0187 | 0.0116 |
| Max | 53500 | 19200 | 53500 | 30000 | 52500 | 53500 |
| n (Patient) | 193 | 121 | 172 | 142 | 155 | 159 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.72 | 0.55 | 0.71 | 0.71 | 0.56 | 0.72 | 0.70 | 0.57 |
| SE | 0.035 | 0.031 | 0.034 | 0.036 | 0.031 | 0.033 | 0.037 | 0.032 | 0.032 |
| p Value | 1.4E−8 | 2.1E−12 | 0.12 | 6.7E−9 | 1.9E−11 | 0.076 | 1.4E−9 | 3.8E−10 | 0.043 |
| nCohort Recovered | 57 | 76 | 193 | 46 | 74 | 172 | 41 | 70 | 155 |
| nCohort Non-recovered | 259 | 239 | 121 | 270 | 241 | 142 | 275 | 245 | 159 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 79% | 82% | 79% | 79% | 81% | 78% | 79% | 81% | 79% |
| Specificity | 35% | 39% | 25% | 37% | 39% | 24% | 41% | 39% | 26% |
| Cutoff Quartile 3 | 155 | 154 | 155 | 155 | 154 | 155 | 155 | 154 | 155 |
| Sensitivity | 56% | 59% | 55% | 56% | 58% | 56% | 55% | 57% | 55% |
| Specificity | 77% | 76% | 53% | 83% | 76% | 55% | 80% | 74% | 55% |
| Cutoff Quartile 4 | 909 | 912 | 902 | 909 | 912 | 902 | 909 | 912 | 902 |
| Sensitivity | 30% | 31% | 29% | 29% | 31% | 28% | 28% | 31% | 28% |
| Specificity | 96% | 95% | 77% | 96% | 95% | 77% | 95% | 94% | 78% |
| OR Quartile 2 | 2.05 | 2.89 | 1.27 | 2.19 | 2.81 | 1.16 | 2.71 | 2.65 | 1.33 |
| p Value | 0.023 | 2.3E−4 | 0.39 | 0.021 | 3.7E−4 | 0.59 | 0.0044 | 9.5E−4 | 0.29 |
| Lower limit of 95% CI | 1.10 | 1.64 | 0.735 | 1.13 | 1.59 | 0.682 | 1.36 | 1.49 | 0.785 |
| Upper limit of 95% CI | 3.82 | 5.08 | 2.20 | 4.26 | 4.95 | 1.96 | 5.38 | 4.71 | 2.25 |
| OR Quartile 3 | 4.30 | 4.56 | 1.42 | 5.94 | 4.31 | 1.59 | 4.95 | 3.85 | 1.54 |
| p Value | 1.7E−5 | 4.3E−7 | 0.13 | 1.3E−5 | 1.2E−6 | 0.042 | 1.0E−4 | 8.2E−6 | 0.055 |
| Lower limit of 95% CI | 2.21 | 2.53 | 0.899 | 2.67 | 2.39 | 1.02 | 2.21 | 2.13 | 0.990 |
| Upper limit of 95% CI | 8.38 | 8.20 | 2.24 | 13.2 | 7.78 | 2.49 | 11.1 | 6.97 | 2.41 |

TABLE 18.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 11.6 | 8.23 | 1.38 | 8.78 | 7.91 | 1.34 | 7.58 | 7.28 | 1.40 |
| p Value | 8.1E−4 | 7.5E−5 | 0.22 | 0.0031 | 1.0E−4 | 0.26 | 0.0060 | 2.0E−4 | 0.19 |
| Lower limit of 95% CI | 2.77 | 2.90 | 0.822 | 2.08 | 2.78 | 0.802 | 1.79 | 2.56 | 0.841 |
| Upper limit of 95% CI | 48.9 | 23.4 | 2.31 | 37.1 | 22.5 | 2.23 | 32.2 | 20.7 | 2.35 |

TABLE 18.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 22.1 | 373 | 18.3 | 355 | 9.44 | 346 |
| Average | 185 | 2330 | 176 | 2230 | 161 | 2170 |
| Stdev | 476 | 6380 | 492 | 6250 | 472 | 6150 |
| p (t-test) | | 0.0016 | | 0.0038 | | 0.0065 |
| Min | 0.0116 | 0.0116 | 0.0187 | 0.0116 | 0.0187 | 0.0116 |
| Max | 3630 | 53500 | 3630 | 53500 | 3630 | 53500 |
| n (Patient) | 90 | 226 | 79 | 237 | 71 | 245 |
| | sCr only | | | | | |
| Median | 18.3 | 403 | 18.3 | 394 | 18.3 | 373 |
| Average | 204 | 2480 | 208 | 2460 | 196 | 2410 |
| Stdev | 473 | 6590 | 477 | 6570 | 455 | 6500 |
| p (t-test) | | 4.5E−4 | | 5.7E−4 | | 8.1E−4 |
| Min | 0.0116 | 0.0116 | 0.0116 | 0.0116 | 0.0187 | 0.0116 |
| Max | 3630 | 53500 | 3630 | 53500 | 3630 | 53500 |
| n (Patient) | 106 | 210 | 104 | 212 | 99 | 217 |
| | UO only | | | | | |
| Median | 115 | 338 | 115 | 248 | 115 | 222 |
| Average | 1880 | 1410 | 2010 | 1260 | 1750 | 1690 |
| Stdev | 6360 | 3070 | 6630 | 2860 | 5640 | 5330 |
| p (t-test) | | 0.48 | | 0.24 | | 0.93 |
| Min | 0.0116 | 0.0116 | 0.0151 | 0.0116 | 0.0151 | 0.0116 |
| Max | 53500 | 19200 | 53500 | 19200 | 52500 | 53500 |
| n (Patient) | 211 | 103 | 193 | 121 | 177 | 137 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | SCr only | UO only | sCr or UO | SCr only | UO only |
| AUC | 0.72 | 0.73 | 0.55 | 0.73 | 0.73 | 0.53 | 0.73 | 0.73 | 0.54 |
| SE | 0.029 | 0.028 | 0.035 | 0.030 | 0.028 | 0.034 | 0.030 | 0.029 | 0.033 |
| p Value | 3.0E−14 | 0 | 0.18 | 3.1E−14 | 6.7E−16 | 0.33 | 8.2E−15 | 3.1E−15 | 0.23 |
| nCohort Recovered | 90 | 106 | 211 | 79 | 104 | 193 | 71 | 99 | 177 |
| nCohort Non-recovered | 226 | 210 | 103 | 237 | 212 | 121 | 245 | 217 | 137 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 81% | 84% | 79% | 81% | 83% | 78% | 82% | 83% | 79% |
| Specificity | 36% | 38% | 24% | 38% | 38% | 24% | 41% | 37% | 25% |
| Cutoff Quartile 3 | 155 | 155 | 155 | 155 | 155 | 155 | 155 | 155 | 155 |
| Sensitivity | 61% | 63% | 57% | 60% | 62% | 56% | 58% | 61% | 55% |
| Specificity | 78% | 75% | 54% | 80% | 75% | 54% | 79% | 75% | 54% |
| Cutoff Quartile 4 | 909 | 909 | 902 | 909 | 909 | 902 | 909 | 909 | 902 |
| Sensitivity | 33% | 35% | 28% | 32% | 34% | 26% | 31% | 34% | 26% |
| Specificity | 96% | 94% | 76% | 95% | 94% | 75% | 96% | 95% | 76% |
| OR Quartile 2 | 2.42 | 3.14 | 1.17 | 2.69 | 3.03 | 1.09 | 3.07 | 2.90 | 1.23 |
| p Value | 0.0015 | 3.1E−5 | 0.58 | 5.5E−4 | 5.2E−5 | 0.76 | 1.3E−4 | 1.1E−4 | 0.44 |

TABLE 18.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.40 | 1.83 | 0.666 | 1.53 | 1.77 | 0.634 | 1.73 | 1.69 | 0.723 |
| Upper limit of 95% CI | 4.17 | 5.37 | 2.07 | 4.70 | 5.19 | 1.87 | 5.44 | 4.98 | 2.10 |
| OR Quartile 3 | 5.49 | 5.21 | 1.55 | 5.89 | 4.95 | 1.50 | 5.23 | 4.69 | 1.40 |
| p Value | 3.3E−9 | 6.5E−10 | 0.072 | 1.0E−8 | 2.1E−9 | 0.083 | 2.0E−7 | 1.1E−8 | 0.14 |
| Lower limit of 95% CI | 3.12 | 3.08 | 0.962 | 3.21 | 2.93 | 0.949 | 2.80 | 2.76 | 0.896 |
| Upper limit of 95% CI | 9.65 | 8.79 | 2.49 | 10.8 | 8.36 | 2.37 | 9.77 | 7.96 | 2.19 |
| OR Quartile 4 | 10.7 | 8.88 | 1.26 | 8.68 | 8.58 | 1.04 | 10.2 | 9.73 | 1.11 |
| p Value | 8.1E−6 | 9.0E−7 | 0.39 | 4.8E−5 | 1.3E−6 | 0.88 | 1.3E−4 | 2.2E−6 | 0.69 |
| Lower limit of 95% CI | 3.77 | 3.72 | 0.740 | 3.06 | 3.59 | 0.617 | 3.11 | 3.79 | 0.665 |
| Upper limit of 95% CI | 30.2 | 21.2 | 2.15 | 24.6 | 20.5 | 1.75 | 33.4 | 25.0 | 1.85 |

TABLE 18.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 39.4 | 403 | 39.5 | 355 | 13.4 | 347 |
| Average | 365 | 2480 | 383 | 2400 | 386 | 2310 |
| Stdev | 1110 | 6700 | 1140 | 6600 | 1180 | 6460 |
| p (t-test) | | 9.4E−4 | | 0.0019 | | 0.0040 |
| Min | 0.0116 | 0.0116 | 0.0116 | 0.0116 | 0.0116 | 0.0116 |
| Max | 7940 | 53500 | 7940 | 53500 | 7940 | 53500 |
| n (Patient) | 114 | 202 | 107 | 209 | 97 | 219 |
| | sCr only | | | | | |
| Median | 36.6 | 423 | 39.4 | 403 | 36.6 | 366 |
| Average | 365 | 2620 | 373 | 2580 | 370 | 2530 |
| Stdev | 1060 | 6900 | 1070 | 6850 | 1080 | 6770 |
| p (t-test) | | 3.0E−4 | | 4.3E−4 | | 6.4E−4 |
| Min | 0.0116 | 0.0116 | 0.0116 | 0.0116 | 0.0116 | 0.0116 |
| Max | 7940 | 53500 | 7940 | 53500 | 7940 | 53500 |
| n (Patient) | 127 | 189 | 124 | 192 | 119 | 197 |
| | UO only | | | | | |
| Median | 118 | 338 | 118 | 237 | 115 | 222 |
| Average | 1870 | 1420 | 1950 | 1310 | 1740 | 1700 |
| Stdev | 6330 | 3100 | 6480 | 2970 | 5520 | 5490 |
| p (t-test) | | 0.50 | | 0.33 | | 0.95 |
| Min | 0.0116 | 0.0116 | 0.0116 | 0.0116 | 0.0116 | 0.0116 |
| Max | 53500 | 19200 | 53500 | 19200 | 52500 | 53500 |
| n (Patient) | 213 | 101 | 203 | 111 | 189 | 125 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.72 | 0.56 | 0.70 | 0.71 | 0.54 | 0.71 | 0.71 | 0.55 |
| SE | 0.029 | 0.028 | 0.035 | 0.030 | 0.029 | 0.034 | 0.030 | 0.029 | 0.033 |
| p Value | 8.5E−13 | 2.1E−14 | 0.10 | 1.4E−11 | 1.1E−12 | 0.19 | 4.2E−12 | 1.2E−12 | 0.15 |
| nCohort Recovered | 114 | 127 | 213 | 107 | 124 | 203 | 97 | 119 | 189 |
| nCohort Non-recovered | 202 | 189 | 101 | 209 | 192 | 111 | 219 | 197 | 125 |
| Cutoff Quartile 2 | 0.0489 | 0.0489 | 0.0489 | 0.0489 | 0.0489 | 0.0489 | 0.0489 | 0.0489 | 0.0489 |

TABLE 18.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 83% | 85% | 80% | 83% | 84% | 80% | 83% | 84% | 81% |
| Specificity | 34% | 35% | 25% | 36% | 35% | 25% | 38% | 35% | 26% |
| Cutoff Quartile 3 | 155 | 155 | 155 | 155 | 155 | 155 | 155 | 155 | 155 |
| Sensitivity | 62% | 64% | 57% | 61% | 63% | 56% | 60% | 62% | 55% |
| Specificity | 72% | 71% | 54% | 72% | 70% | 53% | 72% | 70% | 53% |
| Cutoff Quartile 4 | 909 | 909 | 902 | 909 | 909 | 902 | 909 | 909 | 902 |
| Sensitivity | 35% | 36% | 29% | 33% | 35% | 26% | 32% | 35% | 26% |
| Specificity | 92% | 91% | 77% | 92% | 91% | 75% | 92% | 92% | 76% |
| OR Quartile 2 | 2.48 | 3.03 | 1.34 | 2.65 | 2.76 | 1.36 | 3.03 | 2.81 | 1.47 |
| p Value | 8.0E−4 | 5.3E−5 | 0.32 | 3.6E−4 | 1.9E−4 | 0.29 | 5.8E−5 | 1.5E−4 | 0.17 |
| Lower limit of 95% CI | 1.46 | 1.77 | 0.751 | 1.55 | 1.62 | 0.772 | 1.77 | 1.65 | 0.849 |
| Upper limit of 95% CI | 4.22 | 5.18 | 2.40 | 4.52 | 4.70 | 2.39 | 5.21 | 4.80 | 2.56 |
| OR Quartile 3 | 4.25 | 4.33 | 1.55 | 4.06 | 4.01 | 1.44 | 3.86 | 3.75 | 1.41 |
| p Value | 1.2E−8 | 3.1E−9 | 0.071 | 5.6E−8 | 1.8E−8 | 0.13 | 3.5E−7 | 9.5E−8 | 0.13 |
| Lower limit of 95% CI | 2.58 | 2.67 | 0.963 | 2.45 | 2.47 | 0.903 | 2.30 | 2.31 | 0.898 |
| Upper limit of 95% CI | 6.99 | 7.03 | 2.50 | 6.72 | 6.50 | 2.29 | 6.49 | 6.09 | 2.23 |
| OR Quartile 4 | 6.19 | 5.93 | 1.31 | 5.48 | 5.63 | 1.08 | 5.34 | 5.88 | 1.12 |
| p Value | 1.4E−6 | 3.7E−7 | 0.32 | 6.7E−6 | 7.9E−7 | 0.77 | 2.4E−5 | 1.0E−6 | 0.68 |
| Lower limit of 95% CI | 2.95 | 2.98 | 0.769 | 2.61 | 2.84 | 0.637 | 2.45 | 2.89 | 0.664 |
| Upper limit of 95% CI | 13.0 | 11.8 | 2.24 | 11.5 | 11.2 | 1.84 | 11.6 | 12.0 | 1.87 |

TABLE 18.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 40.2 | 420 | 48.0 | 355 | 39.4 | 351 |
| Average | 430 | 2660 | 455 | 2540 | 464 | 2420 |
| Stdev | 1260 | 7000 | 1300 | 6860 | 1350 | 6690 |
| p (t-test) | | 3.1E−4 | | 8.7E−4 | | 0.0022 |
| Min | 0.0116 | 0.0116 | 0.0116 | 0.0116 | 0.0116 | 0.0116 |
| Max | 8690 | 53500 | 8690 | 53500 | 8690 | 53500 |
| n (Patient) | 134 | 182 | 125 | 191 | 114 | 202 |
| | sCr only | | | | | |
| Median | 40.2 | 436 | 44.1 | 420 | 40.2 | 406 |
| Average | 425 | 2740 | 431 | 2710 | 426 | 2680 |
| Stdev | 1240 | 7110 | 1250 | 7070 | 1250 | 7020 |
| p (t-test) | | 1.7E−4 | | 2.2E−4 | | 2.7E−4 |
| Min | 0.0116 | 0.0116 | 0.0116 | 0.0116 | 0.0116 | 0.0116 |
| Max | 8690 | 53500 | 8690 | 53500 | 8690 | 53500 |
| n (Patient) | 140 | 176 | 138 | 178 | 135 | 181 |
| | UO only | | | | | |
| Median | 118 | 248 | 123 | 223 | 118 | 222 |
| Average | 1860 | 1430 | 1930 | 1320 | 1720 | 1730 |
| Stdev | 6300 | 3130 | 6430 | 3010 | 5470 | 5580 |
| p (t-test) | | 0.52 | | 0.35 | | 0.98 |
| Min | 0.0116 | 0.0116 | 0.0116 | 0.0116 | 0.0116 | 0.0116 |
| Max | 53500 | 19200 | 53500 | 19200 | 52500 | 53500 |
| n (Patient) | 215 | 99 | 206 | 108 | 193 | 121 |

TABLE 18.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.71 | 0.55 | 0.69 | 0.70 | 0.54 | 0.69 | 0.70 | 0.54 |
| SE | 0.029 | 0.029 | 0.035 | 0.030 | 0.029 | 0.034 | 0.030 | 0.029 | 0.034 |
| p Value | 2.3E−12 | 2.8E−13 | 0.13 | 2.5E−10 | 6.1E−12 | 0.25 | 2.2E−10 | 7.9E−12 | 0.19 |
| nCohort Recovered | 134 | 140 | 215 | 125 | 138 | 206 | 114 | 135 | 193 |
| nCohort Non-recovered | 182 | 176 | 99 | 191 | 178 | 108 | 202 | 181 | 121 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 85% | 81% | 83% | 84% | 81% | 84% | 83% | 81% |
| Specificity | 33% | 34% | 25% | 34% | 33% | 25% | 36% | 33% | 26% |
| Cutoff Quartile 3 | 155 | 155 | 155 | 155 | 155 | 155 | 155 | 155 | 155 |
| Sensitivity | 64% | 65% | 58% | 62% | 64% | 56% | 61% | 64% | 55% |
| Specificity | 69% | 69% | 53% | 69% | 68% | 53% | 69% | 68% | 53% |
| Cutoff Quartile 4 | 909 | 909 | 902 | 909 | 909 | 902 | 909 | 909 | 902 |
| Sensitivity | 37% | 38% | 28% | 35% | 37% | 26% | 34% | 37% | 26% |
| Specificity | 91% | 91% | 76% | 90% | 91% | 75% | 90% | 91% | 76% |
| OR Quartile 2 | 2.48 | 2.79 | 1.41 | 2.51 | 2.49 | 1.40 | 2.88 | 2.43 | 1.49 |
| p Value | 8.4E−4 | 1.9E−4 | 0.25 | 6.7E−4 | 8.3E−4 | 0.25 | 1.1E−4 | 0.0010 | 0.16 |
| Lower limit of 95% CI | 1.45 | 1.63 | 0.785 | 1.48 | 1.46 | 0.790 | 1.69 | 1.43 | 0.854 |
| Upper limit of 95% CI | 4.22 | 4.78 | 2.54 | 4.28 | 4.24 | 2.48 | 4.91 | 4.14 | 2.60 |
| OR Quartile 3 | 4.08 | 4.01 | 1.56 | 3.64 | 3.81 | 1.40 | 3.51 | 3.73 | 1.42 |
| p Value | 7.1E−9 | 8.1E−9 | 0.069 | 1.2E−7 | 2.7E−8 | 0.15 | 4.5E−7 | 4.6E−8 | 0.13 |
| Lower limit of 95% CI | 2.54 | 2.50 | 0.965 | 2.26 | 2.38 | 0.880 | 2.16 | 2.33 | 0.899 |
| Upper limit of 95% CI | 6.57 | 6.43 | 2.52 | 5.88 | 6.10 | 2.24 | 5.73 | 5.98 | 2.24 |
| OR Quartile 4 | 5.92 | 5.86 | 1.27 | 5.09 | 5.67 | 1.06 | 4.75 | 6.02 | 1.12 |
| p Value | 1.6E−7 | 8.5E−8 | 0.39 | 1.6E−6 | 1.5E−7 | 0.82 | 8.7E−6 | 1.2E−7 | 0.68 |
| Lower limit of 95% CI | 3.05 | 3.07 | 0.740 | 2.62 | 2.97 | 0.624 | 2.39 | 3.10 | 0.663 |
| Upper limit of 95% CI | 11.5 | 11.2 | 2.17 | 9.90 | 10.8 | 1.81 | 9.44 | 11.7 | 1.88 |

TABLE 18.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 72.4 | 406 | 72.6 | 351 | 72.6 | 351 |
| Average | 1650 | 1810 | 1680 | 1770 | 1680 | 1770 |
| Stdev | 6260 | 4140 | 6300 | 4100 | 6300 | 4100 |
| p (t-test) | 0.80 | | 0.88 | | 0.88 | |
| Min | 0.0116 | 0.0116 | 0.0116 | 0.0116 | 0.0116 | 0.0116 |
| Max | 53500 | 34200 | 53500 | 34200 | 53500 | 34200 |
| n (Patient) | 187 | 129 | 184 | 132 | 184 | 132 |
| | sCr only | | | | | |
| Median | 53.2 | 531 | 54.2 | 492 | 55.3 | 488 |
| Average | 638 | 2810 | 648 | 2760 | 652 | 2740 |
| Stdev | 2630 | 7160 | 2660 | 7110 | 2670 | 7090 |
| p (t-test) | 3.9E−4 | | 5.8E−4 | | 6.6E−4 | |
| Min | 0.0116 | 0.0116 | 0.0116 | 0.0116 | 0.0116 | 0.0116 |
| Max | 30000 | 53500 | 30000 | 53500 | 30000 | 53500 |
| n (Patient) | 159 | 157 | 156 | 160 | 155 | 161 |

TABLE 18.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 116 | 300 | 118 | 248 | 116 | 242 |
| Average | 1840 | 1490 | 1860 | 1450 | 1880 | 1430 |
| Stdev | 6370 | 3110 | 6410 | 3070 | 6450 | 3030 |
| p (t-test) | | 0.60 | | 0.53 | | 0.49 |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 210 | 104 | 207 | 107 | 204 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.70 | 0.57 | 0.63 | 0.69 | 0.56 | 0.63 | 0.69 | 0.57 |
| SE | 0.032 | 0.029 | 0.035 | 0.032 | 0.029 | 0.035 | 0.032 | 0.030 | 0.034 |
| p Value | 3.1E−5 | 3.6E−12 | 0.038 | 7.9E−5 | 4.5E−11 | 0.068 | 7.9E−5 | 1.3E−10 | 0.054 |
| nCohort Recovered | 187 | 159 | 210 | 184 | 156 | 207 | 184 | 155 | 204 |
| nCohort Non-recovered | 129 | 157 | 104 | 132 | 160 | 107 | 132 | 161 | 110 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 85% | 85% | 82% | 85% | 84% | 81% | 85% | 84% | 82% |
| Specificity | 29% | 32% | 26% | 29% | 31% | 26% | 29% | 31% | 26% |
| Cutoff Quartile 3 | 155 | 155 | 155 | 155 | 155 | 155 | 155 | 155 | 155 |
| Sensitivity | 64% | 66% | 60% | 64% | 66% | 58% | 64% | 65% | 58% |
| Specificity | 60% | 66% | 55% | 60% | 66% | 54% | 60% | 66% | 54% |
| Cutoff Quartile 4 | 909 | 909 | 902 | 909 | 909 | 902 | 909 | 909 | 902 |
| Sensitivity | 34% | 39% | 31% | 33% | 38% | 30% | 33% | 38% | 30% |
| Specificity | 81% | 89% | 78% | 81% | 88% | 77% | 81% | 88% | 77% |
| OR Quartile 2 | 2.41 | 2.75 | 1.55 | 2.33 | 2.47 | 1.50 | 2.33 | 2.33 | 1.58 |
| p Value | 0.0029 | 3.4E−4 | 0.14 | 0.0038 | 0.0011 | 0.17 | 0.0038 | 0.0022 | 0.12 |
| Lower limit of 95% CI | 1.35 | 1.58 | 0.862 | 1.31 | 1.43 | 0.840 | 1.31 | 1.36 | 0.887 |
| Upper limit of 95% CI | 4.31 | 4.79 | 2.78 | 4.12 | 4.26 | 2.67 | 4.12 | 4.00 | 2.81 |
| OR Quartile 3 | 2.69 | 3.82 | 1.79 | 2.60 | 3.71 | 1.62 | 2.60 | 3.61 | 1.66 |
| p Value | 2.8E−5 | 1.8E−8 | 0.017 | 4.8E−5 | 3.3E−8 | 0.044 | 4.8E−5 | 5.9E−8 | 0.034 |
| Lower limit of 95% CI | 1.69 | 2.39 | 1.11 | 1.64 | 2.33 | 1.01 | 1.64 | 2.27 | 1.04 |
| Upper limit of 95% CI | 4.29 | 6.08 | 2.88 | 4.13 | 5.91 | 2.60 | 4.13 | 5.74 | 2.65 |
| OR Quartile 4 | 2.25 | 4.98 | 1.54 | 2.13 | 4.72 | 1.45 | 2.13 | 4.64 | 1.47 |
| p Value | 0.0021 | 8.1E−8 | 0.11 | 0.0041 | 2.0E−7 | 0.16 | 0.0041 | 2.8E−7 | 0.15 |
| Lower limit of 95% CI | 1.34 | 2.77 | 0.909 | 1.27 | 2.63 | 0.858 | 1.27 | 2.59 | 0.872 |
| Upper limit of 95% CI | 3.77 | 8.95 | 2.61 | 3.57 | 8.49 | 2.46 | 3.57 | 8.34 | 2.48 |

TABLE 18.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 2350 | 4630 | 2350 | 4520 | 2350 | 4520 |
| Average | 2780 | 5040 | 2970 | 4940 | 2740 | 4940 |
| Stdev | 2070 | 3020 | 2160 | 3030 | 1870 | 3030 |

TABLE 18.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | |
|---|---|---|---|---|---|---|---|
| p (t-test) | | 4.6E−4 | | 0.0047 | | 0.0024 | |
| Min | 62.8 | 413 | 62.8 | 276 | 62.8 | 276 | |
| Max | 8250 | 21200 | 8250 | 21200 | 8050 | 21200 | |
| n (Patient) | 25 | 126 | 21 | 130 | 19 | 132 | | sCr only

| | | | | | | | |
|---|---|---|---|---|---|---|---|
| Median | 3060 | 4590 | 3080 | 4560 | 3240 | 4520 | |
| Average | 3540 | 4950 | 3570 | 4930 | 3720 | 4870 | |
| Stdev | 2350 | 3090 | 2390 | 3080 | 2410 | 3090 | |
| p (t-test) | | 0.023 | | 0.031 | | 0.076 | |
| Min | 842 | 62.8 | 842 | 62.8 | 842 | 62.8 | |
| Max | 10700 | 21200 | 10700 | 21200 | 10700 | 21200 | |
| n (Patient) | 29 | 121 | 28 | 122 | 26 | 124 | |

UO only

| | | | | | | | |
|---|---|---|---|---|---|---|---|
| Median | 4050 | 4670 | 3990 | 4570 | 3790 | 4710 | |
| Average | 4550 | 4910 | 4490 | 4940 | 4200 | 5210 | |
| Stdev | 2870 | 3190 | 2730 | 3300 | 2440 | 3430 | |
| p (t-test) | | 0.47 | | 0.37 | | 0.040 | |
| Min | 62.8 | 513 | 62.8 | 276 | 62.8 | 276 | |
| Max | 13800 | 21200 | 13800 | 21200 | 11800 | 21200 | |
| n (Patient) | 91 | 59 | 84 | 66 | 77 | 73 | |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.76 | 0.66 | 0.54 | 0.73 | 0.65 | 0.54 | 0.75 | 0.63 | 0.59 |
| SE | 0.045 | 0.052 | 0.048 | 0.052 | 0.053 | 0.048 | 0.051 | 0.056 | 0.047 |
| p Value | 7.1E−9 | 0.0020 | 0.41 | 1.3E−5 | 0.0037 | 0.41 | 7.7E−7 | 0.022 | 0.064 |
| nCohort Recovered | 25 | 29 | 91 | 21 | 28 | 84 | 19 | 26 | 77 |
| nCohort Non-recovered | 126 | 121 | 59 | 130 | 122 | 66 | 132 | 124 | 73 |
| Cutoff Quartile 2 | 2740 | 2730 | 2740 | 2740 | 2730 | 2740 | 2740 | 2730 | 2740 |
| Sensitivity | 81% | 79% | 80% | 79% | 78% | 77% | 79% | 77% | 79% |
| Specificity | 56% | 41% | 29% | 52% | 39% | 27% | 53% | 35% | 30% |
| Cutoff Quartile 3 | 4230 | 4260 | 4260 | 4230 | 4260 | 4260 | 4230 | 4260 | 4260 |
| Sensitivity | 58% | 56% | 54% | 56% | 56% | 55% | 56% | 55% | 58% |
| Specificity | 88% | 76% | 53% | 86% | 75% | 54% | 89% | 73% | 57% |
| Cutoff Quartile 4 | 6010 | 6060 | 6060 | 6010 | 6060 | 6060 | 6010 | 6060 | 6060 |
| Sensitivity | 29% | 29% | 20% | 28% | 29% | 23% | 28% | 28% | 26% |
| Specificity | 92% | 90% | 71% | 90% | 89% | 73% | 95% | 88% | 75% |
| OR Quartile 2 | 5.41 | 2.58 | 1.57 | 4.20 | 2.28 | 1.28 | 4.13 | 1.73 | 1.65 |
| p Value | 2.6E−4 | 0.030 | 0.26 | 0.0033 | 0.064 | 0.52 | 0.0051 | 0.23 | 0.19 |
| Lower limit of 95% CI | 2.19 | 1.09 | 0.718 | 1.61 | 0.953 | 0.606 | 1.53 | 0.699 | 0.779 |
| Upper limit of 95% CI | 13.4 | 6.08 | 3.42 | 10.9 | 5.44 | 2.71 | 11.1 | 4.30 | 3.48 |
| OR Quartile 3 | 10.1 | 4.03 | 1.32 | 7.68 | 3.78 | 1.38 | 10.8 | 3.30 | 1.81 |
| p Value | 3.1E−4 | 0.0031 | 0.40 | 0.0017 | 0.0050 | 0.32 | 0.0019 | 0.013 | 0.073 |
| Lower limit of 95% CI | 2.87 | 1.60 | 0.686 | 2.16 | 1.49 | 0.725 | 2.41 | 1.29 | 0.946 |
| Upper limit of 95% CI | 35.5 | 10.2 | 2.55 | 27.4 | 9.55 | 2.64 | 48.8 | 8.40 | 3.45 |
| OR Quartile 4 | 4.60 | 3.53 | 0.638 | 3.64 | 3.35 | 0.780 | 7.01 | 3.01 | 1.07 |
| p Value | 0.046 | 0.050 | 0.26 | 0.093 | 0.060 | 0.52 | 0.063 | 0.087 | 0.85 |
| Lower limit of 95% CI | 1.03 | 1.00 | 0.293 | 0.806 | 0.951 | 0.369 | 0.903 | 0.851 | 0.514 |
| Upper limit of 95% CI | 20.5 | 12.4 | 1.39 | 16.4 | 11.8 | 1.65 | 54.4 | 10.7 | 2.24 |

TABLE 18.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3060 | 4710 | 3080 | 4670 | 3080 | 4590 |
| Average | 3490 | 5090 | 3580 | 5010 | 3480 | 4990 |
| Stdev | 2270 | 3120 | 2360 | 3100 | 2330 | 3080 |
| p (t-test) | | 0.0035 | | 0.012 | | 0.011 |
| Min | 62.8 | 276 | 62.8 | 276 | 62.8 | 276 |
| Max | 11800 | 21200 | 11800 | 21200 | 11800 | 21200 |
| n (Patient) | 40 | 111 | 36 | 115 | 32 | 119 |
| sCr only | | | | | | |
| Median | 3500 | 4700 | 3620 | 4680 | 3800 | 4530 |
| Average | 3860 | 5000 | 3890 | 4980 | 4030 | 4900 |
| Stdev | 2390 | 3160 | 2410 | 3160 | 2440 | 3150 |
| p (t-test) | | 0.034 | | 0.043 | | 0.12 |
| Min | 842 | 62.8 | 842 | 62.8 | 842 | 62.8 |
| Max | 11800 | 21200 | 11800 | 21200 | 11800 | 21200 |
| n (Patient) | 44 | 107 | 43 | 108 | 40 | 111 |
| UO only | | | | | | |
| Median | 4090 | 4690 | 4060 | 4670 | 3920 | 4710 |
| Average | 4590 | 4890 | 4520 | 4970 | 4260 | 5250 |
| Stdev | 2740 | 3460 | 2660 | 3480 | 2400 | 3570 |
| p (t-test) | | 0.56 | | 0.38 | | 0.045 |
| Min | 62.8 | 276 | 62.8 | 276 | 62.8 | 276 |
| Max | 13800 | 21200 | 13800 | 21200 | 11800 | 21200 |
| n (Patient) | 100 | 50 | 93 | 57 | 85 | 65 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.68 | 0.62 | 0.52 | 0.66 | 0.62 | 0.53 | 0.67 | 0.59 | 0.58 |
| SE | 0.046 | 0.048 | 0.050 | 0.049 | 0.049 | 0.049 | 0.050 | 0.051 | 0.047 |
| p Value | 1.3E−4 | 0.010 | 0.66 | 0.0014 | 0.016 | 0.54 | 8.8E−4 | 0.079 | 0.10 |
| nCohort Recovered | 40 | 44 | 100 | 36 | 43 | 93 | 32 | 40 | 85 |
| nCohort Non-recovered | 111 | 107 | 50 | 115 | 108 | 57 | 119 | 111 | 65 |
| Cutoff Quartile 2 | 2740 | 2740 | 2740 | 2740 | 2740 | 2740 | 2740 | 2740 | 2740 |
| Sensitivity | 78% | 77% | 74% | 77% | 76% | 74% | 77% | 75% | 77% |
| Specificity | 35% | 30% | 25% | 33% | 28% | 25% | 34% | 25% | 27% |
| Cutoff Quartile 3 | 4230 | 4230 | 4260 | 4230 | 4230 | 4260 | 4230 | 4230 | 4260 |
| Sensitivity | 59% | 58% | 56% | 57% | 57% | 56% | 57% | 56% | 58% |
| Specificity | 75% | 68% | 53% | 72% | 67% | 54% | 75% | 65% | 56% |
| Cutoff Quartile 4 | 6010 | 6010 | 6060 | 6010 | 6010 | 6060 | 6010 | 6010 | 6060 |
| Sensitivity | 31% | 31% | 24% | 30% | 31% | 25% | 29% | 30% | 28% |
| Specificity | 90% | 89% | 74% | 89% | 88% | 74% | 91% | 88% | 76% |
| OR Quartile 2 | 1.95 | 1.38 | 0.949 | 1.71 | 1.22 | 0.920 | 1.78 | 0.988 | 1.24 |
| p Value | 0.098 | 0.43 | 0.89 | 0.20 | 0.62 | 0.83 | 0.18 | 0.98 | 0.58 |
| Lower limit of 95% CI | 0.885 | 0.626 | 0.436 | 0.754 | 0.549 | 0.433 | 0.766 | 0.429 | 0.584 |
| Upper limit of 95% CI | 4.31 | 3.02 | 2.06 | 3.88 | 2.71 | 1.96 | 4.16 | 2.28 | 2.62 |
| OR Quartile 3 | 4.40 | 2.95 | 1.44 | 3.50 | 2.79 | 1.49 | 4.00 | 2.35 | 1.83 |
| p Value | 3.4E−4 | 0.0042 | 0.30 | 0.0027 | 0.0068 | 0.24 | 0.0020 | 0.026 | 0.071 |
| Lower limit of 95% CI | 1.96 | 1.41 | 0.725 | 1.55 | 1.33 | 0.767 | 1.66 | 1.11 | 0.950 |
| Upper limit of 95% CI | 9.89 | 6.20 | 2.84 | 7.93 | 5.87 | 2.89 | 9.63 | 4.97 | 3.51 |

TABLE 18.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.97 | 3.48 | 0.899 | 3.36 | 3.34 | 0.936 | 4.03 | 2.96 | 1.24 |
| p Value | 0.015 | 0.016 | 0.79 | 0.033 | 0.020 | 0.86 | 0.029 | 0.037 | 0.56 |
| Lower limit of 95% CI | 1.31 | 1.26 | 0.409 | 1.10 | 1.21 | 0.437 | 1.15 | 1.07 | 0.594 |
| Upper limit of 95% CI | 12.0 | 9.62 | 1.98 | 10.2 | 9.26 | 2.00 | 14.1 | 8.23 | 2.61 |

TABLE 18.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3500 | 4670 | 3500 | 4530 | 3500 | 4530 |
| Average | 3980 | 5010 | 3930 | 4990 | 3900 | 4940 |
| Stdev | 2670 | 3100 | 2540 | 3130 | 2570 | 3100 |
| p (t-test) | | 0.047 | | 0.046 | | 0.059 |
| Min | 62.8 | 276 | 62.8 | 276 | 62.8 | 276 |
| Max | 11800 | 21200 | 11800 | 21200 | 11800 | 21200 |
| n (Patient) | 50 | 101 | 46 | 105 | 40 | 111 |
| | sCr only | | | | | |
| Median | 3860 | 4530 | 3930 | 4500 | 3940 | 4480 |
| Average | 4130 | 4960 | 4230 | 4900 | 4350 | 4820 |
| Stdev | 2520 | 3210 | 2520 | 3210 | 2530 | 3200 |
| p (t-test) | | 0.10 | | 0.19 | | 0.38 |
| Min | 703 | 62.8 | 842 | 62.8 | 842 | 62.8 |
| Max | 11800 | 21200 | 11800 | 21200 | 11800 | 21200 |
| n (Patient) | 54 | 97 | 52 | 99 | 49 | 102 |
| | UO only | | | | | |
| Median | 3930 | 4790 | 3930 | 4790 | 3770 | 4790 |
| Average | 4450 | 5150 | 4410 | 5160 | 4270 | 5250 |
| Stdev | 2680 | 3490 | 2640 | 3480 | 2590 | 3400 |
| p (t-test) | | 0.17 | | 0.14 | | 0.048 |
| Min | 62.8 | 276 | 62.8 | 276 | 62.8 | 276 |
| Max | 13800 | 21200 | 13800 | 21200 | 13800 | 21200 |
| n (Patient) | 98 | 52 | 94 | 56 | 86 | 64 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.62 | 0.58 | 0.56 | 0.61 | 0.56 | 0.57 | 0.61 | 0.54 | 0.59 |
| SE | 0.047 | 0.048 | 0.050 | 0.048 | 0.048 | 0.049 | 0.050 | 0.050 | 0.047 |
| p Value | 0.013 | 0.078 | 0.19 | 0.020 | 0.19 | 0.16 | 0.023 | 0.45 | 0.045 |
| nCohort Recovered | 50 | 54 | 98 | 46 | 52 | 94 | 40 | 49 | 86 |
| nCohort Non-recovered | 101 | 97 | 52 | 105 | 99 | 56 | 111 | 102 | 64 |
| Cutoff Quartile 2 | 2740 | 2740 | 2740 | 2740 | 2740 | 2740 | 2740 | 2740 | 2740 |
| Sensitivity | 78% | 76% | 75% | 77% | 75% | 75% | 77% | 74% | 78% |
| Specificity | 32% | 28% | 26% | 30% | 25% | 26% | 30% | 22% | 28% |
| Cutoff Quartile 3 | 4230 | 4230 | 4260 | 4230 | 4230 | 4260 | 4230 | 4230 | 4260 |
| Sensitivity | 58% | 57% | 62% | 57% | 56% | 61% | 57% | 54% | 61% |
| Specificity | 66% | 61% | 56% | 65% | 60% | 56% | 68% | 57% | 58% |
| Cutoff Quartile 4 | 6010 | 6010 | 6060 | 6010 | 6010 | 6060 | 6010 | 6010 | 6060 |
| Sensitivity | 29% | 30% | 27% | 29% | 29% | 27% | 28% | 28% | 28% |
| Specificity | 82% | 83% | 76% | 83% | 83% | 76% | 82% | 82% | 77% |
| OR Quartile 2 | 1.69 | 1.24 | 1.03 | 1.48 | 0.987 | 1.03 | 1.40 | 0.804 | 1.38 |
| p Value | 0.18 | 0.58 | 0.95 | 0.32 | 0.97 | 0.94 | 0.41 | 0.59 | 0.40 |

TABLE 18.8-continued

Comparison of marker levels and the area under the ROC curve (AUC) in EDTA samples for the "recovered"
and "non-recovered" cohorts where recovery starts within 72 hours after sample collection and renal
status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 0.791 | 0.580 | 0.473 | 0.680 | 0.455 | 0.480 | 0.626 | 0.360 | 0.648 |
| Upper limit of 95% CI | 3.61 | 2.64 | 2.23 | 3.21 | 2.14 | 2.20 | 3.14 | 1.79 | 2.95 |
| OR Quartile 3 | 2.73 | 2.06 | 2.05 | 2.50 | 1.85 | 2.00 | 2.73 | 1.56 | 2.17 |
| p Value | 0.0054 | 0.037 | 0.041 | 0.013 | 0.078 | 0.044 | 0.0098 | 0.20 | 0.022 |
| Lower limit of 95% CI | 1.35 | 1.04 | 1.03 | 1.22 | 0.934 | 1.02 | 1.27 | 0.785 | 1.12 |
| Upper limit of 95% CI | 5.53 | 4.06 | 4.07 | 5.13 | 3.65 | 3.92 | 5.83 | 3.10 | 4.19 |
| OR Quartile 4 | 1.83 | 2.13 | 1.14 | 1.90 | 1.98 | 1.13 | 1.83 | 1.77 | 1.29 |
| p Value | 0.16 | 0.076 | 0.74 | 0.15 | 0.11 | 0.75 | 0.20 | 0.19 | 0.50 |
| Lower limit of 95% CI | 0.792 | 0.923 | 0.528 | 0.794 | 0.856 | 0.530 | 0.732 | 0.761 | 0.616 |
| Upper limit of 95% CI | 4.25 | 4.93 | 2.44 | 4.54 | 4.58 | 2.40 | 4.56 | 4.10 | 2.71 |

TABLE 18.9

Comparison of marker levels and the area under the ROC curve (AUC) in EDTA samples for the "recovered"
and "non-recovered" cohorts where recovery starts within 96 hours after sample collection and renal
status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3650 | 4700 | 3620 | 4600 | 3540 | 4630 |
| Average | 4130 | 5000 | 4100 | 4970 | 3970 | 4980 |
| Stdev | 2690 | 3140 | 2620 | 3150 | 2610 | 3120 |
| p (t-test) | | 0.084 | | 0.087 | | 0.053 |
| Min | 62.8 | 276 | 62.8 | 276 | 62.8 | 276 |
| Max | 11800 | 21200 | 11800 | 21200 | 11800 | 21200 |
| n (Patient) | 58 | 93 | 53 | 98 | 47 | 104 |
| sCr only | | | | | | |
| Median | 3860 | 4530 | 3920 | 4520 | 3930 | 4490 |
| Average | 4250 | 4940 | 4310 | 4890 | 4390 | 4830 |
| Stdev | 2600 | 3220 | 2580 | 3230 | 2590 | 3220 |
| p (t-test) | | 0.17 | | 0.25 | | 0.38 |
| Min | 703 | 62.8 | 842 | 62.8 | 842 | 62.8 |
| Max | 11800 | 21200 | 11800 | 21200 | 11800 | 21200 |
| n (Patient) | 60 | 91 | 59 | 92 | 57 | 94 |
| UO only | | | | | | |
| Median | 3930 | 4820 | 3920 | 4790 | 3770 | 4790 |
| Average | 4430 | 5150 | 4400 | 5150 | 4270 | 5250 |
| Stdev | 2710 | 3420 | 2660 | 3420 | 2590 | 3400 |
| p (t-test) | | 0.16 | | 0.14 | | 0.048 |
| Min | 62.8 | 276 | 62.8 | 276 | 62.8 | 276 |
| Max | 13800 | 21200 | 13800 | 21200 | 13800 | 21200 |
| n (Patient) | 96 | 54 | 92 | 58 | 86 | 64 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.60 | 0.57 | 0.57 | 0.59 | 0.56 | 0.57 | 0.61 | 0.54 | 0.60 |
| SE | 0.047 | 0.047 | 0.049 | 0.047 | 0.048 | 0.048 | 0.048 | 0.048 | 0.047 |
| p Value | 0.034 | 0.14 | 0.13 | 0.048 | 0.22 | 0.14 | 0.017 | 0.39 | 0.044 |
| nCohort Recovered | 58 | 60 | 96 | 53 | 59 | 92 | 47 | 57 | 86 |
| nCohort Non-recovered | 93 | 91 | 54 | 98 | 92 | 58 | 104 | 94 | 64 |
| Cutoff Quartile 2 | 2740 | 2740 | 2740 | 2740 | 2740 | 2740 | 2740 | 2740 | 2740 |

TABLE 18.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| Sensitivity | 78% | 77% | 76% | 78% | 76% | 76% | 78% | 76% | 78% |
|---|---|---|---|---|---|---|---|---|---|
| Specificity | 31% | 28% | 26% | 30% | 27% | 26% | 32% | 26% | 28% |
| Cutoff Quartile 3 | 4230 | 4230 | 4260 | 4230 | 4230 | 4260 | 4230 | 4230 | 4260 |
| Sensitivity | 59% | 57% | 61% | 58% | 57% | 60% | 59% | 55% | 61% |
| Specificity | 64% | 60% | 56% | 64% | 59% | 57% | 68% | 58% | 58% |
| Cutoff Quartile 4 | 6010 | 6010 | 6060 | 6010 | 6010 | 6060 | 6010 | 6010 | 6060 |
| Sensitivity | 28% | 29% | 26% | 28% | 28% | 26% | 28% | 28% | 28% |
| Specificity | 79% | 80% | 75% | 79% | 80% | 75% | 81% | 79% | 77% |
| OR Quartile 2 | 1.64 | 1.32 | 1.11 | 1.49 | 1.18 | 1.11 | 1.65 | 1.10 | 1.38 |
| p Value | 0.19 | 0.47 | 0.79 | 0.30 | 0.66 | 0.79 | 0.20 | 0.80 | 0.40 |
| Lower limit of 95% CI | 0.780 | 0.626 | 0.513 | 0.703 | 0.561 | 0.519 | 0.765 | 0.519 | 0.648 |
| Upper limit of 95% CI | 3.46 | 2.77 | 2.40 | 3.18 | 2.50 | 2.37 | 3.56 | 2.34 | 2.95 |
| OR Quartile 3 | 2.55 | 2.00 | 2.02 | 2.49 | 1.90 | 1.98 | 3.03 | 1.70 | 2.17 |
| p Value | 0.0067 | 0.040 | 0.043 | 0.0096 | 0.059 | 0.045 | 0.0028 | 0.12 | 0.022 |
| Lower limit of 95% CI | 1.30 | 1.03 | 1.02 | 1.25 | 0.977 | 1.01 | 1.46 | 0.876 | 1.12 |
| Upper limit of 95% CI | 5.02 | 3.88 | 3.99 | 4.96 | 3.68 | 3.86 | 6.26 | 3.31 | 4.19 |
| OR Quartile 4 | 1.49 | 1.60 | 1.05 | 1.45 | 1.54 | 1.05 | 1.63 | 1.43 | 1.29 |
| p Value | 0.32 | 0.24 | 0.90 | 0.36 | 0.28 | 0.91 | 0.25 | 0.37 | 0.50 |
| Lower limit of 95% CI | 0.682 | 0.734 | 0.489 | 0.654 | 0.708 | 0.492 | 0.702 | 0.657 | 0.616 |
| Upper limit of 95% CI | 3.25 | 3.49 | 2.25 | 3.23 | 3.36 | 2.22 | 3.80 | 3.13 | 2.71 |

TABLE 18.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 4170 | 4480 | 4150 | 4470 | 4150 | 4470 |
| Average | 4620 | 4720 | 4620 | 4720 | 4620 | 4720 |
| Stdev | 2740 | 3290 | 2760 | 3260 | 2760 | 3260 |
| p (t-test) | | 0.83 | | 0.84 | | 0.84 |
| Min | 703 | 62.8 | 703 | 62.8 | 703 | 62.8 |
| Max | 13800 | 21200 | 13800 | 21200 | 13800 | 21200 |
| n (Patient) | 81 | 70 | 80 | 71 | 80 | 71 |
| | sCr only | | | | | |
| Median | 3920 | 4520 | 3920 | 4520 | 3920 | 4520 |
| Average | 4320 | 4940 | 4360 | 4890 | 4360 | 4890 |
| Stdev | 2570 | 3290 | 2570 | 3280 | 2570 | 3280 |
| p (t-test) | | 0.21 | | 0.28 | | 0.28 |
| Min | 703 | 62.8 | 842 | 62.8 | 842 | 62.8 |
| Max | 11800 | 21200 | 11800 | 21200 | 11800 | 21200 |
| n (Patient) | 67 | 84 | 65 | 86 | 65 | 86 |

TABLE 18.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 3940 | 4710 | 3940 | 4670 | 3940 | 4670 |
| Average | 4530 | 4970 | 4570 | 4890 | 4560 | 4900 |
| Stdev | 2690 | 3460 | 2690 | 3440 | 2720 | 3390 |
| p (t-test) | | 0.39 | | 0.52 | | 0.49 |
| Min | 413 | 62.8 | 413 | 62.8 | 413 | 62.8 |
| Max | 13800 | 21200 | 13800 | 21200 | 13800 | 21200 |
| n (Patient) | 95 | 55 | 93 | 57 | 91 | 59 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.50 | 0.56 | 0.54 | 0.51 | 0.55 | 0.53 | 0.51 | 0.55 | 0.53 |
| SE | 0.047 | 0.047 | 0.049 | 0.047 | 0.047 | 0.049 | 0.047 | 0.047 | 0.049 |
| p Value | 0.92 | 0.23 | 0.44 | 0.91 | 0.31 | 0.59 | 0.91 | 0.31 | 0.52 |
| nCohort Recovered | 81 | 67 | 95 | 80 | 65 | 93 | 80 | 65 | 91 |
| nCohort Non-recovered | 70 | 84 | 55 | 71 | 86 | 57 | 71 | 86 | 59 |
| Cutoff Quartile 2 | 2740 | 2740 | 2740 | 2740 | 2740 | 2740 | 2740 | 2740 | 2740 |
| Sensitivity | 73% | 77% | 75% | 73% | 77% | 74% | 73% | 77% | 75% |
| Specificity | 23% | 28% | 25% | 24% | 28% | 25% | 24% | 28% | 25% |
| Cutoff Quartile 3 | 4230 | 4230 | 4260 | 4230 | 4230 | 4260 | 4230 | 4230 | 4260 |
| Sensitivity | 53% | 57% | 56% | 54% | 57% | 56% | 54% | 57% | 56% |
| Specificity | 52% | 58% | 54% | 52% | 58% | 54% | 52% | 58% | 54% |
| Cutoff Quartile 4 | 6010 | 6010 | 6060 | 6010 | 6010 | 6060 | 6010 | 6010 | 6060 |
| Sensitivity | 24% | 26% | 24% | 24% | 26% | 23% | 24% | 26% | 24% |
| Specificity | 74% | 76% | 74% | 74% | 75% | 73% | 74% | 75% | 74% |
| OR Quartile 2 | 0.823 | 1.35 | 0.990 | 0.852 | 1.26 | 0.920 | 0.852 | 1.26 | 0.992 |
| p Value | 0.60 | 0.42 | 0.98 | 0.67 | 0.53 | 0.83 | 0.67 | 0.53 | 0.98 |
| Lower limit of 95% CI | 0.394 | 0.648 | 0.462 | 0.408 | 0.604 | 0.433 | 0.408 | 0.604 | 0.467 |
| Upper limit of 95% CI | 1.72 | 2.83 | 2.12 | 1.78 | 2.65 | 1.96 | 1.78 | 2.65 | 2.11 |
| OR Quartile 3 | 1.21 | 1.86 | 1.50 | 1.27 | 1.86 | 1.49 | 1.27 | 1.86 | 1.48 |
| p Value | 0.56 | 0.062 | 0.24 | 0.46 | 0.061 | 0.24 | 0.46 | 0.061 | 0.24 |
| Lower limit of 95% CI | 0.636 | 0.970 | 0.767 | 0.671 | 0.971 | 0.767 | 0.671 | 0.971 | 0.766 |
| Upper limit of 95% CI | 2.29 | 3.56 | 2.92 | 2.41 | 3.58 | 2.89 | 2.41 | 3.58 | 2.86 |
| OR Quartile 4 | 0.916 | 1.13 | 0.867 | 0.884 | 1.05 | 0.804 | 0.884 | 1.05 | 0.869 |
| p Value | 0.82 | 0.75 | 0.72 | 0.74 | 0.89 | 0.58 | 0.74 | 0.89 | 0.72 |
| Lower limit of 95% CI | 0.438 | 0.538 | 0.401 | 0.423 | 0.500 | 0.372 | 0.423 | 0.500 | 0.406 |
| Upper limit of 95% CI | 1.92 | 2.38 | 1.87 | 1.85 | 2.21 | 1.74 | 1.85 | 2.21 | 1.86 |

Example 19. Use of C—C Motif Chemokine 15 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 15 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 19.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 22.1 | 401 | 36.6 | 366 | 37.9 | 363 |
| Average | 820 | 2170 | 852 | 2130 | 869 | 2110 |
| Stdev | 4380 | 5930 | 4460 | 5880 | 4530 | 5840 |
| p (t-test) | | 0.038 | | 0.051 | | 0.062 |
| Min | 0.0116 | 0.0116 | 0.0187 | 0.0116 | 0.0187 | 0.0116 |
| Max | 34200 | 53500 | 34200 | 53500 | 34200 | 53500 |
| n (Patient) | 107 | 209 | 103 | 213 | 100 | 216 |
| | sCr only | | | | | |
| Median | 22.1 | 414 | 22.1 | 403 | 24.3 | 401 |
| Average | 754 | 2360 | 765 | 2330 | 771 | 2320 |
| Stdev | 4060 | 6190 | 4090 | 6160 | 4110 | 6150 |
| p (t-test) | | 0.011 | | 0.013 | | 0.015 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 125 | 190 | 123 | 192 | 122 | 193 |
| | UO only | | | | | |
| Median | 110 | 347 | 115 | 341 | 118 | 261 |
| Average | 1780 | 1580 | 1880 | 1420 | 1670 | 1810 |
| Stdev | 6210 | 3290 | 6400 | 3100 | 5420 | 5670 |
| p (t-test) | | 0.77 | | 0.49 | | 0.83 |
| Min | 0.0116 | 0.0116 | 0.0187 | 0.0116 | 0.0187 | 0.0116 |
| Max | 53500 | 19200 | 53500 | 19200 | 52500 | 53500 |
| n (Patient) | 221 | 93 | 207 | 107 | 197 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.72 | 0.57 | 0.70 | 0.72 | 0.55 | 0.70 | 0.72 | 0.55 |
| SE | 0.029 | 0.028 | 0.036 | 0.030 | 0.028 | 0.035 | 0.030 | 0.028 | 0.034 |
| p Value | 1.2E−14 | 1.1E−15 | 0.038 | 5.3E−12 | 2.7E−15 | 0.13 | 1.5E−11 | 1.5E−14 | 0.17 |
| nCohort Recovered | 107 | 125 | 221 | 103 | 123 | 207 | 100 | 122 | 197 |
| nCohort Non-recovered | 209 | 190 | 93 | 213 | 192 | 107 | 216 | 193 | 117 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 83% | 85% | 81% | 82% | 85% | 79% | 82% | 84% | 78% |
| Specificity | 36% | 36% | 25% | 35% | 37% | 24% | 35% | 36% | 24% |
| Cutoff Quartile 3 | 155 | 154 | 155 | 155 | 154 | 155 | 155 | 154 | 155 |
| Sensitivity | 63% | 65% | 60% | 62% | 65% | 58% | 61% | 64% | 56% |
| Specificity | 75% | 72% | 54% | 74% | 72% | 54% | 74% | 72% | 54% |
| Cutoff Quartile 4 | 909 | 912 | 902 | 909 | 912 | 902 | 909 | 912 | 902 |
| Sensitivity | 34% | 36% | 30% | 33% | 36% | 27% | 33% | 36% | 28% |
| Specificity | 93% | 92% | 77% | 92% | 92% | 76% | 92% | 92% | 77% |
| OR Quartile 2 | 2.85 | 3.12 | 1.38 | 2.47 | 3.24 | 1.16 | 2.44 | 3.06 | 1.10 |
| p Value | 1.3E−4 | 3.4E−5 | 0.29 | 9.2E−4 | 1.9E−5 | 0.60 | 0.0011 | 4.3E−5 | 0.74 |
| Lower limit of 95% CI | 1.67 | 1.82 | 0.759 | 1.45 | 1.89 | 0.664 | 1.43 | 1.79 | 0.636 |
| Upper limit of 95% CI | 4.87 | 5.35 | 2.51 | 4.23 | 5.56 | 2.04 | 4.18 | 5.24 | 1.89 |
| OR Quartile 3 | 4.98 | 4.72 | 1.80 | 4.50 | 4.77 | 1.62 | 4.47 | 4.65 | 1.51 |
| p Value | 1.3E−9 | 5.8E−10 | 0.020 | 1.3E−8 | 5.4E−10 | 0.044 | 2.1E−8 | 1.0E−9 | 0.081 |
| Lower limit of 95% CI | 2.96 | 2.89 | 1.10 | 2.68 | 2.91 | 1.01 | 2.65 | 2.84 | 0.951 |
| Upper limit of 95% CI | 8.36 | 7.71 | 2.94 | 7.55 | 7.82 | 2.60 | 7.55 | 7.62 | 2.39 |

TABLE 19.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 6.37 | 6.56 | 1.44 | 5.94 | 6.34 | 1.17 | 5.63 | 6.23 | 1.29 |
| p Value | 2.9E−6 | 2.1E−7 | 0.19 | 6.8E−6 | 3.5E−7 | 0.57 | 1.3E−5 | 4.5E−7 | 0.34 |
| Lower limit of 95% CI | 2.93 | 3.22 | 0.835 | 2.73 | 3.11 | 0.686 | 2.59 | 3.06 | 0.766 |
| Upper limit of 95% CI | 13.8 | 13.3 | 2.47 | 12.9 | 12.9 | 1.99 | 12.2 | 12.7 | 2.17 |

TABLE 19.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 48.0 | 434 | 49.4 | 434 | 53.2 | 423 |
| Average | 874 | 2340 | 888 | 2320 | 908 | 2270 |
| Stdev | 4000 | 6310 | 4030 | 6280 | 4090 | 6220 |
| p (t-test) | | 0.018 | | 0.022 | | 0.029 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 135 | 181 | 133 | 183 | 129 | 187 |
| | sCr only | | | | | |
| Median | 48.7 | 436 | 49.4 | 434 | 51.3 | 434 |
| Average | 836 | 2490 | 841 | 2480 | 847 | 2460 |
| Stdev | 3820 | 6530 | 3840 | 6510 | 3850 | 6490 |
| p (t-test) | | 0.0072 | | 0.0080 | | 0.0089 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 148 | 168 | 147 | 169 | 146 | 170 |
| | UO only | | | | | |
| Median | 106 | 354 | 110 | 347 | 113 | 300 |
| Average | 1780 | 1580 | 1820 | 1500 | 1650 | 1850 |
| Stdev | 6170 | 3270 | 6250 | 3180 | 5320 | 5850 |
| p (t-test) | | 0.78 | | 0.63 | | 0.76 |
| Min | 0.0116 | 0.0116 | 0.0116 | 0.0116 | 0.0116 | 0.0116 |
| Max | 53500 | 19200 | 53500 | 19200 | 52500 | 53500 |
| n (Patient) | 225 | 89 | 219 | 95 | 206 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.58 | 0.69 | 0.70 | 0.57 | 0.68 | 0.69 | 0.55 |
| SE | 0.029 | 0.029 | 0.036 | 0.029 | 0.029 | 0.036 | 0.030 | 0.029 | 0.034 |
| p Value | 1.4E−11 | 3.5E−12 | 0.021 | 1.3E−10 | 8.5E−12 | 0.051 | 1.1E−9 | 3.3E−11 | 0.12 |
| nCohort Recovered | 135 | 148 | 225 | 133 | 147 | 219 | 129 | 146 | 206 |
| nCohort Non-recovered | 181 | 168 | 89 | 183 | 169 | 95 | 187 | 170 | 108 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 86% | 81% | 84% | 86% | 80% | 83% | 85% | 79% |
| Specificity | 33% | 34% | 25% | 33% | 34% | 25% | 33% | 34% | 24% |
| Cutoff Quartile 3 | 155 | 155 | 155 | 155 | 155 | 155 | 155 | 155 | 155 |
| Sensitivity | 64% | 65% | 62% | 63% | 64% | 60% | 63% | 64% | 57% |
| Specificity | 69% | 67% | 55% | 68% | 67% | 54% | 68% | 66% | 54% |
| Cutoff Quartile 4 | 909 | 909 | 902 | 909 | 909 | 902 | 909 | 909 | 902 |
| Sensitivity | 35% | 37% | 30% | 35% | 37% | 28% | 34% | 36% | 28% |
| Specificity | 89% | 89% | 77% | 89% | 88% | 76% | 88% | 88% | 76% |
| OR Quartile 2 | 2.62 | 3.06 | 1.40 | 2.52 | 3.11 | 1.31 | 2.34 | 2.93 | 1.18 |
| p Value | 4.1E−4 | 6.7E−5 | 0.28 | 6.7E−4 | 5.2E−5 | 0.37 | 0.0017 | 1.1E−4 | 0.55 |

TABLE 19.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.54 | 1.77 | 0.763 | 1.48 | 1.80 | 0.726 | 1.38 | 1.70 | 0.677 |
| Upper limit of 95% CI | 4.47 | 5.31 | 2.58 | 4.29 | 5.40 | 2.36 | 3.97 | 5.06 | 2.07 |
| OR Quartile 3 | 3.95 | 3.73 | 1.95 | 3.75 | 3.63 | 1.78 | 3.59 | 3.54 | 1.57 |
| p Value | 1.4E−8 | 3.1E−8 | 0.0090 | 4.4E−8 | 5.6E−8 | 0.020 | 1.3E−7 | 1.0E−7 | 0.058 |
| Lower limit of 95% CI | 2.46 | 2.34 | 1.18 | 2.34 | 2.28 | 1.09 | 2.23 | 2.22 | 0.985 |
| Upper limit of 95% CI | 6.35 | 5.95 | 3.22 | 6.02 | 5.79 | 2.91 | 5.77 | 5.63 | 2.52 |
| OR Quartile 4 | 4.38 | 4.51 | 1.45 | 4.23 | 4.43 | 1.28 | 3.95 | 4.36 | 1.23 |
| p Value | 2.8E−6 | 6.9E−7 | 0.18 | 4.6E−6 | 9.2E−7 | 0.38 | 1.3E−5 | 1.2E−6 | 0.44 |
| Lower limit of 95% CI | 2.36 | 2.49 | 0.838 | 2.28 | 2.45 | 0.740 | 2.13 | 2.40 | 0.726 |
| Upper limit of 95% CI | 8.11 | 8.17 | 2.51 | 7.84 | 8.03 | 2.20 | 7.33 | 7.89 | 2.09 |

TABLE 19.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 49.4 | 537 | 49.4 | 497 | 53.2 | 437 |
| Average | 877 | 2500 | 888 | 2470 | 912 | 2420 |
| Stdev | 3820 | 6600 | 3850 | 6560 | 3900 | 6490 |
| p (t-test) | | 0.0082 | | 0.010 | | 0.015 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 153 | 163 | 151 | 165 | 147 | 169 |
| | sCr only | | | | | |
| Median | 53.2 | 517 | 53.2 | 497 | 54.2 | 492 |
| Average | 864 | 2590 | 870 | 2570 | 875 | 2560 |
| Stdev | 3740 | 6730 | 3750 | 6710 | 3760 | 6690 |
| p (t-test) | | 0.0050 | | 0.0056 | | 0.0062 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 160 | 156 | 159 | 157 | 158 | 158 |
| | UO only | | | | | |
| Median | 115 | 354 | 113 | 351 | 115 | 261 |
| Average | 1790 | 1550 | 1800 | 1530 | 1640 | 1900 |
| Stdev | 6200 | 3230 | 6210 | 3220 | 5260 | 5980 |
| p (t-test) | | 0.72 | | 0.69 | | 0.69 |
| Min | 0.0116 | 0.0116 | 0.0116 | 0.0116 | 0.0116 | 0.0116 |
| Max | 53500 | 19200 | 53500 | 19200 | 52500 | 53500 |
| n (Patient) | 223 | 91 | 222 | 92 | 211 | 103 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.58 | 0.70 | 0.69 | 0.58 | 0.68 | 0.69 | 0.56 |
| SE | 0.029 | 0.029 | 0.036 | 0.029 | 0.029 | 0.036 | 0.030 | 0.030 | 0.035 |
| p Value | 9.2E−12 | 2.0E−11 | 0.031 | 2.3E−11 | 4.7E−11 | 0.032 | 9.8E−10 | 1.7E−10 | 0.081 |
| nCohort Recovered | 153 | 160 | 223 | 151 | 159 | 222 | 147 | 158 | 211 |
| nCohort Non-recovered | 163 | 156 | 91 | 165 | 157 | 92 | 169 | 158 | 103 |
| Cutoff Quartile 2 | 0.0489 | 0.0489 | 0.0489 | 0.0489 | 0.0489 | 0.0489 | 0.0489 | 0.0489 | 0.0489 |

TABLE 19.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 84% | 85% | 80% | 84% | 85% | 80% | 83% | 85% | 80% |
| Specificity | 31% | 32% | 25% | 32% | 32% | 25% | 31% | 32% | 25% |
| Cutoff Quartile 3 | 155 | 155 | 155 | 155 | 155 | 155 | 155 | 155 | 155 |
| Sensitivity | 66% | 66% | 62% | 65% | 66% | 61% | 64% | 65% | 57% |
| Specificity | 67% | 66% | 55% | 67% | 65% | 55% | 66% | 65% | 54% |
| Cutoff Quartile 4 | 909 | 909 | 902 | 909 | 909 | 902 | 909 | 909 | 902 |
| Sensitivity | 37% | 38% | 31% | 37% | 38% | 30% | 36% | 37% | 28% |
| Specificity | 88% | 88% | 77% | 88% | 87% | 77% | 88% | 87% | 76% |
| OR Quartile 2 | 2.41 | 2.71 | 1.33 | 2.49 | 2.75 | 1.35 | 2.29 | 2.58 | 1.28 |
| p Value | 0.0014 | 4.3E−4 | 0.35 | 9.4E−4 | 3.4E−4 | 0.32 | 0.0023 | 6.9E−4 | 0.40 |
| Lower limit of 95% CI | 1.40 | 1.56 | 0.729 | 1.45 | 1.58 | 0.744 | 1.34 | 1.49 | 0.720 |
| Upper limit of 95% CI | 4.14 | 4.71 | 2.42 | 4.28 | 4.79 | 2.46 | 3.92 | 4.47 | 2.26 |
| OR Quartile 3 | 4.05 | 3.71 | 1.93 | 3.83 | 3.61 | 1.86 | 3.43 | 3.51 | 1.55 |
| p Value | 5.0E−9 | 3.3E−8 | 0.0095 | 1.7E−8 | 6.0E−8 | 0.014 | 1.8E−7 | 1.1E−7 | 0.072 |
| Lower limit of 95% CI | 2.53 | 2.33 | 1.17 | 2.40 | 2.27 | 1.14 | 2.16 | 2.21 | 0.962 |
| Upper limit of 95% CI | 6.46 | 5.91 | 3.18 | 6.10 | 5.74 | 3.06 | 5.46 | 5.57 | 2.49 |
| OR Quartile 4 | 4.49 | 4.26 | 1.50 | 4.33 | 4.18 | 1.47 | 4.05 | 4.11 | 1.26 |
| p Value | 5.0E−7 | 6.1E−7 | 0.14 | 9.0E−7 | 8.3E−7 | 0.17 | 2.8E−6 | 1.1E−6 | 0.39 |
| Lower limit of 95% CI | 2.50 | 2.41 | 0.870 | 2.41 | 2.37 | 0.852 | 2.26 | 2.33 | 0.740 |
| Upper limit of 95% CI | 8.05 | 7.52 | 2.58 | 7.78 | 7.39 | 2.53 | 7.26 | 7.26 | 2.15 |

TABLE 19.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 53.2 | 555 | 54.2 | 544 | 57.7 | 492 |
| Average | 856 | 2680 | 871 | 2630 | 893 | 2560 |
| Stdev | 3670 | 6870 | 3700 | 6810 | 3740 | 6740 |
| p (t-test) | | 0.0030 | | 0.0043 | | 0.0067 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 167 | 149 | 164 | 152 | 160 | 156 |
| | sCr only | | | | | |
| Median | 55.3 | 555 | 55.7 | 553 | 56.1 | 550 |
| Average | 847 | 2740 | 852 | 2720 | 857 | 2700 |
| Stdev | 3620 | 6950 | 3630 | 6930 | 3640 | 6910 |
| p (t-test) | | 0.0021 | | 0.0024 | | 0.0027 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 171 | 145 | 170 | 146 | 169 | 147 |
| | UO only | | | | | |
| Median | 116 | 340 | 118 | 338 | 118 | 248 |
| Average | 1810 | 1510 | 1820 | 1500 | 1630 | 1920 |
| Stdev | 6210 | 3220 | 6220 | 3210 | 5240 | 6040 |
| p (t-test) | | 0.66 | | 0.64 | | 0.67 |
| Min | 0.0116 | 0.0116 | 0.0116 | 0.0116 | 0.0116 | 0.0116 |
| Max | 53500 | 19200 | 53500 | 19200 | 52500 | 53500 |
| n (Patient) | 222 | 92 | 221 | 93 | 213 | 101 |

TABLE 19.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.57 | 0.69 | 0.70 | 0.57 | 0.68 | 0.69 | 0.56 |
| SE | 0.030 | 0.030 | 0.036 | 0.030 | 0.030 | 0.036 | 0.030 | 0.030 | 0.035 |
| p Value | 1.9E−11 | 9.6E−12 | 0.043 | 1.6E−10 | 2.4E−11 | 0.062 | 5.7E−9 | 9.1E−11 | 0.11 |
| nCohort Recovered | 167 | 171 | 222 | 164 | 170 | 221 | 160 | 169 | 213 |
| nCohort Non-recovered | 149 | 145 | 92 | 152 | 146 | 93 | 156 | 147 | 101 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 85% | 86% | 82% | 84% | 86% | 81% | 83% | 85% | 80% |
| Specificity | 31% | 31% | 25% | 30% | 31% | 25% | 30% | 31% | 25% |
| Cutoff Quartile 3 | 155 | 155 | 155 | 155 | 155 | 155 | 155 | 155 | 155 |
| Sensitivity | 68% | 68% | 61% | 66% | 67% | 60% | 65% | 67% | 57% |
| Specificity | 66% | 65% | 55% | 65% | 65% | 54% | 64% | 64% | 54% |
| Cutoff Quartile 4 | 909 | 909 | 902 | 909 | 909 | 902 | 909 | 909 | 902 |
| Sensitivity | 38% | 39% | 29% | 38% | 38% | 29% | 37% | 38% | 28% |
| Specificity | 87% | 87% | 77% | 87% | 86% | 76% | 86% | 86% | 76% |
| OR Quartile 2 | 2.41 | 2.65 | 1.49 | 2.34 | 2.70 | 1.38 | 2.14 | 2.53 | 1.34 |
| p Value | 0.0018 | 7.1E−4 | 0.20 | 0.0024 | 5.8E−4 | 0.29 | 0.0057 | 0.0012 | 0.32 |
| Lower limit of 95% CI | 1.39 | 1.51 | 0.811 | 1.35 | 1.53 | 0.759 | 1.25 | 1.44 | 0.751 |
| Upper limit of 95% CI | 4.19 | 4.67 | 2.73 | 4.05 | 4.74 | 2.51 | 3.68 | 4.41 | 2.40 |
| OR Quartile 3 | 4.06 | 3.86 | 1.86 | 3.72 | 3.74 | 1.80 | 3.32 | 3.63 | 1.55 |
| p Value | 4.9E−9 | 1.6E−8 | 0.014 | 3.2E−8 | 3.1E−8 | 0.020 | 3.4E−7 | 5.6E−8 | 0.071 |
| Lower limit of 95% CI | 2.54 | 2.41 | 1.14 | 2.33 | 2.35 | 1.10 | 2.09 | 2.28 | 0.963 |
| Upper limit of 95% CI | 6.49 | 6.16 | 3.06 | 5.92 | 5.97 | 2.94 | 5.26 | 5.79 | 2.50 |
| OR Quartile 4 | 4.08 | 4.05 | 1.36 | 3.87 | 3.98 | 1.33 | 3.61 | 3.91 | 1.22 |
| p Value | 7.4E−7 | 6.9E−7 | 0.27 | 1.8E−6 | 9.4E−7 | 0.31 | 5.9E−6 | 1.3E−6 | 0.47 |
| Lower limit of 95% CI | 2.34 | 2.33 | 0.787 | 2.22 | 2.29 | 0.771 | 2.07 | 2.25 | 0.712 |
| Upper limit of 95% CI | 7.13 | 7.03 | 2.34 | 6.76 | 6.90 | 2.29 | 6.29 | 6.78 | 2.09 |

TABLE 19.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 81.2 | 447 | 81.2 | 380 | 81.4 | 354 |
| Average | 1830 | 1510 | 1850 | 1480 | 1860 | 1470 |
| Stdev | 6490 | 2980 | 6520 | 2960 | 6530 | 2950 |
| p (t-test) | 0.61 | | 0.56 | | 0.54 | |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 202 | 114 | 200 | 116 | 199 | 117 |
| | sCr only | | | | | |
| Median | 65.1 | 553 | 65.1 | 553 | 65.1 | 553 |
| Average | 943 | 2790 | 943 | 2790 | 943 | 2790 |
| Stdev | 3600 | 7230 | 3600 | 7230 | 3600 | 7230 |
| p (t-test) | 0.0029 | | 0.0029 | | 0.0029 | |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 184 | 132 | 184 | 132 | 184 | 132 |

TABLE 19.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 108 | 344 | 110 | 341 | 110 | 338 |
| Average | 1790 | 1570 | 1800 | 1550 | 1820 | 1520 |
| Stdev | 6280 | 3180 | 6300 | 3170 | 6320 | 3140 |
| p (t-test) | | 0.73 | | 0.70 | | 0.65 |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 216 | 98 | 215 | 99 | 213 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.61 | 0.67 | 0.59 | 0.61 | 0.67 | 0.58 | 0.61 | 0.67 | 0.58 |
| SE | 0.033 | 0.031 | 0.035 | 0.033 | 0.031 | 0.035 | 0.033 | 0.031 | 0.035 |
| p Value | 6.4E−4 | 2.4E−8 | 0.016 | 0.0012 | 2.4E−8 | 0.024 | 0.0016 | 2.4E−8 | 0.031 |
| nCohort Recovered | 202 | 184 | 216 | 200 | 184 | 215 | 199 | 184 | 213 |
| nCohort Non-recovered | 114 | 132 | 98 | 116 | 132 | 99 | 117 | 132 | 101 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 84% | 82% | 84% | 84% | 81% | 84% | 84% | 81% |
| Specificity | 28% | 29% | 25% | 28% | 29% | 25% | 28% | 29% | 25% |
| Cutoff Quartile 3 | 155 | 155 | 155 | 155 | 155 | 155 | 155 | 155 | 155 |
| Sensitivity | 65% | 67% | 62% | 64% | 67% | 62% | 63% | 67% | 60% |
| Specificity | 58% | 62% | 56% | 58% | 62% | 55% | 58% | 62% | 55% |
| Cutoff Quartile 4 | 909 | 909 | 902 | 909 | 909 | 902 | 909 | 909 | 902 |
| Sensitivity | 33% | 39% | 32% | 33% | 39% | 31% | 32% | 39% | 31% |
| Specificity | 80% | 85% | 78% | 80% | 85% | 78% | 79% | 85% | 77% |
| OR Quartile 2 | 2.05 | 2.14 | 1.52 | 1.94 | 2.14 | 1.41 | 1.97 | 2.14 | 1.47 |
| p Value | 0.017 | 0.0084 | 0.17 | 0.026 | 0.0084 | 0.25 | 0.022 | 0.0084 | 0.20 |
| Lower limit of 95% CI | 1.13 | 1.22 | 0.837 | 1.08 | 1.22 | 0.785 | 1.10 | 1.22 | 0.815 |
| Upper limit of 95% CI | 3.69 | 3.76 | 2.76 | 3.46 | 3.76 | 2.54 | 3.52 | 3.76 | 2.64 |
| OR Quartile 3 | 2.60 | 3.26 | 2.06 | 2.43 | 3.26 | 1.99 | 2.36 | 3.26 | 1.86 |
| p Value | 8.3E−5 | 7.8E−7 | 0.0037 | 2.2E−4 | 7.8E−7 | 0.0055 | 3.5E−4 | 7.8E−7 | 0.012 |
| Lower limit of 95% CI | 1.62 | 2.04 | 1.26 | 1.52 | 2.04 | 1.22 | 1.47 | 2.04 | 1.15 |
| Upper limit of 95% CI | 4.18 | 5.20 | 3.36 | 3.90 | 5.20 | 3.24 | 3.77 | 5.20 | 3.01 |
| OR Quartile 4 | 1.96 | 3.51 | 1.62 | 1.89 | 3.51 | 1.59 | 1.85 | 3.51 | 1.52 |
| p Value | 0.011 | 4.0E−6 | 0.076 | 0.016 | 4.0E−6 | 0.089 | 0.019 | 4.0E−6 | 0.12 |
| Lower limit of 95% CI | 1.17 | 2.06 | 0.950 | 1.13 | 2.06 | 0.931 | 1.10 | 2.06 | 0.895 |
| Upper limit of 95% CI | 3.30 | 5.98 | 2.76 | 3.17 | 5.98 | 2.70 | 3.11 | 5.98 | 2.59 |

TABLE 19.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3380 | 4600 | 3530 | 4530 | 3530 | 4530 |
| Average | 3630 | 5170 | 3680 | 5130 | 3690 | 5090 |
| Stdev | 2270 | 3180 | 2260 | 3190 | 2260 | 3190 |

TABLE 19.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | 0.0028 | | 0.0052 | | 0.0075 | |
| Min | 62.8 | 413 | 62.8 | 413 | 62.8 | 413 |
| Max | 10700 | 21200 | 10700 | 21200 | 10700 | 21200 |
| n (Patient) | 49 | 102 | 48 | 103 | 46 | 105 | sCr only

| | | | | | | |
|---|---|---|---|---|---|---|
| Median | 3700 | 4680 | 3700 | 4680 | 3730 | 4670 |
| Average | 3750 | 5170 | 3750 | 5170 | 3800 | 5120 |
| Stdev | 2150 | 3280 | 2150 | 3280 | 2140 | 3290 |
| p (t-test) | 0.0056 | | 0.0056 | | 0.010 | |
| Min | 276 | 62.8 | 276 | 62.8 | 276 | 62.8 |
| Max | 10700 | 21200 | 10700 | 21200 | 10700 | 21200 |
| n (Patient) | 52 | 98 | 52 | 98 | 51 | 99 |

UO only

| | | | | | | |
|---|---|---|---|---|---|---|
| Median | 4150 | 4470 | 4120 | 4470 | 4050 | 4670 |
| Average | 4550 | 5000 | 4600 | 4860 | 4430 | 5100 |
| Stdev | 2740 | 3510 | 2760 | 3390 | 2640 | 3460 |
| p (t-test) | 0.40 | | 0.61 | | 0.18 | |
| Min | 62.8 | 733 | 62.8 | 513 | 62.8 | 513 |
| Max | 13800 | 21200 | 13800 | 21200 | 13800 | 21200 |
| n (Patient) | 104 | 46 | 97 | 53 | 91 | 59 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.52 | 0.64 | 0.63 | 0.51 | 0.64 | 0.62 | 0.55 |
| SE | 0.046 | 0.046 | 0.052 | 0.047 | 0.046 | 0.050 | 0.047 | 0.047 | 0.048 |
| p Value | 0.0010 | 0.0045 | 0.67 | 0.0027 | 0.0045 | 0.80 | 0.0037 | 0.011 | 0.30 |
| nCohort Recovered | 49 | 52 | 104 | 48 | 52 | 97 | 46 | 51 | 91 |
| nCohort Non-recovered | 102 | 98 | 46 | 103 | 98 | 53 | 105 | 99 | 59 |
| Cutoff Quartile 2 | 2740 | 2730 | 2740 | 2740 | 2730 | 2740 | 2740 | 2730 | 2740 |
| Sensitivity | 79% | 78% | 76% | 79% | 78% | 75% | 78% | 77% | 76% |
| Specificity | 35% | 31% | 26% | 33% | 31% | 26% | 33% | 29% | 26% |
| Cutoff Quartile 3 | 4230 | 4260 | 4260 | 4230 | 4260 | 4260 | 4230 | 4260 | 4260 |
| Sensitivity | 58% | 57% | 52% | 57% | 57% | 53% | 57% | 57% | 56% |
| Specificity | 65% | 63% | 51% | 65% | 63% | 52% | 65% | 63% | 54% |
| Cutoff Quartile 4 | 6010 | 6060 | 6060 | 6010 | 6060 | 6060 | 6010 | 6060 | 6060 |
| Sensitivity | 31% | 33% | 24% | 31% | 33% | 23% | 30% | 32% | 25% |
| Specificity | 88% | 88% | 74% | 88% | 88% | 73% | 87% | 88% | 75% |
| OR Quartile 2 | 2.05 | 1.54 | 1.12 | 1.84 | 1.54 | 1.07 | 1.73 | 1.38 | 1.15 |
| p Value | 0.064 | 0.27 | 0.79 | 0.12 | 0.27 | 0.87 | 0.17 | 0.41 | 0.72 |
| Lower limit of 95% CI | 0.959 | 0.721 | 0.498 | 0.858 | 0.721 | 0.493 | 0.798 | 0.643 | 0.539 |
| Upper limit of 95% CI | 4.38 | 3.27 | 2.50 | 3.95 | 3.27 | 2.32 | 3.73 | 2.95 | 2.46 |
| OR Quartile 3 | 2.58 | 2.32 | 1.13 | 2.45 | 2.32 | 1.19 | 2.50 | 2.19 | 1.48 |
| p Value | 0.0086 | 0.017 | 0.72 | 0.013 | 0.017 | 0.61 | 0.013 | 0.026 | 0.24 |
| Lower limit of 95% CI | 1.27 | 1.16 | 0.566 | 1.20 | 1.16 | 0.609 | 1.22 | 1.10 | 0.766 |
| Upper limit of 95% CI | 5.24 | 4.63 | 2.27 | 4.97 | 4.63 | 2.33 | 5.13 | 4.39 | 2.86 |
| OR Quartile 4 | 3.28 | 3.72 | 0.896 | 3.15 | 3.72 | 0.799 | 2.92 | 3.58 | 1.01 |
| p Value | 0.014 | 0.0067 | 0.79 | 0.018 | 0.0067 | 0.58 | 0.027 | 0.0085 | 0.98 |
| Lower limit of 95% CI | 1.27 | 1.44 | 0.400 | 1.22 | 1.44 | 0.365 | 1.13 | 1.38 | 0.475 |
| Upper limit of 95% CI | 8.48 | 9.61 | 2.01 | 8.17 | 9.61 | 1.75 | 7.58 | 9.26 | 2.14 |

TABLE 19.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3860 | 4500 | 3860 | 4500 | 3860 | 4500 |
| Average | 4290 | 4950 | 4290 | 4950 | 4310 | 4910 |
| Stdev | 2640 | 3220 | 2640 | 3220 | 2640 | 3210 |
| p (t-test) | | 0.18 | | 0.18 | | 0.23 |
| Min | 62.8 | 276 | 62.8 | 276 | 62.8 | 276 |
| Max | 11800 | 21200 | 11800 | 21200 | 11800 | 21200 |
| n (Patient) | 64 | 87 | 64 | 87 | 62 | 89 |
| sCr only | | | | | | |
| Median | 3940 | 4490 | 3940 | 4490 | 4000 | 4480 |
| Average | 4380 | 4890 | 4380 | 4890 | 4430 | 4850 |
| Stdev | 2530 | 3320 | 2530 | 3320 | 2520 | 3330 |
| p (t-test) | | 0.30 | | 0.30 | | 0.40 |
| Min | 703 | 62.8 | 703 | 62.8 | 703 | 62.8 |
| Max | 11800 | 21200 | 11800 | 21200 | 11800 | 21200 |
| n (Patient) | 67 | 84 | 67 | 84 | 66 | 85 |
| UO only | | | | | | |
| Median | 4060 | 4710 | 4050 | 4710 | 3930 | 4780 |
| Average | 4550 | 5020 | 4540 | 5010 | 4420 | 5170 |
| Stdev | 2710 | 3580 | 2730 | 3500 | 2620 | 3520 |
| p (t-test) | | 0.37 | | 0.37 | | 0.14 |
| Min | 62.8 | 276 | 62.8 | 276 | 62.8 | 276 |
| Max | 13800 | 21200 | 13800 | 21200 | 13800 | 21200 |
| n (Patient) | 105 | 45 | 103 | 47 | 95 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.54 | 0.54 | 0.56 | 0.54 | 0.54 | 0.56 | 0.53 | 0.56 |
| SE | 0.047 | 0.047 | 0.052 | 0.047 | 0.047 | 0.051 | 0.047 | 0.047 | 0.049 |
| p Value | 0.18 | 0.41 | 0.50 | 0.18 | 0.41 | 0.43 | 0.22 | 0.57 | 0.19 |
| nCohort Recovered | 64 | 67 | 105 | 64 | 67 | 103 | 62 | 66 | 95 |
| nCohort Non-recovered | 87 | 84 | 45 | 87 | 84 | 47 | 89 | 85 | 55 |
| Cutoff Quartile 2 | 2740 | 2740 | 2740 | 2740 | 2740 | 2740 | 2740 | 2740 | 2740 |
| Sensitivity | 76% | 74% | 73% | 76% | 74% | 74% | 75% | 73% | 75% |
| Specificity | 27% | 24% | 25% | 27% | 24% | 25% | 26% | 23% | 25% |
| Cutoff Quartile 3 | 4230 | 4230 | 4260 | 4230 | 4230 | 4260 | 4230 | 4230 | 4260 |
| Sensitivity | 57% | 56% | 58% | 57% | 56% | 60% | 57% | 55% | 60% |
| Specificity | 59% | 57% | 53% | 59% | 57% | 54% | 60% | 56% | 56% |
| Cutoff Quartile 4 | 6010 | 6010 | 6060 | 6010 | 6010 | 6060 | 6010 | 6010 | 6060 |
| Sensitivity | 28% | 29% | 27% | 28% | 29% | 26% | 27% | 28% | 27% |
| Specificity | 78% | 79% | 75% | 78% | 79% | 75% | 77% | 79% | 76% |
| OR Quartile 2 | 1.14 | 0.884 | 0.905 | 1.14 | 0.884 | 0.985 | 1.06 | 0.793 | 0.990 |
| p Value | 0.73 | 0.75 | 0.81 | 0.73 | 0.75 | 0.97 | 0.88 | 0.54 | 0.98 |
| Lower limit of 95% CI | 0.542 | 0.421 | 0.408 | 0.542 | 0.421 | 0.446 | 0.503 | 0.375 | 0.462 |
| Upper limit of 95% CI | 2.38 | 1.86 | 2.01 | 2.38 | 1.86 | 2.17 | 2.23 | 1.68 | 2.12 |
| OR Quartile 3 | 1.98 | 1.66 | 1.56 | 1.98 | 1.66 | 1.76 | 1.99 | 1.58 | 1.89 |
| p Value | 0.042 | 0.12 | 0.21 | 0.042 | 0.12 | 0.11 | 0.041 | 0.17 | 0.064 |
| Lower limit of 95% CI | 1.03 | 0.871 | 0.773 | 1.03 | 0.871 | 0.872 | 1.03 | 0.826 | 0.964 |

TABLE 19.7-continued

Comparison of marker levels and the area under the ROC curve (AUC) in EDTA samples for the "recovered"
and "non-recovered" cohorts where recovery starts within 48 hours after sample collection and renal status
is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 3.80 | 3.18 | 3.16 | 3.80 | 3.18 | 3.54 | 3.84 | 3.01 | 3.72 |
| OR Quartile 4 | 1.36 | 1.51 | 1.10 | 1.36 | 1.51 | 1.02 | 1.27 | 1.46 | 1.17 |
| p Value | 0.43 | 0.28 | 0.81 | 0.43 | 0.28 | 0.97 | 0.54 | 0.33 | 0.68 |
| Lower limit of 95% CI | 0.639 | 0.711 | 0.499 | 0.639 | 0.711 | 0.460 | 0.594 | 0.686 | 0.551 |
| Upper limit of 95% CI | 2.90 | 3.22 | 2.45 | 2.90 | 3.22 | 2.24 | 2.70 | 3.11 | 2.50 |

TABLE 19.8

Comparison of marker levels and the area under the ROC curve (AUC) in EDTA samples for the "recovered"
and "non-recovered" cohorts where recovery starts within 72 hours after sample collection and renal status
is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 3790 | 4710 | 3860 | 4700 | 3770 | 4700 |
| Average | 4210 | 5090 | 4250 | 5040 | 4230 | 5040 |
| Stdev | 2560 | 3310 | 2550 | 3320 | 2580 | 3280 |
| p (t-test) | | 0.072 | | 0.11 | | 0.095 |
| Min | 62.8 | 276 | 62.8 | 276 | 62.8 | 276 |
| Max | 11800 | 21200 | 11800 | 21200 | 11800 | 21200 |
| n (Patient) | 73 | 78 | 72 | 79 | 70 | 81 |
| sCr only | | | | | | |
| Median | 3930 | 4670 | 3930 | 4670 | 3930 | 4670 |
| Average | 4300 | 5020 | 4300 | 5020 | 4300 | 5020 |
| Stdev | 2500 | 3380 | 2500 | 3380 | 2500 | 3380 |
| p (t-test) | | 0.14 | | 0.14 | | 0.14 |
| Min | 703 | 62.8 | 703 | 62.8 | 703 | 62.8 |
| Max | 11800 | 21200 | 11800 | 21200 | 11800 | 21200 |
| n (Patient) | 74 | 77 | 74 | 77 | 74 | 77 |
| UO only | | | | | | |
| Median | 4050 | 4800 | 4050 | 4800 | 3930 | 4820 |
| Average | 4460 | 5230 | 4470 | 5170 | 4390 | 5230 |
| Stdev | 2610 | 3710 | 2630 | 3650 | 2580 | 3570 |
| p (t-test) | | 0.15 | | 0.19 | | 0.096 |
| Min | 62.8 | 276 | 62.8 | 276 | 62.8 | 276 |
| Max | 13800 | 21200 | 13800 | 21200 | 13800 | 21200 |
| n (Patient) | 105 | 45 | 103 | 47 | 96 | 54 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.56 | 0.56 | 0.57 | 0.56 | 0.55 | 0.58 | 0.56 | 0.58 |
| SE | 0.046 | 0.047 | 0.052 | 0.046 | 0.047 | 0.051 | 0.046 | 0.047 | 0.049 |
| p Value | 0.073 | 0.20 | 0.25 | 0.12 | 0.20 | 0.28 | 0.086 | 0.20 | 0.13 |
| nCohort Recovered | 73 | 74 | 105 | 72 | 74 | 103 | 70 | 74 | 96 |
| nCohort Non-recovered | 78 | 77 | 45 | 79 | 77 | 47 | 81 | 77 | 54 |
| Cutoff Quartile 2 | 2740 | 2740 | 2740 | 2740 | 2740 | 2740 | 2740 | 2740 | 2740 |
| Sensitivity | 77% | 75% | 73% | 76% | 75% | 72% | 77% | 75% | 74% |
| Specificity | 27% | 26% | 25% | 26% | 26% | 24% | 27% | 26% | 25% |
| Cutoff Quartile 3 | 4230 | 4230 | 4260 | 4230 | 4230 | 4260 | 4230 | 4230 | 4260 |
| Sensitivity | 60% | 58% | 62% | 59% | 58% | 62% | 60% | 58% | 63% |
| Specificity | 60% | 58% | 55% | 60% | 58% | 55% | 61% | 58% | 57% |
| Cutoff Quartile 4 | 6010 | 6010 | 6060 | 6010 | 6010 | 6060 | 6010 | 6010 | 6060 |
| Sensitivity | 29% | 30% | 29% | 29% | 30% | 28% | 28% | 30% | 28% |
| Specificity | 79% | 80% | 76% | 79% | 80% | 76% | 79% | 80% | 76% |

TABLE 19.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 1.26 | 1.05 | 0.905 | 1.13 | 1.05 | 0.838 | 1.22 | 1.05 | 0.952 |
| p Value | 0.54 | 0.89 | 0.81 | 0.74 | 0.89 | 0.66 | 0.60 | 0.89 | 0.90 |
| Lower limit of 95% CI | 0.602 | 0.506 | 0.408 | 0.543 | 0.506 | 0.384 | 0.582 | 0.506 | 0.444 |
| Upper limit of 95% CI | 2.63 | 2.20 | 2.01 | 2.36 | 2.20 | 1.83 | 2.54 | 2.20 | 2.04 |
| OR Quartile 3 | 2.30 | 1.95 | 2.03 | 2.18 | 1.95 | 2.00 | 2.44 | 1.95 | 2.28 |
| p Value | 0.012 | 0.043 | 0.052 | 0.019 | 0.043 | 0.055 | 0.0077 | 0.043 | 0.018 |
| Lower limit of 95% CI | 1.20 | 1.02 | 0.994 | 1.14 | 1.02 | 0.987 | 1.27 | 1.02 | 1.15 |
| Upper limit of 95% CI | 4.42 | 3.73 | 4.15 | 4.18 | 3.73 | 4.04 | 4.70 | 3.73 | 4.52 |
| OR Quartile 4 | 1.62 | 1.68 | 1.30 | 1.56 | 1.68 | 1.19 | 1.45 | 1.68 | 1.22 |
| p Value | 0.21 | 0.18 | 0.51 | 0.24 | 0.18 | 0.66 | 0.33 | 0.18 | 0.61 |
| Lower limit of 95% CI | 0.765 | 0.793 | 0.593 | 0.739 | 0.793 | 0.546 | 0.688 | 0.793 | 0.572 |
| Upper limit of 95% CI | 3.42 | 3.54 | 2.85 | 3.30 | 3.54 | 2.61 | 3.07 | 3.54 | 2.60 |

TABLE 19.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 3860 | 4710 | 3920 | 4690 | 3790 | 4690 |
| Average | 4250 | 5090 | 4290 | 5040 | 4260 | 5040 |
| Stdev | 2560 | 3350 | 2550 | 3360 | 2580 | 3310 |
| p (t-test) | | 0.083 | | 0.12 | | 0.11 |
| Min | 62.8 | 276 | 62.8 | 276 | 62.8 | 276 |
| Max | 11800 | 21200 | 11800 | 21200 | 11800 | 21200 |
| n (Patient) | 76 | 75 | 75 | 76 | 73 | 78 |
| | sCr only | | | | | |
| Median | 3930 | 4580 | 3930 | 4580 | 3930 | 4580 |
| Average | 4320 | 5030 | 4320 | 5030 | 4320 | 5030 |
| Stdev | 2500 | 3420 | 2500 | 3420 | 2500 | 3420 |
| p (t-test) | | 0.15 | | 0.15 | | 0.15 |
| Min | 703 | 62.8 | 703 | 62.8 | 703 | 62.8 |
| Max | 11800 | 21200 | 11800 | 21200 | 11800 | 21200 |
| n (Patient) | 77 | 74 | 77 | 74 | 77 | 74 |
| | UO only | | | | | |
| Median | 3930 | 4820 | 3930 | 4820 | 3920 | 4840 |
| Average | 4460 | 5160 | 4460 | 5160 | 4380 | 5230 |
| Stdev | 2670 | 3540 | 2670 | 3540 | 2600 | 3530 |
| p (t-test) | | 0.18 | | 0.18 | | 0.092 |
| Min | 62.8 | 276 | 62.8 | 276 | 62.8 | 276 |
| Max | 13800 | 21200 | 13800 | 21200 | 13800 | 21200 |
| n (Patient) | 100 | 50 | 100 | 50 | 95 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.56 | 0.56 | 0.57 | 0.56 | 0.56 | 0.57 | 0.56 | 0.58 |
| SE | 0.046 | 0.047 | 0.050 | 0.047 | 0.047 | 0.050 | 0.046 | 0.047 | 0.049 |
| p Value | 0.093 | 0.22 | 0.20 | 0.15 | 0.22 | 0.20 | 0.11 | 0.22 | 0.10 |
| nCohort Recovered | 76 | 77 | 100 | 75 | 77 | 100 | 73 | 77 | 95 |
| nCohort Non- | 75 | 74 | 50 | 76 | 74 | 50 | 78 | 74 | 55 |

TABLE 19.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| recovered | | | | | | | | | |
|---|---|---|---|---|---|---|---|---|---|
| Cutoff Quartile 2 | 2740 | 2740 | 2740 | 2740 | 2740 | 2740 | 2740 | 2740 | 2740 |
| Sensitivity | 77% | 76% | 74% | 76% | 76% | 74% | 77% | 76% | 75% |
| Specificity | 28% | 26% | 25% | 27% | 26% | 25% | 27% | 26% | 25% |
| Cutoff Quartile 3 | 4230 | 4230 | 4260 | 4230 | 4230 | 4260 | 4230 | 4230 | 4260 |
| Sensitivity | 60% | 58% | 62% | 59% | 58% | 62% | 60% | 58% | 64% |
| Specificity | 59% | 57% | 56% | 59% | 57% | 56% | 60% | 57% | 58% |
| Cutoff Quartile 4 | 6010 | 6010 | 6060 | 6010 | 6010 | 6060 | 6010 | 6010 | 6060 |
| Sensitivity | 29% | 30% | 26% | 29% | 30% | 26% | 28% | 30% | 27% |
| Specificity | 79% | 79% | 75% | 79% | 79% | 75% | 78% | 79% | 76% |
| OR Quartile 2 | 1.30 | 1.09 | 0.949 | 1.17 | 1.09 | 0.949 | 1.26 | 1.09 | 0.990 |
| p Value | 0.48 | 0.82 | 0.89 | 0.67 | 0.82 | 0.89 | 0.54 | 0.82 | 0.98 |
| Lower limit of 95% CI | 0.623 | 0.523 | 0.436 | 0.561 | 0.523 | 0.436 | 0.602 | 0.523 | 0.462 |
| Upper limit of 95% CI | 2.73 | 2.28 | 2.06 | 2.45 | 2.28 | 2.06 | 2.63 | 2.28 | 2.12 |
| OR Quartile 3 | 2.18 | 1.85 | 2.08 | 2.06 | 1.85 | 2.08 | 2.30 | 1.85 | 2.41 |
| p Value | 0.019 | 0.062 | 0.039 | 0.029 | 0.062 | 0.039 | 0.012 | 0.062 | 0.012 |
| Lower limit of 95% CI | 1.14 | 0.970 | 1.04 | 1.08 | 0.970 | 1.04 | 1.20 | 0.970 | 1.21 |
| Upper limit of 95% CI | 4.17 | 3.53 | 4.16 | 3.94 | 3.53 | 4.16 | 4.42 | 3.53 | 4.77 |
| OR Quartile 4 | 1.56 | 1.61 | 1.05 | 1.50 | 1.61 | 1.05 | 1.40 | 1.61 | 1.17 |
| p Value | 0.24 | 0.21 | 0.89 | 0.28 | 0.21 | 0.89 | 0.37 | 0.21 | 0.68 |
| Lower limit of 95% CI | 0.741 | 0.768 | 0.484 | 0.715 | 0.768 | 0.484 | 0.666 | 0.768 | 0.551 |
| Upper limit of 95% CI | 3.27 | 3.39 | 2.29 | 3.16 | 3.39 | 2.29 | 2.94 | 3.39 | 2.50 |

TABLE 19.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 4060 | 4580 | 4090 | 4500 | 4060 | 4490 |
| Average | 4540 | 4840 | 4580 | 4780 | 4580 | 4780 |
| Stdev | 2720 | 3370 | 2710 | 3380 | 2730 | 3350 |
| p (t-test) | | 0.55 | | 0.68 | | 0.69 |
| Min | 703 | 62.8 | 703 | 62.8 | 703 | 62.8 |
| Max | 13800 | 21200 | 13800 | 21200 | 13800 | 21200 |
| n (Patient) | 89 | 62 | 88 | 63 | 87 | 64 |
| sCr only | | | | | | |
| Median | 3930 | 4690 | 3930 | 4690 | 3930 | 4690 |
| Average | 4310 | 5060 | 4310 | 5060 | 4310 | 5060 |
| Stdev | 2520 | 3420 | 2520 | 3420 | 2520 | 3420 |
| p (t-test) | | 0.12 | | 0.12 | | 0.12 |
| Min | 703 | 62.8 | 703 | 62.8 | 703 | 62.8 |
| Max | 11800 | 21200 | 11800 | 21200 | 11800 | 21200 |
| n (Patient) | 79 | 72 | 79 | 72 | 79 | 72 |

TABLE 19.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 3930 | 4790 | 3930 | 4790 | 3930 | 4750 |
| Average | 4480 | 5080 | 4480 | 5080 | 4520 | 5000 |
| Stdev | 2670 | 3520 | 2670 | 3520 | 2680 | 3490 |
| p (t-test) | | 0.24 | | 0.24 | | 0.34 |
| Min | 413 | 62.8 | 413 | 62.8 | 413 | 62.8 |
| Max | 13800 | 21200 | 13800 | 21200 | 13800 | 21200 |
| n (Patient) | 98 | 52 | 98 | 52 | 96 | 54 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.52 | 0.56 | 0.56 | 0.51 | 0.56 | 0.56 | 0.51 | 0.56 | 0.54 |
| SE | 0.048 | 0.047 | 0.050 | 0.048 | 0.047 | 0.050 | 0.048 | 0.047 | 0.049 |
| p Value | 0.61 | 0.17 | 0.27 | 0.78 | 0.17 | 0.27 | 0.77 | 0.17 | 0.38 |
| nCohort Recovered | 89 | 79 | 98 | 88 | 79 | 98 | 87 | 79 | 96 |
| nCohort Non-recovered | 62 | 72 | 52 | 63 | 72 | 52 | 64 | 72 | 54 |
| Cutoff Quartile 2 | 2740 | 2740 | 2740 | 2740 | 2740 | 2740 | 2740 | 2740 | 2740 |
| Sensitivity | 74% | 78% | 75% | 73% | 78% | 75% | 73% | 78% | 74% |
| Specificity | 25% | 28% | 26% | 24% | 28% | 26% | 24% | 28% | 25% |
| Cutoff Quartile 3 | 4230 | 4230 | 4260 | 4230 | 4230 | 4260 | 4230 | 4230 | 4260 |
| Sensitivity | 56% | 58% | 60% | 56% | 58% | 60% | 56% | 58% | 59% |
| Specificity | 54% | 57% | 55% | 53% | 57% | 55% | 54% | 57% | 55% |
| Cutoff Quartile 4 | 6010 | 6010 | 6060 | 6010 | 6010 | 6060 | 6010 | 6010 | 6060 |
| Sensitivity | 24% | 28% | 25% | 24% | 28% | 25% | 23% | 28% | 24% |
| Specificity | 74% | 77% | 74% | 74% | 77% | 74% | 74% | 77% | 74% |
| OR Quartile 2 | 0.944 | 1.35 | 1.03 | 0.848 | 1.35 | 1.03 | 0.880 | 1.35 | 0.952 |
| p Value | 0.88 | 0.43 | 0.95 | 0.66 | 0.43 | 0.95 | 0.73 | 0.43 | 0.90 |
| Lower limit of 95% CI | 0.448 | 0.643 | 0.473 | 0.404 | 0.643 | 0.473 | 0.419 | 0.643 | 0.444 |
| Upper limit of 95% CI | 1.99 | 2.84 | 2.23 | 1.78 | 2.84 | 2.23 | 1.85 | 2.84 | 2.04 |
| OR Quartile 3 | 1.52 | 1.85 | 1.81 | 1.43 | 1.85 | 1.81 | 1.51 | 1.85 | 1.79 |
| p Value | 0.21 | 0.061 | 0.088 | 0.28 | 0.061 | 0.088 | 0.21 | 0.061 | 0.090 |
| Lower limit of 95% CI | 0.790 | 0.971 | 0.916 | 0.748 | 0.971 | 0.916 | 0.789 | 0.971 | 0.912 |
| Upper limit of 95% CI | 2.91 | 3.54 | 3.58 | 2.74 | 3.54 | 3.58 | 2.89 | 3.54 | 3.52 |
| OR Quartile 4 | 0.916 | 1.30 | 0.973 | 0.883 | 1.30 | 0.973 | 0.852 | 1.30 | 0.900 |
| p Value | 0.82 | 0.48 | 0.95 | 0.75 | 0.48 | 0.95 | 0.67 | 0.48 | 0.79 |
| Lower limit of 95% CI | 0.432 | 0.624 | 0.449 | 0.417 | 0.624 | 0.449 | 0.403 | 0.624 | 0.416 |
| Upper limit of 95% CI | 1.94 | 2.72 | 2.11 | 1.87 | 2.72 | 2.11 | 1.80 | 2.72 | 1.95 |

Example 20. Use of C—C Motif Chemokine 15 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 15 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 20.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 65.6 | 585 | 65.6 | 770 | 77.7 | 784 |
| Average | 1180 | 2680 | 1140 | 3040 | 1460 | 2460 |
| Stdev | 5100 | 6030 | 4920 | 6440 | 5910 | 3940 |
| p (t-test) | | 0.020 | | 0.0044 | | 0.16 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 204 | 112 | 220 | 96 | 235 | 81 |
| sCr only | | | | | | |
| Median | 65.2 | 604 | 65.6 | 803 | 75.3 | 791 |
| Average | 1170 | 2770 | 1110 | 3170 | 1450 | 2490 |
| Stdev | 5060 | 6130 | 4890 | 6520 | 5920 | 3950 |
| p (t-test) | | 0.014 | | 0.0023 | | 0.14 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 207 | 108 | 222 | 93 | 234 | 81 |
| UO only | | | | | | |
| Median | 130 | 344 | 130 | 406 | 129 | 491 |
| Average | 1750 | 1550 | 1730 | 1670 | 1720 | 1720 |
| Stdev | 5760 | 3230 | 5730 | 3330 | 5720 | 3370 |
| p (t-test) | | 0.83 | | 0.95 | | 1.00 |
| Min | 0.0116 | 0.0116 | 0.0116 | 0.0116 | 0.0116 | 0.0116 |
| Max | 53500 | 18400 | 53500 | 18400 | 53500 | 18400 |
| n (Patient) | 274 | 40 | 277 | 37 | 278 | 36 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.71 | 0.58 | 0.73 | 0.74 | 0.60 | 0.72 | 0.72 | 0.61 |
| SE | 0.032 | 0.032 | 0.050 | 0.033 | 0.033 | 0.052 | 0.035 | 0.035 | 0.052 |
| p Value | 3.6E−10 | 2.6E−11 | 0.12 | 4.4E−12 | 2.8E−13 | 0.065 | 1.0E−9 | 6.9E−10 | 0.034 |
| nCohort Non-persistent | 204 | 207 | 274 | 220 | 222 | 277 | 235 | 234 | 278 |
| nCohort Persistent | 112 | 108 | 40 | 96 | 93 | 37 | 81 | 81 | 36 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 88% | 90% | 82% | 90% | 91% | 84% | 90% | 93% | 86% |
| Specificity | 29% | 30% | 24% | 29% | 30% | 24% | 28% | 29% | 24% |
| Cutoff Quartile 3 | 155 | 154 | 155 | 155 | 154 | 155 | 155 | 154 | 155 |
| Sensitivity | 71% | 71% | 68% | 75% | 75% | 70% | 77% | 74% | 72% |
| Specificity | 61% | 61% | 53% | 61% | 60% | 53% | 59% | 58% | 53% |
| Cutoff Quartile 4 | 909 | 912 | 902 | 909 | 912 | 902 | 909 | 912 | 902 |
| Sensitivity | 42% | 44% | 32% | 46% | 48% | 35% | 46% | 47% | 36% |
| Specificity | 84% | 85% | 76% | 84% | 85% | 76% | 82% | 82% | 76% |
| OR Quartile 2 | 2.92 | 3.86 | 1.50 | 3.53 | 4.50 | 1.65 | 3.56 | 5.12 | 2.01 |
| p Value | 9.7E−4 | 1.3E−4 | 0.36 | 5.6E−4 | 1.6E−4 | 0.29 | 0.0015 | 2.7E−4 | 0.16 |
| Lower limit of 95% CI | 1.54 | 1.93 | 0.632 | 1.72 | 2.06 | 0.659 | 1.63 | 2.13 | 0.751 |
| Upper limit of 95% CI | 5.51 | 7.69 | 3.54 | 7.22 | 9.81 | 4.12 | 7.80 | 12.3 | 5.37 |
| OR Quartile 3 | 3.79 | 3.86 | 2.30 | 4.67 | 4.63 | 2.63 | 4.72 | 3.97 | 2.92 |
| p Value | 1.3E−7 | 1.3E−7 | 0.020 | 1.7E−8 | 3.0E−8 | 0.011 | 1.3E−7 | 1.5E−6 | 0.0062 |
| Lower limit of 95% CI | 2.31 | 2.34 | 1.14 | 2.74 | 2.69 | 1.25 | 2.66 | 2.26 | 1.36 |

TABLE 20.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 6.21 | 6.38 | 4.65 | 7.99 | 7.97 | 5.54 | 8.41 | 6.95 | 6.28 |
| OR Quartile 4 | 3.89 | 4.21 | 1.52 | 4.47 | 5.18 | 1.73 | 3.86 | 4.16 | 1.82 |
| p Value | 5.7E−7 | 1.4E−7 | 0.25 | 5.4E−8 | 3.6E−9 | 0.14 | 1.5E−6 | 4.0E−7 | 0.11 |
| Lower limit of 95% CI | 2.28 | 2.47 | 0.741 | 2.61 | 3.00 | 0.835 | 2.23 | 2.40 | 0.871 |
| Upper limit of 95% CI | 6.62 | 7.20 | 3.11 | 7.68 | 8.95 | 3.59 | 6.70 | 7.22 | 3.78 |

TABLE 20.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 59.2 | 576 | 59.2 | 618 | 65.6 | 616 |
| Average | 1170 | 2490 | 1100 | 2820 | 1460 | 2290 |
| Stdev | 5270 | 5700 | 5040 | 6070 | 6080 | 3820 |
| p (t-test) | | 0.034 | | 0.0075 | | 0.21 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 185 | 131 | 203 | 113 | 218 | 98 |
| | sCr only | | | | | |
| Median | 60.0 | 577 | 59.2 | 717 | 65.2 | 616 |
| Average | 1140 | 2610 | 1090 | 2900 | 1460 | 2300 |
| Stdev | 5190 | 5840 | 5020 | 6140 | 6090 | 3820 |
| p (t-test) | | 0.021 | | 0.0050 | | 0.21 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 191 | 124 | 205 | 110 | 217 | 98 |
| | UO only | | | | | |
| Median | 118 | 406 | 118 | 488 | 118 | 521 |
| Average | 1790 | 1450 | 1760 | 1530 | 1760 | 1560 |
| Stdev | 5950 | 2870 | 5910 | 2960 | 5900 | 2980 |
| p (t-test) | | 0.67 | | 0.78 | | 0.81 |
| Min | 0.0116 | 0.0116 | 0.0116 | 0.0116 | 0.0116 | 0.0116 |
| Max | 53500 | 18400 | 53500 | 18400 | 53500 | 18400 |
| n (Patient) | 255 | 59 | 259 | 55 | 260 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.71 | 0.60 | 0.73 | 0.73 | 0.61 | 0.71 | 0.71 | 0.62 |
| SE | 0.030 | 0.031 | 0.042 | 0.031 | 0.031 | 0.044 | 0.033 | 0.033 | 0.044 |
| p Value | 2.7E−11 | 1.4E−11 | 0.020 | 2.3E−13 | 3.9E−14 | 0.014 | 3.3E−10 | 2.8E−10 | 0.0069 |
| nCohort Non-persistent | 185 | 191 | 255 | 203 | 205 | 259 | 218 | 217 | 260 |
| nCohort Persistent | 131 | 124 | 59 | 113 | 110 | 55 | 98 | 98 | 54 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 87% | 89% | 85% | 89% | 91% | 85% | 89% | 91% | 87% |
| Specificity | 31% | 31% | 25% | 31% | 31% | 25% | 29% | 30% | 25% |
| Cutoff Quartile 3 | 155 | 154 | 155 | 155 | 154 | 155 | 155 | 154 | 155 |
| Sensitivity | 70% | 70% | 68% | 73% | 74% | 69% | 74% | 72% | 70% |
| Specificity | 64% | 63% | 54% | 63% | 62% | 54% | 61% | 60% | 54% |
| Cutoff Quartile 4 | 909 | 912 | 902 | 909 | 912 | 902 | 909 | 912 | 902 |
| Sensitivity | 40% | 42% | 31% | 43% | 45% | 33% | 42% | 43% | 33% |
| Specificity | 85% | 86% | 76% | 85% | 86% | 76% | 83% | 83% | 77% |

TABLE 20.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 2.99 | 3.60 | 1.86 | 3.70 | 4.54 | 1.97 | 3.21 | 4.23 | 2.28 |
| p Value | 3.3E−4 | 7.6E−5 | 0.11 | 1.3E−4 | 3.3E−5 | 0.097 | 9.4E−4 | 1.5E−4 | 0.054 |
| Lower limit of 95% CI | 1.64 | 1.91 | 0.867 | 1.90 | 2.22 | 0.884 | 1.61 | 2.01 | 0.984 |
| Upper limit of 95% CI | 5.43 | 6.79 | 4.00 | 7.22 | 9.27 | 4.38 | 6.42 | 8.90 | 5.30 |
| OR Quartile 3 | 4.25 | 3.97 | 2.48 | 4.72 | 4.64 | 2.63 | 4.57 | 3.93 | 2.81 |
| p Value | 3.5E−9 | 2.3E−8 | 0.0029 | 1.8E−9 | 3.5E−9 | 0.0023 | 1.9E−8 | 2.5E−7 | 0.0014 |
| Lower limit of 95% CI | 2.63 | 2.45 | 1.36 | 2.85 | 2.79 | 1.41 | 2.69 | 2.34 | 1.49 |
| Upper limit of 95% CI | 6.88 | 6.45 | 4.52 | 7.83 | 7.73 | 4.90 | 7.76 | 6.61 | 5.30 |
| OR Quartile 4 | 3.85 | 4.39 | 1.40 | 4.42 | 5.06 | 1.58 | 3.41 | 3.65 | 1.63 |
| p Value | 8.8E−7 | 8.6E−8 | 0.29 | 6.1E−8 | 5.0E−9 | 0.16 | 6.4E−6 | 2.0E−6 | 0.13 |
| Lower limit of 95% CI | 2.25 | 2.55 | 0.748 | 2.58 | 2.94 | 0.839 | 2.00 | 2.14 | 0.865 |
| Upper limit of 95% CI | 6.59 | 7.54 | 2.61 | 7.56 | 8.71 | 2.97 | 5.80 | 6.22 | 3.08 |

TABLE 20.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 55.7 | 585 | 55.3 | 692 | 63.1 | 635 |
| Average | 1100 | 2470 | 1030 | 2740 | 1400 | 2290 |
| Stdev | 5340 | 5580 | 5130 | 5840 | 6200 | 3820 |
| p (t-test) | | 0.026 | | 0.0065 | | 0.17 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 174 | 142 | 189 | 127 | 204 | 112 |
| | sCr only | | | | | |
| Median | 56.1 | 596 | 55.7 | 784 | 65.0 | 616 |
| Average | 1070 | 2600 | 1020 | 2850 | 1390 | 2350 |
| Stdev | 5240 | 5720 | 5070 | 5960 | 6150 | 3880 |
| p (t-test) | | 0.014 | | 0.0038 | | 0.14 |
| Min | 0.0116 | 0.0116 | 0.0116 | 0.0116 | 0.0116 | 0.0116 |
| Max | 53500 | 52500 | 53500 | 52500 | 53500 | 19200 |
| n (Patient) | 181 | 134 | 194 | 121 | 207 | 108 |
| | UO only | | | | | |
| Median | 118 | 406 | 118 | 521 | 118 | 521 |
| Average | 1780 | 1510 | 1750 | 1610 | 1750 | 1610 |
| Stdev | 6040 | 2930 | 5980 | 3010 | 5980 | 3010 |
| p (t-test) | | 0.72 | | 0.86 | | 0.86 |
| Min | 0.0116 | 0.0116 | 0.0116 | 0.0116 | 0.0116 | 0.0116 |
| Max | 53500 | 18400 | 53500 | 18400 | 53500 | 18400 |
| n (Patient) | 245 | 69 | 250 | 64 | 250 | 64 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.72 | 0.59 | 0.74 | 0.74 | 0.61 | 0.71 | 0.72 | 0.61 |
| SE | 0.029 | 0.029 | 0.040 | 0.029 | 0.030 | 0.041 | 0.031 | 0.032 | 0.041 |
| p Value | 3.3E−13 | 4.0E−14 | 0.018 | 4.4E−16 | 2.2E−16 | 0.0070 | 1.2E−11 | 1.1E−11 | 0.0070 |
| nCohort Non-persistent | 174 | 181 | 245 | 189 | 194 | 250 | 204 | 207 | 250 |

TABLE 20.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Persistent | 142 | 134 | 69 | 127 | 121 | 64 | 112 | 108 | 64 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 87% | 89% | 84% | 89% | 91% | 86% | 88% | 91% | 86% |
| Specificity | 32% | 33% | 25% | 32% | 32% | 26% | 30% | 31% | 26% |
| Cutoff Quartile 3 | 155 | 154 | 155 | 155 | 154 | 155 | 155 | 154 | 155 |
| Sensitivity | 70% | 70% | 65% | 72% | 73% | 67% | 72% | 71% | 67% |
| Specificity | 66% | 65% | 54% | 65% | 64% | 54% | 62% | 61% | 54% |
| Cutoff Quartile 4 | 909 | 912 | 902 | 909 | 912 | 902 | 909 | 912 | 902 |
| Sensitivity | 40% | 43% | 30% | 44% | 46% | 33% | 42% | 44% | 33% |
| Specificity | 87% | 88% | 76% | 88% | 88% | 77% | 84% | 85% | 77% |
| OR Quartile 2 | 2.99 | 3.84 | 1.79 | 3.75 | 4.81 | 2.10 | 3.25 | 4.39 | 2.10 |
| p Value | 2.1E−4 | 2.2E−5 | 0.11 | 4.3E−5 | 7.9E−6 | 0.055 | 3.9E−4 | 5.0E−5 | 0.055 |
| Lower limit of 95% CI | 1.68 | 2.06 | 0.882 | 1.99 | 2.42 | 0.984 | 1.69 | 2.15 | 0.984 |
| Upper limit of 95% CI | 5.34 | 7.14 | 3.62 | 7.08 | 9.58 | 4.50 | 6.23 | 8.96 | 4.50 |
| OR Quartile 3 | 4.49 | 4.30 | 2.23 | 4.90 | 4.72 | 2.44 | 4.31 | 3.86 | 2.44 |
| p Value | 6.4E−10 | 2.5E−9 | 0.0047 | 2.2E−10 | 8.4E−10 | 0.0025 | 1.1E−8 | 1.3E−7 | 0.0025 |
| Lower limit of 95% CI | 2.79 | 2.66 | 1.28 | 3.00 | 2.88 | 1.37 | 2.61 | 2.34 | 1.37 |
| Upper limit of 95% CI | 7.22 | 6.94 | 3.88 | 8.00 | 7.76 | 4.35 | 7.12 | 6.38 | 4.35 |
| OR Quartile 4 | 4.63 | 5.35 | 1.41 | 5.69 | 6.41 | 1.62 | 3.89 | 4.21 | 1.62 |
| p Value | 7.6E−8 | 5.0E−9 | 0.25 | 1.1E−9 | 1.0E−10 | 0.12 | 5.7E−7 | 1.4E−7 | 0.12 |
| Lower limit of 95% CI | 2.65 | 3.05 | 0.781 | 3.25 | 3.65 | 0.888 | 2.28 | 2.47 | 0.888 |
| Upper limit of 95% CI | 8.10 | 9.39 | 2.55 | 9.96 | 11.2 | 2.94 | 6.62 | 7.20 | 2.94 |

TABLE 20.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 54.2 | 585 | 54.2 | 671 | 60.6 | 616 |
| Average | 1100 | 2450 | 1040 | 2720 | 1160 | 2670 |
| Stdev | 5380 | 5540 | 5150 | 5820 | 5100 | 6000 |
| p (t-test) | | 0.029 | | 0.0073 | | 0.019 |
| Min | 0.0116 | 0.0116 | 0.0116 | 0.0116 | 0.0116 | 0.0116 |
| Max | 53500 | 52500 | 53500 | 52500 | 53500 | 52500 |
| n (Patient) | 172 | 144 | 188 | 128 | 200 | 116 |
| | sCr only | | | | | |
| | Cohort | Cohort | Cohort | Cohort | Cohort | Cohort |
| Median | 56.1 | 585 | 55.3 | 701 | 61.1 | 616 |
| Average | 1080 | 2560 | 1030 | 2790 | 1150 | 2740 |
| Stdev | 5270 | 5680 | 5110 | 5900 | 5060 | 6090 |
| p (t-test) | | 0.017 | | 0.0053 | | 0.014 |
| Min | 0.0116 | 0.0116 | 0.0116 | 0.0116 | 0.0116 | 0.0116 |
| Max | 53500 | 52500 | 53500 | 52500 | 53500 | 52500 |
| n (Patient) | 179 | 136 | 191 | 124 | 203 | 112 |
| | UO only | | | | | |
| Median | 116 | 351 | 116 | 380 | 116 | 380 |
| Average | 1750 | 1650 | 1710 | 1760 | 1710 | 1760 |
| Stdev | 6010 | 3470 | 5940 | 3590 | 5940 | 3590 |
| p (t-test) | | 0.90 | | 0.95 | | 0.95 |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 238 | 76 | 244 | 70 | 244 | 70 |

TABLE 20.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

|  | Persistence Period Duration (hr) | | | | | | | | |
| --- | --- | --- | --- | --- | --- | --- | --- | --- | --- |
|  | 24 | | | 48 | | | 72 | | |
|  | sCr or UO | sCr only | UO only | sCr or UO | sCr only | UO only | sCr or UO | sCr only | UO only |
| AUC | 0.72 | 0.72 | 0.60 | 0.74 | 0.74 | 0.61 | 0.71 | 0.72 | 0.61 |
| SE | 0.029 | 0.030 | 0.038 | 0.029 | 0.030 | 0.040 | 0.031 | 0.031 | 0.040 |
| p Value | 1.3E−13 | 2.7E−13 | 0.011 | 6.7E−16 | 6.7E−16 | 0.0061 | 7.6E−12 | 6.2E−12 | 0.0061 |
| nCohort Non-persistent | 172 | 179 | 238 | 188 | 191 | 244 | 200 | 203 | 244 |
| nCohort Persistent | 144 | 136 | 76 | 128 | 124 | 70 | 116 | 112 | 70 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 87% | 88% | 84% | 89% | 90% | 86% | 89% | 90% | 86% |
| Specificity | 32% | 32% | 26% | 32% | 32% | 26% | 30% | 31% | 26% |
| Cutoff Quartile 3 | 155 | 154 | 155 | 155 | 154 | 155 | 155 | 154 | 155 |
| Sensitivity | 69% | 69% | 66% | 72% | 72% | 67% | 71% | 71% | 67% |
| Specificity | 66% | 64% | 55% | 65% | 64% | 55% | 62% | 61% | 55% |
| Cutoff Quartile 4 | 909 | 912 | 902 | 909 | 912 | 902 | 909 | 912 | 902 |
| Sensitivity | 40% | 42% | 30% | 44% | 45% | 31% | 41% | 43% | 31% |
| Specificity | 88% | 88% | 76% | 88% | 88% | 77% | 84% | 85% | 77% |
| OR Quartile 2 | 3.09 | 3.60 | 1.84 | 3.82 | 4.49 | 2.09 | 3.48 | 4.13 | 2.09 |
| p Value | 1.3E−4 | 3.7E−5 | 0.080 | 3.5E−5 | 1.1E−5 | 0.047 | 1.7E−4 | 5.5E−5 | 0.047 |
| Lower limit of 95% CI | 1.73 | 1.96 | 0.930 | 2.02 | 2.30 | 1.01 | 1.81 | 2.07 | 1.01 |
| Upper limit of 95% CI | 5.52 | 6.61 | 3.63 | 7.20 | 8.75 | 4.33 | 6.67 | 8.24 | 4.33 |
| OR Quartile 3 | 4.47 | 4.02 | 2.35 | 4.72 | 4.50 | 2.49 | 3.93 | 3.76 | 2.49 |
| p Value | 6.6E−10 | 9.4E−9 | 0.0018 | 4.5E−10 | 1.8E−9 | 0.0014 | 4.6E−8 | 1.6E−7 | 0.0014 |
| Lower limit of 95% CI | 2.78 | 2.50 | 1.37 | 2.90 | 2.75 | 1.42 | 2.41 | 2.29 | 1.42 |
| Upper limit of 95% CI | 7.18 | 6.47 | 4.03 | 7.70 | 7.34 | 4.35 | 6.43 | 6.16 | 4.35 |
| OR Quartile 4 | 4.85 | 5.15 | 1.41 | 5.58 | 6.02 | 1.50 | 3.85 | 4.16 | 1.50 |
| p Value | 4.3E−8 | 1.1E−8 | 0.24 | 1.6E−9 | 3.7E−10 | 0.17 | 6.9E−7 | 1.8E−7 | 0.17 |
| Lower limit of 95% CI | 2.76 | 2.94 | 0.795 | 3.19 | 3.43 | 0.837 | 2.26 | 2.44 | 0.837 |
| Upper limit of 95% CI | 8.53 | 9.03 | 2.50 | 9.76 | 10.5 | 2.70 | 6.55 | 7.11 | 2.70 |

TABLE 20.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

|  | Persistence Period Duration (hr) | | | | | |
| --- | --- | --- | --- | --- | --- | --- |
|  | 24 | | 48 | | 72 | |
|  | Non-persistent Cohort | Persistent Cohort | Non-persistent Cohort | Persistent Cohort | Non-persistent Cohort | Persistent Cohort |
| | sCr or UO | | | | | |
| Median | 54.2 | 585 | 53.2 | 692 | 59.6 | 616 |
| Average | 798 | 2760 | 754 | 3040 | 1170 | 2600 |
| Stdev | 3610 | 6900 | 3460 | 7220 | 5150 | 5910 |
| p (t-test) | 0.0014 | | 2.2E−4 | | 0.024 | |
| Min | 0.0116 | 0.0116 | 0.0116 | 0.0116 | 0.0116 | 0.0116 |
| Max | 34200 | 53500 | 34200 | 53500 | 53500 | 52500 |
| n (Patient) | 168 | 148 | 183 | 133 | 196 | 120 |
| | sCr only | | | | | |
| Median | 56.1 | 585 | 55.3 | 701 | 61.1 | 616 |
| Average | 787 | 2890 | 752 | 3130 | 899 | 3130 |
| Stdev | 3540 | 7070 | 3430 | 7350 | 3490 | 7630 |
| p (t-test) | 6.9E−4 | | 1.4E−4 | | 4.7E−4 | |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 175 | 140 | 187 | 128 | 199 | 116 |

TABLE 20.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | UO only | | | | |
|---|---|---|---|---|---|---|---|---|
| Median | 106 | 406 | 104 | 447 | 104 | 447 | | |
| Average | 1730 | 1710 | 1710 | 1760 | 1710 | 1760 | | |
| Stdev | 6070 | 3420 | 6030 | 3470 | 6030 | 3470 | | |
| p (t-test) | | 0.98 | | 0.94 | | 0.94 | | |
| Min | 0.0116 | 0.0116 | 0.0116 | 0.0116 | 0.0116 | 0.0116 | | |
| Max | 53500 | 19200 | 53500 | 19200 | 53500 | 19200 | | |
| n (Patient) | 233 | 81 | 236 | 78 | 236 | 78 | | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.72 | 0.62 | 0.75 | 0.74 | 0.62 | 0.72 | 0.72 | 0.62 |
| SE | 0.029 | 0.029 | 0.037 | 0.029 | 0.029 | 0.038 | 0.031 | 0.031 | 0.038 |
| p Value | 3.4E−14 | 1.0E−13 | 0.0019 | 0 | 2.2E−16 | 0.0012 | 2.3E−12 | 3.5E−12 | 0.0012 |
| nCohort Non-persistent | 168 | 175 | 233 | 183 | 187 | 236 | 196 | 199 | 236 |
| nCohort Persistent | 148 | 140 | 81 | 133 | 128 | 78 | 120 | 116 | 78 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 86% | 87% | 85% | 89% | 89% | 86% | 89% | 89% | 86% |
| Specificity | 32% | 32% | 26% | 33% | 32% | 26% | 31% | 31% | 26% |
| Cutoff Quartile 3 | 155 | 154 | 155 | 155 | 154 | 155 | 155 | 154 | 155 |
| Sensitivity | 69% | 69% | 68% | 72% | 71% | 69% | 71% | 70% | 69% |
| Specificity | 67% | 65% | 56% | 66% | 64% | 56% | 63% | 61% | 56% |
| Cutoff Quartile 4 | 909 | 912 | 902 | 909 | 912 | 902 | 909 | 912 | 902 |
| Sensitivity | 41% | 42% | 32% | 44% | 45% | 33% | 42% | 43% | 33% |
| Specificity | 89% | 89% | 77% | 89% | 89% | 78% | 85% | 85% | 78% |
| OR Quartile 2 | 3.03 | 3.19 | 2.04 | 4.15 | 3.85 | 2.17 | 3.72 | 3.50 | 2.17 |
| p Value | 1.4E−4 | 1.1E−4 | 0.040 | 1.1E−5 | 3.1E−5 | 0.030 | 7.5E−5 | 1.6E−4 | 0.030 |
| Lower limit of 95% CI | 1.71 | 1.77 | 1.03 | 2.20 | 2.04 | 1.08 | 1.94 | 1.83 | 1.08 |
| Upper limit of 95% CI | 5.37 | 5.74 | 4.02 | 7.82 | 7.25 | 4.37 | 7.13 | 6.71 | 4.37 |
| OR Quartile 3 | 4.43 | 3.98 | 2.72 | 5.06 | 4.41 | 2.91 | 4.09 | 3.67 | 2.91 |
| p Value | 6.9E−10 | 1.0E−8 | 2.4E−4 | 6.9E−11 | 2.1E−9 | 1.3E−4 | 1.6E−8 | 1.8E−7 | 1.3E−4 |
| Lower limit of 95% CI | 2.76 | 2.48 | 1.59 | 3.11 | 2.71 | 1.68 | 2.51 | 2.25 | 1.68 |
| Upper limit of 95% CI | 7.12 | 6.38 | 4.63 | 8.24 | 7.16 | 5.01 | 6.67 | 5.98 | 5.01 |
| OR Quartile 4 | 5.35 | 5.65 | 1.61 | 6.50 | 6.55 | 1.73 | 4.11 | 4.44 | 1.73 |
| p Value | 1.4E−8 | 3.4E−9 | 0.096 | 2.0E−10 | 1.2E−10 | 0.057 | 2.3E−7 | 5.8E−8 | 0.057 |
| Lower limit of 95% CI | 3.00 | 3.18 | 0.919 | 3.65 | 3.70 | 0.985 | 2.41 | 2.59 | 0.985 |
| Upper limit of 95% CI | 9.54 | 10.0 | 2.81 | 11.6 | 11.6 | 3.03 | 7.03 | 7.61 | 3.03 |

TABLE 20.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 4090 | 4500 | 4090 | 4500 | 4170 | 4300 |
| Average | 4460 | 5020 | 4470 | 5090 | 4630 | 4780 |
| Stdev | 2710 | 3430 | 2690 | 3590 | 2790 | 3560 |

TABLE 20.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.27 | | 0.24 | | 0.78 |
| Min | 62.8 | 413 | 62.8 | 413 | 62.8 | 413 |
| Max | 11800 | 21200 | 11800 | 21200 | 13800 | 21200 |
| n (Patient) | 96 | 55 | 104 | 47 | 111 | 40 | sCr only

| | | | | | | |
|---|---|---|---|---|---|---|
| Median | 4150 | 4490 | 4120 | 4500 | 4230 | 4300 |
| Average | 4520 | 4930 | 4480 | 5090 | 4660 | 4720 |
| Stdev | 2700 | 3470 | 2660 | 3650 | 2780 | 3560 |
| p (t-test) | | 0.42 | | 0.26 | | 0.91 |
| Min | 276 | 62.8 | 276 | 62.8 | 276 | 62.8 |
| Max | 11800 | 21200 | 11800 | 21200 | 13800 | 21200 |
| n (Patient) | 94 | 56 | 103 | 47 | 108 | 42 |

UO only

| | | | | | | |
|---|---|---|---|---|---|---|
| Median | 4170 | 4800 | 4170 | 4800 | 4150 | 4880 |
| Average | 4560 | 5570 | 4560 | 5570 | 4540 | 5820 |
| Stdev | 2670 | 4660 | 2670 | 4660 | 2680 | 4660 |
| p (t-test) | | 0.17 | | 0.17 | | 0.089 |
| Min | 62.8 | 1120 | 62.8 | 1120 | 62.8 | 1630 |
| Max | 13800 | 21200 | 13800 | 21200 | 13800 | 21200 |
| n (Patient) | 131 | 19 | 131 | 19 | 132 | 18 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.54 | 0.52 | 0.54 | 0.54 | 0.54 | 0.54 | 0.49 | 0.49 | 0.57 |
| SE | 0.049 | 0.049 | 0.072 | 0.051 | 0.051 | 0.072 | 0.054 | 0.053 | 0.074 |
| p Value | 0.44 | 0.65 | 0.54 | 0.43 | 0.43 | 0.54 | 0.89 | 0.80 | 0.32 |
| nCohort Non-persistent | 96 | 94 | 131 | 104 | 103 | 131 | 111 | 108 | 132 |
| nCohort Persistent | 55 | 56 | 19 | 47 | 47 | 19 | 40 | 42 | 18 |
| Cutoff Quartile 2 | 2740 | 2730 | 2740 | 2740 | 2730 | 2740 | 2740 | 2730 | 2740 |
| Sensitivity | 75% | 73% | 68% | 79% | 79% | 68% | 78% | 76% | 72% |
| Specificity | 25% | 24% | 24% | 27% | 27% | 24% | 26% | 26% | 25% |
| Cutoff Quartile 3 | 4230 | 4260 | 4260 | 4230 | 4260 | 4260 | 4230 | 4260 | 4260 |
| Sensitivity | 56% | 54% | 63% | 57% | 55% | 63% | 52% | 50% | 67% |
| Specificity | 53% | 52% | 52% | 53% | 52% | 52% | 50% | 50% | 52% |
| Cutoff Quartile 4 | 6010 | 6060 | 6060 | 6010 | 6060 | 6060 | 6010 | 6060 | 6060 |
| Sensitivity | 29% | 29% | 26% | 28% | 30% | 26% | 20% | 21% | 28% |
| Specificity | 77% | 77% | 75% | 76% | 77% | 75% | 73% | 73% | 75% |
| OR Quartile 2 | 0.976 | 0.885 | 0.700 | 1.36 | 1.38 | 0.700 | 1.22 | 1.12 | 0.867 |
| p Value | 0.95 | 0.75 | 0.50 | 0.46 | 0.44 | 0.50 | 0.65 | 0.79 | 0.80 |
| Lower limit of 95% CI | 0.455 | 0.416 | 0.246 | 0.599 | 0.607 | 0.246 | 0.518 | 0.488 | 0.287 |
| Upper limit of 95% CI | 2.09 | 1.89 | 1.99 | 3.10 | 3.14 | 1.99 | 2.86 | 2.57 | 2.61 |
| OR Quartile 3 | 1.46 | 1.26 | 1.85 | 1.52 | 1.36 | 1.85 | 1.13 | 1.00 | 2.19 |
| p Value | 0.26 | 0.50 | 0.22 | 0.24 | 0.38 | 0.22 | 0.75 | 1.0 | 0.14 |
| Lower limit of 95% CI | 0.751 | 0.647 | 0.685 | 0.756 | 0.682 | 0.685 | 0.546 | 0.490 | 0.776 |
| Upper limit of 95% CI | 2.85 | 2.44 | 5.00 | 3.04 | 2.73 | 5.00 | 2.32 | 2.04 | 6.18 |
| OR Quartile 4 | 1.38 | 1.31 | 1.06 | 1.21 | 1.40 | 1.06 | 0.675 | 0.743 | 1.15 |
| p Value | 0.40 | 0.48 | 0.92 | 0.64 | 0.40 | 0.92 | 0.38 | 0.49 | 0.80 |
| Lower limit of 95% CI | 0.651 | 0.618 | 0.355 | 0.553 | 0.644 | 0.355 | 0.280 | 0.317 | 0.383 |
| Upper limit of 95% CI | 2.93 | 2.77 | 3.17 | 2.64 | 3.03 | 3.17 | 1.63 | 1.74 | 3.48 |

TABLE 20.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 4000 | 4480 | 4000 | 4480 | 4170 | 4420 |
| Average | 4440 | 4980 | 4480 | 4980 | 4640 | 4720 |
| Stdev | 2720 | 3350 | 2750 | 3360 | 2850 | 3300 |
| p (t-test) | | 0.28 | | 0.32 | | 0.88 |
| Min | 62.8 | 413 | 62.8 | 413 | 62.8 | 413 |
| Max | 11800 | 21200 | 11800 | 21200 | 13800 | 21200 |
| n (Patient) | 88 | 63 | 94 | 57 | 101 | 50 |
| *sCr only* | | | | | | |
| Median | 4090 | 4490 | 4060 | 4500 | 4170 | 4370 |
| Average | 4490 | 4930 | 4460 | 5020 | 4640 | 4730 |
| Stdev | 2680 | 3430 | 2650 | 3500 | 2770 | 3440 |
| p (t-test) | | 0.38 | | 0.26 | | 0.87 |
| Min | 276 | 62.8 | 276 | 62.8 | 276 | 62.8 |
| Max | 11800 | 21200 | 11800 | 21200 | 13800 | 21200 |
| n (Patient) | 88 | 62 | 93 | 57 | 99 | 51 |
| *UO only* | | | | | | |
| Median | 4170 | 4670 | 4170 | 4670 | 4150 | 4690 |
| Average | 4600 | 5110 | 4600 | 5110 | 4570 | 5260 |
| Stdev | 2710 | 4090 | 2710 | 4090 | 2710 | 4090 |
| p (t-test) | | 0.42 | | 0.42 | | 0.29 |
| Min | 62.8 | 513 | 62.8 | 513 | 62.8 | 513 |
| Max | 13800 | 21200 | 13800 | 21200 | 13800 | 21200 |
| n (Patient) | 123 | 27 | 123 | 27 | 124 | 26 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.54 | 0.53 | 0.52 | 0.54 | 0.54 | 0.52 | 0.50 | 0.49 | 0.54 |
| SE | 0.048 | 0.048 | 0.062 | 0.049 | 0.049 | 0.062 | 0.050 | 0.050 | 0.063 |
| p Value | 0.39 | 0.55 | 0.80 | 0.39 | 0.39 | 0.80 | 0.98 | 0.89 | 0.57 |
| nCohort Non-persistent | 88 | 88 | 123 | 94 | 93 | 123 | 101 | 99 | 124 |
| nCohort Persistent | 63 | 62 | 27 | 57 | 57 | 27 | 50 | 51 | 26 |
| Cutoff Quartile 2 | 2740 | 2730 | 2740 | 2740 | 2730 | 2740 | 2740 | 2730 | 2740 |
| Sensitivity | 76% | 74% | 70% | 79% | 77% | 70% | 78% | 75% | 73% |
| Specificity | 26% | 25% | 24% | 28% | 27% | 24% | 27% | 25% | 25% |
| Cutoff Quartile 3 | 4230 | 4260 | 4260 | 4230 | 4260 | 4260 | 4230 | 4260 | 4260 |
| Sensitivity | 57% | 55% | 59% | 58% | 56% | 59% | 54% | 51% | 62% |
| Specificity | 55% | 53% | 52% | 54% | 54% | 52% | 51% | 51% | 52% |
| Cutoff Quartile 4 | 6010 | 6060 | 6060 | 6010 | 6060 | 6060 | 6010 | 6060 | 6060 |
| Sensitivity | 27% | 27% | 22% | 26% | 28% | 22% | 20% | 22% | 23% |
| Specificity | 76% | 76% | 74% | 76% | 76% | 74% | 72% | 73% | 74% |
| OR Quartile 2 | 1.13 | 0.958 | 0.766 | 1.43 | 1.24 | 0.766 | 1.29 | 0.988 | 0.905 |
| p Value | 0.75 | 0.91 | 0.57 | 0.37 | 0.58 | 0.57 | 0.53 | 0.97 | 0.84 |
| Lower limit of 95% CI | 0.535 | 0.455 | 0.304 | 0.657 | 0.576 | 0.304 | 0.581 | 0.455 | 0.347 |
| Upper limit of 95% CI | 2.40 | 2.02 | 1.93 | 3.13 | 2.69 | 1.93 | 2.88 | 2.15 | 2.36 |
| OR Quartile 3 | 1.60 | 1.39 | 1.58 | 1.63 | 1.49 | 1.58 | 1.25 | 1.06 | 1.76 |
| p Value | 0.16 | 0.32 | 0.29 | 0.15 | 0.24 | 0.29 | 0.53 | 0.86 | 0.20 |
| Lower limit of 95% CI | 0.834 | 0.725 | 0.678 | 0.839 | 0.767 | 0.678 | 0.632 | 0.540 | 0.742 |
| Upper limit of 95% CI | 3.07 | 2.67 | 3.67 | 3.17 | 2.89 | 3.67 | 2.46 | 2.09 | 4.19 |

TABLE 20.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.18 | 1.21 | 0.812 | 1.10 | 1.26 | 0.812 | 0.652 | 0.733 | 0.862 |
| p Value | 0.66 | 0.62 | 0.68 | 0.80 | 0.55 | 0.68 | 0.31 | 0.45 | 0.77 |
| Lower limit of 95% CI | 0.562 | 0.574 | 0.301 | 0.519 | 0.595 | 0.301 | 0.287 | 0.329 | 0.318 |
| Upper limit of 95% CI | 2.47 | 2.53 | 2.19 | 2.34 | 2.67 | 2.19 | 1.48 | 1.63 | 2.34 |

TABLE 20.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3930 | 4580 | 3930 | 4500 | 4090 | 4480 |
| Average | 4370 | 5030 | 4390 | 5030 | 4530 | 4880 |
| Stdev | 2750 | 3260 | 2730 | 3310 | 2830 | 3270 |
| p (t-test) | | 0.18 | | 0.20 | | 0.49 |
| Min | 62.8 | 413 | 62.8 | 413 | 62.8 | 413 |
| Max | 11800 | 21200 | 11800 | 21200 | 13800 | 21200 |
| n (Patient) | 83 | 68 | 86 | 65 | 94 | 57 |
| | sCr only | | | | | |
| Median | 3930 | 4580 | 3930 | 4580 | 4120 | 4480 |
| Average | 4420 | 4980 | 4430 | 5000 | 4590 | 4810 |
| Stdev | 2720 | 3310 | 2690 | 3380 | 2800 | 3330 |
| p (t-test) | | 0.26 | | 0.25 | | 0.66 |
| Min | 276 | 62.8 | 276 | 62.8 | 276 | 62.8 |
| Max | 11800 | 21200 | 11800 | 21200 | 13800 | 21200 |
| n (Patient) | 82 | 68 | 86 | 64 | 93 | 57 |
| | UO only | | | | | |
| Median | 4060 | 4780 | 4060 | 4780 | 4050 | 4790 |
| Average | 4550 | 5150 | 4550 | 5150 | 4520 | 5270 |
| Stdev | 2750 | 3690 | 2750 | 3690 | 2750 | 3680 |
| p (t-test) | | 0.30 | | 0.30 | | 0.20 |
| Min | 62.8 | 513 | 62.8 | 513 | 62.8 | 513 |
| Max | 13800 | 21200 | 13800 | 21200 | 13800 | 21200 |
| n (Patient) | 115 | 35 | 115 | 35 | 116 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.55 | 0.55 | 0.56 | 0.55 | 0.55 | 0.53 | 0.52 | 0.57 |
| SE | 0.047 | 0.047 | 0.057 | 0.047 | 0.048 | 0.057 | 0.049 | 0.049 | 0.057 |
| p Value | 0.18 | 0.27 | 0.37 | 0.22 | 0.29 | 0.37 | 0.51 | 0.73 | 0.23 |
| nCohort Non-persistent | 83 | 82 | 115 | 86 | 86 | 115 | 94 | 93 | 116 |
| nCohort Persistent | 68 | 68 | 35 | 65 | 64 | 35 | 57 | 57 | 34 |
| Cutoff Quartile 2 | 2740 | 2730 | 2740 | 2740 | 2730 | 2740 | 2740 | 2730 | 2740 |
| Sensitivity | 78% | 76% | 74% | 78% | 77% | 74% | 79% | 75% | 76% |
| Specificity | 28% | 27% | 25% | 28% | 27% | 25% | 28% | 26% | 26% |
| Cutoff Quartile 3 | 4230 | 4260 | 4260 | 4230 | 4260 | 4260 | 4230 | 4260 | 4260 |
| Sensitivity | 59% | 57% | 63% | 58% | 58% | 63% | 56% | 54% | 65% |
| Specificity | 57% | 56% | 54% | 56% | 56% | 54% | 53% | 53% | 54% |
| Cutoff Quartile 4 | 6010 | 6060 | 6060 | 6010 | 6060 | 6060 | 6010 | 6060 | 6060 |
| Sensitivity | 28% | 28% | 26% | 28% | 28% | 26% | 25% | 25% | 26% |
| Specificity | 77% | 77% | 75% | 77% | 77% | 75% | 74% | 74% | 75% |
| OR Quartile 2 | 1.35 | 1.19 | 0.974 | 1.41 | 1.19 | 0.974 | 1.43 | 1.07 | 1.13 |
| p Value | 0.43 | 0.64 | 0.95 | 0.37 | 0.65 | 0.95 | 0.37 | 0.86 | 0.78 |

TABLE 20.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 0.641 | 0.567 | 0.409 | 0.662 | 0.563 | 0.409 | 0.657 | 0.499 | 0.463 |
| Upper limit of 95% CI | 2.86 | 2.51 | 2.32 | 3.00 | 2.52 | 2.32 | 3.13 | 2.29 | 2.77 |
| OR Quartile 3 | 1.87 | 1.72 | 1.98 | 1.78 | 1.73 | 1.98 | 1.45 | 1.33 | 2.18 |
| p Value | 0.060 | 0.10 | 0.085 | 0.083 | 0.100 | 0.085 | 0.27 | 0.40 | 0.054 |
| Lower limit of 95% CI | 0.974 | 0.898 | 0.910 | 0.927 | 0.900 | 0.910 | 0.751 | 0.685 | 0.986 |
| Upper limit of 95% CI | 3.57 | 3.29 | 4.31 | 3.41 | 3.33 | 4.31 | 2.82 | 2.57 | 4.81 |
| OR Quartile 4 | 1.31 | 1.29 | 1.03 | 1.26 | 1.29 | 1.03 | 0.950 | 0.936 | 1.08 |
| p Value | 0.48 | 0.50 | 0.95 | 0.53 | 0.50 | 0.95 | 0.89 | 0.86 | 0.86 |
| Lower limit of 95% CI | 0.625 | 0.615 | 0.431 | 0.604 | 0.616 | 0.431 | 0.444 | 0.437 | 0.452 |
| Upper limit of 95% CI | 2.73 | 2.69 | 2.44 | 2.65 | 2.71 | 2.44 | 2.03 | 2.00 | 2.58 |

TABLE 20.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 3920 | 4690 | 3930 | 4580 | 4060 | 4490 |
| Average | 4350 | 5040 | 4380 | 5040 | 4520 | 4880 |
| Stdev | 2780 | 3210 | 2740 | 3280 | 2860 | 3200 |
| p (t-test) | | 0.16 | | 0.18 | | 0.48 |
| Min | 62.8 | 413 | 62.8 | 413 | 62.8 | 413 |
| Max | 11800 | 21200 | 11800 | 21200 | 13800 | 21200 |
| n (Patient) | 81 | 70 | 85 | 66 | 91 | 60 |
| sCr only | | | | | | |
| Median | 3930 | 4670 | 3930 | 4580 | 4090 | 4490 |
| Average | 4410 | 4990 | 4430 | 4990 | 4570 | 4820 |
| Stdev | 2740 | 3280 | 2720 | 3330 | 2840 | 3260 |
| p (t-test) | | 0.24 | | 0.26 | | 0.62 |
| Min | 276 | 62.8 | 276 | 62.8 | 276 | 62.8 |
| Max | 11800 | 21200 | 11800 | 21200 | 13800 | 21200 |
| n (Patient) | 81 | 69 | 84 | 66 | 90 | 60 |
| UO only | | | | | | |
| Median | 3940 | 4800 | 3990 | 4790 | 3940 | 4800 |
| Average | 4500 | 5200 | 4510 | 5200 | 4480 | 5300 |
| Stdev | 2760 | 3510 | 2750 | 3560 | 2760 | 3540 |
| p (t-test) | | 0.21 | | 0.21 | | 0.14 |
| Min | 62.8 | 513 | 62.8 | 513 | 62.8 | 513 |
| Max | 13800 | 21200 | 13800 | 21200 | 13800 | 21200 |
| n (Patient) | 109 | 41 | 110 | 40 | 111 | 39 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.56 | 0.57 | 0.56 | 0.55 | 0.57 | 0.54 | 0.53 | 0.58 |
| SE | 0.047 | 0.047 | 0.054 | 0.047 | 0.048 | 0.054 | 0.048 | 0.048 | 0.054 |
| p Value | 0.12 | 0.22 | 0.20 | 0.18 | 0.28 | 0.23 | 0.44 | 0.60 | 0.14 |
| nCohort Non-persistent | 81 | 81 | 109 | 85 | 84 | 110 | 91 | 90 | 111 |
| nCohort Persistent | 70 | 69 | 41 | 66 | 66 | 40 | 60 | 60 | 39 |
| Cutoff Quartile 2 | 2740 | 2730 | 2740 | 2740 | 2730 | 2740 | 2740 | 2730 | 2740 |

TABLE 20.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 79% | 77% | 76% | 79% | 77% | 75% | 78% | 77% | 77% |
| Specificity | 28% | 27% | 26% | 28% | 27% | 25% | 27% | 27% | 26% |
| Cutoff Quartile 3 | 4230 | 4260 | 4260 | 4230 | 4260 | 4260 | 4230 | 4260 | 4260 |
| Sensitivity | 60% | 58% | 63% | 59% | 58% | 62% | 57% | 55% | 64% |
| Specificity | 58% | 57% | 55% | 56% | 56% | 55% | 54% | 53% | 55% |
| Cutoff Quartile 4 | 6010 | 6060 | 6060 | 6010 | 6060 | 6060 | 6010 | 6060 | 6060 |
| Sensitivity | 27% | 28% | 24% | 27% | 27% | 25% | 25% | 25% | 26% |
| Specificity | 77% | 77% | 74% | 76% | 76% | 75% | 75% | 74% | 75% |
| OR Quartile 2 | 1.45 | 1.24 | 1.07 | 1.46 | 1.28 | 1.02 | 1.37 | 1.19 | 1.18 |
| p Value | 0.33 | 0.58 | 0.87 | 0.33 | 0.52 | 0.95 | 0.42 | 0.65 | 0.71 |
| Lower limit of 95% CI | 0.688 | 0.587 | 0.466 | 0.686 | 0.606 | 0.445 | 0.636 | 0.559 | 0.500 |
| Upper limit of 95% CI | 3.07 | 2.60 | 2.46 | 3.11 | 2.71 | 2.36 | 2.95 | 2.55 | 2.78 |
| OR Quartile 3 | 2.07 | 1.81 | 2.12 | 1.87 | 1.72 | 2.00 | 1.53 | 1.40 | 2.18 |
| p Value | 0.028 | 0.073 | 0.046 | 0.059 | 0.10 | 0.067 | 0.21 | 0.32 | 0.043 |
| Lower limit of 95% CI | 1.08 | 0.947 | 1.01 | 0.977 | 0.899 | 0.952 | 0.792 | 0.725 | 1.03 |
| Upper limit of 95% CI | 3.97 | 3.47 | 4.44 | 3.60 | 3.31 | 4.20 | 2.94 | 2.69 | 4.63 |
| OR Quartile 4 | 1.22 | 1.24 | 0.933 | 1.22 | 1.20 | 0.976 | 0.986 | 0.971 | 1.02 |
| p Value | 0.60 | 0.57 | 0.87 | 0.60 | 0.63 | 0.95 | 0.97 | 0.94 | 0.96 |
| Lower limit of 95% CI | 0.582 | 0.593 | 0.406 | 0.583 | 0.573 | 0.424 | 0.465 | 0.458 | 0.443 |
| Upper limit of 95% CI | 2.54 | 2.59 | 2.14 | 2.55 | 2.51 | 2.25 | 2.09 | 2.06 | 2.36 |

TABLE 20.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3930 | 4670 | 3930 | 4580 | 4090 | 4480 |
| Average | 4330 | 5030 | 4350 | 5030 | 4590 | 4770 |
| Stdev | 2660 | 3300 | 2640 | 3350 | 2860 | 3190 |
| p (t-test) | | 0.15 | | 0.17 | | 0.71 |
| Min | 276 | 62.8 | 276 | 62.8 | 276 | 62.8 |
| Max | 11800 | 21200 | 11800 | 21200 | 13800 | 21200 |
| n (Patient) | 78 | 73 | 81 | 70 | 88 | 63 |
| | sCr only | | | | | |
| Median | 3930 | 4670 | 3930 | 4580 | 4090 | 4490 |
| Average | 4340 | 5050 | 4360 | 5050 | 4510 | 4900 |
| Stdev | 2640 | 3340 | 2620 | 3390 | 2760 | 3330 |
| p (t-test) | | 0.15 | | 0.16 | | 0.44 |
| Min | 276 | 62.8 | 276 | 62.8 | 276 | 62.8 |
| Max | 11800 | 21200 | 11800 | 21200 | 13800 | 21200 |
| n (Patient) | 79 | 71 | 82 | 68 | 88 | 62 |
| | UO only | | | | | |
| Median | 3930 | 4790 | 3930 | 4790 | 3930 | 4800 |
| Average | 4500 | 5170 | 4500 | 5170 | 4470 | 5270 |

TABLE 20.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 2780 | 3480 | 2780 | 3480 | 2780 | 3460 |
| p (t-test) | | 0.22 | | 0.22 | | 0.15 |
| Min | 62.8 | 513 | 62.8 | 513 | 62.8 | 513 |
| Max | 13800 | 21200 | 13800 | 21200 | 13800 | 21200 |
| n (Patient) | 108 | 42 | 108 | 42 | 109 | 41 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.56 | 0.57 | 0.56 | 0.56 | 0.57 | 0.52 | 0.53 | 0.58 |
| SE | 0.047 | 0.047 | 0.053 | 0.047 | 0.047 | 0.053 | 0.048 | 0.048 | 0.053 |
| p Value | 0.16 | 0.17 | 0.21 | 0.20 | 0.22 | 0.21 | 0.66 | 0.51 | 0.12 |
| nCohort Non-persistent | 78 | 79 | 108 | 81 | 82 | 108 | 88 | 88 | 109 |
| nCohort Persistent | 73 | 71 | 42 | 70 | 68 | 42 | 63 | 62 | 41 |
| Cutoff Quartile 2 | 2740 | 2730 | 2740 | 2740 | 2730 | 2740 | 2740 | 2730 | 2740 |
| Sensitivity | 78% | 77% | 76% | 79% | 78% | 76% | 78% | 77% | 78% |
| Specificity | 28% | 28% | 26% | 28% | 28% | 26% | 27% | 27% | 27% |
| Cutoff Quartile 3 | 4230 | 4260 | 4260 | 4230 | 4260 | 4260 | 4230 | 4260 | 4260 |
| Sensitivity | 59% | 58% | 62% | 59% | 57% | 62% | 56% | 55% | 63% |
| Specificity | 58% | 57% | 55% | 57% | 56% | 55% | 53% | 53% | 55% |
| Cutoff Quartile 4 | 6010 | 6060 | 6060 | 6010 | 6060 | 6060 | 6010 | 6060 | 6060 |
| Sensitivity | 27% | 28% | 24% | 27% | 28% | 24% | 24% | 26% | 24% |
| Specificity | 77% | 77% | 74% | 77% | 77% | 74% | 74% | 75% | 74% |
| OR Quartile 2 | 1.40 | 1.33 | 1.12 | 1.45 | 1.38 | 1.12 | 1.31 | 1.29 | 1.29 |
| p Value | 0.37 | 0.46 | 0.79 | 0.33 | 0.40 | 0.79 | 0.48 | 0.52 | 0.56 |
| Lower limit of 95% CI | 0.666 | 0.631 | 0.488 | 0.688 | 0.651 | 0.488 | 0.616 | 0.603 | 0.549 |
| Upper limit of 95% CI | 2.94 | 2.79 | 2.57 | 3.07 | 2.91 | 2.57 | 2.80 | 2.74 | 3.02 |
| OR Quartile 3 | 1.95 | 1.81 | 1.96 | 1.86 | 1.72 | 1.96 | 1.43 | 1.39 | 2.12 |
| p Value | 0.042 | 0.073 | 0.071 | 0.061 | 0.10 | 0.071 | 0.28 | 0.32 | 0.046 |
| Lower limit of 95% CI | 1.02 | 0.946 | 0.944 | 0.972 | 0.898 | 0.944 | 0.748 | 0.725 | 1.01 |
| Upper limit of 95% CI | 3.73 | 3.46 | 4.06 | 3.55 | 3.29 | 4.06 | 2.74 | 2.67 | 4.44 |
| OR Quartile 4 | 1.26 | 1.33 | 0.893 | 1.22 | 1.29 | 0.893 | 0.883 | 1.04 | 0.933 |
| p Value | 0.54 | 0.45 | 0.79 | 0.60 | 0.50 | 0.79 | 0.75 | 0.91 | 0.87 |
| Lower limit of 95% CI | 0.602 | 0.636 | 0.389 | 0.582 | 0.615 | 0.389 | 0.417 | 0.495 | 0.406 |
| Upper limit of 95% CI | 2.63 | 2.78 | 2.05 | 2.54 | 2.69 | 2.05 | 1.87 | 2.20 | 2.14 |

Example 21. Use of C—C Motif Chemokine 15 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 15 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 21.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 22.1 | 428 | 59.2 | 423 | 58.2 | 565 |
| Average | 764 | 2280 | 881 | 2540 | 859 | 2820 |
| Stdev | 4180 | 6070 | 3730 | 6700 | 3560 | 7110 |
| p (t-test) | | 0.017 | | 0.0070 | | 0.0015 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 118 | 198 | 157 | 159 | 178 | 138 |
| | sCr only | | | | | |
| Median | 22.1 | 428 | 59.2 | 434 | 57.2 | 596 |
| Average | 738 | 2400 | 843 | 2640 | 812 | 2980 |
| Stdev | 4000 | 6250 | 3680 | 6790 | 3510 | 7250 |
| p (t-test) | | 0.0080 | | 0.0036 | | 5.0E−4 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 129 | 186 | 161 | 154 | 183 | 132 |
| | UO only | | | | | |
| Median | 108 | 420 | 127 | 434 | 127 | 585 |
| Average | 1750 | 1620 | 1740 | 1630 | 1710 | 1780 |
| Stdev | 6070 | 2990 | 5930 | 3050 | 5860 | 3210 |
| p (t-test) | | 0.86 | | 0.88 | | 0.94 |
| Min | 0.0116 | 0.0116 | 0.0116 | 0.0116 | 0.0116 | 0.0116 |
| Max | 53500 | 18400 | 53500 | 18400 | 53500 | 18400 |
| n (Patient) | 240 | 74 | 255 | 59 | 262 | 52 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.61 | 0.67 | 0.68 | 0.59 | 0.69 | 0.71 | 0.61 |
| SE | 0.028 | 0.028 | 0.039 | 0.030 | 0.030 | 0.042 | 0.030 | 0.030 | 0.045 |
| p Value | 0 | 2.2E−16 | 0.0048 | 2.6E−8 | 1.5E−9 | 0.026 | 1.1E−10 | 1.5E−12 | 0.011 |
| nCohort Non-persistent | 118 | 129 | 240 | 157 | 161 | 255 | 178 | 183 | 262 |
| nCohort Persistent | 198 | 186 | 74 | 159 | 154 | 59 | 138 | 132 | 52 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 85% | 85% | 85% | 84% | 85% | 81% | 86% | 86% | 83% |
| Specificity | 37% | 36% | 26% | 31% | 32% | 24% | 30% | 31% | 24% |
| Cutoff Quartile 3 | 155 | 154 | 155 | 155 | 154 | 155 | 155 | 154 | 155 |
| Sensitivity | 65% | 66% | 65% | 63% | 64% | 66% | 67% | 70% | 69% |
| Specificity | 75% | 72% | 55% | 63% | 63% | 54% | 63% | 64% | 54% |
| Cutoff Quartile 4 | 909 | 912 | 902 | 909 | 912 | 902 | 909 | 912 | 902 |
| Sensitivity | 36% | 37% | 32% | 36% | 38% | 32% | 40% | 42% | 35% |
| Specificity | 93% | 92% | 77% | 87% | 87% | 76% | 87% | 87% | 77% |
| OR Quartile 2 | 3.33 | 3.38 | 1.99 | 2.25 | 2.64 | 1.40 | 2.57 | 2.79 | 1.54 |
| p Value | 1.2E−5 | 1.1E−5 | 0.054 | 0.0032 | 5.9E−4 | 0.35 | 0.0012 | 6.2E−4 | 0.27 |
| Lower limit of 95% CI | 1.94 | 1.96 | 0.988 | 1.31 | 1.52 | 0.686 | 1.45 | 1.55 | 0.714 |
| Upper limit of 95% CI | 5.71 | 5.81 | 4.03 | 3.87 | 4.59 | 2.87 | 4.55 | 5.03 | 3.34 |
| OR Quartile 3 | 5.36 | 4.92 | 2.22 | 2.89 | 3.11 | 2.26 | 3.59 | 4.08 | 2.62 |
| p Value | 8.1E−11 | 1.7E−10 | 0.0039 | 5.1E−6 | 1.3E−6 | 0.0069 | 8.9E−8 | 8.5E−9 | 0.0030 |
| Lower limit of 95% CI | 3.23 | 3.02 | 1.29 | 1.83 | 1.96 | 1.25 | 2.25 | 2.53 | 1.39 |
| Upper limit of 95% CI | 8.90 | 8.03 | 3.81 | 4.57 | 4.93 | 4.09 | 5.74 | 6.58 | 4.96 |

TABLE 21.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 7.69 | 7.02 | 1.61 | 3.72 | 4.03 | 1.54 | 4.25 | 5.13 | 1.74 |
| p Value | 2.4E−7 | 7.7E−8 | 0.10 | 4.6E−6 | 1.2E−6 | 0.17 | 2.3E−7 | 8.8E−9 | 0.088 |
| Lower limit of 95% CI | 3.54 | 3.45 | 0.911 | 2.12 | 2.29 | 0.832 | 2.46 | 2.94 | 0.921 |
| Upper limit of 95% CI | 16.7 | 14.3 | 2.86 | 6.52 | 7.07 | 2.86 | 7.36 | 8.95 | 3.31 |

TABLE 21.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 22.0 | 423 | 53.2 | 436 | 54.2 | 565 |
| Average | 793 | 2220 | 857 | 2450 | 849 | 2650 |
| Stdev | 4300 | 5980 | 3850 | 6490 | 3700 | 6810 |
| p (t-test) | 0.027 | | 0.0096 | | 0.0034 | |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 111 | 205 | 146 | 170 | 164 | 152 |
| | sCr only | | | | | |
| Median | 22.0 | 428 | 53.2 | 436 | 53.2 | 576 |
| Average | 750 | 2360 | 836 | 2550 | 830 | 2740 |
| Stdev | 4060 | 6190 | 3770 | 6630 | 3650 | 6910 |
| p (t-test) | 0.011 | | 0.0053 | | 0.0020 | |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 125 | 190 | 153 | 162 | 168 | 147 |
| | UO only | | | | | |
| Median | 88.0 | 406 | 110 | 434 | 113 | 565 |
| Average | 1750 | 1650 | 1740 | 1680 | 1700 | 1790 |
| Stdev | 6210 | 3290 | 6030 | 3410 | 5950 | 3540 |
| p (t-test) | 0.87 | | 0.93 | | 0.91 | |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 221 | 93 | 237 | 77 | 244 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.61 | 0.69 | 0.70 | 0.60 | 0.70 | 0.71 | 0.61 |
| SE | 0.028 | 0.028 | 0.036 | 0.029 | 0.029 | 0.038 | 0.029 | 0.029 | 0.040 |
| p Value | 0 | 0 | 0.0025 | 1.2E−10 | 2.9E−11 | 0.0086 | 3.9E−12 | 3.2E−13 | 0.0038 |
| nCohort Non-persistent | 111 | 125 | 221 | 146 | 153 | 237 | 164 | 168 | 244 |
| nCohort Persistent | 205 | 190 | 93 | 170 | 162 | 77 | 152 | 147 | 70 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 86% | 84% | 84% | 86% | 82% | 85% | 86% | 83% |
| Specificity | 38% | 38% | 26% | 32% | 33% | 25% | 31% | 32% | 25% |
| Cutoff Quartile 3 | 155 | 154 | 155 | 155 | 154 | 155 | 155 | 154 | 155 |
| Sensitivity | 64% | 65% | 63% | 64% | 65% | 65% | 68% | 69% | 67% |
| Specificity | 76% | 73% | 56% | 66% | 65% | 55% | 66% | 66% | 55% |
| Cutoff Quartile 4 | 909 | 912 | 902 | 909 | 912 | 902 | 909 | 912 | 902 |
| Sensitivity | 35% | 36% | 31% | 36% | 38% | 31% | 39% | 40% | 33% |
| Specificity | 93% | 92% | 77% | 88% | 88% | 77% | 88% | 88% | 77% |
| OR Quartile 2 | 3.29 | 3.64 | 1.85 | 2.51 | 3.02 | 1.49 | 2.53 | 3.01 | 1.61 |
| p Value | 1.4E−5 | 3.4E−6 | 0.055 | 7.9E−4 | 9.3E−5 | 0.23 | 0.0010 | 1.6E−4 | 0.17 |

TABLE 21.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.92 | 2.11 | 0.987 | 1.47 | 1.74 | 0.779 | 1.46 | 1.70 | 0.811 |
| Upper limit of 95% CI | 5.64 | 6.27 | 3.47 | 4.31 | 5.26 | 2.86 | 4.40 | 5.33 | 3.20 |
| OR Quartile 3 | 5.51 | 5.03 | 2.18 | 3.54 | 3.48 | 2.25 | 4.17 | 4.28 | 2.49 |
| p Value | 1.2E−10 | 1.5E−10 | 0.0022 | 1.0E−7 | 1.4E−7 | 0.0029 | 2.6E−9 | 1.7E−9 | 0.0014 |
| Lower limit of 95% CI | 3.28 | 3.07 | 1.32 | 2.22 | 2.19 | 1.32 | 2.60 | 2.66 | 1.42 |
| Upper limit of 95% CI | 9.25 | 8.24 | 3.59 | 5.63 | 5.53 | 3.84 | 6.66 | 6.86 | 4.35 |
| OR Quartile 4 | 6.82 | 6.56 | 1.55 | 4.36 | 4.53 | 1.50 | 4.57 | 4.96 | 1.64 |
| p Value | 1.2E−6 | 2.1E−7 | 0.11 | 1.2E−6 | 4.3E−7 | 0.16 | 1.8E−7 | 4.0E−8 | 0.094 |
| Lower limit of 95% CI | 3.14 | 3.22 | 0.903 | 2.40 | 2.52 | 0.848 | 2.58 | 2.80 | 0.919 |
| Upper limit of 95% CI | 14.8 | 13.3 | 2.66 | 7.89 | 8.14 | 2.65 | 8.08 | 8.79 | 2.94 |

TABLE 21.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 22.1 | 414 | 53.2 | 434 | 53.2 | 550 |
| Average | 800 | 2210 | 870 | 2420 | 866 | 2560 |
| Stdev | 4320 | 5970 | 3890 | 6440 | 3770 | 6670 |
| p (t-test) | | 0.030 | | 0.012 | | 0.0060 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 110 | 206 | 143 | 173 | 157 | 159 |
| | sCr only | | | | | |
| Median | 22.1 | 414 | 54.2 | 434 | 54.2 | 550 |
| Average | 762 | 2330 | 848 | 2510 | 855 | 2640 |
| Stdev | 4090 | 6160 | 3800 | 6580 | 3720 | 6790 |
| p (t-test) | | 0.013 | | 0.0070 | | 0.0039 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 123 | 192 | 150 | 165 | 162 | 153 |
| | UO only | | | | | |
| Median | 91.3 | 347 | 116 | 351 | 118 | 406 |
| Average | 1810 | 1540 | 1780 | 1570 | 1740 | 1660 |
| Stdev | 6340 | 3150 | 6180 | 3250 | 6100 | 3360 |
| p (t-test) | | 0.67 | | 0.76 | | 0.91 |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 211 | 103 | 224 | 90 | 231 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.72 | 0.59 | 0.68 | 0.69 | 0.58 | 0.70 | 0.70 | 0.59 |
| SE | 0.028 | 0.028 | 0.035 | 0.030 | 0.030 | 0.036 | 0.029 | 0.029 | 0.037 |
| p Value | 4.4E−16 | 1.3E−15 | 0.0084 | 6.1E−10 | 1.5E−10 | 0.029 | 2.2E−11 | 1.4E−11 | 0.016 |
| nCohort Non-persistent | 110 | 123 | 211 | 143 | 150 | 224 | 157 | 162 | 231 |
| nCohort Persistent | 206 | 192 | 103 | 173 | 165 | 90 | 159 | 153 | 83 |
| Cutoff Quartile 2 | 0.0489 | 0.0489 | 0.0489 | 0.0489 | 0.0489 | 0.0489 | 0.0489 | 0.0489 | 0.0489 |

TABLE 21.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| Sensitivity | 84% | 85% | 83% | 83% | 85% | 80% | 84% | 86% | 81% |
|---|---|---|---|---|---|---|---|---|---|
| Specificity | 37% | 37% | 26% | 31% | 33% | 25% | 31% | 32% | 25% |
| Cutoff Quartile 3 | 155 | 154 | 155 | 155 | 154 | 155 | 155 | 154 | 155 |
| Sensitivity | 64% | 65% | 60% | 64% | 64% | 60% | 66% | 67% | 61% |
| Specificity | 75% | 72% | 55% | 66% | 65% | 54% | 66% | 65% | 54% |
| Cutoff Quartile 4 | 909 | 912 | 902 | 909 | 912 | 902 | 909 | 912 | 902 |
| Sensitivity | 34% | 36% | 31% | 36% | 37% | 31% | 38% | 39% | 33% |
| Specificity | 93% | 92% | 78% | 88% | 88% | 77% | 88% | 88% | 77% |
| OR Quartile 2 | 3.12 | 3.24 | 1.66 | 2.28 | 2.72 | 1.30 | 2.43 | 2.81 | 1.37 |
| p Value | 3.3E−5 | 1.9E−5 | 0.093 | 0.0024 | 3.3E−4 | 0.39 | 0.0014 | 2.9E−4 | 0.32 |
| Lower limit of 95% CI | 1.82 | 1.89 | 0.919 | 1.34 | 1.57 | 0.715 | 1.41 | 1.61 | 0.736 |
| Upper limit of 95% CI | 5.33 | 5.56 | 3.02 | 3.88 | 4.69 | 2.37 | 4.19 | 4.92 | 2.56 |
| OR Quartile 3 | 5.37 | 4.77 | 1.85 | 3.46 | 3.39 | 1.76 | 3.82 | 3.79 | 1.88 |
| p Value | 2.2E−10 | 5.4E−10 | 0.012 | 1.7E−7 | 2.4E−7 | 0.025 | 1.8E−8 | 2.3E−8 | 0.016 |
| Lower limit of 95% CI | 3.20 | 2.91 | 1.14 | 2.17 | 2.13 | 1.07 | 2.39 | 2.37 | 1.13 |
| Upper limit of 95% CI | 9.02 | 7.82 | 2.98 | 5.50 | 5.38 | 2.90 | 6.08 | 6.04 | 3.14 |
| OR Quartile 4 | 6.71 | 6.34 | 1.57 | 4.14 | 4.30 | 1.53 | 4.40 | 4.46 | 1.66 |
| p Value | 1.5E−6 | 3.5E−7 | 0.093 | 2.8E−6 | 1.0E−6 | 0.12 | 4.8E−7 | 2.8E−7 | 0.073 |
| Lower limit of 95% CI | 3.09 | 3.11 | 0.927 | 2.29 | 2.40 | 0.889 | 2.47 | 2.52 | 0.954 |
| Upper limit of 95% CI | 14.6 | 12.9 | 2.67 | 7.50 | 7.72 | 2.64 | 7.84 | 7.88 | 2.89 |

TABLE 21.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 22.0 | 406 | 53.2 | 434 | 53.2 | 537 |
| Average | 805 | 2200 | 875 | 2400 | 875 | 2530 |
| Stdev | 4340 | 5950 | 3910 | 6430 | 3800 | 6630 |
| p (t-test) | | 0.032 | | 0.014 | | 0.0073 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 109 | 207 | 142 | 174 | 155 | 161 |
| | sCr only | | | | | |
| Median | 22.1 | 414 | 53.2 | 434 | 53.2 | 544 |
| Average | 762 | 2330 | 853 | 2500 | 860 | 2620 |
| Stdev | 4090 | 6160 | 3820 | 6560 | 3730 | 6770 |
| p (t-test) | | 0.013 | | 0.0077 | | 0.0043 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 123 | 192 | 149 | 166 | 161 | 154 |
| | UO only | | | | | |
| Median | 88.0 | 338 | 115 | 338 | 115 | 341 |
| Average | 1850 | 1480 | 1820 | 1500 | 1790 | 1560 |
| Stdev | 6400 | 3110 | 6250 | 3180 | 6170 | 3270 |

TABLE 21.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

|  | | | | | | | | | |
|---|---|---|---|---|---|---|---|---|---|
| p (t-test) | | 0.58 | | | 0.64 | | | 0.75 | |
| Min | 0.0116 | 0.0116 | 0.0116 | 0.0116 | 0.0116 | 0.0116 | | | |
| Max | 53500 | 19200 | 53500 | 19200 | 53500 | 19200 | | | |
| n (Patient) | 207 | 107 | 219 | 95 | 225 | 89 | | | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.72 | 0.59 | 0.68 | 0.69 | 0.58 | 0.70 | 0.70 | 0.58 |
| SE | 0.028 | 0.028 | 0.034 | 0.030 | 0.030 | 0.036 | 0.029 | 0.029 | 0.036 |
| p Value | 2.2E−16 | 1.3E−15 | 0.011 | 6.8E−10 | 1.7E−10 | 0.035 | 2.4E−11 | 1.6E−11 | 0.021 |
| nCohort Non-persistent | 109 | 123 | 207 | 142 | 149 | 219 | 155 | 161 | 225 |
| nCohort Persistent | 207 | 192 | 107 | 174 | 166 | 95 | 161 | 154 | 89 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 85% | 83% | 83% | 85% | 81% | 84% | 86% | 82% |
| Specificity | 38% | 37% | 27% | 32% | 33% | 25% | 32% | 32% | 25% |
| Cutoff Quartile 3 | 155 | 154 | 155 | 155 | 154 | 155 | 155 | 154 | 155 |
| Sensitivity | 64% | 65% | 60% | 63% | 64% | 60% | 66% | 66% | 62% |
| Specificity | 76% | 72% | 55% | 66% | 65% | 54% | 66% | 65% | 55% |
| Cutoff Quartile 4 | 909 | 912 | 902 | 909 | 912 | 902 | 909 | 912 | 902 |
| Sensitivity | 34% | 36% | 30% | 36% | 37% | 29% | 37% | 38% | 30% |
| Specificity | 93% | 92% | 77% | 88% | 88% | 77% | 88% | 88% | 77% |
| OR Quartile 2 | 3.18 | 3.24 | 1.79 | 2.32 | 2.76 | 1.43 | 2.51 | 2.86 | 1.55 |
| p Value | 2.5E−5 | 1.9E−5 | 0.055 | 0.0020 | 2.6E−4 | 0.24 | 9.0E−4 | 2.3E−4 | 0.17 |
| Lower limit of 95% CI | 1.86 | 1.89 | 0.989 | 1.36 | 1.60 | 0.790 | 1.46 | 1.64 | 0.834 |
| Upper limit of 95% CI | 5.44 | 5.56 | 3.24 | 3.95 | 4.77 | 2.61 | 4.34 | 5.01 | 2.87 |
| OR Quartile 3 | 5.62 | 4.77 | 1.82 | 3.37 | 3.30 | 1.78 | 3.82 | 3.68 | 1.95 |
| p Value | 1.1E−10 | 5.4E−10 | 0.013 | 3.1E−7 | 4.3E−7 | 0.020 | 1.8E−8 | 4.2E−8 | 0.0090 |
| Lower limit of 95% CI | 3.33 | 2.91 | 1.14 | 2.12 | 2.08 | 1.09 | 2.40 | 2.31 | 1.18 |
| Upper limit of 95% CI | 9.49 | 7.82 | 2.93 | 5.36 | 5.23 | 2.91 | 6.08 | 5.86 | 3.22 |
| OR Quartile 4 | 6.59 | 6.34 | 1.45 | 4.07 | 4.23 | 1.38 | 4.25 | 4.38 | 1.45 |
| p Value | 1.9E−6 | 3.5E−7 | 0.16 | 3.6E−6 | 1.4E−6 | 0.25 | 8.7E−7 | 3.8E−7 | 0.18 |
| Lower limit of 95% CI | 3.04 | 3.11 | 0.858 | 2.25 | 2.36 | 0.801 | 2.39 | 2.48 | 0.838 |
| Upper limit of 95% CI | 14.3 | 12.9 | 2.46 | 7.37 | 7.59 | 2.36 | 7.57 | 7.74 | 2.51 |

TABLE 21.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 22.0 | 406 | 53.2 | 434 | 53.2 | 497 |
| Average | 799 | 2170 | 889 | 2350 | 893 | 2450 |
| Stdev | 4420 | 5900 | 3970 | 6340 | 3870 | 6530 |
| p (t-test) | | 0.036 | | 0.019 | | 0.012 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 105 | 211 | 137 | 179 | 149 | 167 |
| | sCr only | | | | | |
| Median | 22.1 | 423 | 53.2 | 436 | 53.2 | 544 |
| Average | 749 | 2320 | 836 | 2470 | 845 | 2590 |

TABLE 21.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 4130 | 6120 | 3860 | 6490 | 3770 | 6690 |
| p (t-test) | | 0.014 | | 0.0082 | | 0.0047 |
| Min | 0.0116 | 0.0116 | 0.0116 | 0.0116 | 0.0116 | 0.0116 |
| Max | 34200 | 53500 | 34200 | 53500 | 34200 | 53500 |
| n (Patient) | 120 | 195 | 145 | 170 | 157 | 158 |

UO only

| | | | | | | |
|---|---|---|---|---|---|---|
| Median | 81.4 | 347 | 88.0 | 341 | 97.4 | 344 |
| Average | 1830 | 1530 | 1820 | 1530 | 1790 | 1570 |
| Stdev | 6480 | 3070 | 6350 | 3120 | 6280 | 3180 |
| p (t-test) | | 0.65 | | 0.66 | | 0.74 |
| Min | 0.0116 | 0.0116 | 0.0116 | 0.0116 | 0.0116 | 0.0116 |
| Max | 53500 | 19200 | 53500 | 19200 | 53500 | 19200 |
| n (Patient) | 201 | 113 | 211 | 103 | 216 | 98 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.61 | 0.68 | 0.70 | 0.59 | 0.69 | 0.71 | 0.59 |
| SE | 0.028 | 0.028 | 0.034 | 0.030 | 0.029 | 0.035 | 0.029 | 0.029 | 0.035 |
| p Value | 0 | 2.2E−16 | 0.0014 | 1.1E−9 | 2.1E−11 | 0.0075 | 4.6E−11 | 1.9E−12 | 0.0076 |
| nCohort Non-persistent | 105 | 120 | 201 | 137 | 145 | 211 | 149 | 157 | 216 |
| nCohort Persistent | 211 | 195 | 113 | 179 | 170 | 103 | 167 | 158 | 98 |
| Cutoff Quartile 2 | 0.0489 | 0.0489 | 0.0489 | 0.0489 | 0.0489 | 0.0489 | 0.0489 | 0.0489 | 0.0489 |
| Sensitivity | 84% | 85% | 84% | 83% | 85% | 83% | 84% | 85% | 83% |
| Specificity | 38% | 37% | 27% | 32% | 33% | 26% | 32% | 32% | 26% |
| Cutoff Quartile 3 | 155 | 154 | 155 | 155 | 154 | 155 | 155 | 154 | 155 |
| Sensitivity | 64% | 65% | 62% | 63% | 64% | 61% | 65% | 66% | 62% |
| Specificity | 77% | 73% | 57% | 66% | 66% | 55% | 66% | 66% | 56% |
| Cutoff Quartile 4 | 909 | 912 | 902 | 909 | 912 | 902 | 909 | 912 | 902 |
| Sensitivity | 34% | 36% | 32% | 35% | 37% | 31% | 37% | 39% | 32% |
| Specificity | 93% | 92% | 79% | 88% | 89% | 78% | 88% | 89% | 78% |
| OR Quartile 2 | 3.20 | 3.18 | 1.99 | 2.35 | 2.74 | 1.66 | 2.58 | 2.82 | 1.67 |
| p Value | 2.2E−5 | 2.4E−5 | 0.023 | 0.0016 | 2.7E−4 | 0.093 | 6.1E−4 | 2.4E−4 | 0.098 |
| Lower limit of 95% CI | 1.87 | 1.86 | 1.10 | 1.38 | 1.59 | 0.919 | 1.50 | 1.62 | 0.911 |
| Upper limit of 95% CI | 5.49 | 5.45 | 3.59 | 4.00 | 4.71 | 3.02 | 4.43 | 4.91 | 3.05 |
| OR Quartile 3 | 5.87 | 5.02 | 2.13 | 3.31 | 3.50 | 1.96 | 3.62 | 3.89 | 2.06 |
| p Value | 8.7E−11 | 2.5E−10 | 0.0016 | 5.0E−7 | 1.3E−7 | 0.0060 | 5.7E−8 | 1.2E−8 | 0.0037 |
| Lower limit of 95% CI | 3.44 | 3.05 | 1.33 | 2.07 | 2.20 | 1.21 | 2.28 | 2.44 | 1.26 |
| Upper limit of 95% CI | 10.0 | 8.28 | 3.42 | 5.27 | 5.58 | 3.17 | 5.77 | 6.20 | 3.36 |
| OR Quartile 4 | 7.25 | 6.91 | 1.72 | 4.11 | 4.75 | 1.57 | 4.19 | 4.86 | 1.62 |
| p Value | 2.1E−6 | 3.0E−7 | 0.041 | 4.7E−6 | 4.6E−7 | 0.093 | 1.6E−6 | 1.3E−7 | 0.076 |
| Lower limit of 95% CI | 3.20 | 3.30 | 1.02 | 2.24 | 2.59 | 0.927 | 2.33 | 2.70 | 0.950 |
| Upper limit of 95% CI | 16.4 | 14.5 | 2.89 | 7.52 | 8.70 | 2.67 | 7.52 | 8.73 | 2.76 |

TABLE 21.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 3500 | 4670 | 3940 | 4690 | 4060 | 4580 |
| Average | 3630 | 5180 | 4270 | 5060 | 4340 | 5090 |
| Stdev | 2250 | 3190 | 2560 | 3340 | 2610 | 3410 |
| p (t-test) | | 0.0024 | | 0.10 | | 0.13 |
| Min | 62.8 | 413 | 62.8 | 413 | 62.8 | 413 |
| Max | 10700 | 21200 | 11800 | 21200 | 11800 | 21200 |
| n (Patient) | 50 | 101 | 75 | 76 | 85 | 66 |
| sCr only | | | | | | |
| Median | 3700 | 4680 | 3950 | 4670 | 3950 | 4720 |
| Average | 3750 | 5170 | 4340 | 4990 | 4300 | 5170 |
| Stdev | 2150 | 3280 | 2490 | 3410 | 2460 | 3570 |
| p (t-test) | | 0.0056 | | 0.19 | | 0.079 |
| Min | 276 | 62.8 | 276 | 62.8 | 276 | 62.8 |
| Max | 10700 | 21200 | 11800 | 21200 | 11800 | 21200 |
| n (Patient) | 52 | 98 | 73 | 77 | 86 | 64 |
| UO only | | | | | | |
| Median | 4050 | 4720 | 4050 | 4840 | 4120 | 4800 |
| Average | 4550 | 5100 | 4490 | 5500 | 4500 | 5660 |
| Stdev | 2770 | 3580 | 2700 | 3890 | 2680 | 4160 |
| p (t-test) | | 0.33 | | 0.096 | | 0.076 |
| Min | 62.8 | 1120 | 62.8 | 1120 | 62.8 | 1630 |
| Max | 13800 | 21200 | 13800 | 21200 | 13800 | 21200 |
| n (Patient) | 112 | 38 | 120 | 30 | 125 | 25 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.54 | 0.56 | 0.55 | 0.58 | 0.56 | 0.57 | 0.58 |
| SE | 0.046 | 0.046 | 0.055 | 0.047 | 0.047 | 0.060 | 0.047 | 0.048 | 0.065 |
| p Value | 8.4E−4 | 0.0045 | 0.44 | 0.17 | 0.32 | 0.16 | 0.24 | 0.17 | 0.22 |
| nCohort Non-persistent | 50 | 52 | 112 | 75 | 73 | 120 | 85 | 86 | 125 |
| nCohort Persistent | 101 | 98 | 38 | 76 | 77 | 30 | 66 | 64 | 25 |
| Cutoff Quartile 2 | 2740 | 2730 | 2740 | 2740 | 2730 | 2740 | 2740 | 2730 | 2740 |
| Sensitivity | 79% | 78% | 76% | 75% | 73% | 80% | 76% | 77% | 80% |
| Specificity | 34% | 31% | 26% | 25% | 23% | 27% | 26% | 27% | 26% |
| Cutoff Quartile 3 | 4230 | 4260 | 4260 | 4230 | 4260 | 4260 | 4230 | 4260 | 4260 |
| Sensitivity | 58% | 57% | 58% | 57% | 56% | 67% | 56% | 58% | 64% |
| Specificity | 66% | 63% | 53% | 56% | 56% | 54% | 54% | 56% | 53% |
| Cutoff Quartile 4 | 6010 | 6060 | 6060 | 6010 | 6060 | 6060 | 6010 | 6060 | 6060 |
| Sensitivity | 32% | 33% | 24% | 29% | 30% | 30% | 29% | 31% | 28% |
| Specificity | 88% | 88% | 74% | 79% | 79% | 76% | 78% | 79% | 75% |
| OR Quartile 2 | 1.96 | 1.54 | 1.13 | 1.02 | 0.810 | 1.45 | 1.09 | 1.19 | 1.43 |
| p Value | 0.081 | 0.27 | 0.79 | 0.96 | 0.58 | 0.45 | 0.82 | 0.65 | 0.50 |
| Lower limit of 95% CI | 0.920 | 0.721 | 0.477 | 0.488 | 0.387 | 0.545 | 0.519 | 0.563 | 0.498 |
| Upper limit of 95% CI | 4.18 | 3.27 | 2.66 | 2.12 | 1.70 | 3.88 | 2.29 | 2.52 | 4.13 |
| OR Quartile 3 | 2.73 | 2.32 | 1.53 | 1.66 | 1.62 | 2.36 | 1.50 | 1.73 | 1.99 |
| p Value | 0.0054 | 0.017 | 0.26 | 0.12 | 0.14 | 0.045 | 0.22 | 0.100 | 0.13 |
| Lower limit of 95% CI | 1.35 | 1.16 | 0.728 | 0.872 | 0.850 | 1.02 | 0.788 | 0.900 | 0.818 |
| Upper limit of 95% CI | 5.53 | 4.63 | 3.22 | 3.16 | 3.09 | 5.47 | 2.87 | 3.33 | 4.84 |

TABLE 21.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.40 | 3.72 | 0.888 | 1.50 | 1.65 | 1.34 | 1.40 | 1.72 | 1.18 |
| p Value | 0.012 | 0.0067 | 0.79 | 0.28 | 0.19 | 0.51 | 0.37 | 0.15 | 0.74 |
| Lower limit of 95% CI | 1.31 | 1.44 | 0.376 | 0.715 | 0.779 | 0.555 | 0.671 | 0.818 | 0.450 |
| Upper limit of 95% CI | 8.80 | 9.61 | 2.10 | 3.16 | 3.48 | 3.26 | 2.94 | 3.60 | 3.09 |

TABLE 21.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3620 | 4600 | 3930 | 4500 | 3940 | 4490 |
| Average | 3690 | 5130 | 4340 | 4950 | 4400 | 4960 |
| Stdev | 2220 | 3210 | 2550 | 3320 | 2610 | 3360 |
| p (t-test) | | 0.0053 | | 0.21 | | 0.26 |
| Min | 62.8 | 276 | 62.8 | 276 | 62.8 | 276 |
| Max | 10700 | 21200 | 11800 | 21200 | 11800 | 21200 |
| n (Patient) | 49 | 102 | 70 | 81 | 79 | 72 |
| | sCr only | | | | | |
| Median | 3730 | 4670 | 4000 | 4490 | 3940 | 4500 |
| Average | 3820 | 5120 | 4410 | 4910 | 4350 | 5030 |
| Stdev | 2120 | 3300 | 2500 | 3390 | 2480 | 3480 |
| p (t-test) | | 0.012 | | 0.31 | | 0.17 |
| Min | 703 | 62.8 | 703 | 62.8 | 703 | 62.8 |
| Max | 10700 | 21200 | 11800 | 21200 | 11800 | 21200 |
| n (Patient) | 51 | 99 | 70 | 80 | 79 | 71 |
| | UO only | | | | | |
| Median | 3940 | 4710 | 3940 | 4840 | 4050 | 4790 |
| Average | 4500 | 5110 | 4440 | 5420 | 4450 | 5520 |
| Stdev | 2770 | 3420 | 2700 | 3640 | 2680 | 3820 |
| p (t-test) | | 0.25 | | 0.078 | | 0.067 |
| Min | 62.8 | 513 | 62.8 | 513 | 62.8 | 513 |
| Max | 13800 | 21200 | 13800 | 21200 | 13800 | 21200 |
| n (Patient) | 103 | 47 | 111 | 39 | 116 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.56 | 0.55 | 0.53 | 0.59 | 0.54 | 0.55 | 0.59 |
| SE | 0.046 | 0.047 | 0.051 | 0.047 | 0.047 | 0.054 | 0.047 | 0.047 | 0.057 |
| p Value | 0.0027 | 0.012 | 0.27 | 0.30 | 0.48 | 0.089 | 0.38 | 0.31 | 0.13 |
| nCohort Non-persistent | 49 | 51 | 103 | 70 | 70 | 111 | 79 | 79 | 116 |
| nCohort Persistent | 102 | 99 | 47 | 81 | 80 | 39 | 72 | 71 | 34 |
| Cutoff Quartile 2 | 2740 | 2730 | 2740 | 2740 | 2730 | 2740 | 2740 | 2730 | 2740 |
| Sensitivity | 78% | 77% | 77% | 74% | 72% | 79% | 75% | 75% | 79% |
| Specificity | 33% | 29% | 26% | 24% | 23% | 27% | 25% | 25% | 27% |
| Cutoff Quartile 3 | 4230 | 4260 | 4260 | 4230 | 4260 | 4260 | 4230 | 4260 | 4260 |
| Sensitivity | 58% | 57% | 60% | 57% | 55% | 67% | 57% | 56% | 65% |
| Specificity | 65% | 63% | 54% | 57% | 56% | 56% | 56% | 56% | 54% |
| Cutoff Quartile 4 | 6010 | 6060 | 6060 | 6010 | 6060 | 6060 | 6010 | 6060 | 6060 |
| Sensitivity | 31% | 32% | 26% | 28% | 29% | 31% | 28% | 30% | 29% |
| Specificity | 88% | 88% | 75% | 79% | 79% | 77% | 77% | 78% | 76% |
| OR Quartile 2 | 1.76 | 1.38 | 1.16 | 0.916 | 0.781 | 1.44 | 1.02 | 0.998 | 1.41 |
| p Value | 0.14 | 0.41 | 0.71 | 0.82 | 0.51 | 0.42 | 0.96 | 1.00 | 0.47 |

TABLE 21.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 0.824 | 0.643 | 0.520 | 0.438 | 0.372 | 0.594 | 0.487 | 0.478 | 0.556 |
| Upper limit of 95% CI | 3.77 | 2.95 | 2.60 | 1.92 | 1.64 | 3.47 | 2.12 | 2.09 | 3.56 |
| OR Quartile 3 | 2.58 | 2.19 | 1.76 | 1.75 | 1.54 | 2.53 | 1.66 | 1.62 | 2.18 |
| p Value | 0.0086 | 0.026 | 0.11 | 0.089 | 0.19 | 0.017 | 0.12 | 0.14 | 0.054 |
| Lower limit of 95% CI | 1.27 | 1.10 | 0.872 | 0.918 | 0.806 | 1.18 | 0.873 | 0.850 | 0.986 |
| Upper limit of 95% CI | 5.24 | 4.39 | 3.54 | 3.34 | 2.93 | 5.43 | 3.17 | 3.09 | 4.81 |
| OR Quartile 4 | 3.28 | 3.58 | 1.02 | 1.45 | 1.48 | 1.45 | 1.30 | 1.53 | 1.31 |
| p Value | 0.014 | 0.0085 | 0.97 | 0.33 | 0.31 | 0.37 | 0.48 | 0.26 | 0.53 |
| Lower limit of 95% CI | 1.27 | 1.38 | 0.460 | 0.688 | 0.700 | 0.647 | 0.624 | 0.731 | 0.559 |
| Upper limit of 95% CI | 8.48 | 9.26 | 2.24 | 3.07 | 3.13 | 3.26 | 2.72 | 3.21 | 3.07 |

TABLE 21.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3620 | 4600 | 3930 | 4580 | 3920 | 4690 |
| Average | 3690 | 5130 | 4300 | 4980 | 4240 | 5090 |
| Stdev | 2220 | 3210 | 2550 | 3310 | 2530 | 3360 |
| p (t-test) | | 0.0053 | | 0.17 | | 0.081 |
| Min | 62.8 | 276 | 62.8 | 276 | 62.8 | 276 |
| Max | 10700 | 21200 | 11800 | 21200 | 11800 | 21200 |
| n (Patient) | 49 | 102 | 69 | 82 | 75 | 76 |
| | sCr only | | | | | |
| Median | 3730 | 4670 | 3940 | 4500 | 3930 | 4670 |
| Average | 3820 | 5120 | 4370 | 4930 | 4300 | 5040 |
| Stdev | 2120 | 3300 | 2500 | 3370 | 2490 | 3430 |
| p (t-test) | | 0.012 | | 0.25 | | 0.13 |
| Min | 703 | 62.8 | 703 | 62.8 | 703 | 62.8 |
| Max | 10700 | 21200 | 11800 | 21200 | 11800 | 21200 |
| n (Patient) | 51 | 99 | 69 | 81 | 75 | 75 |
| | UO only | | | | | |
| Median | 3930 | 4790 | 3920 | 4860 | 3930 | 4910 |
| Average | 4400 | 5250 | 4320 | 5550 | 4340 | 5650 |
| Stdev | 2720 | 3410 | 2660 | 3550 | 2630 | 3690 |
| p (t-test) | | 0.098 | | 0.021 | | 0.018 |
| Min | 62.8 | 513 | 62.8 | 513 | 62.8 | 513 |
| Max | 13800 | 21200 | 13800 | 21200 | 13800 | 21200 |
| n (Patient) | 98 | 52 | 105 | 45 | 110 | 40 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.62 | 0.58 | 0.56 | 0.54 | 0.62 | 0.58 | 0.56 | 0.62 |
| SE | 0.046 | 0.047 | 0.050 | 0.047 | 0.047 | 0.051 | 0.046 | 0.047 | 0.054 |
| p Value | 0.0027 | 0.012 | 0.096 | 0.22 | 0.37 | 0.017 | 0.10 | 0.20 | 0.027 |
| nCohort Non-persistent | 49 | 51 | 98 | 69 | 69 | 105 | 75 | 75 | 110 |
| nCohort Persistent | 102 | 99 | 52 | 82 | 81 | 45 | 76 | 75 | 40 |
| Cutoff Quartile 2 | 2740 | 2730 | 2740 | 2740 | 2730 | 2740 | 2740 | 2730 | 2740 |

TABLE 21.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 78% | 77% | 77% | 74% | 73% | 80% | 76% | 75% | 80% |
| Specificity | 33% | 29% | 27% | 25% | 23% | 28% | 27% | 25% | 27% |
| Cutoff Quartile 3 | 4230 | 4260 | 4260 | 4230 | 4260 | 4260 | 4230 | 4260 | 4260 |
| Sensitivity | 58% | 57% | 62% | 57% | 56% | 69% | 59% | 57% | 68% |
| Specificity | 65% | 63% | 56% | 58% | 57% | 58% | 59% | 57% | 56% |
| Cutoff Quartile 4 | 6010 | 6060 | 6060 | 6010 | 6060 | 6060 | 6010 | 6060 | 6060 |
| Sensitivity | 31% | 32% | 29% | 29% | 30% | 33% | 30% | 31% | 32% |
| Specificity | 88% | 88% | 77% | 80% | 80% | 78% | 80% | 80% | 77% |
| OR Quartile 2 | 1.76 | 1.38 | 1.20 | 0.950 | 0.810 | 1.53 | 1.17 | 1.00 | 1.50 |
| p Value | 0.14 | 0.41 | 0.64 | 0.89 | 0.58 | 0.33 | 0.67 | 1.0 | 0.37 |
| Lower limit of 95% CI | 0.824 | 0.643 | 0.549 | 0.454 | 0.385 | 0.655 | 0.561 | 0.479 | 0.621 |
| Upper limit of 95% CI | 3.77 | 2.95 | 2.64 | 1.99 | 1.70 | 3.56 | 2.45 | 2.09 | 3.62 |
| OR Quartile 3 | 2.58 | 2.19 | 2.05 | 1.85 | 1.62 | 3.07 | 2.06 | 1.81 | 2.68 |
| p Value | 0.0086 | 0.026 | 0.041 | 0.062 | 0.14 | 0.0030 | 0.029 | 0.073 | 0.011 |
| Lower limit of 95% CI | 1.27 | 1.10 | 1.03 | 0.969 | 0.851 | 1.46 | 1.08 | 0.945 | 1.25 |
| Upper limit of 95% CI | 5.24 | 4.39 | 4.07 | 3.54 | 3.10 | 6.44 | 3.94 | 3.45 | 5.74 |
| OR Quartile 4 | 3.28 | 3.58 | 1.32 | 1.63 | 1.65 | 1.78 | 1.74 | 1.77 | 1.64 |
| p Value | 0.014 | 0.0085 | 0.47 | 0.21 | 0.19 | 0.14 | 0.15 | 0.14 | 0.23 |
| Lower limit of 95% CI | 1.27 | 1.38 | 0.618 | 0.764 | 0.777 | 0.823 | 0.822 | 0.837 | 0.737 |
| Upper limit of 95% CI | 8.48 | 9.26 | 2.83 | 3.46 | 3.52 | 3.86 | 3.67 | 3.74 | 3.64 |

TABLE 21.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 3620 | 4600 | 3930 | 4670 | 3860 | 4710 |
| Average | 3690 | 5130 | 4280 | 4980 | 4220 | 5100 |
| Stdev | 2220 | 3210 | 2560 | 3290 | 2540 | 3340 |
| p (t-test) | | 0.0053 | | 0.15 | | 0.072 |
| Min | 62.8 | 276 | 62.8 | 276 | 62.8 | 276 |
| Max | 10700 | 21200 | 11800 | 21200 | 11800 | 21200 |
| n (Patient) | 49 | 102 | 68 | 83 | 74 | 77 |
| | sCr only | | | | | |
| Median | 3730 | 4670 | 3930 | 4580 | 3930 | 4690 |
| Average | 3820 | 5120 | 4350 | 4940 | 4290 | 5050 |
| Stdev | 2120 | 3300 | 2510 | 3350 | 2500 | 3400 |
| p (t-test) | | 0.012 | | 0.23 | | 0.12 |
| Min | 703 | 62.8 | 703 | 62.8 | 703 | 62.8 |
| Max | 10700 | 21200 | 11800 | 21200 | 11800 | 21200 |
| n (Patient) | 51 | 99 | 68 | 82 | 74 | 76 |
| | UO only | | | | | |
| Median | 3920 | 4800 | 3920 | 4860 | 3930 | 4860 |
| Average | 4390 | 5200 | 4340 | 5400 | 4360 | 5470 |
| Stdev | 2750 | 3330 | 2710 | 3410 | 2680 | 3530 |
| p (t-test) | | 0.11 | | 0.041 | | 0.037 |
| Min | 62.8 | 513 | 62.8 | 513 | 62.8 | 513 |
| Max | 13800 | 21200 | 13800 | 21200 | 13800 | 21200 |
| n (Patient) | 95 | 55 | 100 | 50 | 105 | 45 |

TABLE 21.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

|  | Persistence Period Duration (hr) | | | | | | | | |
| --- | --- | --- | --- | --- | --- | --- | --- | --- | --- |
|  | 24 | | | 48 | | | 72 | | |
|  | sCr or UO | sCr only | UO only | sCr or UO | sCr only | UO only | sCr or UO | sCr only | UO only |
| AUC | 0.64 | 0.62 | 0.58 | 0.56 | 0.55 | 0.61 | 0.58 | 0.57 | 0.60 |
| SE | 0.046 | 0.047 | 0.049 | 0.047 | 0.047 | 0.050 | 0.046 | 0.047 | 0.052 |
| p Value | 0.0027 | 0.012 | 0.089 | 0.17 | 0.31 | 0.027 | 0.081 | 0.16 | 0.043 |
| nCohort Non-persistent | 49 | 51 | 95 | 68 | 68 | 100 | 74 | 74 | 105 |
| nCohort Persistent | 102 | 99 | 55 | 83 | 82 | 50 | 77 | 76 | 45 |
| Cutoff Quartile 2 | 2740 | 2730 | 2740 | 2740 | 2730 | 2740 | 2740 | 2730 | 2740 |
| Sensitivity | 78% | 77% | 76% | 75% | 73% | 78% | 77% | 75% | 78% |
| Specificity | 33% | 29% | 26% | 25% | 24% | 27% | 27% | 26% | 27% |
| Cutoff Quartile 3 | 4230 | 4260 | 4260 | 4230 | 4260 | 4260 | 4230 | 4260 | 4260 |
| Sensitivity | 58% | 57% | 62% | 58% | 56% | 66% | 60% | 58% | 64% |
| Specificity | 65% | 63% | 57% | 59% | 57% | 58% | 59% | 58% | 56% |
| Cutoff Quartile 4 | 6010 | 6060 | 6060 | 6010 | 6060 | 6060 | 6010 | 6060 | 6060 |
| Sensitivity | 31% | 32% | 27% | 29% | 29% | 30% | 30% | 30% | 29% |
| Specificity | 88% | 88% | 76% | 79% | 79% | 77% | 80% | 80% | 76% |
| OR Quartile 2 | 1.76 | 1.38 | 1.15 | 0.984 | 0.839 | 1.31 | 1.21 | 1.04 | 1.27 |
| p Value | 0.14 | 0.41 | 0.72 | 0.97 | 0.64 | 0.51 | 0.61 | 0.92 | 0.57 |
| Lower limit of 95% CI | 0.824 | 0.643 | 0.533 | 0.470 | 0.399 | 0.588 | 0.582 | 0.496 | 0.558 |
| Upper limit of 95% CI | 3.77 | 2.95 | 2.50 | 2.06 | 1.76 | 2.92 | 2.53 | 2.16 | 2.90 |
| OR Quartile 3 | 2.58 | 2.19 | 2.13 | 1.96 | 1.72 | 2.68 | 2.18 | 1.91 | 2.32 |
| p Value | 0.0086 | 0.026 | 0.029 | 0.043 | 0.10 | 0.0063 | 0.019 | 0.051 | 0.022 |
| Lower limit of 95% CI | 1.27 | 1.10 | 1.08 | 1.02 | 0.898 | 1.32 | 1.14 | 0.997 | 1.13 |
| Upper limit of 95% CI | 5.24 | 4.39 | 4.20 | 3.75 | 3.29 | 5.44 | 4.17 | 3.65 | 4.79 |
| OR Quartile 4 | 3.28 | 3.58 | 1.17 | 1.57 | 1.60 | 1.43 | 1.68 | 1.71 | 1.30 |
| p Value | 0.014 | 0.0085 | 0.68 | 0.24 | 0.23 | 0.35 | 0.18 | 0.16 | 0.51 |
| Lower limit of 95% CI | 1.27 | 1.38 | 0.551 | 0.737 | 0.749 | 0.669 | 0.793 | 0.807 | 0.593 |
| Upper limit of 95% CI | 8.48 | 9.26 | 2.50 | 3.34 | 3.40 | 3.08 | 3.54 | 3.61 | 2.85 |

TABLE 21.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

|  | Persistence Period Duration (hr) | | | | | |
| --- | --- | --- | --- | --- | --- | --- |
|  | 24 | | 48 | | 72 | |
|  | Non-persistent Cohort | Persistent Cohort | Non-persistent Cohort | Persistent Cohort | Non-persistent Cohort | Persistent Cohort |
| | sCr or UO | | | | | |
| Median | 3620 | 4600 | 3930 | 4490 | 3930 | 4500 |
| Average | 3740 | 5090 | 4360 | 4890 | 4340 | 4950 |
| Stdev | 2190 | 3220 | 2560 | 3280 | 2530 | 3340 |
| p (t-test) | 0.0100 | | 0.28 | | 0.21 | |
| Min | 703 | 62.8 | 703 | 62.8 | 703 | 62.8 |
| Max | 10700 | 21200 | 11800 | 21200 | 11800 | 21200 |
| n (Patient) | 47 | 104 | 65 | 86 | 70 | 81 |
| | sCr only | | | | | |
| Median | 3700 | 4680 | 3930 | 4580 | 3930 | 4690 |
| Average | 3790 | 5120 | 4360 | 4920 | 4290 | 5030 |
| Stdev | 2130 | 3280 | 2540 | 3320 | 2520 | 3370 |
| p (t-test) | 0.010 | | 0.26 | | 0.14 | |
| Min | 703 | 62.8 | 703 | 62.8 | 703 | 62.8 |
| Max | 10700 | 21200 | 11800 | 21200 | 11800 | 21200 |
| n (Patient) | 50 | 100 | 66 | 84 | 72 | 78 |

TABLE 21.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

|  | UO only | | | | | |
|---|---|---|---|---|---|---|
| Median | 3930 | 4750 | 3920 | 4800 | 3930 | 4780 |
| Average | 4430 | 5100 | 4410 | 5180 | 4420 | 5220 |
| Stdev | 2790 | 3280 | 2750 | 3340 | 2730 | 3410 |
| p (t-test) | | 0.19 | | 0.13 | | 0.12 |
| Min | 62.8 | 513 | 62.8 | 513 | 62.8 | 513 |
| Max | 13800 | 21200 | 13800 | 21200 | 13800 | 21200 |
| n (Patient) | 92 | 58 | 95 | 55 | 99 | 51 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.62 | 0.57 | 0.55 | 0.55 | 0.58 | 0.55 | 0.56 | 0.57 |
| SE | 0.047 | 0.047 | 0.049 | 0.047 | 0.047 | 0.049 | 0.047 | 0.047 | 0.050 |
| p Value | 0.0049 | 0.0079 | 0.17 | 0.34 | 0.32 | 0.11 | 0.27 | 0.17 | 0.14 |
| nCohort Non-persistent | 47 | 50 | 92 | 65 | 66 | 95 | 70 | 72 | 99 |
| nCohort Persistent | 104 | 100 | 58 | 86 | 84 | 55 | 81 | 78 | 51 |
| Cutoff Quartile 2 | 2740 | 2730 | 2740 | 2740 | 2730 | 2740 | 2740 | 2730 | 2740 |
| Sensitivity | 78% | 77% | 76% | 74% | 74% | 76% | 75% | 76% | 76% |
| Specificity | 32% | 30% | 26% | 25% | 24% | 26% | 26% | 26% | 26% |
| Cutoff Quartile 3 | 4230 | 4260 | 4260 | 4230 | 4260 | 4260 | 4230 | 4260 | 4260 |
| Sensitivity | 58% | 57% | 59% | 57% | 56% | 62% | 58% | 58% | 61% |
| Specificity | 66% | 64% | 55% | 58% | 58% | 57% | 59% | 58% | 56% |
| Cutoff Quartile 4 | 6010 | 6060 | 6060 | 6010 | 6060 | 6060 | 6010 | 6060 | 6060 |
| Sensitivity | 31% | 32% | 26% | 28% | 29% | 27% | 28% | 29% | 25% |
| Specificity | 87% | 88% | 75% | 78% | 79% | 76% | 79% | 79% | 75% |
| OR Quartile 2 | 1.65 | 1.43 | 1.11 | 0.950 | 0.902 | 1.15 | 1.06 | 1.11 | 1.16 |
| p Value | 0.20 | 0.35 | 0.79 | 0.89 | 0.79 | 0.72 | 0.89 | 0.78 | 0.72 |
| Lower limit of 95% CI | 0.765 | 0.669 | 0.519 | 0.452 | 0.429 | 0.533 | 0.506 | 0.533 | 0.527 |
| Upper limit of 95% CI | 3.56 | 3.08 | 2.37 | 2.00 | 1.90 | 2.50 | 2.20 | 2.32 | 2.54 |
| OR Quartile 3 | 2.64 | 2.36 | 1.76 | 1.86 | 1.72 | 2.13 | 1.95 | 1.91 | 1.94 |
| p Value | 0.0080 | 0.016 | 0.095 | 0.061 | 0.10 | 0.029 | 0.043 | 0.051 | 0.059 |
| Lower limit of 95% CI | 1.29 | 1.17 | 0.906 | 0.971 | 0.899 | 1.08 | 1.02 | 0.998 | 0.974 |
| Upper limit of 95% CI | 5.42 | 4.75 | 3.43 | 3.58 | 3.31 | 4.20 | 3.74 | 3.65 | 3.85 |
| OR Quartile 4 | 3.04 | 3.45 | 1.05 | 1.41 | 1.49 | 1.17 | 1.45 | 1.59 | 1.01 |
| p Value | 0.022 | 0.011 | 0.91 | 0.37 | 0.31 | 0.68 | 0.33 | 0.23 | 0.97 |
| Lower limit of 95% CI | 1.17 | 1.33 | 0.492 | 0.662 | 0.697 | 0.551 | 0.688 | 0.752 | 0.466 |
| Upper limit of 95% CI | 7.87 | 8.93 | 2.22 | 3.00 | 3.17 | 2.50 | 3.07 | 3.36 | 2.20 |

Example 22. Use of C—C Motif Chemokine 18 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 18 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 22.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.870 | 1.22 | 0.716 | 1.23 | 0.716 | 1.18 |
| Average | 0.858 | 2.90 | 0.745 | 2.86 | 0.739 | 2.83 |
| Stdev | 0.658 | 9.70 | 0.561 | 9.57 | 0.588 | 9.49 |
| p (t-test) | | 0.32 | | 0.33 | | 0.35 |
| Min | 0.0264 | 0.00242 | 0.0264 | 0.00242 | 0.0264 | 0.00242 |
| Max | 2.61 | 60.0 | 2.01 | 60.0 | 2.01 | 60.0 |
| n (Patient) | 23 | 109 | 20 | 112 | 18 | 114 |
| sCr only | | | | | | |
| Median | 0.797 | 1.27 | 0.819 | 1.26 | 0.797 | 1.24 |
| Average | 0.783 | 3.07 | 0.794 | 3.04 | 0.786 | 3.02 |
| Stdev | 0.513 | 10.1 | 0.519 | 10.0 | 0.527 | 9.96 |
| p (t-test) | | 0.22 | | 0.23 | | 0.24 |
| Min | 0.0264 | 0.00242 | 0.0264 | 0.00242 | 0.0264 | 0.00242 |
| Max | 2.01 | 60.0 | 2.01 | 60.0 | 2.01 | 60.0 |
| n (Patient) | 30 | 101 | 29 | 102 | 28 | 103 |
| UO only | | | | | | |
| Median | 0.970 | 1.36 | 0.947 | 1.42 | 0.915 | 1.36 |
| Average | 1.06 | 5.16 | 0.957 | 4.78 | 0.923 | 4.33 |
| Stdev | 0.834 | 14.3 | 0.720 | 13.4 | 0.707 | 12.6 |
| p (t-test) | | 0.010 | | 0.014 | | 0.028 |
| Min | 0.00242 | 0.273 | 0.00242 | 0.273 | 0.00242 | 0.273 |
| Max | 4.23 | 60.0 | 3.20 | 60.0 | 3.20 | 60.0 |
| n (Patient) | 83 | 48 | 76 | 55 | 68 | 63 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.69 | 0.67 | 0.70 | 0.68 | 0.71 | 0.70 | 0.68 | 0.71 |
| SE | 0.058 | 0.051 | 0.050 | 0.057 | 0.052 | 0.047 | 0.059 | 0.052 | 0.045 |
| p Value | 0.0071 | 2.4E−4 | 8.4E−4 | 5.7E−4 | 5.5E−4 | 4.6E−6 | 9.9E−4 | 5.0E−4 | 4.7E−6 |
| nCohort Recovered | 23 | 30 | 83 | 20 | 29 | 76 | 18 | 28 | 68 |
| nCohort Non-recovered | 109 | 101 | 48 | 112 | 102 | 55 | 114 | 103 | 63 |
| Cutoff Quartile 2 | 0.561 | 0.557 | 0.569 | 0.561 | 0.557 | 0.569 | 0.561 | 0.557 | 0.569 |
| Sensitivity | 77% | 78% | 90% | 78% | 77% | 91% | 78% | 78% | 89% |
| Specificity | 35% | 37% | 34% | 40% | 34% | 37% | 44% | 36% | 38% |
| Cutoff Quartile 3 | 1.07 | 1.07 | 1.07 | 1.07 | 1.07 | 1.07 | 1.07 | 1.07 | 1.07 |
| Sensitivity | 54% | 56% | 67% | 54% | 56% | 69% | 54% | 55% | 65% |
| Specificity | 70% | 70% | 59% | 75% | 69% | 63% | 72% | 68% | 63% |
| Cutoff Quartile 4 | 1.65 | 1.64 | 1.66 | 1.65 | 1.64 | 1.66 | 1.65 | 1.64 | 1.66 |
| Sensitivity | 28% | 31% | 31% | 28% | 30% | 36% | 27% | 30% | 35% |
| Specificity | 87% | 93% | 78% | 90% | 93% | 83% | 89% | 93% | 84% |
| OR Quartile 2 | 1.79 | 2.08 | 4.38 | 2.32 | 1.81 | 5.83 | 2.85 | 1.93 | 4.95 |
| p Value | 0.24 | 0.10 | 0.0050 | 0.099 | 0.20 | 8.0E−4 | 0.046 | 0.15 | 7.0E−4 |
| Lower limit of 95% CI | 0.681 | 0.862 | 1.56 | 0.854 | 0.738 | 2.08 | 1.02 | 0.784 | 1.96 |
| Upper limit of 95% CI | 4.71 | 5.01 | 12.3 | 6.30 | 4.43 | 16.4 | 7.98 | 4.76 | 12.5 |
| OR Quartile 3 | 2.70 | 3.02 | 2.88 | 3.59 | 2.81 | 3.83 | 2.99 | 2.62 | 3.21 |
| p Value | 0.044 | 0.013 | 0.0052 | 0.020 | 0.021 | 3.6E−4 | 0.050 | 0.033 | 0.0014 |
| Lower limit of 95% CI | 1.03 | 1.26 | 1.37 | 1.22 | 1.17 | 1.83 | 1.00 | 1.08 | 1.57 |
| Upper limit of 95% CI | 7.08 | 7.25 | 6.06 | 10.5 | 6.78 | 8.01 | 8.95 | 6.33 | 6.55 |

TABLE 22.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 2.53 | 6.20 | 1.64 | 3.44 | 5.89 | 2.77 | 2.99 | 5.60 | 2.78 |
| p Value | 0.16 | 0.017 | 0.23 | 0.11 | 0.020 | 0.014 | 0.16 | 0.024 | 0.015 |
| Lower limit of 95% CI | 0.701 | 1.39 | 0.735 | 0.755 | 1.32 | 1.23 | 0.649 | 1.25 | 1.22 |
| Upper limit of 95% CI | 9.14 | 27.7 | 3.66 | 15.7 | 26.3 | 6.23 | 13.8 | 25.1 | 6.36 |

TABLE 22.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| *sCr or UO* | | | | | | |
| Median | 0.695 | 1.32 | 0.659 | 1.32 | 0.604 | 1.30 |
| Average | 0.763 | 3.18 | 0.738 | 3.14 | 0.692 | 3.09 |
| Stdev | 0.593 | 10.2 | 0.599 | 10.1 | 0.577 | 10.0 |
| p (t-test) | | 0.17 | | 0.18 | | 0.19 |
| Min | 0.0264 | 0.00242 | 0.0264 | 0.00242 | 0.0264 | 0.00242 |
| Max | 2.01 | 60.0 | 2.01 | 60.0 | 2.01 | 60.0 |
| n (Patient) | 35 | 97 | 33 | 99 | 30 | 102 |
| *sCr only* | | | | | | |
| Median | 0.735 | 1.35 | 0.774 | 1.35 | 0.735 | 1.34 |
| Average | 0.781 | 3.36 | 0.788 | 3.33 | 0.782 | 3.31 |
| Stdev | 0.564 | 10.6 | 0.569 | 10.6 | 0.575 | 10.5 |
| p (t-test) | | 0.12 | | 0.13 | | 0.13 |
| Min | 0.0264 | 0.00242 | 0.0264 | 0.00242 | 0.0264 | 0.00242 |
| Max | 2.01 | 60.0 | 2.01 | 60.0 | 2.01 | 60.0 |
| n (Patient) | 42 | 90 | 41 | 91 | 40 | 92 |
| *UO only* | | | | | | |
| Median | 0.978 | 1.39 | 0.974 | 1.42 | 0.983 | 1.36 |
| Average | 1.08 | 5.69 | 1.06 | 5.25 | 1.04 | 4.66 |
| Stdev | 0.846 | 15.3 | 0.838 | 14.5 | 0.843 | 13.4 |
| p (t-test) | | 0.0051 | | 0.0091 | | 0.020 |
| Min | 0.00242 | 0.273 | 0.00242 | 0.273 | 0.00242 | 0.273 |
| Max | 4.23 | 60.0 | 4.23 | 60.0 | 4.23 | 60.0 |
| n (Patient) | 89 | 42 | 84 | 47 | 76 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.72 | 0.67 | 0.73 | 0.71 | 0.68 | 0.74 | 0.71 | 0.67 |
| SE | 0.047 | 0.045 | 0.052 | 0.046 | 0.046 | 0.050 | 0.046 | 0.046 | 0.049 |
| p Value | 3.6E−6 | 1.2E−6 | 0.0010 | 1.0E−6 | 3.6E−6 | 4.4E−4 | 1.2E−7 | 3.3E−6 | 5.8E−4 |
| nCohort Recovered | 35 | 42 | 89 | 33 | 41 | 84 | 30 | 40 | 76 |
| nCohort Non-recovered | 97 | 90 | 42 | 99 | 91 | 47 | 102 | 92 | 55 |
| Cutoff Quartile 2 | 0.561 | 0.561 | 0.569 | 0.561 | 0.561 | 0.569 | 0.561 | 0.561 | 0.569 |
| Sensitivity | 81% | 82% | 88% | 82% | 81% | 89% | 82% | 82% | 87% |
| Specificity | 43% | 40% | 31% | 45% | 39% | 33% | 50% | 40% | 34% |
| Cutoff Quartile 3 | 1.07 | 1.07 | 1.07 | 1.07 | 1.07 | 1.07 | 1.07 | 1.07 | 1.07 |
| Sensitivity | 58% | 59% | 69% | 58% | 58% | 68% | 57% | 58% | 64% |
| Specificity | 71% | 69% | 58% | 73% | 68% | 60% | 73% | 68% | 59% |
| Cutoff Quartile 4 | 1.65 | 1.65 | 1.66 | 1.65 | 1.65 | 1.66 | 1.65 | 1.65 | 1.66 |
| Sensitivity | 30% | 32% | 33% | 29% | 32% | 34% | 29% | 32% | 33% |
| Specificity | 89% | 90% | 79% | 88% | 90% | 80% | 90% | 90% | 80% |

TABLE 22.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 3.29 | 3.14 | 3.40 | 3.75 | 2.79 | 4.20 | 4.67 | 2.94 | 3.57 |
| p Value | 0.0056 | 0.0061 | 0.021 | 0.0024 | 0.014 | 0.0064 | 5.9E−4 | 0.010 | 0.0070 |
| Lower limit of 95% CI | 1.42 | 1.39 | 1.21 | 1.60 | 1.23 | 1.50 | 1.94 | 1.29 | 1.42 |
| Upper limit of 95% CI | 7.65 | 7.14 | 9.57 | 8.81 | 6.32 | 11.8 | 11.2 | 6.70 | 8.98 |
| OR Quartile 3 | 3.41 | 3.20 | 3.14 | 3.62 | 3.00 | 3.14 | 3.62 | 2.82 | 2.54 |
| p Value | 0.0040 | 0.0034 | 0.0040 | 0.0035 | 0.0056 | 0.0029 | 0.0050 | 0.0091 | 0.011 |
| Lower limit of 95% CI | 1.48 | 1.47 | 1.44 | 1.53 | 1.38 | 1.48 | 1.48 | 1.29 | 1.24 |
| Upper limit of 95% CI | 7.88 | 6.95 | 6.83 | 8.58 | 6.54 | 6.66 | 8.91 | 6.16 | 5.19 |
| OR Quartile 4 | 3.31 | 4.52 | 1.84 | 3.00 | 4.33 | 2.03 | 3.75 | 4.14 | 1.98 |
| p Value | 0.038 | 0.0084 | 0.14 | 0.057 | 0.010 | 0.084 | 0.041 | 0.013 | 0.094 |
| Lower limit of 95% CI | 1.07 | 1.47 | 0.813 | 0.969 | 1.41 | 0.910 | 1.06 | 1.35 | 0.891 |
| Upper limit of 95% CI | 10.2 | 13.9 | 4.17 | 9.31 | 13.3 | 4.55 | 13.3 | 12.7 | 4.39 |

TABLE 22.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.739 | 1.30 | 0.700 | 1.30 | 0.700 | 1.28 |
| Average | 0.865 | 3.50 | 0.851 | 3.45 | 0.842 | 3.34 |
| Stdev | 0.690 | 11.0 | 0.700 | 10.9 | 0.702 | 10.6 |
| p (t-test) | | 0.100 | | 0.11 | | 0.13 |
| Min | 0.0264 | 0.00242 | 0.0264 | 0.00242 | 0.0264 | 0.00242 |
| Max | 3.02 | 60.0 | 3.02 | 60.0 | 3.02 | 60.0 |
| n (Patient) | 48 | 84 | 46 | 86 | 42 | 90 |
| | sCr only | | | | | |
| Median | 0.797 | 1.34 | 0.819 | 1.33 | 0.819 | 1.28 |
| Average | 0.857 | 3.71 | 0.864 | 3.67 | 0.874 | 3.59 |
| Stdev | 0.614 | 11.4 | 0.617 | 11.3 | 0.622 | 11.2 |
| p (t-test) | | 0.068 | | 0.074 | | 0.086 |
| Min | 0.0264 | 0.00242 | 0.0264 | 0.00242 | 0.0264 | 0.00242 |
| Max | 2.07 | 60.0 | 2.07 | 60.0 | 2.07 | 60.0 |
| n (Patient) | 54 | 78 | 53 | 79 | 51 | 81 |
| | UO only | | | | | |
| Median | 1.02 | 1.36 | 1.00 | 1.36 | 1.00 | 1.36 |
| Average | 1.11 | 5.75 | 1.10 | 5.36 | 1.07 | 4.76 |
| Stdev | 0.842 | 15.5 | 0.855 | 14.8 | 0.863 | 13.7 |
| p (t-test) | | 0.0050 | | 0.0085 | | 0.019 |
| Min | 0.00242 | 0.273 | 0.00242 | 0.273 | 0.00242 | 0.273 |
| Max | 4.23 | 60.0 | 4.23 | 60.0 | 4.23 | 60.0 |
| n (Patient) | 90 | 41 | 86 | 45 | 78 | 53 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.69 | 0.64 | 0.69 | 0.69 | 0.65 | 0.69 | 0.68 | 0.65 |
| SE | 0.046 | 0.045 | 0.054 | 0.046 | 0.046 | 0.052 | 0.047 | 0.046 | 0.050 |
| p Value | 4.4E−5 | 1.7E−5 | 0.010 | 2.5E−5 | 4.2E−5 | 0.0047 | 5.0E−5 | 1.6E−4 | 0.0023 |

TABLE 22.3-continued

Comparison of marker levels and the area under the ROC curve (AUC) in urine samples
for the "recovered" and "non-recovered" cohorts where recovery starts
within 72 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| nCohort Recovered | 48 | 54 | 90 | 46 | 53 | 86 | 42 | 51 | 78 |
| nCohort Non-recovered | 84 | 78 | 41 | 86 | 79 | 45 | 90 | 81 | 53 |
| Cutoff Quartile 2 | 0.561 | 0.561 | 0.569 | 0.561 | 0.561 | 0.569 | 0.561 | 0.561 | 0.569 |
| Sensitivity | 83% | 83% | 85% | 84% | 82% | 87% | 83% | 81% | 87% |
| Specificity | 40% | 37% | 30% | 41% | 36% | 31% | 43% | 35% | 33% |
| Cutoff Quartile 3 | 1.07 | 1.07 | 1.07 | 1.07 | 1.07 | 1.07 | 1.07 | 1.07 | 1.07 |
| Sensitivity | 58% | 59% | 63% | 58% | 58% | 64% | 57% | 57% | 62% |
| Specificity | 65% | 63% | 56% | 65% | 62% | 57% | 64% | 61% | 58% |
| Cutoff Quartile 4 | 1.65 | 1.65 | 1.66 | 1.65 | 1.65 | 1.66 | 1.65 | 1.65 | 1.66 |
| Sensitivity | 32% | 35% | 32% | 31% | 34% | 31% | 31% | 33% | 32% |
| Specificity | 88% | 89% | 78% | 87% | 89% | 78% | 88% | 88% | 79% |
| OR Quartile 2 | 3.28 | 2.94 | 2.50 | 3.62 | 2.59 | 2.97 | 3.75 | 2.40 | 3.29 |
| p Value | 0.0043 | 0.0092 | 0.066 | 0.0021 | 0.020 | 0.028 | 0.0017 | 0.033 | 0.012 |
| Lower limit of 95% CI | 1.45 | 1.31 | 0.942 | 1.59 | 1.16 | 1.12 | 1.64 | 1.08 | 1.30 |
| Upper limit of 95% CI | 7.40 | 6.63 | 6.64 | 8.22 | 5.81 | 7.87 | 8.56 | 5.36 | 8.28 |
| OR Quartile 3 | 2.55 | 2.44 | 2.17 | 2.60 | 2.30 | 2.40 | 2.35 | 2.04 | 2.25 |
| p Value | 0.012 | 0.014 | 0.046 | 0.012 | 0.022 | 0.021 | 0.027 | 0.051 | 0.026 |
| Lower limit of 95% CI | 1.23 | 1.20 | 1.01 | 1.24 | 1.13 | 1.14 | 1.10 | 0.998 | 1.10 |
| Upper limit of 95% CI | 5.32 | 4.99 | 4.63 | 5.47 | 4.69 | 5.06 | 5.02 | 4.16 | 4.60 |
| OR Quartile 4 | 3.32 | 4.24 | 1.62 | 3.05 | 4.07 | 1.59 | 3.34 | 3.75 | 1.83 |
| p Value | 0.015 | 0.0035 | 0.25 | 0.024 | 0.0045 | 0.26 | 0.022 | 0.0075 | 0.14 |
| Lower limit of 95% CI | 1.26 | 1.61 | 0.713 | 1.15 | 1.54 | 0.708 | 1.19 | 1.42 | 0.825 |
| Upper limit of 95% CI | 8.75 | 11.2 | 3.71 | 8.06 | 10.7 | 3.58 | 9.41 | 9.88 | 4.06 |

TABLE 22.4

Comparison of marker levels and the area under the ROC curve (AUC) in urine samples
for the "recovered" and "non-recovered" cohorts where recovery starts
within 96 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.774 | 1.35 | 0.704 | 1.33 | 0.700 | 1.30 |
| Average | 0.862 | 3.74 | 0.846 | 3.61 | 0.837 | 3.45 |
| Stdev | 0.661 | 11.4 | 0.678 | 11.2 | 0.684 | 10.9 |
| p (t-test) | | 0.065 | | 0.080 | | 0.11 |
| Min | 0.0264 | 0.00242 | 0.0264 | 0.00242 | 0.0264 | 0.00242 |
| Max | 3.02 | 60.0 | 3.02 | 60.0 | 3.02 | 60.0 |
| n (Patient) | 55 | 77 | 51 | 81 | 46 | 86 |
| sCr only | | | | | | |
| Median | 0.774 | 1.36 | 0.797 | 1.35 | 0.819 | 1.35 |
| Average | 0.842 | 3.83 | 0.849 | 3.79 | 0.861 | 3.74 |
| Stdev | 0.606 | 11.6 | 0.609 | 11.5 | 0.608 | 11.4 |
| p (t-test) | | 0.054 | | 0.059 | | 0.065 |
| Min | 0.0264 | 0.00242 | 0.0264 | 0.00242 | 0.0264 | 0.00242 |
| Max | 2.07 | 60.0 | 2.07 | 60.0 | 2.07 | 60.0 |
| n (Patient) | 57 | 75 | 56 | 76 | 55 | 77 |
| UO only | | | | | | |
| Median | 1.02 | 1.36 | 1.00 | 1.36 | 1.02 | 1.35 |
| Average | 1.09 | 5.57 | 1.08 | 5.20 | 1.08 | 4.67 |
| Stdev | 0.825 | 15.1 | 0.840 | 14.5 | 0.864 | 13.6 |

TABLE 22.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  |  | 0.0063 |  |  | 0.010 |  |  | 0.022 |  |
|---|---|---|---|---|---|---|---|---|---|
| p (t-test) |  |  |  |  |  |  |  |  |  |
| Min | 0.00242 | 0.233 |  | 0.00242 | 0.233 |  | 0.00242 | 0.233 |  |
| Max | 4.23 | 60.0 |  | 4.23 | 60.0 |  | 4.23 | 60.0 |  |
| n (Patient) | 88 | 43 |  | 84 | 47 |  | 77 | 54 |  |

| | Recovery Period Duration (hr) ||||||||| 
|---|---|---|---|---|---|---|---|---|---|
| | 24 ||| 48 ||| 72 |||
| | sCr or UO | sCr only | UO only | sCr or UO | sCr only | UO only | sCr or UO | sCr only | UO only |
| AUC | 0.70 | 0.71 | 0.64 | 0.71 | 0.70 | 0.65 | 0.70 | 0.69 | 0.64 |
| SE | 0.045 | 0.044 | 0.053 | 0.045 | 0.045 | 0.051 | 0.046 | 0.045 | 0.050 |
| p Value | 5.3E−6 | 1.6E−6 | 0.0064 | 4.1E−6 | 4.5E−6 | 0.0045 | 1.4E−5 | 2.0E−5 | 0.0056 |
| nCohort Recovered | 55 | 57 | 88 | 51 | 56 | 84 | 46 | 55 | 77 |
| nCohort Non-recovered | 77 | 75 | 43 | 81 | 76 | 47 | 86 | 77 | 54 |
| Cutoff Quartile 2 | 0.561 | 0.561 | 0.569 | 0.561 | 0.561 | 0.569 | 0.561 | 0.561 | 0.569 |
| Sensitivity | 84% | 85% | 84% | 85% | 84% | 85% | 85% | 83% | 85% |
| Specificity | 38% | 39% | 30% | 41% | 38% | 31% | 43% | 36% | 32% |
| Cutoff Quartile 3 | 1.07 | 1.07 | 1.07 | 1.07 | 1.07 | 1.07 | 1.07 | 1.07 | 1.07 |
| Sensitivity | 61% | 61% | 63% | 60% | 61% | 64% | 58% | 60% | 61% |
| Specificity | 65% | 65% | 56% | 67% | 64% | 57% | 65% | 64% | 57% |
| Cutoff Quartile 4 | 1.65 | 1.65 | 1.66 | 1.65 | 1.65 | 1.66 | 1.65 | 1.65 | 1.66 |
| Sensitivity | 35% | 36% | 35% | 33% | 36% | 32% | 33% | 35% | 31% |
| Specificity | 89% | 89% | 80% | 88% | 89% | 79% | 89% | 89% | 79% |
| OR Quartile 2 | 3.35 | 3.66 | 2.16 | 4.02 | 3.20 | 2.56 | 4.32 | 2.81 | 2.76 |
| p Value | 0.0040 | 0.0023 | 0.11 | 9.9E−4 | 0.0054 | 0.047 | 5.5E−4 | 0.012 | 0.025 |
| Lower limit of 95% CI | 1.47 | 1.59 | 0.851 | 1.76 | 1.41 | 1.01 | 1.88 | 1.25 | 1.14 |
| Upper limit of 95% CI | 7.61 | 8.41 | 5.47 | 9.22 | 7.27 | 6.47 | 9.90 | 6.33 | 6.73 |
| OR Quartile 3 | 2.97 | 2.93 | 2.12 | 3.06 | 2.76 | 2.35 | 2.60 | 2.60 | 2.10 |
| p Value | 0.0031 | 0.0032 | 0.049 | 0.0028 | 0.0053 | 0.023 | 0.012 | 0.0088 | 0.041 |
| Lower limit of 95% CI | 1.44 | 1.43 | 1.00 | 1.47 | 1.35 | 1.13 | 1.24 | 1.27 | 1.03 |
| Upper limit of 95% CI | 6.10 | 6.00 | 4.48 | 6.37 | 5.64 | 4.91 | 5.47 | 5.30 | 4.26 |
| OR Quartile 4 | 4.41 | 4.78 | 2.08 | 3.75 | 4.59 | 1.72 | 3.96 | 4.41 | 1.75 |
| p Value | 0.0027 | 0.0015 | 0.077 | 0.0075 | 0.0020 | 0.19 | 0.0090 | 0.0027 | 0.17 |
| Lower limit of 95% CI | 1.67 | 1.82 | 0.924 | 1.42 | 1.74 | 0.769 | 1.41 | 1.67 | 0.791 |
| Upper limit of 95% CI | 11.6 | 12.6 | 4.70 | 9.88 | 12.1 | 3.84 | 11.1 | 11.6 | 3.88 |

TABLE 22.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) ||||||
|---|---|---|---|---|---|---|
| | 24 || 48 || 72 ||
| | Recovered Cohort | Non-recovered Cohort | Recovered Cohort | Non-recovered Cohort | Recovered Cohort | Non-recovered Cohort |
| | sCr or UO ||||||
| Median | 1.02 | 1.35 | 1.02 | 1.33 | 1.02 | 1.33 |
| Average | 1.04 | 4.93 | 1.04 | 4.78 | 1.04 | 4.78 |
| Stdev | 0.797 | 13.9 | 0.805 | 13.7 | 0.805 | 13.7 |
| p (t-test) | | 0.013 | | 0.017 | | 0.017 |
| Min | 0.00242 | 0.197 | 0.00242 | 0.197 | 0.00242 | 0.197 |
| Max | 4.23 | 60.0 | 4.23 | 60.0 | 4.23 | 60.0 |
| n (Patient) | 81 | 51 | 79 | 53 | 79 | 53 |
| | sCr only ||||||
| Median | 0.950 | 1.35 | 0.950 | 1.35 | 0.950 | 1.35 |
| Average | 0.990 | 4.19 | 0.990 | 4.19 | 0.990 | 4.19 |

TABLE 22.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 0.779 | 12.5 | 0.779 | 12.5 | 0.779 | 12.5 |
| p (t-test) | | 0.037 | | 0.037 | | 0.037 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 68 | 64 | 68 | 64 | 68 | 64 |
| UO only | | | | | | |
| Median | 1.02 | 1.39 | 1.02 | 1.35 | 1.02 | 1.35 |
| Average | 1.09 | 5.46 | 1.10 | 5.26 | 1.10 | 5.18 |
| Stdev | 0.828 | 15.0 | 0.836 | 14.7 | 0.841 | 14.5 |
| p (t-test) | | 0.0073 | | 0.0098 | | 0.011 |
| Min | 0.00242 | 0.233 | 0.00242 | 0.233 | 0.00242 | 0.233 |
| Max | 4.23 | 60.0 | 4.23 | 60.0 | 4.23 | 60.0 |
| n (Patient) | 87 | 44 | 85 | 46 | 84 | 47 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.66 | 0.64 | 0.65 | 0.66 | 0.63 | 0.65 | 0.66 | 0.63 |
| SE | 0.050 | 0.047 | 0.053 | 0.050 | 0.047 | 0.052 | 0.050 | 0.047 | 0.052 |
| p Value | 0.0020 | 7.5E−4 | 0.0087 | 0.0029 | 7.5E−4 | 0.012 | 0.0029 | 7.5E−4 | 0.011 |
| nCohort Recovered | 81 | 68 | 87 | 79 | 68 | 85 | 79 | 68 | 84 |
| nCohort Non-recovered | 51 | 64 | 44 | 53 | 64 | 46 | 53 | 64 | 47 |
| Cutoff Quartile 2 | 0.561 | 0.561 | 0.569 | 0.561 | 0.561 | 0.569 | 0.561 | 0.561 | 0.569 |
| Sensitivity | 86% | 84% | 84% | 87% | 84% | 85% | 87% | 84% | 85% |
| Specificity | 32% | 34% | 30% | 33% | 34% | 31% | 33% | 34% | 31% |
| Cutoff Quartile 3 | 1.07 | 1.07 | 1.07 | 1.07 | 1.07 | 1.07 | 1.07 | 1.07 | 1.07 |
| Sensitivity | 59% | 61% | 61% | 58% | 61% | 61% | 58% | 61% | 62% |
| Specificity | 56% | 60% | 55% | 56% | 60% | 55% | 56% | 60% | 56% |
| Cutoff Quartile 4 | 1.65 | 1.65 | 1.66 | 1.65 | 1.65 | 1.66 | 1.65 | 1.65 | 1.66 |
| Sensitivity | 35% | 34% | 34% | 34% | 34% | 33% | 34% | 34% | 32% |
| Specificity | 81% | 84% | 79% | 81% | 84% | 79% | 81% | 84% | 79% |
| OR Quartile 2 | 2.97 | 2.76 | 2.25 | 3.22 | 2.76 | 2.46 | 3.22 | 2.76 | 2.56 |
| p Value | 0.021 | 0.018 | 0.087 | 0.013 | 0.018 | 0.058 | 0.013 | 0.018 | 0.047 |
| Lower limit of 95% CI | 1.18 | 1.19 | 0.890 | 1.28 | 1.19 | 0.971 | 1.28 | 1.19 | 1.01 |
| Upper limit of 95% CI | 7.49 | 6.40 | 5.71 | 8.12 | 6.40 | 6.21 | 8.12 | 6.40 | 6.47 |
| OR Quartile 3 | 1.79 | 2.37 | 1.95 | 1.77 | 2.37 | 1.92 | 1.77 | 2.37 | 2.05 |
| p Value | 0.11 | 0.016 | 0.076 | 0.11 | 0.016 | 0.079 | 0.11 | 0.016 | 0.054 |
| Lower limit of 95% CI | 0.879 | 1.18 | 0.933 | 0.876 | 1.18 | 0.927 | 0.876 | 1.18 | 0.987 |
| Upper limit of 95% CI | 3.63 | 4.76 | 4.09 | 3.58 | 4.76 | 3.99 | 3.58 | 4.76 | 4.24 |
| OR Quartile 4 | 2.40 | 2.71 | 1.98 | 2.19 | 2.71 | 1.80 | 2.19 | 2.71 | 1.72 |
| p Value | 0.033 | 0.018 | 0.098 | 0.054 | 0.018 | 0.15 | 0.054 | 0.018 | 0.19 |
| Lower limit of 95% CI | 1.08 | 1.19 | 0.881 | 0.986 | 1.19 | 0.804 | 0.986 | 1.19 | 0.769 |
| Upper limit of 95% CI | 5.36 | 6.20 | 4.46 | 4.88 | 6.20 | 4.04 | 4.88 | 6.20 | 3.84 |

Example 23. Use of C—C Motif Chemokine 18 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 18 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 23.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non covered Cohort |
| sCr or UO | | | | | | |
| Median | 0.822 | 1.30 | 0.822 | 1.30 | 0.822 | 1.28 |
| Average | 0.944 | 3.40 | 0.944 | 3.40 | 0.955 | 3.34 |
| Stdev | 0.827 | 10.9 | 0.827 | 10.9 | 0.843 | 10.7 |
| p (t-test) | | 0.13 | | 0.13 | | 0.15 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 46 | 86 | 46 | 86 | 44 | 88 |
| sCr only | | | | | | |
| Median | 0.819 | 1.34 | 0.819 | 1.34 | 0.870 | 1.31 |
| Average | 0.934 | 3.71 | 0.934 | 3.71 | 0.952 | 3.63 |
| Stdev | 0.778 | 11.5 | 0.778 | 11.5 | 0.787 | 11.4 |
| p (t-test) | | 0.077 | | 0.077 | | 0.090 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 55 | 76 | 55 | 76 | 53 | 78 |
| UO only | | | | | | |
| Median | 1.02 | 1.42 | 0.974 | 1.43 | 1.00 | 1.36 |
| Average | 1.71 | 4.64 | 1.70 | 4.33 | 1.74 | 4.02 |
| Stdev | 6.16 | 13.3 | 6.33 | 12.5 | 6.48 | 12.0 |
| p (t-test) | | 0.086 | | 0.11 | | 0.16 |
| Min | 0.00242 | 0.273 | 0.00242 | 0.273 | 0.00242 | 0.273 |
| Max | 60.0 | 60.0 | 60.0 | 60.0 | 60.0 | 60.0 |
| n (Patient) | 93 | 38 | 88 | 43 | 84 | 47 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.67 | 0.66 | 0.66 | 0.67 | 0.69 | 0.65 | 0.66 | 0.66 |
| SE | 0.048 | 0.047 | 0.055 | 0.048 | 0.047 | 0.051 | 0.049 | 0.047 | 0.051 |
| p Value | 8.0E-4 | 2.0E-4 | 0.0031 | 8.0E-4 | 2.0E-4 | 2.0E-4 | 0.0020 | 8.6E-4 | 0.0019 |
| nCohort Recovered | 46 | 55 | 93 | 46 | 55 | 88 | 44 | 53 | 84 |
| nCohort Non-recovered | 86 | 76 | 38 | 86 | 76 | 43 | 88 | 78 | 47 |
| Cutoff Quartile 2 | 0.561 | 0.557 | 0.569 | 0.561 | 0.557 | 0.569 | 0.561 | 0.557 | 0.569 |
| Sensitivity | 81% | 83% | 87% | 81% | 83% | 88% | 81% | 81% | 87% |
| Specificity | 37% | 36% | 30% | 37% | 36% | 32% | 36% | 34% | 32% |
| Cutoff Quartile 3 | 1.07 | 1.07 | 1.07 | 1.07 | 1.07 | 1.07 | 1.07 | 1.07 | 1.07 |

TABLE 23.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Sensitivity | 58% | 61% | 68% | 58% | 61% | 70% | 57% | 59% | 64% |
| Specificity | 65% | 64% | 57% | 65% | 64% | 59% | 64% | 62% | 57% |
| Cutoff Quartile 4 | 1.65 | 1.64 | 1.66 | 1.65 | 1.64 | 1.66 | 1.65 | 1.64 | 1.66 |
| Sensitivity | 29% | 33% | 34% | 29% | 33% | 37% | 28% | 32% | 34% |
| Specificity | 83% | 85% | 78% | 83% | 85% | 81% | 82% | 85% | 80% |
| OR Quartile 2 | 2.56 | 2.77 | 2.84 | 2.56 | 2.77 | 3.55 | 2.39 | 2.16 | 3.24 |
| p Value | 0.022 | 0.014 | 0.049 | 0.022 | 0.014 | 0.016 | 0.035 | 0.059 | 0.018 |
| Lower limit of 95% CI | 1.14 | 1.23 | 1.01 | 1.14 | 1.23 | 1.26 | 1.06 | 0.970 | 1.23 |
| Upper limit of 95% CI | 5.76 | 6.23 | 8.04 | 5.76 | 6.23 | 9.98 | 5.37 | 4.81 | 8.55 |
| OR Quartile 3 | 2.60 | 2.68 | 2.87 | 2.60 | 2.68 | 3.33 | 2.30 | 2.37 | 2.35 |
| p Value | 0.012 | 0.0069 | 0.0096 | 0.012 | 0.0069 | 0.0024 | 0.028 | 0.018 | 0.023 |
| Lower limit of 95% CI | 1.24 | 1.31 | 1.29 | 1.24 | 1.31 | 1.53 | 1.09 | 1.16 | 1.13 |
| Upper limit of 95% CI | 5.47 | 5.49 | 6.37 | 5.47 | 5.49 | 7.25 | 4.85 | 4.85 | 4.91 |
| OR Quartile 4 | 1.95 | 2.88 | 1.90 | 1.95 | 2.88 | 2.47 | 1.79 | 2.65 | 2.03 |
| p Value | 0.14 | 0.020 | 0.13 | 0.14 | 0.020 | 0.029 | 0.20 | 0.032 | 0.084 |
| Lower limit of 95% CI | 0.797 | 1.18 | 0.825 | 0.797 | 1.18 | 1.10 | 0.729 | 1.09 | 0.910 |
| Upper limit of 95% CI | 4.76 | 7.01 | 4.37 | 4.76 | 7.01 | 5.59 | 4.37 | 6.46 | 4.55 |

TABLE 23.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.940 | 1.33 | 0.940 | 1.33 | 0.960 | 1.32 |
| Average | 0.935 | 3.76 | 0.935 | 3.76 | 0.944 | 3.68 |
| Stdev | 0.763 | 11.6 | 0.763 | 11.6 | 0.774 | 11.5 |
| p (t-test) | | 0.069 | | 0.069 | | 0.079 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 57 | 75 | 57 | 75 | 55 | 77 |
| | sCr only | | | | | |
| Median | 0.905 | 1.36 | 0.905 | 1.36 | 0.950 | 1.35 |
| Average | 0.928 | 4.06 | 0.928 | 4.06 | 0.943 | 3.96 |
| Stdev | 0.731 | 12.1 | 0.731 | 12.1 | 0.738 | 12.0 |
| p (t-test) | | 0.041 | | 0.041 | | 0.050 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 64 | 68 | 64 | 68 | 62 | 70 |
| | UO only | | | | | |
| Median | 0.983 | 1.36 | 0.974 | 1.42 | 1.00 | 1.36 |
| Average | 1.71 | 4.72 | 1.69 | 4.60 | 1.75 | 4.10 |
| Stdev | 6.13 | 13.4 | 6.20 | 13.1 | 6.41 | 12.2 |

TABLE 23.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.080 | | | 0.086 | | | 0.15 | |
| Min | 0.00242 | 0.310 | | 0.00242 | 0.310 | | 0.00242 | 0.310 | |
| Max | 60.0 | 60.0 | | 60.0 | 60.0 | | 60.0 | 60.0 | |
| n (Patient) | 94 | 37 | | 92 | 39 | | 86 | 45 | |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.69 | 0.67 | 0.67 | 0.69 | 0.69 | 0.66 | 0.67 | 0.65 |
| SE | 0.046 | 0.046 | 0.055 | 0.046 | 0.046 | 0.053 | 0.047 | 0.046 | 0.052 |
| p Value | 2.0E−4 | 3.2E−5 | 0.0023 | 2.0E−4 | 3.2E−5 | 3.9E−4 | 5.4E−4 | 1.7E−4 | 0.0039 |
| nCohort Recovered | 57 | 64 | 94 | 57 | 64 | 92 | 55 | 62 | 86 |
| nCohort Non-recovered | 75 | 68 | 37 | 75 | 68 | 39 | 77 | 70 | 45 |
| Cutoff Quartile 2 | 0.561 | 0.561 | 0.569 | 0.561 | 0.561 | 0.569 | 0.561 | 0.561 | 0.569 |
| Sensitivity | 84% | 85% | 89% | 84% | 85% | 90% | 83% | 83% | 89% |
| Specificity | 37% | 36% | 31% | 37% | 36% | 32% | 36% | 34% | 33% |
| Cutoff Quartile 3 | 1.07 | 1.07 | 1.07 | 1.07 | 1.07 | 1.07 | 1.07 | 1.07 | 1.07 |
| Sensitivity | 59% | 60% | 70% | 59% | 60% | 72% | 57% | 59% | 64% |
| Specificity | 61% | 61% | 57% | 61% | 61% | 59% | 60% | 60% | 57% |
| Cutoff Quartile 4 | 1.65 | 1.65 | 1.66 | 1.65 | 1.65 | 1.66 | 1.65 | 1.65 | 1.66 |
| Sensitivity | 33% | 37% | 32% | 33% | 37% | 36% | 32% | 36% | 31% |
| Specificity | 86% | 88% | 78% | 86% | 88% | 79% | 85% | 87% | 78% |
| OR Quartile 2 | 3.06 | 3.25 | 3.68 | 3.06 | 3.25 | 4.03 | 2.81 | 2.48 | 3.86 |
| p Value | 0.0074 | 0.0061 | 0.023 | 0.0074 | 0.0061 | 0.015 | 0.012 | 0.029 | 0.010 |
| Lower limit of 95% CI | 1.35 | 1.40 | 1.19 | 1.35 | 1.40 | 1.31 | 1.25 | 1.10 | 1.37 |
| Upper limit of 95% CI | 6.95 | 7.56 | 11.4 | 6.95 | 7.56 | 12.4 | 6.33 | 5.59 | 10.9 |
| OR Quartile 3 | 2.26 | 2.37 | 3.19 | 2.26 | 2.37 | 3.62 | 2.00 | 2.09 | 2.40 |
| p Value | 0.023 | 0.016 | 0.0053 | 0.023 | 0.016 | 0.0019 | 0.053 | 0.037 | 0.021 |
| Lower limit of 95% CI | 1.12 | 1.18 | 1.41 | 1.12 | 1.18 | 1.61 | 0.990 | 1.04 | 1.14 |
| Upper limit of 95% CI | 4.57 | 4.76 | 7.21 | 4.57 | 4.76 | 8.14 | 4.04 | 4.19 | 5.06 |
| OR Quartile 4 | 3.06 | 4.07 | 1.67 | 3.06 | 4.07 | 2.15 | 2.82 | 3.75 | 1.59 |
| p Value | 0.014 | 0.0020 | 0.23 | 0.014 | 0.0020 | 0.069 | 0.022 | 0.0036 | 0.26 |
| Lower limit of 95% CI | 1.26 | 1.67 | 0.719 | 1.26 | 1.67 | 0.942 | 1.16 | 1.54 | 0.708 |
| Upper limit of 95% CI | 7.44 | 9.91 | 3.87 | 7.44 | 9.91 | 4.92 | 6.87 | 9.12 | 3.58 |

TABLE 23.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.970 | 1.35 | 0.970 | 1.35 | 0.970 | 1.33 |
| Average | 0.991 | 4.05 | 0.991 | 4.05 | 0.987 | 3.96 |
| Stdev | 0.774 | 12.2 | 0.774 | 12.2 | 0.785 | 12.1 |

TABLE 23.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.047 | | 0.047 | | 0.053 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 65 | 67 | 65 | 67 | 63 | 69 | sCr only

| | | | | | | |
|---|---|---|---|---|---|---|
| Median | 0.960 | 1.36 | 0.960 | 1.36 | 0.965 | 1.36 |
| Average | 0.948 | 4.18 | 0.948 | 4.18 | 0.955 | 4.13 |
| Stdev | 0.723 | 12.4 | 0.723 | 12.4 | 0.726 | 12.3 |
| p (t-test) | | 0.035 | | 0.035 | | 0.039 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 67 | 65 | 67 | 65 | 66 | 66 |

UO only

| | | | | | | |
|---|---|---|---|---|---|---|
| Median | 1.02 | 1.36 | 1.02 | 1.36 | 1.02 | 1.35 |
| Average | 1.72 | 4.78 | 1.72 | 4.78 | 1.76 | 4.27 |
| Stdev | 6.10 | 13.6 | 6.10 | 13.6 | 6.30 | 12.7 |
| p (t-test) | | 0.078 | | 0.078 | | 0.13 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 95 | 36 | 95 | 36 | 89 | 42 |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.68 | 0.64 | 0.65 | 0.68 | 0.64 | 0.65 | 0.67 | 0.63 |
| SE | 0.048 | 0.047 | 0.056 | 0.048 | 0.047 | 0.056 | 0.047 | 0.047 | 0.053 |
| p Value | 0.0014 | 1.1E−4 | 0.012 | 0.0014 | 1.1E−4 | 0.012 | 0.0014 | 2.5E−4 | 0.012 |
| nCohort Recovered | 65 | 67 | 95 | 65 | 67 | 95 | 63 | 66 | 89 |
| nCohort Non-recovered | 67 | 65 | 36 | 67 | 65 | 36 | 69 | 66 | 42 |
| Cutoff Quartile 2 | 0.561 | 0.561 | 0.569 | 0.561 | 0.561 | 0.569 | 0.561 | 0.561 | 0.569 |
| Sensitivity | 84% | 85% | 86% | 84% | 85% | 86% | 84% | 83% | 88% |
| Specificity | 34% | 34% | 29% | 34% | 34% | 29% | 35% | 33% | 31% |
| Cutoff Quartile 3 | 1.07 | 1.07 | 1.07 | 1.07 | 1.07 | 1.07 | 1.07 | 1.07 | 1.07 |
| Sensitivity | 58% | 60% | 64% | 58% | 60% | 64% | 58% | 59% | 62% |
| Specificity | 58% | 60% | 55% | 58% | 60% | 55% | 59% | 59% | 55% |
| Cutoff Quartile 4 | 1.65 | 1.65 | 1.66 | 1.65 | 1.65 | 1.66 | 1.65 | 1.65 | 1.66 |
| Sensitivity | 34% | 37% | 33% | 34% | 37% | 33% | 33% | 36% | 31% |
| Specificity | 85% | 87% | 78% | 85% | 87% | 78% | 84% | 86% | 78% |
| OR Quartile 2 | 2.60 | 2.88 | 2.59 | 2.60 | 2.88 | 2.59 | 2.83 | 2.50 | 3.40 |
| p Value | 0.023 | 0.014 | 0.073 | 0.023 | 0.014 | 0.073 | 0.014 | 0.030 | 0.021 |
| Lower limit of 95% CI | 1.14 | 1.24 | 0.914 | 1.14 | 1.24 | 0.914 | 1.24 | 1.10 | 1.21 |
| Upper limit of 95% CI | 5.95 | 6.67 | 7.35 | 5.95 | 6.67 | 7.35 | 6.47 | 5.71 | 9.57 |
| OR Quartile 3 | 1.96 | 2.22 | 2.14 | 1.96 | 2.22 | 2.14 | 1.96 | 2.09 | 1.99 |
| p Value | 0.057 | 0.025 | 0.059 | 0.057 | 0.025 | 0.059 | 0.056 | 0.038 | 0.072 |
| Lower limit of 95% CI | 0.981 | 1.11 | 0.970 | 0.981 | 1.11 | 0.970 | 0.982 | 1.04 | 0.940 |
| Upper limit of 95% CI | 3.92 | 4.46 | 4.72 | 3.92 | 4.46 | 4.72 | 3.92 | 4.18 | 4.21 |
| OR Quartile 4 | 2.87 | 3.77 | 1.76 | 2.87 | 3.77 | 1.76 | 2.65 | 3.62 | 1.55 |
| p Value | 0.014 | 0.0026 | 0.19 | 0.014 | 0.0026 | 0.19 | 0.023 | 0.0035 | 0.30 |
| Lower limit of 95% CI | 1.24 | 1.59 | 0.756 | 1.24 | 1.59 | 0.756 | 1.14 | 1.53 | 0.680 |
| Upper limit of 95% CI | 6.67 | 8.95 | 4.10 | 6.67 | 8.95 | 4.10 | 6.14 | 8.58 | 3.52 |

TABLE 23.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.970 | 1.35 | 0.979 | 1.34 | 0.979 | 1.33 |
| Average | 1.84 | 3.31 | 1.86 | 3.27 | 1.88 | 3.20 |
| Stdev | 7.14 | 10.4 | 7.20 | 10.3 | 7.30 | 10.2 |
| p (t-test) | | 0.34 | | 0.36 | | 0.39 |
| Min | 0.0264 | 0.00242 | 0.0264 | 0.00242 | 0.0264 | 0.00242 |
| Max | 60.0 | 60.0 | 60.0 | 60.0 | 60.0 | 60.0 |
| n (Patient) | 69 | 63 | 68 | 64 | 66 | 66 |
| sCr only | | | | | | |
| Median | 0.965 | 1.36 | 0.965 | 1.36 | 0.970 | 1.36 |
| Average | 1.79 | 3.39 | 1.79 | 3.39 | 1.81 | 3.34 |
| Stdev | 7.09 | 10.5 | 7.09 | 10.5 | 7.14 | 10.4 |
| p (t-test) | | 0.30 | | 0.30 | | 0.32 |
| Min | 0.0264 | 0.00242 | 0.0264 | 0.00242 | 0.0264 | 0.00242 |
| Max | 60.0 | 60.0 | 60.0 | 60.0 | 60.0 | 60.0 |
| n (Patient) | 70 | 62 | 70 | 62 | 69 | 63 |
| UO only | | | | | | |
| Median | 1.02 | 1.36 | 1.04 | 1.36 | 1.02 | 1.35 |
| Average | 1.73 | 4.44 | 1.75 | 4.35 | 1.76 | 4.14 |
| Stdev | 6.23 | 13.0 | 6.26 | 12.8 | 6.37 | 12.4 |
| p (t-test) | | 0.11 | | 0.12 | | 0.15 |
| Min | 0.00242 | 0.233 | 0.00242 | 0.233 | 0.00242 | 0.233 |
| Max | 60.0 | 60.0 | 60.0 | 60.0 | 60.0 | 60.0 |
| n (Patient) | 91 | 40 | 90 | 41 | 87 | 44 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.67 | 0.64 | 0.64 | 0.67 | 0.63 | 0.64 | 0.66 | 0.63 |
| SE | 0.048 | 0.047 | 0.054 | 0.048 | 0.047 | 0.054 | 0.048 | 0.048 | 0.053 |
| p Value | 0.0024 | 4.1E−4 | 0.0096 | 0.0040 | 4.1E−4 | 0.016 | 0.0040 | 8.4E−4 | 0.012 |
| nCohort Recovered | 69 | 70 | 91 | 68 | 70 | 90 | 66 | 69 | 87 |
| nCohort Non-recovered | 63 | 62 | 40 | 64 | 62 | 41 | 66 | 63 | 44 |
| Cutoff Quartile 2 | 0.561 | 0.561 | 0.569 | 0.561 | 0.561 | 0.569 | 0.561 | 0.561 | 0.569 |
| Sensitivity | 83% | 84% | 85% | 83% | 84% | 85% | 83% | 83% | 86% |
| Specificity | 32% | 33% | 30% | 32% | 33% | 30% | 33% | 32% | 31% |
| Cutoff Quartile 3 | 1.07 | 1.07 | 1.07 | 1.07 | 1.07 | 1.07 | 1.07 | 1.07 | 1.07 |
| Sensitivity | 59% | 60% | 62% | 58% | 60% | 61% | 58% | 59% | 61% |
| Specificity | 58% | 59% | 55% | 57% | 59% | 54% | 58% | 58% | 55% |
| Cutoff Quartile 4 | 1.65 | 1.65 | 1.66 | 1.65 | 1.65 | 1.66 | 1.65 | 1.65 | 1.66 |
| Sensitivity | 35% | 37% | 35% | 34% | 37% | 34% | 33% | 37% | 32% |
| Specificity | 84% | 86% | 79% | 84% | 86% | 79% | 83% | 86% | 78% |
| OR Quartile 2 | 2.21 | 2.54 | 2.39 | 2.30 | 2.54 | 2.50 | 2.50 | 2.21 | 2.85 |
| p Value | 0.059 | 0.029 | 0.081 | 0.047 | 0.029 | 0.066 | 0.030 | 0.059 | 0.035 |
| Lower limit of 95% CI | 0.970 | 1.10 | 0.899 | 1.01 | 1.10 | 0.942 | 1.10 | 0.970 | 1.08 |
| Upper limit of 95% CI | 5.05 | 5.90 | 6.35 | 5.26 | 5.90 | 6.64 | 5.71 | 5.05 | 7.54 |
| OR Quartile 3 | 1.96 | 2.09 | 2.03 | 1.84 | 2.09 | 1.87 | 1.84 | 1.96 | 1.95 |
| p Value | 0.056 | 0.037 | 0.068 | 0.083 | 0.037 | 0.10 | 0.083 | 0.056 | 0.076 |
| Lower limit of 95% CI | 0.982 | 1.04 | 0.949 | 0.924 | 1.04 | 0.880 | 0.923 | 0.982 | 0.933 |
| Upper limit of 95% CI | 3.92 | 4.19 | 4.35 | 3.68 | 4.19 | 3.96 | 3.67 | 3.92 | 4.09 |

TABLE 23.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| OR Quartile 4 | 2.83 | 3.54 | 2.04 | 2.71 | 3.54 | 1.94 | 2.50 | 3.39 | 1.67 |
|---|---|---|---|---|---|---|---|---|---|
| p Value | 0.014 | 0.0034 | 0.090 | 0.018 | 0.0034 | 0.11 | 0.030 | 0.0046 | 0.22 |
| Lower limit of 95% CI | 1.24 | 1.52 | 0.896 | 1.19 | 1.52 | 0.853 | 1.10 | 1.46 | 0.741 |
| Upper limit of 95% CI | 6.47 | 8.24 | 4.65 | 6.20 | 8.24 | 4.40 | 5.71 | 7.89 | 3.77 |

TABLE 23.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 1.02 | 1.36 | 1.04 | 1.35 | 1.02 | 1.35 |
| Average | 1.73 | 4.22 | 1.75 | 4.13 | 1.75 | 4.07 |
| Stdev | 6.30 | 12.5 | 6.33 | 12.4 | 6.37 | 12.2 |
| p (t-test) | | 0.13 | | 0.14 | | 0.15 |
| Min | 0.00242 | 0.197 | 0.00242 | 0.197 | 0.00242 | 0.197 |
| Max | 60.0 | 60.0 | 60.0 | 60.0 | 60.0 | 60.0 |
| n (Patient) | 89 | 43 | 88 | 44 | 87 | 45 |
| sCr only | | | | | | |
| Median | 0.989 | 1.36 | 0.989 | 1.36 | 0.989 | 1.36 |
| Average | 1.78 | 3.68 | 1.78 | 3.68 | 1.78 | 3.68 |
| Stdev | 6.68 | 11.3 | 6.68 | 11.3 | 6.68 | 11.3 |
| p (t-test) | | 0.23 | | 0.23 | | 0.23 |
| Min | 0.0264 | 0.00242 | 0.0264 | 0.00242 | 0.0264 | 0.00242 |
| Max | 60.0 | 60.0 | 60.0 | 60.0 | 60.0 | 60.0 |
| n (Patient) | 79 | 53 | 79 | 53 | 79 | 53 |
| UO only | | | | | | |
| Median | 1.05 | 1.35 | 1.05 | 1.35 | 1.05 | 1.34 |
| Average | 1.74 | 4.43 | 1.75 | 4.33 | 1.76 | 4.26 |
| Stdev | 6.23 | 13.0 | 6.26 | 12.8 | 6.30 | 12.7 |
| p (t-test) | | 0.11 | | 0.12 | | 0.13 |
| Min | 0.00242 | 0.233 | 0.00242 | 0.233 | 0.00242 | 0.233 |
| Max | 60.0 | 60.0 | 60.0 | 60.0 | 60.0 | 60.0 |
| n (Patient) | 91 | 40 | 90 | 41 | 89 | 42 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.64 | 0.63 | 0.62 | 0.64 | 0.62 | 0.63 | 0.64 | 0.62 |
| SE | 0.053 | 0.050 | 0.054 | 0.053 | 0.050 | 0.054 | 0.052 | 0.050 | 0.054 |
| p Value | 0.011 | 0.0054 | 0.017 | 0.018 | 0.0054 | 0.027 | 0.016 | 0.0054 | 0.023 |
| nCohort Recovered | 89 | 79 | 91 | 88 | 79 | 90 | 87 | 79 | 89 |
| nCohort Non-recovered | 43 | 53 | 40 | 44 | 53 | 41 | 45 | 53 | 42 |
| Cutoff Quartile 2 | 0.561 | 0.561 | 0.569 | 0.561 | 0.561 | 0.569 | 0.561 | 0.561 | 0.569 |
| Sensitivity | 84% | 81% | 85% | 84% | 81% | 85% | 84% | 81% | 86% |
| Specificity | 29% | 29% | 30% | 30% | 29% | 30% | 30% | 29% | 30% |
| Cutoff Quartile 3 | 1.07 | 1.07 | 1.07 | 1.07 | 1.07 | 1.07 | 1.07 | 1.07 | 1.07 |
| Sensitivity | 60% | 62% | 60% | 59% | 62% | 59% | 60% | 62% | 60% |
| Specificity | 55% | 58% | 54% | 55% | 58% | 53% | 55% | 58% | 54% |
| Cutoff Quartile 4 | 1.65 | 1.65 | 1.66 | 1.65 | 1.65 | 1.66 | 1.65 | 1.65 | 1.66 |
| Sensitivity | 35% | 36% | 35% | 34% | 36% | 34% | 33% | 36% | 33% |
| Specificity | 80% | 82% | 79% | 80% | 82% | 79% | 79% | 82% | 79% |

TABLE 23.5-continued

Comparison of marker levels and the area under the ROC curve (AUC) in urine samples
for the "recovered" and "non-recovered" cohorts where recovery starts
within 168 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| OR Quartile 2 | 2.12 | 1.77 | 2.39 | 2.22 | 1.77 | 2.50 | 2.31 | 1.77 | 2.61 |
| p Value | 0.11 | 0.19 | 0.081 | 0.093 | 0.19 | 0.066 | 0.076 | 0.19 | 0.054 |
| Lower limit of 95% CI | 0.838 | 0.761 | 0.899 | 0.876 | 0.761 | 0.942 | 0.915 | 0.761 | 0.985 |
| Upper limit of 95% CI | 5.38 | 4.10 | 6.35 | 5.61 | 4.10 | 6.64 | 5.85 | 4.10 | 6.93 |
| OR Quartile 3 | 1.87 | 2.30 | 1.75 | 1.73 | 2.30 | 1.61 | 1.85 | 2.30 | 1.72 |
| p Value | 0.097 | 0.022 | 0.15 | 0.14 | 0.022 | 0.21 | 0.10 | 0.022 | 0.15 |
| Lower limit of 95% CI | 0.894 | 1.13 | 0.823 | 0.833 | 1.13 | 0.765 | 0.889 | 1.13 | 0.818 |
| Upper limit of 95% CI | 3.93 | 4.69 | 3.72 | 3.61 | 4.69 | 3.40 | 3.83 | 4.69 | 3.62 |
| OR Quartile 4 | 2.11 | 2.59 | 2.04 | 2.01 | 2.59 | 1.94 | 1.92 | 2.59 | 1.84 |
| p Value | 0.071 | 0.020 | 0.090 | 0.091 | 0.020 | 0.11 | 0.11 | 0.020 | 0.14 |
| Lower limit of 95% CI | 0.937 | 1.16 | 0.896 | 0.894 | 1.16 | 0.853 | 0.854 | 1.16 | 0.813 |
| Upper limit of 95% CI | 4.76 | 5.81 | 4.65 | 4.52 | 5.81 | 4.40 | 4.30 | 5.81 | 4.17 |

Example 24. Use of C—C Motif Chemokine 18 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 18 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 24.1

Comparison of marker levels and the area under the ROC curve (AUC) in urine samples
for the "persistent" and "non-persistent" cohorts where persistence
starts within 24 hours after sample collection and renal status is assessed by serum
creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.989 | 1.36 | 0.978 | 1.54 | 0.989 | 1.54 |
| Average | 1.70 | 4.28 | 1.66 | 4.64 | 1.68 | 4.94 |
| Stdev | 6.30 | 12.5 | 6.16 | 13.1 | 6.04 | 13.8 |
| p (t-test) | | 0.12 | | 0.078 | | 0.062 |
| Min | 0.00242 | 0.233 | 0.00242 | 0.233 | 0.00242 | 0.310 |
| Max | 60.0 | 60.0 | 60.0 | 60.0 | 60.0 | 60.0 |
| n (Patient) | 89 | 43 | 93 | 39 | 97 | 35 |
| sCr only | | | | | | |
| Median | 0.978 | 1.39 | 0.983 | 1.59 | 1.00 | 1.54 |
| Average | 1.69 | 4.37 | 1.65 | 4.81 | 1.69 | 4.90 |
| Stdev | 6.30 | 12.6 | 6.13 | 13.4 | 6.07 | 13.8 |

TABLE 24.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.11 | | 0.066 | | 0.066 |
| Min | 0.00242 | 0.233 | 0.00242 | 0.233 | 0.00242 | 0.233 |
| Max | 60.0 | 60.0 | 60.0 | 60.0 | 60.0 | 60.0 |
| n (Patient) | 89 | 42 | 94 | 37 | 96 | 35 |

UO only

| | | | | | | |
|---|---|---|---|---|---|---|
| Median | 1.06 | 1.58 | 1.06 | 1.74 | 1.06 | 1.74 |
| Average | 1.65 | 8.26 | 1.64 | 9.16 | 1.64 | 9.16 |
| Stdev | 5.60 | 18.9 | 5.55 | 19.9 | 5.55 | 19.9 |
| p (t-test) | | 0.0030 | | 0.0013 | | 0.0013 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 113 | 18 | 115 | 16 | 115 | 16 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.68 | 0.71 | 0.70 | 0.70 | 0.73 | 0.68 | 0.67 | 0.73 |
| SE | 0.052 | 0.052 | 0.072 | 0.053 | 0.054 | 0.075 | 0.055 | 0.056 | 0.075 |
| p Value | 0.0013 | 4.8E−4 | 0.0046 | 2.2E−4 | 2.6E−4 | 0.0018 | 8.4E−4 | 0.0026 | 0.0018 |
| nCohort Non-persistent | 89 | 89 | 113 | 93 | 94 | 115 | 97 | 96 | 115 |
| nCohort Persistent | 43 | 42 | 18 | 39 | 37 | 16 | 35 | 35 | 16 |
| Cutoff Quartile 2 | 0.561 | 0.557 | 0.569 | 0.561 | 0.557 | 0.569 | 0.561 | 0.557 | 0.569 |
| Sensitivity | 88% | 88% | 94% | 87% | 86% | 94% | 89% | 86% | 94% |
| Specificity | 31% | 31% | 28% | 30% | 30% | 28% | 30% | 29% | 28% |
| Cutoff Quartile 3 | 1.07 | 1.07 | 1.07 | 1.07 | 1.07 | 1.07 | 1.07 | 1.07 | 1.07 |
| Sensitivity | 65% | 69% | 72% | 72% | 70% | 75% | 71% | 69% | 75% |
| Specificity | 57% | 58% | 53% | 59% | 57% | 53% | 58% | 56% | 53% |
| Cutoff Quartile 4 | 1.65 | 1.64 | 1.66 | 1.65 | 1.64 | 1.66 | 1.65 | 1.64 | 1.66 |
| Sensitivity | 35% | 36% | 44% | 38% | 41% | 50% | 37% | 37% | 50% |
| Specificity | 80% | 80% | 78% | 81% | 81% | 78% | 79% | 79% | 78% |
| OR Quartile 2 | 3.49 | 3.40 | 6.72 | 2.93 | 2.72 | 5.78 | 3.31 | 2.47 | 5.78 |
| p Value | 0.018 | 0.021 | 0.070 | 0.042 | 0.060 | 0.096 | 0.038 | 0.090 | 0.096 |
| Lower limit of 95% CI | 1.24 | 1.21 | 0.858 | 1.04 | 0.959 | 0.733 | 1.07 | 0.870 | 0.733 |
| Upper limit of 95% CI | 9.81 | 9.57 | 52.6 | 8.27 | 7.69 | 45.6 | 10.2 | 7.02 | 45.6 |
| OR Quartile 3 | 2.51 | 3.14 | 2.94 | 3.68 | 3.19 | 3.39 | 3.41 | 2.81 | 3.39 |
| p Value | 0.017 | 0.0040 | 0.053 | 0.0016 | 0.0053 | 0.044 | 0.0040 | 0.014 | 0.044 |
| Lower limit of 95% CI | 1.18 | 1.44 | 0.984 | 1.64 | 1.41 | 1.03 | 1.48 | 1.24 | 1.03 |
| Upper limit of 95% CI | 5.33 | 6.83 | 8.80 | 8.29 | 7.21 | 11.1 | 7.88 | 6.37 | 11.1 |
| OR Quartile 4 | 2.11 | 2.19 | 2.82 | 2.60 | 2.88 | 3.60 | 2.28 | 2.25 | 3.60 |
| p Value | 0.071 | 0.060 | 0.049 | 0.023 | 0.013 | 0.020 | 0.056 | 0.060 | 0.020 |
| Lower limit of 95% CI | 0.937 | 0.969 | 1.00 | 1.14 | 1.25 | 1.23 | 0.978 | 0.965 | 1.23 |
| Upper limit of 95% CI | 4.76 | 4.96 | 7.89 | 5.94 | 6.63 | 10.6 | 5.29 | 5.22 | 10.6 |

TABLE 24.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.970 | 1.36 | 0.960 | 1.54 | 0.970 | 1.54 |
| Average | 1.73 | 3.75 | 1.67 | 4.12 | 1.68 | 4.32 |
| Stdev | 6.68 | 11.3 | 6.45 | 12.0 | 6.30 | 12.5 |
| p (t-test) | | 0.20 | | 0.13 | | 0.11 |
| Min | 0.0156 | 0.00242 | 0.00242 | 0.233 | 0.00242 | 0.310 |
| Max | 60.0 | 60.0 | 60.0 | 60.0 | 60.0 | 60.0 |
| n (Patient) | 79 | 53 | 85 | 47 | 89 | 43 |
| sCr only | | | | | | |
| Median | 0.965 | 1.36 | 0.965 | 1.43 | 0.978 | 1.39 |
| Average | 1.72 | 3.84 | 1.68 | 4.09 | 1.71 | 4.20 |
| Stdev | 6.64 | 11.5 | 6.48 | 12.0 | 6.37 | 12.4 |
| p (t-test) | | 0.18 | | 0.14 | | 0.13 |
| Min | 0.0156 | 0.00242 | 0.00242 | 0.233 | 0.00242 | 0.233 |
| Max | 60.0 | 60.0 | 60.0 | 60.0 | 60.0 | 60.0 |
| n (Patient) | 80 | 51 | 84 | 47 | 87 | 44 |
| UO only | | | | | | |
| Median | 1.05 | 1.48 | 1.05 | 1.58 | 1.05 | 1.58 |
| Average | 1.67 | 6.52 | 1.66 | 7.02 | 1.66 | 7.02 |
| Stdev | 5.75 | 16.5 | 5.70 | 17.2 | 5.70 | 17.2 |
| p (t-test) | | 0.015 | | 0.0093 | | 0.0093 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 107 | 24 | 109 | 22 | 109 | 22 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.68 | 0.68 | 0.71 | 0.70 | 0.69 | 0.70 | 0.67 | 0.69 |
| SE | 0.049 | 0.049 | 0.065 | 0.049 | 0.050 | 0.067 | 0.051 | 0.052 | 0.067 |
| p Value | 3.3E−4 | 2.6E−4 | 0.0068 | 2.0E−5 | 8.2E−5 | 0.0039 | 7.5E−5 | 9.1E−4 | 0.0039 |
| nCohort Non-persistent | 79 | 80 | 107 | 85 | 84 | 109 | 89 | 87 | 109 |
| nCohort Persistent | 53 | 51 | 24 | 47 | 47 | 22 | 43 | 44 | 22 |
| Cutoff Quartile 2 | 0.561 | 0.557 | 0.569 | 0.561 | 0.557 | 0.569 | 0.561 | 0.557 | 0.569 |
| Sensitivity | 87% | 86% | 92% | 87% | 87% | 91% | 88% | 86% | 91% |
| Specificity | 33% | 32% | 29% | 32% | 32% | 28% | 31% | 31% | 28% |
| Cutoff Quartile 3 | 1.07 | 1.07 | 1.07 | 1.07 | 1.07 | 1.07 | 1.07 | 1.07 | 1.07 |
| Sensitivity | 62% | 65% | 67% | 68% | 66% | 68% | 70% | 66% | 68% |
| Specificity | 58% | 59% | 53% | 60% | 58% | 53% | 60% | 57% | 53% |
| Cutoff Quartile 4 | 1.65 | 1.64 | 1.66 | 1.65 | 1.64 | 1.66 | 1.65 | 1.64 | 1.66 |
| Sensitivity | 38% | 37% | 42% | 40% | 38% | 45% | 40% | 36% | 45% |
| Specificity | 84% | 82% | 79% | 84% | 82% | 79% | 82% | 80% | 79% |
| OR Quartile 2 | 3.22 | 3.03 | 4.49 | 3.18 | 3.24 | 3.97 | 3.49 | 2.85 | 3.97 |
| p Value | 0.013 | 0.019 | 0.051 | 0.019 | 0.018 | 0.074 | 0.018 | 0.035 | 0.074 |
| Lower limit of 95% CI | 1.28 | 1.20 | 0.995 | 1.20 | 1.23 | 0.876 | 1.24 | 1.08 | 0.876 |
| Upper limit of 95% CI | 8.12 | 7.63 | 20.2 | 8.40 | 8.55 | 18.0 | 9.81 | 7.54 | 18.0 |
| OR Quartile 3 | 2.30 | 2.61 | 2.28 | 3.20 | 2.71 | 2.44 | 3.40 | 2.61 | 2.44 |
| p Value | 0.022 | 0.0096 | 0.082 | 0.0024 | 0.0085 | 0.073 | 0.0020 | 0.013 | 0.073 |
| Lower limit of 95% CI | 1.13 | 1.26 | 0.900 | 1.51 | 1.29 | 0.921 | 1.56 | 1.23 | 0.921 |
| Upper limit of 95% CI | 4.69 | 5.40 | 5.78 | 6.78 | 5.70 | 6.45 | 7.38 | 5.56 | 6.45 |

TABLE 24.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.08 | 2.80 | 2.61 | 3.44 | 2.86 | 3.12 | 2.98 | 2.35 | 3.12 |
| p Value | 0.0068 | 0.013 | 0.044 | 0.0030 | 0.011 | 0.020 | 0.0087 | 0.039 | 0.020 |
| Lower limit of 95% CI | 1.36 | 1.25 | 1.03 | 1.52 | 1.27 | 1.20 | 1.32 | 1.05 | 1.20 |
| Upper limit of 95% CI | 6.94 | 6.29 | 6.63 | 7.79 | 6.42 | 8.11 | 6.75 | 5.30 | 8.11 |

TABLE 24.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.965 | 1.35 | 0.960 | 1.36 | 0.965 | 1.39 |
| Average | 1.79 | 3.50 | 1.73 | 3.75 | 1.72 | 3.88 |
| Stdev | 6.90 | 10.8 | 6.68 | 11.3 | 6.56 | 11.6 |
| p (t-test) | | 0.27 | | 0.20 | | 0.17 |
| Min | 0.0156 | 0.00242 | 0.00242 | 0.233 | 0.00242 | 0.310 |
| Max | 60.0 | 60.0 | 60.0 | 60.0 | 60.0 | 60.0 |
| n (Patient) | 74 | 58 | 79 | 53 | 82 | 50 |
| | sCr only | | | | | |
| Median | 0.960 | 1.36 | 0.960 | 1.39 | 0.970 | 1.39 |
| Average | 1.75 | 3.68 | 1.71 | 3.90 | 1.72 | 3.98 |
| Stdev | 6.77 | 11.2 | 6.60 | 11.6 | 6.52 | 11.9 |
| p (t-test) | | 0.22 | | 0.17 | | 0.16 |
| Min | 0.0156 | 0.00242 | 0.00242 | 0.233 | 0.00242 | 0.233 |
| Max | 60.0 | 60.0 | 60.0 | 60.0 | 60.0 | 60.0 |
| n (Patient) | 77 | 54 | 81 | 50 | 83 | 48 |
| | UO only | | | | | |
| Median | 1.05 | 1.36 | 1.05 | 1.45 | 1.05 | 1.45 |
| Average | 1.69 | 5.61 | 1.67 | 6.16 | 1.67 | 6.16 |
| Stdev | 5.89 | 15.1 | 5.80 | 15.9 | 5.80 | 15.9 |
| p (t-test) | | 0.035 | | 0.020 | | 0.020 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 102 | 29 | 105 | 26 | 105 | 26 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.67 | 0.64 | 0.68 | 0.69 | 0.67 | 0.68 | 0.67 | 0.67 |
| SE | 0.048 | 0.049 | 0.061 | 0.049 | 0.049 | 0.063 | 0.049 | 0.050 | 0.063 |
| p Value | 0.0011 | 4.5E-4 | 0.018 | 2.3E-4 | 1.6E-4 | 0.0058 | 2.3E-4 | 5.2E-4 | 0.0058 |
| nCohort Non-persistent | 74 | 77 | 102 | 79 | 81 | 105 | 82 | 83 | 105 |
| nCohort Persistent | 58 | 54 | 29 | 53 | 50 | 26 | 50 | 48 | 26 |
| Cutoff Quartile 2 | 0.561 | 0.557 | 0.569 | 0.561 | 0.557 | 0.569 | 0.561 | 0.557 | 0.569 |
| Sensitivity | 84% | 85% | 86% | 85% | 86% | 88% | 86% | 85% | 88% |
| Specificity | 32% | 32% | 28% | 32% | 32% | 29% | 32% | 31% | 29% |
| Cutoff Quartile 3 | 1.07 | 1.07 | 1.07 | 1.07 | 1.07 | 1.07 | 1.07 | 1.07 | 1.07 |
| Sensitivity | 60% | 63% | 62% | 64% | 64% | 65% | 66% | 65% | 65% |
| Specificity | 58% | 58% | 53% | 59% | 58% | 53% | 60% | 58% | 53% |
| Cutoff Quartile 4 | 1.65 | 1.64 | 1.66 | 1.65 | 1.64 | 1.66 | 1.65 | 1.64 | 1.66 |
| Sensitivity | 34% | 35% | 38% | 36% | 36% | 42% | 36% | 35% | 42% |
| Specificity | 82% | 82% | 78% | 82% | 81% | 79% | 82% | 81% | 79% |

TABLE 24.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 2.61 | 2.76 | 2.48 | 2.60 | 2.90 | 3.07 | 2.85 | 2.67 | 3.07 |
| p Value | 0.029 | 0.025 | 0.12 | 0.035 | 0.024 | 0.085 | 0.026 | 0.038 | 0.085 |
| Lower limit of 95% CI | 1.10 | 1.14 | 0.794 | 1.07 | 1.15 | 0.857 | 1.13 | 1.06 | 0.857 |
| Upper limit of 95% CI | 6.18 | 6.73 | 7.76 | 6.34 | 7.32 | 11.0 | 7.19 | 6.74 | 11.0 |
| OR Quartile 3 | 2.11 | 2.39 | 1.84 | 2.63 | 2.46 | 2.16 | 2.88 | 2.50 | 2.16 |
| p Value | 0.036 | 0.017 | 0.16 | 0.0084 | 0.015 | 0.092 | 0.0046 | 0.014 | 0.092 |
| Lower limit of 95% CI | 1.05 | 1.17 | 0.791 | 1.28 | 1.19 | 0.883 | 1.38 | 1.20 | 0.883 |
| Upper limit of 95% CI | 4.25 | 4.88 | 4.29 | 5.39 | 5.08 | 5.28 | 6.00 | 5.21 | 5.28 |
| OR Quartile 4 | 2.47 | 2.44 | 2.22 | 2.59 | 2.47 | 2.77 | 2.51 | 2.30 | 2.77 |
| p Value | 0.028 | 0.030 | 0.077 | 0.020 | 0.027 | 0.028 | 0.025 | 0.043 | 0.028 |
| Lower limit of 95% CI | 1.10 | 1.09 | 0.916 | 1.16 | 1.11 | 1.11 | 1.12 | 1.03 | 1.11 |
| Upper limit of 95% CI | 5.54 | 5.46 | 5.39 | 5.81 | 5.53 | 6.87 | 5.62 | 5.13 | 6.87 |

TABLE 24.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 0.960 | 1.36 | 0.950 | 1.39 | 0.965 | 1.39 |
| Average | 1.79 | 3.47 | 1.73 | 3.71 | 1.74 | 3.77 |
| Stdev | 6.95 | 10.7 | 6.73 | 11.2 | 6.64 | 11.4 |
| p (t-test) | | 0.28 | | 0.21 | | 0.20 |
| Min | 0.0156 | 0.00242 | 0.00242 | 0.233 | 0.00242 | 0.233 |
| Max | 60.0 | 60.0 | 60.0 | 60.0 | 60.0 | 60.0 |
| n (Patient) | 73 | 59 | 78 | 54 | 80 | 52 |
| *sCr only* | | | | | | |
| Median | 0.960 | 1.36 | 0.960 | 1.39 | 0.970 | 1.39 |
| Average | 1.77 | 3.59 | 1.73 | 3.79 | 1.74 | 3.86 |
| Stdev | 6.86 | 11.0 | 6.68 | 11.4 | 6.60 | 11.6 |
| p (t-test) | | 0.25 | | 0.19 | | 0.18 |
| Min | 0.0156 | 0.00242 | 0.00242 | 0.233 | 0.00242 | 0.233 |
| Max | 60.0 | 60.0 | 60.0 | 60.0 | 60.0 | 60.0 |
| n (Patient) | 75 | 56 | 79 | 52 | 81 | 50 |
| *UO only* | | | | | | |
| Median | 1.05 | 1.36 | 1.05 | 1.45 | 1.05 | 1.45 |
| Average | 1.70 | 5.11 | 1.67 | 5.54 | 1.67 | 5.54 |
| Stdev | 6.01 | 14.2 | 5.92 | 14.8 | 5.92 | 14.8 |
| p (t-test) | | 0.056 | | 0.036 | | 0.036 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 98 | 33 | 101 | 30 | 101 | 30 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.67 | 0.65 | 0.69 | 0.68 | 0.67 | 0.67 | 0.67 | 0.67 |
| SE | 0.048 | 0.048 | 0.058 | 0.048 | 0.049 | 0.059 | 0.049 | 0.050 | 0.059 |
| p Value | 5.6E-4 | 4.5E-4 | 0.011 | 1.0E-4 | 1.7E-4 | 0.0037 | 3.5E-4 | 5.5E-4 | 0.0037 |

TABLE 24.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-persistent | 73 | 75 | 98 | 78 | 79 | 101 | 80 | 81 | 101 |
| nCohort Persistent | 59 | 56 | 33 | 54 | 52 | 30 | 52 | 50 | 30 |
| Cutoff Quartile 2 | 0.561 | 0.557 | 0.569 | 0.561 | 0.557 | 0.569 | 0.561 | 0.557 | 0.569 |
| Sensitivity | 85% | 84% | 88% | 85% | 85% | 90% | 85% | 84% | 90% |
| Specificity | 33% | 32% | 30% | 32% | 32% | 30% | 31% | 31% | 30% |
| Cutoff Quartile 3 | 1.07 | 1.07 | 1.07 | 1.07 | 1.07 | 1.07 | 1.07 | 1.07 | 1.07 |
| Sensitivity | 61% | 62% | 61% | 65% | 63% | 63% | 65% | 64% | 63% |
| Specificity | 59% | 59% | 53% | 60% | 58% | 53% | 60% | 58% | 53% |
| Cutoff Quartile 4 | 1.65 | 1.64 | 1.66 | 1.65 | 1.64 | 1.66 | 1.65 | 1.64 | 1.66 |
| Sensitivity | 36% | 36% | 39% | 37% | 37% | 43% | 37% | 36% | 43% |
| Specificity | 84% | 83% | 80% | 83% | 82% | 80% | 82% | 81% | 80% |
| OR Quartile 2 | 2.72 | 2.46 | 3.05 | 2.71 | 2.55 | 3.80 | 2.50 | 2.34 | 3.80 |
| p Value | 0.023 | 0.041 | 0.054 | 0.028 | 0.040 | 0.039 | 0.043 | 0.061 | 0.039 |
| Lower limit of 95% CI | 1.15 | 1.04 | 0.983 | 1.12 | 1.05 | 1.07 | 1.03 | 0.961 | 1.07 |
| Upper limit of 95% CI | 6.44 | 5.82 | 9.45 | 6.60 | 6.20 | 13.5 | 6.08 | 5.71 | 13.5 |
| OR Quartile 3 | 2.24 | 2.37 | 1.74 | 2.79 | 2.42 | 1.98 | 2.83 | 2.46 | 1.98 |
| p Value | 0.024 | 0.017 | 0.18 | 0.0051 | 0.016 | 0.11 | 0.0049 | 0.015 | 0.11 |
| Lower limit of 95% CI | 1.11 | 1.16 | 0.779 | 1.36 | 1.18 | 0.857 | 1.37 | 1.19 | 0.857 |
| Upper limit of 95% CI | 4.52 | 4.81 | 3.88 | 5.73 | 4.97 | 4.59 | 5.85 | 5.08 | 4.59 |
| OR Quartile 4 | 2.81 | 2.65 | 2.54 | 2.94 | 2.67 | 3.10 | 2.71 | 2.47 | 3.10 |
| p Value | 0.013 | 0.018 | 0.033 | 0.0092 | 0.017 | 0.011 | 0.015 | 0.027 | 0.011 |
| Lower limit of 95% CI | 1.24 | 1.18 | 1.08 | 1.31 | 1.19 | 1.29 | 1.21 | 1.11 | 1.29 |
| Upper limit of 95% CI | 6.36 | 5.96 | 5.95 | 6.63 | 5.99 | 7.41 | 6.08 | 5.53 | 7.41 |

TABLE 24.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.960 | 1.36 | 0.950 | 1.39 | 0.965 | 1.39 |
| Average | 1.79 | 3.47 | 1.73 | 3.71 | 1.74 | 3.77 |
| Stdev | 6.95 | 10.7 | 6.73 | 11.2 | 6.64 | 11.4 |
| p (t-test) | | 0.28 | | 0.21 | | 0.20 |
| Min | 0.0156 | 0.00242 | 0.00242 | 0.233 | 0.00242 | 0.233 |
| Max | 60.0 | 60.0 | 60.0 | 60.0 | 60.0 | 60.0 |
| n (Patient) | 73 | 59 | 78 | 54 | 80 | 52 |
| | sCr only | | | | | |
| Median | 0.965 | 1.36 | 0.965 | 1.36 | 0.979 | 1.36 |
| Average | 1.79 | 3.53 | 1.75 | 3.72 | 1.76 | 3.78 |
| Stdev | 6.90 | 10.9 | 6.72 | 11.3 | 6.64 | 11.5 |
| p (t-test) | | 0.27 | | 0.21 | | 0.20 |
| Min | 0.0264 | 0.00242 | 0.00242 | 0.0156 | 0.00242 | 0.0156 |
| Max | 60.0 | 60.0 | 60.0 | 60.0 | 60.0 | 60.0 |
| n (Patient) | 74 | 57 | 78 | 53 | 80 | 51 |

TABLE 24.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

|  | UO only | | | | | |
|---|---|---|---|---|---|---|
| Median | 1.05 | 1.36 | 1.05 | 1.36 | 1.05 | 1.36 |
| Average | 1.71 | 4.88 | 1.70 | 5.12 | 1.70 | 5.12 |
| Stdev | 6.07 | 13.8 | 6.01 | 14.2 | 6.01 | 14.2 |
| p (t-test) | | 0.070 | | 0.055 | | 0.055 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 96 | 35 | 98 | 33 | 98 | 33 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.65 | 0.64 | 0.69 | 0.67 | 0.65 | 0.67 | 0.65 | 0.65 |
| SE | 0.048 | 0.049 | 0.057 | 0.048 | 0.049 | 0.058 | 0.049 | 0.050 | 0.058 |
| p Value | 5.6E−4 | 0.0016 | 0.013 | 1.0E−4 | 7.0E−4 | 0.0093 | 3.5E−4 | 0.0020 | 0.0093 |
| nCohort Non-persistent | 73 | 74 | 96 | 78 | 78 | 98 | 80 | 80 | 98 |
| nCohort Persistent | 59 | 57 | 35 | 54 | 53 | 33 | 52 | 51 | 33 |
| Cutoff Quartile 2 | 0.561 | 0.557 | 0.569 | 0.561 | 0.557 | 0.569 | 0.561 | 0.557 | 0.569 |
| Sensitivity | 85% | 82% | 89% | 85% | 83% | 88% | 85% | 82% | 88% |
| Specificity | 33% | 31% | 30% | 32% | 31% | 30% | 31% | 30% | 30% |
| Cutoff Quartile 3 | 1.07 | 1.07 | 1.07 | 1.07 | 1.07 | 1.07 | 1.07 | 1.07 | 1.07 |
| Sensitivity | 61% | 61% | 60% | 65% | 62% | 61% | 65% | 63% | 61% |
| Specificity | 59% | 58% | 53% | 60% | 58% | 53% | 60% | 57% | 53% |
| Cutoff Quartile 4 | 1.65 | 1.64 | 1.66 | 1.65 | 1.64 | 1.66 | 1.65 | 1.64 | 1.66 |
| Sensitivity | 36% | 35% | 37% | 37% | 36% | 39% | 37% | 35% | 39% |
| Specificity | 84% | 82% | 79% | 83% | 82% | 80% | 82% | 81% | 80% |
| OR Quartile 2 | 2.72 | 2.12 | 3.35 | 2.71 | 2.17 | 3.05 | 2.50 | 2.00 | 3.05 |
| p Value | 0.023 | 0.080 | 0.036 | 0.028 | 0.078 | 0.054 | 0.043 | 0.12 | 0.054 |
| Lower limit of 95% CI | 1.15 | 0.914 | 1.08 | 1.12 | 0.916 | 0.983 | 1.03 | 0.843 | 0.983 |
| Upper limit of 95% CI | 6.44 | 4.92 | 10.4 | 6.60 | 5.15 | 9.45 | 6.08 | 4.75 | 9.45 |
| OR Quartile 3 | 2.24 | 2.21 | 1.70 | 2.79 | 2.25 | 1.74 | 2.83 | 2.28 | 1.74 |
| p Value | 0.024 | 0.028 | 0.19 | 0.0051 | 0.026 | 0.18 | 0.0049 | 0.025 | 0.18 |
| Lower limit of 95% CI | 1.11 | 1.09 | 0.775 | 1.36 | 1.10 | 0.779 | 1.37 | 1.11 | 0.779 |
| Upper limit of 95% CI | 4.52 | 4.47 | 3.73 | 5.73 | 4.60 | 3.88 | 5.85 | 4.68 | 3.88 |
| OR Quartile 4 | 2.81 | 2.54 | 2.25 | 2.94 | 2.55 | 2.54 | 2.71 | 2.36 | 2.54 |
| p Value | 0.013 | 0.024 | 0.060 | 0.0092 | 0.023 | 0.033 | 0.015 | 0.036 | 0.033 |
| Lower limit of 95% CI | 1.24 | 1.13 | 0.965 | 1.31 | 1.14 | 1.08 | 1.21 | 1.06 | 1.08 |
| Upper limit of 95% CI | 6.36 | 5.70 | 5.22 | 6.63 | 5.72 | 5.95 | 6.08 | 5.28 | 5.95 |

Example 25. Use of C—C Motif Chemokine 18 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 18 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 25.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.845 | 1.33 | 0.979 | 1.34 | 0.989 | 1.36 |
| Average | 0.977 | 3.63 | 1.02 | 4.25 | 1.02 | 4.55 |
| Stdev | 0.836 | 11.4 | 0.798 | 12.7 | 0.777 | 13.2 |
| p (t-test) | | 0.091 | | 0.036 | | 0.023 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 54 | 78 | 70 | 62 | 75 | 57 |
| | sCr only | | | | | |
| Median | 0.870 | 1.31 | 0.970 | 1.35 | 0.989 | 1.44 |
| Average | 0.984 | 3.75 | 1.000 | 4.38 | 1.00 | 4.75 |
| Stdev | 0.819 | 11.7 | 0.777 | 12.9 | 0.752 | 13.6 |
| p (t-test) | | 0.077 | | 0.030 | | 0.017 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 57 | 74 | 71 | 60 | 77 | 54 |
| | UO only | | | | | |
| Median | 0.983 | 1.59 | 1.02 | 1.59 | 1.04 | 1.61 |
| Average | 1.64 | 5.80 | 1.64 | 6.89 | 1.63 | 7.41 |
| Stdev | 5.89 | 15.1 | 5.73 | 16.8 | 5.67 | 17.5 |
| p (t-test) | | 0.025 | | 0.0095 | | 0.0058 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 102 | 29 | 108 | 23 | 110 | 21 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.65 | 0.73 | 0.64 | 0.66 | 0.74 | 0.65 | 0.66 | 0.74 |
| SE | 0.047 | 0.048 | 0.057 | 0.048 | 0.048 | 0.063 | 0.049 | 0.049 | 0.066 |
| p Value | 0.0011 | 0.0017 | 5.0E−5 | 0.0038 | 0.0012 | 1.8E−4 | 0.0017 | 8.2E−4 | 2.7E−4 |
| nCohort Non-persistent | 54 | 57 | 102 | 70 | 71 | 108 | 75 | 77 | 110 |
| nCohort Persistent | 78 | 74 | 29 | 62 | 60 | 23 | 57 | 54 | 21 |
| Cutoff Quartile 2 | 0.561 | 0.557 | 0.569 | 0.561 | 0.557 | 0.569 | 0.561 | 0.557 | 0.569 |
| Sensitivity | 83% | 82% | 97% | 85% | 85% | 96% | 86% | 85% | 95% |
| Specificity | 37% | 35% | 31% | 34% | 34% | 30% | 33% | 32% | 29% |
| Cutoff Quartile 3 | 1.07 | 1.07 | 1.07 | 1.07 | 1.07 | 1.07 | 1.07 | 1.07 | 1.07 |
| Sensitivity | 59% | 59% | 79% | 58% | 62% | 78% | 60% | 61% | 76% |
| Specificity | 63% | 61% | 58% | 57% | 59% | 56% | 57% | 57% | 55% |
| Cutoff Quartile 4 | 1.65 | 1.64 | 1.66 | 1.65 | 1.64 | 1.66 | 1.65 | 1.64 | 1.66 |
| Sensitivity | 29% | 31% | 38% | 32% | 33% | 43% | 35% | 37% | 48% |
| Specificity | 81% | 82% | 78% | 81% | 82% | 79% | 83% | 83% | 79% |
| OR Quartile 2 | 2.94 | 2.54 | 12.8 | 3.07 | 2.89 | 9.26 | 3.06 | 2.76 | 8.21 |
| p Value | 0.0092 | 0.024 | 0.014 | 0.011 | 0.016 | 0.033 | 0.014 | 0.025 | 0.044 |
| Lower limit of 95% CI | 1.31 | 1.13 | 1.67 | 1.30 | 1.22 | 1.20 | 1.26 | 1.14 | 1.06 |
| Upper limit of 95% CI | 6.63 | 5.70 | 98.3 | 7.27 | 6.86 | 71.7 | 7.44 | 6.73 | 63.7 |
| OR Quartile 3 | 2.44 | 2.33 | 5.26 | 1.85 | 2.33 | 4.50 | 1.99 | 2.10 | 3.84 |
| p Value | 0.014 | 0.019 | 9.1E−4 | 0.082 | 0.018 | 0.0055 | 0.054 | 0.041 | 0.014 |
| Lower limit of 95% CI | 1.20 | 1.15 | 1.97 | 0.924 | 1.15 | 1.56 | 0.987 | 1.03 | 1.31 |
| Upper limit of 95% CI | 4.99 | 4.73 | 14.0 | 3.69 | 4.71 | 13.0 | 4.00 | 4.26 | 11.2 |

TABLE 25.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.84 | 2.12 | 2.22 | 2.09 | 2.23 | 2.84 | 2.58 | 2.90 | 3.44 |
| p Value | 0.16 | 0.080 | 0.077 | 0.073 | 0.051 | 0.030 | 0.022 | 0.010 | 0.013 |
| Lower limit of 95% CI | 0.793 | 0.914 | 0.916 | 0.934 | 0.996 | 1.11 | 1.15 | 1.28 | 1.30 |
| Upper limit of 95% CI | 4.27 | 4.92 | 5.39 | 4.67 | 5.00 | 7.31 | 5.79 | 6.53 | 9.09 |

TABLE 25.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.774 | 1.33 | 0.965 | 1.31 | 0.965 | 1.35 |
| Average | 0.895 | 3.51 | 0.997 | 4.00 | 0.988 | 4.19 |
| Stdev | 0.778 | 11.0 | 0.784 | 12.2 | 0.766 | 12.5 |
| p (t-test) | | 0.10 | | 0.051 | | 0.037 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 49 | 83 | 64 | 68 | 68 | 64 |
| | sCr only | | | | | |
| Median | 0.797 | 1.35 | 0.950 | 1.35 | 0.960 | 1.36 |
| Average | 0.903 | 3.70 | 0.953 | 4.16 | 0.952 | 4.32 |
| Stdev | 0.750 | 11.5 | 0.734 | 12.4 | 0.721 | 12.7 |
| p (t-test) | | 0.076 | | 0.038 | | 0.030 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 54 | 77 | 66 | 65 | 69 | 62 |
| | UO only | | | | | |
| Median | 0.974 | 1.42 | 1.00 | 1.43 | 1.02 | 1.54 |
| Average | 1.69 | 4.77 | 1.68 | 5.39 | 1.68 | 5.66 |
| Stdev | 6.13 | 13.4 | 5.95 | 14.6 | 5.89 | 15.1 |
| p (t-test) | | 0.073 | | 0.042 | | 0.032 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 94 | 37 | 100 | 31 | 102 | 29 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.69 | 0.69 | 0.65 | 0.67 | 0.68 | 0.66 | 0.68 | 0.67 |
| SE | 0.046 | 0.046 | 0.054 | 0.048 | 0.047 | 0.058 | 0.047 | 0.047 | 0.060 |
| p Value | 4.1E−5 | 4.7E−5 | 5.7E−4 | 0.0023 | 3.2E−4 | 0.0024 | 8.2E−4 | 1.8E−4 | 0.0039 |
| nCohort Non-persistent | 49 | 54 | 94 | 64 | 66 | 100 | 68 | 69 | 102 |
| nCohort Persistent | 83 | 77 | 37 | 68 | 65 | 31 | 64 | 62 | 29 |
| Cutoff Quartile 2 | 0.561 | 0.557 | 0.569 | 0.561 | 0.557 | 0.569 | 0.561 | 0.557 | 0.569 |
| Sensitivity | 83% | 83% | 92% | 84% | 85% | 90% | 84% | 85% | 90% |
| Specificity | 39% | 37% | 32% | 34% | 35% | 30% | 34% | 35% | 29% |
| Cutoff Quartile 3 | 1.07 | 1.07 | 1.07 | 1.07 | 1.07 | 1.07 | 1.07 | 1.07 | 1.07 |
| Sensitivity | 60% | 61% | 73% | 57% | 60% | 71% | 59% | 60% | 69% |
| Specificity | 67% | 65% | 59% | 58% | 59% | 56% | 59% | 58% | 55% |
| Cutoff Quartile 4 | 1.65 | 1.64 | 1.66 | 1.65 | 1.64 | 1.66 | 1.65 | 1.64 | 1.66 |
| Sensitivity | 31% | 34% | 32% | 32% | 34% | 35% | 34% | 35% | 38% |
| Specificity | 86% | 87% | 78% | 83% | 83% | 78% | 84% | 84% | 78% |

TABLE 25.2-continued

Comparison of marker levels and the area under the ROC curve (AUC) in urine samples
for the "persistent" and "non-persistent" cohorts where persistence
starts within 48 hours after sample collection and renal status is assessed by serum
creatinine (sCr) only, urine output (UO) only, or serum creatinine or urine output RIFLE criteria.

| | | | | | | | | | |
|---|---|---|---|---|---|---|---|---|---|
| OR Quartile 2 | 3.12 | 2.90 | 5.31 | 2.71 | 2.94 | 4.00 | 2.76 | 3.14 | 3.61 |
| p Value | 0.0060 | 0.010 | 0.0092 | 0.018 | 0.012 | 0.032 | 0.018 | 0.0093 | 0.047 |
| Lower limit of 95% CI | 1.38 | 1.28 | 1.51 | 1.19 | 1.27 | 1.13 | 1.19 | 1.33 | 1.02 |
| Upper limit of 95% CI | 7.03 | 6.53 | 18.7 | 6.20 | 6.83 | 14.2 | 6.40 | 7.44 | 12.8 |
| OR Quartile 3 | 3.12 | 2.89 | 3.81 | 1.84 | 2.17 | 3.11 | 2.09 | 2.04 | 2.71 |
| p Value | 0.0026 | 0.0040 | 0.0017 | 0.083 | 0.030 | 0.011 | 0.038 | 0.045 | 0.026 |
| Lower limit of 95% CI | 1.49 | 1.40 | 1.65 | 0.924 | 1.08 | 1.30 | 1.04 | 1.02 | 1.12 |
| Upper limit of 95% CI | 6.56 | 5.94 | 8.76 | 3.68 | 4.35 | 7.43 | 4.18 | 4.10 | 6.51 |
| OR Quartile 4 | 2.74 | 3.42 | 1.67 | 2.30 | 2.56 | 1.95 | 2.71 | 2.90 | 2.22 |
| p value | 0.033 | 0.0090 | 0.23 | 0.047 | 0.026 | 0.13 | 0.018 | 0.012 | 0.077 |
| Lower limit of 95% CI | 1.09 | 1.36 | 0.719 | 1.01 | 1.12 | 0.813 | 1.19 | 1.27 | 0.916 |
| Upper limit of 95% CI | 6.90 | 8.62 | 3.87 | 5.26 | 5.85 | 4.68 | 6.20 | 6.64 | 5.39 |

TABLE 25.3

Comparison of marker levels and the area under the ROC curve (AUC) in urine samples
for the "persistent" and "non-persistent" cohorts where persistence
starts within 72 hours after sample collection and renal status is assessed by serum
creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 0.774 | 1.33 | 0.965 | 1.31 | 0.979 | 1.34 |
| Average | 0.895 | 3.51 | 0.997 | 4.00 | 1.00 | 4.08 |
| Stdev | 0.778 | 11.0 | 0.784 | 12.2 | 0.773 | 12.3 |
| p (t-test) | | 0.10 | | 0.051 | | 0.045 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 49 | 83 | 64 | 68 | 66 | 66 |
| *sCr only* | | | | | | |
| Median | 0.819 | 1.34 | 0.960 | 1.34 | 0.970 | 1.35 |
| Average | 0.911 | 3.66 | 0.960 | 4.11 | 0.967 | 4.20 |
| Stdev | 0.755 | 11.4 | 0.737 | 12.3 | 0.727 | 12.5 |
| p (t-test) | | 0.082 | | 0.042 | | 0.037 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 53 | 78 | 65 | 66 | 67 | 64 |
| *UO only* | | | | | | |
| Median | 1.02 | 1.35 | 1.05 | 1.35 | 1.06 | 1.34 |
| Average | 1.75 | 4.29 | 1.74 | 4.73 | 1.73 | 4.93 |
| Stdev | 6.30 | 12.7 | 6.10 | 13.6 | 6.04 | 14.0 |
| p (t-test) | | 0.13 | | 0.085 | | 0.071 |
| Min | 0.00242 | 0.310 | 0.00242 | 0.310 | 0.00242 | 0.310 |
| Max | 60.0 | 60.0 | 60.0 | 60.0 | 60.0 | 60.0 |
| n (Patient) | 89 | 42 | 95 | 36 | 97 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.64 | 0.65 | 0.66 | 0.62 | 0.64 | 0.66 | 0.62 |
| SE | 0.046 | 0.046 | 0.053 | 0.048 | 0.047 | 0.057 | 0.048 | 0.048 | 0.058 |
| p Value | 4.1E-5 | 1.1E-4 | 0.0096 | 0.0023 | 6.6E-4 | 0.031 | 0.0028 | 8.3E-4 | 0.046 |

TABLE 25.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-persistent | 49 | 53 | 89 | 64 | 65 | 95 | 66 | 67 | 97 |
| nCohort Persistent | 83 | 78 | 42 | 68 | 66 | 36 | 66 | 64 | 34 |
| Cutoff Quartile 2 | 0.561 | 0.557 | 0.569 | 0.561 | 0.557 | 0.569 | 0.561 | 0.557 | 0.569 |
| Sensitivity | 83% | 82% | 88% | 84% | 83% | 86% | 83% | 83% | 85% |
| Specificity | 39% | 36% | 31% | 34% | 34% | 29% | 33% | 33% | 29% |
| Cutoff Quartile 3 | 1.07 | 1.07 | 1.07 | 1.07 | 1.07 | 1.07 | 1.07 | 1.07 | 1.07 |
| Sensitivity | 60% | 60% | 64% | 57% | 59% | 61% | 58% | 58% | 59% |
| Specificity | 67% | 64% | 56% | 58% | 58% | 54% | 58% | 57% | 53% |
| Cutoff Quartile 4 | 1.65 | 1.64 | 1.66 | 1.65 | 1.64 | 1.66 | 1.65 | 1.64 | 1.66 |
| Sensitivity | 31% | 33% | 29% | 32% | 33% | 31% | 33% | 34% | 32% |
| Specificity | 86% | 87% | 76% | 83% | 83% | 77% | 83% | 84% | 77% |
| OR Quartile 2 | 3.12 | 2.55 | 3.40 | 2.71 | 2.56 | 2.59 | 2.50 | 2.36 | 2.35 |
| p Value | 0.0060 | 0.023 | 0.021 | 0.018 | 0.026 | 0.073 | 0.030 | 0.042 | 0.11 |
| Lower limit of 95% CI | 1.38 | 1.14 | 1.21 | 1.19 | 1.12 | 0.914 | 1.10 | 1.03 | 0.827 |
| Upper limit of 95% CI | 7.03 | 5.72 | 9.57 | 6.20 | 5.85 | 7.35 | 5.71 | 5.38 | 6.70 |
| OR Quartile 3 | 3.12 | 2.71 | 2.31 | 1.84 | 2.03 | 1.82 | 1.84 | 1.80 | 1.58 |
| p Value | 0.0026 | 0.0067 | 0.030 | 0.083 | 0.046 | 0.13 | 0.083 | 0.098 | 0.25 |
| Lower limit of 95% CI | 1.49 | 1.32 | 1.08 | 0.924 | 1.01 | 0.833 | 0.923 | 0.898 | 0.718 |
| Upper limit of 95% CI | 6.56 | 5.58 | 4.92 | 3.68 | 4.08 | 3.98 | 3.67 | 3.59 | 3.49 |
| OR Quartile 4 | 2.74 | 3.29 | 1.30 | 2.30 | 2.45 | 1.46 | 2.50 | 2.67 | 1.63 |
| p Value | 0.033 | 0.012 | 0.54 | 0.047 | 0.033 | 0.39 | 0.030 | 0.020 | 0.27 |
| Lower limit of 95% CI | 1.09 | 1.30 | 0.565 | 1.01 | 1.07 | 0.621 | 1.10 | 1.17 | 0.689 |
| Upper limit of 95% CI | 6.90 | 8.28 | 2.97 | 5.26 | 5.61 | 3.43 | 5.71 | 6.10 | 3.86 |

TABLE 25.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.774 | 1.33 | 0.960 | 1.33 | 0.970 | 1.35 |
| Average | 0.895 | 3.51 | 0.985 | 3.96 | 0.991 | 4.05 |
| Stdev | 0.778 | 11.0 | 0.785 | 12.1 | 0.774 | 12.2 |
| p (t-test) | | 0.10 | | 0.053 | | 0.047 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 49 | 83 | 63 | 69 | 65 | 67 |
| sCr only | | | | | | |
| Median | 0.819 | 1.34 | 0.950 | 1.35 | 0.965 | 1.36 |
| Average | 0.911 | 3.66 | 0.949 | 4.07 | 0.955 | 4.16 |
| Stdev | 0.755 | 11.4 | 0.736 | 12.2 | 0.726 | 12.4 |
| p (t-test) | | 0.082 | | 0.044 | | 0.038 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 53 | 78 | 64 | 67 | 66 | 65 |

TABLE 25.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

|  | UO only | | | | | |
|---|---|---|---|---|---|---|
| Median | 1.00 | 1.36 | 1.05 | 1.35 | 1.06 | 1.34 |
| Average | 1.75 | 4.11 | 1.76 | 4.39 | 1.75 | 4.55 |
| Stdev | 6.41 | 12.2 | 6.23 | 13.0 | 6.16 | 13.3 |
| p (t-test) |  | 0.15 |  | 0.12 |  | 0.10 |
| Min | 0.00242 | 0.233 | 0.00242 | 0.233 | 0.00242 | 0.233 |
| Max | 60.0 | 60.0 | 60.0 | 60.0 | 60.0 | 60.0 |
| n (Patient) | 86 | 45 | 91 | 40 | 93 | 38 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.64 | 0.65 | 0.67 | 0.62 | 0.65 | 0.67 | 0.61 |
| SE | 0.046 | 0.046 | 0.052 | 0.047 | 0.047 | 0.055 | 0.048 | 0.047 | 0.056 |
| p Value | 4.1E−5 | 1.1E−4 | 0.0059 | 0.0012 | 2.9E−4 | 0.032 | 0.0014 | 3.8E−4 | 0.047 |
| nCohort Non-persistent | 49 | 53 | 86 | 63 | 64 | 91 | 65 | 66 | 93 |
| nCohort Persistent | 83 | 78 | 45 | 69 | 67 | 40 | 67 | 65 | 38 |
| Cutoff Quartile 2 | 0.561 | 0.557 | 0.569 | 0.561 | 0.557 | 0.569 | 0.561 | 0.557 | 0.569 |
| Sensitivity | 83% | 82% | 87% | 84% | 84% | 85% | 84% | 83% | 84% |
| Specificity | 39% | 36% | 31% | 35% | 34% | 30% | 34% | 33% | 29% |
| Cutoff Quartile 3 | 1.07 | 1.07 | 1.07 | 1.07 | 1.07 | 1.07 | 1.07 | 1.07 | 1.07 |
| Sensitivity | 60% | 60% | 64% | 58% | 60% | 60% | 58% | 58% | 58% |
| Specificity | 67% | 64% | 57% | 59% | 59% | 54% | 58% | 58% | 53% |
| Cutoff Quartile 4 | 1.65 | 1.64 | 1.66 | 1.65 | 1.64 | 1.66 | 1.65 | 1.64 | 1.66 |
| Sensitivity | 31% | 33% | 31% | 33% | 34% | 32% | 34% | 35% | 34% |
| Specificity | 86% | 87% | 78% | 84% | 84% | 78% | 85% | 85% | 78% |
| OR Quartile 2 | 3.12 | 2.55 | 2.97 | 2.83 | 2.67 | 2.39 | 2.60 | 2.45 | 2.18 |
| p Value | 0.0060 | 0.023 | 0.028 | 0.014 | 0.020 | 0.081 | 0.023 | 0.033 | 0.12 |
| Lower limit of 95% CI | 1.38 | 1.14 | 1.12 | 1.24 | 1.17 | 0.899 | 1.14 | 1.07 | 0.819 |
| Upper limit of 95% CI | 7.03 | 5.72 | 7.87 | 6.47 | 6.10 | 6.35 | 5.95 | 5.61 | 5.81 |
| OR Quartile 3 | 3.12 | 2.71 | 2.40 | 1.96 | 2.17 | 1.75 | 1.96 | 1.91 | 1.53 |
| p Value | 0.0026 | 0.0067 | 0.021 | 0.056 | 0.030 | 0.15 | 0.057 | 0.068 | 0.27 |
| Lower limit of 95% CI | 1.49 | 1.32 | 1.14 | 0.982 | 1.08 | 0.823 | 0.981 | 0.954 | 0.715 |
| Upper limit of 95% CI | 6.56 | 5.58 | 5.06 | 3.92 | 4.35 | 3.72 | 3.92 | 3.82 | 3.28 |
| OR Quartile 4 | 2.74 | 3.29 | 1.59 | 2.65 | 2.82 | 1.71 | 2.87 | 3.07 | 1.90 |
| p Value | 0.033 | 0.012 | 0.26 | 0.023 | 0.016 | 0.20 | 0.014 | 0.0092 | 0.13 |
| Lower limit of 95% CI | 1.09 | 1.30 | 0.708 | 1.14 | 1.22 | 0.748 | 1.24 | 1.32 | 0.825 |
| Upper limit of 95% CI | 6.90 | 8.28 | 3.58 | 6.14 | 6.55 | 3.91 | 6.67 | 7.13 | 4.37 |

TABLE 25.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.774 | 1.33 | 0.950 | 1.33 | 0.965 | 1.34 |
| Average | 0.895 | 3.51 | 0.980 | 3.93 | 0.986 | 4.01 |
| Stdev | 0.778 | 11.0 | 0.791 | 12.0 | 0.779 | 12.2 |
| p (t-test) |  | 0.10 |  | 0.056 |  | 0.049 |

TABLE 25.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 49 | 83 | 62 | 70 | 64 | 68 | sCr only

| | | | | | | |
|---|---|---|---|---|---|---|
| Median | 0.819 | 1.34 | 0.950 | 1.35 | 0.965 | 1.36 |
| Average | 0.911 | 3.66 | 0.949 | 4.07 | 0.955 | 4.16 |
| Stdev | 0.755 | 11.4 | 0.736 | 12.2 | 0.726 | 12.4 |
| p (t-test) | | 0.082 | | 0.044 | | 0.038 |
| Min | 0.0264 | 0.00242 | 0.0264 | 0.00242 | 0.0264 | 0.00242 |
| Max | 4.23 | 60.0 | 4.23 | 60.0 | 4.23 | 60.0 |
| n (Patient) | 53 | 78 | 64 | 67 | 66 | 65 |

UO only

| | | | | | | |
|---|---|---|---|---|---|---|
| Median | 1.00 | 1.36 | 1.04 | 1.35 | 1.05 | 1.33 |
| Average | 1.77 | 3.98 | 1.78 | 4.17 | 1.77 | 4.30 |
| Stdev | 6.48 | 12.0 | 6.33 | 12.5 | 6.26 | 12.8 |
| p (t-test) | | 0.17 | | 0.15 | | 0.13 |
| Min | 0.00242 | 0.233 | 0.00242 | 0.233 | 0.00242 | 0.233 |
| Max | 60.0 | 60.0 | 60.0 | 60.0 | 60.0 | 60.0 |
| n (Patient) | 84 | 47 | 88 | 43 | 90 | 41 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.64 | 0.66 | 0.67 | 0.62 | 0.65 | 0.67 | 0.61 |
| SE | 0.046 | 0.046 | 0.052 | 0.047 | 0.047 | 0.054 | 0.047 | 0.047 | 0.054 |
| p Value | 4.1E-5 | 1.1E-4 | 0.0064 | 8.8E-4 | 2.9E-4 | 0.030 | 0.0011 | 3.8E-4 | 0.045 |
| nCohort Non-persistent | 49 | 53 | 84 | 62 | 64 | 88 | 64 | 66 | 90 |
| nCohort Persistent | 83 | 78 | 47 | 70 | 67 | 43 | 68 | 65 | 41 |
| Cutoff Quartile 2 | 0.561 | 0.557 | 0.569 | 0.561 | 0.557 | 0.569 | 0.561 | 0.557 | 0.569 |
| Sensitivity | 83% | 82% | 87% | 84% | 84% | 86% | 84% | 83% | 85% |
| Specificity | 39% | 36% | 32% | 35% | 34% | 31% | 34% | 33% | 30% |
| Cutoff Quartile 3 | 1.07 | 1.07 | 1.07 | 1.07 | 1.07 | 1.07 | 1.07 | 1.07 | 1.07 |
| Sensitivity | 60% | 60% | 64% | 59% | 60% | 60% | 59% | 58% | 59% |
| Specificity | 67% | 64% | 57% | 60% | 59% | 55% | 59% | 58% | 53% |
| Cutoff Quartile 4 | 1.65 | 1.64 | 1.66 | 1.65 | 1.64 | 1.66 | 1.65 | 1.64 | 1.66 |
| Sensitivity | 31% | 33% | 30% | 33% | 34% | 30% | 34% | 35% | 32% |
| Specificity | 86% | 87% | 77% | 84% | 84% | 77% | 84% | 85% | 78% |
| OR Quartile 2 | 3.12 | 2.55 | 3.24 | 2.95 | 2.67 | 2.73 | 2.71 | 2.45 | 2.50 |
| p Value | 0.0060 | 0.023 | 0.018 | 0.010 | 0.020 | 0.043 | 0.018 | 0.033 | 0.066 |
| Lower limit of 95% CI | 1.38 | 1.14 | 1.23 | 1.29 | 1.17 | 1.03 | 1.19 | 1.07 | 0.942 |
| Upper limit of 95% CI | 7.03 | 5.72 | 8.55 | 6.75 | 6.10 | 7.23 | 6.20 | 5.61 | 6.64 |
| OR Quartile 3 | 3.12 | 2.71 | 2.35 | 2.09 | 2.17 | 1.84 | 2.09 | 1.91 | 1.61 |
| p Value | 0.0026 | 0.0067 | 0.023 | 0.037 | 0.030 | 0.11 | 0.038 | 0.068 | 0.21 |
| Lower limit of 95% CI | 1.49 | 1.32 | 1.13 | 1.04 | 1.08 | 0.874 | 1.04 | 0.954 | 0.765 |
| Upper limit of 95% CI | 6.56 | 5.58 | 4.91 | 4.19 | 4.35 | 3.85 | 4.18 | 3.82 | 3.40 |
| OR Quartile 4 | 2.74 | 3.29 | 1.45 | 2.54 | 2.82 | 1.47 | 2.76 | 3.07 | 1.62 |
| p Value | 0.033 | 0.012 | 0.37 | 0.029 | 0.016 | 0.35 | 0.018 | 0.0092 | 0.25 |
| Lower limit of 95% CI | 1.09 | 1.30 | 0.647 | 1.10 | 1.22 | 0.649 | 1.19 | 1.32 | 0.713 |
| Upper limit of 95% CI | 6.90 | 8.28 | 3.25 | 5.90 | 6.55 | 3.34 | 6.40 | 7.13 | 3.71 |

Example 26. Use of C—C Motif Chemokine 23 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 23 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 26.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00282 | 0.0144 | 0.00258 | 0.0130 | 0.00282 | 0.0123 |
| Average | 0.00875 | 0.134 | 0.00707 | 0.129 | 0.00774 | 0.127 |
| Stdev | 0.0140 | 0.372 | 0.00989 | 0.366 | 0.0103 | 0.363 |
| p (t-test) | | 0.012 | | 0.025 | | 0.037 |
| Min | 7.19E−7 | 3.28E−9 | 7.19E−7 | 3.28E−9 | 7.19E−7 | 3.28E−9 |
| Max | 0.0790 | 2.47 | 0.0380 | 2.47 | 0.0380 | 2.47 |
| n (Patient) | 57 | 260 | 46 | 271 | 41 | 276 |
| | sCr only | | | | | |
| Median | 0.00278 | 0.0172 | 0.00278 | 0.0168 | 0.00282 | 0.0162 |
| Average | 0.00748 | 0.144 | 0.00760 | 0.143 | 0.00783 | 0.141 |
| Stdev | 0.0121 | 0.386 | 0.0123 | 0.384 | 0.0125 | 0.382 |
| p (t-test) | | 0.0022 | | 0.0027 | | 0.0038 |
| Min | 3.28E−9 | 3.28E−9 | 3.28E−9 | 3.28E−9 | 3.28E−9 | 3.28E−9 |
| Max | 0.0790 | 2.47 | 0.0790 | 2.47 | 0.0790 | 2.47 |
| n (Patient) | 76 | 240 | 74 | 242 | 70 | 246 |
| | UO only | | | | | |
| Median | 0.00780 | 0.0134 | 0.00783 | 0.0129 | 0.00764 | 0.0134 |
| Average | 0.0920 | 0.144 | 0.0859 | 0.144 | 0.0865 | 0.137 |
| Stdev | 0.347 | 0.331 | 0.338 | 0.345 | 0.350 | 0.332 |
| p (t-test) | | 0.19 | | 0.14 | | 0.19 |
| Min | 6.85E−7 | 3.28E−9 | 6.85E−7 | 3.28E−9 | 6.85E−7 | 3.28E−9 |
| Max | 2.47 | 1.82 | 2.47 | 1.92 | 2.47 | 1.92 |
| n (Patient) | 194 | 121 | 173 | 142 | 156 | 159 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.73 | 0.57 | 0.71 | 0.73 | 0.57 | 0.69 | 0.72 | 0.57 |
| SE | 0.035 | 0.030 | 0.033 | 0.037 | 0.030 | 0.033 | 0.040 | 0.031 | 0.032 |
| p Value | 9.9E−9 | 5.1E−15 | 0.036 | 1.9E−8 | 5.0E−14 | 0.034 | 2.0E−6 | 1.1E−12 | 0.020 |
| nCohort Recovered | 57 | 76 | 194 | 46 | 74 | 173 | 41 | 70 | 156 |
| nCohort Non-recovered | 260 | 240 | 121 | 271 | 242 | 142 | 276 | 246 | 159 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 78% | 80% | 78% | 78% | 80% | 78% | 77% | 80% | 78% |
| Specificity | 40% | 42% | 27% | 43% | 42% | 28% | 39% | 41% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 56% | 59% | 55% | 55% | 59% | 54% | 54% | 58% | 54% |
| Specificity | 75% | 79% | 53% | 76% | 78% | 53% | 73% | 77% | 54% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 30% | 32% | 36% | 30% | 32% | 35% | 29% | 32% | 33% |
| Specificity | 98% | 99% | 82% | 100% | 99% | 83% | 100% | 99% | 83% |
| OR Quartile 2 | 2.46 | 2.99 | 1.27 | 2.76 | 2.91 | 1.37 | 2.16 | 2.77 | 1.39 |
| p Value | 0.0035 | 1.1E−4 | 0.37 | 0.0022 | 1.8E−4 | 0.23 | 0.028 | 4.3E−4 | 0.21 |
| Lower limit of 95% CI | 1.34 | 1.71 | 0.748 | 1.44 | 1.67 | 0.818 | 1.09 | 1.57 | 0.834 |
| Upper limit of 95% CI | 4.52 | 5.21 | 2.17 | 5.30 | 5.10 | 2.31 | 4.30 | 4.89 | 2.32 |
| OR Quartile 3 | 3.87 | 5.43 | 1.40 | 3.83 | 5.15 | 1.35 | 3.15 | 4.61 | 1.37 |

TABLE 26.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| p Value | 4.6E−5 | 5.0E−8 | 0.14 | 2.5E−4 | 1.4E−7 | 0.19 | 0.0021 | 1.0E−6 | 0.16 |
|---|---|---|---|---|---|---|---|---|---|
| Lower limit of 95% CI | 2.02 | 2.96 | 0.890 | 1.87 | 2.80 | 0.862 | 1.52 | 2.50 | 0.882 |
| Upper limit of 95% CI | 7.42 | 9.99 | 2.22 | 7.85 | 9.47 | 2.10 | 6.55 | 8.50 | 2.14 |
| OR Quartile 4 | 24.4 | 36.1 | 2.60 | 39.1 | 34.7 | 2.51 | 34.0 | 32.0 | 2.50 |
| p Value | 0.0017 | 4.2E−4 | 3.3E−4 | 0.010 | 4.8E−4 | 5.7E−4 | 0.014 | 6.5E−4 | 7.9E−4 |
| Lower limit of 95% CI | 3.32 | 4.93 | 1.54 | 2.38 | 4.74 | 1.49 | 2.07 | 4.37 | 1.46 |
| Upper limit of 95% CI | 180 | 265 | 4.37 | 642 | 254 | 4.24 | 559 | 235 | 4.27 |

TABLE 26.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00296 | 0.0184 | 0.00282 | 0.0168 | 0.00285 | 0.0162 |
| Average | 0.00925 | 0.152 | 0.00872 | 0.145 | 0.00897 | 0.141 |
| Stdev | 0.0164 | 0.395 | 0.0154 | 0.387 | 0.0157 | 0.382 |
| p (t-test) | | 7.3E−4 | | 0.0019 | | 0.0039 |
| Min | 7.09E−7 | 3.28E−9 | 7.09E−7 | 3.28E−9 | 7.09E−7 | 3.28E−9 |
| Max | 0.102 | 2.47 | 0.102 | 2.47 | 0.102 | 2.47 |
| n (Patient) | 90 | 227 | 79 | 238 | 71 | 246 |
| | sCr only | | | | | |
| Median | 0.00328 | 0.0222 | 0.00328 | 0.0220 | 0.00329 | 0.0213 |
| Average | 0.00870 | 0.163 | 0.00881 | 0.161 | 0.00872 | 0.158 |
| Stdev | 0.0153 | 0.408 | 0.0154 | 0.406 | 0.0155 | 0.402 |
| p (t-test) | | 1.3E−4 | | 1.6E−4 | | 2.7E−4 |
| Min | 3.28E−9 | 3.28E−9 | 3.28E−9 | 3.28E−9 | 3.28E−9 | 3.28E−9 |
| Max | 0.102 | 2.47 | 0.102 | 2.47 | 0.102 | 2.47 |
| n (Patient) | 106 | 211 | 104 | 213 | 99 | 218 |
| | UO only | | | | | |
| Median | 0.00764 | 0.0192 | 0.00780 | 0.0175 | 0.00764 | 0.0169 |
| Average | 0.0920 | 0.153 | 0.0981 | 0.134 | 0.0990 | 0.129 |
| Stdev | 0.336 | 0.351 | 0.350 | 0.328 | 0.361 | 0.315 |
| p (t-test) | | 0.14 | | 0.37 | | 0.44 |
| Min | 6.85E−7 | 3.28E−9 | 6.85E−7 | 3.28E−9 | 6.85E−7 | 3.28E−9 |
| Max | 2.47 | 1.82 | 2.47 | 1.82 | 2.47 | 1.82 |
| n (Patient) | 212 | 103 | 194 | 121 | 178 | 137 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.75 | 0.59 | 0.73 | 0.75 | 0.57 | 0.72 | 0.74 | 0.57 |
| SE | 0.029 | 0.027 | 0.035 | 0.030 | 0.027 | 0.033 | 0.031 | 0.028 | 0.033 |
| p Value | 7.5E−15 | 0 | 0.012 | 3.1E−14 | 0 | 0.035 | 6.9E−12 | 0 | 0.026 |
| nCohort Recovered | 90 | 106 | 212 | 79 | 104 | 194 | 71 | 99 | 178 |
| nCohort Non-recovered | 227 | 211 | 103 | 238 | 213 | 121 | 246 | 218 | 137 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 81% | 82% | 78% | 81% | 82% | 79% | 80% | 82% | 79% |
| Specificity | 39% | 40% | 26% | 42% | 39% | 28% | 41% | 39% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 60% | 64% | 59% | 59% | 63% | 56% | 57% | 62% | 55% |
| Specificity | 76% | 77% | 54% | 76% | 77% | 54% | 75% | 77% | 54% |

TABLE 26.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 4 | 0.0477 | 0.0477 | 0.0478 | 0.0477 | 0.0477 | 0.0478 | 0.0477 | 0.0477 | 0.0478 |
| Sensitivity | 34% | 36% | 36% | 33% | 36% | 33% | 32% | 35% | 32% |
| Specificity | 97% | 97% | 80% | 97% | 97% | 80% | 97% | 97% | 80% |
| OR Quartile 2 | 2.65 | 3.09 | 1.25 | 2.99 | 3.00 | 1.48 | 2.71 | 2.89 | 1.45 |
| p Value | 3.8E−4 | 2.7E−5 | 0.43 | 9.5E−5 | 4.5E−5 | 0.15 | 5.6E−4 | 8.4E−5 | 0.16 |
| Lower limit of 95% CI | 1.55 | 1.82 | 0.717 | 1.73 | 1.77 | 0.863 | 1.54 | 1.70 | 0.861 |
| Upper limit of 95% CI | 4.53 | 5.23 | 2.18 | 5.19 | 5.08 | 2.54 | 4.77 | 4.91 | 2.46 |
| OR Quartile 3 | 4.71 | 6.07 | 1.72 | 4.51 | 5.77 | 1.48 | 3.95 | 5.48 | 1.46 |
| p Value | 3.3E−8 | 3.9E−11 | 0.026 | 3.1E−7 | 1.3E−10 | 0.091 | 5.2E−6 | 7.1E−10 | 0.098 |
| Lower limit of 95% CI | 2.72 | 3.56 | 1.07 | 2.53 | 3.38 | 0.939 | 2.19 | 3.19 | 0.932 |
| Upper limit of 95% CI | 8.15 | 10.4 | 2.77 | 8.03 | 9.85 | 2.34 | 7.14 | 9.41 | 2.28 |
| OR Quartile 4 | 14.9 | 19.7 | 2.27 | 18.8 | 19.1 | 1.96 | 16.0 | 17.5 | 1.93 |
| p Value | 7.7E−6 | 7.6E−7 | 0.0022 | 5.8E−5 | 1.0E−6 | 0.011 | 1.5E−4 | 2.1E−6 | 0.012 |
| Lower limit of 95% CI | 4.56 | 6.05 | 1.34 | 4.49 | 5.85 | 1.17 | 3.83 | 5.36 | 1.15 |
| Upper limit of 95% CI | 48.6 | 64.3 | 3.84 | 78.4 | 62.1 | 3.29 | 67.0 | 57.0 | 3.24 |

TABLE 26.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00324 | 0.0215 | 0.00306 | 0.0200 | 0.00321 | 0.0178 |
| Average | 0.0146 | 0.165 | 0.0151 | 0.160 | 0.0158 | 0.153 |
| Stdev | 0.0391 | 0.415 | 0.0403 | 0.409 | 0.0422 | 0.401 |
| p (t-test) | | 1.3E−4 | | 3.0E−4 | | 8.6E−4 |
| Min | 3.28E−9 | 3.28E−9 | 3.28E−9 | 3.28E−9 | 3.28E−9 | 3.28E−9 |
| Max | 0.361 | 2.47 | 0.361 | 2.47 | 0.361 | 2.47 |
| n (Patient) | 114 | 203 | 107 | 210 | 97 | 220 |
| | sCr only | | | | | |
| Median | 0.00365 | 0.0249 | 0.00367 | 0.0232 | 0.00365 | 0.0226 |
| Average | 0.0139 | 0.176 | 0.0142 | 0.174 | 0.0142 | 0.170 |
| Stdev | 0.0371 | 0.427 | 0.0375 | 0.424 | 0.0382 | 0.420 |
| p (t-test) | | 2.6E−5 | | 3.9E−5 | | 7.2E−5 |
| Min | 3.28E−9 | 3.28E−9 | 3.28E−9 | 3.28E−9 | 3.28E−9 | 3.28E−9 |
| Max | 0.361 | 2.47 | 0.361 | 2.47 | 0.361 | 2.47 |
| n (Patient) | 127 | 190 | 124 | 193 | 119 | 198 |
| | UO only | | | | | |
| Median | 0.00730 | 0.0207 | 0.00764 | 0.0182 | 0.00724 | 0.0182 |
| Average | 0.0934 | 0.151 | 0.0971 | 0.139 | 0.0964 | 0.135 |
| Stdev | 0.335 | 0.354 | 0.342 | 0.340 | 0.350 | 0.328 |
| p (t-test) | | 0.16 | | 0.30 | | 0.32 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 214 | 101 | 204 | 111 | 190 | 125 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.73 | 0.59 | 0.72 | 0.73 | 0.57 | 0.71 | 0.72 | 0.59 |
| SE | 0.028 | 0.028 | 0.035 | 0.029 | 0.028 | 0.034 | 0.029 | 0.028 | 0.033 |

TABLE 26.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 1.8E-15 | 0 | 0.0072 | 2.2E-14 | 6.7E-16 | 0.029 | 7.5E-13 | 1.1E-15 | 0.0092 |
| nCohort Recovered | 114 | 127 | 214 | 107 | 124 | 204 | 97 | 119 | 190 |
| nCohort Non-recovered | 203 | 190 | 101 | 210 | 193 | 111 | 220 | 198 | 125 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 82% | 83% | 79% | 82% | 83% | 79% | 82% | 82% | 80% |
| Specificity | 38% | 37% | 27% | 39% | 37% | 27% | 40% | 37% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 63% | 65% | 61% | 61% | 64% | 58% | 60% | 64% | 58% |
| Specificity | 72% | 72% | 55% | 71% | 72% | 54% | 71% | 72% | 55% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 36% | 38% | 34% | 35% | 38% | 32% | 33% | 37% | 32% |
| Specificity | 94% | 94% | 79% | 93% | 94% | 78% | 93% | 94% | 79% |
| OR Quartile 2 | 2.81 | 2.90 | 1.42 | 3.02 | 2.86 | 1.45 | 3.03 | 2.73 | 1.59 |
| p Value | 1.1E-4 | 6.7E-5 | 0.23 | 3.8E-5 | 8.2E-5 | 0.19 | 4.4E-5 | 1.6E-4 | 0.093 |
| Lower limit of 95% CI | 1.67 | 1.72 | 0.803 | 1.79 | 1.70 | 0.833 | 1.78 | 1.62 | 0.926 |
| Upper limit of 95% CI | 4.74 | 4.90 | 2.50 | 5.11 | 4.82 | 2.52 | 5.15 | 4.60 | 2.73 |
| OR Quartile 3 | 4.28 | 4.94 | 1.95 | 3.83 | 4.57 | 1.59 | 3.63 | 4.56 | 1.64 |
| p Value | 1.0E-8 | 1.8E-10 | 0.0065 | 1.5E-7 | 1.2E-9 | 0.050 | 9.5E-7 | 1.9E-9 | 0.033 |
| Lower limit of 95% CI | 2.60 | 3.02 | 1.21 | 2.32 | 2.80 | 0.999 | 2.17 | 2.78 | 1.04 |
| Upper limit of 95% CI | 7.04 | 8.07 | 3.17 | 6.32 | 7.46 | 2.54 | 6.07 | 7.48 | 2.59 |
| OR Quartile 4 | 8.58 | 10.7 | 1.91 | 7.61 | 10.2 | 1.67 | 6.38 | 9.34 | 1.82 |
| p Value | 2.5E-7 | 1.3E-8 | 0.017 | 1.1E-6 | 2.6E-8 | 0.052 | 9.1E-6 | 8.1E-8 | 0.022 |
| Lower limit of 95% CI | 3.79 | 4.73 | 1.12 | 3.36 | 4.50 | 0.994 | 2.82 | 4.13 | 1.09 |
| Upper limit of 95% CI | 19.4 | 24.2 | 3.23 | 17.2 | 23.0 | 2.82 | 14.5 | 21.1 | 3.05 |

TABLE 26.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00383 | 0.0238 | 0.00365 | 0.0217 | 0.00348 | 0.0194 |
| Average | 0.0158 | 0.181 | 0.0164 | 0.173 | 0.0171 | 0.164 |
| Stdev | 0.0389 | 0.434 | 0.0402 | 0.426 | 0.0419 | 0.416 |
| p (t-test) | | 1.5E-5 | | 5.3E-5 | | 2.0E-4 |
| Min | 3.28E-9 | 3.28E-9 | 3.28E-9 | 3.28E-9 | 3.28E-9 | 3.28E-9 |
| Max | 0.361 | 2.47 | 0.361 | 2.47 | 0.361 | 2.47 |
| n (Patient) | 134 | 183 | 125 | 192 | 114 | 203 |
| | sCr only | | | | | |
| Median | 0.00383 | 0.0285 | 0.00396 | 0.0284 | 0.00379 | 0.0272 |
| Average | 0.0150 | 0.187 | 0.0152 | 0.185 | 0.0151 | 0.183 |
| Stdev | 0.0379 | 0.440 | 0.0382 | 0.438 | 0.0385 | 0.435 |
| p (t-test) | | 5.8E-6 | | 8.0E-6 | | 1.2E-5 |
| Min | 3.28E-9 | 3.28E-9 | 3.28E-9 | 3.28E-9 | 3.28E-9 | 3.28E-9 |
| Max | 0.361 | 2.47 | 0.361 | 2.47 | 0.361 | 2.47 |
| n (Patient) | 140 | 177 | 138 | 179 | 135 | 182 |
| | UO only | | | | | |
| Median | 0.00717 | 0.0215 | 0.00711 | 0.0199 | 0.00710 | 0.0184 |
| Average | 0.0925 | 0.154 | 0.0956 | 0.143 | 0.0948 | 0.139 |
| Stdev | 0.333 | 0.357 | 0.340 | 0.344 | 0.347 | 0.333 |

TABLE 26.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  | | | | | | | | | |
|---|---|---|---|---|---|---|---|---|---|
| p (t-test) | | 0.14 | | | 0.24 | | | 0.26 | |
| Min | 3.28E−9 | 3.28E−9 | | 3.28E−9 | 3.28E−9 | | 3.28E−9 | 3.28E−9 | |
| Max | 2.47 | 1.82 | | 2.47 | 1.82 | | 2.47 | 1.82 | |
| n (Patient) | 216 | 99 | | 207 | 108 | | 194 | 121 | |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.74 | 0.61 | 0.71 | 0.73 | 0.59 | 0.70 | 0.73 | 0.59 |
| SE | 0.028 | 0.028 | 0.035 | 0.029 | 0.028 | 0.034 | 0.029 | 0.028 | 0.033 |
| p Value | 5.1E−15 | 0 | 0.0024 | 1.1E−13 | 4.4E−16 | 0.0073 | 5.9E−12 | 0 | 0.0063 |
| nCohort Recovered | 134 | 140 | 216 | 125 | 138 | 207 | 114 | 135 | 194 |
| nCohort Non-recovered | 183 | 177 | 99 | 192 | 179 | 108 | 203 | 182 | 121 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 83% | 84% | 80% | 83% | 84% | 80% | 82% | 84% | 79% |
| Specificity | 35% | 36% | 27% | 37% | 36% | 28% | 38% | 37% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 64% | 66% | 65% | 62% | 65% | 61% | 61% | 65% | 60% |
| Specificity | 69% | 70% | 56% | 68% | 70% | 56% | 68% | 70% | 56% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 38% | 40% | 34% | 36% | 40% | 32% | 34% | 39% | 32% |
| Specificity | 93% | 94% | 79% | 92% | 93% | 79% | 91% | 93% | 79% |
| OR Quartile 2 | 2.55 | 3.05 | 1.48 | 2.81 | 2.94 | 1.49 | 2.81 | 3.10 | 1.48 |
| p Value | 4.3E−4 | 3.8E−5 | 0.18 | 1.1E−4 | 6.2E−5 | 0.17 | 1.1E−4 | 2.7E−5 | 0.15 |
| Lower limit of 95% CI | 1.51 | 1.79 | 0.836 | 1.66 | 1.73 | 0.849 | 1.67 | 1.83 | 0.863 |
| Upper limit of 95% CI | 4.29 | 5.18 | 2.64 | 4.73 | 4.98 | 2.60 | 4.74 | 5.27 | 2.54 |
| OR Quartile 3 | 4.12 | 4.55 | 2.37 | 3.46 | 4.31 | 1.96 | 3.33 | 4.49 | 1.85 |
| p Value | 5.7E−9 | 4.8E−10 | 5.8E−4 | 3.0E−7 | 1.7E−9 | 0.0053 | 1.2E−6 | 8.4E−10 | 0.0091 |
| Lower limit of 95% CI | 2.56 | 2.82 | 1.45 | 2.15 | 2.68 | 1.22 | 2.05 | 2.78 | 1.16 |
| Upper limit of 95% CI | 6.63 | 7.33 | 3.88 | 5.57 | 6.94 | 3.16 | 5.41 | 7.24 | 2.92 |
| OR Quartile 4 | 7.68 | 9.75 | 1.99 | 6.60 | 9.42 | 1.78 | 5.47 | 8.95 | 1.83 |
| p Value | 1.8E−8 | 1.6E−9 | 0.011 | 1.9E−7 | 2.7E−9 | 0.031 | 2.7E−6 | 6.1E−9 | 0.022 |
| Lower limit of 95% CI | 3.78 | 4.66 | 1.17 | 3.24 | 4.50 | 1.05 | 2.69 | 4.28 | 1.09 |
| Upper limit of 95% CI | 15.6 | 20.4 | 3.37 | 13.4 | 19.7 | 3.00 | 11.1 | 18.7 | 3.07 |

TABLE 26.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00615 | 0.0222 | 0.00601 | 0.0213 | 0.00601 | 0.0213 |
| Average | 0.0697 | 0.172 | 0.0707 | 0.168 | 0.0707 | 0.168 |
| Stdev | 0.294 | 0.392 | 0.297 | 0.388 | 0.297 | 0.388 |
| p (t-test) | | 0.0086 | | 0.012 | | 0.012 |
| Min | 3.28E−9 | 3.28E−9 | 3.28E−9 | 3.28E−9 | 3.28E−9 | 3.28E−9 |
| Max | 2.43 | 2.47 | 2.43 | 2.47 | 2.43 | 2.47 |
| n (Patient) | 188 | 129 | 185 | 132 | 185 | 132 |
| | sCr only | | | | | |
| Median | 0.00460 | 0.0298 | 0.00458 | 0.0284 | 0.00443 | 0.0284 |
| Average | 0.0332 | 0.191 | 0.0336 | 0.187 | 0.0338 | 0.186 |

TABLE 26.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Stdev | 0.161 | 0.443 | 0.163 | 0.439 | 0.163 | 0.438 |
| p (t-test) | | 3.2E−5 | | 4.9E−5 | | 5.7E−5 |
| Min | 3.28E−9 | 3.28E−9 | 3.28E−9 | 3.28E−9 | 3.28E−9 | 3.28E−9 |
| Max | 1.92 | 2.47 | 1.92 | 2.47 | 1.92 | 2.47 |
| n (Patient) | 160 | 157 | 157 | 160 | 156 | 161 |

UO only

| | | | | | | |
|---|---|---|---|---|---|---|
| Median | 0.00709 | 0.0213 | 0.00710 | 0.0207 | 0.00709 | 0.0209 |
| Average | 0.0861 | 0.164 | 0.0872 | 0.160 | 0.0868 | 0.159 |
| Stdev | 0.328 | 0.363 | 0.330 | 0.359 | 0.332 | 0.355 |
| p (t-test) | | 0.056 | | 0.074 | | 0.075 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 211 | 104 | 208 | 107 | 205 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.71 | 0.61 | 0.65 | 0.71 | 0.61 | 0.65 | 0.71 | 0.61 |
| SE | 0.032 | 0.029 | 0.034 | 0.032 | 0.029 | 0.034 | 0.032 | 0.029 | 0.034 |
| p Value | 2.6E−6 | 3.5E−13 | 9.2E−4 | 3.0E−6 | 3.9E−13 | 0.0021 | 3.0E−6 | 3.8E−13 | 0.0013 |
| nCohort Recovered | 188 | 160 | 211 | 185 | 157 | 208 | 185 | 156 | 205 |
| nCohort Non-recovered | 129 | 157 | 104 | 132 | 160 | 107 | 132 | 161 | 110 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 83% | 83% | 80% | 83% | 84% | 79% | 83% | 84% | 79% |
| Specificity | 30% | 33% | 27% | 31% | 34% | 27% | 31% | 34% | 27% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 67% | 68% | 65% | 66% | 68% | 64% | 66% | 68% | 64% |
| Specificity | 61% | 68% | 57% | 61% | 68% | 57% | 61% | 68% | 57% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 36% | 41% | 35% | 35% | 40% | 34% | 35% | 40% | 34% |
| Specificity | 82% | 90% | 80% | 82% | 90% | 79% | 82% | 90% | 80% |
| OR Quartile 2 | 2.12 | 2.50 | 1.50 | 2.23 | 2.63 | 1.46 | 2.23 | 2.67 | 1.42 |
| p Value | 0.0080 | 7.9E−4 | 0.16 | 0.0046 | 4.0E−4 | 0.19 | 0.0046 | 3.2E−4 | 0.21 |
| Lower limit of 95% CI | 1.22 | 1.46 | 0.851 | 1.28 | 1.54 | 0.834 | 1.28 | 1.57 | 0.818 |
| Upper limit of 95% CI | 3.68 | 4.26 | 2.64 | 3.87 | 4.48 | 2.55 | .3.87 | 4.56 | 2.47 |
| OR Quartile 3 | 3.15 | 4.44 | 2.54 | 3.03 | 4.57 | 2.29 | 3.03 | 4.44 | 2.33 |
| p Value | 1.6E−6 | 5.6E−10 | 1.8E−4 | 3.0E−6 | 2.9E−10 | 7.3E−4 | 3.0E−6 | 5.6E−10 | 5.2E−4 |
| Lower limit of 95% CI | 1.97 | 2.77 | 1.56 | 1.90 | 2.85 | 1.41 | 1.90 | 2.77 | 1.44 |
| Upper limit of 95% CI | 5.04 | 7.12 | 4.13 | 4.83 | 7.34 | 3.69 | 4.83 | 7.12 | 3.75 |
| OR Quartile 4 | 2.51 | 6.19 | 2.07 | 2.38 | 5.88 | 1.95 | 2.38 | 5.77 | 1.97 |
| p Value | 4.9E−4 | 3.8E−9 | 0.0066 | 0.0010 | 1.0E−8 | 0.013 | 0.0010 | 1.4E−8 | 0.011 |
| Lower limit of 95% CI | 1.50 | 3.38 | 1.22 | 1.42 | 3.20 | 1.15 | 1.42 | 3.15 | 1.17 |
| Upper limit of 95% CI | 4.21 | 11.4 | 3.50 | 3.98 | 10.8 | 3.28 | 3.98 | 10.6 | 3.31 |

Example 27. Use of C—C Motif Chemokine 23 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 23 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 27.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 0.00335 | 0.0207 | 0.00326 | 0.0192 | 0.00296 | 0.0192 |
| Average | 0.0505 | 0.143 | 0.0522 | 0.140 | 0.0531 | 0.138 |
| Stdev | 0.299 | 0.357 | 0.305 | 0.354 | 0.311 | 0.351 |
| p (t-test) | | 0.022 | | 0.031 | | 0.039 |
| Min | 6.85E−7 | 3.28E−9 | 6.85E−7 | 3.28E−9 | 6.85E−7 | 3.28E−9 |
| Max | 2.47 | 2.43 | 2.47 | 2.43 | 2.47 | 2.43 |
| n (Patient) | 108 | 209 | 104 | 213 | 100 | 217 |
| sCr only | | | | | | |
| Median | 0.00335 | 0.0249 | 0.00335 | 0.0235 | 0.00335 | 0.0231 |
| Average | 0.0443 | 0.156 | 0.0449 | 0.154 | 0.0456 | 0.153 |
| Stdev | 0.277 | 0.372 | 0.279 | 0.370 | 0.282 | 0.368 |
| p (t-test) | | 0.0042 | | 0.0052 | | 0.0063 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 126 | 190 | 124 | 192 | 122 | 194 |
| UO only | | | | | | |
| Median | 0.00809 | 0.0175 | 0.00780 | 0.0169 | 0.00744 | 0.0175 |
| Average | 0.0873 | 0.171 | 0.0900 | 0.155 | 0.0930 | 0.144 |
| Stdev | 0.327 | 0.370 | 0.337 | 0.348 | 0.345 | 0.335 |
| p (t-test) | | 0.048 | | 0.11 | | 0.20 |
| Min | 6.85E−7 | 3.28E−9 | 6.85E−7 | 3.28E−9 | 6.85E−7 | 3.28E−9 |
| Max | 2.47 | 1.82 | 2.47 | 1.82 | 2.47 | 1.82 |
| n (Patient) | 222 | 93 | 208 | 107 | 198 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.74 | 0.57 | 0.70 | 0.74 | 0.58 | 0.72 | 0.73 | 0.59 |
| SE | 0.029 | 0.027 | 0.036 | 0.029 | 0.028 | 0.034 | 0.029 | 0.028 | 0.034 |
| p Value | 9.9E−13 | 0 | 0.042 | 3.1E−12 | 0 | 0.021 | 1.4E−13 | 0 | 0.011 |
| nCohort Recovered | 108 | 126 | 222 | 104 | 124 | 208 | 100 | 122 | 198 |
| nCohort Non-recovered | 209 | 190 | 93 | 213 | 192 | 107 | 217 | 194 | 117 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 80% | 83% | 75% | 81% | 83% | 79% | 81% | 82% | 79% |
| Specificity | 35% | 37% | 25% | 37% | 37% | 27% | 38% | 37% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 62% | 66% | 58% | 61% | 65% | 57% | 60% | 64% | 57% |

TABLE 27.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| Specificity | 72% | 74% | 53% | 71% | 73% | 53% | 72% | 73% | 54% |
|---|---|---|---|---|---|---|---|---|---|
| Cutoff Quartile 4 | 0.0477 | 0.0468 | 0.0478 | 0.0477 | 0.0468 | 0.0478 | 0.0477 | 0.0468 | 0.0478 |
| Sensitivity | 36% | 38% | 39% | 35% | 38% | 38% | 35% | 38% | 38% |
| Specificity | 95% | 95% | 81% | 95% | 95% | 82% | 96% | 95% | 82% |
| OR Quartile 2 | 2.22 | 2.94 | 1.03 | 2.42 | 2.84 | 1.35 | 2.63 | 2.75 | 1.49 |
| p Value | 0.0027 | 5.6E−5 | 0.93 | 9.9E−4 | 9.0E−5 | 0.29 | 3.3E−4 | 1.4E−4 | 0.15 |
| Lower limit of 95% CI | 1.32 | 1.74 | 0.586 | 1.43 | 1.68 | 0.773 | 1.55 | 1.63 | 0.863 |
| Upper limit of 95% CI | 3.75 | 4.96 | 1.80 | 4.08 | 4.79 | 2.34 | 4.46 | 4.63 | 2.57 |
| OR Quartile 3 | 4.19 | 5.42 | 1.57 | 3.79 | 5.14 | 1.52 | 3.92 | 4.89 | 1.58 |
| p Value | 2.7E−8 | 2.8E−11 | 0.070 | 2.4E−7 | 1.0E−10 | 0.082 | 2.0E−7 | 3.6E−10 | 0.053 |
| Lower limit of 95% CI | 2.53 | 3.30 | 0.963 | 2.29 | 3.13 | 0.949 | 2.34 | 2.98 | 0.994 |
| Upper limit of 95% CI | 6.95 | 8.91 | 2.56 | 6.28 | 8.45 | 2.43 | 6.55 | 8.02 | 2.50 |
| OR Quartile 4 | 11.5 | 12.5 | 2.63 | 10.8 | 12.1 | 2.78 | 12.9 | 11.7 | 2.81 |
| p Value | 3.5E−7 | 1.3E−8 | 3.9E−4 | 7.5E−7 | 2.1E−8 | 1.4E−4 | 1.4E−6 | 3.2E−8 | 1.1E−4 |
| Lower limit of 95% CI | 4.50 | 5.23 | 1.54 | 4.20 | 5.05 | 1.64 | 4.58 | 4.88 | 1.66 |
| Upper limit of 95% CI | 29.5 | 29.8 | 4.48 | 27.6 | 28.8 | 4.70 | 36.5 | 27.9 | 4.73 |

TABLE 27.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00396 | 0.0222 | 0.00396 | 0.0220 | 0.00368 | 0.0217 |
| Average | 0.0487 | 0.158 | 0.0494 | 0.157 | 0.0503 | 0.153 |
| Stdev | 0.268 | 0.380 | 0.270 | 0.378 | 0.275 | 0.374 |
| p (t-test) | | 0.0045 | | 0.0055 | | 0.0081 |
| Min | 6.85E−7 | 3.28E−9 | 6.85E−7 | 3.28E−9 | 6.85E−7 | 3.28E−9 |
| Max | 2.47 | 2.43 | 2.47 | 2.43 | 2.47 | 2.43 |
| n (Patient) | 136 | 181 | 134 | 183 | 129 | 188 |
| | sCr only | | | | | |
| Median | 0.00420 | 0.0272 | 0.00413 | 0.0260 | 0.00413 | 0.0259 |
| Average | 0.0452 | 0.170 | 0.0455 | 0.169 | 0.0460 | 0.167 |
| Stdev | 0.257 | 0.392 | 0.257 | 0.391 | 0.259 | 0.389 |
| p (t-test) | | 0.0011 | | 0.0012 | | 0.0015 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 149 | 168 | 148 | 169 | 146 | 171 |
| | UO only | | | | | |
| Median | 0.00730 | 0.0220 | 0.00744 | 0.0215 | 0.00722 | 0.0209 |
| Average | 0.0877 | 0.173 | 0.0889 | 0.165 | 0.0927 | 0.149 |
| Stdev | 0.326 | 0.374 | 0.330 | 0.363 | 0.340 | 0.344 |
| p (t-test) | | 0.045 | | 0.069 | | 0.17 |
| Min | 6.85E−7 | 3.28E−9 | 6.85E−7 | 3.28E−9 | 6.85E−7 | 3.28E−9 |
| Max | 2.47 | 1.82 | 2.47 | 1.82 | 2.47 | 1.82 |
| n (Patient) | 226 | 89 | 220 | 95 | 207 | 108 |

TABLE 27.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.72 | 0.61 | 0.69 | 0.72 | 0.61 | 0.69 | 0.71 | 0.61 |
| SE | 0.029 | 0.028 | 0.036 | 0.029 | 0.028 | 0.035 | 0.029 | 0.029 | 0.034 |
| p Value | 1.5E−10 | 3.1E−14 | 0.0017 | 2.5E−10 | 3.3E−14 | 0.0019 | 3.4E−11 | 1.9E−13 | 0.0020 |
| nCohort Recovered | 136 | 149 | 226 | 134 | 148 | 220 | 129 | 146 | 207 |
| nCohort Non-recovered | 181 | 168 | 89 | 183 | 169 | 95 | 188 | 171 | 108 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 81% | 83% | 80% | 81% | 83% | 81% | 81% | 82% | 81% |
| Specificity | 32% | 34% | 27% | 33% | 34% | 28% | 34% | 34% | 29% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 63% | 67% | 64% | 62% | 66% | 62% | 62% | 65% | 60% |
| Specificity | 67% | 68% | 55% | 66% | 68% | 55% | 67% | 68% | 55% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 38% | 40% | 38% | 37% | 40% | 38% | 37% | 39% | 36% |
| Specificity | 91% | 91% | 80% | 91% | 91% | 80% | 91% | 91% | 81% |
| OR Quartile 2 | 2.00 | 2.42 | 1.46 | 2.07 | 2.46 | 1.64 | 2.26 | 2.37 | 1.75 |
| p Value | 0.0086 | 9.7E−4 | 0.21 | 0.0058 | 7.7E−4 | 0.10 | 0.0020 | 0.0012 | 0.054 |
| Lower limit of 95% CI | 1.19 | 1.43 | 0.804 | 1.23 | 1.46 | 0.908 | 1.35 | 1.41 | 0.990 |
| Upper limit of 95% CI | 3.34 | 4.09 | 2.64 | 3.46 | 4.16 | 2.97 | 3.80 | 4.00 | 3.11 |
| OR Quartile 3 | 3.44 | 4.34 | 2.20 | 3.27 | 4.22 | 2.00 | 3.22 | 4.00 | 1.85 |
| p Value | 2.2E−7 | 1.0E−9 | 0.0022 | 6.6E−7 | 2.0E−9 | 0.0057 | 1.0E−6 | 7.0E−9 | 0.011 |
| Lower limit of 95% CI | 2.16 | 2.71 | 1.33 | 2.05 | 2.64 | 1.22 | 2.01 | 2.50 | 1.15 |
| Upper limit of 95% CI | 5.49 | 6.95 | 3.66 | 5.21 | 6.76 | 3.28 | 5.15 | 6.39 | 2.97 |
| OR Quartile 4 | 6.22 | 6.94 | 2.49 | 6.01 | 6.82 | 2.51 | 6.22 | 6.59 | 2.36 |
| p Value | 7.0E−8 | 4.5E−9 | 9.1E−4 | 1.2E−7 | 6.1E−9 | 6.9E−4 | 1.7E−7 | 1.1E−8 | 0.0013 |
| Lower limit of 95% CI | 3.20 | 3.63 | 1.45 | 3.09 | 3.57 | 1.48 | 3.13 | 3.45 | 1.40 |
| Upper limit of 95% CI | 12.1 | 13.3 | 4.26 | 11.7 | 13.0 | 4.27 | 12.3 | 12.6 | 3.98 |

TABLE 27.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00427 | 0.0260 | 0.00427 | 0.0259 | 0.00396 | 0.0232 |
| Average | 0.0490 | 0.170 | 0.0496 | 0.168 | 0.0506 | 0.164 |
| Stdev | 0.255 | 0.397 | 0.257 | 0.395 | 0.260 | 0.391 |
| p (t-test) | | 0.0015 | | 0.0019 | | 0.0029 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 154 | 163 | 152 | 165 | 148 | 169 |
| | sCr only | | | | | |
| Median | 0.00427 | 0.0295 | 0.00427 | 0.0293 | 0.00427 | 0.0289 |
| Average | 0.0471 | 0.177 | 0.0473 | 0.176 | 0.0476 | 0.175 |
| Stdev | 0.250 | 0.404 | 0.251 | 0.403 | 0.251 | 0.402 |
| p (t-test) | | 6.0E−4 | | 6.8E−4 | | 7.9E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 161 | 156 | 160 | 157 | 159 | 158 |

TABLE 27.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | UO only | | | |
|---|---|---|---|---|---|---|
| Median | 0.00710 | 0.0222 | 0.00711 | 0.0221 | 0.00717 | 0.0212 |
| Average | 0.0895 | 0.167 | 0.0899 | 0.165 | 0.0934 | 0.150 |
| Stdev | 0.328 | 0.370 | 0.328 | 0.368 | 0.336 | 0.351 |
| p (t-test) | | 0.068 | | 0.075 | | 0.17 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 224 | 91 | 223 | 92 | 212 | 103 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.72 | 0.62 | 0.70 | 0.72 | 0.62 | 0.70 | 0.72 | 0.61 |
| SE | 0.029 | 0.029 | 0.036 | 0.029 | 0.029 | 0.036 | 0.029 | 0.029 | 0.035 |
| p Value | 7.9E−13 | 7.8E−15 | 4.9E−4 | 3.3E−12 | 8.7E−15 | 6.1E−4 | 2.7E−12 | 5.9E−14 | 0.0013 |
| nCohort Recovered | 154 | 161 | 224 | 152 | 160 | 223 | 148 | 159 | 212 |
| nCohort Non-recovered | 163 | 156 | 91 | 165 | 157 | 92 | 169 | 158 | 103 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 84% | 85% | 81% | 84% | 85% | 82% | 84% | 85% | 83% |
| Specificity | 34% | 35% | 28% | 34% | 35% | 28% | 35% | 35% | 29% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 65% | 67% | 67% | 64% | 67% | 66% | 63% | 66% | 62% |
| Specificity | 66% | 66% | 57% | 65% | 66% | 57% | 65% | 66% | 56% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 39% | 41% | 37% | 39% | 41% | 37% | 38% | 41% | 35% |
| Specificity | 90% | 90% | 80% | 89% | 90% | 80% | 89% | 90% | 80% |
| OR Quartile 2 | 2.77 | 3.08 | 1.67 | 2.66 | 3.14 | 1.70 | 2.85 | 2.95 | 1.91 |
| p Value | 1.9E−4 | 5.7E−5 | 0.097 | 3.1E−4 | 4.4E−5 | 0.085 | 1.2E−4 | 9.5E−5 | 0.032 |
| Lower limit of 95% CI | 1.62 | 1.78 | 0.912 | 1.56 | 1.81 | 0.930 | 1.67 | 1.71 | 1.06 |
| Upper limit of 95% CI | 4.72 | 5.34 | 3.04 | 4.52 | 5.43 | 3.10 | 4.85 | 5.09 | 3.44 |
| OR Quartile 3 | 3.54 | 4.08 | 2.66 | 3.36 | 3.96 | 2.56 | 3.19 | 3.85 | 2.06 |
| p Value | 8.4E−8 | 3.9E−9 | 1.7E−4 | 2.7E−7 | 7.3E−9 | 2.9E−4 | 8.0E−7 | 1.4E−8 | 0.0033 |
| Lower limit of 95% CI | 2.23 | 2.56 | 1.60 | 2.12 | 2.49 | 1.54 | 2.01 | 2.42 | 1.27 |
| Upper limit of 95% CI | 5.63 | 6.51 | 4.44 | 5.32 | 6.32 | 4.24 | 5.05 | 6.14 | 3.33 |
| OR Quartile 4 | 5.58 | 6.30 | 2.37 | 5.39 | 6.19 | 2.32 | 5.03 | 6.09 | 2.11 |
| p Value | 2.7E−8 | 2.7E−9 | 0.0016 | 5.0E−8 | 3.8E−9 | 0.0021 | 1.7E−7 | 5.4E−9 | 0.0053 |
| Lower limit of 95% CI | 3.04 | 3.44 | 1.39 | 2.94 | 3.38 | 1.36 | 2.75 | 3.32 | 1.25 |
| Upper limit of 95% CI | 10.2 | 11.6 | 4.06 | 9.87 | 11.4 | 3.96 | 9.21 | 11.2 | 3.57 |

TABLE 27.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 0.00443 | 0.0285 | 0.00428 | 0.0272 | 0.00427 | 0.0249 |
| Average | 0.0480 | 0.183 | 0.0488 | 0.179 | 0.0497 | 0.175 |
| Stdev | 0.245 | 0.412 | 0.248 | 0.409 | 0.251 | 0.405 |

TABLE 27.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 4.1E−4 | | 6.1E−4 | | 0.0010 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 168 | 149 | 165 | 152 | 161 | 156 | sCr only

| | | | | | | |
|---|---|---|---|---|---|---|
| Median | 0.00443 | 0.0336 | 0.00428 | 0.0317 | 0.00443 | 0.0298 |
| Average | 0.0468 | 0.188 | 0.0471 | 0.186 | 0.0473 | 0.185 |
| Stdev | 0.243 | 0.417 | 0.243 | 0.416 | 0.244 | 0.415 |
| p (t-test) | | 2.2E−4 | | 2.5E−4 | | 2.9E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 172 | 145 | 171 | 146 | 170 | 147 |

UO only

| | | | | | | |
|---|---|---|---|---|---|---|
| Median | 0.00711 | 0.0227 | 0.00710 | 0.0222 | 0.00710 | 0.0215 |
| Average | 0.0898 | 0.165 | 0.0902 | 0.164 | 0.0927 | 0.153 |
| Stdev | 0.328 | 0.368 | 0.329 | 0.366 | 0.335 | 0.354 |
| p (t-test) | | 0.074 | | 0.081 | | 0.15 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 223 | 92 | 222 | 93 | 214 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.71 | 0.72 | 0.62 | 0.70 | 0.72 | 0.62 | 0.70 | 0.72 | 0.62 |
| SE | 0.029 | 0.029 | 0.036 | 0.029 | 0.029 | 0.036 | 0.029 | 0.029 | 0.035 |
| p Value | 8.1E−13 | 1.0E−14 | 4.6E−4 | 3.6E−12 | 1.2E−14 | 4.9E−4 | 3.5E−12 | 8.0E−14 | 8.7E−4 |
| nCohort Recovered | 168 | 172 | 223 | 165 | 171 | 222 | 161 | 170 | 214 |
| nCohort Non-recovered | 149 | 145 | 92 | 152 | 146 | 93 | 156 | 147 | 101 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 85% | 86% | 82% | 84% | 86% | 82% | 85% | 86% | 82% |
| Specificity | 33% | 34% | 28% | 33% | 35% | 28% | 34% | 34% | 29% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 67% | 68% | 68% | 66% | 68% | 68% | 65% | 67% | 64% |
| Specificity | 65% | 65% | 57% | 64% | 65% | 57% | 64% | 65% | 57% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 41% | 43% | 37% | 40% | 42% | 37% | 39% | 42% | 35% |
| Specificity | 89% | 90% | 80% | 88% | 89% | 80% | 88% | 89% | 79% |
| OR Quartile 2 | 2.74 | 3.26 | 1.70 | 2.67 | 3.32 | 1.73 | 2.85 | 3.11 | 1.84 |
| p Value | 3.1E−4 | 4.4E−5 | 0.085 | 4.0E−4 | 3.4E−5 | 0.074 | 1.6E−4 | 7.3E−5 | 0.043 |
| Lower limit of 95% CI | 1.58 | 1.85 | 0.930 | 1.55 | 1.88 | 0.949 | 1.66 | 1.77 | 1.02 |
| Upper limit of 95% CI | 4.74 | 5.76 | 3.10 | 4.59 | 5.85 | 3.16 | 4.91 | 5.44 | 3.32 |
| OR Quartile 3 | 3.77 | 4.02 | 2.93 | 3.46 | 3.90 | 2.81 | 3.26 | 3.78 | 2.35 |
| p Value | 2.4E−8 | 6.5E−9 | 4.2E−5 | 1.5E−7 | 1.2E−8 | 7.2E−5 | 4.7E−7 | 2.3E−8 | 6.1E−4 |
| Lower limit of 95% CI | 2.37 | 2.51 | 1.75 | 2.18 | 2.44 | 1.69 | 2.06 | 2.37 | 1.44 |
| Upper limit of 95% CI | 6.01 | 6.43 | 4.89 | 5.49 | 6.22 | 4.67 | 5.16 | 6.03 | 3.83 |
| OR Quartile 4 | 5.44 | 6.39 | 2.32 | 5.15 | 6.27 | 2.27 | 4.80 | 6.16 | 2.05 |
| p Value | 9.7E−9 | 6.6E−10 | 0.0021 | 2.7E−8 | 9.5E−10 | 0.0027 | 9.8E−8 | 1.4E−9 | 0.0077 |
| Lower limit of 95% CI | 3.05 | 3.55 | 1.36 | 2.89 | 3.48 | 1.33 | 2.70 | 3.42 | 1.21 |
| Upper limit of 95% CI | 9.69 | 11.5 | 3.96 | 9.18 | 11.3 | 3.87 | 8.54 | 11.1 | 3.47 |

TABLE 27.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

|  | Recovery Period Duration (hr) | | | | | |
|---|---|---|---|---|---|---|
|  | 24 | | 48 | | 72 | |
|  | Recovered Cohort | Non-recovered Cohort | Recovered Cohort | Non-recovered Cohort | Recovered Cohort | Non-recovered Cohort |
|  | sCr or UO | | | | | |
| Median | 0.00638 | 0.0249 | 0.00638 | 0.0235 | 0.00651 | 0.0232 |
| Average | 0.0834 | 0.161 | 0.0842 | 0.158 | 0.0846 | 0.157 |
| Stdev | 0.333 | 0.350 | 0.334 | 0.348 | 0.335 | 0.347 |
| p (t-test) |  | 0.052 |  | 0.063 |  | 0.069 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 203 | 114 | 201 | 116 | 200 | 117 |
|  | sCr only | | | | | |
| Median | 0.00574 | 0.0344 | 0.00574 | 0.0344 | 0.00574 | 0.0344 |
| Average | 0.0509 | 0.196 | 0.0509 | 0.196 | 0.0509 | 0.196 |
| Stdev | 0.238 | 0.433 | 0.238 | 0.433 | 0.238 | 0.433 |
| p (t-test) |  | 1.7E−4 |  | 1.7E−4 |  | 1.7E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 185 | 132 | 185 | 132 | 185 | 132 |
|  | UO only | | | | | |
| Median | 0.00708 | 0.0235 | 0.00701 | 0.0232 | 0.00709 | 0.0222 |
| Average | 0.0838 | 0.174 | 0.0841 | 0.172 | 0.0849 | 0.169 |
| Stdev | 0.324 | 0.372 | 0.325 | 0.370 | 0.326 | 0.367 |
| p (t-test) |  | 0.029 |  | 0.033 |  | 0.041 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 217 | 98 | 216 | 99 | 214 | 101 |

|  | Recovery Period Duration (hr) | | | | | | | | |
|---|---|---|---|---|---|---|---|---|---|
|  | 24 | | | 48 | | | 72 | | |
|  | sCr or UO | sCr only | UO only | sCr or UO | sCr only | UO only | sCr or UO | sCr only | UO only |
| AUC | 0.65 | 0.71 | 0.64 | 0.64 | 0.71 | 0.64 | 0.64 | 0.71 | 0.63 |
| SE | 0.033 | 0.030 | 0.035 | 0.033 | 0.030 | 0.035 | 0.033 | 0.030 | 0.035 |
| p Value | 4.7E−6 | 7.9E−12 | 6.6E−5 | 1.1E−5 | 7.9E−12 | 7.0E−5 | 1.5E−5 | 7.9E−12 | 1.9E−4 |
| nCohort Recovered | 203 | 185 | 217 | 201 | 185 | 216 | 200 | 185 | 214 |
| nCohort Non-recovered | 114 | 132 | 98 | 116 | 132 | 99 | 117 | 132 | 101 |
| Cutoff Quartile 2 | 0.00202 | 0.00202 | 0.00207 | 0.00202 | 0.00202 | 0.00207 | 0.00202 | 0.00202 | 0.00207 |
| Sensitivity | 83% | 84% | 83% | 83% | 84% | 83% | 83% | 84% | 82% |
| Specificity | 30% | 31% | 29% | 29% | 31% | 29% | 30% | 31% | 29% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 69% | 71% | 69% | 68% | 71% | 69% | 68% | 71% | 67% |
| Specificity | 61% | 65% | 59% | 60% | 65% | 58% | 60% | 65% | 58% |
| Cutoff Quartile 4 | 0.0477 | 0.0477 | 0.0478 | 0.0477 | 0.0477 | 0.0478 | 0.0477 | 0.0477 | 0.0478 |
| Sensitivity | 37% | 42% | 37% | 36% | 42% | 36% | 36% | 42% | 36% |
| Specificity | 81% | 87% | 80% | 81% | 87% | 80% | 81% | 87% | 80% |
| OR Quartile 2 | 2.10 | 2.41 | 1.91 | 1.99 | 2.41 | 1.94 | 2.03 | 2.41 | 1.84 |
| p Value | 0.012 | 0.0021 | 0.035 | 0.017 | 0.0021 | 0.030 | 0.015 | 0.0021 | 0.043 |
| Lower limit of 95% CI | 1.18 | 1.38 | 1.05 | 1.13 | 1.38 | 1.07 | 1.15 | 1.38 | 1.02 |
| Upper limit of 95% CI | 3.74 | 4.23 | 3.47 | 3.52 | 4.23 | 3.54 | 3.59 | 4.23 | 3.32 |
| OR Quartile 3 | 3.47 | 4.57 | 3.20 | 3.23 | 4.57 | 3.07 | 3.12 | 4.57 | 2.84 |
| p Value | 5.7E−7 | 7.0E−10 | 7.1E−6 | 1.9E−6 | 7.0E−10 | 1.3E−5 | 3.3E−6 | 7.0E−10 | 3.8E−5 |
| Lower limit of 95% CI | 2.13 | 2.82 | 1.93 | 1.99 | 2.82 | 1.86 | 1.93 | 2.82 | 1.73 |
| Upper limit of 95% CI | 5.65 | 7.40 | 5.31 | 5.23 | 7.40 | 5.08 | 5.04 | 7.40 | 4.66 |

TABLE 27.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| OR Quartile 4 | 2.53 | 4.94 | 2.35 | 2.43 | 4.94 | 2.30 | 2.39 | 4.94 | 2.20 |
|---|---|---|---|---|---|---|---|---|---|
| p Value | 4.5E−4 | 1.3E−8 | 0.0016 | 7.6E−4 | 1.3E−8 | 0.0020 | 9.7E−4 | 1.3E−8 | 0.0033 |
| Lower limit of 95% CI | 1.51 | 2.85 | 1.38 | 1.45 | 2.85 | 1.36 | 1.42 | 2.85 | 1.30 |
| Upper limit of 95% CI | 4.26 | 8.57 | 3.99 | 4.09 | 8.57 | 3.90 | 4.00 | 8.57 | 3.73 |

Example 28. Use of C—C Motif Chemokine 23 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 23 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 28.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.00597 | 0.0390 | 0.00601 | 0.0499 | 0.00709 | 0.0479 |
| Average | 0.0619 | 0.201 | 0.0592 | 0.231 | 0.0780 | 0.208 |
| Stdev | 0.283 | 0.412 | 0.273 | 0.438 | 0.320 | 0.380 |
| p (t-test) | | 4.5E−4 | | 3.0E−5 | | 0.0029 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 1.82 |
| n (Patient) | 205 | 112 | 221 | 96 | 236 | 81 |
| sCr only | | | | | | |
| Median | 0.00599 | 0.0390 | 0.00630 | 0.0479 | 0.00694 | 0.0443 |
| Average | 0.0644 | 0.202 | 0.0621 | 0.230 | 0.0812 | 0.199 |
| Stdev | 0.284 | 0.417 | 0.274 | 0.444 | 0.323 | 0.379 |
| p (t-test) | | 6.2E−4 | | 5.8E−5 | | 0.0072 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 1.82 |
| n (Patient) | 208 | 108 | 223 | 93 | 235 | 81 |
| UO only | | | | | | |
| Median | 0.00870 | 0.0349 | 0.00864 | 0.0832 | 0.00859 | 0.0861 |
| Average | 0.0897 | 0.265 | 0.0887 | 0.286 | 0.0884 | 0.294 |
| Stdev | 0.311 | 0.484 | 0.309 | 0.497 | 0.309 | 0.502 |

TABLE 28.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.0023 | | | 9.0E−4 | | | 6.2E−4 | |
| Min | 3.28E−9 | 3.28E−9 | | 3.28E−9 | 3.28E−9 | | 3.28E−9 | 3.28E−9 | |
| Max | 2.47 | 1.82 | | 2.47 | 1.82 | | 2.47 | 1.82 | |
| n (Patient) | 275 | 40 | | 278 | 37 | | 279 | 36 | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.70 | 0.63 | 0.73 | 0.72 | 0.66 | 0.70 | 0.69 | 0.68 |
| SE | 0.032 | 0.032 | 0.050 | 0.032 | 0.033 | 0.051 | 0.036 | 0.036 | 0.051 |
| p Value | 9.9E−11 | 1.6E−10 | 0.011 | 6.3E−13 | 2.0E−11 | 0.0017 | 4.1E−8 | 1.1E−7 | 4.7E−4 |
| nCohort Non-persistent | 205 | 208 | 275 | 221 | 223 | 278 | 236 | 235 | 279 |
| nCohort Persistent | 112 | 108 | 40 | 96 | 93 | 37 | 81 | 81 | 36 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 84% | 85% | 78% | 86% | 87% | 81% | 84% | 86% | 83% |
| Specificity | 30% | 30% | 25% | 30% | 30% | 26% | 28% | 29% | 26% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 72% | 73% | 68% | 76% | 75% | 73% | 73% | 74% | 75% |
| Specificity | 62% | 62% | 52% | 61% | 61% | 53% | 58% | 58% | 53% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 47% | 47% | 48% | 52% | 51% | 51% | 51% | 48% | 53% |
| Specificity | 87% | 87% | 78% | 86% | 86% | 78% | 83% | 83% | 78% |
| OR Quartile 2 | 2.21 | 2.50 | 1.18 | 2.72 | 2.90 | 1.50 | 2.03 | 2.59 | 1.77 |
| p Value | 0.0080 | 0.0031 | 0.69 | 0.0026 | 0.0019 | 0.36 | 0.035 | 0.0073 | 0.22 |
| Lower limit of 95% CI | 1.23 | 1.36 | 0.534 | 1.42 | 1.48 | 0.630 | 1.05 | 1.29 | 0.709 |
| Upper limit of 95% CI | 3.98 | 4.59 | 2.59 | 5.22 | 5.67 | 3.56 | 3.92 | 5.19 | 4.43 |
| OR Quartile 3 | 4.25 | 4.45 | 2.28 | 4.98 | 4.67 | 3.03 | 3.65 | 3.99 | 3.39 |
| p Value | 1.5E−8 | 9.3E−9 | 0.021 | 6.0E−9 | 2.5E−8 | 0.0044 | 4.6E−6 | 1.3E−6 | 0.0025 |
| Lower limit of 95% CI | 2.58 | 2.67 | 1.13 | 2.90 | 2.71 | 1.41 | 2.10 | 2.28 | 1.54 |
| Upper limit of 95% CI | 7.02 | 7.40 | 4.61 | 8.56 | 8.03 | 6.50 | 6.34 | 7.00 | 7.47 |
| OR Quartile 4 | 5.92 | 5.75 | 3.24 | 6.92 | 6.10 | 3.84 | 5.18 | 4.53 | 4.08 |
| p Value | 2.2E−10 | 4.2E−10 | 7.4E−4 | 8.7E−12 | 1.4E−10 | 1.9E−4 | 6.3E−9 | 8.7E−8 | 1.1E−4 |
| Lower limit of 95% CI | 3.42 | 3.32 | 1.64 | 3.97 | 3.51 | 1.89 | 2.97 | 2.60 | 2.00 |
| Upper limit of 95% CI | 10.3 | 9.96 | 6.42 | 12.1 | 10.6 | 7.76 | 9.02 | 7.87 | 8.33 |

TABLE 28.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.00500 | 0.0347 | 0.00576 | 0.0465 | 0.00630 | 0.0472 |
| Average | 0.0512 | 0.196 | 0.0487 | 0.224 | 0.0681 | 0.207 |
| Stdev | 0.245 | 0.429 | 0.234 | 0.456 | 0.294 | 0.413 |

TABLE 28.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 1.6E−4 | | 8.6E−6 | | 7.0E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.34 |
| n (Patient) | 186 | 131 | 204 | 113 | 219 | 98 | sCr only

| | | | | | | |
|---|---|---|---|---|---|---|
| Median | 0.00576 | 0.0338 | 0.00578 | 0.0422 | 0.00615 | 0.0387 |
| Average | 0.0548 | 0.199 | 0.0526 | 0.222 | 0.0724 | 0.198 |
| Stdev | 0.244 | 0.439 | 0.236 | 0.461 | 0.297 | 0.412 |
| p (t-test) | | 2.1E−4 | | 2.2E−5 | | 0.0023 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.34 |
| n (Patient) | 192 | 124 | 206 | 110 | 218 | 98 |

UO only

| | | | | | | |
|---|---|---|---|---|---|---|
| Median | 0.00780 | 0.0298 | 0.00780 | 0.0355 | 0.00778 | 0.0410 |
| Average | 0.0894 | 0.210 | 0.0882 | 0.224 | 0.0879 | 0.228 |
| Stdev | 0.319 | 0.414 | 0.317 | 0.425 | 0.316 | 0.428 |
| p (t-test) | | 0.014 | | 0.0073 | | 0.0059 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 256 | 59 | 260 | 55 | 261 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.71 | 0.65 | 0.74 | 0.73 | 0.67 | 0.72 | 0.70 | 0.68 |
| SE | 0.030 | 0.031 | 0.042 | 0.030 | 0.031 | 0.043 | 0.033 | 0.033 | 0.043 |
| p Value | 2.1E−13 | 1.3E−11 | 4.3E−4 | 6.7E−16 | 8.0E−14 | 8.4E−5 | 2.1E−11 | 8.4E−10 | 2.3E−5 |
| nCohort Non-persistent | 186 | 192 | 256 | 204 | 206 | 260 | 219 | 218 | 261 |
| nCohort Persistent | 131 | 124 | 59 | 113 | 110 | 55 | 98 | 98 | 54 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 84% | 85% | 81% | 87% | 87% | 84% | 86% | 87% | 85% |
| Specificity | 31% | 31% | 27% | 31% | 32% | 27% | 30% | 30% | 27% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 72% | 72% | 71% | 76% | 75% | 75% | 74% | 74% | 76% |
| Specificity | 65% | 64% | 55% | 64% | 64% | 55% | 61% | 61% | 55% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 45% | 44% | 46% | 50% | 47% | 47% | 50% | 46% | 48% |
| Specificity | 89% | 87% | 80% | 88% | 87% | 80% | 86% | 84% | 80% |
| OR Quartile 2 | 2.37 | 2.51 | 1.58 | 2.99 | 3.16 | 1.88 | 2.53 | 2.84 | 2.15 |
| p Value | 0.0025 | 0.0017 | 0.21 | 5.3E−4 | 3.7E−4 | 0.10 | 0.0042 | 0.0017 | 0.061 |
| Lower limit of 95% CI | 1.36 | 1.41 | 0.775 | 1.61 | 1.68 | 0.876 | 1.34 | 1.48 | 0.967 |
| Upper limit of 95% CI | 4.16 | 4.47 | 3.22 | 5.54 | 5.95 | 4.05 | 4.78 | 5.45 | 4.78 |
| OR Quartile 3 | 4.73 | 4.53 | 2.98 | 5.72 | 5.37 | 3.58 | 4.52 | 4.57 | 3.88 |
| p Value | 3.5E−10 | 1.5E−9 | 5.0E−4 | 4.4E−11 | 2.2E−10 | 1.3E−4 | 2.3E−8 | 1.9E−8 | 7.2E−5 |
| Lower limit of 95% CI | 2.91 | 2.78 | 1.61 | 3.40 | 3.20 | 1.86 | 2.66 | 2.69 | 1.99 |
| Upper limit of 95% CI | 7.68 | 7.40 | 5.51 | 9.60 | 9.02 | 6.88 | 7.66 | 7.76 | 7.58 |
| OR Quartile 4 | 6.44 | 5.15 | 3.31 | 7.37 | 5.94 | 3.50 | 6.06 | 4.59 | 3.64 |
| p Value | 1.5E−10 | 5.2E−9 | 8.2E−5 | 3.7E−12 | 2.3E−10 | 5.5E−5 | 1.2E−10 | 3.1E−8 | 3.6E−5 |
| Lower limit of 95% CI | 3.64 | 2.97 | 1.82 | 4.19 | 3.43 | 1.90 | 3.50 | 2.68 | 1.97 |
| Upper limit of 95% CI | 11.4 | 8.93 | 6.01 | 12.9 | 10.3 | 6.44 | 10.5 | 7.89 | 6.73 |

TABLE 28.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

|  | Persistence Period Duration (hr) | | | | | |
|---|---|---|---|---|---|---|
|  | 24 | | 48 | | 72 | |
|  | Non-persistent Cohort | Persistent Cohort | Non-persistent Cohort | Persistent Cohort | Non-persistent Cohort | Persistent Cohort |
| sCr or UO | | | | | | |
| Median | 0.00463 | 0.0344 | 0.00466 | 0.0443 | 0.00597 | 0.0434 |
| Average | 0.0451 | 0.193 | 0.0427 | 0.214 | 0.0589 | 0.207 |
| Stdev | 0.240 | 0.421 | 0.230 | 0.440 | 0.280 | 0.415 |
| p (t-test) |  | 1.1E−4 |  | 9.0E−6 |  | 1.9E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.34 |
| n (Patient) | 175 | 142 | 190 | 127 | 205 | 112 |
| sCr only | | | | | | |
| Median | 0.00500 | 0.0344 | 0.00531 | 0.0425 | 0.00599 | 0.0387 |
| Average | 0.0479 | 0.198 | 0.0462 | 0.217 | 0.0622 | 0.206 |
| Stdev | 0.239 | 0.430 | 0.231 | 0.449 | 0.280 | 0.421 |
| p (t-test) |  | 9.9E−5 |  | 1.2E−5 |  | 3.3E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.34 |
| n (Patient) | 182 | 134 | 195 | 121 | 208 | 108 |
| UO only | | | | | | |
| Median | 0.00765 | 0.0238 | 0.00751 | 0.0272 | 0.00751 | 0.0272 |
| Average | 0.0863 | 0.203 | 0.0849 | 0.218 | 0.0849 | 0.218 |
| Stdev | 0.314 | 0.415 | 0.311 | 0.428 | 0.311 | 0.428 |
| p (t-test) |  | 0.012 |  | 0.0053 |  | 0.0053 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 246 | 69 | 251 | 64 | 251 | 64 |

|  | Persistence Period Duration (hr) | | | | | | | | |
|---|---|---|---|---|---|---|---|---|---|
|  | 24 | | | 48 | | | 72 | | |
|  | sCr or UO | sCr only | UO only | sCr or UO | sCr only | UO only | sCr or UO | sCr only | UO only |
| AUC | 0.73 | 0.72 | 0.63 | 0.75 | 0.75 | 0.66 | 0.72 | 0.71 | 0.66 |
| SE | 0.029 | 0.029 | 0.040 | 0.029 | 0.029 | 0.040 | 0.031 | 0.032 | 0.040 |
| p Value | 7.8E−15 | 2.9E−14 | 9.5E−4 | 0 | 0 | 9.0E−5 | 9.3E−13 | 1.4E−11 | 9.0E−5 |
| nCohort Non-persistent | 175 | 182 | 246 | 190 | 195 | 251 | 205 | 208 | 251 |
| nCohort Persistent | 142 | 134 | 69 | 127 | 121 | 64 | 112 | 108 | 64 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 84% | 85% | 81% | 87% | 88% | 84% | 86% | 87% | 84% |
| Specificity | 32% | 32% | 27% | 33% | 33% | 27% | 31% | 31% | 27% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 71% | 72% | 68% | 76% | 75% | 72% | 74% | 74% | 72% |
| Specificity | 67% | 66% | 55% | 67% | 66% | 55% | 63% | 62% | 55% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 44% | 44% | 42% | 48% | 47% | 44% | 47% | 45% | 44% |
| Specificity | 90% | 89% | 80% | 90% | 89% | 80% | 87% | 86% | 80% |
| OR Quartile 2 | 2.43 | 2.73 | 1.58 | 3.13 | 3.45 | 2.05 | 2.66 | 3.05 | 2.05 |
| p Value | 0.0015 | 5.1E−4 | 0.18 | 1.6E−4 | 8.5E−5 | 0.054 | 0.0016 | 5.6E−4 | 0.054 |
| Lower limit of 95% CI | 1.41 | 1.55 | 0.811 | 1.73 | 1.86 | 0.987 | 1.45 | 1.62 | 0.987 |
| Upper limit of 95% CI | 4.21 | 4.82 | 3.07 | 5.68 | 6.40 | 4.25 | 4.88 | 5.75 | 4.25 |
| OR Quartile 3 | 4.97 | 4.89 | 2.60 | 6.24 | 5.80 | 3.17 | 4.86 | 4.76 | 3.17 |
| p Value | 6.1E−11 | 1.4E−10 | 9.3E−4 | 1.2E−12 | 1.2E−11 | 1.6E−4 | 1.2E−9 | 2.6E−9 | 1.6E−4 |
| Lower limit of 95% CI | 3.07 | 3.01 | 1.48 | 3.77 | 3.49 | 1.74 | 2.92 | 2.85 | 1.74 |

TABLE 28.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 8.03 | 7.94 | 4.57 | 10.3 | 9.63 | 5.77 | 8.08 | 7.96 | 5.77 |
| OR Quartile 4 | 7.41 | 6.37 | 2.84 | 8.32 | 7.00 | 3.05 | 5.92 | 4.93 | 3.05 |
| p Value | 6.0E−11 | 3.0E−10 | 3.3E−4 | 1.7E−12 | 2.1E−11 | 1.7E−4 | 2.2E−10 | 7.8E−9 | 1.7E−4 |
| Lower limit of 95% CI | 4.07 | 3.58 | 1.61 | 4.62 | 3.96 | 1.70 | 3.42 | 2.87 | 1.70 |
| Upper limit of 95% CI | 13.5 | 11.3 | 5.03 | 15.0 | 12.4 | 5.46 | 10.3 | 8.47 | 5.46 |

TABLE 28.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.00463 | 0.0338 | 0.00470 | 0.0434 | 0.00578 | 0.0422 |
| Average | 0.0456 | 0.190 | 0.0429 | 0.212 | 0.0478 | 0.221 |
| Stdev | 0.241 | 0.418 | 0.231 | 0.439 | 0.227 | 0.458 |
| p (t-test) | | 1.5E−4 | | 1.1E−5 | | 9.8E−6 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 173 | 144 | 189 | 128 | 201 | 116 |
| | sCr only | | | | | |
| Median | 0.00552 | 0.0338 | 0.00552 | 0.0422 | 0.00599 | 0.0387 |
| Average | 0.0484 | 0.195 | 0.0462 | 0.212 | 0.0508 | 0.222 |
| Stdev | 0.240 | 0.428 | 0.233 | 0.444 | 0.228 | 0.465 |
| p (t-test) | | 1.4E−4 | | 1.9E−5 | | 1.6E−5 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 180 | 136 | 192 | 124 | 204 | 112 |
| | UO only | | | | | |
| Median | 0.00751 | 0.0235 | 0.00751 | 0.0272 | 0.00751 | 0.0272 |
| Average | 0.0865 | 0.192 | 0.0847 | 0.207 | 0.0847 | 0.207 |
| Stdev | 0.318 | 0.400 | 0.314 | 0.413 | 0.314 | 0.413 |
| p (t-test) | | 0.019 | | 0.0080 | | 0.0080 |
| Min | 3.28E−9 | 3.28E−9 | 3.28E−9 | 3.28E−9 | 3.28E−9 | 3.28E−9 |
| Max | 2.47 | 1.82 | 2.47 | 1.82 | 2.47 | 1.82 |
| n (Patient) | 239 | 76 | 245 | 70 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.72 | 0.63 | 0.75 | 0.74 | 0.66 | 0.72 | 0.71 | 0.66 |
| SE | 0.029 | 0.030 | 0.038 | 0.029 | 0.029 | 0.039 | 0.031 | 0.031 | 0.039 |
| p Value | 1.7E−14 | 3.4E−13 | 4.9E−4 | 0 | 2.2E−16 | 3.8E−5 | 2.7E−13 | 7.6E−12 | 3.8E−5 |
| nCohort Non-persistent | 173 | 180 | 239 | 189 | 192 | 245 | 201 | 204 | 245 |
| nCohort Persistent | 144 | 136 | 76 | 128 | 124 | 70 | 116 | 112 | 70 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 84% | 85% | 83% | 87% | 87% | 86% | 86% | 87% | 86% |
| Specificity | 32% | 32% | 28% | 33% | 33% | 28% | 31% | 31% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 70% | 71% | 67% | 75% | 74% | 71% | 74% | 73% | 71% |
| Specificity | 66% | 66% | 55% | 67% | 66% | 56% | 64% | 63% | 56% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 44% | 43% | 41% | 48% | 47% | 43% | 47% | 46% | 43% |

TABLE 28.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Specificity | 90% | 89% | 80% | 90% | 89% | 80% | 87% | 86% | 80% |
| OR Quartile 2 | 2.52 | 2.60 | 1.85 | 3.19 | 3.30 | 2.35 | 2.85 | 2.96 | 2.35 |
| p Value | 9.5E-4 | 8.2E-4 | 0.068 | 1.3E-4 | 1.1E-4 | 0.021 | 7.0E-4 | 6.0E-4 | 0.021 |
| Lower limit of 95% CI | 1.46 | 1.49 | 0.955 | 1.76 | 1.80 | 1.14 | 1.56 | 1.59 | 1.14 |
| Upper limit of 95% CI | 4.36 | 4.56 | 3.58 | 5.77 | 6.04 | 4.86 | 5.23 | 5.49 | 4.86 |
| OR Quartile 3 | 4.66 | 4.57 | 2.52 | 6.00 | 5.49 | 3.17 | 5.03 | 4.60 | 3.17 |
| p Value | 2.5E-10 | 5.6E-10 | 8.5E-4 | 2.5E-12 | 2.6E-11 | 8.8E-5 | 3.8E-10 | 3.2E-9 | 8.8E-5 |
| Lower limit of 95% CI | 2.89 | 2.83 | 1.46 | 3.63 | 3.33 | 1.78 | 3.03 | 2.78 | 1.78 |
| Upper limit of 95% CI | 7.50 | 7.38 | 4.33 | 9.91 | 9.05 | 5.65 | 8.33 | 7.63 | 5.65 |
| OR Quartile 4 | 7.14 | 6.13 | 2.74 | 8.15 | 7.16 | 3.00 | 5.86 | 5.26 | 3.00 |
| p Value | 1.3E-10 | 6.6E-10 | 3.8E-4 | 2.6E-12 | 1.9E-11 | 1.5E-4 | 3.0E-10 | 2.5E-9 | 1.5E-4 |
| Lower limit of 95% CI | 3.92 | 3.45 | 1.57 | 4.53 | 4.03 | 1.70 | 3.38 | 3.05 | 1.70 |
| Upper limit of 95% CI | 13.0 | 10.9 | 4.78 | 14.7 | 12.7 | 5.29 | 10.2 | 9.07 | 5.29 |

TABLE 28.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.00463 | 0.0317 | 0.00466 | 0.0384 | 0.00578 | 0.0369 |
| Average | 0.0464 | 0.185 | 0.0438 | 0.205 | 0.0485 | 0.214 |
| Stdev | 0.244 | 0.413 | 0.234 | 0.432 | 0.229 | 0.452 |
| p (t-test) | | 2.6E-4 | | 2.7E-5 | | 2.1E-5 |
| Min | 3.28E-9 | 3.28E-9 | 3.28E-9 | 3.28E-9 | 3.28E-9 | 3.28E-9 |
| Max | 2.47 | 2.43 | 2.47 | 2.43 | 2.47 | 2.43 |
| n (Patient) | 169 | 148 | 184 | 133 | 197 | 120 |
| sCr only | | | | | | |
| Median | 0.00552 | 0.0317 | 0.00552 | 0.0369 | 0.00599 | 0.0351 |
| Average | 0.0493 | 0.190 | 0.0469 | 0.206 | 0.0516 | 0.215 |
| Stdev | 0.243 | 0.423 | 0.235 | 0.438 | 0.231 | 0.458 |
| p (t-test) | | 2.5E-4 | | 3.8E-5 | | 3.5E-5 |
| Min | 3.28E-9 | 3.28E-9 | 3.28E-9 | 3.28E-9 | 3.28E-9 | 3.28E-9 |
| Max | 2.47 | 2.43 | 2.47 | 2.43 | 2.47 | 2.43 |
| n (Patient) | 176 | 140 | 188 | 128 | 200 | 116 |
| UO only | | | | | | |
| Median | 0.00717 | 0.0285 | 0.00722 | 0.0291 | 0.00722 | 0.0291 |
| Average | 0.0798 | 0.205 | 0.0791 | 0.212 | 0.0791 | 0.212 |
| Stdev | 0.312 | 0.402 | 0.311 | 0.409 | 0.311 | 0.409 |
| p (t-test) | | 0.0045 | | 0.0028 | | 0.0028 |
| Min | 3.28E-9 | 3.28E-9 | 3.28E-9 | 3.28E-9 | 3.28E-9 | 3.28E-9 |
| Max | 2.47 | 1.82 | 2.47 | 1.82 | 2.47 | 1.82 |
| n (Patient) | 234 | 81 | 237 | 78 | 237 | 78 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.72 | 0.71 | 0.66 | 0.74 | 0.73 | 0.66 | 0.72 | 0.70 | 0.66 |
| SE | 0.029 | 0.030 | 0.037 | 0.029 | 0.030 | 0.037 | 0.031 | 0.031 | 0.037 |
| p Value | 7.2E-14 | 2.8E-12 | 2.1E-5 | 0 | 4.7E-15 | 1.1E-5 | 2.3E-12 | 7.2E-11 | 1.1E-5 |

TABLE 28.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-persistent | 169 | 176 | 234 | 184 | 188 | 237 | 197 | 200 | 237 |
| nCohort Persistent | 148 | 140 | 81 | 133 | 128 | 78 | 120 | 116 | 78 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 84% | 84% | 84% | 86% | 86% | 85% | 86% | 85% | 85% |
| Specificity | 33% | 32% | 28% | 33% | 32% | 28% | 31% | 31% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 69% | 69% | 69% | 73% | 73% | 71% | 72% | 72% | 71% |
| Specificity | 66% | 65% | 56% | 66% | 65% | 57% | 63% | 62% | 57% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 43% | 42% | 42% | 46% | 45% | 42% | 45% | 44% | 42% |
| Specificity | 90% | 89% | 81% | 90% | 89% | 81% | 87% | 86% | 81% |
| OR Quartile 2 | 2.49 | 2.37 | 2.05 | 3.17 | 2.94 | 2.17 | 2.78 | 2.62 | 2.17 |
| p Value | 9.7E−4 | 0.0020 | 0.032 | 1.1E−4 | 3.0E−4 | 0.025 | 7.4E−4 | 0.0015 | 0.025 |
| Lower limit of 95% CI | 1.45 | 1.37 | 1.06 | 1.77 | 1.64 | 1.10 | 1.54 | 1.44 | 1.10 |
| Upper limit of 95% CI | 4.29 | 4.11 | 3.97 | 5.68 | 5.27 | 4.27 | 5.04 | 4.75 | 4.27 |
| OR Quartile 3 | 4.36 | 4.25 | 2.90 | 5.30 | 5.03 | 3.11 | 4.58 | 4.19 | 3.11 |
| p Value | 9.9E−10 | 2.3E−9 | 1.0E−4 | 2.4E−11 | 1.2E−10 | 5.3E−5 | 1.7E−9 | 1.4E−8 | 5.3E−5 |
| Lower limit of 95% CI | 2.72 | 2.65 | 1.69 | 3.25 | 3.08 | 1.79 | 2.79 | 2.56 | 1.79 |
| Upper limit of 95% CI | 6.99 | 6.84 | 4.96 | 8.65 | 8.22 | 5.39 | 7.51 | 6.87 | 5.39 |
| OR Quartile 4 | 6.63 | 5.68 | 3.04 | 7.36 | 6.59 | 3.04 | 5.38 | 4.82 | 3.04 |
| p Value | 5.6E−10 | 3.0E−9 | 7.1E−5 | 2.2E−11 | 1.0E−10 | 7.8E−5 | 1.7E−9 | 1.3E−8 | 7.8E−5 |
| Lower limit of 95% CI | 3.64 | 3.20 | 1.76 | 4.10 | 3.72 | 1.75 | 3.11 | 2.80 | 1.75 |
| Upper limit of 95% CI | 12.0 | 10.1 | 5.26 | 13.2 | 11.7 | 5.29 | 9.30 | 8.29 | 5.29 |

Example 29. Use of C—C Motif Chemokine 23 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 23 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 29.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.00330 | 0.0226 | 0.00434 | 0.0230 | 0.00458 | 0.0289 |
| Average | 0.0467 | 0.150 | 0.0475 | 0.175 | 0.0486 | 0.192 |
| Stdev | 0.285 | 0.365 | 0.250 | 0.402 | 0.239 | 0.426 |
| p (t-test) | | 0.0087 | | 8.3E−4 | | 1.7E−4 |

TABLE 29.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 6.85E-7 | 3.28E-9 | 6.85E-7 | 3.28E-9 | 3.28E-9 | 3.28E-9 |
| Max | 2.47 | 2.43 | 2.47 | 2.43 | 2.47 | 2.43 |
| n (Patient) | 119 | 198 | 158 | 159 | 179 | 138 | sCr only

| | | | | | | |
|---|---|---|---|---|---|---|
| Median | 0.00367 | 0.0249 | 0.00428 | 0.0259 | 0.00460 | 0.0351 |
| Average | 0.0479 | 0.156 | 0.0473 | 0.179 | 0.0487 | 0.199 |
| Stdev | 0.277 | 0.374 | 0.250 | 0.406 | 0.238 | 0.433 |
| p (t-test) | | 0.0055 | | 5.6E-4 | | 9.8E-5 |
| Min | 3.28E-9 | 3.28E-9 | 3.28E-9 | 3.28E-9 | 3.28E-9 | 3.28E-9 |
| Max | 2.47 | 2.43 | 2.47 | 2.43 | 2.47 | 2.43 |
| n (Patient) | 130 | 186 | 162 | 154 | 184 | 132 |

UO only

| | | | | | | |
|---|---|---|---|---|---|---|
| Median | 0.00834 | 0.0202 | 0.00834 | 0.0367 | 0.00834 | 0.0554 |
| Average | 0.0863 | 0.195 | 0.0833 | 0.236 | 0.0824 | 0.261 |
| Stdev | 0.317 | 0.404 | 0.308 | 0.442 | 0.304 | 0.464 |
| p (t-test) | | 0.016 | | 0.0018 | | 5.1E-4 |
| Min | 6.85E-7 | 3.28E-9 | 6.85E-7 | 3.28E-9 | 3.28E-9 | 3.28E-9 |
| Max | 2.47 | 1.82 | 2.47 | 1.82 | 2.47 | 1.82 |
| n (Patient) | 241 | 74 | 256 | 59 | 263 | 52 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.60 | 0.69 | 0.71 | 0.63 | 0.71 | 0.72 | 0.66 |
| SE | 0.028 | 0.028 | 0.039 | 0.030 | 0.029 | 0.042 | 0.030 | 0.030 | 0.044 |
| p Value | 4.4E-16 | 2.2E-16 | 0.0089 | 2.1E-10 | 1.2E-12 | 0.0019 | 2.9E-12 | 2.0E-13 | 2.9E-4 |
| nCohort Non-persistent | 119 | 130 | 241 | 158 | 162 | 256 | 179 | 184 | 263 |
| nCohort Persistent | 198 | 186 | 74 | 159 | 154 | 59 | 138 | 132 | 52 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 82% | 83% | 78% | 82% | 83% | 76% | 85% | 86% | 79% |
| Specificity | 36% | 36% | 26% | 32% | 33% | 25% | 32% | 33% | 26% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 64% | 66% | 61% | 65% | 67% | 66% | 67% | 69% | 69% |
| Specificity | 72% | 72% | 53% | 65% | 66% | 54% | 63% | 64% | 54% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 37% | 38% | 41% | 39% | 40% | 47% | 42% | 43% | 52% |
| Specificity | 95% | 94% | 80% | 89% | 90% | 80% | 88% | 88% | 80% |
| OR Quartile 2 | 2.55 | 2.73 | 1.28 | 2.08 | 2.39 | 1.09 | 2.67 | 2.88 | 1.30 |
| p Value | 4.3E-4 | 1.7E-4 | 0.43 | 0.0063 | 0.0014 | 0.79 | 5.9E-4 | 3.2E-4 | 0.48 |
| Lower limit of 95% CI | 1.51 | 1.62 | 0.688 | 1.23 | 1.40 | 0.564 | 1.53 | 1.62 | 0.632 |
| Upper limit of 95% CI | 4.28 | 4.60 | 2.39 | 3.50 | 4.08 | 2.12 | 4.68 | 5.12 | 2.67 |
| OR Quartile 3 | 4.56 | 4.98 | 1.76 | 3.35 | 3.93 | 2.24 | 3.54 | 3.88 | 2.60 |
| p Value | 1.9E-9 | 1.2E-10 | 0.037 | 2.7E-7 | 9.5E-9 | 0.0075 | 1.2E-7 | 2.3E-8 | 0.0033 |
| Lower limit of 95% CI | 2.78 | 3.05 | 1.03 | 2.11 | 2.46 | 1.24 | 2.22 | 2.41 | 1.38 |
| Upper limit of 95% CI | 7.48 | 8.12 | 2.99 | 5.31 | 6.27 | 4.06 | 5.65 | 6.24 | 4.92 |
| OR Quartile 4 | 11.2 | 9.42 | 2.67 | 4.97 | 5.75 | 3.63 | 5.17 | 5.60 | 4.38 |
| p Value | 5.0E-8 | 1.4E-8 | 5.9E-4 | 7.8E-8 | 9.3E-9 | 2.2E-5 | 8.7E-9 | 2.0E-9 | 3.3E-6 |
| Lower limit of 95% CI | 4.71 | 4.34 | 1.53 | 2.77 | 3.16 | 2.00 | 2.96 | 3.19 | 2.35 |
| Upper limit of 95% CI | 26.8 | 20.4 | 4.68 | 8.93 | 10.4 | 6.59 | 9.06 | 9.83 | 8.17 |

TABLE 29.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.00314 | 0.0220 | 0.00406 | 0.0249 | 0.00406 | 0.0317 |
| Average | 0.0484 | 0.146 | 0.0463 | 0.167 | 0.0462 | 0.182 |
| Stdev | 0.294 | 0.360 | 0.258 | 0.390 | 0.247 | 0.409 |
| p (t-test) | | 0.015 | | 0.0015 | | 3.6E−4 |
| Min | 6.85E−7 | 3.28E−9 | 6.85E−7 | 3.28E−9 | 3.28E−9 | 3.28E−9 |
| Max | 2.47 | 2.43 | 2.47 | 2.43 | 2.47 | 2.43 |
| n (Patient) | 112 | 205 | 147 | 170 | 165 | 152 |
| sCr only | | | | | | |
| Median | 0.00335 | 0.0249 | 0.00413 | 0.0272 | 0.00420 | 0.0341 |
| Average | 0.0485 | 0.153 | 0.0481 | 0.172 | 0.0484 | 0.184 |
| Stdev | 0.281 | 0.371 | 0.256 | 0.397 | 0.247 | 0.413 |
| p (t-test) | | 0.0074 | | 0.0012 | | 3.9E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 126 | 190 | 154 | 162 | 169 | 147 |
| UO only | | | | | | |
| Median | 0.00730 | 0.0215 | 0.00744 | 0.0285 | 0.00737 | 0.0326 |
| Average | 0.0880 | 0.169 | 0.0843 | 0.197 | 0.0833 | 0.212 |
| Stdev | 0.328 | 0.367 | 0.318 | 0.396 | 0.314 | 0.412 |
| p (t-test) | | 0.055 | | 0.011 | | 0.0053 |
| Min | 6.85E−7 | 3.28E−9 | 6.85E−7 | 3.28E−9 | 3.28E−9 | 3.28E−9 |
| Max | 2.47 | 1.82 | 2.47 | 1.82 | 2.47 | 1.82 |
| n (Patient) | 222 | 93 | 238 | 77 | 245 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.74 | 0.61 | 0.71 | 0.72 | 0.64 | 0.73 | 0.74 | 0.66 |
| SE | 0.028 | 0.027 | 0.036 | 0.029 | 0.028 | 0.038 | 0.028 | 0.028 | 0.039 |
| p Value | 2.2E−16 | 0 | 0.0013 | 2.4E−13 | 8.0E−15 | 1.9E−4 | 2.2E−16 | 0 | 2.7E−5 |
| nCohort Non-persistent | 112 | 126 | 222 | 147 | 154 | 238 | 165 | 169 | 245 |
| nCohort Persistent | 205 | 190 | 93 | 170 | 162 | 77 | 152 | 147 | 70 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 82% | 83% | 81% | 82% | 84% | 79% | 86% | 86% | 81% |
| Specificity | 38% | 37% | 27% | 33% | 34% | 26% | 35% | 35% | 27% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 63% | 65% | 63% | 66% | 67% | 69% | 68% | 69% | 71% |
| Specificity | 73% | 73% | 55% | 68% | 68% | 56% | 67% | 67% | 56% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 37% | 38% | 39% | 39% | 40% | 44% | 42% | 42% | 47% |
| Specificity | 96% | 94% | 81% | 90% | 90% | 81% | 90% | 90% | 81% |
| OR Quartile 2 | 2.72 | 2.94 | 1.58 | 2.33 | 2.74 | 1.37 | 3.12 | 3.41 | 1.62 |
| p Value | 1.7E−4 | 5.6E−5 | 0.13 | 0.0015 | 2.2E−4 | 0.32 | 5.8E−5 | 2.3E−5 | 0.16 |
| Lower limit of 95% CI | 1.62 | 1.74 | 0.873 | 1.38 | 1.61 | 0.737 | 1.79 | 1.93 | 0.831 |
| Upper limit of 95% CI | 4.59 | 4.96 | 2.86 | 3.93 | 4.69 | 2.55 | 5.43 | 6.01 | 3.14 |
| OR Quartile 3 | 4.64 | 5.08 | 2.16 | 4.11 | 4.41 | 2.80 | 4.33 | 4.57 | 3.17 |
| p Value | 2.6E−9 | 1.1E−10 | 0.0025 | 3.7E−9 | 7.3E−10 | 2.2E−4 | 1.0E−9 | 3.5E−10 | 8.8E−5 |
| Lower limit of 95% CI | 2.80 | 3.10 | 1.31 | 2.57 | 2.75 | 1.62 | 2.71 | 2.84 | 1.78 |

TABLE 29.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 7.69 | 8.33 | 3.55 | 6.57 | 7.06 | 4.83 | 6.94 | 7.35 | 5.65 |
| OR Quartile 4 | 12.3 | 10.4 | 2.63 | 6.03 | 6.05 | 3.39 | 6.77 | 6.52 | 3.86 |
| p Value | 1.6E−7 | 2.0E−8 | 3.9E−4 | 2.4E−8 | 1.2E−8 | 1.6E−5 | 6.9E−10 | 8.3E−10 | 3.2E−6 |
| Lower limit of 95% CI | 4.82 | 4.58 | 1.54 | 3.21 | 3.26 | 1.95 | 3.69 | 3.58 | 2.19 |
| Upper limit of 95% CI | 31.6 | 23.5 | 4.48 | 11.3 | 11.2 | 5.91 | 12.4 | 11.9 | 6.81 |

TABLE 29.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 0.00321 | 0.0217 | 0.00424 | 0.0232 | 0.00424 | 0.0285 |
| Average | 0.0488 | 0.145 | 0.0472 | 0.164 | 0.0478 | 0.174 |
| Stdev | 0.295 | 0.359 | 0.261 | 0.388 | 0.252 | 0.401 |
| p (t-test) | | 0.016 | | 0.0022 | | 8.8E−4 |
| Min | 6.85E−7 | 3.28E−9 | 6.85E−7 | 3.28E−9 | 3.28E−9 | 3.28E−9 |
| Max | 2.47 | 2.43 | 2.47 | 2.43 | 2.47 | 2.43 |
| n (Patient) | 111 | 206 | 144 | 173 | 158 | 159 |
| sCr only | | | | | | |
| Median | 0.00352 | 0.0235 | 0.00427 | 0.0259 | 0.00427 | 0.0293 |
| Average | 0.0493 | 0.152 | 0.0490 | 0.169 | 0.0500 | 0.177 |
| Stdev | 0.283 | 0.369 | 0.259 | 0.394 | 0.252 | 0.407 |
| p (t-test) | | 0.0091 | | 0.0018 | | 8.9E−4 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 124 | 192 | 151 | 165 | 163 | 153 |
| UO only | | | | | | |
| Median | 0.00717 | 0.0212 | 0.00722 | 0.0235 | 0.00717 | 0.0260 |
| Average | 0.0910 | 0.155 | 0.0880 | 0.172 | 0.0869 | 0.182 |
| Stdev | 0.336 | 0.351 | 0.327 | 0.371 | 0.322 | 0.384 |
| p (t-test) | | 0.12 | | 0.050 | | 0.029 |
| Min | 6.85E−7 | 3.28E−9 | 6.85E−7 | 3.28E−9 | 3.28E−9 | 3.28E−9 |
| Max | 2.47 | 1.82 | 2.47 | 1.82 | 2.47 | 1.82 |
| n (Patient) | 212 | 103 | 225 | 90 | 232 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.61 | 0.70 | 0.71 | 0.62 | 0.72 | 0.72 | 0.64 |
| SE | 0.028 | 0.028 | 0.035 | 0.029 | 0.029 | 0.036 | 0.028 | 0.029 | 0.037 |
| p Value | 6.7E−16 | 2.2E−16 | 0.0019 | 3.1E−12 | 4.3E−13 | 5.8E−4 | 8.4E−15 | 3.6E−14 | 1.3E−4 |
| nCohort Non-persistent | 111 | 124 | 212 | 144 | 151 | 225 | 158 | 163 | 232 |
| nCohort Persistent | 206 | 192 | 103 | 173 | 165 | 90 | 159 | 153 | 83 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 82% | 83% | 81% | 82% | 83% | 80% | 85% | 85% | 82% |
| Specificity | 38% | 37% | 28% | 33% | 34% | 27% | 35% | 34% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 63% | 65% | 63% | 65% | 66% | 67% | 67% | 67% | 69% |
| Specificity | 73% | 73% | 56% | 67% | 68% | 56% | 66% | 66% | 56% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 36% | 38% | 37% | 38% | 39% | 40% | 40% | 41% | 42% |

TABLE 29.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Specificity | 95% | 94% | 81% | 90% | 90% | 81% | 90% | 90% | 81% |
| OR Quartile 2 | 2.78 | 2.84 | 1.60 | 2.29 | 2.50 | 1.49 | 3.00 | 2.96 | 1.73 |
| p Value | 1.3E−4 | 9.0E−5 | 0.11 | 0.0018 | 6.9E−4 | 0.19 | 7.4E−5 | 1.1E−4 | 0.089 |
| Lower limit of 95% CI | 1.65 | 1.68 | 0.902 | 1.36 | 1.47 | 0.821 | 1.74 | 1.71 | 0.921 |
| Upper limit of 95% CI | 4.69 | 4.79 | 2.84 | 3.85 | 4.23 | 2.70 | 5.17 | 5.12 | 3.24 |
| OR Quartile 3 | 4.52 | 4.83 | 2.19 | 3.79 | 4.05 | 2.59 | 3.96 | 4.05 | 2.84 |
| p Value | 4.7E−9 | 3.9E−10 | 0.0015 | 2.3E−8 | 5.0E−9 | 2.6E−4 | 7.4E−9 | 5.0E−9 | 1.2E−4 |
| Lower limit of 95% CI | 2.73 | 2.95 | 1.35 | 2.37 | 2.54 | 1.55 | 2.48 | 2.53 | 1.67 |
| Upper limit of 95% CI | 7.50 | 7.90 | 3.55 | 6.05 | 6.48 | 4.32 | 6.32 | 6.46 | 4.84 |
| OR Quartile 4 | 12.1 | 10.0 | 2.44 | 5.73 | 5.75 | 2.82 | 5.98 | 5.85 | 3.12 |
| p Value | 2.0E−7 | 3.2E−8 | 8.9E−4 | 5.9E−8 | 3.0E−8 | 1.5E−4 | 7.4E−9 | 6.6E−9 | 4.4E−5 |
| Lower limit of 95% CI | 4.74 | 4.43 | 1.44 | 3.05 | 3.10 | 1.65 | 3.26 | 3.22 | 1.81 |
| Upper limit of 95% CI | 31.1 | 22.7 | 4.12 | 10.8 | 10.7 | 4.83 | 11.0 | 10.6 | 5.38 |

TABLE 29.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.00314 | 0.0215 | 0.00420 | 0.0231 | 0.00424 | 0.0284 |
| Average | 0.0492 | 0.144 | 0.0475 | 0.164 | 0.0484 | 0.172 |
| Stdev | 0.296 | 0.358 | 0.262 | 0.387 | 0.254 | 0.399 |
| p (t-test) | | 0.018 | | 0.0024 | | 0.0011 |
| Min | 6.85E−7 | 3.28E−9 | 6.85E−7 | 3.28E−9 | 3.28E−9 | 3.28E−9 |
| Max | 2.47 | 2.43 | 2.47 | 2.43 | 2.47 | 2.43 |
| n (Patient) | 110 | 207 | 143 | 174 | 156 | 161 |
| | sCr only | | | | | |
| Median | 0.00352 | 0.0235 | 0.00424 | 0.0249 | 0.00427 | 0.0289 |
| Average | 0.0493 | 0.152 | 0.0493 | 0.168 | 0.0503 | 0.176 |
| Stdev | 0.283 | 0.369 | 0.259 | 0.393 | 0.253 | 0.405 |
| p (t-test) | | 0.0091 | | 0.0020 | | 0.0010 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 124 | 192 | 150 | 166 | 162 | 154 |
| | UO only | | | | | |
| Median | 0.00710 | 0.0207 | 0.00717 | 0.0222 | 0.00717 | 0.0232 |
| Average | 0.0925 | 0.150 | 0.0897 | 0.163 | 0.0888 | 0.170 |
| Stdev | 0.339 | 0.345 | 0.330 | 0.363 | 0.326 | 0.373 |
| p (t-test) | | 0.16 | | 0.079 | | 0.056 |
| Min | 6.85E−7 | 3.28E−9 | 6.85E−7 | 3.28E−9 | 3.28E−9 | 3.28E−9 |
| Max | 2.47 | 1.82 | 2.47 | 1.82 | 2.47 | 1.82 |
| n (Patient) | 208 | 107 | 220 | 95 | 226 | 89 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.73 | 0.61 | 0.70 | 0.71 | 0.62 | 0.71 | 0.72 | 0.63 |
| SE | 0.028 | 0.028 | 0.034 | 0.029 | 0.029 | 0.035 | 0.029 | 0.029 | 0.036 |

TABLE 29.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 6.7E−16 | 2.2E−16 | 0.0020 | 4.7E−12 | 6.7E−13 | 6.9E−4 | 7.8E−14 | 6.0E−14 | 3.6E−4 |
| nCohort Non-persistent | 110 | 124 | 208 | 143 | 150 | 220 | 156 | 162 | 226 |
| nCohort Persistent | 207 | 192 | 107 | 174 | 166 | 95 | 161 | 154 | 89 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 82% | 83% | 81% | 82% | 83% | 81% | 84% | 85% | 82% |
| Specificity | 38% | 37% | 28% | 34% | 34% | 28% | 35% | 35% | 28% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 62% | 65% | 63% | 64% | 66% | 66% | 66% | 67% | 67% |
| Specificity | 73% | 73% | 56% | 67% | 67% | 57% | 66% | 66% | 57% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 36% | 38% | 36% | 38% | 39% | 38% | 40% | 40% | 39% |
| Specificity | 95% | 94% | 80% | 90% | 90% | 80% | 90% | 90% | 81% |
| OR Quartile 2 | 2.84 | 2.84 | 1.72 | 2.33 | 2.54 | 1.64 | 2.88 | 3.01 | 1.76 |
| p Value | 9.5E−5 | 9.0E−5 | 0.062 | 0.0015 | 5.5E−4 | 0.10 | 1.2E−4 | 8.3E−5 | 0.070 |
| Lower limit of 95% CI | 1.68 | 1.68 | 0.972 | 1.38 | 1.50 | 0.908 | 1.68 | 1.74 | 0.954 |
| Upper limit of 95% CI | 4.79 | 4.79 | 3.05 | 3.92 | 4.31 | 2.97 | 4.94 | 5.21 | 3.26 |
| OR Quartile 3 | 4.41 | 4.83 | 2.15 | 3.69 | 3.94 | 2.59 | 3.75 | 3.93 | 2.70 |
| p Value | 8.5E−9 | 3.9E−10 | 0.0017 | 4.2E−8 | 9.3E−9 | 2.0E−4 | 2.5E−8 | 9.5E−9 | 1.6E−4 |
| Lower limit of 95% CI | 2.66 | 2.95 | 1.34 | 2.31 | 2.47 | 1.57 | 2.35 | 2.46 | 1.61 |
| Upper limit of 95% CI | 7.31 | 7.90 | 3.47 | 5.89 | 6.29 | 4.28 | 5.96 | 6.27 | 4.52 |
| OR Quartile 4 | 11.9 | 10.0 | 2.24 | 5.63 | 5.65 | 2.51 | 5.77 | 5.75 | 2.68 |
| p Value | 2.4E−7 | 3.2E−8 | 0.0025 | 7.9E−8 | 4.1E−8 | 6.9E−4 | 1.4E−8 | 9.3E−9 | 3.3E−4 |
| Lower limit of 95% CI | 4.66 | 4.43 | 1.33 | 3.00 | 3.04 | 1.48 | 3.15 | 3.16 | 1.57 |
| Upper limit of 95% CI | 30.6 | 22.7 | 3.78 | 10.6 | 10.5 | 4.27 | 10.6 | 10.4 | 4.59 |

TABLE 29.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 0.00294 | 0.0212 | 0.00396 | 0.0222 | 0.00413 | 0.0259 |
| Average | 0.0503 | 0.142 | 0.0487 | 0.159 | 0.0498 | 0.166 |
| Stdev | 0.302 | 0.355 | 0.267 | 0.382 | 0.259 | 0.393 |
| p (t-test) | | 0.024 | | 0.0039 | | 0.0022 |
| Min | 6.85E−7 | 3.28E−9 | 6.85E−7 | 3.28E−9 | 3.28E−9 | 3.28E−9 |
| Max | 2.47 | 2.43 | 2.47 | 2.43 | 2.47 | 2.43 |
| n (Patient) | 106 | 211 | 138 | 179 | 150 | 167 |
| | sCr only | | | | | |
| Median | 0.00330 | 0.0232 | 0.00396 | 0.0249 | 0.00413 | 0.0289 |
| Average | 0.0499 | 0.150 | 0.0498 | 0.164 | 0.0508 | 0.172 |
| Stdev | 0.287 | 0.366 | 0.263 | 0.389 | 0.256 | 0.401 |
| p (t-test) | | 0.011 | | 0.0028 | | 0.0015 |
| Min | 3.28E−9 | 3.28E−9 | 3.28E−9 | 3.28E−9 | 3.28E−9 | 3.28E−9 |
| Max | 2.47 | 2.43 | 2.47 | 2.43 | 2.47 | 2.43 |
| n (Patient) | 121 | 195 | 146 | 170 | 158 | 158 |

TABLE 29.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 0.00675 | 0.0215 | 0.00709 | 0.0232 | 0.00708 | 0.0249 |
| Average | 0.0858 | 0.158 | 0.0841 | 0.169 | 0.0836 | 0.175 |
| Stdev | 0.335 | 0.350 | 0.327 | 0.364 | 0.324 | 0.372 |
| p (t-test) | | 0.070 | | 0.038 | | 0.028 |
| Min | 6.85E−7 | 3.28E−9 | 6.85E−7 | 3.28E−9 | 3.28E−9 | 3.28E−9 |
| Max | 2.47 | 1.82 | 2.47 | 1.82 | 2.47 | 1.82 |
| n (Patient) | 202 | 113 | 212 | 103 | 217 | 98 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.73 | 0.74 | 0.63 | 0.70 | 0.72 | 0.63 | 0.71 | 0.72 | 0.64 |
| SE | 0.028 | 0.028 | 0.033 | 0.029 | 0.028 | 0.034 | 0.029 | 0.028 | 0.035 |
| p Value | 0 | 0 | 1.5E−4 | 2.8E−12 | 3.9E−14 | 1.1E−4 | 2.3E−13 | 3.6E−15 | 3.8E−5 |
| nCohort Non-persistent | 106 | 121 | 202 | 138 | 146 | 212 | 150 | 158 | 217 |
| nCohort Persistent | 211 | 195 | 113 | 179 | 170 | 103 | 167 | 158 | 98 |
| Cutoff Quartile 2 | 0.00202 | 0.00200 | 0.00207 | 0.00202 | 0.00200 | 0.00207 | 0.00202 | 0.00200 | 0.00207 |
| Sensitivity | 82% | 83% | 82% | 83% | 84% | 82% | 84% | 85% | 83% |
| Specificity | 40% | 38% | 29% | 35% | 35% | 28% | 35% | 35% | 29% |
| Cutoff Quartile 3 | 0.0104 | 0.0104 | 0.0104 | 0.0104 | 0.0104 | 0.0104 | 0.0104 | 0.0104 | 0.0104 |
| Sensitivity | 63% | 65% | 65% | 64% | 66% | 67% | 65% | 68% | 68% |
| Specificity | 75% | 74% | 58% | 68% | 69% | 58% | 67% | 68% | 58% |
| Cutoff Quartile 4 | 0.0477 | 0.0468 | 0.0478 | 0.0477 | 0.0468 | 0.0478 | 0.0477 | 0.0468 | 0.0478 |
| Sensitivity | 36% | 37% | 35% | 37% | 38% | 37% | 38% | 39% | 38% |
| Specificity | 95% | 94% | 81% | 90% | 90% | 81% | 89% | 89% | 81% |
| OR Quartile 2 | 3.09 | 3.01 | 1.92 | 2.55 | 2.72 | 1.75 | 2.96 | 3.22 | 1.91 |
| p Value | 2.7E−5 | 3.8E−5 | 0.025 | 4.5E−4 | 2.1E−4 | 0.060 | 7.1E−5 | 3.0E−5 | 0.035 |
| Lower limit of 95% CI | 1.82 | 1.78 | 1.08 | 1.51 | 1.60 | 0.976 | 1.73 | 1.86 | 1.05 |
| Upper limit of 95% CI | 5.23 | 5.09 | 3.39 | 4.29 | 4.62 | 3.12 | 5.06 | 5.58 | 3.47 |
| OR Quartile 3 | 4.89 | 5.42 | 2.51 | 3.84 | 4.45 | 2.80 | 3.76 | 4.40 | 2.99 |
| p Value | 2.0E−9 | 4.6E−11 | 1.5E−4 | 2.1E−8 | 6.8E−10 | 4.1E−5 | 2.5E−8 | 7.3E−10 | 2.0E−5 |
| Lower limit of 95% CI | 2.91 | 3.28 | 1.56 | 2.40 | 2.77 | 1.71 | 2.36 | 2.75 | 1.81 |
| Upper limit of 95% CI | 8.21 | 8.97 | 4.04 | 6.15 | 7.15 | 4.59 | 5.99 | 7.05 | 4.95 |
| OR Quartile 4 | 11.1 | 9.53 | 2.29 | 5.17 | 5.27 | 2.44 | 5.20 | 5.36 | 2.53 |
| p Value | 5.2E−7 | 6.3E−8 | 0.0018 | 3.2E−7 | 1.3E−7 | 8.9E−4 | 9.1E−8 | 3.4E−8 | 6.0E−4 |
| Lower limit of 95% CI | 4.35 | 4.21 | 1.36 | 2.75 | 2.84 | 1.44 | 2.84 | 2.95 | 1.49 |
| Upper limit of 95% CI | 28.6 | 21.6 | 3.85 | 9.72 | 9.78 | 4.12 | 9.53 | 9.72 | 4.29 |

Example 30. Use of C—C Motif Chemokine 24 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 24 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) where the recovery period can start from the time of sample collection to 24, 48, 72, 96 or 168 hours after sample collection. "Non-recovered" indicates those patients whose maximum RIFLE stage during a period of 24, 48 or 72 hours is risk of injury (R), injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 30.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 9.06 | 33.1 | 10.0 | 32.0 | 11.0 | 31.8 |
| Average | 45.2 | 80.7 | 42.4 | 79.7 | 44.4 | 78.8 |
| Stdev | 111 | 153 | 104 | 152 | 110 | 151 |
| p (t-test) | | 0.098 | | 0.11 | | 0.16 |
| Min | 0.00127 | 0.00127 | 0.00127 | 0.00127 | 0.00127 | 0.00127 |
| Max | 670 | 1150 | 670 | 1150 | 670 | 1150 |
| n (Patient) | 57 | 259 | 46 | 270 | 41 | 275 |
| | sCr only | | | | | |
| Median | 11.9 | 35.0 | 11.5 | 36.2 | 10.0 | 37.4 |
| Average | 54.4 | 79.7 | 54.2 | 79.5 | 52.8 | 79.5 |
| Stdev | 147 | 146 | 149 | 145 | 152 | 144 |
| p (t-test) | | 0.19 | | 0.19 | | 0.18 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 76 | 239 | 74 | 241 | 70 | 245 |
| | UO only | | | | | |
| Median | 19.3 | 47.2 | 18.3 | 43.7 | 18.4 | 40.8 |
| Average | 52.4 | 109 | 49.3 | 104 | 44.3 | 103 |
| Stdev | 115 | 182 | 113 | 175 | 79.7 | 186 |
| p (t-test) | | 8.4E−4 | | 8.6E−4 | | 3.2E−4 |
| Min | 0.00127 | 0.00127 | 0.00127 | 0.00127 | 0.00127 | 0.00127 |
| Max | 1140 | 1150 | 1140 | 1150 | 670 | 1150 |
| n (Patient) | 193 | 121 | 172 | 142 | 155 | 159 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.62 | 0.66 | 0.64 | 0.63 | 0.66 | 0.63 | 0.65 | 0.64 |
| SE | 0.037 | 0.035 | 0.032 | 0.041 | 0.035 | 0.031 | 0.043 | 0.035 | 0.031 |
| p Value | 8.8E−5 | 4.2E−4 | 3.1E−7 | 8.5E−4 | 1.5E−4 | 1.3E−7 | 0.0027 | 1.7E−5 | 8.6E−6 |
| nCohort Recovered | 57 | 76 | 193 | 46 | 74 | 172 | 41 | 70 | 155 |
| nCohort Non-recovered | 259 | 239 | 121 | 270 | 241 | 142 | 275 | 245 | 159 |
| Cutoff Quartile 2 | 4.17 | 4.15 | 4.13 | 4.17 | 4.15 | 4.13 | 4.17 | 4.15 | 4.13 |
| Sensitivity | 78% | 79% | 87% | 77% | 79% | 85% | 77% | 79% | 82% |
| Specificity | 40% | 37% | 33% | 39% | 38% | 34% | 39% | 40% | 33% |
| Cutoff Quartile 3 | 29.6 | 29.3 | 28.8 | 29.6 | 29.3 | 28.8 | 29.6 | 29.3 | 28.8 |
| Sensitivity | 54% | 55% | 65% | 53% | 56% | 63% | 53% | 56% | 60% |
| Specificity | 68% | 66% | 60% | 67% | 68% | 61% | 68% | 70% | 61% |
| Cutoff Quartile 4 | 74.9 | 74.4 | 74.6 | 74.9 | 74.4 | 74.6 | 74.9 | 74.4 | 74.6 |
| Sensitivity | 28% | 28% | 39% | 27% | 28% | 36% | 27% | 28% | 35% |
| Specificity | 88% | 84% | 83% | 87% | 85% | 84% | 85% | 86% | 85% |
| OR Quartile 2 | 2.45 | 2.15 | 3.18 | 2.20 | 2.27 | 2.93 | 2.15 | 2.54 | 2.29 |
| p Value | 0.0037 | 0.0073 | 1.8E−4 | 0.019 | 0.0043 | 1.7E−4 | 0.029 | 0.0013 | 0.0021 |
| Lower limit of 95% CI | 1.34 | 1.23 | 1.73 | 1.14 | 1.29 | 1.67 | 1.08 | 1.44 | 1.35 |
| Upper limit of 95% CI | 4.50 | 3.76 | 5.83 | 4.25 | 3.98 | 5.14 | 4.28 | 4.48 | 3.89 |
| OR Quartile 3 | 2.55 | 2.37 | 2.77 | 2.33 | 2.61 | 2.71 | 2.40 | 2.96 | 2.35 |
| p Value | 0.0026 | 0.0017 | 2.3E−5 | 0.012 | 6.2E−4 | 2.0E−5 | 0.014 | 1.9E−4 | 2.2E−4 |
| Lower limit of 95% CI | 1.39 | 1.39 | 1.73 | 1.20 | 1.51 | 1.71 | 1.19 | 1.67 | 1.49 |

TABLE 30.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Upper limit of 95% CI | 4.69 | 4.06 | 4.45 | 4.51 | 4.52 | 4.29 | 4.83 | 5.23 | 3.69 |
| OR Quartile 4 | 2.75 | 2.08 | 3.20 | 2.47 | 2.25 | 2.88 | 2.11 | 2.35 | 2.89 |
| p Value | 0.018 | 0.035 | 1.5E−5 | 0.049 | 0.023 | 9.2E−5 | 0.11 | 0.021 | 1.3E−4 |
| Lower limit of 95% CI | 1.19 | 1.05 | 1.89 | 1.01 | 1.12 | 1.70 | 0.852 | 1.14 | 1.68 |
| Upper limit of 95% CI | 6.35 | 4.09 | 5.41 | 6.07 | 4.53 | 4.90 | 5.22 | 4.86 | 4.97 |

TABLE 30.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 12.5 | 38.0 | 12.2 | 33.1 | 12.2 | 33.1 |
| Average | 34.3 | 90.3 | 37.0 | 86.7 | 37.2 | 85.1 |
| Stdev | 77.1 | 164 | 81.7 | 161 | 85.6 | 158 |
| p (t-test) | | 0.0020 | | 0.0088 | | 0.015 |
| Min | 0.00127 | 0.00127 | 0.00127 | 0.00127 | 0.00127 | 0.00127 |
| Max | 670 | 1150 | 670 | 1150 | 670 | 1150 |
| n (Patient) | 90 | 226 | 79 | 237 | 71 | 245 |
| | sCr only | | | | | |
| Median | 13.6 | 38.0 | 12.9 | 38.4 | 11.7 | 39.2 |
| Average | 47.3 | 88.0 | 47.0 | 87.7 | 45.5 | 87.5 |
| Stdev | 125 | 154 | 127 | 154 | 129 | 152 |
| p (t-test) | | 0.019 | | 0.020 | | 0.018 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 106 | 210 | 104 | 212 | 99 | 217 |
| | UO only | | | | | |
| Median | 22.7 | 51.1 | 20.4 | 49.9 | 21.0 | 43.2 |
| Average | 52.2 | 119 | 50.8 | 111 | 46.6 | 110 |
| Stdev | 112 | 193 | 113 | 183 | 83.6 | 196 |
| p (t-test) | | 1.2E−4 | | 3.3E−4 | | 1.4E−4 |
| Min | 0.00127 | 0.00127 | 0.00127 | 0.00127 | 0.00127 | 0.00127 |
| Max | 1140 | 1150 | 1140 | 1150 | 670 | 1150 |
| n (Patient) | 211 | 103 | 193 | 121 | 177 | 137 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.64 | 0.67 | 0.63 | 0.64 | 0.66 | 0.63 | 0.66 | 0.64 |
| SE | 0.032 | 0.032 | 0.034 | 0.034 | 0.032 | 0.032 | 0.035 | 0.031 | 0.032 |
| p Value | 1.9E−6 | 2.1E−5 | 3.8E−7 | 1.2E−4 | 7.4E−6 | 4.5E−7 | 1.6E−4 | 4.3E−7 | 1.8E−5 |
| nCohort Recovered | 90 | 106 | 211 | 79 | 104 | 193 | 71 | 99 | 177 |
| nCohort Non-recovered | 226 | 210 | 103 | 237 | 212 | 121 | 245 | 217 | 137 |
| Cutoff Quartile 2 | 4.17 | 4.17 | 4.13 | 4.17 | 4.17 | 4.13 | 4.17 | 4.17 | 4.13 |
| Sensitivity | 80% | 80% | 86% | 78% | 81% | 85% | 78% | 81% | 82% |
| Specificity | 37% | 36% | 31% | 35% | 37% | 32% | 37% | 38% | 31% |
| Cutoff Quartile 3 | 29.6 | 29.6 | 28.8 | 29.6 | 29.6 | 28.8 | 29.6 | 29.6 | 28.8 |
| Sensitivity | 56% | 57% | 66% | 54% | 57% | 64% | 54% | 58% | 61% |
| Specificity | 66% | 63% | 58% | 63% | 64% | 59% | 65% | 67% | 58% |
| Cutoff Quartile 4 | 74.9 | 74.9 | 74.6 | 74.9 | 74.9 | 74.6 | 74.9 | 74.9 | 74.6 |
| Sensitivity | 31% | 31% | 43% | 30% | 31% | 39% | 29% | 31% | 37% |
| Specificity | 91% | 87% | 83% | 90% | 88% | 83% | 90% | 89% | 84% |

TABLE 30.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 2.27 | 2.30 | 2.83 | 2.00 | 2.40 | 2.64 | 2.09 | 2.67 | 2.12 |
| p Value | 0.0029 | 0.0018 | 0.0013 | 0.014 | 0.0011 | 0.0011 | 0.011 | 2.7E−4 | 0.0066 |
| Lower limit of 95% CI | 1.32 | 1.36 | 1.50 | 1.15 | 1.42 | 1.47 | 1.18 | 1.58 | 1.23 |
| Upper limit of 95% CI | 3.88 | 3.89 | 5.34 | 3.49 | 4.06 | 4.75 | 3.70 | 4.54 | 3.66 |
| OR Quartile 3 | 2.44 | 2.25 | 2.66 | 2.06 | 2.41 | 2.47 | 2.18 | 2.72 | 2.14 |
| p Value | 5.7E−4 | 9.5E−4 | 9.2E−5 | 0.0069 | 3.8E−4 | 1.5E−4 | 0.0052 | 8.1E−5 | 0.0010 |
| Lower limit of 95% CI | 1.47 | 1.39 | 1.63 | 1.22 | 1.48 | 1.55 | 1.26 | 1.65 | 1.36 |
| Upper limit of 95% CI | 4.06 | 3.63 | 4.35 | 3.48 | 3.91 | 3.95 | 3.78 | 4.47 | 3.37 |
| OR Quartile 4 | 4.70 | 2.95 | 3.75 | 3.80 | 3.16 | 3.20 | 3.81 | 3.65 | 3.16 |
| p Value | 9.9E−5 | 8.4E−4 | 1.2E−6 | 8.3E−4 | 5.1E−4 | 1.5E−5 | 0.0015 | 2.3E−4 | 2.3E−5 |
| Lower limit of 95% CI | 2.16 | 1.56 | 2.20 | 1.74 | 1.65 | 1.89 | 1.66 | 1.83 | 1.85 |
| Upper limit of 95% CI | 10.2 | 5.55 | 6.39 | 8.30 | 6.06 | 5.41 | 8.70 | 7.27 | 5.37 |

TABLE 30.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 17.2 | 39.4 | 15.8 | 37.8 | 12.9 | 38.2 |
| Average | 42.9 | 92.0 | 44.2 | 89.7 | 42.7 | 88.3 |
| Stdev | 85.0 | 169 | 87.6 | 167 | 89.9 | 164 |
| p (t-test) | | 0.0040 | | 0.0086 | | 0.010 |
| Min | 0.00127 | 0.00127 | 0.00127 | 0.00127 | 0.00127 | 0.00127 |
| Max | 670 | 1150 | 670 | 1150 | 670 | 1150 |
| n (Patient) | 114 | 202 | 107 | 209 | 97 | 219 |
| | sCr only | | | | | |
| Median | 17.6 | 40.2 | 16.4 | 40.3 | 14.3 | 41.4 |
| Average | 49.6 | 90.9 | 49.7 | 90.2 | 47.1 | 90.8 |
| Stdev | 119 | 160 | 120 | 159 | 122 | 157 |
| p (t-test) | | 0.014 | | 0.016 | | 0.0100 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 127 | 189 | 124 | 192 | 119 | 197 |
| | UO only | | | | | |
| Median | 20.4 | 54.9 | 20.3 | 51.1 | 20.3 | 49.9 |
| Average | 53.0 | 119 | 53.5 | 112 | 54.5 | 104 |
| Stdev | 114 | 192 | 117 | 185 | 120 | 176 |
| p (t-test) | | 1.8E−4 | | 6.9E−4 | | 0.0033 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 213 | 101 | 203 | 111 | 189 | 125 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.63 | 0.68 | 0.63 | 0.63 | 0.67 | 0.64 | 0.65 | 0.65 |
| SE | 0.032 | 0.031 | 0.033 | 0.032 | 0.031 | 0.033 | 0.032 | 0.031 | 0.032 |
| p Value | 4.4E−5 | 5.7E−5 | 4.6E−8 | 9.2E−5 | 3.0E−5 | 2.3E−7 | 3.2E−5 | 7.6E−7 | 1.9E−6 |
| nCohort Recovered | 114 | 127 | 213 | 107 | 124 | 203 | 97 | 119 | 189 |
| nCohort Non- | 202 | 189 | 101 | 209 | 192 | 111 | 219 | 197 | 125 |

TABLE 30.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| recovered | | | | | | | | | |
|---|---|---|---|---|---|---|---|---|---|
| Cutoff Quartile 2 | 4.17 | 4.17 | 4.13 | 4.17 | 4.17 | 4.13 | 4.17 | 4.17 | 4.13 |
| Sensitivity | 80% | 81% | 86% | 80% | 81% | 86% | 80% | 82% | 85% |
| Specificity | 34% | 34% | 31% | 36% | 35% | 31% | 36% | 36% | 32% |
| Cutoff Quartile 3 | 29.6 | 29.6 | 28.8 | 29.6 | 29.6 | 28.8 | 29.6 | 29.6 | 28.8 |
| Sensitivity | 57% | 58% | 68% | 56% | 58% | 67% | 56% | 59% | 64% |
| Specificity | 62% | 61% | 59% | 62% | 62% | 59% | 64% | 65% | 59% |
| Cutoff Quartile 4 | 74.9 | 74.9 | 74.6 | 74.9 | 74.9 | 74.6 | 74.9 | 74.9 | 74.6 |
| Sensitivity | 32% | 32% | 43% | 31% | 32% | 40% | 31% | 32% | 38% |
| Specificity | 87% | 85% | 83% | 86% | 85% | 83% | 88% | 87% | 84% |
| OR Quartile 2 | 2.11 | 2.18 | 2.73 | 2.26 | 2.30 | 2.67 | 2.25 | 2.53 | 2.59 |
| p Value | 0.0049 | 0.0032 | 0.0020 | 0.0023 | 0.0016 | 0.0015 | 0.0028 | 4.7E−4 | 0.0012 |
| Lower limit of 95% CI | 1.25 | 1.30 | 1.45 | 1.34 | 1.37 | 1.46 | 1.32 | 1.50 | 1.46 |
| Upper limit of 95% CI | 3.54 | 3.65 | 5.15 | 3.81 | 3.86 | 4.90 | 3.81 | 4.26 | 4.62 |
| OR Quartile 3 | 2.18 | 2.17 | 3.06 | 2.05 | 2.25 | 2.89 | 2.27 | 2.63 | 2.59 |
| p Value | 0.0011 | 9.5E−4 | 1.2E−5 | 0.0032 | 6.1E−4 | 1.7E−5 | 0.0011 | 5.9E−5 | 6.6E−5 |
| Lower limit of 95% CI | 1.36 | 1.37 | 1.86 | 1.27 | 1.41 | 1.78 | 1.39 | 1.64 | 1.62 |
| Upper limit of 95% CI | 3.49 | 3.43 | 5.05 | 3.29 | 3.56 | 4.69 | 3.72 | 4.21 | 4.12 |
| OR Quartile 4 | 3.06 | 2.64 | 3.65 | 2.71 | 2.74 | 3.15 | 3.12 | 3.34 | 3.18 |
| p Value | 3.9E−4 | 9.4E−4 | 2.0E−6 | 0.0016 | 7.2E−4 | 1.9E−5 | 8.6E−4 | 1.3E−4 | 1.7E−5 |
| Lower limit of 95% CI | 1.65 | 1.49 | 2.14 | 1.46 | 1.53 | 1.86 | 1.60 | 1.80 | 1.87 |
| Upper limit of 95% CI | 5.68 | 4.70 | 6.21 | 5.03 | 4.92 | 5.34 | 6.10 | 6.19 | 5.38 |

TABLE 30.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 17.9 | 40.3 | 16.9 | 38.2 | 15.9 | 39.4 |
| Average | 53.8 | 89.4 | 55.9 | 86.4 | 45.0 | 90.8 |
| Stdev | 124 | 159 | 128 | 156 | 91.0 | 168 |
| p (t-test) | | 0.032 | | 0.070 | | 0.0073 |
| Min | 0.00127 | 0.00127 | 0.00127 | 0.00127 | 0.00127 | 0.00127 |
| Max | 1070 | 1150 | 1070 | 1150 | 670 | 1150 |
| n (Patient) | 134 | 182 | 125 | 191 | 114 | 202 |
| sCr only | | | | | | |
| Median | 17.2 | 40.6 | 16.4 | 40.6 | 15.8 | 41.4 |
| Average | 51.7 | 92.3 | 51.8 | 91.8 | 49.7 | 92.7 |
| Stdev | 119 | 163 | 120 | 162 | 120 | 161 |
| p (t-test) | | 0.014 | | 0.016 | | 0.0097 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 140 | 176 | 138 | 178 | 135 | 181 |
| UO only | | | | | | |
| Median | 20.3 | 55.1 | 20.4 | 52.8 | 20.3 | 50.6 |
| Average | 57.4 | 111 | 58.4 | 104 | 54.5 | 106 |
| Stdev | 133 | 167 | 136 | 162 | 119 | 178 |

TABLE 30.4-continued

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

|  |  |  |  |  |  |  |
|---|---|---|---|---|---|---|
| p (t-test) |  | 0.0027 |  | 0.0082 |  | 0.0026 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 215 | 99 | 206 | 108 | 193 | 121 |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.63 | 0.69 | 0.62 | 0.64 | 0.67 | 0.64 | 0.65 | 0.66 |
| SE | 0.031 | 0.031 | 0.033 | 0.031 | 0.031 | 0.033 | 0.031 | 0.031 | 0.032 |
| p Value | 2.9E−5 | 1.6E−5 | 1.0E−8 | 9.7E−5 | 1.1E−5 | 3.1E−7 | 7.4E−6 | 8.2E−7 | 6.9E−7 |
| nCohort Recovered | 134 | 140 | 215 | 125 | 138 | 206 | 114 | 135 | 193 |
| nCohort Non-recovered | 182 | 176 | 99 | 191 | 178 | 108 | 202 | 181 | 121 |
| Cutoff Quartile 2 | 4.17 | 4.17 | 4.13 | 4.17 | 4.17 | 4.13 | 4.17 | 4.17 | 4.13 |
| Sensitivity | 82% | 82% | 88% | 82% | 83% | 86% | 81% | 83% | 86% |
| Specificity | 34% | 34% | 31% | 35% | 35% | 31% | 36% | 36% | 32% |
| Cutoff Quartile 3 | 29.6 | 29.6 | 28.8 | 29.6 | 29.6 | 28.8 | 29.6 | 29.6 | 28.8 |
| Sensitivity | 58% | 59% | 70% | 57% | 59% | 67% | 57% | 60% | 64% |
| Specificity | 61% | 61% | 59% | 61% | 62% | 59% | 63% | 63% | 59% |
| Cutoff Quartile 4 | 74.9 | 74.9 | 74.6 | 74.9 | 74.9 | 74.6 | 74.9 | 74.9 | 74.6 |
| Sensitivity | 32% | 32% | 43% | 31% | 33% | 41% | 32% | 34% | 39% |
| Specificity | 85% | 84% | 83% | 84% | 85% | 83% | 87% | 87% | 83% |
| OR Quartile 2 | 2.36 | 2.44 | 3.28 | 2.42 | 2.53 | 2.79 | 2.42 | 2.67 | 2.90 |
| p Value | 0.0012 | 8.0E−4 | 5.0E−4 | 8.4E−4 | 5.0E−4 | 0.0012 | 8.5E−4 | 2.3E−4 | 4.6E−4 |
| Lower limit of 95% CI | 1.40 | 1.45 | 1.68 | 1.44 | 1.50 | 1.50 | 1.44 | 1.58 | 1.60 |
| Upper limit of 95% CI | 3.97 | 4.11 | 6.41 | 4.07 | 4.26 | 5.19 | 4.08 | 4.50 | 5.25 |
| OR Quartile 3 | 2.20 | 2.30 | 3.32 | 2.06 | 2.31 | 2.85 | 2.31 | 2.52 | 2.62 |
| p Value | 7.0E−4 | 3.2E−4 | 3.6E−6 | 0.0020 | 3.2E−4 | 2.5E−5 | 5.0E−4 | 8.1E−5 | 6.0E−5 |
| Lower limit of 95% CI | 1.39 | 1.46 | 2.00 | 1.30 | 1.46 | 1.75 | 1.44 | 1.59 | 1.64 |
| Upper limit of 95% CI | 3.47 | 3.62 | 5.51 | 3.26 | 3.64 | 4.63 | 3.71 | 3.98 | 4.19 |
| OR Quartile 4 | 2.73 | 2.57 | 3.82 | 2.35 | 2.69 | 3.36 | 3.06 | 3.30 | 3.20 |
| p Value | 5.1E−4 | 8.4E−4 | 9.2E−7 | 0.0033 | 5.3E−4 | 7.1E−6 | 3.9E−4 | 6.1E−5 | 1.5E−5 |
| Lower limit of 95% CI | 1.55 | 1.48 | 2.24 | 1.33 | 1.54 | 1.98 | 1.65 | 1.84 | 1.89 |
| Upper limit of 95% CI | 4.82 | 4.47 | 6.52 | 4.14 | 4.72 | 5.70 | 5.68 | 5.93 | 5.41 |

TABLE 30.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 19.2 | 44.7 | 19.3 | 44.7 | 19.3 | 44.7 |
| Average | 58.6 | 97.0 | 59.3 | 95.2 | 59.3 | 95.2 |
| Stdev | 138 | 155 | 139 | 154 | 139 | 154 |

TABLE 30.5-continued

Comparison of marker levels and the area under the ROC curve (AUC) in urine samples
for the "recovered" and "non-recovered" cohorts where recovery starts
within 168 hours after sample collection and renal status is assessed by serum creatinine
(sCr) only, urine output (UO) only, or serum creatinine or urine output RIFLE criteria.

| | | | | | | |
|---|---|---|---|---|---|---|
| p (t-test) | | 0.022 | | 0.031 | | 0.031 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 187 | 129 | 184 | 132 | 184 | 132 | sCr only

| | | | | | | |
|---|---|---|---|---|---|---|
| Median | 18.4 | 42.2 | 19.7 | 41.6 | 19.2 | 41.8 |
| Average | 52.9 | 96.0 | 53.8 | 94.3 | 53.0 | 94.8 |
| Stdev | 117 | 168 | 118 | 167 | 118 | 167 |
| p (t-test) | | 0.0087 | | 0.014 | | 0.011 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 159 | 157 | 156 | 160 | 155 | 161 |

UO only

| | | | | | | |
|---|---|---|---|---|---|---|
| Median | 20.4 | 54.2 | 20.4 | 53.9 | 20.4 | 52.5 |
| Average | 58.5 | 106 | 59.0 | 104 | 59.0 | 102 |
| Stdev | 135 | 164 | 136 | 163 | 137 | 161 |
| p (t-test) | | 0.0068 | | 0.011 | | 0.012 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 210 | 104 | 207 | 107 | 204 | 110 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.64 | 0.68 | 0.65 | 0.63 | 0.67 | 0.65 | 0.63 | 0.67 |
| SE | 0.032 | 0.031 | 0.033 | 0.032 | 0.031 | 0.033 | 0.032 | 0.031 | 0.033 |
| p Value | 4.0E−7 | 1.0E−5 | 7.1E−8 | 2.2E−6 | 6.0E−5 | 2.6E−7 | 2.2E−6 | 2.7E−5 | 1.6E−7 |
| nCohort Recovered | 187 | 159 | 210 | 184 | 156 | 207 | 184 | 155 | 204 |
| nCohort Non-recovered | 129 | 157 | 104 | 132 | 160 | 107 | 132 | 161 | 110 |
| Cutoff Quartile 2 | 4.17 | 4.17 | 4.13 | 4.17 | 4.17 | 4.13 | 4.17 | 4.17 | 4.13 |
| Sensitivity | 86% | 83% | 88% | 85% | 82% | 87% | 85% | 82% | 87% |
| Specificity | 33% | 33% | 31% | 32% | 32% | 31% | 32% | 32% | 32% |
| Cutoff Quartile 3 | 29.6 | 29.6 | 28.8 | 29.6 | 29.6 | 28.8 | 29.6 | 29.6 | 28.8 |
| Sensitivity | 65% | 62% | 68% | 64% | 61% | 67% | 64% | 61% | 67% |
| Specificity | 60% | 62% | 59% | 60% | 61% | 59% | 60% | 61% | 59% |
| Cutoff Quartile 4 | 74.9 | 74.9 | 74.6 | 74.9 | 74.9 | 74.6 | 74.9 | 74.9 | 74.6 |
| Sensitivity | 37% | 35% | 41% | 36% | 34% | 40% | 36% | 35% | 40% |
| Specificity | 83% | 85% | 83% | 83% | 85% | 83% | 83% | 85% | 83% |
| OR Quartile 2 | 2.99 | 2.34 | 3.21 | 2.64 | 2.13 | 3.04 | 2.64 | 2.17 | 3.21 |
| p Value | 2.4E−4 | 0.0017 | 4.4E−4 | 7.9E−4 | 0.0047 | 5.9E−4 | 7.9E−4 | 0.0038 | 3.1E−4 |
| Lower limit of 95% CI | 1.66 | 1.38 | 1.67 | 1.50 | 1.26 | 1.61 | 1.50 | 1.28 | 1.70 |
| Upper limit of 95% CI | 5.36 | 3.98 | 6.15 | 4.66 | 3.60 | 5.73 | 4.66 | 3.66 | 6.04 |
| OR Quartile 3 | 2.85 | 2.60 | 3.10 | 2.75 | 2.40 | 2.95 | 2.75 | 2.46 | 3.00 |
| p Value | 1.0E−5 | 3.7E−5 | 7.7E−6 | 1.8E−5 | 1.5E−4 | 1.5E−5 | 1.8E−5 | 9.4E−5 | 9.8E−6 |
| Lower limit of 95% CI | 1.79 | 1.65 | 1.89 | 1.73 | 1.53 | 1.81 | 1.73 | 1.57 | 1.84 |
| Upper limit of 95% CI | 4.54 | 4.09 | 5.10 | 4.37 | 3.77 | 4.82 | 4.37 | 3.87 | 4.87 |
| OR Quartile 4 | 2.98 | 3.03 | 3.41 | 2.82 | 2.88 | 3.19 | 2.82 | 3.06 | 3.22 |
| p Value | 4.6E−5 | 6.4E−5 | 5.9E−6 | 1.1E−4 | 1.4E−4 | 1.6E−5 | 1.1E−4 | 6.5E−5 | 1.4E−5 |
| Lower limit of 95% CI | 1.76 | 1.76 | 2.01 | 1.67 | 1.67 | 1.88 | 1.67 | 1.77 | 1.90 |
| Upper limit of 95% CI | 5.04 | 5.23 | 5.79 | 4.76 | 4.96 | 5.41 | 4.76 | 5.30 | 5.45 |

TABLE 30.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 330 | 375 | 245 | 375 | 364 | 374 |
| Average | 391 | 540 | 385 | 536 | 399 | 532 |
| Stdev | 281 | 543 | 298 | 536 | 310 | 533 |
| p (t-test) | | 0.19 | | 0.21 | | 0.29 |
| Min | 50.8 | 46.8 | 50.8 | 46.8 | 50.8 | 46.8 |
| Max | 1070 | 4690 | 1070 | 4690 | 1070 | 4690 |
| n (Patient) | 25 | 126 | 21 | 130 | 19 | 132 |
| sCr only | | | | | | |
| Median | 330 | 374 | 287 | 375 | 304 | 374 |
| Average | 428 | 535 | 423 | 535 | 433 | 531 |
| Stdev | 402 | 536 | 408 | 534 | 422 | 530 |
| p (t-test) | | 0.32 | | 0.30 | | 0.38 |
| Min | 46.8 | 50.8 | 46.8 | 50.8 | 46.8 | 50.8 |
| Max | 1880 | 4690 | 1880 | 4690 | 1880 | 4690 |
| n (Patient) | 29 | 121 | 28 | 122 | 26 | 124 |
| UO only | | | | | | |
| Median | 364 | 380 | 330 | 384 | 337 | 380 |
| Average | 494 | 528 | 499 | 519 | 456 | 563 |
| Stdev | 552 | 427 | 573 | 407 | 341 | 632 |
| p (t-test) | | 0.69 | | 0.81 | | 0.19 |
| Min | 50.8 | 46.8 | 50.8 | 46.8 | 50.8 | 46.8 |
| Max | 4690 | 1880 | 4690 | 1880 | 1540 | 4690 |
| n (Patient) | 91 | 59 | 84 | 66 | 77 | 73 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.58 | 0.58 | 0.54 | 0.59 | 0.59 | 0.55 | 0.58 | 0.59 | 0.54 |
| SE | 0.060 | 0.057 | 0.049 | 0.064 | 0.057 | 0.048 | 0.067 | 0.059 | 0.047 |
| p Value | 0.18 | 0.14 | 0.44 | 0.14 | 0.097 | 0.32 | 0.23 | 0.13 | 0.40 |
| nCohort Recovered | 25 | 29 | 91 | 21 | 28 | 84 | 19 | 26 | 77 |
| nCohort Non-recovered | 126 | 121 | 59 | 130 | 122 | 66 | 132 | 124 | 73 |
| Cutoff Quartile 2 | 218 | 217 | 217 | 218 | 217 | 217 | 218 | 217 | 217 |
| Sensitivity | 76% | 77% | 76% | 76% | 77% | 79% | 77% | 77% | 77% |
| Specificity | 32% | 34% | 26% | 33% | 36% | 29% | 37% | 38% | 27% |
| Cutoff Quartile 3 | 373 | 372 | 372 | 373 | 372 | 372 | 373 | 372 | 372 |
| Sensitivity | 52% | 51% | 53% | 52% | 52% | 53% | 51% | 51% | 52% |
| Specificity | 56% | 55% | 52% | 57% | 57% | 52% | 53% | 54% | 52% |
| Cutoff Quartile 4 | 674 | 661 | 661 | 674 | 661 | 661 | 674 | 661 | 661 |
| Sensitivity | 27% | 26% | 29% | 26% | 26% | 26% | 26% | 26% | 26% |
| Specificity | 84% | 79% | 77% | 81% | 79% | 75% | 79% | 77% | 75% |
| OR Quartile 2 | 1.51 | 1.75 | 1.15 | 1.60 | 1.87 | 1.49 | 1.90 | 2.14 | 1.24 |
| p Value | 0.39 | 0.21 | 0.72 | 0.36 | 0.17 | 0.31 | 0.22 | 0.095 | 0.58 |
| Lower limit of 95% CI | 0.591 | 0.729 | 0.539 | 0.592 | 0.773 | 0.697 | 0.689 | 0.875 | 0.590 |
| Upper limit of 95% CI | 3.84 | 4.19 | 2.46 | 4.31 | 4.50 | 3.17 | 5.25 | 5.25 | 2.59 |
| OR Quartile 3 | 1.36 | 1.29 | 1.18 | 1.42 | 1.42 | 1.24 | 1.15 | 1.20 | 1.17 |
| p Value | 0.49 | 0.54 | 0.62 | 0.46 | 0.40 | 0.51 | 0.78 | 0.67 | 0.62 |
| Lower limit of 95% CI | 0.572 | 0.573 | 0.614 | 0.559 | 0.622 | 0.651 | 0.437 | 0.516 | 0.618 |
| Upper limit of 95% CI | 3.22 | 2.92 | 2.28 | 3.59 | 3.26 | 2.37 | 3.00 | 2.81 | 2.23 |

TABLE 30.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.94 | 1.38 | 1.35 | 1.51 | 1.30 | 1.04 | 1.30 | 1.16 | 1.07 |
| p Value | 0.25 | 0.52 | 0.43 | 0.49 | 0.60 | 0.92 | 0.66 | 0.77 | 0.85 |
| Lower limit of 95% CI | 0.621 | 0.515 | 0.640 | 0.473 | 0.485 | 0.496 | 0.404 | 0.428 | 0.514 |
| Upper limit of 95% CI | 6.06 | 3.69 | 2.84 | 4.79 | 3.50 | 2.18 | 4.19 | 3.14 | 2.24 |

TABLE 30.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 347 | 376 | 344 | 376 | 344 | 374 |
| Average | 454 | 537 | 458 | 533 | 471 | 527 |
| Stdev | 394 | 548 | 411 | 540 | 433 | 532 |
| p (t-test) | | 0.38 | | 0.44 | | 0.59 |
| Min | 50.8 | 46.8 | 50.8 | 46.8 | 50.8 | 46.8 |
| Max | 1880 | 4690 | 1880 | 4690 | 1880 | 4690 |
| n (Patient) | 40 | 111 | 36 | 115 | 32 | 119 |
| sCr only | | | | | | |
| Median | 327 | 380 | 324 | 386 | 291 | 380 |
| Average | 434 | 548 | 431 | 549 | 436 | 544 |
| Stdev | 392 | 552 | 396 | 549 | 410 | 543 |
| p (t-test) | | 0.21 | | 0.20 | | 0.26 |
| Min | 46.8 | 50.8 | 46.8 | 50.8 | 46.8 | 50.8 |
| Max | 1880 | 4690 | 1880 | 4690 | 1880 | 4690 |
| n (Patient) | 44 | 107 | 43 | 108 | 40 | 111 |
| UO only | | | | | | |
| Median | 350 | 394 | 332 | 396 | 337 | 392 |
| Average | 480 | 563 | 481 | 551 | 444 | 591 |
| Stdev | 530 | 452 | 548 | 426 | 329 | 663 |
| p (t-test) | | 0.35 | | 0.42 | | 0.078 |
| Min | 50.8 | 46.8 | 50.8 | 46.8 | 50.8 | 46.8 |
| Max | 4690 | 1880 | 4690 | 1880 | 1540 | 4690 |
| n (Patient) | 100 | 50 | 93 | 57 | 85 | 65 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.55 | 0.58 | 0.56 | 0.55 | 0.59 | 0.57 | 0.55 | 0.59 | 0.56 |
| SE | 0.052 | 0.050 | 0.050 | 0.054 | 0.050 | 0.049 | 0.056 | 0.051 | 0.048 |
| p Value | 0.35 | 0.097 | 0.23 | 0.32 | 0.073 | 0.13 | 0.37 | 0.073 | 0.24 |
| nCohort Recovered | 40 | 44 | 100 | 36 | 43 | 93 | 32 | 40 | 85 |
| nCohort Non-recovered | 111 | 107 | 50 | 115 | 108 | 57 | 119 | 111 | 65 |
| Cutoff Quartile 2 | 218 | 218 | 217 | 218 | 218 | 217 | 218 | 218 | 217 |
| Sensitivity | 76% | 78% | 78% | 76% | 78% | 81% | 76% | 78% | 77% |
| Specificity | 28% | 32% | 27% | 28% | 33% | 29% | 31% | 35% | 27% |
| Cutoff Quartile 3 | 373 | 373 | 372 | 373 | 373 | 372 | 373 | 373 | 372 |
| Sensitivity | 51% | 52% | 54% | 51% | 53% | 56% | 51% | 52% | 54% |
| Specificity | 52% | 55% | 52% | 53% | 56% | 54% | 53% | 55% | 53% |
| Cutoff Quartile 4 | 674 | 674 | 661 | 674 | 674 | 661 | 674 | 674 | 661 |
| Sensitivity | 27% | 28% | 34% | 26% | 28% | 30% | 25% | 27% | 29% |
| Specificity | 80% | 82% | 79% | 78% | 81% | 77% | 75% | 80% | 78% |

TABLE 30.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 1.18 | 1.61 | 1.31 | 1.20 | 1.69 | 1.71 | 1.48 | 1.95 | 1.24 |
| p Value | 0.69 | 0.23 | 0.51 | 0.68 | 0.19 | 0.19 | 0.37 | 0.098 | 0.58 |
| Lower limit of 95% CI | 0.521 | 0.740 | 0.588 | 0.514 | 0.772 | 0.772 | 0.626 | 0.885 | 0.584 |
| Upper limit of 95% CI | 2.67 | 3.52 | 2.92 | 2.78 | 3.70 | 3.79 | 3.49 | 4.31 | 2.62 |
| OR Quartile 3 | 1.17 | 1.32 | 1.27 | 1.18 | 1.41 | 1.49 | 1.19 | 1.34 | 1.31 |
| p Value | 0.68 | 0.44 | 0.49 | 0.67 | 0.34 | 0.24 | 0.66 | 0.43 | 0.41 |
| Lower limit of 95% CI | 0.566 | 0.652 | 0.644 | 0.556 | 0.694 | 0.767 | 0.545 | 0.647 | 0.687 |
| Upper limit of 95% CI | 2.41 | 2.66 | 2.51 | 2.49 | 2.87 | 2.89 | 2.61 | 2.76 | 2.51 |
| OR Quartile 4 | 1.48 | 1.75 | 1.94 | 1.24 | 1.68 | 1.46 | 1.01 | 1.48 | 1.43 |
| p Value | 0.38 | 0.21 | 0.087 | 0.64 | 0.24 | 0.32 | 0.98 | 0.38 | 0.34 |
| Lower limit of 95% CI | 0.614 | 0.731 | 0.908 | 0.508 | 0.701 | 0.690 | 0.411 | 0.614 | 0.685 |
| Upper limit of 95% CI | 3.57 | 4.20 | 4.13 | 3.01 | 4.04 | 3.08 | 2.49 | 3.57 | 3.00 |

TABLE 30.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 369 | 374 | 327 | 380 | 327 | 376 |
| Average | 469 | 538 | 457 | 541 | 463 | 534 |
| Stdev | 383 | 565 | 394 | 555 | 414 | 543 |
| p (t-test) | | 0.44 | | 0.36 | | 0.45 |
| Min | 50.8 | 46.8 | 50.8 | 46.8 | 50.8 | 46.8 |
| Max | 1880 | 4690 | 1880 | 4690 | 1880 | 4690 |
| n (Patient) | 50 | 101 | 46 | 105 | 40 | 111 |
| sCr only | | | | | | |
| Median | 327 | 380 | 311 | 392 | 298 | 394 |
| Average | 447 | 553 | 436 | 557 | 430 | 556 |
| Stdev | 386 | 568 | 389 | 563 | 395 | 556 |
| p (t-test) | | 0.22 | | 0.17 | | 0.16 |
| Min | 46.8 | 50.8 | 46.8 | 50.8 | 46.8 | 50.8 |
| Max | 1880 | 4690 | 1880 | 4690 | 1880 | 4690 |
| n (Patient) | 54 | 97 | 52 | 99 | 49 | 102 |
| UO only | | | | | | |
| Median | 331 | 397 | 329 | 397 | 334 | 390 |
| Average | 474 | 572 | 477 | 559 | 493 | 527 |
| Stdev | 534 | 443 | 544 | 432 | 563 | 419 |
| p (t-test) | | 0.26 | | 0.34 | | 0.68 |
| Min | 50.8 | 46.8 | 50.8 | 46.8 | 50.8 | 46.8 |
| Max | 4690 | 1880 | 4690 | 1880 | 4690 | 1880 |
| n (Patient) | 98 | 52 | 94 | 56 | 86 | 64 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.53 | 0.57 | 0.58 | 0.55 | 0.59 | 0.58 | 0.55 | 0.60 | 0.54 |
| SE | 0.050 | 0.048 | 0.050 | 0.050 | 0.048 | 0.049 | 0.052 | 0.048 | 0.048 |
| p Value | 0.60 | 0.14 | 0.10 | 0.31 | 0.067 | 0.12 | 0.30 | 0.039 | 0.37 |

TABLE 30.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Recovered | 50 | 54 | 98 | 46 | 52 | 94 | 40 | 49 | 86 |
| nCohort Non-recovered | 101 | 97 | 52 | 105 | 99 | 56 | 111 | 102 | 64 |
| Cutoff Quartile 2 | 218 | 218 | 217 | 218 | 218 | 217 | 218 | 218 | 217 |
| Sensitivity | 74% | 77% | 79% | 75% | 78% | 79% | 77% | 78% | 77% |
| Specificity | 24% | 30% | 28% | 26% | 31% | 28% | 30% | 33% | 27% |
| Cutoff Quartile 3 | 373 | 373 | 372 | 373 | 373 | 372 | 373 | 373 | 372 |
| Sensitivity | 50% | 53% | 58% | 52% | 54% | 59% | 52% | 54% | 55% |
| Specificity | 50% | 54% | 54% | 54% | 56% | 55% | 55% | 57% | 53% |
| Cutoff Quartile 4 | 674 | 674 | 661 | 674 | 674 | 661 | 674 | 674 | 661 |
| Sensitivity | 27% | 28% | 33% | 27% | 28% | 30% | 26% | 28% | 28% |
| Specificity | 78% | 80% | 79% | 78% | 81% | 78% | 78% | 82% | 77% |
| OR Quartile 2 | 0.911 | 1.44 | 1.42 | 1.07 | 1.56 | 1.40 | 1.40 | 1.76 | 1.19 |
| p Value | 0.82 | 0.35 | 0.39 | 0.86 | 0.25 | 0.40 | 0.41 | 0.14 | 0.65 |
| Lower limit of 95% CI | 0.414 | 0.676 | 0.637 | 0.485 | 0.731 | 0.641 | 0.626 | 0.824 | 0.563 |
| Upper limit of 95% CI | 2.00 | 3.05 | 3.15 | 2.37 | 3.31 | 3.06 | 3.14 | 3.77 | 2.52 |
| OR Quartile 3 | 1.02 | 1.29 | 1.61 | 1.31 | 1.45 | 1.78 | 1.34 | 1.56 | 1.39 |
| p Value | 0.95 | 0.46 | 0.17 | 0.45 | 0.28 | 0.093 | 0.43 | 0.20 | 0.32 |
| Lower limit of 95% CI | 0.518 | 0.660 | 0.815 | 0.653 | 0.740 | 0.909 | 0.647 | 0.785 | 0.725 |
| Upper limit of 95% CI | 2.01 | 2.51 | 3.17 | 2.62 | 2.85 | 3.47 | 2.76 | 3.10 | 2.66 |
| OR Quartile 4 | 1.29 | 1.51 | 1.78 | 1.31 | 1.66 | 1.52 | 1.22 | 1.77 | 1.29 |
| p Value | 0.53 | 0.31 | 0.13 | 0.52 | 0.23 | 0.28 | 0.65 | 0.19 | 0.50 |
| Lower limit of 95% CI | 0.581 | 0.679 | 0.838 | 0.575 | 0.732 | 0.717 | 0.518 | 0.761 | 0.616 |
| Upper limit of 95% CI | 2.88 | 3.35 | 3.79 | 2.98 | 3.75 | 3.20 | 2.86 | 4.10 | 2.71 |

TABLE 30.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 381 | 371 | 330 | 378 | 330 | 375 |
| Average | 484 | 535 | 460 | 545 | 466 | 537 |
| Stdev | 385 | 578 | 384 | 569 | 400 | 555 |
| p (t-test) | | 0.55 | | 0.33 | | 0.43 |
| Min | 50.8 | 46.8 | 50.8 | 46.8 | 50.8 | 46.8 |
| Max | 1880 | 4690 | 1880 | 4690 | 1880 | 4690 |
| n (Patient) | 58 | 93 | 53 | 98 | 47 | 104 |
| sCr only | | | | | | |
| Median | 347 | 376 | 330 | 378 | 324 | 386 |
| Average | 454 | 555 | 447 | 559 | 439 | 561 |
| Stdev | 380 | 581 | 379 | 579 | 382 | 573 |
| p (t-test) | | 0.24 | | 0.19 | | 0.15 |
| Min | 46.8 | 50.8 | 46.8 | 50.8 | 46.8 | 50.8 |
| Max | 1880 | 4690 | 1880 | 4690 | 1880 | 4690 |
| n (Patient) | 60 | 91 | 59 | 92 | 57 | 94 |
| UO only | | | | | | |
| Median | 331 | 397 | 329 | 397 | 334 | 390 |
| Average | 481 | 555 | 477 | 557 | 491 | 531 |
| Stdev | 542 | 432 | 546 | 432 | 560 | 424 |

TABLE 30.9-continued

Comparison of marker levels and the area under the ROC curve (AUC) in EDTA samples
for the "recovered" and "non-recovered" cohorts where recovery starts
within 96 hours after sample collection and renal status is assessed by serum creatinine
(sCr) only, urine output (UO) only, or serum creatinine or urine output RIFLE criteria.

| | | | | | | | | | |
|---|---|---|---|---|---|---|---|---|---|
| p (t-test) | | 0.39 | | | 0.35 | | | 0.63 | |
| Min | 50.8 | 46.8 | | 50.8 | 46.8 | | 50.8 | 46.8 | |
| Max | 4690 | 1880 | | 4690 | 1880 | | 4690 | 1880 | |
| n (Patient) | 96 | 54 | | 92 | 58 | | 86 | 64 | |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.51 | 0.56 | 0.57 | 0.55 | 0.57 | 0.57 | 0.55 | 0.58 | 0.54 |
| SE | 0.048 | 0.047 | 0.049 | 0.049 | 0.047 | 0.048 | 0.050 | 0.047 | 0.048 |
| p Value | 0.82 | 0.21 | 0.16 | 0.34 | 0.15 | 0.13 | 0.36 | 0.077 | 0.36 |
| nCohort Recovered | 58 | 60 | 96 | 53 | 59 | 92 | 47 | 57 | 86 |
| nCohort Non-recovered | 93 | 91 | 54 | 98 | 92 | 58 | 104 | 94 | 64 |
| Cutoff Quartile 2 | 218 | 218 | 217 | 218 | 218 | 217 | 218 | 218 | 217 |
| Sensitivity | 75% | 78% | 78% | 77% | 78% | 78% | 77% | 79% | 77% |
| Specificity | 26% | 30% | 27% | 28% | 31% | 27% | 30% | 32% | 27% |
| Cutoff Quartile 3 | 373 | 373 | 372 | 373 | 373 | 372 | 373 | 373 | 372 |
| Sensitivity | 49% | 52% | 57% | 52% | 52% | 59% | 52% | 53% | 55% |
| Specificity | 48% | 52% | 54% | 53% | 53% | 55% | 53% | 54% | 53% |
| Cutoff Quartile 4 | 674 | 674 | 661 | 674 | 674 | 661 | 674 | 674 | 661 |
| Sensitivity | 25% | 26% | 30% | 26% | 27% | 29% | 25% | 28% | 28% |
| Specificity | 74% | 77% | 77% | 75% | 78% | 77% | 74% | 79% | 77% |
| OR Quartile 2 | 1.06 | 1.52 | 1.30 | 1.29 | 1.58 | 1.29 | 1.41 | 1.71 | 1.19 |
| p Value | 0.88 | 0.27 | 0.51 | 0.51 | 0.23 | 0.51 | 0.38 | 0.16 | 0.65 |
| Lower limit of 95% CI | 0.500 | 0.724 | 0.594 | 0.603 | 0.752 | 0.598 | 0.652 | 0.810 | 0.563 |
| Upper limit of 95% CI | 2.25 | 3.20 | 2.85 | 2.75 | 3.32 | 2.79 | 3.07 | 3.60 | 2.52 |
| OR Quartile 3 | 0.913 | 1.14 | 1.59 | 1.22 | 1.21 | 1.76 | 1.23 | 1.35 | 1.39 |
| p Value | 0.79 | 0.69 | 0.17 | 0.57 | 0.57 | 0.095 | 0.56 | 0.37 | 0.32 |
| Lower limit of 95% CI | 0.474 | 0.595 | 0.813 | 0.622 | 0.628 | 0.906 | 0.616 | 0.700 | 0.725 |
| Upper limit of 95% CI | 1.76 | 2.19 | 3.12 | 2.37 | 2.32 | 3.43 | 2.45 | 2.62 | 2.66 |
| OR Quartile 4 | 0.942 | 1.18 | 1.42 | 1.05 | 1.32 | 1.40 | 0.972 | 1.43 | 1.29 |
| p Value | 0.88 | 0.67 | 0.37 | 0.89 | 0.48 | 0.37 | 0.94 | 0.37 | 0.50 |
| Lower limit of 95% CI | 0.443 | 0.551 | 0.667 | 0.486 | 0.612 | 0.665 | 0.440 | 0.657 | 0.616 |
| Upper limit of 95% CI | 2.00 | 2.51 | 3.01 | 2.28 | 2.85 | 2.96 | 2.15 | 3.13 | 2.71 |

TABLE 30.10

Comparison of marker levels and the area under the ROC curve (AUC) in EDTA samples
for the "recovered" and "non-recovered" cohorts where recovery starts
within 168 hours after sample collection and renal status is assessed by serum creatinine
(sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 364 | 386 | 348 | 392 | 348 | 392 |
| Average | 529 | 499 | 520 | 510 | 520 | 510 |
| Stdev | 611 | 368 | 610 | 376 | 610 | 376 |
| p (t-test) | | 0.72 | | 0.90 | | 0.90 |

TABLE 30.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 50.8 | 46.8 | 50.8 | 46.8 | 50.8 | 46.8 |
| Max | 4690 | 1540 | 4690 | 1540 | 4690 | 1540 |
| n (Patient) | 81 | 70 | 80 | 71 | 80 | 71 | sCr only

| | | | | | | |
|---|---|---|---|---|---|---|
| Median | 364 | 378 | 364 | 378 | 364 | 378 |
| Average | 456 | 563 | 455 | 561 | 455 | 561 |
| Stdev | 375 | 597 | 374 | 593 | 374 | 593 |
| p (t-test) | | 0.20 | | 0.21 | | 0.21 |
| Min | 46.8 | 50.8 | 46.8 | 50.8 | 46.8 | 50.8 |
| Max | 1880 | 4690 | 1880 | 4690 | 1880 | 4690 |
| n (Patient) | 67 | 84 | 65 | 86 | 65 | 86 |

UO only

| | | | | | | |
|---|---|---|---|---|---|---|
| Median | 328 | 428 | 328 | 428 | 328 | 428 |
| Average | 479 | 558 | 475 | 561 | 475 | 558 |
| Stdev | 555 | 405 | 553 | 413 | 559 | 408 |
| p (t-test) | | 0.36 | | 0.31 | | 0.33 |
| Min | 50.8 | 46.8 | 50.8 | 46.8 | 50.8 | 46.8 |
| Max | 4690 | 1880 | 4690 | 1880 | 4690 | 1880 |
| n (Patient) | 95 | 55 | 93 | 57 | 91 | 59 |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.53 | 0.56 | 0.59 | 0.54 | 0.56 | 0.59 | 0.54 | 0.56 | 0.59 |
| SE | 0.047 | 0.047 | 0.049 | 0.047 | 0.047 | 0.048 | 0.047 | 0.047 | 0.048 |
| p Value | 0.59 | 0.20 | 0.059 | 0.43 | 0.21 | 0.062 | 0.43 | 0.21 | 0.058 |
| nCohort Recovered | 81 | 67 | 95 | 80 | 65 | 93 | 80 | 65 | 91 |
| nCohort Non-recovered | 70 | 84 | 55 | 71 | 86 | 57 | 71 | 86 | 59 |
| Cutoff Quartile 2 | 218 | 218 | 217 | 218 | 218 | 217 | 218 | 218 | 217 |
| Sensitivity | 76% | 79% | 80% | 76% | 78% | 79% | 76% | 78% | 80% |
| Specificity | 26% | 30% | 28% | 26% | 29% | 28% | 26% | 29% | 29% |
| Cutoff Quartile 3 | 373 | 373 | 372 | 373 | 373 | 372 | 373 | 373 | 372 |
| Sensitivity | 53% | 52% | 60% | 54% | 52% | 60% | 54% | 52% | 59% |
| Specificity | 52% | 52% | 56% | 52% | 52% | 56% | 52% | 52% | 56% |
| Cutoff Quartile 4 | 674 | 674 | 661 | 674 | 674 | 661 | 674 | 674 | 661 |
| Sensitivity | 26% | 27% | 31% | 27% | 28% | 32% | 27% | 28% | 32% |
| Specificity | 75% | 78% | 78% | 76% | 78% | 78% | 76% | 78% | 79% |
| OR Quartile 2 | 1.09 | 1.56 | 1.59 | 1.13 | 1.46 | 1.46 | 1.13 | 1.46 | 1.57 |
| p Value | 0.82 | 0.24 | 0.26 | 0.74 | 0.32 | 0.35 | 0.74 | 0.32 | 0.26 |
| Lower limit of 95% CI | 0.521 | 0.746 | 0.716 | 0.540 | 0.696 | 0.666 | 0.540 | 0.696 | 0.718 |
| Upper limit of 95% CI | 2.28 | 3.27 | 3.52 | 2.37 | 3.05 | 3.18 | 2.37 | 3.05 | 3.42 |
| OR Quartile 3 | 1.21 | 1.20 | 1.89 | 1.27 | 1.20 | 1.87 | 1.27 | 1.20 | 1.86 |
| p Value | 0.56 | 0.57 | 0.064 | 0.46 | 0.57 | 0.066 | 0.46 | 0.57 | 0.067 |
| Lower limit of 95% CI | 0.636 | 0.633 | 0.964 | 0.671 | 0.632 | 0.960 | 0.671 | 0.632 | 0.957 |
| Upper limit of 95% CI | 2.29 | 2.29 | 3.72 | 2.41 | 2.29 | 3.66 | 2.41 | 2.29 | 3.61 |
| OR Quartile 4 | 1.06 | 1.31 | 1.58 | 1.17 | 1.41 | 1.68 | 1.17 | 1.41 | 1.80 |
| p Value | 0.89 | 0.48 | 0.23 | 0.67 | 0.37 | 0.17 | 0.67 | 0.37 | 0.12 |
| Lower limit of 95% CI | 0.506 | 0.618 | 0.745 | 0.562 | 0.662 | 0.799 | 0.562 | 0.662 | 0.855 |
| Upper limit of 95% CI | 2.20 | 2.76 | 3.34 | 2.45 | 3.00 | 3.55 | 2.45 | 3.00 | 3.79 |

Example 31. Use of C—C Motif Chemokine 24 for Evaluating Renal Status in Patients Admitted to the ICU: Recovery to RIFLE 0 and R from RIFLE I and F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 24 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 24, 48 or 72 hours is non-injury (RIFLE 0) or risk of injury (R) where the recovery period can start from the time of sample collection to 24, 48, 72, 96 or 168 hours after sample collection. "Non-recovered" indicates those patients whose maximum RIFLE stage during a period of 24, 48 or 72 hours is injury (I) or failure (F) where the recovery period can start from the time of sample collection to 24, 48, 72, 96 or 168 hours after sample collection. If a patient dies or is placed on renal replacement therapy (RRT) at any time from sample collection to 24, 48, 72, 96 or 168 hours after sample collection, the patient is considered "non-recovered".

The ability to distinguish the "recovered" and "non-recovered" cohorts is determined using receiver operating characteristic (ROC) analysis.

TABLE 31.1

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 12.9 | 40.4 | 12.2 | 40.4 | 12.5 | 39.7 |
| Average | 40.8 | 91.5 | 39.2 | 91.3 | 40.0 | 90.2 |
| Stdev | 87.7 | 166 | 88.2 | 165 | 89.4 | 164 |
| p (t-test) | | 0.0035 | | 0.0029 | | 0.0044 |
| Min | 0.00127 | 0.00127 | 0.00127 | 0.00127 | 0.00127 | 0.00127 |
| Max | 670 | 1150 | 670 | 1150 | 670 | 1150 |
| n (Patient) | 107 | 209 | 103 | 213 | 100 | 216 |
| sCr only | | | | | | |
| Median | 15.8 | 39.8 | 14.5 | 40.3 | 14.5 | 40.4 |
| Average | 51.4 | 88.2 | 51.4 | 87.7 | 51.2 | 87.7 |
| Stdev | 125 | 157 | 126 | 156 | 127 | 156 |
| p (t-test) | | 0.029 | | 0.031 | | 0.031 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 125 | 190 | 123 | 192 | 122 | 193 |
| UO only | | | | | | |
| Median | 20.4 | 51.1 | 18.4 | 51.1 | 18.4 | 50.6 |
| Average | 54.7 | 121 | 51.1 | 119 | 52.0 | 112 |
| Stdev | 117 | 193 | 117 | 184 | 120 | 178 |
| p (t-test) | | 2.5E−4 | | 9.3E−5 | | 4.7E−4 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 221 | 93 | 207 | 107 | 197 | 117 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.68 | 0.66 | 0.64 | 0.71 | 0.66 | 0.64 | 0.69 |
| SE | 0.031 | 0.031 | 0.034 | 0.031 | 0.031 | 0.032 | 0.031 | 0.031 | 0.032 |
| p Value | 1.5E−6 | 2.5E−5 | 9.7E−8 | 1.7E−7 | 1.3E−5 | 8.3E−11 | 4.8E−7 | 7.2E−6 | 1.3E−9 |
| nCohort Recovered | 107 | 125 | 221 | 103 | 123 | 207 | 100 | 122 | 197 |
| nCohort Non-recovered | 209 | 190 | 93 | 213 | 192 | 107 | 216 | 193 | 117 |
| Cutoff Quartile 2 | 4.17 | 4.15 | 4.13 | 4.17 | 4.15 | 4.13 | 4.17 | 4.15 | 4.13 |
| Sensitivity | 80% | 81% | 88% | 81% | 81% | 90% | 81% | 81% | 88% |
| Specificity | 36% | 34% | 31% | 37% | 35% | 33% | 37% | 35% | 33% |
| Cutoff Quartile 3 | 29.6 | 29.3 | 28.8 | 29.6 | 29.3 | 28.8 | 29.6 | 29.3 | 28.8 |
| Sensitivity | 59% | 59% | 69% | 59% | 60% | 71% | 58% | 60% | 68% |
| Specificity | 67% | 64% | 58% | 69% | 65% | 61% | 68% | 66% | 61% |
| Cutoff Quartile 4 | 74.9 | 74.4 | 74.6 | 74.9 | 74.4 | 74.6 | 74.9 | 74.4 | 74.6 |
| Sensitivity | 32% | 32% | 43% | 32% | 32% | 43% | 31% | 32% | 40% |
| Specificity | 88% | 86% | 82% | 89% | 85% | 84% | 89% | 86% | 84% |
| OR Quartile 2 | 2.26 | 2.24 | 3.31 | 2.45 | 2.33 | 4.27 | 2.43 | 2.37 | 3.62 |

TABLE 31.1-continued

Comparison of marker levels and the area under the ROC curve (AUC) in urine samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 0.0023 | 0.0022 | 6.8E−4 | 8.2E−4 | 0.0014 | 3.6E−5 | 9.6E−4 | 0.0011 | 6.6E−5 |
| Lower limit of 95% CI | 1.34 | 1.34 | 1.66 | 1.45 | 1.39 | 2.15 | 1.44 | 1.41 | 1.92 |
| Upper limit of 95% CI | 3.81 | 3.76 | 6.61 | 4.15 | 3.91 | 8.50 | 4.12 | 3.99 | 6.82 |
| OR Quartile 3 | 2.94 | 2.61 | 3.04 | 3.21 | 2.78 | 3.81 | 2.98 | 2.87 | 3.37 |
| p Value | 1.5E−5 | 5.5E−5 | 2.2E−5 | 4.5E−6 | 2.0E−5 | 1.8E−7 | 1.9E−5 | 1.2E−5 | 8.4E−7 |
| Lower limit of 95% CI | 1.80 | 1.64 | 1.82 | 1.95 | 1.74 | 2.31 | 1.80 | 1.79 | 2.08 |
| Upper limit of 95% CI | 4.80 | 4.16 | 5.08 | 5.29 | 4.44 | 6.30 | 4.90 | 4.60 | 5.46 |
| OR Quartile 4 | 3.34 | 2.81 | 3.52 | 3.92 | 2.72 | 3.98 | 3.72 | 2.92 | 3.46 |
| p Value | 2.7E−4 | 5.3E−4 | 4.3E−6 | 1.0E−4 | 8.2E−4 | 4.0E−7 | 1.9E−4 | 4.1E−4 | 4.2E−6 |
| Lower limit of 95% CI | 1.74 | 1.57 | 2.06 | 1.97 | 1.51 | 2.33 | 1.87 | 1.61 | 2.04 |
| Upper limit of 95% CI | 6.39 | 5.04 | 6.02 | 7.81 | 4.88 | 6.78 | 7.40 | 5.30 | 5.88 |

TABLE 31.2

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 16.9 | 43.2 | 14.5 | 43.2 | 14.5 | 42.2 |
| Average | 38.1 | 101 | 37.6 | 101 | 37.1 | 100.0 |
| Stdev | 73.1 | 178 | 73.5 | 177 | 73.5 | 176 |
| p (t-test) | | 1.3E−4 | | 1.3E−4 | | 1.5E−4 |
| Min | 0.00127 | 0.00127 | 0.00127 | 0.00127 | 0.00127 | 0.00127 |
| Max | 670 | 1150 | 670 | 1150 | 670 | 1150 |
| n (Patient) | 135 | 181 | 133 | 183 | 129 | 187 |
| sCr only | | | | | | |
| Median | 17.9 | 42.7 | 17.6 | 42.2 | 17.2 | 42.7 |
| Average | 46.2 | 99.1 | 46.2 | 98.8 | 46.0 | 98.6 |
| Stdev | 111 | 168 | 111 | 168 | 112 | 167 |
| p (t-test) | | 0.0012 | | 0.0014 | | 0.0014 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 148 | 168 | 147 | 169 | 146 | 170 |
| UO only | | | | | | |
| Median | 20.4 | 69.8 | 19.9 | 69.8 | 19.7 | 55.0 |
| Average | 53.3 | 127 | 51.1 | 127 | 51.6 | 117 |
| Stdev | 117 | 195 | 115 | 192 | 118 | 183 |
| p (t-test) | | 4.9E−5 | | 1.9E−5 | | 1.5E−4 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 225 | 89 | 219 | 95 | 206 | 108 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.66 | 0.65 | 0.70 | 0.67 | 0.65 | 0.71 | 0.67 | 0.66 | 0.69 |
| SE | 0.030 | 0.030 | 0.034 | 0.030 | 0.030 | 0.033 | 0.030 | 0.030 | 0.032 |
| p Value | 1.2E−7 | 4.5E−7 | 2.9E−9 | 3.9E−8 | 3.6E−7 | 1.4E−10 | 3.7E−8 | 1.8E−7 | 2.7E−9 |
| nCohort Recovered | 135 | 148 | 225 | 133 | 147 | 219 | 129 | 146 | 206 |

TABLE 31.2-continued

Comparison of marker levels and the area under the ROC curve (AUC) in urine samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-recovered | 181 | 168 | 89 | 183 | 169 | 95 | 187 | 170 | 108 |
| Cutoff Quartile 2 | 4.17 | 4.17 | 4.13 | 4.17 | 4.17 | 4.13 | 4.17 | 4.17 | 4.13 |
| Sensitivity | 82% | 83% | 89% | 82% | 83% | 89% | 82% | 83% | 87% |
| Specificity | 34% | 34% | 31% | 35% | 34% | 32% | 35% | 34% | 32% |
| Cutoff Quartile 3 | 29.6 | 29.6 | 28.8 | 29.6 | 29.6 | 28.8 | 29.6 | 29.6 | 28.8 |
| Sensitivity | 61% | 61% | 72% | 61% | 62% | 73% | 60% | 62% | 69% |
| Specificity | 64% | 63% | 59% | 65% | 63% | 60% | 65% | 64% | 60% |
| Cutoff Quartile 4 | 74.9 | 74.9 | 74.6 | 74.9 | 74.9 | 74.6 | 74.9 | 74.9 | 74.6 |
| Sensitivity | 34% | 35% | 47% | 34% | 34% | 47% | 34% | 35% | 44% |
| Specificity | 87% | 86% | 84% | 88% | 86% | 84% | 88% | 86% | 84% |
| OR Quartile 2 | 2.32 | 2.45 | 3.49 | 2.40 | 2.49 | 3.91 | 2.41 | 2.53 | 3.10 |
| p Value | 0.0015 | 8.5E−4 | 6.2E−4 | 9.3E−4 | 6.8E−4 | 1.8E−4 | 8.9E−4 | 5.3E−4 | 4.8E−4 |
| Lower limit of 95% CI | 1.38 | 1.45 | 1.71 | 1.43 | 1.47 | 1.91 | 1.43 | 1.50 | 1.64 |
| Upper limit of 95% CI | 3.89 | 4.14 | 7.15 | 4.04 | 4.21 | 7.99 | 4.05 | 4.28 | 5.83 |
| OR Quartile 3 | 2.81 | 2.68 | 3.63 | 2.98 | 2.76 | 3.95 | 2.85 | 2.83 | 3.44 |
| p Value | 1.2E−5 | 2.2E−5 | 2.1E−6 | 4.0E−6 | 1.4E−5 | 3.0E−7 | 1.0E−5 | 8.1E−6 | 1.0E−6 |
| Lower limit of 95% CI | 1.77 | 1.70 | 2.13 | 1.87 | 1.75 | 2.34 | 1.79 | 1.79 | 2.09 |
| Upper limit of 95% CI | 4.46 | 4.23 | 6.19 | 4.75 | 4.35 | 6.68 | 4.54 | 4.48 | 5.64 |
| OR Quartile 4 | 3.62 | 3.19 | 4.54 | 3.84 | 3.14 | 4.90 | 3.95 | 3.35 | 4.19 |
| p Value | 2.2E−5 | 5.0E−5 | 5.4E−8 | 1.3E−5 | 6.5E−5 | 1.0E−8 | 1.3E−5 | 3.0E−5 | 1.6E−7 |
| Lower limit of 95% CI | 2.00 | 1.82 | 2.63 | 2.10 | 1.79 | 2.84 | 2.13 | 1.90 | 2.45 |
| Upper limit of 95% CI | 6.55 | 5.59 | 7.83 | 7.03 | 5.49 | 8.44 | 7.33 | 5.91 | 7.16 |

TABLE 31.3

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 16.9 | 44.6 | 16.9 | 44.6 | 15.9 | 44.6 |
| Average | 49.3 | 97.8 | 49.6 | 96.9 | 49.2 | 96.2 |
| Stdev | 117 | 166 | 118 | 166 | 119 | 164 |
| p (t-test) | | 0.0031 | | 0.0040 | | 0.0042 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 153 | 163 | 151 | 165 | 147 | 169 |
| | sCr only | | | | | |
| Median | 17.2 | 44.7 | 16.9 | 44.6 | 16.4 | 44.7 |
| Average | 47.8 | 102 | 47.8 | 101 | 47.6 | 101 |
| Stdev | 112 | 171 | 112 | 170 | 113 | 170 |
| p (t-test) | | 0.0010 | | 0.0011 | | 0.0011 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 160 | 156 | 159 | 157 | 158 | 158 |
| | UO only | | | | | |
| Median | 23.0 | 58.3 | 22.9 | 56.7 | 21.0 | 54.5 |
| Average | 59.8 | 110 | 59.8 | 109 | 60.6 | 102 |
| Stdev | 137 | 163 | 138 | 162 | 141 | 155 |

TABLE 31.3-continued

Comparison of marker levels and the area under the ROC curve (AUC) in urine samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.0062 | | | 0.0068 | | | 0.019 | |
| Min | 0.00127 | 0.00127 | 0.00127 | 0.00127 | 0.00127 | 0.00127 | | | |
| Max | 1140 | 1150 | 1140 | 1150 | 1140 | 1150 | | | |
| n (Patient) | 223 | 91 | 222 | 92 | 211 | 103 | | | |

| | Recovery Period Duration (hr) ||||||||| 
|---|---|---|---|---|---|---|---|---|---|
| | 24 ||| 48 ||| 72 |||
| | sCr or UO | sCr only | UO only | sCr or UO | sCr only | UO only | sCr or UO | sCr only | UO only |
| AUC | 0.66 | 0.67 | 0.68 | 0.66 | 0.67 | 0.68 | 0.67 | 0.67 | 0.66 |
| SE | 0.030 | 0.030 | 0.035 | 0.030 | 0.030 | 0.035 | 0.030 | 0.030 | 0.034 |
| p Value | 8.2E−8 | 3.1E−8 | 4.0E−7 | 1.1E−7 | 2.5E−8 | 3.1E−7 | 3.3E−8 | 1.2E−8 | 1.1E−6 |
| nCohort Recovered | 153 | 160 | 223 | 151 | 159 | 222 | 147 | 158 | 211 |
| nCohort Non-recovered | 163 | 156 | 91 | 165 | 157 | 92 | 169 | 158 | 103 |
| Cutoff Quartile 2 | 4.17 | 4.17 | 4.13 | 4.17 | 4.17 | 4.13 | 4.17 | 4.17 | 4.13 |
| Sensitivity | 83% | 84% | 86% | 83% | 84% | 86% | 83% | 84% | 85% |
| Specificity | 33% | 34% | 30% | 34% | 34% | 30% | 35% | 34% | 30% |
| Cutoff Quartile 3 | 29.6 | 29.6 | 28.8 | 29.6 | 29.6 | 28.8 | 29.6 | 29.6 | 28.8 |
| Sensitivity | 63% | 63% | 68% | 62% | 64% | 68% | 62% | 64% | 67% |
| Specificity | 63% | 63% | 57% | 64% | 64% | 58% | 64% | 64% | 58% |
| Cutoff Quartile 4 | 74.9 | 74.9 | 74.6 | 74.9 | 74.9 | 74.6 | 74.9 | 74.9 | 74.6 |
| Sensitivity | 36% | 36% | 45% | 35% | 36% | 45% | 35% | 36% | 42% |
| Specificity | 86% | 86% | 83% | 86% | 86% | 83% | 86% | 86% | 83% |
| OR Quartile 2 | 2.41 | 2.67 | 2.52 | 2.50 | 2.72 | 2.57 | 2.68 | 2.76 | 2.55 |
| p Value | 0.0011 | 3.6E−4 | 0.0055 | 6.9E−4 | 2.8E−4 | 0.0046 | 2.7E−4 | 2.2E−4 | 0.0031 |
| Lower limit of 95% CI | 1.42 | 1.56 | 1.31 | 1.47 | 1.58 | 1.34 | 1.58 | 1.61 | 1.37 |
| Upper limit of 95% CI | 4.09 | 4.58 | 4.85 | 4.23 | 4.65 | 4.94 | 4.54 | 4.74 | 4.75 |
| OR Quartile 3 | 2.90 | 2.97 | 2.88 | 2.90 | 3.06 | 2.96 | 2.91 | 3.14 | 2.84 |
| p Value | 5.1E−6 | 3.0E−6 | 5.6E−5 | 5.0E−6 | 1.8E−6 | 3.6E−5 | 4.9E−6 | 1.0E−6 | 3.5E−5 |
| Lower limit of 95% CI | 1.83 | 1.88 | 1.72 | 1.84 | 1.93 | 1.77 | 1.84 | 1.98 | 1.73 |
| Upper limit of 95% CI | 4.57 | 4.70 | 4.82 | 4.58 | 4.83 | 4.95 | 4.60 | 4.97 | 4.65 |
| OR Quartile 4 | 3.47 | 3.34 | 3.99 | 3.36 | 3.28 | 3.89 | 3.41 | 3.49 | 3.48 |
| p Value | 1.4E−5 | 1.7E−5 | 5.2E−7 | 2.3E−5 | 2.3E−5 | 7.9E−7 | 2.3E−5 | 1.0E−5 | 4.1E−6 |
| Lower limit of 95% CI | 1.98 | 1.93 | 2.32 | 1.91 | 1.89 | 2.27 | 1.93 | 2.00 | 2.05 |
| Upper limit of 95% CI | 6.09 | 5.78 | 6.86 | 5.88 | 5.68 | 6.68 | 6.01 | 6.08 | 5.93 |

TABLE 31.4

Comparison of marker levels and the area under the ROC curve (AUC) in urine samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) ||||||
|---|---|---|---|---|---|---|
| | 24 || 48 || 72 ||
| | Recovered Cohort | Non-recovered Cohort | Recovered Cohort | Non-recovered Cohort | Recovered Cohort | Non-recovered Cohort |
| | sCr or UO ||||||
| Median | 16.5 | 49.9 | 16.7 | 48.2 | 16.2 | 48.2 |
| Average | 53.9 | 97.2 | 54.5 | 95.6 | 54.2 | 94.9 |
| Stdev | 127 | 163 | 128 | 161 | 129 | 160 |

TABLE 31.4-continued

Comparison of marker levels and the area under the ROC curve (AUC) in urine samples
for the "recovered" and "non-recovered" cohorts where recovery starts
within 96 hours after sample collection and renal status is assessed by serum creatinine
(sCr) only, urine output (UO) only, or serum creatinine or urine output RIFLE criteria.

| | | | | | | |
|---|---|---|---|---|---|---|
| p (t-test) | | 0.0083 | | 0.012 | | 0.013 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 167 | 149 | 164 | 152 | 160 | 156 | sCr only

| | | | | | | |
|---|---|---|---|---|---|---|
| Median | 16.9 | 49.9 | 16.7 | 49.5 | 16.5 | 49.9 |
| Average | 52.1 | 100 | 52.2 | 100 | 52.0 | 99.9 |
| Stdev | 123 | 167 | 123 | 166 | 124 | 166 |
| p (t-test) | | 0.0033 | | 0.0036 | | 0.0036 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 171 | 145 | 170 | 146 | 169 | 147 |

UO only

| | | | | | | |
|---|---|---|---|---|---|---|
| Median | 20.7 | 64.0 | 21.0 | 58.3 | 21.0 | 54.7 |
| Average | 59.5 | 110 | 59.8 | 108 | 60.5 | 103 |
| Stdev | 138 | 161 | 138 | 161 | 140 | 156 |
| p (t-test) | | 0.0057 | | 0.0072 | | 0.016 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 222 | 92 | 221 | 93 | 213 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.67 | 0.69 | 0.67 | 0.68 | 0.69 | 0.67 | 0.68 | 0.67 |
| SE | 0.030 | 0.030 | 0.034 | 0.030 | 0.030 | 0.034 | 0.030 | 0.030 | 0.034 |
| p Value | 8.1E−9 | 1.0E−8 | 1.3E−8 | 3.3E−8 | 8.2E−9 | 4.6E−8 | 1.1E−8 | 3.8E−9 | 5.5E−7 |
| nCohort Recovered | 167 | 171 | 222 | 164 | 170 | 221 | 160 | 169 | 213 |
| nCohort Non-recovered | 149 | 145 | 92 | 152 | 146 | 93 | 156 | 147 | 101 |
| Cutoff Quartile 2 | 4.17 | 4.17 | 4.13 | 4.17 | 4.17 | 4.13 | 4.17 | 4.17 | 4.13 |
| Sensitivity | 84% | 84% | 88% | 84% | 84% | 87% | 84% | 84% | 86% |
| Specificity | 33% | 33% | 31% | 33% | 33% | 30% | 34% | 33% | 31% |
| Cutoff Quartile 3 | 29.6 | 29.6 | 28.8 | 29.6 | 29.6 | 28.8 | 29.6 | 29.6 | 28.8 |
| Sensitivity | 66% | 66% | 71% | 65% | 66% | 70% | 65% | 66% | 67% |
| Specificity | 64% | 63% | 59% | 64% | 64% | 58% | 64% | 64% | 58% |
| Cutoff Quartile 4 | 74.9 | 74.9 | 74.6 | 74.9 | 74.9 | 74.6 | 74.9 | 74.9 | 74.6 |
| Sensitivity | 37% | 37% | 46% | 36% | 37% | 45% | 36% | 37% | 43% |
| Specificity | 86% | 85% | 83% | 85% | 85% | 83% | 86% | 86% | 83% |
| OR Quartile 2 | 2.56 | 2.58 | 3.25 | 2.49 | 2.63 | 2.94 | 2.67 | 2.67 | 2.73 |
| p Value | 7.0E−4 | 6.9E−4 | 8.3E−4 | 8.8E−4 | 5.5E−4 | 0.0016 | 3.6E−4 | 4.4E−4 | 0.0020 |
| Lower limit of 95% CI | 1.49 | 1.49 | 1.63 | 1.46 | 1.52 | 1.50 | 1.56 | 1.54 | 1.45 |
| Upper limit of 95% CI | 4.40 | 4.47 | 6.49 | 4.27 | 4.55 | 5.74 | 4.58 | 4.62 | 5.15 |
| OR Quartile 3 | 3.43 | 3.26 | 3.40 | 3.32 | 3.34 | 3.26 | 3.32 | 3.43 | 2.87 |
| p Value | 1.9E−7 | 5.6E−7 | 4.3E−6 | 3.4E−7 | 3.2E−7 | 7.8E−6 | 3.4E−7 | 1.8E−7 | 3.2E−5 |
| Lower limit of 95% CI | 2.16 | 2.05 | 2.02 | 2.10 | 2.10 | 1.94 | 2.09 | 2.16 | 1.75 |
| Upper limit of 95% CI | 5.45 | 5.17 | 5.73 | 5.27 | 5.31 | 5.46 | 5.26 | 5.46 | 4.72 |
| OR Quartile 4 | 3.49 | 3.47 | 4.20 | 3.31 | 3.40 | 4.10 | 3.34 | 3.61 | 3.65 |
| p Value | 7.2E−6 | 6.9E−6 | 2.0E−7 | 1.7E−5 | 9.2E−6 | 3.1E−7 | 1.7E−5 | 4.0E−6 | 2.0E−6 |
| Lower limit of 95% CI | 2.02 | 2.02 | 2.44 | 1.92 | 1.98 | 2.39 | 1.93 | 2.09 | 2.14 |
| Upper limit of 95% CI | 6.02 | 5.96 | 7.22 | 5.70 | 5.85 | 7.03 | 5.78 | 6.24 | 6.21 |

TABLE 31.5

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 19.7 | 49.9 | 20.1 | 48.2 | 19.9 | 49.2 |
| Average | 60.2 | 99.3 | 60.8 | 97.7 | 60.8 | 97.3 |
| Stdev | 141 | 153 | 141 | 152 | 142 | 152 |
| p (t-test) | | 0.022 | | 0.030 | | 0.032 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 202 | 114 | 200 | 116 | 199 | 117 |
| | sCr only | | | | | |
| Median | 18.8 | 46.0 | 18.8 | 46.0 | 18.8 | 46.0 |
| Average | 53.6 | 103 | 53.6 | 103 | 53.6 | 103 |
| Stdev | 120 | 173 | 120 | 173 | 120 | 173 |
| p (t-test) | | 0.0028 | | 0.0028 | | 0.0028 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 184 | 132 | 184 | 132 | 184 | 132 |
| | UO only | | | | | |
| Median | 21.9 | 54.2 | 22.7 | 53.9 | 22.7 | 53.9 |
| Average | 61.1 | 103 | 61.4 | 102 | 61.7 | 101 |
| Stdev | 140 | 158 | 140 | 157 | 141 | 156 |
| p (t-test) | | 0.019 | | 0.023 | | 0.028 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 216 | 98 | 215 | 99 | 213 | 101 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.66 | 0.67 | 0.66 | 0.66 | 0.67 | 0.66 | 0.66 | 0.67 |
| SE | 0.032 | 0.031 | 0.034 | 0.033 | 0.031 | 0.034 | 0.032 | 0.031 | 0.034 |
| p Value | 1.7E−7 | 4.6E−7 | 3.0E−7 | 8.0E−7 | 4.6E−7 | 8.5E−7 | 5.6E−7 | 4.6E−7 | 1.0E−6 |
| nCohort Recovered | 202 | 184 | 216 | 200 | 184 | 215 | 199 | 184 | 213 |
| nCohort Non-recovered | 114 | 132 | 98 | 116 | 132 | 99 | 117 | 132 | 101 |
| Cutoff Quartile 2 | 4.17 | 4.17 | 4.13 | 4.17 | 4.17 | 4.13 | 4.17 | 4.17 | 4.13 |
| Sensitivity | 87% | 84% | 88% | 86% | 84% | 87% | 86% | 84% | 87% |
| Specificity | 32% | 32% | 31% | 32% | 32% | 31% | 32% | 32% | 31% |
| Cutoff Quartile 3 | 29.6 | 29.6 | 28.8 | 29.6 | 29.6 | 28.8 | 29.6 | 29.6 | 28.8 |
| Sensitivity | 68% | 65% | 68% | 66% | 65% | 68% | 67% | 65% | 67% |
| Specificity | 60% | 61% | 58% | 60% | 61% | 58% | 60% | 61% | 58% |
| Cutoff Quartile 4 | 74.9 | 74.9 | 74.6 | 74.9 | 74.9 | 74.6 | 74.9 | 74.9 | 74.6 |
| Sensitivity | 39% | 39% | 42% | 39% | 39% | 41% | 38% | 39% | 41% |
| Specificity | 83% | 85% | 82% | 83% | 85% | 82% | 83% | 85% | 82% |
| OR Quartile 2 | 3.06 | 2.43 | 3.22 | 2.87 | 2.43 | 2.93 | 2.92 | 2.43 | 3.04 |
| p Value | 3.9E−4 | 0.0019 | 6.1E−4 | 6.4E−4 | 0.0019 | 0.0012 | 5.2E−4 | 0.0019 | 8.1E−4 |
| Lower limit of 95% CI | 1.65 | 1.39 | 1.65 | 1.57 | 1.39 | 1.53 | 1.60 | 1.39 | 1.59 |
| Upper limit of 95% CI | 5.68 | 4.26 | 6.29 | 5.27 | 4.26 | 5.62 | 5.36 | 4.26 | 5.83 |
| OR Quartile 3 | 3.11 | 2.91 | 3.03 | 2.90 | 2.91 | 2.91 | 2.98 | 2.91 | 2.87 |
| p Value | 4.1E−6 | 6.7E−6 | 1.7E−5 | 1.2E−5 | 6.7E−6 | 2.9E−5 | 7.7E−6 | 6.7E−6 | 3.2E−5 |
| Lower limit of 95% CI | 1.92 | 1.83 | 1.83 | 1.80 | 1.83 | 1.76 | 1.85 | 1.83 | 1.75 |
| Upper limit of 95% CI | 5.04 | 4.63 | 5.01 | 4.68 | 4.63 | 4.80 | 4.80 | 4.63 | 4.72 |
| OR Quartile 4 | 3.22 | 3.51 | 3.37 | 3.09 | 3.51 | 3.29 | 3.03 | 3.51 | 3.15 |
| p Value | 1.3E−5 | 4.0E−6 | 7.8E−6 | 2.5E−5 | 4.0E−6 | 1.1E−5 | 3.4E−5 | 4.0E−6 | 2.2E−5 |
| Lower limit of 95% CI | 1.90 | 2.06 | 1.98 | 1.83 | 2.06 | 1.93 | 1.80 | 2.06 | 1.85 |

TABLE 31.5-continued

Comparison of marker levels and the area under the ROC curve (AUC) in urine samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | | | | | | | | |
|---|---|---|---|---|---|---|---|---|
| Upper limit of 95% CI | 5.45 | 5.98 | 5.74 | 5.23 | 5.98 | 5.60 | 5.12 | 5.98 | 5.35 |

TABLE 31.6

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| *sCr or UO* | | | | | | |
| Median | 330 | 386 | 344 | 380 | 368 | 376 |
| Average | 417 | 562 | 419 | 560 | 429 | 553 |
| Stdev | 315 | 579 | 318 | 576 | 321 | 573 |
| p (t-test) | | 0.10 | | 0.11 | | 0.17 |
| Min | 50.8 | 46.8 | 50.8 | 46.8 | 50.8 | 46.8 |
| Max | 1640 | 4690 | 1640 | 4690 | 1640 | 4690 |
| n (Patient) | 49 | 102 | 48 | 103 | 46 | 105 |
| *sCr only* | | | | | | |
| Median | 327 | 386 | 327 | 386 | 330 | 380 |
| Average | 437 | 555 | 437 | 555 | 441 | 552 |
| Stdev | 379 | 569 | 379 | 569 | 382 | 567 |
| p (t-test) | | 0.18 | | 0.18 | | 0.21 |
| Min | 46.8 | 50.8 | 46.8 | 50.8 | 46.8 | 50.8 |
| Max | 1880 | 4690 | 1880 | 4690 | 1880 | 4690 |
| n (Patient) | 52 | 98 | 52 | 98 | 51 | 99 |
| *UO only* | | | | | | |
| Median | 368 | 384 | 371 | 376 | 364 | 392 |
| Average | 505 | 514 | 485 | 549 | 487 | 540 |
| Stdev | 546 | 404 | 538 | 440 | 550 | 428 |
| p (t-test) | | 0.92 | | 0.47 | | 0.53 |
| Min | 50.8 | 46.8 | 50.8 | 46.8 | 50.8 | 46.8 |
| Max | 4690 | 1880 | 4690 | 1880 | 4690 | 1880 |
| n (Patient) | 104 | 46 | 97 | 53 | 91 | 59 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.57 | 0.53 | 0.57 | 0.57 | 0.56 | 0.55 | 0.57 | 0.56 |
| SE | 0.049 | 0.048 | 0.052 | 0.049 | 0.048 | 0.050 | 0.050 | 0.049 | 0.048 |
| p Value | 0.15 | 0.13 | 0.54 | 0.16 | 0.13 | 0.25 | 0.29 | 0.16 | 0.25 |
| nCohort Recovered | 49 | 52 | 104 | 48 | 52 | 97 | 46 | 51 | 91 |
| nCohort Non-recovered | 102 | 98 | 46 | 103 | 98 | 53 | 105 | 99 | 59 |
| Cutoff Quartile 2 | 218 | 217 | 217 | 218 | 217 | 217 | 218 | 217 | 217 |
| Sensitivity | 75% | 77% | 78% | 76% | 77% | 79% | 75% | 77% | 78% |
| Specificity | 27% | 29% | 27% | 27% | 29% | 28% | 26% | 29% | 27% |
| Cutoff Quartile 3 | 373 | 372 | 372 | 373 | 372 | 372 | 373 | 372 | 372 |
| Sensitivity | 53% | 53% | 52% | 52% | 53% | 51% | 51% | 53% | 53% |
| Specificity | 55% | 56% | 51% | 54% | 56% | 51% | 52% | 55% | 52% |
| Cutoff Quartile 4 | 674 | 661 | 661 | 674 | 661 | 661 | 674 | 661 | 661 |
| Sensitivity | 29% | 29% | 30% | 29% | 29% | 32% | 29% | 28% | 31% |

TABLE 31.6-continued

Comparison of marker levels and the area under the ROC curve (AUC) in EDTA samples for the "recovered" and "non-recovered" cohorts where recovery starts within 24 hours after sample collection and renal status is assessed by serum creatinine (sCr) only, urine output (UO) only, or serum creatinine or urine output RIFLE criteria.

| Specificity | 84% | 81% | 77% | 83% | 81% | 78% | 83% | 80% | 78% |
|---|---|---|---|---|---|---|---|---|---|
| OR Quartile 2 | 1.11 | 1.32 | 1.33 | 1.16 | 1.32 | 1.47 | 1.07 | 1.38 | 1.34 |
| p Value | 0.79 | 0.47 | 0.50 | 0.71 | 0.47 | 0.34 | 0.86 | 0.41 | 0.46 |
| Lower limit of 95% CI | 0.511 | 0.618 | 0.582 | 0.531 | 0.618 | 0.663 | 0.485 | 0.643 | 0.621 |
| Upper limit of 95% CI | 2.42 | 2.83 | 3.02 | 2.53 | 2.83 | 3.27 | 2.37 | 2.95 | 2.89 |
| OR Quartile 3 | 1.38 | 1.43 | 1.13 | 1.30 | 1.43 | 1.06 | 1.16 | 1.35 | 1.18 |
| p Value | 0.36 | 0.30 | 0.72 | 0.45 | 0.30 | 0.86 | 0.68 | 0.39 | 0.62 |
| Lower limit of 95% CI | 0.697 | 0.725 | 0.566 | 0.655 | 0.725 | 0.543 | 0.577 | 0.684 | 0.614 |
| Upper limit of 95% CI | 2.74 | 2.80 | 2.27 | 2.59 | 2.80 | 2.07 | 2.31 | 2.65 | 2.28 |
| OR Quartile 4 | 2.14 | 1.68 | 1.46 | 2.05 | 1.68 | 1.71 | 1.90 | 1.62 | 1.56 |
| p Value | 0.087 | 0.21 | 0.34 | 0.10 | 0.21 | 0.16 | 0.15 | 0.25 | 0.24 |
| Lower limit of 95% CI | 0.895 | 0.742 | 0.671 | 0.861 | 0.742 | 0.805 | 0.794 | 0.714 | 0.741 |
| Upper limit of 95% CI | 5.09 | 3.80 | 3.17 | 4.90 | 3.80 | 3.63 | 4.54 | 3.66 | 3.28 |

TABLE 31.7

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 331 | 392 | 331 | 392 | 348 | 380 |
| Average | 453 | 561 | 453 | 561 | 461 | 553 |
| Stdev | 367 | 594 | 367 | 594 | 369 | 590 |
| p (t-test) | | 0.20 | | 0.20 | | 0.28 |
| Min | 50.8 | 46.8 | 50.8 | 46.8 | 50.8 | 46.8 |
| Max | 1880 | 4690 | 1880 | 4690 | 1880 | 4690 |
| n (Patient) | 64 | 87 | 64 | 87 | 62 | 89 |
| | sCr only | | | | | |
| Median | 330 | 394 | 330 | 394 | 331 | 392 |
| Average | 446 | 570 | 446 | 570 | 449 | 566 |
| Stdev | 368 | 599 | 368 | 599 | 370 | 596 |
| p (t-test) | | 0.14 | | 0.14 | | 0.16 |
| Min | 46.8 | 50.8 | 46.8 | 50.8 | 46.8 | 50.8 |
| Max | 1880 | 4690 | 1880 | 4690 | 1880 | 4690 |
| n (Patient) | 67 | 84 | 67 | 84 | 66 | 85 |
| | UO only | | | | | |
| Median | 337 | 396 | 337 | 396 | 337 | 396 |
| Average | 493 | 543 | 487 | 554 | 496 | 529 |
| Stdev | 544 | 404 | 542 | 413 | 557 | 403 |
| p (t-test) | | 0.58 | | 0.45 | | 0.70 |
| Min | 50.8 | 46.8 | 50.8 | 46.8 | 50.8 | 46.8 |
| Max | 4690 | 1700 | 4690 | 1700 | 4690 | 1700 |
| n (Patient) | 105 | 45 | 103 | 47 | 95 | 55 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.55 | 0.57 | 0.56 | 0.55 | 0.57 | 0.57 | 0.53 | 0.56 | 0.55 |
| SE | 0.047 | 0.047 | 0.052 | 0.047 | 0.047 | 0.051 | 0.048 | 0.047 | 0.049 |

TABLE 31.7-continued

Comparison of marker levels and the area under the ROC curve (AUC) in EDTA samples for the "recovered" and "non-recovered" cohorts where recovery starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p Value | 0.29 | 0.15 | 0.23 | 0.29 | 0.15 | 0.16 | 0.46 | 0.18 | 0.34 |
| nCohort Recovered | 64 | 67 | 105 | 64 | 67 | 103 | 62 | 66 | 95 |
| nCohort Non-recovered | 87 | 84 | 45 | 87 | 84 | 47 | 89 | 85 | 55 |
| Cutoff Quartile 2 | 218 | 218 | 217 | 218 | 218 | 217 | 218 | 218 | 217 |
| Sensitivity | 75% | 76% | 80% | 75% | 76% | 81% | 74% | 76% | 76% |
| Specificity | 25% | 27% | 28% | 25% | 27% | 28% | 24% | 27% | 26% |
| Cutoff Quartile 3 | 373 | 373 | 372 | 373 | 373 | 372 | 373 | 373 | 372 |
| Sensitivity | 54% | 55% | 56% | 54% | 55% | 55% | 53% | 54% | 55% |
| Specificity | 55% | 55% | 52% | 55% | 55% | 52% | 53% | 55% | 53% |
| Cutoff Quartile 4 | 674 | 674 | 661 | 674 | 674 | 661 | 674 | 674 | 661 |
| Sensitivity | 29% | 30% | 33% | 29% | 30% | 34% | 28% | 29% | 31% |
| Specificity | 80% | 81% | 78% | 80% | 81% | 79% | 79% | 80% | 78% |
| OR Quartile 2 | 0.985 | 1.18 | 1.53 | 0.985 | 1.18 | 1.65 | 0.916 | 1.22 | 1.15 |
| p Value | 0.97 | 0.67 | 0.33 | 0.97 | 0.67 | 0.24 | 0.82 | 0.60 | 0.72 |
| Lower limit of 95% CI | 0.468 | 0.562 | 0.655 | 0.468 | 0.562 | 0.711 | 0.432 | 0.583 | 0.533 |
| Upper limit of 95% CI | 2.07 | 2.46 | 3.56 | 2.07 | 2.46 | 3.85 | 1.94 | 2.55 | 2.50 |
| OR Quartile 3 | 1.42 | 1.49 | 1.38 | 1.42 | 1.49 | 1.36 | 1.27 | 1.42 | 1.33 |
| p Value | 0.29 | 0.22 | 0.37 | 0.29 | 0.22 | 0.38 | 0.47 | 0.29 | 0.40 |
| Lower limit of 95% CI | 0.742 | 0.783 | 0.682 | 0.742 | 0.783 | 0.682 | 0.665 | 0.742 | 0.685 |
| Upper limit of 95% CI | 2.71 | 2.85 | 2.77 | 2.71 | 2.85 | 2.73 | 2.44 | 2.70 | 2.60 |
| OR Quartile 4 | 1.58 | 1.76 | 1.78 | 1.58 | 1.76 | 1.90 | 1.47 | 1.70 | 1.58 |
| p Value | 0.24 | 0.15 | 0.14 | 0.24 | 0.15 | 0.10 | 0.32 | 0.17 | 0.23 |
| Lower limit of 95% CI | 0.736 | 0.819 | 0.823 | 0.736 | 0.819 | 0.884 | 0.684 | 0.790 | 0.745 |
| Upper limit of 95% CI | 3.40 | 3.78 | 3.86 | 3.40 | 3.78 | 4.09 | 3.17 | 3.65 | 3.34 |

TABLE 31.8

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 332 | 386 | 348 | 380 | 348 | 380 |
| Average | 461 | 566 | 467 | 559 | 460 | 563 |
| Stdev | 373 | 612 | 372 | 611 | 363 | 610 |
| p (t-test) | | 0.21 | | 0.27 | | 0.22 |
| Min | 50.8 | 46.8 | 50.8 | 46.8 | 50.8 | 46.8 |
| Max | 1880 | 4690 | 1880 | 4690 | 1880 | 4690 |
| n (Patient) | 73 | 78 | 72 | 79 | 70 | 81 |
| sCr only | | | | | | |
| Median | 331 | 392 | 331 | 392 | 331 | 392 |
| Average | 448 | 580 | 448 | 580 | 448 | 580 |
| Stdev | 366 | 616 | 366 | 616 | 366 | 616 |
| p (t-test) | | 0.11 | | 0.11 | | 0.11 |
| Min | 46.8 | 50.8 | 46.8 | 50.8 | 46.8 | 50.8 |
| Max | 1880 | 4690 | 1880 | 4690 | 1880 | 4690 |
| n (Patient) | 74 | 77 | 74 | 77 | 74 | 77 |
| UO only | | | | | | |
| Median | 332 | 396 | 330 | 397 | 334 | 394 |
| Average | 500 | 526 | 487 | 554 | 496 | 528 |
| Stdev | 550 | 385 | 546 | 401 | 555 | 405 |
| p (t-test) | | 0.78 | | 0.45 | | 0.71 |

TABLE 31.8-continued

Comparison of marker levels and the area under the ROC curve (AUC) in EDTA samples for the "recovered" and "non-recovered" cohorts where recovery starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Min | 50.8 | | 46.8 | 50.8 | | 46.8 | 50.8 | | 46.8 |
| Max | 4690 | | 1700 | 4690 | | 1700 | 4690 | | 1700 |
| n (Patient) | 105 | | 45 | 103 | | 47 | 96 | | 54 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.55 | 0.57 | 0.56 | 0.54 | 0.57 | 0.58 | 0.54 | 0.57 | 0.54 |
| SE | 0.047 | 0.047 | 0.052 | 0.047 | 0.047 | 0.051 | 0.047 | 0.047 | 0.049 |
| p Value | 0.29 | 0.13 | 0.28 | 0.42 | 0.13 | 0.11 | 0.41 | 0.13 | 0.37 |
| nCohort Recovered | 73 | 74 | 105 | 72 | 74 | 103 | 70 | 74 | 96 |
| nCohort Non-recovered | 78 | 77 | 45 | 79 | 77 | 47 | 81 | 77 | 54 |
| Cutoff Quartile 2 | 218 | 218 | 217 | 218 | 218 | 217 | 218 | 218 | 217 |
| Sensitivity | 77% | 78% | 80% | 76% | 78% | 81% | 75% | 78% | 76% |
| Specificity | 27% | 28% | 28% | 26% | 28% | 28% | 26% | 28% | 26% |
| Cutoff Quartile 3 | 373 | 373 | 372 | 373 | 373 | 372 | 373 | 373 | 372 |
| Sensitivity | 54% | 55% | 58% | 53% | 55% | 60% | 53% | 55% | 56% |
| Specificity | 53% | 54% | 53% | 53% | 54% | 54% | 53% | 54% | 53% |
| Cutoff Quartile 4 | 674 | 674 | 661 | 674 | 674 | 661 | 674 | 674 | 661 |
| Sensitivity | 27% | 29% | 29% | 27% | 29% | 32% | 27% | 29% | 30% |
| Specificity | 77% | 78% | 76% | 76% | 78% | 78% | 77% | 78% | 77% |
| OR Quartile 2 | 1.26 | 1.40 | 1.53 | 1.13 | 1.40 | 1.65 | 1.06 | 1.40 | 1.11 |
| p Value | 0.54 | 0.37 | 0.33 | 0.74 | 0.37 | 0.24 | 0.89 | 0.37 | 0.79 |
| Lower limit of 95% CI | 0.602 | 0.668 | 0.655 | 0.543 | 0.668 | 0.711 | 0.506 | 0.668 | 0.513 |
| Upper limit of 95% CI | 2.63 | 2.93 | 3.56 | 2.36 | 2.93 | 3.85 | 2.20 | 2.93 | 2.40 |
| OR Quartile 3 | 1.34 | 1.41 | 1.56 | 1.27 | 1.41 | 1.76 | 1.27 | 1.41 | 1.42 |
| p Value | 0.37 | 0.29 | 0.21 | 0.47 | 0.29 | 0.11 | 0.47 | 0.29 | 0.31 |
| Lower limit of 95% CI | 0.706 | 0.744 | 0.773 | 0.669 | 0.744 | 0.872 | 0.668 | 0.744 | 0.725 |
| Upper limit of 95% CI | 2.54 | 2.68 | 3.16 | 2.41 | 2.68 | 3.54 | 2.41 | 2.68 | 2.77 |
| OR Quartile 4 | 1.21 | 1.45 | 1.30 | 1.17 | 1.45 | 1.63 | 1.26 | 1.45 | 1.42 |
| p Value | 0.61 | 0.33 | 0.51 | 0.67 | 0.33 | 0.21 | 0.54 | 0.33 | 0.37 |
| Lower limit of 95% CI | 0.580 | 0.690 | 0.593 | 0.560 | 0.690 | 0.756 | 0.599 | 0.690 | 0.667 |
| Upper limit of 95% CI | 2.54 | 3.05 | 2.85 | 2.45 | 3.05 | 3.52 | 2.64 | 3.05 | 3.01 |

TABLE 31.9

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| | sCr or UO | | | | | |
| Median | 348 | 392 | 364 | 386 | 364 | 386 |
| Average | 456 | 575 | 461 | 568 | 455 | 571 |
| Stdev | 368 | 621 | 368 | 620 | 359 | 619 |
| p (t-test) | | 0.15 | | 0.20 | | 0.16 |

TABLE 31.9-continued

Comparison of marker levels and the area under the ROC curve (AUC) in EDTA samples for the "recovered" and "non-recovered" cohorts where recovery starts within 96 hours after sample collection and renal status is assessed by serum creatinine (sCr) only, urine output (UO) only, or serum creatinine or urine output RIFLE criteria.

| | | | | | | |
|---|---|---|---|---|---|---|
| Min | 50.8 | 46.8 | 50.8 | 46.8 | 50.8 | 46.8 |
| Max | 1880 | 4690 | 1880 | 4690 | 1880 | 4690 |
| n (Patient) | 76 | 75 | 75 | 76 | 73 | 78 | sCr only

| | | | | | | |
|---|---|---|---|---|---|---|
| Median | 330 | 397 | 330 | 397 | 330 | 397 |
| Average | 439 | 594 | 439 | 594 | 439 | 594 |
| Stdev | 363 | 623 | 363 | 623 | 363 | 623 |
| p (t-test) | | 0.063 | | 0.063 | | 0.063 |
| Min | 46.8 | 50.8 | 46.8 | 50.8 | 46.8 | 50.8 |
| Max | 1880 | 4690 | 1880 | 4690 | 1880 | 4690 |
| n (Patient) | 77 | 74 | 77 | 74 | 77 | 74 |

UO only

| | | | | | | |
|---|---|---|---|---|---|---|
| Median | 329 | 412 | 329 | 412 | 332 | 396 |
| Average | 487 | 550 | 487 | 550 | 493 | 532 |
| Stdev | 551 | 398 | 551 | 398 | 555 | 407 |
| p (t-test) | | 0.47 | | 0.47 | | 0.65 |
| Min | 50.8 | 46.8 | 50.8 | 46.8 | 50.8 | 46.8 |
| Max | 4690 | 1700 | 4690 | 1700 | 4690 | 1700 |
| n (Patient) | 100 | 50 | 100 | 50 | 95 | 55 |

| | Recovery Period Duration (hr) | | | | | | | |
|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.59 | 0.58 | 0.55 | 0.59 | 0.58 | 0.55 | 0.59 | 0.55 |
| SE | 0.047 | 0.046 | 0.050 | 0.047 | 0.046 | 0.050 | 0.047 | 0.046 | 0.049 |
| p Value | 0.22 | 0.052 | 0.11 | 0.33 | 0.052 | 0.11 | 0.32 | 0.052 | 0.31 |
| nCohort Recovered | 76 | 77 | 100 | 75 | 77 | 100 | 73 | 77 | 95 |
| nCohort Non-recovered | 75 | 74 | 50 | 76 | 74 | 50 | 78 | 74 | 55 |
| Cutoff Quartile 2 | 218 | 218 | 217 | 218 | 218 | 217 | 218 | 218 | 217 |
| Sensitivity | 77% | 80% | 80% | 76% | 80% | 80% | 76% | 80% | 76% |
| Specificity | 28% | 30% | 28% | 27% | 30% | 28% | 26% | 30% | 26% |
| Cutoff Quartile 3 | 373 | 373 | 372 | 373 | 373 | 372 | 373 | 373 | 372 |
| Sensitivity | 53% | 55% | 60% | 53% | 55% | 60% | 53% | 55% | 56% |
| Specificity | 53% | 55% | 55% | 52% | 55% | 55% | 52% | 55% | 54% |
| Cutoff Quartile 4 | 674 | 674 | 661 | 674 | 674 | 661 | 674 | 674 | 661 |
| Sensitivity | 28% | 30% | 30% | 28% | 30% | 30% | 28% | 30% | 29% |
| Specificity | 78% | 79% | 77% | 77% | 79% | 77% | 78% | 79% | 77% |
| OR Quartile 2 | 1.30 | 1.68 | 1.56 | 1.17 | 1.68 | 1.56 | 1.09 | 1.68 | 1.15 |
| p Value | 0.48 | 0.18 | 0.29 | 0.67 | 0.18 | 0.29 | 0.81 | 0.18 | 0.72 |
| Lower limit of 95% CI | 0.623 | 0.793 | 0.686 | 0.561 | 0.793 | 0.686 | 0.524 | 0.793 | 0.533 |
| Upper limit of 95% CI | 2.73 | 3.54 | 3.53 | 2.45 | 3.54 | 3.53 | 2.28 | 3.54 | 2.50 |
| OR Quartile 3 | 1.27 | 1.49 | 1.83 | 1.20 | 1.49 | 1.83 | 1.20 | 1.49 | 1.50 |
| p Value | 0.46 | 0.22 | 0.085 | 0.57 | 0.22 | 0.085 | 0.57 | 0.22 | 0.24 |
| Lower limit of 95% CI | 0.670 | 0.785 | 0.920 | 0.636 | 0.785 | 0.920 | 0.635 | 0.785 | 0.767 |
| Upper limit of 95% CI | 2.41 | 2.83 | 3.65 | 2.28 | 2.83 | 3.65 | 2.28 | 2.83 | 2.92 |
| OR Quartile 4 | 1.35 | 1.61 | 1.43 | 1.30 | 1.61 | 1.43 | 1.40 | 1.61 | 1.36 |
| p Value | 0.43 | 0.21 | 0.35 | 0.48 | 0.21 | 0.35 | 0.37 | 0.21 | 0.42 |
| Lower limit of 95% CI | 0.645 | 0.768 | 0.669 | 0.623 | 0.768 | 0.669 | 0.666 | 0.768 | 0.642 |
| Upper limit of 95% CI | 2.82 | 3.39 | 3.08 | 2.73 | 3.39 | 3.08 | 2.94 | 3.39 | 2.89 |

TABLE 31.10

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| | Recovery Period Duration (hr) | | | | | |
|---|---|---|---|---|---|---|
| | 24 | | 48 | | 72 | |
| | Recovered Cohort | Non-recovered Cohort | Recovered Cohort | Non-recovered Cohort | Recovered Cohort | Non-recovered Cohort |
| sCr or UO | | | | | | |
| Median | 332 | 397 | 334 | 396 | 332 | 397 |
| Average | 509 | 525 | 514 | 518 | 505 | 529 |
| Stdev | 590 | 377 | 591 | 378 | 589 | 386 |
| p (t-test) | | 0.85 | | 0.96 | | 0.78 |
| Min | 50.8 | 46.8 | 50.8 | 46.8 | 50.8 | 46.8 |
| Max | 4690 | 1540 | 4690 | 1540 | 4690 | 1540 |
| n (Patient) | 89 | 62 | 88 | 63 | 87 | 64 |
| sCr only | | | | | | |
| Median | 332 | 397 | 332 | 397 | 332 | 397 |
| Average | 451 | 586 | 451 | 586 | 451 | 586 |
| Stdev | 373 | 625 | 373 | 625 | 373 | 625 |
| p (t-test) | | 0.11 | | 0.11 | | 0.11 |
| Min | 46.8 | 50.8 | 46.8 | 50.8 | 46.8 | 50.8 |
| Max | 1880 | 4690 | 1880 | 4690 | 1880 | 4690 |
| n (Patient) | 79 | 72 | 79 | 72 | 79 | 72 |
| UO only | | | | | | |
| Median | 326 | 448 | 326 | 448 | 326 | 448 |
| Average | 489 | 544 | 489 | 544 | 485 | 548 |
| Stdev | 565 | 368 | 565 | 368 | 564 | 379 |
| p (t-test) | | 0.53 | | 0.53 | | 0.47 |
| Min | 50.8 | 46.8 | 50.8 | 46.8 | 50.8 | 46.8 |
| Max | 4690 | 1510 | 4690 | 1510 | 4690 | 1510 |
| n (Patient) | 98 | 52 | 98 | 52 | 96 | 54 |

| | Recovery Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.58 | 0.59 | 0.55 | 0.58 | 0.59 | 0.56 | 0.58 | 0.59 |
| SE | 0.048 | 0.047 | 0.050 | 0.048 | 0.047 | 0.050 | 0.048 | 0.047 | 0.049 |
| p Value | 0.22 | 0.096 | 0.068 | 0.34 | 0.096 | 0.068 | 0.23 | 0.096 | 0.072 |
| nCohort Recovered | 89 | 79 | 98 | 88 | 79 | 98 | 87 | 79 | 96 |
| nCohort Non-recovered | 62 | 72 | 52 | 63 | 72 | 52 | 64 | 72 | 54 |
| Cutoff Quartile 2 | 218 | 218 | 217 | 218 | 218 | 217 | 218 | 218 | 217 |
| Sensitivity | 77% | 79% | 81% | 76% | 79% | 81% | 77% | 79% | 80% |
| Specificity | 27% | 29% | 29% | 26% | 29% | 29% | 26% | 29% | 28% |
| Cutoff Quartile 3 | 373 | 373 | 372 | 373 | 373 | 372 | 373 | 373 | 372 |
| Sensitivity | 56% | 56% | 62% | 56% | 56% | 62% | 56% | 56% | 61% |
| Specificity | 54% | 54% | 56% | 53% | 54% | 56% | 54% | 54% | 56% |
| Cutoff Quartile 4 | 674 | 674 | 661 | 674 | 674 | 661 | 674 | 674 | 661 |
| Sensitivity | 27% | 29% | 31% | 27% | 29% | 31% | 28% | 29% | 31% |
| Specificity | 76% | 78% | 78% | 76% | 78% | 78% | 77% | 78% | 78% |
| OR Quartile 2 | 1.27 | 1.56 | 1.68 | 1.13 | 1.56 | 1.68 | 1.17 | 1.56 | 1.53 |
| p Value | 0.54 | 0.24 | 0.21 | 0.75 | 0.24 | 0.21 | 0.67 | 0.24 | 0.30 |
| Lower limit of 95% CI | 0.594 | 0.739 | 0.742 | 0.535 | 0.739 | 0.742 | 0.555 | 0.739 | 0.689 |
| Upper limit of 95% CI | 2.70 | 3.30 | 3.80 | 2.40 | 3.30 | 3.80 | 2.48 | 3.30 | 3.40 |
| OR Quartile 3 | 1.52 | 1.49 | 2.05 | 1.43 | 1.49 | 2.05 | 1.51 | 1.49 | 2.02 |
| p Value | 0.21 | 0.22 | 0.041 | 0.28 | 0.22 | 0.041 | 0.21 | 0.22 | 0.043 |
| Lower limit of 95% CI | 0.790 | 0.786 | 1.03 | 0.748 | 0.786 | 1.03 | 0.789 | 0.786 | 1.02 |

TABLE 31.10-continued

Comparison of marker levels and the area under the ROC curve (AUC) in EDTA samples for the "recovered" and "non-recovered" cohorts where recovery starts within 168 hours after sample collection and renal status is assessed by serum creatinine (sCr) only, urine output (UO) only, or serum creatinine or urine output RIFLE criteria.

| Upper limit of 95% CI | 2.91 | 2.84 | 4.07 | 2.74 | 2.84 | 4.07 | 2.89 | 2.84 | 3.99 |
|---|---|---|---|---|---|---|---|---|---|
| OR Quartile 4 | 1.22 | 1.50 | 1.54 | 1.18 | 1.50 | 1.54 | 1.31 | 1.50 | 1.64 |
| p Value | 0.59 | 0.28 | 0.27 | 0.66 | 0.28 | 0.27 | 0.47 | 0.28 | 0.20 |
| Lower limit of 95% CI | 0.582 | 0.717 | 0.721 | 0.562 | 0.717 | 0.721 | 0.626 | 0.717 | 0.774 |
| Upper limit of 95% CI | 2.57 | 3.14 | 3.27 | 2.47 | 3.14 | 3.27 | 2.75 | 3.14 | 3.48 |

Example 32. Use of C—C Motif Chemokine 24 for Evaluating Renal Status in Patients Admitted to the ICU: Persistent at RIFLE F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 24 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is failure (F) where the persistence period can start from the time of sample collection to 24, 48, 72, 96 or 168 hours after sample collection. "Non-persistent" indicates those patients who are not persistent at failure (F) and whose minimum RIFLE stage during a period of 24, 48 or 72 hours is non-injury (RIFLE 0), risk of injury (R), or injury (I) where the persistence period can start from the time of sample collection to 24, 48, 72, 96 or 168 hours after sample collection. If a patient dies after failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 32.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 19.2 | 54.8 | 19.9 | 72.5 | 23.1 | 73.8 |
| Average | 53.8 | 112 | 53.2 | 123 | 61.3 | 112 |
| Stdev | 120 | 180 | 116 | 191 | 136 | 168 |
| p (t-test) | | 7.2E−4 | | 8.7E−5 | | 0.0070 |
| Min | 0.00127 | 0.00127 | 0.00127 | 0.00127 | 0.00127 | 0.00127 |
| Max | 1070 | 1150 | 1070 | 1150 | 1140 | 1150 |
| n (Patient) | 204 | 112 | 220 | 96 | 235 | 81 |
| sCr only | | | | | | |
| Median | 19.4 | 50.8 | 20.7 | 54.5 | 23.1 | 54.5 |
| Average | 58.7 | 102 | 59.1 | 108 | 66.1 | 95.1 |
| Stdev | 140 | 153 | 137 | 162 | 153 | 121 |
| p (t-test) | | 0.012 | | 0.0062 | | 0.12 |
| Min | 0.00127 | 0.00127 | 0.00127 | 0.00127 | 0.00127 | 0.00127 |
| Max | 1150 | 1140 | 1150 | 1140 | 1150 | 679 |
| n (Patient) | 207 | 108 | 222 | 93 | 234 | 81 |
| UO only | | | | | | |
| Median | 25.9 | 97.0 | 26.1 | 105 | 25.9 | 109 |
| Average | 66.2 | 129 | 66.0 | 135 | 65.9 | 138 |
| Stdev | 138 | 191 | 137 | 197 | 137 | 199 |
| p (t-test) | | 0.011 | | 0.0069 | | 0.0050 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 274 | 40 | 277 | 37 | 278 | 36 |

TABLE 32.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.69 | 0.68 | 0.72 | 0.72 | 0.69 | 0.73 | 0.69 | 0.68 | 0.74 |
| SE | 0.032 | 0.033 | 0.048 | 0.033 | 0.034 | 0.049 | 0.036 | 0.036 | 0.049 |
| p Value | 3.1E−9 | 4.3E−8 | 5.3E−6 | 4.3E−11 | 1.9E−8 | 2.8E−6 | 7.3E−8 | 1.1E−6 | 1.2E−6 |
| nCohort Non-persistent | 204 | 207 | 274 | 220 | 222 | 277 | 235 | 234 | 278 |
| nCohort Persistent | 112 | 108 | 40 | 96 | 93 | 37 | 81 | 81 | 36 |
| Cutoff Quartile 2 | 4.17 | 4.15 | 4.13 | 4.17 | 4.15 | 4.13 | 4.17 | 4.15 | 4.13 |
| Sensitivity | 86% | 86% | 92% | 90% | 89% | 95% | 89% | 89% | 94% |
| Specificity | 31% | 31% | 28% | 31% | 31% | 28% | 30% | 30% | 28% |
| Cutoff Quartile 3 | 29.6 | 29.3 | 28.8 | 29.6 | 29.3 | 28.8 | 29.6 | 29.3 | 28.8 |
| Sensitivity | 68% | 67% | 75% | 71% | 69% | 76% | 69% | 68% | 78% |
| Specificity | 60% | 58% | 54% | 59% | 58% | 53% | 57% | 56% | 54% |
| Cutoff Quartile 4 | 74.9 | 74.4 | 74.6 | 74.9 | 74.4 | 74.6 | 74.9 | 74.4 | 74.6 |
| Sensitivity | 43% | 43% | 57% | 47% | 44% | 59% | 47% | 44% | 61% |
| Specificity | 85% | 84% | 80% | 85% | 83% | 79% | 83% | 82% | 79% |
| OR Quartile 2 | 2.68 | 2.77 | 4.73 | 3.93 | 3.74 | 6.74 | 3.39 | 3.41 | 6.51 |
| p Value | 0.0014 | 0.0013 | 0.012 | 1.7E−4 | 3.0E−4 | 0.0099 | 0.0013 | 0.0013 | 0.011 |
| Lower limit of 95% CI | 1.46 | 1.49 | 1.42 | 1.92 | 1.83 | 1.58 | 1.61 | 1.62 | 1.53 |
| Upper limit of 95% CI | 4.92 | 5.16 | 15.8 | 8.03 | 7.65 | 28.7 | 7.17 | 7.21 | 27.8 |
| OR Quartile 3 | 3.14 | 2.81 | 3.47 | 3.51 | 3.01 | 3.57 | 2.92 | 2.69 | 4.04 |
| p Value | 3.8E−6 | 3.0E−5 | 0.0012 | 1.8E−6 | 2.6E−5 | 0.0015 | 9.3E−5 | 2.7E−4 | 8.5E−4 |
| Lower limit of 95% CI | 1.93 | 1.73 | 1.63 | 2.09 | 1.80 | 1.62 | 1.71 | 1.58 | 1.78 |
| Upper limit of 95% CI | 5.10 | 4.58 | 7.38 | 5.88 | 5.02 | 7.84 | 5.00 | 4.59 | 9.18 |
| OR Quartile 4 | 4.19 | 3.91 | 5.27 | 4.83 | 3.82 | 5.66 | 4.18 | 3.55 | 6.09 |
| p Value | 1.6E−7 | 5.2E−7 | 2.6E−6 | 1.3E−8 | 1.1E−6 | 2.2E−6 | 3.7E−7 | 6.0E−6 | 1.2E−6 |
| Lower limit of 95% CI | 2.45 | 2.30 | 2.64 | 2.81 | 2.23 | 2.76 | 2.41 | 2.05 | 2.93 |
| Upper limit of 95% CI | 7.15 | 6.67 | 10.5 | 8.30 | 6.54 | 11.6 | 7.26 | 6.15 | 12.7 |

TABLE 32.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 16.9 | 54.6 | 18.0 | 63.7 | 20.4 | 59.3 |
| Average | 52.1 | 106 | 51.2 | 116 | 59.6 | 107 |
| Stdev | 123 | 169 | 119 | 179 | 139 | 157 |
| p (t-test) | 0.0012 | | 1.5E−4 | | 0.0077 | |
| Min | 0.00127 | 0.00127 | 0.00127 | 0.00127 | 0.00127 | 0.00127 |
| Max | 1070 | 1150 | 1070 | 1150 | 1140 | 1150 |
| n (Patient) | 185 | 131 | 203 | 113 | 218 | 98 |
| | sCr only | | | | | |
| Median | 18.3 | 50.9 | 18.4 | 54.6 | 20.4 | 50.9 |
| Average | 59.3 | 95.6 | 58.3 | 102 | 66.3 | 89.6 |
| Stdev | 146 | 144 | 141 | 151 | 158 | 113 |
| p (t-test) | 0.031 | | 0.011 | | 0.19 | |
| Min | 0.00127 | 0.00127 | 0.00127 | 0.00127 | 0.00127 | 0.00127 |
| Max | 1150 | 1140 | 1150 | 1140 | 1150 | 679 |
| n (Patient) | 191 | 124 | 205 | 110 | 217 | 98 |

TABLE 32.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | UO only | | | | | |
|---|---|---|---|---|---|---|
| Median | 24.4 | 78.9 | 24.4 | 82.3 | 24.4 | 86.0 |
| Average | 62.8 | 124 | 62.5 | 129 | 62.3 | 131 |
| Stdev | 135 | 182 | 134 | 187 | 134 | 188 |
| p (t-test) | | 0.0040 | | 0.0021 | | 0.0016 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 255 | 59 | 259 | 55 | 260 | 54 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.70 | 0.68 | 0.69 | 0.73 | 0.70 | 0.70 | 0.70 | 0.68 | 0.71 |
| SE | 0.030 | 0.031 | 0.041 | 0.031 | 0.032 | 0.042 | 0.033 | 0.034 | 0.042 |
| p Value | 2.8E−11 | 6.6E−9 | 1.9E−6 | 1.8E−13 | 1.7E−10 | 1.0E−6 | 1.4E−9 | 1.3E−7 | 5.6E−7 |
| nCohort Non-persistent | 185 | 191 | 255 | 203 | 205 | 259 | 218 | 217 | 260 |
| nCohort Persistent | 131 | 124 | 59 | 113 | 110 | 55 | 98 | 98 | 54 |
| Cutoff Quartile 2 | 4.17 | 4.15 | 4.13 | 4.17 | 4.15 | 4.13 | 4.17 | 4.15 | 4.13 |
| Sensitivity | 86% | 86% | 90% | 90% | 90% | 91% | 90% | 90% | 91% |
| Specificity | 33% | 32% | 29% | 33% | 33% | 29% | 32% | 32% | 28% |
| Cutoff Quartile 3 | 29.6 | 29.3 | 28.8 | 29.6 | 29.3 | 28.8 | 29.6 | 29.3 | 28.8 |
| Sensitivity | 68% | 67% | 71% | 72% | 70% | 73% | 70% | 68% | 74% |
| Specificity | 63% | 61% | 55% | 62% | 60% | 55% | 59% | 58% | 55% |
| Cutoff Quartile 4 | 74.9 | 74.4 | 74.6 | 74.9 | 74.4 | 74.6 | 74.9 | 74.4 | 74.6 |
| Sensitivity | 40% | 40% | 51% | 44% | 42% | 53% | 45% | 42% | 54% |
| Specificity | 86% | 84% | 81% | 86% | 84% | 81% | 84% | 82% | 81% |
| OR Quartile 2 | 3.09 | 3.03 | 3.54 | 4.67 | 4.47 | 4.00 | 4.08 | 4.10 | 3.90 |
| p Value | 1.6E−4 | 2.6E−4 | 0.0052 | 1.1E−5 | 2.0E−5 | 0.0046 | 1.1E−4 | 1.1E−4 | 0.0054 |
| Lower limit of 95% CI | 1.72 | 1.67 | 1.46 | 2.35 | 2.25 | 1.53 | 2.00 | 2.01 | 1.49 |
| Upper limit of 95% CI | 5.54 | 5.48 | 8.60 | 9.28 | 8.88 | 10.4 | 8.32 | 8.38 | 10.2 |
| OR Quartile 3 | 3.56 | 3.13 | 3.01 | 4.14 | 3.57 | 3.24 | 3.45 | 2.99 | 3.49 |
| p Value | 1.4E−7 | 2.3E−6 | 4.5E−4 | 2.2E−8 | 4.6E−7 | 3.4E−4 | 2.0E−6 | 2.0E−5 | 1.9E−4 |
| Lower limit of 95% CI | 2.22 | 1.95 | 1.63 | 2.52 | 2.18 | 1.70 | 2.07 | 1.81 | 1.81 |
| Upper limit of 95% CI | 5.72 | 5.03 | 5.56 | 6.81 | 5.86 | 6.15 | 5.75 | 4.95 | 6.73 |
| OR Quartile 4 | 4.16 | 3.51 | 4.35 | 4.76 | 3.75 | 4.66 | 4.26 | 3.39 | 4.87 |
| p Value | 2.6E−7 | 3.6E−6 | 1.4E−6 | 1.5E−8 | 1.1E−6 | 8.5E−7 | 1.3E−7 | 7.1E−6 | 5.0E−7 |
| Lower limit of 95% CI | 2.42 | 2.06 | 2.39 | 2.77 | 2.20 | 2.53 | 2.49 | 1.99 | 2.63 |
| Upper limit of 95% CI | 7.14 | 5.96 | 7.91 | 8.18 | 6.37 | 8.60 | 7.29 | 5.77 | 9.03 |

TABLE 32.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 18.2 | 50.6 | 18.3 | 54.6 | 20.7 | 50.9 |
| Average | 52.1 | 102 | 50.2 | 110 | 59.8 | 101 |
| Stdev | 123 | 167 | 118 | 175 | 141 | 153 |

TABLE 32.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.0026 | | 3.1E−4 | | 0.017 |
| Min | 0.00127 | 0.00127 | 0.00127 | 0.00127 | 0.00127 | 0.00127 |
| Max | 1070 | 1150 | 1070 | 1150 | 1140 | 1150 |
| n (Patient) | 174 | 142 | 189 | 127 | 204 | 112 | sCr only

| | | | | | | |
|---|---|---|---|---|---|---|
| Median | 19.2 | 48.2 | 19.7 | 50.6 | 22.7 | 48.2 |
| Average | 58.8 | 93.6 | 59.1 | 96.8 | 68.0 | 84.3 |
| Stdev | 146 | 145 | 144 | 146 | 161 | 110 |
| p (t-test) | | 0.036 | | 0.026 | | 0.35 |
| Min | 0.00127 | 0.00127 | 0.00127 | 0.00127 | 0.00127 | 0.00127 |
| Max | 1150 | 1140 | 1150 | 1140 | 1150 | 679 |
| n (Patient) | 181 | 134 | 194 | 121 | 207 | 108 |

UO only

| | | | | | | |
|---|---|---|---|---|---|---|
| Median | 24.4 | 73.5 | 24.9 | 73.6 | 24.9 | 73.6 |
| Average | 62.2 | 117 | 62.0 | 122 | 62.0 | 122 |
| Stdev | 135 | 177 | 134 | 182 | 134 | 182 |
| p (t-test) | | 0.0063 | | 0.0035 | | 0.0035 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 245 | 69 | 250 | 64 | 250 | 64 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.65 | 0.67 | 0.70 | 0.67 | 0.67 | 0.67 | 0.65 | 0.67 |
| SE | 0.031 | 0.032 | 0.039 | 0.031 | 0.032 | 0.040 | 0.033 | 0.033 | 0.040 |
| p Value | 4.2E−8 | 1.1E−6 | 1.3E−5 | 1.2E−10 | 5.1E−8 | 1.5E−5 | 1.2E−7 | 8.7E−6 | 1.5E−5 |
| nCohort Non-persistent | 174 | 181 | 245 | 189 | 194 | 250 | 204 | 207 | 250 |
| nCohort Persistent | 142 | 134 | 69 | 127 | 121 | 64 | 112 | 108 | 64 |
| Cutoff Quartile 2 | 4.17 | 4.15 | 4.13 | 4.17 | 4.15 | 4.13 | 4.17 | 4.15 | 4.13 |
| Sensitivity | 82% | 82% | 86% | 85% | 85% | 86% | 85% | 85% | 86% |
| Specificity | 30% | 30% | 28% | 32% | 31% | 28% | 30% | 30% | 28% |
| Cutoff Quartile 3 | 29.6 | 29.3 | 28.8 | 29.6 | 29.3 | 28.8 | 29.6 | 29.3 | 28.8 |
| Sensitivity | 64% | 63% | 68% | 68% | 66% | 69% | 67% | 65% | 69% |
| Specificity | 61% | 60% | 55% | 62% | 60% | 55% | 59% | 57% | 55% |
| Cutoff Quartile 4 | 74.9 | 74.4 | 74.6 | 74.9 | 74.4 | 74.6 | 74.9 | 74.4 | 74.6 |
| Sensitivity | 39% | 38% | 46% | 42% | 40% | 47% | 41% | 39% | 47% |
| Specificity | 86% | 85% | 81% | 86% | 84% | 80% | 84% | 82% | 80% |
| OR Quartile 2 | 1.95 | 2.00 | 2.31 | 2.64 | 2.62 | 2.38 | 2.44 | 2.52 | 2.38 |
| p Value | 0.014 | 0.012 | 0.024 | 9.4E−4 | 0.0012 | 0.025 | 0.0034 | 0.0029 | 0.025 |
| Lower limit of 95% CI | 1.15 | 1.16 | 1.12 | 1.49 | 1.46 | 1.11 | 1.34 | 1.37 | 1.11 |
| Upper limit of 95% CI | 3.33 | 3.44 | 4.78 | 4.70 | 4.71 | 5.07 | 4.43 | 4.62 | 5.07 |
| OR Quartile 3 | 2.85 | 2.57 | 2.62 | 3.41 | 2.90 | 2.67 | 2.96 | 2.49 | 2.67 |
| p Value | 7.8E−6 | 6.0E−5 | 8.3E−4 | 3.9E−7 | 1.0E−5 | 1.0E−3 | 1.1E−5 | 2.0E−4 | 1.0E−3 |
| Lower limit of 95% CI | 1.80 | 1.62 | 1.49 | 2.12 | 1.81 | 1.49 | 1.82 | 1.54 | 1.49 |
| Upper limit of 95% CI | 4.51 | 4.07 | 4.62 | 5.47 | 4.66 | 4.78 | 4.79 | 4.03 | 4.78 |
| OR Quartile 4 | 3.95 | 3.36 | 3.64 | 4.49 | 3.46 | 3.62 | 3.61 | 2.92 | 3.62 |
| p Value | 8.7E−7 | 8.4E−6 | 8.8E−6 | 6.2E−8 | 4.4E−6 | 1.5E−5 | 2.0E−6 | 6.3E−5 | 1.5E−5 |
| Lower limit of 95% CI | 2.29 | 1.97 | 2.06 | 2.61 | 2.04 | 2.02 | 2.13 | 1.73 | 2.02 |
| Upper limit of 95% CI | 6.83 | 5.72 | 6.44 | 7.73 | 5.87 | 6.48 | 6.13 | 4.94 | 6.48 |

TABLE 32.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 18.2 | 49.9 | 18.2 | 54.6 | 19.7 | 50.9 |
| Average | 52.4 | 100 | 50.3 | 110 | 59.0 | 101 |
| Stdev | 123 | 167 | 119 | 174 | 141 | 152 |
| p (t-test) | | 0.0035 | | 3.6E−4 | | 0.015 |
| Min | 0.00127 | 0.00127 | 0.00127 | 0.00127 | 0.00127 | 0.00127 |
| Max | 1070 | 1150 | 1070 | 1150 | 1140 | 1150 |
| n (Patient) | 172 | 144 | 188 | 128 | 200 | 116 |
| | sCr only | | | | | |
| Median | 18.4 | 48.2 | 18.4 | 50.9 | 20.4 | 49.9 |
| Average | 58.8 | 93.0 | 56.9 | 99.2 | 65.2 | 88.8 |
| Stdev | 146 | 144 | 142 | 149 | 160 | 116 |
| p (t-test) | | 0.039 | | 0.012 | | 0.17 |
| Min | 0.00127 | 0.00127 | 0.00127 | 0.00127 | 0.00127 | 0.00127 |
| Max | 1150 | 1140 | 1150 | 1140 | 1150 | 679 |
| n (Patient) | 179 | 136 | 191 | 124 | 203 | 112 |
| | UO only | | | | | |
| Median | 23.8 | 71.6 | 24.1 | 73.6 | 24.1 | 73.6 |
| Average | 62.3 | 111 | 61.9 | 117 | 61.9 | 117 |
| Stdev | 137 | 169 | 135 | 175 | 135 | 175 |
| p (t-test) | | 0.011 | | 0.0053 | | 0.0053 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 238 | 76 | 244 | 70 | 244 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.67 | 0.66 | 0.67 | 0.70 | 0.68 | 0.68 | 0.68 | 0.66 | 0.68 |
| SE | 0.031 | 0.031 | 0.037 | 0.031 | 0.031 | 0.038 | 0.032 | 0.033 | 0.038 |
| p Value | 6.9E−8 | 5.4E−7 | 3.6E−6 | 1.1E−10 | 6.6E−9 | 2.2E−6 | 2.2E−8 | 6.5E−7 | 2.2E−6 |
| nCohort Non-persistent | 172 | 179 | 238 | 188 | 191 | 244 | 200 | 203 | 244 |
| nCohort Persistent | 144 | 136 | 76 | 128 | 124 | 70 | 116 | 112 | 70 |
| Cutoff Quartile 2 | 4.17 | 4.15 | 4.13 | 4.17 | 4.15 | 4.13 | 4.17 | 4.15 | 4.13 |
| Sensitivity | 82% | 82% | 87% | 85% | 85% | 87% | 85% | 86% | 87% |
| Specificity | 31% | 31% | 29% | 32% | 32% | 29% | 31% | 31% | 29% |
| Cutoff Quartile 3 | 29.6 | 29.3 | 28.8 | 29.6 | 29.3 | 28.8 | 29.6 | 29.3 | 28.8 |
| Sensitivity | 64% | 64% | 68% | 68% | 67% | 70% | 67% | 66% | 70% |
| Specificity | 62% | 60% | 56% | 62% | 61% | 56% | 60% | 59% | 56% |
| Cutoff Quartile 4 | 74.9 | 74.4 | 74.6 | 74.9 | 74.4 | 74.6 | 74.9 | 74.4 | 74.6 |
| Sensitivity | 38% | 38% | 46% | 41% | 40% | 47% | 41% | 40% | 47% |
| Specificity | 86% | 85% | 82% | 86% | 85% | 81% | 84% | 83% | 81% |
| OR Quartile 2 | 2.02 | 2.07 | 2.69 | 2.69 | 2.76 | 2.73 | 2.62 | 2.70 | 2.73 |
| p Value | 0.0098 | 0.0087 | 0.0071 | 7.6E−4 | 6.6E−4 | 0.0090 | 0.0015 | 0.0013 | 0.0090 |
| Lower limit of 95% CI | 1.19 | 1.20 | 1.31 | 1.51 | 1.54 | 1.28 | 1.44 | 1.47 | 1.28 |
| Upper limit of 95% CI | 3.45 | 3.56 | 5.55 | 4.78 | 4.96 | 5.79 | 4.75 | 4.95 | 5.79 |
| OR Quartile 3 | 2.84 | 2.70 | 2.74 | 3.50 | 3.13 | 2.94 | 3.08 | 2.76 | 2.94 |
| p Value | 8.0E−6 | 2.4E−5 | 3.0E−4 | 2.3E−7 | 2.3E−6 | 2.1E−4 | 4.4E−6 | 3.5E−5 | 2.1E−4 |
| Lower limit of 95% CI | 1.80 | 1.70 | 1.59 | 2.18 | 1.95 | 1.66 | 1.91 | 1.71 | 1.66 |
| Upper limit of 95% CI | 4.49 | 4.28 | 4.74 | 5.62 | 5.03 | 5.20 | 4.98 | 4.46 | 5.20 |

TABLE 32.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.81 | 3.49 | 3.76 | 4.40 | 3.77 | 3.84 | 3.85 | 3.34 | 3.84 |
| p Value | 1.6E−6 | 5.0E−6 | 3.1E−6 | 8.9E−8 | 1.1E−6 | 3.5E−6 | 6.9E−7 | 7.5E−6 | 3.5E−6 |
| Lower limit of 95% CI | 2.21 | 2.04 | 2.16 | 2.56 | 2.21 | 2.17 | 2.26 | 1.97 | 2.17 |
| Upper limit of 95% CI | 6.58 | 5.96 | 6.57 | 7.58 | 6.44 | 6.78 | 6.55 | 5.66 | 6.78 |

TABLE 32.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 18.2 | 49.9 | 18.3 | 54.5 | 19.7 | 50.9 |
| Average | 52.8 | 98.7 | 50.9 | 107 | 59.5 | 98.5 |
| Stdev | 125 | 165 | 120 | 172 | 143 | 150 |
| p (t-test) | | 0.0053 | | 7.7E−4 | | 0.021 |
| Min | 0.00127 | 0.00127 | 0.00127 | 0.00127 | 0.00127 | 0.00127 |
| Max | 1070 | 1150 | 1070 | 1150 | 1140 | 1150 |
| n (Patient) | 168 | 148 | 183 | 133 | 196 | 120 |
| | sCr only | | | | | |
| Median | 18.4 | 48.2 | 18.4 | 50.9 | 20.4 | 49.9 |
| Average | 59.4 | 91.3 | 57.4 | 97.1 | 65.8 | 86.9 |
| Stdev | 148 | 142 | 144 | 147 | 161 | 114 |
| p (t-test) | | 0.054 | | 0.018 | | 0.22 |
| Min | 0.00127 | 0.00127 | 0.00127 | 0.00127 | 0.00127 | 0.00127 |
| Max | 1150 | 1140 | 1150 | 1140 | 1150 | 679 |
| n (Patient) | 175 | 140 | 187 | 128 | 199 | 116 |
| | UO only | | | | | |
| Median | 23.7 | 55.1 | 23.8 | 62.5 | 23.8 | 62.5 |
| Average | 62.5 | 108 | 62.3 | 110 | 62.3 | 110 |
| Stdev | 138 | 165 | 137 | 168 | 137 | 168 |
| p (t-test) | | 0.017 | | 0.012 | | 0.012 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 233 | 81 | 236 | 78 | 236 | 78 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.662 | 0.65 | 0.67 | 0.69 | 0.67 | 0.67 | 0.68 | 0.65 | 0.67 |
| SE | 0.031 | 0.031 | 0.037 | 0.031 | 0.031 | 0.037 | 0.032 | 0.033 | 0.037 |
| p Value | 1.3E−7 | 1.6E−6 | 4.5E−6 | 6.4E−10 | 2.7E−8 | 2.4E−6 | 2.6E−8 | 2.2E−6 | 2.4E−6 |
| nCohort Non-persistent | 168 | 175 | 233 | 183 | 187 | 236 | 196 | 199 | 236 |
| nCohort Persistent | 148 | 140 | 81 | 133 | 128 | 78 | 120 | 116 | 78 |
| Cutoff Quartile 2 | 4.17 | 4.15 | 4.13 | 4.17 | 4.15 | 4.13 | 4.17 | 4.15 | 4.13 |
| Sensitivity | 82% | 81% | 86% | 85% | 84% | 87% | 86% | 84% | 87% |
| Specificity | 31% | 30% | 29% | 32% | 32% | 29% | 32% | 31% | 29% |
| Cutoff Quartile 3 | 29.6 | 29.3 | 28.8 | 29.6 | 29.3 | 28.8 | 29.6 | 29.3 | 28.8 |
| Sensitivity | 64% | 64% | 68% | 67% | 66% | 69% | 67% | 66% | 69% |
| Specificity | 62% | 61% | 56% | 62% | 61% | 56% | 60% | 59% | 56% |
| Cutoff Quartile 4 | 74.9 | 74.4 | 74.6 | 74.9 | 74.4 | 74.6 | 74.9 | 74.4 | 74.6 |
| Sensitivity | 38% | 38% | 44% | 41% | 40% | 45% | 41% | 40% | 45% |
| Specificity | 86% | 85% | 82% | 86% | 85% | 81% | 85% | 83% | 81% |
| OR Quartile 2 | 2.01 | 1.90 | 2.62 | 2.69 | 2.49 | 2.81 | 2.80 | 2.41 | 2.81 |
| p Value | 0.0099 | 0.018 | 0.0066 | 6.4E−4 | 0.0017 | 0.0050 | 6.8E−4 | 0.0033 | 0.0050 |

TABLE 32.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.18 | 1.12 | 1.31 | 1.52 | 1.41 | 1.37 | 1.55 | 1.34 | 1.37 |
| Upper limit of 95% CI | 3.41 | 3.25 | 5.26 | 4.74 | 4.39 | 5.78 | 5.08 | 4.32 | 5.78 |
| OR Quartile 3 | 2.83 | 2.68 | 2.72 | 3.34 | 3.09 | 2.91 | 3.03 | 2.71 | 2.91 |
| p Value | 8.3E−6 | 2.5E−5 | 2.4E−4 | 4.6E−7 | 2.6E−6 | 1.3E−4 | 5.0E−6 | 4.0E−5 | 1.3E−4 |
| Lower limit of 95% CI | 1.79 | 1.69 | 1.59 | 2.09 | 1.93 | 1.68 | 1.88 | 1.68 | 1.68 |
| Upper limit of 95% CI | 4.47 | 4.24 | 4.63 | 5.34 | 4.94 | 5.01 | 4.87 | 4.36 | 5.01 |
| OR Quartile 4 | 3.84 | 3.49 | 3.53 | 4.32 | 3.76 | 3.55 | 3.82 | 3.31 | 3.55 |
| p Value | 1.7E−6 | 5.4E−6 | 6.6E−6 | 1.5E−7 | 1.2E−6 | 7.2E−6 | 8.2E−7 | 8.8E−6 | 7.2E−6 |
| Lower limit of 95% CI | 2.21 | 2.04 | 2.04 | 2.50 | 2.20 | 2.04 | 2.24 | 1.95 | 2.04 |
| Upper limit of 95% CI | 6.66 | 5.98 | 6.12 | 7.46 | 6.42 | 6.18 | 6.50 | 5.60 | 6.18 |

TABLE 32.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 372 | 376 | 348 | 396 | 373 | 356 |
| Average | 482 | 573 | 466 | 624 | 527 | 483 |
| Stdev | 382 | 682 | 376 | 722 | 557 | 359 |
| p (t-test) | | 0.30 | | 0.080 | | 0.64 |
| Min | 46.8 | 63.9 | 46.8 | 66.1 | 46.8 | 66.1 |
| Max | 1880 | 4690 | 1880 | 4690 | 4690 | 1700 |
| n (Patient) | 96 | 55 | 104 | 47 | 111 | 40 |
| | sCr only | | | | | |
| Median | 368 | 384 | 364 | 392 | 372 | 356 |
| Average | 473 | 582 | 476 | 598 | 521 | 496 |
| Stdev | 380 | 679 | 385 | 717 | 557 | 381 |
| p (t-test) | | 0.21 | | 0.18 | | 0.79 |
| Min | 46.8 | 63.9 | 46.8 | 63.9 | 46.8 | 63.9 |
| Max | 1880 | 4690 | 1880 | 4690 | 4690 | 1700 |
| n (Patient) | 94 | 56 | 103 | 47 | 108 | 42 |
| | UO only | | | | | |
| Median | 364 | 392 | 364 | 392 | 350 | 394 |
| Average | 518 | 435 | 518 | 435 | 517 | 441 |
| Stdev | 531 | 260 | 531 | 260 | 529 | 265 |
| p (t-test) | | 0.50 | | 0.50 | | 0.55 |
| Min | 46.8 | 66.1 | 46.8 | 66.1 | 46.8 | 66.1 |
| Max | 4690 | 1050 | 4690 | 1050 | 4690 | 1050 |
| n (Patient) | 131 | 19 | 131 | 19 | 132 | 18 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.52 | 0.54 | 0.51 | 0.57 | 0.55 | 0.51 | 0.52 | 0.52 | 0.51 |
| SE | 0.049 | 0.049 | 0.071 | 0.051 | 0.051 | 0.071 | 0.054 | 0.053 | 0.073 |
| p Value | 0.61 | 0.42 | 0.94 | 0.15 | 0.33 | 0.94 | 0.74 | 0.69 | 0.89 |
| nCohort Non-persistent | 96 | 94 | 131 | 104 | 103 | 131 | 111 | 108 | 132 |
| nCohort Persistent | 55 | 56 | 19 | 47 | 47 | 19 | 40 | 42 | 18 |

TABLE 32.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Cutoff Quartile 2 | 218 | 217 | 217 | 218 | 217 | 217 | 218 | 217 | 217 |
| Sensitivity | 76% | 77% | 84% | 83% | 81% | 84% | 82% | 81% | 83% |
| Specificity | 26% | 27% | 27% | 29% | 28% | 27% | 28% | 28% | 27% |
| Cutoff Quartile 3 | 373 | 372 | 372 | 373 | 372 | 372 | 373 | 372 | 372 |
| Sensitivity | 51% | 52% | 58% | 55% | 53% | 58% | 50% | 50% | 61% |
| Specificity | 50% | 51% | 51% | 52% | 51% | 51% | 50% | 50% | 52% |
| Cutoff Quartile 4 | 674 | 661 | 661 | 674 | 661 | 661 | 674 | 661 | 661 |
| Sensitivity | 27% | 29% | 16% | 30% | 28% | 16% | 22% | 24% | 17% |
| Specificity | 76% | 77% | 73% | 77% | 76% | 73% | 74% | 74% | 73% |
| OR Quartile 2 | 1.14 | 1.20 | 1.94 | 1.98 | 1.65 | 1.94 | 1.83 | 1.63 | 1.80 |
| p Value | 0.74 | 0.65 | 0.31 | 0.13 | 0.24 | 0.31 | 0.20 | 0.27 | 0.37 |
| Lower limit of 95% CI | 0.526 | 0.554 | 0.534 | 0.827 | 0.711 | 0.534 | 0.732 | 0.680 | 0.492 |
| Upper limit of 95% CI | 2.46 | 2.59 | 7.08 | 4.72 | 3.85 | 7.08 | 4.56 | 3.93 | 6.61 |
| OR Quartile 3 | 1.04 | 1.12 | 1.44 | 1.34 | 1.20 | 1.44 | 0.982 | 1.00 | 1.67 |
| p Value | 0.91 | 0.74 | 0.46 | 0.41 | 0.60 | 0.46 | 0.96 | 1.0 | 0.32 |
| Lower limit of 95% CI | 0.534 | 0.578 | 0.544 | 0.669 | 0.604 | 0.544 | 0.477 | 0.490 | 0.610 |
| Upper limit of 95% CI | 2.01 | 2.17 | 3.81 | 2.67 | 2.40 | 3.81 | 2.02 | 2.04 | 4.57 |
| OR Quartile 4 | 1.19 | 1.31 | 0.514 | 1.41 | 1.19 | 0.514 | 0.821 | 0.893 | 0.554 |
| p Value | 0.65 | 0.48 | 0.31 | 0.38 | 0.66 | 0.31 | 0.65 | 0.79 | 0.37 |
| Lower limit of 95% CI | 0.559 | 0.618 | 0.141 | 0.652 | 0.546 | 0.141 | 0.349 | 0.389 | 0.151 |
| Upper limit of 95% CI | 2.54 | 2.77 | 1.87 | 3.07 | 2.61 | 1.87 | 1.93 | 2.05 | 2.03 |

TABLE 32.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 348 | 396 | 348 | 396 | 373 | 356 |
| Average | 451 | 605 | 448 | 626 | 514 | 518 |
| Stdev | 359 | 662 | 353 | 689 | 557 | 409 |
| p (t-test) | | 0.068 | | 0.037 | | 0.96 |
| Min | 46.8 | 63.9 | 46.8 | 63.9 | 46.8 | 63.9 |
| Max | 1880 | 4690 | 1880 | 4690 | 4690 | 1700 |
| n (Patient) | 88 | 63 | 94 | 57 | 101 | 50 |
| | sCr only | | | | | |
| Median | 331 | 397 | 330 | 397 | 364 | 392 |
| Average | 442 | 616 | 437 | 639 | 497 | 547 |
| Stdev | 354 | 668 | 348 | 690 | 555 | 422 |
| p (t-test) | | 0.040 | | 0.019 | | 0.58 |
| Min | 46.8 | 63.9 | 46.8 | 63.9 | 46.8 | 63.9 |
| Max | 1880 | 4690 | 1880 | 4690 | 4690 | 1700 |
| n (Patient) | 88 | 62 | 93 | 57 | 99 | 51 |
| | UO only | | | | | |
| Median | 364 | 392 | 364 | 392 | 350 | 394 |
| Average | 508 | 505 | 508 | 505 | 507 | 512 |
| Stdev | 531 | 374 | 531 | 374 | 529 | 380 |

TABLE 32.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| p (t-test) | | 0.97 | | | 0.97 | | | 0.96 | |
| Min | 46.8 | 66.1 | | 46.8 | 66.1 | | 46.8 | 66.1 | |
| Max | 4690 | 1510 | | 4690 | 1510 | | 4690 | 1510 | |
| n (Patient) | 123 | 27 | | 123 | 27 | | 124 | 26 | |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.58 | 0.54 | 0.58 | 0.60 | 0.54 | 0.53 | 0.56 | 0.54 |
| SE | 0.048 | 0.048 | 0.062 | 0.048 | 0.048 | 0.062 | 0.050 | 0.050 | 0.063 |
| p Value | 0.12 | 0.077 | 0.57 | 0.091 | 0.041 | 0.57 | 0.53 | 0.22 | 0.53 |
| nCohort Non-persistent | 88 | 88 | 123 | 94 | 93 | 123 | 101 | 99 | 124 |
| nCohort Persistent | 63 | 62 | 27 | 57 | 57 | 27 | 50 | 51 | 26 |
| Cutoff Quartile 2 | 218 | 217 | 217 | 218 | 217 | 217 | 218 | 217 | 217 |
| Sensitivity | 79% | 79% | 81% | 81% | 81% | 81% | 80% | 80% | 81% |
| Specificity | 28% | 28% | 27% | 29% | 29% | 27% | 28% | 28% | 27% |
| Cutoff Quartile 3 | 373 | 372 | 372 | 373 | 372 | 372 | 373 | 372 | 372 |
| Sensitivity | 54% | 55% | 56% | 54% | 56% | 56% | 50% | 53% | 58% |
| Specificity | 52% | 53% | 51% | 52% | 54% | 51% | 50% | 52% | 52% |
| Cutoff Quartile 4 | 674 | 661 | 661 | 674 | 661 | 661 | 674 | 661 | 661 |
| Sensitivity | 30% | 31% | 26% | 32% | 32% | 26% | 26% | 27% | 27% |
| Specificity | 78% | 78% | 75% | 79% | 78% | 75% | 75% | 76% | 75% |
| OR Quartile 2 | 1.53 | 1.50 | 1.61 | 1.69 | 1.71 | 1.61 | 1.53 | 1.62 | 1.52 |
| p Value | 0.28 | 0.30 | 0.37 | 0.20 | 0.19 | 0.37 | 0.31 | 0.25 | 0.43 |
| Lower limit of 95% CI | 0.709 | 0.695 | 0.565 | 0.761 | 0.772 | 0.565 | 0.677 | 0.714 | 0.531 |
| Upper limit of 95% CI | 3.28 | 3.22 | 4.61 | 3.73 | 3.79 | 4.61 | 3.48 | 3.66 | 4.37 |
| OR Quartile 3 | 1.28 | 1.39 | 1.31 | 1.30 | 1.49 | 1.31 | 0.980 | 1.20 | 1.45 |
| p Value | 0.45 | 0.32 | 0.52 | 0.44 | 0.24 | 0.52 | 0.95 | 0.61 | 0.39 |
| Lower limit of 95% CI | 0.671 | 0.725 | 0.568 | 0.671 | 0.767 | 0.568 | 0.498 | 0.608 | 0.619 |
| Upper limit of 95% CI | 2.46 | 2.67 | 3.03 | 2.51 | 2.89 | 3.03 | 1.93 | 2.35 | 3.42 |
| OR Quartile 4 | 1.57 | 1.60 | 1.04 | 1.71 | 1.68 | 1.04 | 1.07 | 1.18 | 1.11 |
| p Value | 0.23 | 0.21 | 0.94 | 0.16 | 0.17 | 0.94 | 0.87 | 0.67 | 0.84 |
| Lower limit of 95% CI | 0.748 | 0.765 | 0.401 | 0.810 | 0.799 | 0.401 | 0.491 | 0.549 | 0.424 |
| Upper limit of 95% CI | 3.29 | 3.37 | 2.69 | 3.60 | 3.55 | 2.69 | 2.32 | 2.55 | 2.88 |

TABLE 32.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 332 | 394 | 331 | 396 | 348 | 392 |
| Average | 451 | 594 | 448 | 605 | 505 | 531 |
| Stdev | 361 | 644 | 358 | 655 | 572 | 397 |

TABLE 32.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.086 | | 0.062 | | 0.76 |
| Min | 46.8 | 50.8 | 46.8 | 50.8 | 46.8 | 63.9 |
| Max | 1880 | 4690 | 1880 | 4690 | 4690 | 1700 |
| n (Patient) | 83 | 68 | 86 | 65 | 94 | 57 | sCr only

| | | | | | | |
|---|---|---|---|---|---|---|
| Median | 331 | 394 | 331 | 394 | 332 | 392 |
| Average | 443 | 599 | 444 | 608 | 494 | 547 |
| Stdev | 357 | 647 | 353 | 662 | 567 | 413 |
| p (t-test) | | 0.063 | | 0.051 | | 0.54 |
| Min | 46.8 | 50.8 | 46.8 | 50.8 | 46.8 | 63.9 |
| Max | 1880 | 4690 | 1880 | 4690 | 4690 | 1700 |
| n (Patient) | 82 | 68 | 86 | 64 | 93 | 57 |

UO only

| | | | | | | |
|---|---|---|---|---|---|---|
| Median | 332 | 396 | 332 | 396 | 331 | 397 |
| Average | 498 | 540 | 498 | 540 | 496 | 547 |
| Stdev | 538 | 383 | 538 | 383 | 536 | 386 |
| p (t-test) | | 0.66 | | 0.66 | | 0.61 |
| Min | 46.8 | 66.1 | 46.8 | 66.1 | 46.8 | 66.1 |
| Max | 4690 | 1510 | 4690 | 1510 | 4690 | 1510 |
| n (Patient) | 115 | 35 | 115 | 35 | 116 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.58 | 0.57 | 0.58 | 0.58 | 0.57 | 0.56 | 0.57 | 0.57 |
| SE | 0.047 | 0.047 | 0.057 | 0.047 | 0.047 | 0.057 | 0.049 | 0.049 | 0.057 |
| p Value | 0.15 | 0.11 | 0.22 | 0.11 | 0.11 | 0.22 | 0.23 | 0.15 | 0.20 |
| nCohort Non-persistent | 83 | 82 | 115 | 86 | 86 | 115 | 94 | 93 | 116 |
| nCohort Persistent | 68 | 68 | 35 | 65 | 64 | 35 | 57 | 57 | 34 |
| Cutoff Quartile 2 | 218 | 217 | 217 | 218 | 217 | 217 | 218 | 217 | 217 |
| Sensitivity | 78% | 78% | 83% | 78% | 78% | 83% | 81% | 81% | 82% |
| Specificity | 28% | 28% | 28% | 28% | 28% | 28% | 29% | 29% | 28% |
| Cutoff Quartile 3 | 373 | 372 | 372 | 373 | 372 | 372 | 373 | 372 | 372 |
| Sensitivity | 54% | 54% | 60% | 55% | 55% | 60% | 54% | 54% | 62% |
| Specificity | 53% | 54% | 53% | 53% | 53% | 53% | 52% | 53% | 53% |
| Cutoff Quartile 4 | 674 | 661 | 661 | 674 | 661 | 661 | 674 | 661 | 661 |
| Sensitivity | 31% | 31% | 31% | 31% | 30% | 31% | 28% | 28% | 32% |
| Specificity | 80% | 79% | 77% | 79% | 78% | 77% | 77% | 76% | 77% |
| OR Quartile 2 | 1.35 | 1.38 | 1.86 | 1.41 | 1.38 | 1.86 | 1.69 | 1.71 | 1.78 |
| p Value | 0.43 | 0.40 | 0.21 | 0.37 | 0.40 | 0.21 | 0.20 | 0.19 | 0.25 |
| Lower limit of 95% CI | 0.641 | 0.651 | 0.707 | 0.662 | 0.648 | 0.707 | 0.761 | 0.772 | 0.673 |
| Upper limit of 95% CI | 2.86 | 2.91 | 4.91 | 3.00 | 2.95 | 4.91 | 3.73 | 3.79 | 4.70 |
| OR Quartile 3 | 1.35 | 1.38 | 1.69 | 1.43 | 1.39 | 1.69 | 1.30 | 1.33 | 1.85 |
| p Value | 0.36 | 0.33 | 0.18 | 0.28 | 0.32 | 0.18 | 0.44 | 0.40 | 0.12 |
| Lower limit of 95% CI | 0.708 | 0.725 | 0.785 | 0.747 | 0.725 | 0.785 | 0.671 | 0.685 | 0.848 |
| Upper limit of 95% CI | 2.56 | 2.63 | 3.66 | 2.73 | 2.66 | 3.66 | 2.51 | 2.57 | 4.05 |
| OR Quartile 4 | 1.73 | 1.71 | 1.49 | 1.68 | 1.49 | 1.49 | 1.28 | 1.26 | 1.58 |
| p Value | 0.15 | 0.16 | 0.35 | 0.17 | 0.29 | 0.35 | 0.52 | 0.55 | 0.29 |
| Lower limit of 95% CI | 0.827 | 0.814 | 0.649 | 0.801 | 0.711 | 0.649 | 0.604 | 0.595 | 0.682 |
| Upper limit of 95% CI | 3.64 | 3.59 | 3.44 | 3.52 | 3.12 | 3.44 | 2.70 | 2.67 | 3.64 |

TABLE 32.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 332 | 394 | 330 | 397 | 330 | 397 |
| Average | 455 | 585 | 447 | 603 | 498 | 541 |
| Stdev | 363 | 638 | 360 | 650 | 576 | 398 |
| p (t-test) | | 0.12 | | 0.063 | | 0.61 |
| Min | 50.8 | 46.8 | 46.8 | 50.8 | 46.8 | 63.9 |
| Max | 1880 | 4690 | 1880 | 4690 | 4690 | 1700 |
| n (Patient) | 81 | 70 | 85 | 66 | 91 | 60 |
| | sCr only | | | | | |
| Median | 330 | 396 | 329 | 397 | 329 | 397 |
| Average | 442 | 598 | 440 | 608 | 492 | 547 |
| Stdev | 359 | 642 | 356 | 652 | 576 | 403 |
| p (t-test) | | 0.064 | | 0.045 | | 0.52 |
| Min | 46.8 | 50.8 | 46.8 | 50.8 | 46.8 | 63.9 |
| Max | 1880 | 4690 | 1880 | 4690 | 4690 | 1700 |
| n (Patient) | 81 | 69 | 84 | 66 | 90 | 60 |
| | UO only | | | | | |
| Median | 332 | 396 | 331 | 397 | 330 | 397 |
| Average | 503 | 520 | 499 | 531 | 497 | 537 |
| Stdev | 549 | 369 | 548 | 365 | 546 | 368 |
| p (t-test) | | 0.86 | | 0.73 | | 0.68 |
| Min | 50.8 | 46.8 | 46.8 | 66.1 | 46.8 | 66.1 |
| Max | 4690 | 1510 | 4690 | 1510 | 4690 | 1510 |
| n (Patient) | 109 | 41 | 110 | 40 | 111 | 39 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.58 | 0.55 | 0.58 | 0.59 | 0.57 | 0.58 | 0.58 | 0.58 |
| SE | 0.047 | 0.047 | 0.054 | 0.047 | 0.047 | 0.054 | 0.048 | 0.048 | 0.054 |
| p Value | 0.22 | 0.092 | 0.30 | 0.095 | 0.067 | 0.18 | 0.12 | 0.083 | 0.16 |
| nCohort Non-persistent | 81 | 81 | 109 | 85 | 84 | 110 | 91 | 90 | 111 |
| nCohort Persistent | 70 | 69 | 41 | 66 | 66 | 40 | 60 | 60 | 39 |
| Cutoff Quartile 2 | 218 | 217 | 217 | 218 | 217 | 217 | 218 | 217 | 217 |
| Sensitivity | 77% | 78% | 80% | 79% | 79% | 82% | 82% | 82% | 82% |
| Specificity | 27% | 28% | 28% | 28% | 29% | 28% | 30% | 30% | 28% |
| Cutoff Quartile 3 | 373 | 372 | 372 | 373 | 372 | 372 | 373 | 372 | 372 |
| Sensitivity | 54% | 55% | 59% | 56% | 56% | 60% | 57% | 57% | 62% |
| Specificity | 53% | 54% | 53% | 54% | 55% | 54% | 54% | 54% | 54% |
| Cutoff Quartile 4 | 674 | 661 | 661 | 674 | 661 | 661 | 674 | 661 | 661 |
| Sensitivity | 30% | 30% | 29% | 30% | 30% | 30% | 28% | 28% | 31% |
| Specificity | 79% | 79% | 76% | 79% | 79% | 76% | 77% | 77% | 77% |
| OR Quartile 2 | 1.26 | 1.43 | 1.57 | 1.46 | 1.49 | 1.85 | 1.88 | 1.91 | 1.77 |
| p Value | 0.54 | 0.35 | 0.32 | 0.33 | 0.31 | 0.19 | 0.12 | 0.11 | 0.22 |
| Lower limit of 95% CI | 0.599 | 0.675 | 0.650 | 0.686 | 0.697 | 0.741 | 0.850 | 0.863 | 0.708 |
| Upper limit of 95% CI | 2.64 | 3.02 | 3.77 | 3.11 | 3.17 | 4.62 | 4.16 | 4.22 | 4.43 |
| OR Quartile 3 | 1.34 | 1.46 | 1.61 | 1.50 | 1.54 | 1.74 | 1.53 | 1.56 | 1.88 |
| p Value | 0.37 | 0.25 | 0.20 | 0.22 | 0.19 | 0.14 | 0.21 | 0.18 | 0.096 |
| Lower limit of 95% CI | 0.707 | 0.765 | 0.777 | 0.788 | 0.807 | 0.832 | 0.792 | 0.809 | 0.893 |
| Upper limit of 95% CI | 2.55 | 2.78 | 3.32 | 2.87 | 2.95 | 3.62 | 2.94 | 3.02 | 3.97 |

TABLE 32.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.61 | 1.65 | 1.32 | 1.62 | 1.59 | 1.38 | 1.32 | 1.30 | 1.45 |
| p Value | 0.21 | 0.19 | 0.50 | 0.20 | 0.22 | 0.43 | 0.47 | 0.49 | 0.37 |
| Lower limit of 95% CI | 0.770 | 0.785 | 0.591 | 0.773 | 0.761 | 0.618 | 0.626 | 0.617 | 0.647 |
| Upper limit of 95% CI | 3.38 | 3.46 | 2.95 | 3.39 | 3.34 | 3.10 | 2.77 | 2.73 | 3.26 |

TABLE 32.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| *sCr or UO* | | | | | | |
| Median | 331 | 396 | 330 | 397 | 329 | 397 |
| Average | 451 | 584 | 448 | 593 | 496 | 542 |
| Stdev | 360 | 630 | 357 | 640 | 581 | 399 |
| p (t-test) | | 0.11 | | 0.082 | | 0.59 |
| Min | 50.8 | 46.8 | 50.8 | 46.8 | 50.8 | 46.8 |
| Max | 1880 | 4690 | 1880 | 4690 | 4690 | 1700 |
| n (Patient) | 78 | 73 | 81 | 70 | 88 | 63 |
| *sCr only* | | | | | | |
| Median | 330 | 396 | 329 | 397 | 329 | 397 |
| Average | 446 | 590 | 443 | 599 | 496 | 539 |
| Stdev | 361 | 636 | 358 | 646 | 581 | 401 |
| p (t-test) | | 0.086 | | 0.063 | | 0.61 |
| Min | 46.8 | 50.8 | 46.8 | 50.8 | 46.8 | 63.9 |
| Max | 1880 | 4690 | 1880 | 4690 | 4690 | 1700 |
| n (Patient) | 79 | 71 | 82 | 68 | 88 | 62 |
| *UO only* | | | | | | |
| Median | 334 | 394 | 334 | 394 | 332 | 396 |
| Average | 506 | 513 | 506 | 513 | 504 | 518 |
| Stdev | 551 | 366 | 551 | 366 | 549 | 370 |
| p (t-test) | | 0.93 | | 0.93 | | 0.88 |
| Min | 50.8 | 46.8 | 50.8 | 46.8 | 50.8 | 46.8 |
| Max | 4690 | 1510 | 4690 | 1510 | 4690 | 1510 |
| n (Patient) | 108 | 42 | 108 | 42 | 109 | 41 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.57 | 0.55 | 0.57 | 0.58 | 0.55 | 0.58 | 0.57 | 0.55 |
| SE | 0.047 | 0.047 | 0.053 | 0.047 | 0.047 | 0.053 | 0.048 | 0.048 | 0.054 |
| p Value | 0.19 | 0.13 | 0.35 | 0.14 | 0.095 | 0.35 | 0.11 | 0.12 | 0.33 |
| nCohort Non-persistent | 78 | 79 | 108 | 81 | 82 | 108 | 88 | 88 | 109 |
| nCohort Persistent | 73 | 71 | 42 | 70 | 68 | 42 | 63 | 62 | 41 |
| Cutoff Quartile 2 | 218 | 217 | 217 | 218 | 217 | 217 | 218 | 217 | 217 |
| Sensitivity | 77% | 77% | 81% | 77% | 78% | 81% | 81% | 81% | 80% |
| Specificity | 27% | 28% | 28% | 27% | 28% | 28% | 30% | 30% | 28% |
| Cutoff Quartile 3 | 373 | 372 | 372 | 373 | 372 | 372 | 373 | 372 | 372 |
| Sensitivity | 55% | 55% | 57% | 56% | 56% | 57% | 57% | 56% | 59% |
| Specificity | 54% | 54% | 53% | 54% | 55% | 53% | 55% | 55% | 53% |
| Cutoff Quartile 4 | 674 | 661 | 661 | 674 | 661 | 661 | 674 | 661 | 661 |
| Sensitivity | 30% | 30% | 29% | 30% | 29% | 29% | 29% | 27% | 29% |
| Specificity | 79% | 78% | 76% | 79% | 78% | 76% | 77% | 76% | 76% |

TABLE 32.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| OR Quartile 2 | 1.21 | 1.33 | 1.63 | 1.26 | 1.38 | 1.63 | 1.78 | 1.75 | 1.57 |
|---|---|---|---|---|---|---|---|---|---|
| p Value | 0.61 | 0.46 | 0.27 | 0.54 | 0.40 | 0.27 | 0.15 | 0.16 | 0.32 |
| Lower limit of 95% CI | 0.580 | 0.631 | 0.680 | 0.599 | 0.651 | 0.680 | 0.819 | 0.802 | 0.650 |
| Upper limit of 95% CI | 2.54 | 2.79 | 3.93 | 2.64 | 2.91 | 3.93 | 3.88 | 3.81 | 3.77 |
| OR Quartile 3 | 1.41 | 1.46 | 1.49 | 1.50 | 1.54 | 1.49 | 1.60 | 1.56 | 1.61 |
| p Value | 0.29 | 0.25 | 0.28 | 0.22 | 0.19 | 0.28 | 0.16 | 0.19 | 0.20 |
| Lower limit of 95% CI | 0.745 | 0.765 | 0.726 | 0.786 | 0.807 | 0.726 | 0.834 | 0.809 | 0.777 |
| Upper limit of 95% CI | 2.68 | 2.77 | 3.06 | 2.85 | 2.94 | 3.06 | 3.07 | 2.99 | 3.32 |
| OR Quartile 4 | 1.67 | 1.53 | 1.26 | 1.61 | 1.48 | 1.26 | 1.36 | 1.21 | 1.32 |
| p Value | 0.18 | 0.26 | 0.57 | 0.21 | 0.30 | 0.57 | 0.42 | 0.62 | 0.50 |
| Lower limit of 95% CI | 0.795 | 0.731 | 0.566 | 0.770 | 0.708 | 0.566 | 0.649 | 0.574 | 0.591 |
| Upper limit of 95% CI | 3.51 | 3.21 | 2.81 | 3.38 | 3.10 | 2.81 | 2.85 | 2.53 | 2.95 |

Example 33. Use of C—C Motif Chemokine 24 for Evaluating Renal Status in Patients Admitted to the ICU: Persistent at RIFLE I or F Patients from the intensive care unit (ICU) with RIFLE stage of injury (I) or failure (F) are enrolled in the following study. EDTA anti-coagulated blood samples (10 mL) and urine samples (50 mL) are collected from each patient at enrollment, and at every 12 hours up to day 3, and then every 24 hours thereafter up to day 7 while the subject is hospitalized. C—C motif chemokine 24 is measured in the enrollment samples by standard immunoassay methods using commercially available assay reagents.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 24, 48 or 72 hours is injury (I) or failure (F) where the persistence period can start from the time of sample collection to 24, 48, 72, 96 or 168 hours after sample collection. "Non-persistent" indicates those patients who are not persistent at injury (I) or failure (F) and whose minimum RIFLE stage during a period of 24, 48 or 72 hours is non-injury (RIFLE 0) or risk of injury (R) where the persistence period can start from the time of sample collection to 24, 48, 72, 96 or 168 hours after sample collection. If a patient dies after injury (I) or failure (F) or is placed on renal replacement therapy (RRT) at any time from sample collection to 24, 48, 72, 96 or 168 hours after sample collection, the patient is considered "persistent".

The ability to distinguish the "persistent" and "non-persistent" cohorts is determined using receiver operating characteristic (ROC) analysis.

TABLE 33.1

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 15.2 | 39.8 | 19.3 | 42.2 | 19.8 | 44.7 |
| Average | 54.0 | 86.4 | 51.3 | 97.0 | 52.6 | 102 |
| Stdev | 132 | 153 | 117 | 168 | 115 | 175 |
| p (t-test) | | 0.056 | | 0.0054 | | 0.0026 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 118 | 198 | 157 | 159 | 178 | 138 |
| | sCr only | | | | | |
| Median | 17.6 | 38.9 | 19.3 | 42.0 | 20.4 | 46.0 |
| Average | 54.6 | 86.7 | 50.8 | 97.3 | 53.1 | 102 |
| Stdev | 127 | 157 | 116 | 169 | 114 | 178 |
| p (t-test) | | 0.054 | | 0.0046 | | 0.0033 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 129 | 186 | 161 | 154 | 183 | 132 |

TABLE 33.1-continued

Comparison of marker levels and the area under the ROC curve (AUC) in urine samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

|  | UO only | | | | | |
|---|---|---|---|---|---|---|
| Median | 22.9 | 73.9 | 24.4 | 89.6 | 25.6 | 97.6 |
| Average | 57.8 | 127 | 59.3 | 138 | 60.8 | 142 |
| Stdev | 131 | 181 | 130 | 191 | 131 | 197 |
| p (t-test) |  | 3.2E−4 |  | 1.7E−4 |  | 2.6E−4 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 240 | 74 | 255 | 59 | 262 | 52 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.63 | 0.62 | 0.70 | 0.64 | 0.64 | 0.71 | 0.65 | 0.65 | 0.71 |
| SE | 0.032 | 0.032 | 0.037 | 0.031 | 0.031 | 0.040 | 0.031 | 0.032 | 0.043 |
| p Value | 5.0E−5 | 1.9E−4 | 4.1E−8 | 1.2E−5 | 6.5E−6 | 1.2E−7 | 1.1E−6 | 4.2E−6 | 6.4E−7 |
| nCohort Non-persistent | 118 | 129 | 240 | 157 | 161 | 255 | 178 | 183 | 262 |
| nCohort Persistent | 198 | 186 | 74 | 159 | 154 | 59 | 138 | 132 | 52 |
| Cutoff Quartile 2 | 4.17 | 4.15 | 4.13 | 4.17 | 4.15 | 4.13 | 4.17 | 4.15 | 4.13 |
| Sensitivity | 80% | 81% | 89% | 81% | 82% | 90% | 83% | 83% | 90% |
| Specificity | 34% | 33% | 30% | 31% | 32% | 29% | 31% | 31% | 28% |
| Cutoff Quartile 3 | 29.6 | 29.3 | 28.8 | 29.6 | 29.3 | 28.8 | 29.6 | 29.3 | 28.8 |
| Sensitivity | 58% | 59% | 72% | 60% | 60% | 73% | 62% | 62% | 71% |
| Specificity | 64% | 62% | 57% | 60% | 60% | 55% | 60% | 58% | 54% |
| Cutoff Quartile 4 | 74.9 | 74.4 | 74.6 | 74.9 | 74.4 | 74.6 | 74.9 | 74.4 | 74.6 |
| Sensitivity | 31% | 32% | 49% | 35% | 35% | 54% | 37% | 36% | 56% |
| Specificity | 86% | 84% | 82% | 85% | 84% | 82% | 84% | 83% | 81% |
| OR Quartile 2 | 2.09 | 2.08 | 3.47 | 1.95 | 2.09 | 3.54 | 2.30 | 2.26 | 3.70 |
| p Value | 0.0052 | 0.0053 | 0.0019 | 0.012 | 0.0063 | 0.0052 | 0.0030 | 0.0039 | 0.0076 |
| Lower limit of 95% CI | 1.25 | 1.24 | 1.58 | 1.16 | 1.23 | 1.46 | 1.33 | 1.30 | 1.42 |
| Upper limit of 95% CI | 3.51 | 3.49 | 7.59 | 3.29 | 3.53 | 8.60 | 3.97 | 3.94 | 9.67 |
| OR Quartile 3 | 2.42 | 2.31 | 3.30 | 2.21 | 2.25 | 3.32 | 2.43 | 2.31 | 2.92 |
| p Value | 2.3E−4 | 3.6E−4 | 3.6E−5 | 5.3E−4 | 4.2E−4 | 1.6E−4 | 1.3E−4 | 3.5E−4 | 0.0012 |
| Lower limit of 95% CI | 1.51 | 1.46 | 1.87 | 1.41 | 1.43 | 1.78 | 1.54 | 1.46 | 1.53 |
| Upper limit of 95% CI | 3.86 | 3.66 | 5.81 | 3.47 | 3.53 | 6.21 | 3.84 | 3.65 | 5.58 |
| OR Quartile 4 | 2.71 | 2.53 | 4.34 | 2.93 | 2.94 | 5.25 | 3.14 | 2.80 | 5.35 |
| p Value | 0.0010 | 0.0013 | 3.2E−7 | 1.1E−4 | 9.1E−5 | 6.9E−8 | 2.4E−5 | 1.2E−4 | 1.7E−7 |
| Lower limit of 95% CI | 1.49 | 1.43 | 2.47 | 1.70 | 1.71 | 2.87 | 1.85 | 1.66 | 2.85 |
| Upper limit of 95% CI | 4.91 | 4.47 | 7.62 | 5.05 | 5.04 | 9.58 | 5.34 | 4.73 | 10.0 |

TABLE 33.2

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 14.3 | 40.4 | 17.9 | 42.7 | 17.9 | 44.7 |
| Average | 47.1 | 89.0 | 47.9 | 97.0 | 49.1 | 101 |
| Stdev | 125 | 155 | 115 | 166 | 114 | 171 |

TABLE 33.2-continued

Comparison of marker levels and the area under the ROC curve (AUC) in urine samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.015 | | 0.0028 | | 0.0014 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 111 | 205 | 146 | 170 | 164 | 152 | sCr only

| | | | | | | |
|---|---|---|---|---|---|---|
| Median | 15.8 | 39.7 | 18.3 | 42.7 | 17.9 | 44.7 |
| Average | 48.6 | 90.0 | 45.9 | 99.7 | 47.6 | 103 |
| Stdev | 119 | 159 | 109 | 170 | 110 | 174 |
| p (t-test) | | 0.014 | | 9.9E−4 | | 6.6E−4 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 125 | 190 | 153 | 162 | 168 | 147 |

UO only

| | | | | | | |
|---|---|---|---|---|---|---|
| Median | 19.9 | 55.1 | 23.0 | 74.0 | 23.8 | 74.7 |
| Average | 57.2 | 114 | 59.1 | 121 | 60.7 | 121 |
| Stdev | 135 | 165 | 134 | 173 | 135 | 176 |
| p (t-test) | | 0.0015 | | 0.0013 | | 0.0023 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 221 | 93 | 237 | 77 | 244 | 70 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.63 | 0.70 | 0.65 | 0.66 | 0.70 | 0.67 | 0.67 | 0.69 |
| SE | 0.031 | 0.031 | 0.034 | 0.031 | 0.031 | 0.037 | 0.030 | 0.031 | 0.038 |
| p Value | 1.6E−6 | 2.1E−5 | 4.1E−9 | 6.2E−7 | 3.8E−7 | 6.0E−8 | 5.1E−8 | 3.5E−8 | 4.0E−7 |
| nCohort Non-persistent | 111 | 125 | 221 | 146 | 153 | 237 | 164 | 168 | 244 |
| nCohort Persistent | 205 | 190 | 93 | 170 | 162 | 77 | 152 | 147 | 70 |
| Cutoff Quartile 2 | 4.17 | 4.15 | 4.13 | 4.17 | 4.15 | 4.13 | 4.17 | 4.15 | 4.13 |
| Sensitivity | 80% | 81% | 88% | 82% | 83% | 88% | 84% | 84% | 89% |
| Specificity | 35% | 34% | 31% | 33% | 33% | 30% | 33% | 33% | 29% |
| Cutoff Quartile 3 | 29.6 | 29.3 | 28.8 | 29.6 | 29.3 | 28.8 | 29.6 | 29.3 | 28.8 |
| Sensitivity | 59% | 59% | 72% | 61% | 61% | 73% | 63% | 64% | 71% |
| Specificity | 67% | 64% | 59% | 62% | 61% | 57% | 62% | 62% | 56% |
| Cutoff Quartile 4 | 74.9 | 74.4 | 74.6 | 74.9 | 74.4 | 74.6 | 74.9 | 74.4 | 74.6 |
| Sensitivity | 32% | 32% | 46% | 35% | 35% | 49% | 37% | 37% | 50% |
| Specificity | 88% | 86% | 84% | 86% | 86% | 83% | 86% | 85% | 82% |
| OR Quartile 2 | 2.23 | 2.24 | 3.31 | 2.20 | 2.39 | 3.17 | 2.49 | 2.70 | 3.18 |
| p Value | 0.0025 | 0.0022 | 6.8E−4 | 0.0030 | 0.0012 | 0.0026 | 8.8E−4 | 4.0E−4 | 0.0039 |
| Lower limit of 95% CI | 1.33 | 1.34 | 1.66 | 1.31 | 1.41 | 1.50 | 1.46 | 1.56 | 1.45 |
| Upper limit of 95% CI | 3.76 | 3.76 | 6.61 | 3.70 | 4.06 | 6.70 | 4.27 | 4.67 | 6.98 |
| OR Quartile 3 | 2.88 | 2.61 | 3.75 | 2.54 | 2.50 | 3.59 | 2.82 | 2.88 | 3.20 |
| p Value | 1.8E−5 | 5.5E−5 | 8.6E−7 | 5.7E−5 | 7.3E−5 | 8.8E−6 | 8.5E−6 | 6.1E−6 | 7.7E−5 |
| Lower limit of 95% CI | 1.78 | 1.64 | 2.22 | 1.61 | 1.59 | 2.04 | 1.79 | 1.82 | 1.80 |
| Upper limit of 95% CI | 4.67 | 4.16 | 6.35 | 4.01 | 3.94 | 6.31 | 4.45 | 4.56 | 5.70 |
| OR Quartile 4 | 3.58 | 2.81 | 4.42 | 3.35 | 3.23 | 4.66 | 3.58 | 3.32 | 4.55 |
| p Value | 1.2E−4 | 5.3E−4 | 7.7E−8 | 3.0E−5 | 3.4E−5 | 7.0E−8 | 5.7E−6 | 1.4E−5 | 2.0E−7 |
| Lower limit of 95% CI | 1.87 | 1.57 | 2.57 | 1.90 | 1.86 | 2.66 | 2.06 | 1.93 | 2.57 |
| Upper limit of 95% CI | 6.85 | 5.04 | 7.60 | 5.91 | 5.63 | 8.15 | 6.20 | 5.71 | 8.05 |

TABLE 33.3

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 13.6 | 40.3 | 16.9 | 43.2 | 16.9 | 44.6 |
| Average | 47.4 | 88.7 | 47.8 | 96.2 | 49.6 | 98.7 |
| Stdev | 125 | 155 | 116 | 164 | 116 | 168 |
| p (t-test) | | 0.017 | | 0.0032 | | 0.0027 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 110 | 206 | 143 | 173 | 157 | 159 |
| sCr only | | | | | | |
| Median | 14.5 | 39.7 | 17.2 | 43.2 | 17.2 | 44.6 |
| Average | 48.7 | 89.5 | 45.9 | 98.8 | 48.0 | 101 |
| Stdev | 120 | 159 | 110 | 169 | 111 | 172 |
| p (t-test) | | 0.015 | | 0.0012 | | 0.0013 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 123 | 192 | 150 | 165 | 162 | 153 |
| UO only | | | | | | |
| Median | 20.3 | 54.7 | 22.9 | 64.0 | 23.7 | 69.8 |
| Average | 58.5 | 106 | 60.1 | 109 | 61.7 | 109 |
| Stdev | 138 | 159 | 138 | 163 | 138 | 164 |
| p (t-test) | | 0.0064 | | 0.0069 | | 0.012 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 211 | 103 | 224 | 90 | 231 | 83 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.65 | 0.64 | 0.68 | 0.66 | 0.66 | 0.68 | 0.66 | 0.66 | 0.67 |
| SE | 0.031 | 0.031 | 0.033 | 0.030 | 0.030 | 0.035 | 0.030 | 0.030 | 0.036 |
| p Value | 1.9E−6 | 1.4E−5 | 9.0E−8 | 2.5E−7 | 1.7E−7 | 2.3E−7 | 6.2E−8 | 6.7E−8 | 1.6E−6 |
| nCohort Non-persistent | 110 | 123 | 211 | 143 | 150 | 224 | 157 | 162 | 231 |
| nCohort Persistent | 206 | 192 | 103 | 173 | 165 | 90 | 159 | 153 | 83 |
| Cutoff Quartile 2 | 4.17 | 4.15 | 4.13 | 4.17 | 4.15 | 4.13 | 4.17 | 4.15 | 4.13 |
| Sensitivity | 81% | 81% | 85% | 82% | 83% | 86% | 83% | 84% | 86% |
| Specificity | 35% | 35% | 30% | 34% | 34% | 29% | 33% | 33% | 29% |
| Cutoff Quartile 3 | 29.6 | 29.3 | 28.8 | 29.6 | 29.3 | 28.8 | 29.6 | 29.3 | 28.8 |
| Sensitivity | 59% | 59% | 69% | 61% | 61% | 70% | 63% | 63% | 69% |
| Specificity | 66% | 64% | 59% | 63% | 62% | 58% | 63% | 62% | 57% |
| Cutoff Quartile 4 | 74.9 | 74.4 | 74.6 | 74.9 | 74.4 | 74.6 | 74.9 | 74.4 | 74.6 |
| Sensitivity | 32% | 32% | 43% | 35% | 35% | 46% | 36% | 36% | 46% |
| Specificity | 88% | 86% | 83% | 87% | 86% | 83% | 86% | 85% | 82% |
| OR Quartile 2 | 2.28 | 2.33 | 2.55 | 2.31 | 2.52 | 2.47 | 2.42 | 2.56 | 2.42 |
| p Value | 0.0019 | 0.0014 | 0.0031 | 0.0016 | 6.1E−4 | 0.0066 | 0.0011 | 6.3E−4 | 0.010 |
| Lower limit of 95% CI | 1.35 | 1.39 | 1.37 | 1.37 | 1.49 | 1.29 | 1.42 | 1.49 | 1.23 |
| Upper limit of 95% CI | 3.84 | 3.91 | 4.75 | 3.90 | 4.28 | 4.76 | 4.12 | 4.39 | 4.75 |
| OR Quartile 3 | 2.81 | 2.62 | 3.22 | 2.62 | 2.57 | 3.23 | 2.89 | 2.87 | 2.87 |
| p Value | 2.8E−5 | 5.3E−5 | 4.3E−6 | 3.5E−5 | 4.6E−5 | 1.1E−5 | 5.1E−6 | 6.3E−6 | 1.0E−4 |
| Lower limit of 95% CI | 1.73 | 1.64 | 1.96 | 1.66 | 1.63 | 1.91 | 1.83 | 1.82 | 1.69 |
| Upper limit of 95% CI | 4.55 | 4.19 | 5.31 | 4.14 | 4.06 | 5.44 | 4.57 | 4.53 | 4.89 |

TABLE 33.3-continued

Comparison of marker levels and the area under the ROC curve (AUC) in urine samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 3.52 | 2.97 | 3.75 | 3.47 | 3.33 | 4.10 | 3.43 | 3.23 | 3.91 |
| p Value | 1.4E-4 | 3.3E-4 | 1.2E-6 | 2.3E-5 | 2.6E-5 | 3.4E-7 | 1.4E-5 | 2.5E-5 | 1.1E-6 |
| Lower limit of 95% CI | 1.84 | 1.64 | 2.20 | 1.95 | 1.90 | 2.38 | 1.97 | 1.87 | 2.26 |
| Upper limit of 95% CI | 6.73 | 5.39 | 6.39 | 6.16 | 5.84 | 7.04 | 5.97 | 5.57 | 6.77 |

TABLE 33.4

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 14.3 | 40.2 | 16.4 | 42.7 | 15.9 | 44.6 |
| Average | 47.8 | 88.2 | 47.9 | 95.9 | 49.6 | 98.1 |
| Stdev | 126 | 155 | 117 | 164 | 117 | 167 |
| p (t-test) | | 0.019 | | 0.0036 | | 0.0032 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 109 | 207 | 142 | 174 | 155 | 161 |
| | sCr only | | | | | |
| Median | 14.5 | 39.7 | 16.9 | 42.7 | 16.9 | 44.6 |
| Average | 48.7 | 89.5 | 45.9 | 98.4 | 48.1 | 100 |
| Stdev | 120 | 159 | 111 | 168 | 112 | 171 |
| p (t-test) | | 0.015 | | 0.0014 | | 0.0014 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 123 | 192 | 149 | 166 | 161 | 154 |
| | UO only | | | | | |
| Median | 19.9 | 54.5 | 20.4 | 55.1 | 22.7 | 55.1 |
| Average | 58.7 | 104 | 60.2 | 106 | 62.0 | 105 |
| Stdev | 139 | 157 | 139 | 159 | 140 | 159 |
| p (t-test) | | 0.0091 | | 0.010 | | 0.019 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 207 | 107 | 219 | 95 | 225 | 89 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.64 | 0.67 | 0.66 | 0.66 | 0.68 | 0.67 | 0.67 | 0.68 |
| SE | 0.031 | 0.031 | 0.033 | 0.030 | 0.030 | 0.034 | 0.030 | 0.030 | 0.035 |
| p Value | 4.8E-6 | 1.4E-5 | 1.4E-7 | 2.2E-7 | 1.5E-7 | 1.1E-7 | 3.4E-8 | 5.9E-8 | 5.9E-7 |
| nCohort Non-persistent | 109 | 123 | 207 | 142 | 149 | 219 | 155 | 161 | 225 |
| nCohort Persistent | 207 | 192 | 107 | 174 | 166 | 95 | 161 | 154 | 89 |
| Cutoff Quartile 2 | 4.17 | 4.15 | 4.13 | 4.17 | 4.15 | 4.13 | 4.17 | 4.15 | 4.13 |
| Sensitivity | 80% | 81% | 85% | 82% | 83% | 86% | 83% | 84% | 87% |
| Specificity | 35% | 35% | 30% | 34% | 34% | 30% | 34% | 34% | 30% |
| Cutoff Quartile 3 | 29.6 | 29.3 | 28.8 | 29.6 | 29.3 | 28.8 | 29.6 | 29.3 | 28.8 |
| Sensitivity | 58% | 59% | 68% | 61% | 61% | 69% | 63% | 64% | 69% |
| Specificity | 66% | 64% | 59% | 63% | 62% | 58% | 64% | 63% | 57% |
| Cutoff Quartile 4 | 74.9 | 74.4 | 74.6 | 74.9 | 74.4 | 74.6 | 74.9 | 74.4 | 74.6 |
| Sensitivity | 32% | 32% | 42% | 34% | 35% | 44% | 35% | 36% | 44% |
| Specificity | 88% | 86% | 84% | 87% | 86% | 83% | 86% | 85% | 82% |
| OR Quartile 2 | 2.17 | 2.33 | 2.49 | 2.36 | 2.56 | 2.72 | 2.51 | 2.60 | 2.72 |
| p Value | 0.0037 | 0.0014 | 0.0033 | 0.0013 | 4.8E-4 | 0.0026 | 7.0E-4 | 5.0E-4 | 0.0035 |

TABLE 33.4-continued

Comparison of marker levels and the area under the ROC curve (AUC) in urine samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| Lower limit of 95% CI | 1.29 | 1.39 | 1.35 | 1.40 | 1.51 | 1.42 | 1.47 | 1.52 | 1.39 |
| Upper limit of 95% CI | 3.65 | 3.91 | 4.57 | 3.97 | 4.35 | 5.22 | 4.26 | 4.46 | 5.33 |
| OR Quartile 3 | 2.74 | 2.62 | 3.14 | 2.70 | 2.65 | 3.20 | 3.06 | 2.95 | 2.93 |
| p Value | 4.4E−5 | 5.3E−5 | 5.2E−6 | 2.1E−5 | 2.8E−5 | 8.7E−6 | 1.8E−6 | 3.8E−6 | 5.1E−5 |
| Lower limit of 95% CI | 1.69 | 1.64 | 1.92 | 1.71 | 1.68 | 1.92 | 1.93 | 1.86 | 1.74 |
| Upper limit of 95% CI | 4.44 | 4.19 | 5.14 | 4.26 | 4.17 | 5.35 | 4.83 | 4.66 | 4.92 |
| OR Quartile 4 | 3.46 | 2.97 | 3.69 | 3.41 | 3.27 | 3.90 | 3.31 | 3.17 | 3.61 |
| p Value | 1.8E−4 | 3.3E−4 | 1.5E−6 | 3.0E−5 | 3.4E−5 | 7.0E−7 | 2.3E−5 | 3.3E−5 | 3.3E−6 |
| Lower limit of 95% CI | 1.81 | 1.64 | 2.17 | 1.92 | 1.87 | 2.28 | 1.90 | 1.84 | 2.10 |
| Upper limit of 95% CI | 6.61 | 5.39 | 6.28 | 6.06 | 5.74 | 6.67 | 5.77 | 5.47 | 6.19 |

TABLE 33.5

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 14.3 | 39.2 | 14.5 | 43.2 | 15.8 | 44.6 |
| Average | 48.8 | 87.0 | 48.1 | 94.4 | 50.2 | 95.8 |
| Stdev | 128 | 153 | 119 | 162 | 119 | 164 |
| p (t-test) | | 0.029 | | 0.0052 | | 0.0055 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 105 | 211 | 137 | 179 | 149 | 167 |
| | sCr only | | | | | |
| Median | 14.5 | 39.2 | 15.8 | 42.7 | 15.9 | 44.6 |
| Average | 49.2 | 88.6 | 46.1 | 97.0 | 48.3 | 98.7 |
| Stdev | 122 | 158 | 112 | 166 | 113 | 169 |
| p (t-test) | | 0.020 | | 0.0020 | | 0.0021 |
| Min | 0.00127 | 0.00127 | 0.00127 | 0.00127 | 0.00127 | 0.00127 |
| Max | 1070 | 1150 | 1070 | 1150 | 1070 | 1150 |
| n (Patient) | 120 | 195 | 145 | 170 | 157 | 158 |
| | UO only | | | | | |
| Median | 19.9 | 50.6 | 20.4 | 54.5 | 21.9 | 52.8 |
| Average | 59.5 | 100 | 61.3 | 101 | 63.2 | 98.3 |
| Stdev | 141 | 154 | 142 | 154 | 143 | 154 |
| p (t-test) | | 0.018 | | 0.026 | | 0.050 |
| Min | 0.00127 | 0.00127 | 0.00127 | 0.00127 | 0.00127 | 0.00127 |
| Max | 1140 | 1150 | 1140 | 1150 | 1140 | 1150 |
| n (Patient) | 201 | 113 | 211 | 103 | 216 | 98 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.64 | 0.64 | 0.67 | 0.66 | 0.66 | 0.67 | 0.67 | 0.67 | 0.66 |
| SE | 0.032 | 0.031 | 0.033 | 0.030 | 0.030 | 0.034 | 0.030 | 0.030 | 0.034 |
| p Value | 8.0E−6 | 1.6E−5 | 2.9E−7 | 8.7E−8 | 9.6E−8 | 3.2E−7 | 2.4E−8 | 3.9E−8 | 1.7E−6 |
| nCohort Non-persistent | 105 | 120 | 201 | 137 | 145 | 211 | 149 | 157 | 216 |
| nCohort Persistent | 211 | 195 | 113 | 179 | 170 | 103 | 167 | 158 | 98 |
| Cutoff Quartile 2 | 4.17 | 4.15 | 4.13 | 4.17 | 4.15 | 4.13 | 4.17 | 4.15 | 4.13 |

TABLE 33.5-continued

Comparison of marker levels and the area under the ROC curve (AUC) in urine samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| Sensitivity | 81% | 82% | 85% | 83% | 84% | 86% | 84% | 84% | 87% |
|---|---|---|---|---|---|---|---|---|---|
| Specificity | 36% | 36% | 31% | 35% | 35% | 31% | 35% | 34% | 31% |
| Cutoff Quartile 3 | 29.6 | 29.3 | 28.8 | 29.6 | 29.3 | 28.8 | 29.6 | 29.3 | 28.8 |
| Sensitivity | 58% | 59% | 67% | 61% | 61% | 68% | 63% | 63% | 67% |
| Specificity | 66% | 64% | 60% | 64% | 63% | 59% | 64% | 63% | 58% |
| Cutoff Quartile 4 | 74.9 | 74.4 | 74.6 | 74.9 | 74.4 | 74.6 | 74.9 | 74.4 | 74.6 |
| Sensitivity | 31% | 32% | 41% | 34% | 35% | 42% | 35% | 35% | 41% |
| Specificity | 88% | 86% | 84% | 87% | 86% | 83% | 86% | 85% | 82% |
| OR Quartile 2 | 2.35 | 2.47 | 2.52 | 2.57 | 2.75 | 2.83 | 2.78 | 2.79 | 2.88 |
| p Value | 0.0014 | 6.6E−4 | 0.0024 | 3.9E−4 | 1.8E−4 | 0.0013 | 1.7E−4 | 1.9E−4 | 0.0015 |
| Lower limit of 95% CI | 1.39 | 1.47 | 1.39 | 1.53 | 1.62 | 1.50 | 1.63 | 1.63 | 1.50 |
| Upper limit of 95% CI | 3.97 | 4.15 | 4.57 | 4.34 | 4.67 | 5.34 | 4.73 | 4.78 | 5.52 |
| OR Quartile 3 | 2.63 | 2.57 | 3.04 | 2.80 | 2.66 | 3.02 | 3.07 | 2.94 | 2.83 |
| p Value | 1.0E−4 | 8.0E−5 | 6.5E−6 | 1.2E−5 | 2.8E−5 | 1.3E−5 | 1.7E−6 | 3.8E−6 | 4.7E−5 |
| Lower limit of 95% CI | 1.61 | 1.61 | 1.88 | 1.76 | 1.68 | 1.84 | 1.94 | 1.86 | 1.72 |
| Upper limit of 95% CI | 4.28 | 4.12 | 4.94 | 4.43 | 4.19 | 4.97 | 4.86 | 4.65 | 4.68 |
| OR Quartile 4 | 3.22 | 2.82 | 3.50 | 3.42 | 3.32 | 3.48 | 3.24 | 3.20 | 3.13 |
| p Value | 4.2E−4 | 6.3E−4 | 3.6E−6 | 3.7E−5 | 3.4E−5 | 4.1E−6 | 3.9E−5 | 3.4E−5 | 2.6E−5 |
| Lower limit of 95% CI | 1.68 | 1.56 | 2.06 | 1.91 | 1.88 | 2.05 | 1.85 | 1.85 | 1.84 |
| Upper limit of 95% CI | 6.17 | 5.12 | 5.93 | 6.13 | 5.86 | 5.93 | 5.68 | 5.54 | 5.33 |

TABLE 33.6

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 347 | 380 | 364 | 378 | 373 | 355 |
| Average | 446 | 549 | 470 | 559 | 487 | 552 |
| Stdev | 374 | 566 | 370 | 620 | 381 | 644 |
| p (t-test) | | 0.24 | | 0.29 | | 0.44 |
| Min | 50.8 | 46.8 | 50.8 | 46.8 | 50.8 | 46.8 |
| Max | 1880 | 4690 | 1880 | 4690 | 1880 | 4690 |
| n (Patient) | 50 | 101 | 75 | 76 | 85 | 66 |
| sCr only | | | | | | |
| Median | 327 | 386 | 371 | 374 | 376 | 332 |
| Average | 437 | 555 | 481 | 545 | 491 | 544 |
| Stdev | 379 | 569 | 387 | 610 | 393 | 642 |
| p (t-test) | | 0.18 | | 0.45 | | 0.54 |
| Min | 46.8 | 50.8 | 46.8 | 50.8 | 46.8 | 50.8 |
| Max | 1880 | 4690 | 1880 | 4690 | 1880 | 4690 |
| n (Patient) | 52 | 98 | 73 | 77 | 86 | 64 |
| UO only | | | | | | |
| Median | 334 | 397 | 331 | 412 | 330 | 428 |
| Average | 504 | 520 | 504 | 524 | 509 | 503 |
| Stdev | 545 | 370 | 537 | 354 | 539 | 287 |

TABLE 33.6-continued

Comparison of marker levels and the area under the ROC curve (AUC) in EDTA samples for the "persistent" and "non-persistent" cohorts where persistence starts within 24 hours after sample collection and renal status is assessed by serum creatinine (sCr) only, urine output (UO) only, or serum creatinine or urine output RIFLE criteria.

| | | | | | | | | |
|---|---|---|---|---|---|---|---|---|
| p (t-test) | | 0.87 | | | 0.84 | | | 0.96 |
| Min | 50.8 | 46.8 | | 50.8 | 46.8 | | 50.8 | 46.8 |
| Max | 4690 | 1700 | | 4690 | 1700 | | 4690 | 1050 |
| n (Patient) | 112 | 38 | | 120 | 30 | | 125 | 25 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.55 | 0.57 | 0.55 | 0.53 | 0.52 | 0.57 | 0.51 | 0.51 | 0.57 |
| SE | 0.049 | 0.048 | 0.055 | 0.047 | 0.047 | 0.060 | 0.048 | 0.048 | 0.065 |
| p Value | 0.27 | 0.13 | 0.37 | 0.58 | 0.72 | 0.25 | 0.88 | 0.86 | 0.29 |
| nCohort Non-persistent | 50 | 52 | 112 | 75 | 73 | 120 | 85 | 86 | 125 |
| nCohort Persistent | 101 | 98 | 38 | 76 | 77 | 30 | 66 | 64 | 25 |
| Cutoff Quartile 2 | 218 | 217 | 217 | 218 | 217 | 217 | 218 | 217 | 217 |
| Sensitivity | 75% | 77% | 79% | 74% | 74% | 83% | 74% | 77% | 84% |
| Specificity | 26% | 29% | 27% | 24% | 25% | 28% | 25% | 27% | 27% |
| Cutoff Quartile 3 | 373 | 372 | 372 | 373 | 372 | 372 | 373 | 372 | 372 |
| Sensitivity | 52% | 53% | 58% | 53% | 51% | 63% | 50% | 48% | 68% |
| Specificity | 54% | 56% | 53% | 52% | 51% | 53% | 49% | 49% | 54% |
| Cutoff Quartile 4 | 674 | 661 | 661 | 674 | 661 | 661 | 674 | 661 | 661 |
| Sensitivity | 29% | 29% | 34% | 30% | 29% | 33% | 27% | 25% | 32% |
| Specificity | 82% | 81% | 78% | 80% | 78% | 77% | 76% | 74% | 76% |
| OR Quartile 2 | 1.07 | 1.32 | 1.37 | 0.884 | 0.933 | 1.90 | 0.946 | 1.19 | 1.96 |
| p Value | 0.87 | 0.47 | 0.48 | 0.74 | 0.85 | 0.23 | 0.88 | 0.65 | 0.25 |
| Lower limit of 95% CI | 0.491 | 0.618 | 0.566 | 0.424 | 0.446 | 0.670 | 0.451 | 0.563 | 0.628 |
| Upper limit of 95% CI | 2.32 | 2.83 | 3.32 | 1.85 | 1.95 | 5.37 | 1.98 | 2.52 | 6.13 |
| OR Quartile 3 | 1.30 | 1.43 | 1.53 | 1.20 | 1.05 | 1.97 | 0.977 | 0.897 | 2.45 |
| p Value | 0.45 | 0.30 | 0.26 | 0.57 | 0.87 | 0.11 | 0.94 | 0.74 | 0.053 |
| Lower limit of 95% CI | 0.657 | 0.725 | 0.728 | 0.636 | 0.556 | 0.865 | 0.513 | 0.469 | 0.987 |
| Upper limit of 95% CI | 2.56 | 2.80 | 3.22 | 2.28 | 2.00 | 4.50 | 1.86 | 1.71 | 6.10 |
| OR Quartile 4 | 1.83 | 1.68 | 1.81 | 1.74 | 1.42 | 1.64 | 1.22 | 0.970 | 1.49 |
| p Value | 0.16 | 0.21 | 0.15 | 0.15 | 0.35 | 0.26 | 0.60 | 0.94 | 0.40 |
| Lower limit of 95% CI | 0.792 | 0.742 | 0.810 | 0.822 | 0.678 | 0.689 | 0.583 | 0.460 | 0.585 |
| Upper limit of 95% CI | 4.25 | 3.80 | 4.04 | 3.67 | 3.00 | 3.92 | 2.55 | 2.04 | 3.80 |

TABLE 33.7

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| | sCr or UO | | | | | |
| Median | 330 | 386 | 368 | 376 | 373 | 355 |
| Average | 443 | 550 | 468 | 556 | 473 | 561 |
| Stdev | 377 | 563 | 366 | 610 | 364 | 635 |

TABLE 33.7-continued

Comparison of marker levels and the area under the ROC curve (AUC) in EDTA samples for the "persistent" and "non-persistent" cohorts where persistence starts within 48 hours after sample collection and renal status is assessed by serum creatinine (sCr) only, urine output (UO) only, or serum creatinine or urine output RIFLE criteria.

| | | | | | | |
|---|---|---|---|---|---|---|
| p (t-test) | | 0.23 | | 0.29 | | 0.29 |
| Min | 50.8 | 46.8 | 50.8 | 46.8 | 50.8 | 46.8 |
| Max | 1880 | 4690 | 1880 | 4690 | 1880 | 4690 |
| n (Patient) | 49 | 102 | 70 | 81 | 79 | 72 | sCr only

| | | | | | | |
|---|---|---|---|---|---|---|
| Median | 324 | 392 | 348 | 378 | 371 | 374 |
| Average | 434 | 555 | 453 | 567 | 458 | 576 |
| Stdev | 382 | 566 | 362 | 613 | 360 | 639 |
| p (t-test) | | 0.17 | | 0.18 | | 0.16 |
| Min | 46.8 | 50.8 | 46.8 | 50.8 | 46.8 | 50.8 |
| Max | 1880 | 4690 | 1880 | 4690 | 1880 | 4690 |
| n (Patient) | 51 | 99 | 70 | 80 | 79 | 71 |

UO only

| | | | | | | |
|---|---|---|---|---|---|---|
| Median | 364 | 392 | 337 | 396 | 334 | 397 |
| Average | 493 | 540 | 494 | 548 | 500 | 535 |
| Stdev | 540 | 421 | 533 | 420 | 535 | 393 |
| p (t-test) | | 0.60 | | 0.57 | | 0.72 |
| Min | 50.8 | 46.8 | 50.8 | 46.8 | 50.8 | 46.8 |
| Max | 4690 | 1700 | 4690 | 1700 | 4690 | 1510 |
| n (Patient) | 103 | 47 | 111 | 39 | 116 | 34 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.58 | 0.54 | 0.53 | 0.55 | 0.56 | 0.52 | 0.54 | 0.56 |
| SE | 0.049 | 0.048 | 0.051 | 0.047 | 0.047 | 0.054 | 0.047 | 0.047 | 0.057 |
| p Value | 0.22 | 0.097 | 0.39 | 0.58 | 0.32 | 0.28 | 0.69 | 0.36 | 0.33 |
| nCohort Non-persistent | 49 | 51 | 103 | 70 | 70 | 111 | 79 | 79 | 116 |
| nCohort Persistent | 102 | 99 | 47 | 81 | 80 | 39 | 72 | 71 | 34 |
| Cutoff Quartile 2 | 218 | 217 | 217 | 218 | 217 | 217 | 218 | 217 | 217 |
| Sensitivity | 75% | 77% | 77% | 74% | 75% | 79% | 75% | 76% | 79% |
| Specificity | 27% | 29% | 26% | 24% | 26% | 27% | 25% | 27% | 27% |
| Cutoff Quartile 3 | 373 | 372 | 372 | 373 | 372 | 372 | 373 | 372 | 372 |
| Sensitivity | 53% | 54% | 53% | 52% | 52% | 56% | 50% | 51% | 59% |
| Specificity | 55% | 57% | 51% | 51% | 53% | 52% | 49% | 51% | 53% |
| Cutoff Quartile 4 | 674 | 661 | 661 | 674 | 661 | 661 | 674 | 661 | 661 |
| Sensitivity | 28% | 28% | 34% | 30% | 30% | 33% | 28% | 28% | 32% |
| Specificity | 82% | 80% | 79% | 80% | 80% | 77% | 77% | 77% | 77% |
| OR Quartile 2 | 1.11 | 1.38 | 1.16 | 0.916 | 1.04 | 1.44 | 1.02 | 1.15 | 1.41 |
| p Value | 0.79 | 0.41 | 0.71 | 0.82 | 0.92 | 0.42 | 0.96 | 0.71 | 0.47 |
| Lower limit of 95% CI | 0.511 | 0.643 | 0.520 | 0.438 | 0.497 | 0.594 | 0.487 | 0.549 | 0.556 |
| Upper limit of 95% CI | 2.42 | 2.95 | 2.60 | 1.92 | 2.17 | 3.47 | 2.12 | 2.41 | 3.56 |
| OR Quartile 3 | 1.38 | 1.52 | 1.20 | 1.14 | 1.24 | 1.42 | 0.975 | 1.05 | 1.58 |
| p Value | 0.36 | 0.23 | 0.60 | 0.69 | 0.51 | 0.35 | 0.94 | 0.87 | 0.24 |
| Lower limit of 95% CI | 0.697 | 0.769 | 0.604 | 0.601 | 0.652 | 0.679 | 0.515 | 0.556 | 0.731 |
| Upper limit of 95% CI | 2.74 | 3.00 | 2.40 | 2.16 | 2.36 | 2.95 | 1.85 | 2.00 | 3.44 |
| OR Quartile 4 | 1.77 | 1.62 | 1.90 | 1.68 | 1.71 | 1.72 | 1.30 | 1.33 | 1.58 |
| p Value | 0.19 | 0.25 | 0.10 | 0.18 | 0.16 | 0.18 | 0.48 | 0.45 | 0.29 |
| Lower limit of 95% CI | 0.761 | 0.714 | 0.884 | 0.791 | 0.805 | 0.772 | 0.624 | 0.636 | 0.682 |
| Upper limit of 95% CI | 4.10 | 3.66 | 4.09 | 3.58 | 3.65 | 3.83 | 2.72 | 2.78 | 3.64 |

TABLE 33.8

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 330 | 386 | 364 | 378 | 364 | 378 |
| Average | 443 | 550 | 465 | 557 | 463 | 567 |
| Stdev | 377 | 563 | 368 | 606 | 368 | 620 |
| p (t-test) | | 0.23 | | 0.27 | | 0.22 |
| Min | 50.8 | 46.8 | 50.8 | 46.8 | 50.8 | 46.8 |
| Max | 1880 | 4690 | 1880 | 4690 | 1880 | 4690 |
| n (Patient) | 49 | 102 | 69 | 82 | 75 | 76 |
| sCr only | | | | | | |
| Median | 324 | 392 | 332 | 380 | 332 | 380 |
| Average | 434 | 555 | 450 | 568 | 450 | 578 |
| Stdev | 382 | 566 | 364 | 610 | 364 | 624 |
| p (t-test) | | 0.17 | | 0.16 | | 0.13 |
| Min | 46.8 | 50.8 | 46.8 | 50.8 | 46.8 | 50.8 |
| Max | 1880 | 4690 | 1880 | 4690 | 1880 | 4690 |
| n (Patient) | 51 | 99 | 69 | 81 | 75 | 75 |
| UO only | | | | | | |
| Median | 334 | 394 | 332 | 396 | 331 | 397 |
| Average | 491 | 538 | 495 | 538 | 501 | 527 |
| Stdev | 551 | 408 | 544 | 403 | 546 | 376 |
| p (t-test) | | 0.59 | | 0.63 | | 0.78 |
| Min | 50.8 | 46.8 | 50.8 | 46.8 | 50.8 | 46.8 |
| Max | 4690 | 1700 | 4690 | 1700 | 4690 | 1510 |
| n (Patient) | 98 | 52 | 105 | 45 | 110 | 40 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.58 | 0.55 | 0.53 | 0.55 | 0.56 | 0.54 | 0.56 | 0.56 |
| SE | 0.049 | 0.048 | 0.050 | 0.047 | 0.047 | 0.052 | 0.047 | 0.047 | 0.054 |
| p Value | 0.22 | 0.097 | 0.28 | 0.49 | 0.26 | 0.25 | 0.38 | 0.18 | 0.30 |
| nCohort Non-persistent | 49 | 51 | 98 | 69 | 69 | 105 | 75 | 75 | 110 |
| nCohort Persistent | 102 | 99 | 52 | 82 | 81 | 45 | 76 | 75 | 40 |
| Cutoff Quartile 2 | 218 | 217 | 217 | 218 | 217 | 217 | 218 | 217 | 217 |
| Sensitivity | 75% | 77% | 77% | 74% | 75% | 80% | 76% | 77% | 80% |
| Specificity | 27% | 29% | 27% | 25% | 26% | 28% | 27% | 28% | 27% |
| Cutoff Quartile 3 | 373 | 372 | 372 | 373 | 372 | 372 | 373 | 372 | 372 |
| Sensitivity | 53% | 54% | 56% | 52% | 53% | 58% | 53% | 53% | 60% |
| Specificity | 55% | 57% | 53% | 52% | 54% | 53% | 52% | 53% | 54% |
| Cutoff Quartile 4 | 674 | 661 | 661 | 674 | 661 | 661 | 674 | 661 | 661 |
| Sensitivity | 28% | 28% | 33% | 29% | 30% | 31% | 28% | 28% | 30% |
| Specificity | 82% | 80% | 79% | 80% | 80% | 77% | 77% | 77% | 76% |
| OR Quartile 2 | 1.11 | 1.38 | 1.20 | 0.950 | 1.08 | 1.53 | 1.17 | 1.33 | 1.50 |
| p Value | 0.79 | 0.41 | 0.64 | 0.89 | 0.84 | 0.33 | 0.67 | 0.45 | 0.37 |
| Lower limit of 95% CI | 0.511 | 0.643 | 0.549 | 0.454 | 0.515 | 0.655 | 0.561 | 0.634 | 0.621 |
| Upper limit of 95% CI | 2.42 | 2.95 | 2.64 | 1.99 | 2.25 | 3.56 | 2.45 | 2.78 | 3.62 |
| OR Quartile 3 | 1.38 | 1.52 | 1.43 | 1.20 | 1.31 | 1.56 | 1.20 | 1.31 | 1.74 |
| p Value | 0.36 | 0.23 | 0.30 | 0.57 | 0.41 | 0.21 | 0.57 | 0.41 | 0.14 |
| Lower limit of 95% CI | 0.697 | 0.769 | 0.725 | 0.634 | 0.687 | 0.773 | 0.636 | 0.688 | 0.832 |
| Upper limit of 95% CI | 2.74 | 3.00 | 2.80 | 2.28 | 2.49 | 3.16 | 2.28 | 2.48 | 3.62 |

TABLE 33.8-continued

Comparison of marker levels and the area under the ROC curve (AUC) in EDTA samples for the "persistent" and "non-persistent" cohorts where persistence starts within 72 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 4 | 1.77 | 1.62 | 1.78 | 1.63 | 1.65 | 1.52 | 1.30 | 1.33 | 1.38 |
| p Value | 0.19 | 0.25 | 0.13 | 0.21 | 0.19 | 0.29 | 0.48 | 0.45 | 0.43 |
| Lower limit of 95% CI | 0.761 | 0.714 | 0.838 | 0.764 | 0.777 | 0.700 | 0.623 | 0.634 | 0.618 |
| Upper limit of 95% CI | 4.10 | 3.66 | 3.79 | 3.46 | 3.52 | 3.32 | 2.73 | 2.78 | 3.10 |

TABLE 33.9

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 330 | 386 | 348 | 380 | 348 | 380 |
| Average | 443 | 550 | 465 | 557 | 463 | 566 |
| Stdev | 377 | 563 | 370 | 602 | 370 | 616 |
| p (t-test) | | 0.23 | | 0.27 | | 0.22 |
| Min | 50.8 | 46.8 | 50.8 | 46.8 | 50.8 | 46.8 |
| Max | 1880 | 4690 | 1880 | 4690 | 1880 | 4690 |
| n (Patient) | 49 | 102 | 68 | 83 | 74 | 77 |
| sCr only | | | | | | |
| Median | 324 | 392 | 331 | 386 | 331 | 386 |
| Average | 434 | 555 | 449 | 567 | 449 | 577 |
| Stdev | 382 | 566 | 366 | 606 | 366 | 620 |
| p (t-test) | | 0.17 | | 0.16 | | 0.13 |
| Min | 46.8 | 50.8 | 46.8 | 50.8 | 46.8 | 50.8 |
| Max | 1880 | 4690 | 1880 | 4690 | 1880 | 4690 |
| n (Patient) | 51 | 99 | 68 | 82 | 74 | 76 |
| UO only | | | | | | |
| Median | 330 | 397 | 329 | 412 | 328 | 428 |
| Average | 483 | 551 | 486 | 550 | 493 | 541 |
| Stdev | 554 | 408 | 551 | 399 | 552 | 375 |
| p (t-test) | | 0.43 | | 0.47 | | 0.60 |
| Min | 50.8 | 46.8 | 50.8 | 46.8 | 50.8 | 46.8 |
| Max | 4690 | 1700 | 4690 | 1700 | 4690 | 1510 |
| n (Patient) | 95 | 55 | 100 | 50 | 105 | 45 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.56 | 0.58 | 0.57 | 0.54 | 0.56 | 0.58 | 0.55 | 0.57 | 0.58 |
| SE | 0.049 | 0.048 | 0.049 | 0.047 | 0.047 | 0.050 | 0.047 | 0.047 | 0.052 |
| p Value | 0.22 | 0.097 | 0.13 | 0.45 | 0.22 | 0.11 | 0.34 | 0.16 | 0.14 |
| nCohort Non-persistent | 49 | 51 | 95 | 68 | 68 | 100 | 74 | 74 | 105 |
| nCohort Persistent | 102 | 99 | 55 | 83 | 82 | 50 | 77 | 76 | 45 |
| Cutoff Quartile 2 | 218 | 217 | 217 | 218 | 217 | 217 | 218 | 217 | 217 |
| Sensitivity | 75% | 77% | 78% | 75% | 76% | 80% | 77% | 78% | 80% |
| Specificity | 27% | 29% | 27% | 25% | 26% | 28% | 27% | 28% | 28% |
| Cutoff Quartile 3 | 373 | 372 | 372 | 373 | 372 | 372 | 373 | 372 | 372 |
| Sensitivity | 53% | 54% | 58% | 53% | 54% | 60% | 53% | 54% | 62% |
| Specificity | 55% | 57% | 55% | 53% | 54% | 55% | 53% | 54% | 55% |
| Cutoff Quartile 4 | 674 | 661 | 661 | 674 | 661 | 661 | 674 | 661 | 661 |
| Sensitivity | 28% | 28% | 33% | 29% | 29% | 32% | 27% | 28% | 31% |
| Specificity | 82% | 80% | 79% | 79% | 79% | 78% | 77% | 77% | 77% |

TABLE 33.9-continued

Comparison of marker levels and the area under the ROC curve (AUC) in EDTA samples for the "persistent" and "non-persistent" cohorts where persistence starts within 96 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| OR Quartile 2 | 1.11 | 1.38 | 1.35 | 0.984 | 1.12 | 1.56 | 1.21 | 1.38 | 1.53 |
| p Value | 0.79 | 0.41 | 0.45 | 0.97 | 0.77 | 0.29 | 0.61 | 0.40 | 0.33 |
| Lower limit of 95% CI | 0.511 | 0.643 | 0.617 | 0.470 | 0.534 | 0.686 | 0.582 | 0.657 | 0.655 |
| Upper limit of 95% CI | 2.42 | 2.95 | 2.95 | 2.06 | 2.33 | 3.53 | 2.53 | 2.88 | 3.56 |
| OR Quartile 3 | 1.38 | 1.52 | 1.68 | 1.27 | 1.38 | 1.83 | 1.27 | 1.38 | 2.03 |
| p Value | 0.36 | 0.23 | 0.13 | 0.47 | 0.33 | 0.085 | 0.47 | 0.33 | 0.052 |
| Lower limit of 95% CI | 0.697 | 0.769 | 0.860 | 0.668 | 0.725 | 0.920 | 0.670 | 0.725 | 0.994 |
| Upper limit of 95% CI | 2.74 | 3.00 | 3.29 | 2.41 | 2.63 | 3.65 | 2.40 | 2.62 | 4.15 |
| OR Quartile 4 | 1.77 | 1.62 | 1.82 | 1.57 | 1.60 | 1.67 | 1.26 | 1.28 | 1.52 |
| p Value | 0.19 | 0.25 | 0.12 | 0.24 | 0.23 | 0.19 | 0.54 | 0.51 | 0.29 |
| Lower limit of 95% CI | 0.761 | 0.714 | 0.863 | 0.737 | 0.749 | 0.781 | 0.601 | 0.611 | 0.700 |
| Upper limit of 95% CI | 4.10 | 3.66 | 3.86 | 3.34 | 3.40 | 3.57 | 2.63 | 2.68 | 3.32 |

TABLE 33.10

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | Persistence Period Duration (hr) | | | | | |
|---|---|---|---|---|---|---|
| | 24 | | 48 | | 72 | |
| | Non-persistent Cohort | Persistent Cohort | Non-persistent Cohort | Persistent Cohort | Non-persistent Cohort | Persistent Cohort |
| sCr or UO | | | | | | |
| Median | 330 | 386 | 330 | 394 | 331 | 392 |
| Average | 432 | 553 | 442 | 570 | 447 | 574 |
| Stdev | 374 | 561 | 357 | 599 | 358 | 611 |
| p (t-test) | | 0.18 | | 0.13 | | 0.13 |
| Min | 50.8 | 46.8 | 50.8 | 46.8 | 50.8 | 46.8 |
| Max | 1880 | 4690 | 1880 | 4690 | 1880 | 4690 |
| n (Patient) | 47 | 104 | 65 | 86 | 70 | 81 |
| sCr only | | | | | | |
| Median | 327 | 386 | 331 | 386 | 331 | 386 |
| Average | 436 | 553 | 450 | 564 | 449 | 573 |
| Stdev | 386 | 564 | 371 | 599 | 371 | 612 |
| p (t-test) | | 0.19 | | 0.18 | | 0.14 |
| Min | 46.8 | 50.8 | 46.8 | 50.8 | 46.8 | 50.8 |
| Max | 1880 | 4690 | 1880 | 4690 | 1880 | 4690 |
| n (Patient) | 50 | 100 | 66 | 84 | 72 | 78 |
| UO only | | | | | | |
| Median | 329 | 412 | 328 | 428 | 328 | 428 |
| Average | 484 | 545 | 484 | 548 | 495 | 533 |
| Stdev | 563 | 399 | 558 | 400 | 561 | 378 |
| p (t-test) | | 0.48 | | 0.46 | | 0.67 |
| Min | 50.8 | 46.8 | 50.8 | 46.8 | 50.8 | 46.8 |
| Max | 4690 | 1700 | 4690 | 1700 | 4690 | 1510 |
| n (Patient) | 92 | 58 | 95 | 55 | 99 | 51 |

| | Persistence Period Duration (hr) | | | | | | | | |
|---|---|---|---|---|---|---|---|---|---|
| | 24 | | | 48 | | | 72 | | |
| | sCr or UO | sCr only | UO only | sCr or UO | sCr only | UO only | sCr or UO | sCr only | UO only |
| AUC | 0.57 | 0.58 | 0.58 | 0.56 | 0.56 | 0.58 | 0.56 | 0.57 | 0.57 |
| SE | 0.049 | 0.049 | 0.048 | 0.047 | 0.047 | 0.049 | 0.047 | 0.047 | 0.050 |
| p Value | 0.14 | 0.10 | 0.11 | 0.18 | 0.20 | 0.10 | 0.20 | 0.14 | 0.18 |

TABLE 33.10-continued

Comparison of marker levels and the area under the ROC curve (AUC) in EDTA samples for the "persistent" and "non-persistent" cohorts where persistence starts within 168 hours after sample collection and renal status is assessed by serum creatinine (sCr) only, urine output (UO) only, or serum creatinine or urine output RIFLE criteria.

| | | | | | | | | | |
|---|---|---|---|---|---|---|---|---|---|
| nCohort Non-persistent | 47 | 50 | 92 | 65 | 66 | 95 | 70 | 72 | 99 |
| nCohort Persistent | 104 | 100 | 58 | 86 | 84 | 55 | 81 | 78 | 51 |
| Cutoff Quartile 2 | 218 | 217 | 217 | 218 | 217 | 217 | 218 | 217 | 217 |
| Sensitivity | 76% | 77% | 79% | 76% | 76% | 80% | 77% | 78% | 78% |
| Specificity | 28% | 30% | 28% | 26% | 27% | 28% | 27% | 29% | 27% |
| Cutoff Quartile 3 | 373 | 372 | 372 | 373 | 372 | 372 | 373 | 372 | 372 |
| Sensitivity | 53% | 53% | 59% | 55% | 54% | 60% | 54% | 54% | 61% |
| Specificity | 55% | 56% | 55% | 55% | 55% | 56% | 54% | 54% | 56% |
| Cutoff Quartile 4 | 674 | 661 | 661 | 674 | 661 | 661 | 674 | 661 | 661 |
| Sensitivity | 29% | 28% | 31% | 30% | 29% | 31% | 28% | 27% | 29% |
| Specificity | 83% | 80% | 78% | 82% | 79% | 78% | 79% | 76% | 77% |
| OR Quartile 2 | 1.21 | 1.43 | 1.51 | 1.10 | 1.20 | 1.59 | 1.22 | 1.48 | 1.36 |
| p Value | 0.64 | 0.35 | 0.30 | 0.81 | 0.63 | 0.26 | 0.60 | 0.30 | 0.45 |
| Lower limit of 95% CI | 0.553 | 0.669 | 0.692 | 0.523 | 0.573 | 0.716 | 0.582 | 0.705 | 0.612 |
| Upper limit of 95% CI | 2.64 | 3.08 | 3.30 | 2.30 | 2.51 | 3.52 | 2.54 | 3.10 | 3.04 |
| OR Quartile 3 | 1.39 | 1.44 | 1.76 | 1.50 | 1.38 | 1.89 | 1.41 | 1.38 | 1.94 |
| p Value | 0.35 | 0.30 | 0.095 | 0.22 | 0.32 | 0.064 | 0.29 | 0.33 | 0.059 |
| Lower limit of 95% CI | 0.696 | 0.725 | 0.906 | 0.783 | 0.725 | 0.964 | 0.743 | 0.725 | 0.974 |
| Upper limit of 95% CI | 2.78 | 2.84 | 3.43 | 2.86 | 2.64 | 3.72 | 2.68 | 2.62 | 3.85 |
| OR Quartile 4 | 1.98 | 1.56 | 1.62 | 1.91 | 1.49 | 1.58 | 1.45 | 1.19 | 1.38 |
| p Value | 0.13 | 0.29 | 0.20 | 0.10 | 0.31 | 0.23 | 0.33 | 0.64 | 0.41 |
| Lower limit of 95% CI | 0.827 | 0.686 | 0.769 | 0.880 | 0.697 | 0.745 | 0.688 | 0.569 | 0.643 |
| Upper limit of 95% CI | 4.72 | 3.53 | 3.41 | 4.16 | 3.17 | 3.34 | 3.07 | 2.50 | 2.95 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of treating a subject having acute kidney injury, the method comprising:
   (a) detecting a level of Metalloproteinase inhibitor 2 in a body fluid sample obtained from the subject;
   (b) determining the subject is at an increased risk of persistent acute kidney injury when the detected level of Metalloproteinase inhibitor 2 is above a predetermined threshold level of Metalloproteinase inhibitor 2, wherein persistent acute kidney injury is a minimum RIFLE stage of RIFLE stage R during a period no less than 24 hours, the period beginning within 7 days after sample collection; and
   (c) treating the subject based on the subject's increased risk of persistent acute kidney injury for persistent acute kidney injury, wherein the treatment comprises renal replacement therapy, withdrawing delivery of compounds that are known to be damaging to the kidney, delaying procedures that are known to be damaging to the kidney, or modifying diuretic administration.

2. The method of claim 1, wherein persistent acute kidney injury is a minimum RIFLE stage of RIFLE stage F during the period.

3. The method of claim 1, wherein the subject has RIFLE stage R acute kidney injury.

4. The method of claim 1, wherein the subject has RIFLE stage I acute kidney injury.

5. The method of claim 1, wherein the subject has RIFLE stage F acute kidney injury.

6. The method of claim 1, wherein the period is no less than 48 hours.

7. The method of claim 1, wherein the period is no less than 72 hours.

8. The method of claim 1, wherein the sample is a urine sample.

9. The method of claim 1, wherein persistent acute kidney injury is a minimum RIFLE stage of RIFLE stage I during the period.

10. The method of claim 9, wherein the subject has RIFLE stage I or F acute kidney injury.

11. The method of claim 9, wherein the period is no less than 48 hours.

12. The method of claim 9, wherein the period is no less than 72 hours.

13. The method of claim 9, wherein the period starts within 48 hours after sample collection.

14. The method of claim 9, wherein the period starts within 72 hours after sample collection.

15. The method of claim 9, wherein the period starts within 96 hours after sample collection.

16. The method of claim 2, wherein the subject has RIFLE stage I or F acute kidney injury.

17. The method of claim 2, wherein the period is no less than 48 hours.

18. The method of claim 2, wherein the period is no less than 72 hours.

19. The method of claim 2, wherein the period starts within 72 hours after sample collection.

20. The method of claim 2, wherein the period starts within 96 hours after sample collection.

\* \* \* \* \*

SEQUENCE LISTING

<160> NUMBER OF SEQ ID NOS: 7

<210> SEQ ID NO 1
<211> LENGTH: 207
<212> TYPE: PRT
<213> ORGANISM: Homo sapiens
<220> FEATURE:
<221> NAME/KEY: misc_feature
<223> OTHER INFORMATION: Metalloproteinase inhibitor 1 precursor

```
<400> SEQUENCE: 1

Met Ala Pro Phe Glu Pro Leu Ala Ser Gly Ile Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 2
<211> LENGTH: 220
<212> TYPE: PRT
<213> ORGANISM: Homo sapiens
<220> FEATURE:
<221> NAME/KEY: misc_feature
<223> OTHER INFORMATION: Metalloproteinase inhibitor 2 precursor human
      precursor

<400> SEQUENCE: 2

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
```

```
                130             135             140
Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
                195                 200                 205

Pro Pro Lys Gln Glu Phe Leu Asp Ile Glu Asp Pro
            210                 215                 220

<210> SEQ ID NO 3
<211> LENGTH: 224
<212> TYPE: PRT
<213> ORGANISM: Homo sapiens
<220> FEATURE:
<221> NAME/KEY: misc_feature
<223> OTHER INFORMATION: Metalloproteinase inhibitor 4 precursor human
      precursor

<400> SEQUENCE: 3

Met Pro Gly Ser Pro Arg Pro Ala Pro Ser Trp Val Leu Leu Leu Arg
1               5                   10                  15

Leu Leu Ala Leu Leu Arg Pro Pro Gly Leu Gly Glu Ala Cys Ser Cys
            20                  25                  30

Ala Pro Ala His Pro Gln Gln His Ile Cys His Ser Ala Leu Val Ile
        35                  40                  45

Arg Ala Lys Ile Ser Ser Glu Lys Val Val Pro Ala Ser Ala Asp Pro
50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
                85                  90                  95

Phe Asp Ser Ser Leu Cys Gly Val Lys Leu Glu Ala Asn Ser Gln Lys
            100                 105                 110

Gln Tyr Leu Leu Thr Gly Gln Val Leu Ser Asp Gly Lys Val Phe Ile
        115                 120                 125

His Leu Cys Asn Tyr Ile Glu Pro Trp Glu Asp Leu Ser Leu Val Gln
130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
            180                 185                 190

Gln His Tyr Val Cys Met Lys His Val Asp Gly Thr Cys Ser Trp Tyr
        195                 200                 205

Arg Gly His Leu Pro Leu Arg Lys Glu Phe Val Asp Ile Val Gln Pro
210                 215                 220

<210> SEQ ID NO 4
<211> LENGTH: 113
<212> TYPE: PRT
<213> ORGANISM: Homo sapiens
<220> FEATURE:
<221> NAME/KEY: misc_feature
<223> OTHER INFORMATION: C-C motif chemokine 15 precursor human
``` precursor

<400> SEQUENCE: 4

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
            20                  25                  30

Met Ser Lys Leu Pro Leu Glu Asn Pro Val Val Leu Asn Ser Phe His
        35                  40                  45

Phe Ala Ala Asp Cys Cys Thr Ser Tyr Ile Ser Gln Ser Ile Pro Cys
    50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Lys Leu Lys Pro Tyr Ser
            100                 105                 110

Ile

<210> SEQ ID NO 5
<211> LENGTH: 89
<212> TYPE: PRT
<213> ORGANISM: Homo sapiens
<220> FEATURE:
<221> NAME/KEY: misc_feature
<223> OTHER INFORMATION: C-C motif chemokine 18 precursor human
      precursor

<400> SEQUENCE: 5

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 6
<211> LENGTH: 120
<212> TYPE: PRT
<213> ORGANISM: Homo sapiens
<220> FEATURE:
<221> NAME/KEY: misc_feature
<223> OTHER INFORMATION: C-C motif chemokine 23 precursor

<400> SEQUENCE: 6

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

```
Cys Ser Leu Leu Glu Ser Tyr Phe Glu Thr Asn Ser Glu Cys Ser Lys
 65                  70                  75                  80

Pro Gly Val Ile Phe Leu Thr Lys Lys Gly Arg Arg Phe Cys Ala Asn
                 85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120

<210> SEQ ID NO 7
<211> LENGTH: 119
<212> TYPE: PRT
<213> ORGANISM: Homo sapiens
<220> FEATURE:
<221> NAME/KEY: misc_feature
<223> OTHER INFORMATION: C-C motif chemokine 24 precursor

<400> SEQUENCE: 7

Met Ala Gly Leu Met Thr Ile Val Thr Ser Leu Leu Phe Leu Gly Val
 1               5                  10                  15

Cys Ala His His Ile Ile Pro Thr Gly Ser Val Val Ile Pro Ser Pro
                 20                  25                  30

Cys Cys Met Phe Phe Val Ser Lys Arg Ile Pro Glu Asn Arg Val Val
             35                  40                  45

Ser Tyr Gln Leu Ser Ser Arg Ser Thr Cys Leu Lys Ala Gly Val Ile
         50                  55                  60

Phe Thr Thr Lys Lys Gly Gln Gln Phe Cys Gly Asp Pro Lys Gln Glu
 65                  70                  75                  80

Trp Val Gln Arg Tyr Met Lys Asn Leu Asp Ala Lys Gln Lys Lys Ala
                 85                  90                  95

Ser Pro Arg Ala Arg Ala Val Ala Val Lys Gly Pro Val Gln Arg Tyr
            100                 105                 110

Pro Gly Asn Gln Thr Thr Cys
        115
```